United States Patent
Meyers et al.

(10) Patent No.: US 7,611,879 B2
(45) Date of Patent: Nov. 3, 2009

(54) 27877, 18080, 14081, 32140, 50352, 16658, 14223, 16002, 50566, 65552 AND 65577 MOLECULES AND USES THEREFOR

(75) Inventors: Rachel E. Meyers, Newton, MA (US); William James Cook, Hanover, NH (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/981,466

(22) Filed: Oct. 31, 2007

(65) Prior Publication Data

US 2008/0234468 A1    Sep. 25, 2008

Related U.S. Application Data

(60) Division of application No. 11/429,599, filed on May 5, 2006, now Pat. No. 7,351,566, which is a division of application No. 10/391,364, filed on Mar. 18, 2003, now Pat. No. 7,094,587, which is a continuation-in-part of application No. 09/717,926, filed on Nov. 21, 2000, now Pat. No. 6,569,657, said application No. 10/391,364 is a continuation-in-part of application No. 10/294,039, filed on Nov. 13, 2002, now abandoned, and a continuation-in-part of application No. 10/268,036, filed on Oct. 9, 2002, now abandoned, and a continuation-in-part of application No. 10/266,035, filed on Oct. 7, 2002, now abandoned, and a continuation-in-part of application No. 10/163,316, filed on Jun. 5, 2002, now abandoned, and a continuation-in-part of application No. 10/103,377, filed on Mar. 21, 2002, now abandoned, and a continuation-in-part of application No. 09/950,370, filed on Sep. 10, 2001, now abandoned, and a continuation-in-part of application No. 09/945,327, filed on Aug. 31, 2001, now abandoned, and a continuation-in-part of application No. 09/922,138, filed on Aug. 3, 2001, now abandoned.

(60) Provisional application No. 60/214,707, filed on Jun. 27, 2000, provisional application No. 60/231,084, filed on Sep. 8, 2000, provisional application No. 60/338,587, filed on Nov. 13, 2001, provisional application No. 60/328,198, filed on Oct. 9, 2001, provisional application No. 60/327,820, filed on Oct. 9, 2001, provisional application No. 60/229,299, filed on Sep. 1, 2000, provisional application No. 60/229,425, filed on Aug. 31, 2000, provisional application No. 60/297,863, filed on Jun. 13, 2001, provisional application No. 60/278,347, filed on Mar. 23, 2001.

(51) Int. Cl.
    *C12N 9/04*    (2006.01)
    *C07K 1/00*    (2006.01)

(52) U.S. Cl. ...................................... 435/190; 530/350

(58) Field of Classification Search ................. 435/190; 530/350
    See application file for complete search history.

(56) References Cited

U.S. PATENT DOCUMENTS 6,136,599 A  *  10/2000  Cho ............................ 435/325

FOREIGN PATENT DOCUMENTS

WO    WO02/00863    *    1/2002

OTHER PUBLICATIONS

Meyers et al., Geneseq database accession No. ABB08241, Apr. 2002, see hit #1 in the attcahed Geneseq search results.*
Cook et al. Isolation and characterization of cDNA clones for rat liver 10-formyltetrahydrofolate dehydrogenase. J. Biol. Chem. 266 (8), 4965-4973 (1991).*
Cook, R. J., et al., "Isolation and Characterization of cDNA Clones for Rat Liver 10-Formyltetrahydrofolate Dehydrogenase," *The Journal of Biological Chemistry*, Mar. 15, 1991, pp. 1965-1973, vol. 266, No. 8.
Hong, M. et al., "Isolation and Characterization of cDNA Clone for Human Liver 10-Formyltetrahydrofolate Dehydrogenase," *Biochemistry and Molecular Biology International*, Mar. 1999, pp. 407-415, vol. 47, No. 3.
Yoshida, A., et al., "Human Aldehyde Dehydrogenase Gene Family," *European Journal of Biochemistry*. Feb. 1998, pp. 549-557, vol. 251, No. 3.
EMBL Database Report for Accession No. AA424371, 1997 Unpublished (XP-002212692).
EMBL Database Report for Accession No. AF052732, Sep. 21, 1998 (XP-002212693).
EMBL Database Report for Accession No. M59861, May 1, 1991 (XP-002212694).

* cited by examiner

*Primary Examiner*—Maryam Monshipouri

(57) ABSTRACT

The invention provides isolated nucleic acids molecules, designated 27877, 18080, 14081, 32140, 50352, 16658, 14223, 16002, 50566, 65552 and 65577 nucleic acid molecules. The invention also provides antisense nucleic acid molecules, recombinant expression vectors containing 27877, 18080, 14081, 32140, 50352, 16658, 14223, 16002, 50566, 65552 and 65577 nucleic acid molecules, host cells into which the expression vectors have been introduced, and nonhuman transgenic animals in which a 27877, 18080, 14081, 32140, 50352, 16658, 14223, 16002, 50566, 65552 or 65577 gene has been introduced or disrupted. The invention still further provides isolated 27877, 18080, 14081, 32140, 50352, 16658, 14223, 16002, 50566, 65552 or 65577 proteins, fusion proteins, antigenic peptides and anti-27877, 18080, 14081, 32140, 50352, 16658, 14223, 16002, 50566, 65552 or 65577 antibodies. Diagnostic and therapeutic methods utilizing compositions of the invention are also provided.

6 Claims, No Drawings

SEQUENCE LISTING

<160> NUMBER OF SEQ ID NOS: 93

<210> SEQ ID NO 1
<211> LENGTH: 2981
<212> TYPE: DNA
<213> ORGANISM: Homo sapiens
<220> FEATURE:
<221> NAME/KEY: CDS
<222> LOCATION: (202)...(2826)

<400> SEQUENCE: 1

```
cacgaggccg gcggcagaac gcagctgcgg cggctgcggg tctcgtgggg gcggagcggt        60
cgccgctgcc gccgcagctc gggtcgggat ttgaaagatt agaaacttcg ggtggagagg       120
gcggcggcgt tgaatgtgtg gcggaagcgc tgggggtcac ggctccgcgc gccgccggac       180
agccggcggc gtctccacag c atg aat tac ccg ggc cgc ggg tcc cca cgg        231
                        Met Asn Tyr Pro Gly Arg Gly Ser Pro Arg
                          1               5                  10 agc ccc gag cat aac ggc cga ggc ggc ggc ggc ggc gcc tgg gag ctg        279
Ser Pro Glu His Asn Gly Arg Gly Gly Gly Gly Gly Ala Trp Glu Leu
             15                  20                  25 ggc tca gac gcg agg cca gcg ttc ggc ggc ggc gtc tgc tgc ttc gag        327
Gly Ser Asp Ala Arg Pro Ala Phe Gly Gly Gly Val Cys Cys Phe Glu
         30                  35                  40 cac ctg ccc ggc ggg gac ccg gac gac ggc gac gtg ccc ctg gcc ctg        375
His Leu Pro Gly Gly Asp Pro Asp Asp Gly Asp Val Pro Leu Ala Leu
     45                  50                  55 ctg cgc ggg gaa ccc ggg ctg cat ttg gcg ccg ggc acc gac gac cac        423
Leu Arg Gly Glu Pro Gly Leu His Leu Ala Pro Gly Thr Asp Asp His
 60                  65                  70 aac cac cac ctc gcg ctg gac ccc tgc ctc agt gac gag aac tat gac        471
Asn His His Leu Ala Leu Asp Pro Cys Leu Ser Asp Glu Asn Tyr Asp
 75                  80                  85                  90 ttt agc tcc gcc gag tcg ggc tcc tcg ctg cgc tac tac agc gag ggt        519
Phe Ser Ser Ala Glu Ser Gly Ser Ser Leu Arg Tyr Tyr Ser Glu Gly
                 95                 100                 105 gag agc ggc ggc ggc ggc ggc agc tcc ttg tcg ctg cat ccg ccg            567
Glu Ser Gly Gly Gly Gly Gly Ser Ser Leu Ser Leu His Pro Pro
            110                 115                 120 cag cag cct ccg ctg gtc ccg acg aac tcg ggg ggc ggc gcg aca            615
Gln Gln Pro Pro Leu Val Pro Thr Asn Ser Gly Gly Gly Ala Thr
        125                 130                 135 gga ggg tcc ccc ggg gaa agg aaa cgt acc cgg ctt ggc ggc ccg gcg        663
Gly Gly Ser Pro Gly Glu Arg Lys Arg Thr Arg Leu Gly Gly Pro Ala
    140                 145                 150 gcc cgg cac cgc tat gag gta gtg acg gag ctg ggc ccg gag gag gta        711
Ala Arg His Arg Tyr Glu Val Val Thr Glu Leu Gly Pro Glu Glu Val
155                 160                 165                 170 cgc tgg ttc tac aag gag gac aag aag acc tgg aag ccc ttc atc ggc        759
Arg Trp Phe Tyr Lys Glu Asp Lys Lys Thr Trp Lys Pro Phe Ile Gly
                175                 180                 185 tac gac tcg ctc cgc atc gag ctc gcc ttc cgg acc ctg ctg cag acc        807
Tyr Asp Ser Leu Arg Ile Glu Leu Ala Phe Arg Thr Leu Leu Gln Thr
            190                 195                 200 acg ggt gcc cgg ccc cag ggc ggg gac cgg gac ggc gac cat gtg tgc        855
Thr Gly Ala Arg Pro Gln Gly Gly Asp Arg Asp Gly Asp His Val Cys
        205                 210                 215 tcc ccc acg agc cca gcc tcc agt tcc gga gaa gat gac gat gag gac        903
Ser Pro Thr Ser Pro Ala Ser Ser Ser Gly Glu Asp Asp Asp Glu Asp
```

```
                220                 225                 230
cgc gcc tgc ggc ttc tgc cag agt acg acg ggg cac gag ccg gag atg      951
Arg Ala Cys Gly Phe Cys Gln Ser Thr Thr Gly His Glu Pro Glu Met
235                 240                 245                 250 gtg gag ctt gtg aac atc gag cct gtg tgc gtg cgg ggc ggc ctc tac      999
Val Glu Leu Val Asn Ile Glu Pro Val Cys Val Arg Gly Gly Leu Tyr
                    255                 260                 265 gag gtg gat gtg acc caa gga gag tgc tac ccg gtg tac tgg aac cag     1047
Glu Val Asp Val Thr Gln Gly Glu Cys Tyr Pro Val Tyr Trp Asn Gln
                270                 275                 280 gct gat aaa ata cca gta atg cgt gga cag tgg ttt att gac ggc act     1095
Ala Asp Lys Ile Pro Val Met Arg Gly Gln Trp Phe Ile Asp Gly Thr
            285                 290                 295 tgg cag cct cta gaa gag gaa gaa agt aat tta att gag caa gaa cat     1143
Trp Gln Pro Leu Glu Glu Glu Glu Ser Asn Leu Ile Glu Gln Glu His
        300                 305                 310 ctc aat tgt ttt agg ggc cag cag atg cag gaa aat ttc gat att gaa     1191
Leu Asn Cys Phe Arg Gly Gln Gln Met Gln Glu Asn Phe Asp Ile Glu
315                 320                 325                 330 gtg tca aaa tcc ata gat gga aaa gat gct gtt cat agt ttc aag ttg     1239
Val Ser Lys Ser Ile Asp Gly Lys Asp Ala Val His Ser Phe Lys Leu
                    335                 340                 345 agt cga aac cat gtg gac tgg cac agt gtg gat gaa gta tat ctt tat     1287
Ser Arg Asn His Val Asp Trp His Ser Val Asp Glu Val Tyr Leu Tyr
                350                 355                 360 agt gat gca aca aca tct aaa att gca aga aca gtt acc caa aaa ctg     1335
Ser Asp Ala Thr Thr Ser Lys Ile Ala Arg Thr Val Thr Gln Lys Leu
            365                 370                 375 gga ttt tct aaa gca tca agt agt ggt acc aga ctt cat aga ggt tat     1383
Gly Phe Ser Lys Ala Ser Ser Ser Gly Thr Arg Leu His Arg Gly Tyr
        380                 385                 390 gta gaa gaa gcc aca tta gaa gac aag cca tca cag act acc cat att     1431
Val Glu Glu Ala Thr Leu Glu Asp Lys Pro Ser Gln Thr Thr His Ile
395                 400                 405                 410 gta ttt gtt gtg cat ggc att ggg cag aaa atg gac caa gga aga att     1479
Val Phe Val Val His Gly Ile Gly Gln Lys Met Asp Gln Gly Arg Ile
                    415                 420                 425 atc aaa aat aca gct atg atg aga gaa gct gca aga aaa ata gaa gaa     1527
Ile Lys Asn Thr Ala Met Met Arg Glu Ala Ala Arg Lys Ile Glu Glu
                430                 435                 440 agg cat ttt tcc aac cat gca aca cat gtt gaa ttt ctg cct gtt gag     1575
Arg His Phe Ser Asn His Ala Thr His Val Glu Phe Leu Pro Val Glu
            445                 450                 455 tgg cgg tca aaa ctt act ctt gat gga gac act gtt gat tcc att act     1623
Trp Arg Ser Lys Leu Thr Leu Asp Gly Asp Thr Val Asp Ser Ile Thr
        460                 465                 470 cct gac aaa gta cga ggt tta agg gat atg ctg aac agc agt gca atg     1671
Pro Asp Lys Val Arg Gly Leu Arg Asp Met Leu Asn Ser Ser Ala Met
475                 480                 485                 490 gac ata atg tat tat act agt cca ctt tat aga gat gaa cta gtt aaa     1719
Asp Ile Met Tyr Tyr Thr Ser Pro Leu Tyr Arg Asp Glu Leu Val Lys
                    495                 500                 505 ggc ctt cag caa gag ctg aat cga ttg tat tcc ctt ttc tgt tct cgg     1767
Gly Leu Gln Gln Glu Leu Asn Arg Leu Tyr Ser Leu Phe Cys Ser Arg
                510                 515                 520 aat cca gac ttt gaa gaa aaa ggg ggt aaa gtc tca ata gta tca cat     1815
Asn Pro Asp Phe Glu Glu Lys Gly Gly Lys Val Ser Ile Val Ser His
            525                 530                 535 tcc ttg gga tgt gta att act tat gac ata atg act ggc tgg aat cca     1863
```

```
                Ser Leu Gly Cys Val Ile Thr Tyr Asp Ile Met Thr Gly Trp Asn Pro
                    540                 545                 550 gtt cgg ctg tat gaa cag ttg ctg caa aag gaa gaa gag ttg cct gat      1911
Val Arg Leu Tyr Glu Gln Leu Leu Gln Lys Glu Glu Glu Leu Pro Asp
555                 560                 565                 570 gaa cga tgg atg agc tat gaa gaa cga cat ctt ctt gat gaa ctc tat      1959
Glu Arg Trp Met Ser Tyr Glu Glu Arg His Leu Leu Asp Glu Leu Tyr
                575                 580                 585 ata aca aaa cga cgg ctg aag gaa ata gaa gaa cgg ctt cac gga ttg      2007
Ile Thr Lys Arg Arg Leu Lys Glu Ile Glu Glu Arg Leu His Gly Leu
            590                 595                 600 aaa gca tca tct atg aca caa aca cct gcc tta aaa ttt aag gtt gag      2055
Lys Ala Ser Ser Met Thr Gln Thr Pro Ala Leu Lys Phe Lys Val Glu
        605                 610                 615 aat ttc ttc tgt atg gga tcc cca tta gca gtt ttc ttg gcg ttg cgt      2103
Asn Phe Phe Cys Met Gly Ser Pro Leu Ala Val Phe Leu Ala Leu Arg
    620                 625                 630 ggc atc cgc cca gga aat act gga agt caa gac cat att ttg cct aga      2151
Gly Ile Arg Pro Gly Asn Thr Gly Ser Gln Asp His Ile Leu Pro Arg
635                 640                 645                 650 gag att tgt aac cgg tta cta aat att ttt cat cct aca gat cca gtg      2199
Glu Ile Cys Asn Arg Leu Leu Asn Ile Phe His Pro Thr Asp Pro Val
                655                 660                 665 gct tat aga tta gaa cca tta ata ctg aaa cac tac agc aac att tca      2247
Ala Tyr Arg Leu Glu Pro Leu Ile Leu Lys His Tyr Ser Asn Ile Ser
            670                 675                 680 cct gtc cag atc cac tgg tac aat act tca aat cct tta cct tat gaa      2295
Pro Val Gln Ile His Trp Tyr Asn Thr Ser Asn Pro Leu Pro Tyr Glu
        685                 690                 695 cat atg aag cca agc ttt ctc aac cca gct aaa gaa cct acc tca gtt      2343
His Met Lys Pro Ser Phe Leu Asn Pro Ala Lys Glu Pro Thr Ser Val
    700                 705                 710 tca gag aat gaa ggc att tca acc ata cca agc cct gtg acc tca cca      2391
Ser Glu Asn Glu Gly Ile Ser Thr Ile Pro Ser Pro Val Thr Ser Pro
715                 720                 725                 730 gtt ttg tcc cgc cga cac tat gga gaa tct ata aca aat ata ggc aaa      2439
Val Leu Ser Arg Arg His Tyr Gly Glu Ser Ile Thr Asn Ile Gly Lys
                735                 740                 745 gca agc ata tta ggg gct gct agc att gga aag gga ctt gga gga atg      2487
Ala Ser Ile Leu Gly Ala Ala Ser Ile Gly Lys Gly Leu Gly Gly Met
            750                 755                 760 ttg ttc tca aga ttt gga cgt tca tct aca aca cag tca tct gaa aca      2535
Leu Phe Ser Arg Phe Gly Arg Ser Ser Thr Thr Gln Ser Ser Glu Thr
        765                 770                 775 tca aaa gac tca atg gaa gat gag aag aag cca gtt gcc tca cct tct      2583
Ser Lys Asp Ser Met Glu Asp Glu Lys Lys Pro Val Ala Ser Pro Ser
    780                 785                 790 gct acc acc gta ggg aca cag acc ctt cca cat agc agt tct ggc ttc      2631
Ala Thr Thr Val Gly Thr Gln Thr Leu Pro His Ser Ser Ser Gly Phe
795                 800                 805                 810 ctc gat tct gca ttg gag ttg gat cac agg att gat ttt gaa ctc aga      2679
Leu Asp Ser Ala Leu Glu Leu Asp His Arg Ile Asp Phe Glu Leu Arg
                815                 820                 825 gaa ggc ctt gtg gag agc cgc tat tgg tca gct gtc acg tcg cat act      2727
Glu Gly Leu Val Glu Ser Arg Tyr Trp Ser Ala Val Thr Ser His Thr
            830                 835                 840 gcc tat tgg tca tcc ttg gat gtt gcc ctt ttt ctt tta acc ttc atg      2775
Ala Tyr Trp Ser Ser Leu Asp Val Ala Leu Phe Leu Leu Thr Phe Met
        845                 850                 855
```

```
tat aaa cat gag cac gat gat gat gca aaa ccc aat tta gat cca atc       2823
Tyr Lys His Glu His Asp Asp Asp Ala Lys Pro Asn Leu Asp Pro Ile
    860                 865                 870 tga actcttgaag gacatgaatg gcctaaaact gattttttt tttttccgtt              2876
* aaaatgtgtg tgtcaagata cggagatttc agggttaaag tatatttcag ttttctttag      2936
ggcaacatat atttgaattt aaaagcactt tatttaaaaa aaaaa                      2981
```

<210> SEQ ID NO 2
<211> LENGTH: 874
<212> TYPE: PRT
<213> ORGANISM: Homo sapiens

<400> SEQUENCE: 2

```
Met Asn Tyr Pro Gly Arg Gly Ser Pro Arg Ser Pro Glu His Asn Gly
1               5                   10                  15

Arg Gly Gly Gly Gly Ala Trp Glu Leu Gly Ser Asp Ala Arg Pro
            20                  25                  30

Ala Phe Gly Gly Gly Val Cys Cys Phe Glu His Leu Pro Gly Gly Asp
        35                  40                  45

Pro Asp Asp Gly Asp Val Pro Leu Ala Leu Leu Arg Gly Glu Pro Gly
    50                  55                  60

Leu His Leu Ala Pro Gly Thr Asp Asp His Asn His His Leu Ala Leu
65                  70                  75                  80

Asp Pro Cys Leu Ser Asp Glu Asn Tyr Asp Phe Ser Ser Ala Glu Ser
                85                  90                  95

Gly Ser Ser Leu Arg Tyr Tyr Ser Glu Gly Glu Ser Gly Gly Gly Gly
            100                 105                 110

Gly Gly Ser Ser Leu Ser Leu His Pro Pro Gln Gln Pro Leu Val
        115                 120                 125

Pro Thr Asn Ser Gly Gly Gly Ala Thr Gly Gly Ser Pro Gly Glu
    130                 135                 140

Arg Lys Arg Thr Arg Leu Gly Gly Pro Ala Ala Arg His Arg Tyr Glu
145                 150                 155                 160

Val Val Thr Glu Leu Gly Pro Glu Glu Val Arg Trp Phe Tyr Lys Glu
                165                 170                 175

Asp Lys Lys Thr Trp Lys Pro Phe Ile Gly Tyr Asp Ser Leu Arg Ile
            180                 185                 190

Glu Leu Ala Phe Arg Thr Leu Leu Gln Thr Thr Gly Ala Arg Pro Gln
        195                 200                 205

Gly Gly Asp Arg Asp Gly Asp His Val Cys Ser Pro Thr Ser Pro Ala
    210                 215                 220

Ser Ser Ser Gly Glu Asp Asp Glu Asp Arg Ala Cys Gly Phe Cys
225                 230                 235                 240

Gln Ser Thr Thr Gly His Glu Pro Glu Met Val Glu Leu Val Asn Ile
                245                 250                 255

Glu Pro Val Cys Val Arg Gly Gly Leu Tyr Glu Val Asp Val Thr Gln
            260                 265                 270

Gly Glu Cys Tyr Pro Val Tyr Trp Asn Gln Ala Asp Lys Ile Pro Val
        275                 280                 285

Met Arg Gly Gln Trp Phe Ile Asp Gly Thr Trp Gln Pro Leu Glu Glu
    290                 295                 300

Glu Glu Ser Asn Leu Ile Glu Gln Glu His Leu Asn Cys Phe Arg Gly
305                 310                 315                 320
```

-continued

```
Gln Gln Met Gln Glu Asn Phe Asp Ile Glu Val Ser Lys Ser Ile Asp
                325                 330                 335

Gly Lys Asp Ala Val His Ser Phe Lys Leu Ser Arg Asn His Val Asp
            340                 345                 350

Trp His Ser Val Asp Glu Val Tyr Leu Tyr Ser Asp Ala Thr Thr Ser
        355                 360                 365

Lys Ile Ala Arg Thr Val Thr Gln Lys Leu Gly Phe Ser Lys Ala Ser
    370                 375                 380

Ser Ser Gly Thr Arg Leu His Arg Gly Tyr Val Glu Glu Ala Thr Leu
385                 390                 395                 400

Glu Asp Lys Pro Ser Gln Thr Thr His Ile Val Phe Val Val His Gly
                405                 410                 415

Ile Gly Gln Lys Met Asp Gln Gly Arg Ile Ile Lys Asn Thr Ala Met
            420                 425                 430

Met Arg Glu Ala Ala Arg Lys Ile Glu Glu Arg His Phe Ser Asn His
        435                 440                 445

Ala Thr His Val Glu Phe Leu Pro Val Glu Trp Arg Ser Lys Leu Thr
    450                 455                 460

Leu Asp Gly Asp Thr Val Asp Ser Ile Thr Pro Asp Lys Val Arg Gly
465                 470                 475                 480

Leu Arg Asp Met Leu Asn Ser Ser Ala Met Asp Ile Met Tyr Tyr Thr
                485                 490                 495

Ser Pro Leu Tyr Arg Asp Glu Leu Val Lys Gly Leu Gln Gln Glu Leu
            500                 505                 510

Asn Arg Leu Tyr Ser Leu Phe Cys Ser Arg Asn Pro Asp Phe Glu Glu
        515                 520                 525

Lys Gly Gly Lys Val Ser Ile Val Ser His Ser Leu Gly Cys Val Ile
    530                 535                 540

Thr Tyr Asp Ile Met Thr Gly Trp Asn Pro Val Arg Leu Tyr Glu Gln
545                 550                 555                 560

Leu Leu Gln Lys Glu Glu Leu Pro Asp Glu Arg Trp Met Ser Tyr
                565                 570                 575

Glu Glu Arg His Leu Leu Asp Glu Leu Tyr Ile Thr Lys Arg Arg Leu
            580                 585                 590

Lys Glu Ile Glu Glu Arg Leu His Gly Leu Lys Ala Ser Ser Met Thr
        595                 600                 605

Gln Thr Pro Ala Leu Lys Phe Lys Val Glu Asn Phe Phe Cys Met Gly
    610                 615                 620

Ser Pro Leu Ala Val Phe Leu Ala Leu Arg Gly Ile Arg Pro Gly Asn
625                 630                 635                 640

Thr Gly Ser Gln Asp His Ile Leu Pro Arg Glu Ile Cys Asn Arg Leu
                645                 650                 655

Leu Asn Ile Phe His Pro Thr Asp Pro Val Ala Tyr Arg Leu Glu Pro
            660                 665                 670

Leu Ile Leu Lys His Tyr Ser Asn Ile Ser Pro Val Gln Ile His Trp
        675                 680                 685

Tyr Asn Thr Ser Asn Pro Leu Pro Tyr Glu His Met Lys Pro Ser Phe
    690                 695                 700

Leu Asn Pro Ala Lys Glu Pro Thr Ser Val Ser Glu Asn Glu Gly Ile
705                 710                 715                 720

Ser Thr Ile Pro Ser Pro Val Thr Ser Pro Val Leu Ser Arg Arg His
                725                 730                 735

Tyr Gly Glu Ser Ile Thr Asn Ile Gly Lys Ala Ser Ile Leu Gly Ala
```

```
                    740                 745                 750
Ala Ser Ile Gly Lys Gly Leu Gly Gly Met Leu Phe Ser Arg Phe Gly
                755                 760                 765

Arg Ser Ser Thr Thr Gln Ser Ser Glu Thr Ser Lys Asp Ser Met Glu
            770                 775                 780

Asp Glu Lys Lys Pro Val Ala Ser Pro Ser Ala Thr Thr Val Gly Thr
785                 790                 795                 800

Gln Thr Leu Pro His Ser Ser Gly Phe Leu Asp Ser Ala Leu Glu
                805                 810                 815

Leu Asp His Arg Ile Asp Phe Glu Leu Arg Glu Gly Leu Val Glu Ser
                820                 825                 830

Arg Tyr Trp Ser Ala Val Thr Ser His Thr Ala Tyr Trp Ser Ser Leu
            835                 840                 845

Asp Val Ala Leu Phe Leu Leu Thr Phe Met Tyr Lys His Glu His Asp
            850                 855                 860

Asp Asp Ala Lys Pro Asn Leu Asp Pro Ile
865                 870

<210> SEQ ID NO 3
<211> LENGTH: 2622
<212> TYPE: DNA
<213> ORGANISM: Homo sapiens
<220> FEATURE:
<221> NAME/KEY: CDS
<222> LOCATION: (1)...(2622)

<400> SEQUENCE: 3 atg aat tac ccg ggc cgc ggg tcc cca cgg agc ccc gag cat aac ggc     48
Met Asn Tyr Pro Gly Arg Gly Ser Pro Arg Ser Pro Glu His Asn Gly
1               5                   10                  15 cga ggc ggc ggc ggc gcc tgg gag ctg ggc tca gac gcg agg cca         96
Arg Gly Gly Gly Gly Ala Trp Glu Leu Gly Ser Asp Ala Arg Pro
            20                  25                  30 gcg ttc ggc ggc ggc gtc tgc tgc ttc gag cac ctg ccc ggc ggg gac    144
Ala Phe Gly Gly Gly Val Cys Cys Phe Glu His Leu Pro Gly Gly Asp
        35                  40                  45 ccg gac gac ggc gac gtg ccc ctg gcc ctg ctg cgc ggg gaa ccc ggg    192
Pro Asp Asp Gly Asp Val Pro Leu Ala Leu Leu Arg Gly Glu Pro Gly
    50                  55                  60 ctg cat ttg gcg ccg ggc acc gac gac cac aac cac cac ctc gcg ctg    240
Leu His Leu Ala Pro Gly Thr Asp Asp His Asn His His Leu Ala Leu
65                  70                  75                  80 gac ccc tgc ctc agt gac gag aac tat gac ttt agc tcc gcc gag tcg    288
Asp Pro Cys Leu Ser Asp Glu Asn Tyr Asp Phe Ser Ser Ala Glu Ser
                85                  90                  95 ggc tcc tcg ctg cgc tac tac agc gag ggt gag agc ggc ggc ggc ggc    336
Gly Ser Ser Leu Arg Tyr Tyr Ser Glu Gly Glu Ser Gly Gly Gly Gly
            100                 105                 110 ggc ggc agc tcc ttg tcg ctg cat ccg ccg cag cag cct ccg ctg gtc    384
Gly Gly Ser Ser Leu Ser Leu His Pro Pro Gln Gln Pro Pro Leu Val
        115                 120                 125 ccg acg aac tcg ggg ggc ggc ggc gcg aca gga ggg tcc ccc ggg gaa    432
Pro Thr Asn Ser Gly Gly Gly Gly Ala Thr Gly Gly Ser Pro Gly Glu
    130                 135                 140 agg aaa cgt acc cgg ctt ggc ggc ccg gcg gcc cgg cac cgc tat gag    480
Arg Lys Arg Thr Arg Leu Gly Gly Pro Ala Ala Arg His Arg Tyr Glu
145                 150                 155                 160 gta gtg acg gag ctg ggc ccg gag gag gta cgc tgg ttc tac aag gag    528
Val Val Thr Glu Leu Gly Pro Glu Glu Val Arg Trp Phe Tyr Lys Glu
```

-continued

|  |  |  | 165 |  |  |  | 170 |  |  |  | 175 |  |  |
|---|---|---|---|---|---|---|---|---|---|---|---|---|---|

```
gac aag aag acc tgg aag ccc ttc atc ggc tac gac tcg ctc cgc atc      576
Asp Lys Lys Thr Trp Lys Pro Phe Ile Gly Tyr Asp Ser Leu Arg Ile
            180                 185                 190 gag ctc gcc ttc cgg acc ctg ctg cag acc acg ggt gcc cgg ccc cag      624
Glu Leu Ala Phe Arg Thr Leu Leu Gln Thr Thr Gly Ala Arg Pro Gln
        195                 200                 205 ggc ggg gac cgg gac ggc gac cat gtg tgc tcc ccc acg agc cca gcc      672
Gly Gly Asp Arg Asp Gly Asp His Val Cys Ser Pro Thr Ser Pro Ala
    210                 215                 220 tcc agt tcc gga gaa gat gac gat gag gac cgc gcc tgc ggc ttc tgc      720
Ser Ser Ser Gly Glu Asp Asp Asp Glu Asp Arg Ala Cys Gly Phe Cys
225                 230                 235                 240 cag agt acg acg ggg cac gag ccg gag atg gtg gag ctt gtg aac atc      768
Gln Ser Thr Thr Gly His Glu Pro Glu Met Val Glu Leu Val Asn Ile
            245                 250                 255 gag cct gtg tgc gtg cgg ggc ggc ctc tac gag gtg gat gtg acc caa      816
Glu Pro Val Cys Val Arg Gly Gly Leu Tyr Glu Val Asp Val Thr Gln
        260                 265                 270 gga gag tgc tac ccg gtg tac tgg aac cag gct gat aaa ata cca gta      864
Gly Glu Cys Tyr Pro Val Tyr Trp Asn Gln Ala Asp Lys Ile Pro Val
    275                 280                 285 atg cgt gga cag tgg ttt att gac ggc act tgg cag cct cta gaa gag      912
Met Arg Gly Gln Trp Phe Ile Asp Gly Thr Trp Gln Pro Leu Glu Glu
290                 295                 300 gaa gaa agt aat tta att gag caa gaa cat ctc aat tgt ttt agg ggc      960
Glu Glu Ser Asn Leu Ile Glu Gln Glu His Leu Asn Cys Phe Arg Gly
            305                 310                 315                 320 cag cag atg cag gaa aat ttc gat att gaa gtg tca aaa tcc ata gat     1008
Gln Gln Met Gln Glu Asn Phe Asp Ile Glu Val Ser Lys Ser Ile Asp
        325                 330                 335 gga aaa gat gct gtt cat agt ttc aag ttg agt cga aac cat gtg gac     1056
Gly Lys Asp Ala Val His Ser Phe Lys Leu Ser Arg Asn His Val Asp
    340                 345                 350 tgg cac agt gtg gat gaa gta tat ctt tat agt gat gca aca aca tct     1104
Trp His Ser Val Asp Glu Val Tyr Leu Tyr Ser Asp Ala Thr Thr Ser
355                 360                 365 aaa att gca aga aca gtt acc caa aaa ctg gga ttt tct aaa gca tca     1152
Lys Ile Ala Arg Thr Val Thr Gln Lys Leu Gly Phe Ser Lys Ala Ser
370                 375                 380 agt agt ggt acc aga ctt cat aga ggt tat gta gaa gaa gcc aca tta     1200
Ser Ser Gly Thr Arg Leu His Arg Gly Tyr Val Glu Glu Ala Thr Leu
385                 390                 395                 400 gaa gac aag cca tca cag act acc cat att gta ttt gtg cat ggc         1248
Glu Asp Lys Pro Ser Gln Thr Thr His Ile Val Phe Val His Gly
            405                 410                 415 att ggg cag aaa atg gac caa gga aga att atc aaa aat aca gct atg     1296
Ile Gly Gln Lys Met Asp Gln Gly Arg Ile Ile Lys Asn Thr Ala Met
        420                 425                 430 atg aga gaa gct gca aga aaa ata gaa gaa agg cat ttt tcc aac cat     1344
Met Arg Glu Ala Ala Arg Lys Ile Glu Glu Arg His Phe Ser Asn His
    435                 440                 445 gca aca cat gtt gaa ttt ctg cct gtt gag tgg cgg tca aaa ctt act     1392
Ala Thr His Val Glu Phe Leu Pro Val Glu Trp Arg Ser Lys Leu Thr
450                 455                 460 ctt gat gga gac act gtt gat tcc att act cct gac aaa gta cga ggt     1440
Leu Asp Gly Asp Thr Val Asp Ser Ile Thr Pro Asp Lys Val Arg Gly
465                 470                 475                 480 tta agg gat atg ctg aac agc agt gca atg gac ata atg tat tat act     1488
```

```
Leu Arg Asp Met Leu Asn Ser Ser Ala Met Asp Ile Met Tyr Tyr Thr
            485                 490                 495 agt cca ctt tat aga gat gaa cta gtt aaa ggc ctt cag caa gag ctg      1536
Ser Pro Leu Tyr Arg Asp Glu Leu Val Lys Gly Leu Gln Gln Glu Leu
            500                 505                 510 aat cga ttg tat tcc ctt ttc tgt tct cgg aat cca gac ttt gaa gaa      1584
Asn Arg Leu Tyr Ser Leu Phe Cys Ser Arg Asn Pro Asp Phe Glu Glu
            515                 520                 525 aaa ggg ggt aaa gtc tca ata gta tca cat tcc ttg gga tgt gta att      1632
Lys Gly Gly Lys Val Ser Ile Val Ser His Ser Leu Gly Cys Val Ile
530                 535                 540 act tat gac ata atg act ggc tgg aat cca gtt cgg ctg tat gaa cag      1680
Thr Tyr Asp Ile Met Thr Gly Trp Asn Pro Val Arg Leu Tyr Glu Gln
545                 550                 555                 560 ttg ctg caa aag gaa gaa gag ttg cct gat gaa cga tgg atg agc tat      1728
Leu Leu Gln Lys Glu Glu Glu Leu Pro Asp Glu Arg Trp Met Ser Tyr
                565                 570                 575 gaa gaa cga cat ctt ctt gat gaa ctc tat ata aca aaa cga cgg ctg      1776
Glu Glu Arg His Leu Leu Asp Glu Leu Tyr Ile Thr Lys Arg Arg Leu
                580                 585                 590 aag gaa ata gaa gaa cgg ctt cac gga ttg aaa gca tca tct atg aca      1824
Lys Glu Ile Glu Glu Arg Leu His Gly Leu Lys Ala Ser Ser Met Thr
                595                 600                 605 caa aca cct gcc tta aaa ttt aag gtt gag aat ttc ttc tgt atg gga      1872
Gln Thr Pro Ala Leu Lys Phe Lys Val Glu Asn Phe Phe Cys Met Gly
610                 615                 620 tcc cca tta gca gtt ttc ttg gcg ttg cgt ggc atc cgc cca gga aat      1920
Ser Pro Leu Ala Val Phe Leu Ala Leu Arg Gly Ile Arg Pro Gly Asn
625                 630                 635                 640 act gga agt caa gac cat att ttg cct aga gag att tgt aac cgg tta      1968
Thr Gly Ser Gln Asp His Ile Leu Pro Arg Glu Ile Cys Asn Arg Leu
                645                 650                 655 cta aat att ttt cat cct aca gat cca gtg gct tat aga tta gaa cca      2016
Leu Asn Ile Phe His Pro Thr Asp Pro Val Ala Tyr Arg Leu Glu Pro
                660                 665                 670 tta ata ctg aaa cac tac agc aac att tca cct gtc cag atc cac tgg      2064
Leu Ile Leu Lys His Tyr Ser Asn Ile Ser Pro Val Gln Ile His Trp
                675                 680                 685 tac aat act tca aat cct tta cct tat gaa cat atg aag cca agc ttt      2112
Tyr Asn Thr Ser Asn Pro Leu Pro Tyr Glu His Met Lys Pro Ser Phe
        690                 695                 700 ctc aac cca gct aaa gaa cct acc tca gtt tca gag aat gaa ggc att      2160
Leu Asn Pro Ala Lys Glu Pro Thr Ser Val Ser Glu Asn Glu Gly Ile
705                 710                 715                 720 tca acc ata cca agc cct gtg acc tca cca gtt ttg tcc cgc cga cac      2208
Ser Thr Ile Pro Ser Pro Val Thr Ser Pro Val Leu Ser Arg Arg His
                725                 730                 735 tat gga gaa tct ata aca aat ata ggc aaa gca agc ata tta ggg gct      2256
Tyr Gly Glu Ser Ile Thr Asn Ile Gly Lys Ala Ser Ile Leu Gly Ala
                740                 745                 750 gct agc att gga aag gga ctt gga gga atg ttg ttc tca aga ttt gga      2304
Ala Ser Ile Gly Lys Gly Leu Gly Gly Met Leu Phe Ser Arg Phe Gly
            755                 760                 765 cgt tca tct aca aca cag tca tct gaa aca tca aaa gac tca atg gaa      2352
Arg Ser Ser Thr Thr Gln Ser Ser Glu Thr Ser Lys Asp Ser Met Glu
            770                 775                 780 gat gag aag aag cca gtt gcc tca cct tct gct acc acc gta ggg aca      2400
Asp Glu Lys Lys Pro Val Ala Ser Pro Ser Ala Thr Thr Val Gly Thr
785                 790                 795                 800
```

-continued

| | | |
|---|---|---|
| cag acc ctt cca cat agc agt tct ggc ttc ctc gat tct gca ttg gag<br>Gln Thr Leu Pro His Ser Ser Ser Gly Phe Leu Asp Ser Ala Leu Glu<br>805                     810                   815 | 2448 |
| ttg gat cac agg att gat ttt gaa ctc aga gaa ggc ctt gtg gag agc<br>Leu Asp His Arg Ile Asp Phe Glu Leu Arg Glu Gly Leu Val Glu Ser<br>820                     825                   830 | 2496 |
| cgc tat tgg tca gct gtc acg tcg cat act gcc tat tgg tca tcc ttg<br>Arg Tyr Trp Ser Ala Val Thr Ser His Thr Ala Tyr Trp Ser Ser Leu<br>835                     840                   845 | 2544 |
| gat gtt gcc ctt ttt ctt tta acc ttc atg tat aaa cat gag cac gat<br>Asp Val Ala Leu Phe Leu Leu Thr Phe Met Tyr Lys His Glu His Asp<br>850                     855                   860 | 2592 |
| gat gat gca aaa ccc aat tta gat cca atc<br>Asp Asp Ala Lys Pro Asn Leu Asp Pro Ile<br>865                     870 | 2622 |

<210> SEQ ID NO 4
<211> LENGTH: 3065
<212> TYPE: DNA
<213> ORGANISM: Homo sapiens
<220> FEATURE:
<221> NAME/KEY: CDS
<222> LOCATION: (202)...(2910)

<400> SEQUENCE: 4

| | |
|---|---|
| cacgaggccg gcggcagaac gcagctgcgg cggctgcggg tctcgtgggg gcggagcggt | 60 |
| cgccgctgcc gccgcagctc gggtcgggat ttgaaagatt agaaacttcg ggtggagagg | 120 |
| gcggcggcgt tgaatgtgtg gcggaagcgc tgggggtcac ggctccgcgc gccgccggac | 180 |
| agccggcggc gtctccacag c atg aat tac ccg ggc cgc ggg tcc cca cgg<br>                                     Met Asn Tyr Pro Gly Arg Gly Ser Pro Arg<br>                                     1               5                   10 | 231 |
| agc ccc gag cat aac ggc cga ggc ggc ggc ggc gcc tgg gag ctg<br>Ser Pro Glu His Asn Gly Arg Gly Gly Gly Gly Ala Trp Glu Leu<br>                15                   20                   25 | 279 |
| ggc tca gac gcg agg cca gcg ttc ggc ggc ggc gtc tgc tgc ttc gag<br>Gly Ser Asp Ala Arg Pro Ala Phe Gly Gly Gly Val Cys Cys Phe Glu<br>                30                   35                   40 | 327 |
| cac ctg ccc ggc ggg gac ccg gac gac ggc gac gtg ccc ctg gcc ctg<br>His Leu Pro Gly Gly Asp Pro Asp Asp Gly Asp Val Pro Leu Ala Leu<br>                45                   50                   55 | 375 |
| ctg cgc ggg gaa ccc ggg ctg cat ttg gcg ccg ggc acc gac gac cac<br>Leu Arg Gly Glu Pro Gly Leu His Leu Ala Pro Gly Thr Asp Asp His<br>        60                   65                   70 | 423 |
| aac cac cac ctc gcg ctg gac ccc tgc ctc agt gac gag aac tat gac<br>Asn His His Leu Ala Leu Asp Pro Cys Leu Ser Asp Glu Asn Tyr Asp<br>75                   80                   85                   90 | 471 |
| ttt agc tcc gcc gag tcg ggc tcc tcg ctg cgc tac tac agc gag ggt<br>Phe Ser Ser Ala Glu Ser Gly Ser Ser Leu Arg Tyr Tyr Ser Glu Gly<br>                95                  100                 105 | 519 |
| gag agc ggc ggc ggc ggc ggc agc tcc ttg tcg ctg cat ccg ccg<br>Glu Ser Gly Gly Gly Gly Gly Ser Ser Leu Ser Leu His Pro Pro<br>               110                  115                120 | 567 |
| cag cag cct ccg ctg gtc ccg acg aac tcg ggg ggc ggc ggc gcg aca<br>Gln Gln Pro Pro Leu Val Pro Thr Asn Ser Gly Gly Gly Gly Ala Thr<br>             125                   130                135 | 615 |
| gga ggg tcc ccc ggg gaa agg aaa cgt acc cgg ctt ggc ggc ccg gcg<br>Gly Gly Ser Pro Gly Glu Arg Lys Arg Thr Arg Leu Gly Gly Pro Ala<br>        140                   145                   150 | 663 |
| gcc cgg cac cgc tat gag gta gtg acg gag ctg ggc ccg gag gag gta<br>Ala Arg His Arg Tyr Glu Val Val Thr Glu Leu Gly Pro Glu Glu Val | 711 |

```
                                      -continued
      155                 160                 165                 170
cgc tgg ttc tac aag gag gac aag aag acc tgg aag ccc ttc atc ggc        759
Arg Trp Phe Tyr Lys Glu Asp Lys Lys Thr Trp Lys Pro Phe Ile Gly
            175                 180                 185 tac gac tcg ctc cgc atc gag ctc gcc ttc cgg acc ctg ctg cag acc        807
Tyr Asp Ser Leu Arg Ile Glu Leu Ala Phe Arg Thr Leu Leu Gln Thr
            190                 195                 200 acg ggt gcc cgg ccc cag ggc ggg gac cgg gac ggc gac cat gtg tgc        855
Thr Gly Ala Arg Pro Gln Gly Gly Asp Arg Asp Gly Asp His Val Cys
            205                 210                 215 tcc ccc acg agc cca gcc tcc agt tcc gga gaa gat gac gat gag gac        903
Ser Pro Thr Ser Pro Ala Ser Ser Ser Gly Glu Asp Asp Asp Glu Asp
            220                 225                 230 cgc gcc tgc ggc ttc tgc cag agt acg acg ggg cac gag ccg gag atg        951
Arg Ala Cys Gly Phe Cys Gln Ser Thr Thr Gly His Glu Pro Glu Met
235                 240                 245                 250 gtg gag ctt gtg aac atc gag cct gtg tgc gtg cgg ggc ggc ctc tac        999
Val Glu Leu Val Asn Ile Glu Pro Val Cys Val Arg Gly Gly Leu Tyr
            255                 260                 265 gag gtg gat gtg acc caa gga gag tgc tac ccg gtg tac tgg aac cag       1047
Glu Val Asp Val Thr Gln Gly Glu Cys Tyr Pro Val Tyr Trp Asn Gln
            270                 275                 280 gct gat aaa ata cca gta atg cgt gga cag tgg ttt att gac ggc act       1095
Ala Asp Lys Ile Pro Val Met Arg Gly Gln Trp Phe Ile Asp Gly Thr
            285                 290                 295 tgg cag cct cta gaa gag gaa gaa agt aat tta att gag caa gaa cat       1143
Trp Gln Pro Leu Glu Glu Glu Glu Ser Asn Leu Ile Glu Gln Glu His
            300                 305                 310 ctc aat tgt ttt agg ggc cag cag atg cag gaa aat ttc gat att gaa       1191
Leu Asn Cys Phe Arg Gly Gln Gln Met Gln Glu Asn Phe Asp Ile Glu
315                 320                 325                 330 gtg tca aaa tcc ata gat gga aaa gat gct gtt cat agt ttc aag ttg       1239
Val Ser Lys Ser Ile Asp Gly Lys Asp Ala Val His Ser Phe Lys Leu
            335                 340                 345 agt cga aac cat gtg gac tgg cac agt gtg gat gaa gta tat ctt tat       1287
Ser Arg Asn His Val Asp Trp His Ser Val Asp Glu Val Tyr Leu Tyr
            350                 355                 360 agt gat gca aca aca tct aaa att gca aga aca gtt acc caa aaa ctg       1335
Ser Asp Ala Thr Thr Ser Lys Ile Ala Arg Thr Val Thr Gln Lys Leu
            365                 370                 375 gga ttt tct aaa gca tca agt agt ggt acc aga ctt cat aga ggt tat       1383
Gly Phe Ser Lys Ala Ser Ser Ser Gly Thr Arg Leu His Arg Gly Tyr
            380                 385                 390 gta gaa gaa gcc aca tta gaa gac aag cca tca cag act acc cat att       1431
Val Glu Glu Ala Thr Leu Glu Asp Lys Pro Ser Gln Thr Thr His Ile
395                 400                 405                 410 gta ttt gtt gtg cat ggc att ggg cag aaa atg gac caa gga aga att       1479
Val Phe Val Val His Gly Ile Gly Gln Lys Met Asp Gln Gly Arg Ile
            415                 420                 425 atc aaa aat aca gct atg atg aga gaa gct gca aga aaa ata gaa gaa       1527
Ile Lys Asn Thr Ala Met Met Arg Glu Ala Ala Arg Lys Ile Glu Glu
            430                 435                 440 agg cat ttt tcc aac cat gca aca cat gtt gaa ttt ctg cct gtt gag       1575
Arg His Phe Ser Asn His Ala Thr His Val Glu Phe Leu Pro Val Glu
            445                 450                 455 tgg cgg tca aaa ctt act ctt gat gga gac act gtt gat tcc att act       1623
Trp Arg Ser Lys Leu Thr Leu Asp Gly Asp Thr Val Asp Ser Ile Thr
460                 465                 470 cct gac aaa gta cga ggt tta agg gat atg ctg aac agc agt gca atg       1671
```

```
Pro Asp Lys Val Arg Gly Leu Arg Asp Met Leu Asn Ser Ser Ala Met
475                 480                 485                 490 gac ata atg tat tat act agt cca ctt tat aga gat gaa cta gtt aaa          1719
Asp Ile Met Tyr Tyr Thr Ser Pro Leu Tyr Arg Asp Glu Leu Val Lys
                495                 500                 505 ggc ctt cag caa gag ctg aat cga ttg tat tcc ctt ttc tgt tct cgg          1767
Gly Leu Gln Gln Glu Leu Asn Arg Leu Tyr Ser Leu Phe Cys Ser Arg
            510                 515                 520 aat cca gac ttt gaa gaa aaa ggg ggt aaa gtc tca ata gta tca cat          1815
Asn Pro Asp Phe Glu Glu Lys Gly Gly Lys Val Ser Ile Val Ser His
        525                 530                 535 tcc ttg gga tgt gta att act tat gac ata atg act ggc tgg aat cca          1863
Ser Leu Gly Cys Val Ile Thr Tyr Asp Ile Met Thr Gly Trp Asn Pro
    540                 545                 550 gtt cgg ctg tat gaa cag ttg ctg caa aag gaa gaa gag ttg cct gat          1911
Val Arg Leu Tyr Glu Gln Leu Leu Gln Lys Glu Glu Glu Leu Pro Asp
555                 560                 565                 570 gaa cga tgg atg agc tat gaa gaa cga cat ctt ctt gat gaa ctc tat          1959
Glu Arg Trp Met Ser Tyr Glu Glu Arg His Leu Leu Asp Glu Leu Tyr
                575                 580                 585 ata aca aaa cga cgg ctg aag gaa ata gaa gaa cgg ctt cac gga ttg          2007
Ile Thr Lys Arg Arg Leu Lys Glu Ile Glu Glu Arg Leu His Gly Leu
            590                 595                 600 aaa gca tca tct atg aca caa aca cct gcc tta aaa ttt aag gtt gag          2055
Lys Ala Ser Ser Met Thr Gln Thr Pro Ala Leu Lys Phe Lys Val Glu
        605                 610                 615 aat ttc ttc tgt atg gga tcc cca tta gca gtt ttc ttg gcg ttg cgt          2103
Asn Phe Phe Cys Met Gly Ser Pro Leu Ala Val Phe Leu Ala Leu Arg
    620                 625                 630 ggc atc cgc cca gga aat act gga agt caa gac cat att ttg cct aga          2151
Gly Ile Arg Pro Gly Asn Thr Gly Ser Gln Asp His Ile Leu Pro Arg
635                 640                 645                 650 gag att tgt aac cgg tta cta aat att ttt cat cct aca gat cca gtg          2199
Glu Ile Cys Asn Arg Leu Leu Asn Ile Phe His Pro Thr Asp Pro Val
                655                 660                 665 gct tat aga tta gaa cca tta ata ctg aaa cac tac agc aac att tca          2247
Ala Tyr Arg Leu Glu Pro Leu Ile Leu Lys His Tyr Ser Asn Ile Ser
            670                 675                 680 cct gtc cag atc cac tgg tac aat act tca aat cct tta cct tat gaa          2295
Pro Val Gln Ile His Trp Tyr Asn Thr Ser Asn Pro Leu Pro Tyr Glu
        685                 690                 695 cat atg aag cca agc ttt ctc aac cca gct aaa gaa cct acc tca gtt          2343
His Met Lys Pro Ser Phe Leu Asn Pro Ala Lys Glu Pro Thr Ser Val
    700                 705                 710 tca gag aat gaa ggc att tca acc ata cca agc cct gtg acc tca cca          2391
Ser Glu Asn Glu Gly Ile Ser Thr Ile Pro Ser Pro Val Thr Ser Pro
715                 720                 725                 730 gtt ttg tcc cgc cga cac tat gga gaa tct ata aca aat ata ggc aaa          2439
Val Leu Ser Arg Arg His Tyr Gly Glu Ser Ile Thr Asn Ile Gly Lys
                735                 740                 745 gca agc ata tta ggg gct gct agc att gga aag gga ctt gga gga atg          2487
Ala Ser Ile Leu Gly Ala Ala Ser Ile Gly Lys Gly Leu Gly Gly Met
            750                 755                 760 ttg ttc tca aga ttt gga cgt tca tct aca aca cag tca tct gaa aca          2535
Leu Phe Ser Arg Phe Gly Arg Ser Ser Thr Thr Gln Ser Ser Glu Thr
        765                 770                 775 tca aaa gac tca atg gaa gat gag aag aag cca gtt gcc tca cct tct          2583
Ser Lys Asp Ser Met Glu Asp Glu Lys Lys Pro Val Ala Ser Pro Ser
    780                 785                 790
```

```
gct acc acc gta ggg aca cag acc ctt cca cat agc agt tct ggc ttc      2631
Ala Thr Thr Val Gly Thr Gln Thr Leu Pro His Ser Ser Ser Gly Phe
795                 800                 805                 810 ctc gat tct gca tat ttc aga ctt caa gaa tcg ttc ttt aat ctc cca      2679
Leu Asp Ser Ala Tyr Phe Arg Leu Gln Glu Ser Phe Phe Asn Leu Pro
                815                 820                 825 caa ctt ctt ttt ccg gaa aat gta atg cag aat aaa gat aat gcc ctc      2727
Gln Leu Leu Phe Pro Glu Asn Val Met Gln Asn Lys Asp Asn Ala Leu
            830                 835                 840 gtg gag ttg gat cac agg att gat ttt gaa ctc aga gaa ggc ctt gtg      2775
Val Glu Leu Asp His Arg Ile Asp Phe Glu Leu Arg Glu Gly Leu Val
        845                 850                 855 gag agc cgc tat tgg tca gct gtc acg tcg cat act gcc tat tgg tca      2823
Glu Ser Arg Tyr Trp Ser Ala Val Thr Ser His Thr Ala Tyr Trp Ser
860                 865                 870 tcc ttg gat gtt gcc ctt ttt ctt tta acc ttc atg tat aaa cat gag      2871
Ser Leu Asp Val Ala Leu Phe Leu Leu Thr Phe Met Tyr Lys His Glu
875                 880                 885                 890 cac gat gat gat gca aaa ccc aat tta gat cca atc tga actcttgaag       2920
His Asp Asp Asp Ala Lys Pro Asn Leu Asp Pro Ile *
                895                 900 gacatgaatg gcctaaaact gattttttt ttttccgtt aaaatgtgtg tgtcaagata       2980
cggagatttc agggttaaag tatatttcag ttttctttag ggcaacatat atttgaattt     3040
aaaagcactt tatttaaaaa aaaaa                                          3065

<210> SEQ ID NO 5
<211> LENGTH: 902
<212> TYPE: PRT
<213> ORGANISM: Homo sapiens

<400> SEQUENCE: 5

Met Asn Tyr Pro Gly Arg Gly Ser Pro Arg Ser Pro Glu His Asn Gly
1               5                   10                  15

Arg Gly Gly Gly Gly Ala Trp Glu Leu Gly Ser Asp Ala Arg Pro
            20                  25                  30

Ala Phe Gly Gly Gly Val Cys Cys Phe Glu His Leu Pro Gly Gly Asp
        35                  40                  45

Pro Asp Asp Gly Asp Val Pro Leu Ala Leu Leu Arg Gly Glu Pro Gly
    50                  55                  60

Leu His Leu Ala Pro Gly Thr Asp Asp His Asn His Leu Ala Leu
65                  70                  75                  80

Asp Pro Cys Leu Ser Asp Glu Asn Tyr Asp Phe Ser Ser Ala Glu Ser
                85                  90                  95

Gly Ser Ser Leu Arg Tyr Tyr Ser Glu Gly Glu Ser Gly Gly Gly Gly
            100                 105                 110

Gly Gly Ser Ser Leu Ser Leu His Pro Pro Gln Gln Pro Leu Val
        115                 120                 125

Pro Thr Asn Ser Gly Gly Gly Ala Thr Gly Gly Ser Pro Gly Glu
    130                 135                 140

Arg Lys Arg Thr Arg Leu Gly Gly Pro Ala Ala Arg His Arg Tyr Glu
145                 150                 155                 160

Val Val Thr Glu Leu Gly Pro Glu Glu Val Arg Trp Phe Tyr Lys Glu
                165                 170                 175

Asp Lys Lys Thr Trp Lys Pro Phe Ile Gly Tyr Asp Ser Leu Arg Ile
            180                 185                 190

Glu Leu Ala Phe Arg Thr Leu Leu Gln Thr Thr Gly Ala Arg Pro Gln
```

```
                195                 200                 205
Gly Gly Asp Arg Asp Gly Asp His Val Cys Ser Pro Thr Ser Pro Ala
    210                 215                 220

Ser Ser Ser Gly Glu Asp Asp Glu Asp Arg Ala Cys Gly Phe Cys
225                 230                 235                 240

Gln Ser Thr Thr Gly His Glu Pro Glu Met Val Glu Leu Val Asn Ile
            245                 250                 255

Glu Pro Val Cys Val Arg Gly Gly Leu Tyr Glu Val Asp Val Thr Gln
            260                 265                 270

Gly Glu Cys Tyr Pro Val Tyr Trp Asn Gln Ala Asp Lys Ile Pro Val
        275                 280                 285

Met Arg Gly Gln Trp Phe Ile Asp Gly Thr Trp Gln Pro Leu Glu Glu
    290                 295                 300

Glu Glu Ser Asn Leu Ile Glu Gln Glu His Leu Asn Cys Phe Arg Gly
305                 310                 315                 320

Gln Gln Met Gln Glu Asn Phe Asp Ile Glu Val Ser Lys Ser Ile Asp
                325                 330                 335

Gly Lys Asp Ala Val His Ser Phe Lys Leu Ser Arg Asn His Val Asp
            340                 345                 350

Trp His Ser Val Asp Glu Val Tyr Leu Tyr Ser Asp Ala Thr Thr Ser
        355                 360                 365

Lys Ile Ala Arg Thr Val Thr Gln Lys Leu Gly Phe Ser Lys Ala Ser
    370                 375                 380

Ser Ser Gly Thr Arg Leu His Arg Gly Tyr Val Glu Glu Ala Thr Leu
385                 390                 395                 400

Glu Asp Lys Pro Ser Gln Thr Thr His Ile Val Phe Val Val His Gly
                405                 410                 415

Ile Gly Gln Lys Met Asp Gln Gly Arg Ile Ile Lys Asn Thr Ala Met
            420                 425                 430

Met Arg Glu Ala Ala Arg Lys Ile Glu Glu Arg His Phe Ser Asn His
        435                 440                 445

Ala Thr His Val Glu Phe Leu Pro Val Glu Trp Arg Ser Lys Leu Thr
    450                 455                 460

Leu Asp Gly Asp Thr Val Asp Ser Ile Thr Pro Asp Lys Val Arg Gly
465                 470                 475                 480

Leu Arg Asp Met Leu Asn Ser Ser Ala Met Asp Ile Met Tyr Tyr Thr
                485                 490                 495

Ser Pro Leu Tyr Arg Asp Glu Leu Val Lys Gly Leu Gln Gln Glu Leu
            500                 505                 510

Asn Arg Leu Tyr Ser Leu Phe Cys Ser Arg Asn Pro Asp Phe Glu Glu
        515                 520                 525

Lys Gly Gly Lys Val Ser Ile Val Ser His Ser Leu Gly Cys Val Ile
    530                 535                 540

Thr Tyr Asp Ile Met Thr Gly Trp Asn Pro Val Arg Leu Tyr Glu Gln
545                 550                 555                 560

Leu Leu Gln Lys Glu Glu Leu Pro Asp Glu Arg Trp Met Ser Tyr
                565                 570                 575

Glu Glu Arg His Leu Leu Asp Glu Leu Tyr Ile Thr Lys Arg Arg Leu
            580                 585                 590

Lys Glu Ile Glu Glu Arg Leu His Gly Leu Lys Ala Ser Ser Met Thr
        595                 600                 605

Gln Thr Pro Ala Leu Lys Phe Lys Val Glu Asn Phe Phe Cys Met Gly
    610                 615                 620
```

```
Ser Pro Leu Ala Val Phe Leu Ala Leu Arg Gly Ile Arg Pro Gly Asn
625                 630                 635                 640

Thr Gly Ser Gln Asp His Ile Leu Pro Arg Glu Ile Cys Asn Arg Leu
            645                 650                 655

Leu Asn Ile Phe His Pro Thr Asp Pro Val Ala Tyr Arg Leu Glu Pro
            660                 665                 670

Leu Ile Leu Lys His Tyr Ser Asn Ile Ser Pro Val Gln Ile His Trp
            675                 680                 685

Tyr Asn Thr Ser Asn Pro Leu Pro Tyr Glu His Met Lys Pro Ser Phe
            690                 695                 700

Leu Asn Pro Ala Lys Glu Pro Thr Ser Val Ser Glu Asn Glu Gly Ile
705                 710                 715                 720

Ser Thr Ile Pro Ser Pro Val Thr Ser Pro Val Leu Ser Arg Arg His
                725                 730                 735

Tyr Gly Glu Ser Ile Thr Asn Ile Gly Lys Ala Ser Ile Leu Gly Ala
                740                 745                 750

Ala Ser Ile Gly Lys Gly Leu Gly Gly Met Leu Phe Ser Arg Phe Gly
            755                 760                 765

Arg Ser Ser Thr Thr Gln Ser Ser Glu Thr Ser Lys Asp Ser Met Glu
770                 775                 780

Asp Glu Lys Lys Pro Val Ala Ser Pro Ser Ala Thr Thr Val Gly Thr
785                 790                 795                 800

Gln Thr Leu Pro His Ser Ser Ser Gly Phe Leu Asp Ser Ala Tyr Phe
                805                 810                 815

Arg Leu Gln Glu Ser Phe Phe Asn Leu Pro Gln Leu Leu Phe Pro Glu
                820                 825                 830

Asn Val Met Gln Asn Lys Asp Asn Ala Leu Val Glu Leu Asp His Arg
                835                 840                 845

Ile Asp Phe Glu Leu Arg Glu Gly Leu Val Glu Ser Arg Tyr Trp Ser
                850                 855                 860

Ala Val Thr Ser His Thr Ala Tyr Trp Ser Ser Leu Asp Val Ala Leu
865                 870                 875                 880

Phe Leu Leu Thr Phe Met Tyr Lys His Glu His Asp Asp Ala Lys
                885                 890                 895

Pro Asn Leu Asp Pro Ile
            900

<210> SEQ ID NO 6
<211> LENGTH: 2706
<212> TYPE: DNA
<213> ORGANISM: Homo sapiens
<220> FEATURE:
<221> NAME/KEY: CDS
<222> LOCATION: (1)...(2706)

<400> SEQUENCE: 6 atg aat tac ccg ggc cgc ggg tcc cca cgg agc ccc gag cat aac ggc      48
Met Asn Tyr Pro Gly Arg Gly Ser Pro Arg Ser Pro Glu His Asn Gly
 1               5                  10                  15 cga ggc ggc ggc ggc gcc tgg gag ctg ggc tca gac gcg agg cca           96
Arg Gly Gly Gly Gly Ala Trp Glu Leu Gly Ser Asp Ala Arg Pro
                20                  25                  30 gcg ttc ggc ggc ggc gtc tgc tgc ttc gag cac ctg ccc ggc ggg gac     144
Ala Phe Gly Gly Gly Val Cys Cys Phe Glu His Leu Pro Gly Gly Asp
             35                  40                  45 ccg gac gac ggc gac gtg ccc ctg gcc ctg ctg cgc ggg gaa ccc ggg     192
```

```
Pro Asp Asp Gly Asp Val Pro Leu Ala Leu Leu Arg Gly Glu Pro Gly
    50              55                  60 ctg cat ttg gcg ccg ggc acc gac gac cac aac cac cac ctc gcg ctg      240
Leu His Leu Ala Pro Gly Thr Asp Asp His Asn His His Leu Ala Leu
 65              70                  75                      80 gac ccc tgc ctc agt gac gag aac tat gac ttt agc tcc gcc gag tcg      288
Asp Pro Cys Leu Ser Asp Glu Asn Tyr Asp Phe Ser Ser Ala Glu Ser
                 85                  90                  95 ggc tcc tcg ctg cgc tac tac agc gag ggt gag agc ggc ggc ggc ggc      336
Gly Ser Ser Leu Arg Tyr Tyr Ser Glu Gly Glu Ser Gly Gly Gly Gly
                100                 105                 110 ggc ggc agc tcc ttg tcg ctg cat ccg ccg cag cag cct ccg ctg gtc      384
Gly Gly Ser Ser Leu Ser Leu His Pro Pro Gln Gln Pro Pro Leu Val
            115                 120                 125 ccg acg aac tcg ggg ggc ggc ggc gcg aca gga ggg tcc ccc ggg gaa      432
Pro Thr Asn Ser Gly Gly Gly Gly Ala Thr Gly Gly Ser Pro Gly Glu
        130                 135                 140 agg aaa cgt acc cgg ctt ggc ggc ccg gcg gcc cgg cac cgc tat gag      480
Arg Lys Arg Thr Arg Leu Gly Gly Pro Ala Ala Arg His Arg Tyr Glu
145                 150                 155                 160 gta gtg acg gag ctg ggc ccg gag gag gta cgc tgg ttc tac aag gag      528
Val Val Thr Glu Leu Gly Pro Glu Glu Val Arg Trp Phe Tyr Lys Glu
                165                 170                 175 gac aag aag acc tgg aag ccc ttc atc ggc tac gac tcg ctc cgc atc      576
Asp Lys Lys Thr Trp Lys Pro Phe Ile Gly Tyr Asp Ser Leu Arg Ile
            180                 185                 190 gag ctc gcc ttc cgg acc ctg ctg cag acc acg ggt gcc cgg ccc cag      624
Glu Leu Ala Phe Arg Thr Leu Leu Gln Thr Thr Gly Ala Arg Pro Gln
        195                 200                 205 ggc ggg gac cgg gac ggc gac cat gtg tgc tcc ccc acg agc cca gcc      672
Gly Gly Asp Arg Asp Gly Asp His Val Cys Ser Pro Thr Ser Pro Ala
    210                 215                 220 tcc agt tcc gga gaa gat gac gat gag gac cgc gcc tgc ggc ttc tgc      720
Ser Ser Ser Gly Glu Asp Asp Asp Glu Asp Arg Ala Cys Gly Phe Cys
225                 230                 235                 240 cag agt acg acg ggg cac gag ccg gag atg gtg gag ctt gtg aac atc      768
Gln Ser Thr Thr Gly His Glu Pro Glu Met Val Glu Leu Val Asn Ile
                245                 250                 255 gag cct gtg tgc gtg cgg ggc ggc ctc tac gag gtg gat gtg acc caa      816
Glu Pro Val Cys Val Arg Gly Gly Leu Tyr Glu Val Asp Val Thr Gln
            260                 265                 270 gga gag tgc tac ccg gtg tac tgg aac cag gct gat aaa ata cca gta      864
Gly Glu Cys Tyr Pro Val Tyr Trp Asn Gln Ala Asp Lys Ile Pro Val
        275                 280                 285 atg cgt gga cag tgg ttt att gac ggc act tgg cag cct cta gaa gag      912
Met Arg Gly Gln Trp Phe Ile Asp Gly Thr Trp Gln Pro Leu Glu Glu
    290                 295                 300 gaa gaa agt aat tta att gag caa gaa cat ctc aat tgt ttt agg ggc      960
Glu Glu Ser Asn Leu Ile Glu Gln Glu His Leu Asn Cys Phe Arg Gly
305                 310                 315                 320 cag cag atg cag gaa aat ttc gat att gaa gtg tca aaa tcc ata gat     1008
Gln Gln Met Gln Glu Asn Phe Asp Ile Glu Val Ser Lys Ser Ile Asp
                325                 330                 335 gga aaa gat gct gtt cat agt ttc aag ttg agt cga aac cat gtg gac     1056
Gly Lys Asp Ala Val His Ser Phe Lys Leu Ser Arg Asn His Val Asp
            340                 345                 350 tgg cac agt gtg gat gaa gta tat ctt tat agt gat gca aca aca tct     1104
Trp His Ser Val Asp Glu Val Tyr Leu Tyr Ser Asp Ala Thr Thr Ser
        355                 360                 365
```

-continued

```
aaa att gca aga aca gtt acc caa aaa ctg gga ttt tct aaa gca tca      1152
Lys Ile Ala Arg Thr Val Thr Gln Lys Leu Gly Phe Ser Lys Ala Ser
    370                 375                 380 agt agt ggt acc aga ctt cat aga ggt tat gta gaa gaa gcc aca tta      1200
Ser Ser Gly Thr Arg Leu His Arg Gly Tyr Val Glu Glu Ala Thr Leu
385                 390                 395                 400 gaa gac aag cca tca cag act acc cat att gta ttt gtg cat ggc          1248
Glu Asp Lys Pro Ser Gln Thr Thr His Ile Val Phe Val Val His Gly
                405                 410                 415 att ggg cag aaa atg gac caa gga aga att atc aaa aat aca gct atg      1296
Ile Gly Gln Lys Met Asp Gln Gly Arg Ile Ile Lys Asn Thr Ala Met
        420                 425                 430 atg aga gaa gct gca aga aaa ata gaa gaa agg cat ttt tcc aac cat      1344
Met Arg Glu Ala Ala Arg Lys Ile Glu Glu Arg His Phe Ser Asn His
                435                 440                 445 gca aca cat gtt gaa ttt ctg cct gtt gag tgg cgg tca aaa ctt act      1392
Ala Thr His Val Glu Phe Leu Pro Val Glu Trp Arg Ser Lys Leu Thr
    450                 455                 460 ctt gat gga gac act gtt gat tcc att act cct gac aaa gta cga ggt     1440
Leu Asp Gly Asp Thr Val Asp Ser Ile Thr Pro Asp Lys Val Arg Gly
465                 470                 475                 480 tta agg gat atg ctg aac agc agt gca atg gac ata atg tat tat act     1488
Leu Arg Asp Met Leu Asn Ser Ser Ala Met Asp Ile Met Tyr Tyr Thr
                485                 490                 495 agt cca ctt tat aga gat gaa cta gtt aaa ggc ctt cag caa gag ctg     1536
Ser Pro Leu Tyr Arg Asp Glu Leu Val Lys Gly Leu Gln Gln Glu Leu
        500                 505                 510 aat cga ttg tat tcc ctt ttc tgt tct cgg aat cca gac ttt gaa gaa     1584
Asn Arg Leu Tyr Ser Leu Phe Cys Ser Arg Asn Pro Asp Phe Glu Glu
                515                 520                 525 aaa ggg ggt aaa gtc tca ata gta tca cat tcc ttg gga tgt gta att     1632
Lys Gly Gly Lys Val Ser Ile Val Ser His Ser Leu Gly Cys Val Ile
    530                 535                 540 act tat gac ata atg act ggc tgg aat cca gtt cgg ctg tat gaa cag     1680
Thr Tyr Asp Ile Met Thr Gly Trp Asn Pro Val Arg Leu Tyr Glu Gln
545                 550                 555                 560 ttg ctg caa aag gaa gaa gag ttg cct gat gaa cga tgg atg agc tat     1728
Leu Leu Gln Lys Glu Glu Glu Leu Pro Asp Glu Arg Trp Met Ser Tyr
                565                 570                 575 gaa gaa cga cat ctt ctt gat gaa ctc tat ata aca aaa cga cgg ctg     1776
Glu Glu Arg His Leu Leu Asp Glu Leu Tyr Ile Thr Lys Arg Arg Leu
        580                 585                 590 aag gaa ata gaa gaa cgg ctt cac gga ttg aaa gca tca tct atg aca     1824
Lys Glu Ile Glu Glu Arg Leu His Gly Leu Lys Ala Ser Ser Met Thr
                595                 600                 605 caa aca cct gcc tta aaa ttt aag gtt gag aat ttc ttc tgt atg gga     1872
Gln Thr Pro Ala Leu Lys Phe Lys Val Glu Asn Phe Phe Cys Met Gly
    610                 615                 620 tcc cca tta gca gtt ttc ttg gcg ttg cgt ggc atc cgc cca gga aat     1920
Ser Pro Leu Ala Val Phe Leu Ala Leu Arg Gly Ile Arg Pro Gly Asn
625                 630                 635                 640 act gga agt caa gac cat att ttg cct aga gag att tgt aac cgg tta     1968
Thr Gly Ser Gln Asp His Ile Leu Pro Arg Glu Ile Cys Asn Arg Leu
                645                 650                 655 cta aat att ttt cat cct aca gat cca gtg gct tat aga tta gaa cca     2016
Leu Asn Ile Phe His Pro Thr Asp Pro Val Ala Tyr Arg Leu Glu Pro
        660                 665                 670 tta ata ctg aaa cac tac agc aac att tca cct gtc cag atc cac tgg     2064
Leu Ile Leu Lys His Tyr Ser Asn Ile Ser Pro Val Gln Ile His Trp
                675                 680                 685
```

| | | | | | | | | | | | | | | |
|---|---|---|---|---|---|---|---|---|---|---|---|---|---|---|
| tac | aat | act | tca | aat | cct | tta | cct | tat | gaa | cat | atg | aag | cca | agc | ttt | 2112 |
| Tyr | Asn | Thr | Ser | Asn | Pro | Leu | Pro | Tyr | Glu | His | Met | Lys | Pro | Ser | Phe |
| | 690 | | | | 695 | | | | 700 | | | | | | |

```
tac aat act tca aat cct tta cct tat gaa cat atg aag cca agc ttt    2112
Tyr Asn Thr Ser Asn Pro Leu Pro Tyr Glu His Met Lys Pro Ser Phe
    690                 695                 700 ctc aac cca gct aaa gaa cct acc tca gtt tca gag aat gaa ggc att    2160
Leu Asn Pro Ala Lys Glu Pro Thr Ser Val Ser Glu Asn Glu Gly Ile
705                 710                 715                 720 tca acc ata cca agc cct gtg acc tca cca gtt ttg tcc cgc cga cac    2208
Ser Thr Ile Pro Ser Pro Val Thr Ser Pro Val Leu Ser Arg Arg His
                725                 730                 735 tat gga gaa tct ata aca aat ata ggc aaa gca agc ata tta ggg gct    2256
Tyr Gly Glu Ser Ile Thr Asn Ile Gly Lys Ala Ser Ile Leu Gly Ala
            740                 745                 750 gct agc att gga aag gga ctt gga gga atg ttg ttc tca aga ttt gga    2304
Ala Ser Ile Gly Lys Gly Leu Gly Gly Met Leu Phe Ser Arg Phe Gly
        755                 760                 765 cgt tca tct aca aca cag tca tct gaa aca tca aaa gac tca atg gaa    2352
Arg Ser Ser Thr Thr Gln Ser Ser Glu Thr Ser Lys Asp Ser Met Glu
770                 775                 780 gat gag aag aag cca gtt gcc tca cct tct gct acc acc gta ggg aca    2400
Asp Glu Lys Lys Pro Val Ala Ser Pro Ser Ala Thr Thr Val Gly Thr
785                 790                 795                 800 cag acc ctt cca cat agc agt tct ggc ttc ctc gat tct gca tat ttc    2448
Gln Thr Leu Pro His Ser Ser Ser Gly Phe Leu Asp Ser Ala Tyr Phe
                805                 810                 815 aga ctt caa gaa tcg ttc ttt aat ctc cca caa ctt ctt ttt ccg gaa    2496
Arg Leu Gln Glu Ser Phe Phe Asn Leu Pro Gln Leu Leu Phe Pro Glu
            820                 825                 830 aat gta atg cag aat aaa gat aat gcc ctc gtg gag ttg gat cac agg    2544
Asn Val Met Gln Asn Lys Asp Asn Ala Leu Val Glu Leu Asp His Arg
        835                 840                 845 att gat ttt gaa ctc aga gaa ggc ctt gtg gag agc cgc tat tgg tca    2592
Ile Asp Phe Glu Leu Arg Glu Gly Leu Val Glu Ser Arg Tyr Trp Ser
850                 855                 860 gct gtc acg tcg cat act gcc tat tgg tca tcc ttg gat gtt gcc ctt    2640
Ala Val Thr Ser His Thr Ala Tyr Trp Ser Ser Leu Asp Val Ala Leu
865                 870                 875                 880 ttt ctt tta acc ttc atg tat aaa cat gag cac gat gat gat gca aaa    2688
Phe Leu Leu Thr Phe Met Tyr Lys His Glu His Asp Asp Asp Ala Lys
                885                 890                 895 ccc aat tta gat cca atc                                            2706
Pro Asn Leu Asp Pro Ile
            900

<210> SEQ ID NO 7
<211> LENGTH: 2625
<212> TYPE: DNA
<213> ORGANISM: Bos taurus

<400> SEQUENCE: 7
atgaattacc cgggccatgg gtctccgcgg agctccgagc gtaacggcgg ccggggcggc     60
gacggcgccg cctgggagct gggctcggac acggaacccg cgttcggggg cagcgtctgc    120
cgcttcgacc acctgccagt cggggagcct ggcgatgacg aggtgcccct ggccctgctg    180
cgcggggagc ccgggctgca cttggcgccg ggagcggagg accacaacca tcacctggcg    240
ctggacccct gcctcagtga cgataactat gacttcagct cggccgagtc gggctcctcg    300
ctgcgctact acagcgaggg cgagagtgga ggcggcggca gctcctcgtc gctgcacccg    360
cctcagcagc cgctggtccc gtcgaactcg gggggcggcg gggcggctgg aggaggcccc    420
```

-continued

| | |
|---|---|
| ggtgagagga agcgcacccg gcccggcggc gcggccgccc ggcacagata cgaggtggtg | 480 |
| acggagctgg gcccggagga ggtgcgctgg ttctacaagg aggacaagaa gacctggaag | 540 |
| cccttcatcg gctacgactc gctccgcatc gagcttgcct tccgaacgct actgcaggcc | 600 |
| acggggccc gagcccgggc ccaagacccg gacgcgacc atgtgtgcgg cccggcctca | 660 |
| cccgcgggtc cggcctccag ctccgtggag gacgaagacg aggaccgcgt ctgcggcttc | 720 |
| tgcccgcgca ttgcgggcca cgggcgcgag atggaggagc tggtgaacat cgagcgggtg | 780 |
| tgtgtgcggg gcggcctcta cgaggtggat gtgacccaag gagaatgcta cccggtgtac | 840 |
| tggaaccagt ctgataaaat accagtaatg cgtggacagt ggtttattga tggtacctgg | 900 |
| cagccactag aagaagaaga aagtaattta attgagcaag aacatcttag ccgttttaga | 960 |
| ggacagcaga tgcaggaaag ttttgatatt gaagtgtcga acccataga tggaaaagat | 1020 |
| gctattcata gtttcaaatt gagtcgaaac cacgtggact ggcacagtgt ggatgaagta | 1080 |
| tatctttata gtgatgcaac aacatccaaa attgcaagaa cagttactca aaaactggga | 1140 |
| ttttctaaag catcaagtag tgggaccaga cttcatagag gttatgtaga agaagcgaca | 1200 |
| ttagaagaca agccatctca gactacccat atcgtatttg ttgtgcatgg cattggacag | 1260 |
| aaaatggacc aaggaagaat tatcaaaaat actgccatga tgagagaggc tgcaagaaaa | 1320 |
| atagaagaaa ggcattttc caaccatgca acacatgttg aatttctgcc tgttgagtgg | 1380 |
| cggtcaaaac ttactcttga tggagacact gttgattcca ttactccaga caaagtgcga | 1440 |
| ggtttaaggg atatgttaaa cagcagtgca atggacataa tgtattatac tagcccactg | 1500 |
| tatagagatg aactagttaa aggccttcag caagagctca atcgattata ttcccttttc | 1560 |
| tgttcccgga atccaaactt tgaggaaaaa ggggtaaag tctcaatagt gtcacattcc | 1620 |
| ttgggatgtg tgatcactta tgacataatg actggctgga atccagttcg actctatgaa | 1680 |
| cagttgctgc agaaggaaga agagttgcct gatgaacgat ggatgagcta cgaagaacgt | 1740 |
| catcttcttg atgaactcta taacaaaa cgacggctac gagaaattga agaacggcta | 1800 |
| catggattga aagcatcatc tatgacacaa acacctgcct taaaatttaa ggttgaaaat | 1860 |
| ttcttctgta tgggatcccc actagcagtt ttttggcac tgcgtggcat ccgcccagga | 1920 |
| aacactggaa gtcaagacca tatttttgccc agagagattt gtaaccgatt actaaacatt | 1980 |
| ttccatccaa cagatccagt ggcttataga ttagaaccat taatactgaa acactacagc | 2040 |
| aacatttcac ctgtgcagat ccactggtat aatacatcca atcctctacc ttatgagtat | 2100 |
| atgaagccaa gctttcttca cccagcgaaa gatcctacct caatttcaga gaatgaaggc | 2160 |
| atctcaacaa taccaagccc tgtgacttcg ccagtcttgt ctcgccgaca ctatggggaa | 2220 |
| tctataacaa atataggcaa agcaagcata ttaggggctg caagcattgg aaagggactt | 2280 |
| ggaggaatgt tgttctcaag atttggacgt tcatctgcat cacagccatc tgagacatca | 2340 |
| agggactcca tagaagacga gaagaagcca gttgcctccc cgcccatgac caccgtggca | 2400 |
| acgcagaccc ttccacacag cagttctggc tttcttgact ctgcattgga actggatcac | 2460 |
| agaattgact ttgaactcag agaaggcctt gtggagagcc gctattggtc agctgtcacg | 2520 |
| tcgcatactg cctattggtc atccttggat gttgccctct tcctgttaac cttcatgtac | 2580 |
| aaacacgagc acgataataa tgtgaaaccc agtttagatc cagtc | 2625 |

<210> SEQ ID NO 8
<211> LENGTH: 875
<212> TYPE: PRT
<213> ORGANISM: Bos taurus

```
<400> SEQUENCE: 8

Met Asn Tyr Pro Gly His Gly Ser Pro Arg Ser Ser Glu Arg Asn Gly
1               5                   10                  15

Gly Arg Gly Gly Asp Gly Ala Ala Trp Glu Leu Gly Ser Asp Thr Glu
            20                  25                  30

Pro Ala Phe Gly Gly Ser Val Cys Arg Phe Asp His Leu Pro Val Gly
            35                  40                  45

Glu Pro Gly Asp Asp Glu Val Pro Leu Ala Leu Leu Arg Gly Glu Pro
    50                  55                  60

Gly Leu His Leu Ala Pro Gly Ala Glu Asp His Asn His His Leu Ala
65                  70                  75                  80

Leu Asp Pro Cys Leu Ser Asp Asp Asn Tyr Asp Phe Ser Ser Ala Glu
                85                  90                  95

Ser Gly Ser Ser Leu Arg Tyr Tyr Ser Glu Gly Glu Ser Gly Gly Gly
            100                 105                 110

Gly Ser Ser Ser Ser Leu His Pro Pro Gln Gln Pro Leu Val Pro Ser
            115                 120                 125

Asn Ser Gly Gly Gly Gly Ala Ala Gly Gly Pro Gly Glu Arg Lys
            130                 135                 140

Arg Thr Arg Pro Gly Gly Ala Ala Ala Arg His Arg Tyr Glu Val Val
145                 150                 155                 160

Thr Glu Leu Gly Pro Glu Glu Val Arg Trp Phe Tyr Lys Glu Asp Lys
                165                 170                 175

Lys Thr Trp Lys Pro Phe Ile Gly Tyr Asp Ser Leu Arg Ile Glu Leu
            180                 185                 190

Ala Phe Arg Thr Leu Leu Gln Ala Thr Gly Ala Arg Ala Arg Ala Gln
            195                 200                 205

Asp Pro Asp Gly Asp His Val Cys Gly Pro Ala Ser Pro Ala Gly Pro
    210                 215                 220

Ala Ser Ser Ser Val Glu Asp Glu Asp Glu Asp Arg Val Cys Gly Phe
225                 230                 235                 240

Cys Pro Arg Ile Ala Gly His Gly Arg Glu Met Glu Glu Leu Val Asn
                245                 250                 255

Ile Glu Arg Val Cys Val Arg Gly Gly Leu Tyr Glu Val Asp Val Thr
            260                 265                 270

Gln Gly Glu Cys Tyr Pro Val Tyr Trp Asn Gln Ser Asp Lys Ile Pro
            275                 280                 285

Val Met Arg Gly Gln Trp Phe Ile Asp Gly Thr Trp Gln Pro Leu Glu
    290                 295                 300

Glu Glu Glu Ser Asn Leu Ile Glu Gln Glu His Leu Ser Arg Phe Arg
305                 310                 315                 320

Gly Gln Gln Met Gln Glu Ser Phe Asp Ile Glu Val Ser Lys Pro Ile
                325                 330                 335

Asp Gly Lys Asp Ala Ile His Ser Phe Lys Leu Ser Arg Asn His Val
            340                 345                 350

Asp Trp His Ser Val Asp Glu Val Tyr Leu Tyr Ser Asp Ala Thr Thr
            355                 360                 365

Ser Lys Ile Ala Arg Thr Val Thr Gln Lys Leu Gly Phe Ser Lys Ala
    370                 375                 380

Ser Ser Ser Gly Thr Arg Leu His Arg Gly Tyr Val Glu Glu Ala Thr
385                 390                 395                 400

Leu Glu Asp Lys Pro Ser Gln Thr Thr His Ile Val Phe Val Val His
```

-continued

```
                405                 410                 415
Gly Ile Gly Gln Lys Met Asp Gln Gly Arg Ile Ile Lys Asn Thr Ala
            420                 425                 430
Met Met Arg Glu Ala Ala Arg Lys Ile Glu Glu Arg His Phe Ser Asn
            435                 440                 445
His Ala Thr His Val Glu Phe Leu Pro Val Glu Trp Arg Ser Lys Leu
            450                 455                 460
Thr Leu Asp Gly Asp Thr Val Asp Ser Ile Thr Pro Asp Lys Val Arg
465                 470                 475                 480
Gly Leu Arg Asp Met Leu Asn Ser Ser Ala Met Asp Ile Met Tyr Tyr
                485                 490                 495
Thr Ser Pro Leu Tyr Arg Asp Glu Leu Val Lys Gly Leu Gln Gln Glu
            500                 505                 510
Leu Asn Arg Leu Tyr Ser Leu Phe Cys Ser Arg Asn Pro Asn Phe Glu
            515                 520                 525
Glu Lys Gly Gly Lys Val Ser Ile Val Ser His Ser Leu Gly Cys Val
            530                 535                 540
Ile Thr Tyr Asp Ile Met Thr Gly Trp Asn Pro Val Arg Leu Tyr Glu
545                 550                 555                 560
Gln Leu Leu Gln Lys Glu Glu Leu Pro Asp Glu Arg Trp Met Ser
                565                 570                 575
Tyr Glu Glu Arg His Leu Leu Asp Glu Leu Tyr Ile Thr Lys Arg Arg
            580                 585                 590
Leu Arg Glu Ile Glu Arg Leu His Gly Leu Lys Ala Ser Ser Met
            595                 600                 605
Thr Gln Thr Pro Ala Leu Lys Phe Lys Val Glu Asn Phe Phe Cys Met
            610                 615                 620
Gly Ser Pro Leu Ala Val Phe Leu Ala Leu Arg Gly Ile Arg Pro Gly
625                 630                 635                 640
Asn Thr Gly Ser Gln Asp His Ile Leu Pro Arg Glu Ile Cys Asn Arg
                645                 650                 655
Leu Leu Asn Ile Phe His Pro Thr Asp Pro Val Ala Tyr Arg Leu Glu
            660                 665                 670
Pro Leu Ile Leu Lys His Tyr Ser Asn Ile Ser Pro Val Gln Ile His
            675                 680                 685
Trp Tyr Asn Thr Ser Asn Pro Leu Pro Tyr Glu Tyr Met Lys Pro Ser
            690                 695                 700
Phe Leu His Pro Ala Lys Asp Pro Thr Ser Ile Ser Glu Asn Glu Gly
705                 710                 715                 720
Ile Ser Thr Ile Pro Ser Pro Val Thr Ser Pro Val Leu Ser Arg Arg
                725                 730                 735
His Tyr Gly Glu Ser Ile Thr Asn Ile Gly Lys Ala Ser Ile Leu Gly
            740                 745                 750
Ala Ala Ser Ile Gly Lys Gly Leu Gly Met Leu Phe Ser Arg Phe
            755                 760                 765
Gly Arg Ser Ser Ala Ser Gln Pro Ser Glu Thr Ser Arg Asp Ser Ile
            770                 775                 780
Glu Asp Glu Lys Lys Pro Val Ala Ser Pro Met Thr Thr Val Ala
785                 790                 795                 800
Thr Gln Thr Leu Pro His Ser Ser Gly Phe Leu Asp Ser Ala Leu
                805                 810                 815
Glu Leu Asp His Arg Ile Asp Phe Glu Leu Arg Glu Gly Leu Val Glu
            820                 825                 830
```

```
Ser Arg Tyr Trp Ser Ala Val Thr Ser His Thr Ala Tyr Trp Ser Ser
        835                 840                 845

Leu Asp Val Ala Leu Phe Leu Leu Thr Phe Met Tyr Lys His Glu His
    850                 855                 860

Asp Asn Asn Val Lys Pro Ser Leu Asp Pro Val
865                 870                 875

<210> SEQ ID NO 9
<211> LENGTH: 5
<212> TYPE: PRT
<213> ORGANISM: Artificial Sequence
<220> FEATURE:
<223> OTHER INFORMATION: Consensus amino acid sequence

<400> SEQUENCE: 9

Ser His Ser Leu Gly
 1               5

<210> SEQ ID NO 10
<211> LENGTH: 5
<212> TYPE: PRT
<213> ORGANISM: Artificial Sequence
<220> FEATURE:
<223> OTHER INFORMATION: Consensus amino acid sequence
<220> FEATURE:
<221> NAME/KEY: VARIANT
<222> LOCATION: (1)...(2)
<223> OTHER INFORMATION: Xaa = Any Amino Acid
<220> FEATURE:
<221> NAME/KEY: VARIANT
<222> LOCATION: (4)...(4)
<223> OTHER INFORMATION: Xaa = Any Amino Acid

<400> SEQUENCE: 10

Xaa Xaa Ser Xaa Gly
 1               5

<210> SEQ ID NO 11
<211> LENGTH: 1921
<212> TYPE: DNA
<213> ORGANISM: Homo sapiens
<220> FEATURE:
<221> NAME/KEY: CDS
<222> LOCATION: (33)...(1391)

<400> SEQUENCE: 11
cctgttgctg atgctgccgt gcggtacttg tc atg gag ctg gca ctg cgg cgc        53
                                    Met Glu Leu Ala Leu Arg Arg
                                     1               5 tct ccc gtc ccg cgg tgg ttg ctg ctg ctg ccg ctg ctg ctg ggc ctg       101
Ser Pro Val Pro Arg Trp Leu Leu Leu Leu Pro Leu Leu Leu Gly Leu
        10                  15                  20 aac gca gga gct gtc att gac tgg ccc aca gag gag ggc aag gaa gta       149
Asn Ala Gly Ala Val Ile Asp Trp Pro Thr Glu Glu Gly Lys Glu Val
    25                  30                  35 tgg gat tat gtg acg gtc cgc aag gat gcc tac atg ttc tgg tgg ctc       197
Trp Asp Tyr Val Thr Val Arg Lys Asp Ala Tyr Met Phe Trp Trp Leu
40                  45                  50                  55 tat tat gcc acc aac tcc tgc aag aac ttc tca gaa ctg ccc ctg gtc       245
Tyr Tyr Ala Thr Asn Ser Cys Lys Asn Phe Ser Glu Leu Pro Leu Val
                60                  65                  70 atg tgg ctt cag ggc ggt cca ggc ggt tct agc act gga ttt gga aac       293
Met Trp Leu Gln Gly Gly Pro Gly Gly Ser Ser Thr Gly Phe Gly Asn
            75                  80                  85
```

```
ttt gag gaa att ggg ccc ctt gac agt gat ctc aaa cca cgg aaa acc      341
Phe Glu Glu Ile Gly Pro Leu Asp Ser Asp Leu Lys Pro Arg Lys Thr
         90              95             100 acc tgg ctc cag gct gcc agt ctc cta ttt gtg gat aat ccc gtg ggc      389
Thr Trp Leu Gln Ala Ala Ser Leu Leu Phe Val Asp Asn Pro Val Gly
105             110             115 act ggg ttc agt tat gtg aat ggt agt ggt gcc tat gcc aag gac ctg      437
Thr Gly Phe Ser Tyr Val Asn Gly Ser Gly Ala Tyr Ala Lys Asp Leu
120             125             130             135 gct atg gtg gct tca gac atg atg gtt ctc ctg aag acc ttc ttc agt      485
Ala Met Val Ala Ser Asp Met Met Val Leu Leu Lys Thr Phe Phe Ser
                140             145             150 tgc cac aaa gaa ttc cag aca gtt cca ttc tac att ttc tca gag tcc      533
Cys His Lys Glu Phe Gln Thr Val Pro Phe Tyr Ile Phe Ser Glu Ser
            155             160             165 tat gga gga aaa atg gca gct ggc att ggt cta gag ctt tat aag gcc      581
Tyr Gly Gly Lys Met Ala Ala Gly Ile Gly Leu Glu Leu Tyr Lys Ala
        170             175             180 att cag cga ggg acc atc aag tgc aac ttt gcg ggg gtt gcc ttg ggt      629
Ile Gln Arg Gly Thr Ile Lys Cys Asn Phe Ala Gly Val Ala Leu Gly
185             190             195 gat tcc tgg atc tcc ccc gtg gat tcg gtg ctc tcc tgg gga cct tac      677
Asp Ser Trp Ile Ser Pro Val Asp Ser Val Leu Ser Trp Gly Pro Tyr
200             205             210             215 ctg tac agc atg tct ctt ctc gaa gac aaa ggt ctg gca gag gtg tct      725
Leu Tyr Ser Met Ser Leu Leu Glu Asp Lys Gly Leu Ala Glu Val Ser
                220             225             230 aag gtt gca gag caa gta ctg aat gcc gta aat aag ggg ctc tac aga      773
Lys Val Ala Glu Gln Val Leu Asn Ala Val Asn Lys Gly Leu Tyr Arg
            235             240             245 gag gcc aca gag ctg tgg ggg aaa gca gaa atg atc att gaa cag aac      821
Glu Ala Thr Glu Leu Trp Gly Lys Ala Glu Met Ile Ile Glu Gln Asn
        250             255             260 aca gat ggg gtg aac ttc tat aac atc tta act aaa agc act ccc acg      869
Thr Asp Gly Val Asn Phe Tyr Asn Ile Leu Thr Lys Ser Thr Pro Thr
265             270             275 tct aca atg gag tcg agt cta gaa ttc aca cag agc cac cta gtt tgt      917
Ser Thr Met Glu Ser Ser Leu Glu Phe Thr Gln Ser His Leu Val Cys
280             285             290             295 ctt tgt cag cgc cac gtg aga cac cta caa cga gat gcc tta agc cag      965
Leu Cys Gln Arg His Val Arg His Leu Gln Arg Asp Ala Leu Ser Gln
                300             305             310 ctc atg aat ggc ccc atc aga aag aag ctc aaa att att cct gag gat     1013
Leu Met Asn Gly Pro Ile Arg Lys Lys Leu Lys Ile Ile Pro Glu Asp
            315             320             325 caa tcc tgg gga ggc cag gct acc aac gtc ttt gtg aac atg gag gag     1061
Gln Ser Trp Gly Gly Gln Ala Thr Asn Val Phe Val Asn Met Glu Glu
        330             335             340 gac ttc atg aag cca gtc att agc att gtg gac gag ttg ctg gag gca     1109
Asp Phe Met Lys Pro Val Ile Ser Ile Val Asp Glu Leu Leu Glu Ala
345             350             355 ggg atc aac gtg acg gtg tat aat gga cag ctg gat ctc atc gta gat     1157
Gly Ile Asn Val Thr Val Tyr Asn Gly Gln Leu Asp Leu Ile Val Asp
360             365             370             375 acc atg ggt cag gag gcc tgg gtg cgg aaa ctg aag tgg cca gaa ctg     1205
Thr Met Gly Gln Glu Ala Trp Val Arg Lys Leu Lys Trp Pro Glu Leu
                380             385             390 cct aaa ttc agt cag ctg aag tgg aag gcc ctg tac agt gac cct aaa     1253
Pro Lys Phe Ser Gln Leu Lys Trp Lys Ala Leu Tyr Ser Asp Pro Lys
            395             400             405
```

-continued

```
tct ttg gaa aca tct gct ttt gtc aag tcc tac aag aac ctt gct ttc    1301
Ser Leu Glu Thr Ser Ala Phe Val Lys Ser Tyr Lys Asn Leu Ala Phe
        410                 415                 420 tac tgg att ctg aaa gct ggt cat atg gtt cct tct gac caa ggg gac    1349
Tyr Trp Ile Leu Lys Ala Gly His Met Val Pro Ser Asp Gln Gly Asp
425                 430                 435 atg gct ctg aag atg atg aga ctg gtg act cag caa gaa tag            1391
Met Ala Leu Lys Met Met Arg Leu Val Thr Gln Gln Glu *
440                 445                 450 gatggatggg gctggagatg agctggtttg gccttggggc acagagctga gctgaggccg  1451
ctgaagctgt aggaagcgcc attcttccct gtatctaact ggggctgtga tcaagaaggt  1511
tctgaccagc ttctgcagag gataaaatca ttgtctctgg aggcaatttg gaaattattt  1571
ctgcttctta aaaaaaccta agatttttta aaaaattgat ttgttttgat caaaataaag  1631
gatgataata gatattattt tttcttatga cagaagcaaa tgatgtgatt tatagaaaaa  1691
ctgggaaata caggtaccca aagagtaaat caacatctgt atccccctt cccagggta    1751
agcactgtta ccaatttagc atatgtcctt gcagaatttt ttttctata tatacatata   1811
tatttttac caaaatgaat cattactcta tgttgttta ctatttgttt gacatatcag    1871
tatatctgaa acacctttc atgtcaataa atgttcttct ctaacattaa               1921
```

<210> SEQ ID NO 12
<211> LENGTH: 452
<212> TYPE: PRT
<213> ORGANISM: Homo sapiens

<400> SEQUENCE: 12

```
Met Glu Leu Ala Leu Arg Arg Ser Pro Val Pro Arg Trp Leu Leu
1               5                   10                  15

Leu Pro Leu Leu Leu Gly Leu Asn Ala Gly Ala Val Ile Asp Trp Pro
                20                  25                  30

Thr Glu Glu Gly Lys Glu Val Trp Asp Tyr Val Thr Arg Lys Asp
        35                  40                  45

Ala Tyr Met Phe Trp Trp Leu Tyr Ala Thr Asn Ser Cys Lys Asn
    50                  55                  60

Phe Ser Glu Leu Pro Leu Val Met Trp Leu Gln Gly Pro Gly Gly
65                  70                  75                  80

Ser Ser Thr Gly Phe Gly Asn Phe Glu Glu Ile Gly Pro Leu Asp Ser
                85                  90                  95

Asp Leu Lys Pro Arg Lys Thr Thr Trp Leu Gln Ala Ala Ser Leu Leu
            100                 105                 110

Phe Val Asp Asn Pro Val Gly Thr Gly Phe Ser Tyr Val Asn Gly Ser
        115                 120                 125

Gly Ala Tyr Ala Lys Asp Leu Ala Met Val Ala Ser Asp Met Met Val
    130                 135                 140

Leu Leu Lys Thr Phe Phe Ser Cys His Lys Glu Phe Gln Thr Val Pro
145                 150                 155                 160

Phe Tyr Ile Phe Ser Glu Ser Tyr Gly Gly Lys Met Ala Ala Gly Ile
                165                 170                 175

Gly Leu Glu Leu Tyr Lys Ala Ile Gln Arg Gly Thr Ile Lys Cys Asn
            180                 185                 190

Phe Ala Gly Val Ala Leu Gly Asp Ser Trp Ile Ser Pro Val Asp Ser
        195                 200                 205

Val Leu Ser Trp Gly Pro Tyr Leu Tyr Ser Met Ser Leu Leu Glu Asp
```

```
                    210                 215                 220
Lys Gly Leu Ala Glu Val Ser Lys Val Ala Glu Gln Val Leu Asn Ala
225                 230                 235                 240

Val Asn Lys Gly Leu Tyr Arg Glu Ala Thr Glu Leu Trp Gly Lys Ala
                245                 250                 255

Glu Met Ile Ile Glu Gln Asn Thr Asp Gly Val Asn Phe Tyr Asn Ile
                260                 265                 270

Leu Thr Lys Ser Thr Pro Thr Ser Thr Met Glu Ser Ser Leu Glu Phe
            275                 280                 285

Thr Gln Ser His Leu Val Cys Leu Cys Gln Arg His Val Arg His Leu
        290                 295                 300

Gln Arg Asp Ala Leu Ser Gln Leu Met Asn Gly Pro Ile Arg Lys Lys
305                 310                 315                 320

Leu Lys Ile Ile Pro Glu Asp Gln Ser Trp Gly Gly Gln Ala Thr Asn
                325                 330                 335

Val Phe Val Asn Met Glu Glu Asp Phe Met Lys Pro Val Ile Ser Ile
                340                 345                 350

Val Asp Glu Leu Leu Glu Ala Gly Ile Asn Val Thr Val Tyr Asn Gly
            355                 360                 365

Gln Leu Asp Leu Ile Val Asp Thr Met Gly Gln Glu Ala Trp Val Arg
        370                 375                 380

Lys Leu Lys Trp Pro Glu Leu Pro Lys Phe Ser Gln Leu Lys Trp Lys
385                 390                 395                 400

Ala Leu Tyr Ser Asp Pro Lys Ser Leu Glu Thr Ser Ala Phe Val Lys
                405                 410                 415

Ser Tyr Lys Asn Leu Ala Phe Tyr Trp Ile Leu Lys Ala Gly His Met
                420                 425                 430

Val Pro Ser Asp Gln Gly Asp Met Ala Leu Lys Met Met Arg Leu Val
            435                 440                 445

Thr Gln Gln Glu
    450

<210> SEQ ID NO 13
<211> LENGTH: 1359
<212> TYPE: DNA
<213> ORGANISM: Homo sapiens
<220> FEATURE:
<221> NAME/KEY: CDS
<222> LOCATION: (1)...(1359)

<400> SEQUENCE: 13 atg gag ctg gca ctg cgg cgc tct ccc gtc ccg cgg tgg ttg ctg ctg      48
Met Glu Leu Ala Leu Arg Arg Ser Pro Val Pro Arg Trp Leu Leu Leu
 1               5                  10                  15 ctg ccg ctg ctg ctg ggc ctg aac gca gga gct gtc att gac tgg ccc      96
Leu Pro Leu Leu Leu Gly Leu Asn Ala Gly Ala Val Ile Asp Trp Pro
                20                  25                  30 aca gag gag ggc aag gaa gta tgg gat tat gtg acg gtc cgc aag gat     144
Thr Glu Glu Gly Lys Glu Val Trp Asp Tyr Val Thr Val Arg Lys Asp
            35                  40                  45 gcc tac atg ttc tgg tgg ctc tat tat gcc acc aac tcc tgc aag aac     192
Ala Tyr Met Phe Trp Trp Leu Tyr Tyr Ala Thr Asn Ser Cys Lys Asn
        50                  55                  60 ttc tca gaa ctg ccc ctg gtc atg tgg ctt cag ggc ggt cca ggc ggt     240
Phe Ser Glu Leu Pro Leu Val Met Trp Leu Gln Gly Gly Pro Gly Gly
65                  70                  75                  80 tct agc act gga ttt gga aac ttt gag gaa att ggg ccc ctt gac agt     288
```

```
                Ser Ser Thr Gly Phe Gly Asn Phe Glu Glu Ile Gly Pro Leu Asp Ser
                                85                  90                  95 gat ctc aaa cca cgg aaa acc acc tgg ctc cag gct gcc agt ctc cta        336
Asp Leu Lys Pro Arg Lys Thr Thr Trp Leu Gln Ala Ala Ser Leu Leu
        100                 105                 110 ttt gtg gat aat ccc gtg ggc act ggg ttc agt tat gtg aat ggt agt        384
Phe Val Asp Asn Pro Val Gly Thr Gly Phe Ser Tyr Val Asn Gly Ser
            115                 120                 125 ggt gcc tat gcc aag gac ctg gct atg gtg gct tca gac atg atg gtt        432
Gly Ala Tyr Ala Lys Asp Leu Ala Met Val Ala Ser Asp Met Met Val
130                 135                 140 ctc ctg aag acc ttc ttc agt tgc cac aaa gaa ttc cag aca gtt cca        480
Leu Leu Lys Thr Phe Phe Ser Cys His Lys Glu Phe Gln Thr Val Pro
145                 150                 155                 160 ttc tac att ttc tca gag tcc tat gga gga aaa atg gca gct ggc att        528
Phe Tyr Ile Phe Ser Glu Ser Tyr Gly Gly Lys Met Ala Ala Gly Ile
                165                 170                 175 ggt cta gag ctt tat aag gcc att cag cga ggg acc atc aag tgc aac        576
Gly Leu Glu Leu Tyr Lys Ala Ile Gln Arg Gly Thr Ile Lys Cys Asn
            180                 185                 190 ttt gcg ggg gtt gcc ttg ggt gat tcc tgg atc tcc ccc gtg gat tcg        624
Phe Ala Gly Val Ala Leu Gly Asp Ser Trp Ile Ser Pro Val Asp Ser
        195                 200                 205 gtg ctc tcc tgg gga cct tac ctg tac agc atg tct ctt ctc gaa gac        672
Val Leu Ser Trp Gly Pro Tyr Leu Tyr Ser Met Ser Leu Leu Glu Asp
    210                 215                 220 aaa ggt ctg gca gag gtg tct aag gtt gca gag caa gta ctg aat gcc        720
Lys Gly Leu Ala Glu Val Ser Lys Val Ala Glu Gln Val Leu Asn Ala
225                 230                 235                 240 gta aat aag ggg ctc tac aga gag gcc aca gag ctg tgg ggg aaa gca        768
Val Asn Lys Gly Leu Tyr Arg Glu Ala Thr Glu Leu Trp Gly Lys Ala
                245                 250                 255 gaa atg atc att gaa cag aac aca gat ggg gtg aac ttc tat aac atc        816
Glu Met Ile Ile Glu Gln Asn Thr Asp Gly Val Asn Phe Tyr Asn Ile
            260                 265                 270 tta act aaa agc act ccc acg tct aca atg gag tcg agt cta gaa ttc        864
Leu Thr Lys Ser Thr Pro Thr Ser Thr Met Glu Ser Ser Leu Glu Phe
        275                 280                 285 aca cag agc cac cta gtt tgt ctt tgt cag cgc cac gtg aga cac cta        912
Thr Gln Ser His Leu Val Cys Leu Cys Gln Arg His Val Arg His Leu
    290                 295                 300 caa cga gat gcc tta agc cag ctc atg aat ggc ccc atc aga aag aag        960
Gln Arg Asp Ala Leu Ser Gln Leu Met Asn Gly Pro Ile Arg Lys Lys
305                 310                 315                 320 ctc aaa att att cct gag gat caa tcc tgg gga ggc cag gct acc aac       1008
Leu Lys Ile Ile Pro Glu Asp Gln Ser Trp Gly Gly Gln Ala Thr Asn
                325                 330                 335 gtc ttt gtg aac atg gag gag gac ttc atg aag cca gtc att agc att       1056
Val Phe Val Asn Met Glu Glu Asp Phe Met Lys Pro Val Ile Ser Ile
            340                 345                 350 gtg gac gag ttg ctg gag gca ggg atc aac gtg acg gtg tat aat gga       1104
Val Asp Glu Leu Leu Glu Ala Gly Ile Asn Val Thr Val Tyr Asn Gly
        355                 360                 365 cag ctg gat ctc atc gta gat acc atg ggt cag gag gcc tgg gtg cgg       1152
Gln Leu Asp Leu Ile Val Asp Thr Met Gly Gln Glu Ala Trp Val Arg
    370                 375                 380 aaa ctg aag tgg cca gaa ctg cct aaa ttc agt cag ctg aag tgg aag       1200
Lys Leu Lys Trp Pro Glu Leu Pro Lys Phe Ser Gln Leu Lys Trp Lys
385                 390                 395                 400
```

```
gcc ctg tac agt gac cct aaa tct ttg gaa aca tct gct ttt gtc aag    1248
Ala Leu Tyr Ser Asp Pro Lys Ser Leu Glu Thr Ser Ala Phe Val Lys
            405                 410                 415 tcc tac aag aac ctt gct ttc tac tgg att ctg aaa gct ggt cat atg    1296
Ser Tyr Lys Asn Leu Ala Phe Tyr Trp Ile Leu Lys Ala Gly His Met
        420                 425                 430 gtt cct tct gac caa ggg gac atg gct ctg aag atg atg aga ctg gtg    1344
Val Pro Ser Asp Gln Gly Asp Met Ala Leu Lys Met Met Arg Leu Val
    435                 440                 445 act cag caa gaa tag                                                1359
Thr Gln Gln Glu *
    450
```

<210> SEQ ID NO 14
<211> LENGTH: 209
<212> TYPE: PRT
<213> ORGANISM: Homo sapiens
<220> FEATURE:
<221> NAME/KEY: VARIANT
<222> LOCATION: (22)...(24)
<223> OTHER INFORMATION: Xaa = Any Amino Acid

<400> SEQUENCE: 14

```
Tyr Leu Thr Val Asn Asp Thr His Gly Lys Asn Leu Phe Tyr Trp Phe
1               5                   10                  15

Phe Glu Ser Arg Asn Xaa Xaa Xaa Asp Pro Lys Gln Asp Pro Val Val
            20                  25                  30

Leu Trp Leu Asn Gly Gly Pro Gly Cys Ser Ser Leu Leu Phe Tyr Glu
        35                  40                  45

Asn Gly Pro Phe Ser Ile Ser Ser Asp Gly Ser Lys Ser Leu Pro Ser
    50                  55                  60

Leu Ser Leu Asn Pro Tyr Ser Trp Asn Asn Val Ala Asn Met Ile Tyr
65                  70                  75                  80

Leu Asp Gln Pro Val Gly Val Gly Phe Ser Tyr Ser Asp Ser Asp Asp
                85                  90                  95

Asp Tyr Thr Thr Thr Asn Asp Val Glu Ala Ala Lys Asp Leu Tyr Asn
            100                 105                 110

Phe Leu Gln Asp Phe Phe Gln Leu Phe Pro Glu Leu Leu Lys Asn Asp
        115                 120                 125

Phe Tyr Ile Ala Gly Glu Ser Tyr Ala Gly His Tyr Ile Pro Thr Phe
    130                 135                 140

Ala Ser Glu Ile Val Gln Gly Asn Lys Lys Asn Pro Gly Pro Asn Ile
145                 150                 155                 160

Asn Leu Lys Gly Leu Ala Ile Gly Asn Gly Leu Thr Asp Pro Leu Ile
                165                 170                 175

Gln Tyr Asn Ala Tyr Val Pro Phe Ala Tyr Glu His Gly Gly Glu Leu
            180                 185                 190

Ser Val Leu Ile Ser Glu Glu Tyr Ser Lys Ile Ser Lys Ser Phe Pro
        195                 200                 205

Arg
```

<210> SEQ ID NO 15
<211> LENGTH: 119
<212> TYPE: PRT
<213> ORGANISM: Homo sapiens

<400> SEQUENCE: 15

```
Val Tyr Gln Lys Phe Leu Asp Thr Gly Asp Trp Met Arg Ser Phe Leu
1               5                   10                  15
```

```
Val Lys Leu Leu Ser Leu Leu Glu Gln Gly Tyr Arg Val Leu Ile Tyr
            20                  25                  30

Ala Gly Asp Leu Asp Met Ile Cys Asn Trp Leu Gly Asn Glu Ala Trp
            35                  40                  45

Val Asn Ser Leu Glu Trp Ser Gly Lys Lys Gln Phe Gln Ala Ser Ser
 50                  55                  60

Trp Arg Pro Trp Leu Val Asp Gly Ala Asp Ser Glu Val Ala Gly
 65                  70                  75                  80

Phe Val Lys Thr Tyr Glu Lys His Leu Thr Phe Leu Thr Val Arg Gly
                85                  90                  95

Ala Gly His Met Val Pro Tyr Asp Lys Pro Gln Ala Ala Leu Gln Met
            100                 105                 110

Val Lys Arg Trp Ile Ala Gly
            115

<210> SEQ ID NO 16
<211> LENGTH: 8
<212> TYPE: PRT
<213> ORGANISM: Artificial Sequence
<220> FEATURE:
<223> OTHER INFORMATION: Consensus amino acid sequence
<220> FEATURE:
<221> NAME/KEY: VARIANT
<222> LOCATION: (1)...(1)
<223> OTHER INFORMATION: Xaa at postion 1 can be L, I, V or M
<220> FEATURE:
<221> NAME/KEY: VARIANT
<222> LOCATION: (2)...(2)
<223> OTHER INFORMATION: Xaa = Any Amino Acid
<220> FEATURE:
<221> NAME/KEY: VARIANT
<222> LOCATION: (3)...(3)
<223> OTHER INFORMATION: Xaa at postion 3 can be G, T or A
<220> FEATURE:
<221> NAME/KEY: VARIANT
<222> LOCATION: (7)...(7)
<223> OTHER INFORMATION: Xaa at position 7 can be A or G
<220> FEATURE:
<221> NAME/KEY: VARIANT
<222> LOCATION: (8)...(8)
<223> OTHER INFORMATION: Xaa at position 8 can be G or S

<400> SEQUENCE: 16

Xaa Xaa Xaa Glu Ser Tyr Xaa Xaa
 1               5

<210> SEQ ID NO 17
<211> LENGTH: 18
<212> TYPE: PRT
<213> ORGANISM: Artificial Sequence
<220> FEATURE:
<223> OTHER INFORMATION: Consensus amino acid sequence
<220> FEATURE:
<221> NAME/KEY: VARIANT
<222> LOCATION: (1)...(1)
<223> OTHER INFORMATION: Xaa at position 1 can be L, I, V or F
<220> FEATURE:
<221> NAME/KEY: VARIANT
<222> LOCATION: (2)...(3)
<223> OTHER INFORMATION: Xaa = Any Amino Acid
<220> FEATURE:
<221> NAME/KEY: VARIANT
<222> LOCATION: (4)...(4)
<223> OTHER INFORMATION: Xaa at position 4 can be L, I, V, S, T or A
<220> FEATURE:
<221> NAME/KEY: VARIANT
<222> LOCATION: (5)...(5)
<223> OTHER INFORMATION: Xaa = Any Amino Acid
<220> FEATURE:
```

```
<221> NAME/KEY: VARIANT
<222> LOCATION: (6)...(6)
<223> OTHER INFORMATION: Xaa at position 6 can be I, V, P, S or T
<220> FEATURE:
<221> NAME/KEY: VARIANT
<222> LOCATION: (7)...(7)
<223> OTHER INFORMATION: Xaa = Any Amino Acid
<220> FEATURE:
<221> NAME/KEY: VARIANT
<222> LOCATION: (8)...(8)
<223> OTHER INFORMATION: Xaa at position 8 can be G, S, D, N, Q or L
<220> FEATURE:
<221> NAME/KEY: VARIANT
<222> LOCATION: (9)...(9)
<223> OTHER INFORMATION: Xaa at position 9 can be S, A, G or V
<220> FEATURE:
<221> NAME/KEY: VARIANT
<222> LOCATION: (10)...(10)
<223> OTHER INFORMATION: Xaa at position 9 can be S or G
<220> FEATURE:
<221> NAME/KEY: VARIANT
<222> LOCATION: (12)...(12)
<223> OTHER INFORMATION: Xaa = Any Amino Acid
<220> FEATURE:
<221> NAME/KEY: VARIANT
<222> LOCATION: (13)...(13)
<223> OTHER INFORMATION: Xaa at position 9 can be I, V, A or Q
<220> FEATURE:
<221> NAME/KEY: VARIANT
<222> LOCATION: (15)...(17)
<223> OTHER INFORMATION: Xaa = Any Amino Acid
<220> FEATURE:
<221> NAME/KEY: VARIANT
<222> LOCATION: (18)...(18)
<223> OTHER INFORMATION: Xaa at position 18 can be P, S or A

<400> SEQUENCE: 17

Xaa Xaa Xaa Xaa Xaa Xaa Xaa Xaa Xaa Xaa His Xaa Xaa Pro Xaa Xaa
 1               5                  10                  15

Xaa Xaa

<210> SEQ ID NO 18
<211> LENGTH: 8
<212> TYPE: PRT
<213> ORGANISM: Artificial Sequence
<220> FEATURE:
<223> OTHER INFORMATION: Consensus amino acid sequence

<400> SEQUENCE: 18

Ile Phe Ser Glu Ser Tyr Gly Gly
 1               5

<210> SEQ ID NO 19
<211> LENGTH: 14
<212> TYPE: PRT
<213> ORGANISM: Artificial Sequence
<220> FEATURE:
<223> OTHER INFORMATION: Consensus amino acid sequence

<400> SEQUENCE: 19

Leu Ala Phe Tyr Trp Ile Leu Lys Ala Gly His Met Val Pro
 1               5                  10

<210> SEQ ID NO 20
<211> LENGTH: 980
<212> TYPE: DNA
<213> ORGANISM: Homo sapiens
<220> FEATURE:
<221> NAME/KEY: CDS
<222> LOCATION: (18)...(800)

<400> SEQUENCE: 20
```

```
cctgtggtcg ccccagg atg ctg aac cga atg gtg ggc ggg cag gac acg        50
                   Met Leu Asn Arg Met Val Gly Gly Gln Asp Thr
                    1               5                  10 cag gag ggc gag tgg ccc tgg caa gtc agc atc cag cgc aac gga agc        98
Gln Glu Gly Glu Trp Pro Trp Gln Val Ser Ile Gln Arg Asn Gly Ser
             15                  20                  25 cac ttc tgc ggg ggc agc ctc atc gcg gag cag tgg gtc ctg acg gct       146
His Phe Cys Gly Gly Ser Leu Ile Ala Glu Gln Trp Val Leu Thr Ala
         30                  35                  40 gcg cac tgc ttc cgc aac acc tct gag acg tcc ctg tac cag gtc ctg       194
Ala His Cys Phe Arg Asn Thr Ser Glu Thr Ser Leu Tyr Gln Val Leu
     45                  50                  55 ctg ggg gca agg cag cta gtg cag ccg gga cca cac gct atg tat gcc       242
Leu Gly Ala Arg Gln Leu Val Gln Pro Gly Pro His Ala Met Tyr Ala
 60                  65                  70                  75 cgg gtg agg cag gtg gag agc aac ccc ctg tac cag ggc acg gcc tcc       290
Arg Val Arg Gln Val Glu Ser Asn Pro Leu Tyr Gln Gly Thr Ala Ser
                 80                  85                  90 agc gct gac gtg gcc ctg gtg gag ctg gag gca cca gtg ccc ttc acc       338
Ser Ala Asp Val Ala Leu Val Glu Leu Glu Ala Pro Val Pro Phe Thr
             95                 100                 105 aat tac atc ctc ccc gtg tgc ctg cct gac ccc tcg gtg atc ttt gag       386
Asn Tyr Ile Leu Pro Val Cys Leu Pro Asp Pro Ser Val Ile Phe Glu
         110                 115                 120 acg ggc atg aac tgc tgg gtc act ggc tgg ggc agc ccc agt gag gaa       434
Thr Gly Met Asn Cys Trp Val Thr Gly Trp Gly Ser Pro Ser Glu Glu
     125                 130                 135 gac ctc ctg ccc gaa ccg cgg atc ctg cag aaa ctc gct gtg ccc atc       482
Asp Leu Leu Pro Glu Pro Arg Ile Leu Gln Lys Leu Ala Val Pro Ile
140                 145                 150                 155 atc gac aca ccc aag tgc aac ctg ctc tac agc aaa gac acc gag ttt       530
Ile Asp Thr Pro Lys Cys Asn Leu Leu Tyr Ser Lys Asp Thr Glu Phe
                 160                 165                 170 ggc tac caa ccc aaa acc atc aag aat gac atg ctg tgc gcc ggc ttc       578
Gly Tyr Gln Pro Lys Thr Ile Lys Asn Asp Met Leu Cys Ala Gly Phe
             175                 180                 185 gag gag ggc aag aag gat gcc tgc aag ggc gac tcg ggc ggc ccc ctg       626
Glu Glu Gly Lys Lys Asp Ala Cys Lys Gly Asp Ser Gly Gly Pro Leu
         190                 195                 200 gtg tgc ctc gtg ggt cag tcg tgg ctg cag gcg ggg gtg atc agc tgg       674
Val Cys Leu Val Gly Gln Ser Trp Leu Gln Ala Gly Val Ile Ser Trp
     205                 210                 215 ggt gag ggc tgt gcc cgc cag aac cgc cca ggt gtc tac atc cgt gtc       722
Gly Glu Gly Cys Ala Arg Gln Asn Arg Pro Gly Val Tyr Ile Arg Val
220                 225                 230                 235 acc gcc cac cac aac tgg atc cat cgg atc atc ccc aaa ctg cag ttc       770
Thr Ala His His Asn Trp Ile His Arg Ile Ile Pro Lys Leu Gln Phe
                 240                 245                 250 cag cca gcg agg ttg ggc ggc cag aag tga gaccccggg gccaggagcc          820
Gln Pro Ala Arg Leu Gly Gly Gln Lys  *
             255                 260 ccttgagcag agctctgcac ccagcctgcc cgcccacacc atcctgctgg tcctcccagc     880
gctgctgttg cacctgtgag ccccaccaga ctcatttgta aatagcgctc cttcctcccc     940
tctcaaatac ccttattta tttatgtttc tcccaataaa                            980

<210> SEQ ID NO 21
<211> LENGTH: 260
<212> TYPE: PRT
```

<213> ORGANISM: Homo sapiens

<400> SEQUENCE: 21

```
Met Leu Asn Arg Met Val Gly Gly Gln Asp Thr Gln Glu Gly Glu Trp
 1               5                  10                  15

Pro Trp Gln Val Ser Ile Gln Arg Asn Gly Ser His Phe Cys Gly Gly
            20                  25                  30

Ser Leu Ile Ala Glu Gln Trp Val Leu Thr Ala Ala His Cys Phe Arg
        35                  40                  45

Asn Thr Ser Glu Thr Ser Leu Tyr Gln Val Leu Leu Gly Ala Arg Gln
    50                  55                  60

Leu Val Gln Pro Gly Pro His Ala Met Tyr Ala Arg Val Arg Gln Val
65                  70                  75                  80

Glu Ser Asn Pro Leu Tyr Gln Gly Thr Ala Ser Ala Asp Val Ala
                85                  90                  95

Leu Val Glu Leu Glu Ala Pro Val Pro Phe Thr Asn Tyr Ile Leu Pro
            100                 105                 110

Val Cys Leu Pro Asp Pro Ser Val Ile Phe Glu Thr Gly Met Asn Cys
        115                 120                 125

Trp Val Thr Gly Trp Gly Ser Pro Ser Glu Glu Asp Leu Leu Pro Glu
    130                 135                 140

Pro Arg Ile Leu Gln Lys Leu Ala Val Pro Ile Ile Asp Thr Pro Lys
145                 150                 155                 160

Cys Asn Leu Leu Tyr Ser Lys Asp Thr Glu Phe Gly Tyr Gln Pro Lys
                165                 170                 175

Thr Ile Lys Asn Asp Met Leu Cys Ala Gly Phe Glu Glu Gly Lys Lys
            180                 185                 190

Asp Ala Cys Lys Gly Asp Ser Gly Gly Pro Leu Val Cys Leu Val Gly
        195                 200                 205

Gln Ser Trp Leu Gln Ala Gly Val Ile Ser Trp Gly Glu Gly Cys Ala
    210                 215                 220

Arg Gln Asn Arg Pro Gly Val Tyr Ile Arg Val Thr Ala His His Asn
225                 230                 235                 240

Trp Ile His Arg Ile Ile Pro Lys Leu Gln Phe Gln Pro Ala Arg Leu
                245                 250                 255

Gly Gly Gln Lys
            260
```

<210> SEQ ID NO 22
<211> LENGTH: 783
<212> TYPE: DNA
<213> ORGANISM: Homo sapiens
<220> FEATURE:
<221> NAME/KEY: CDS
<222> LOCATION: (1)...(783)

<400> SEQUENCE: 22

```
atg ctg aac cga atg gtg ggc ggg cag gac acg cag gag ggc gag tgg     48
Met Leu Asn Arg Met Val Gly Gly Gln Asp Thr Gln Glu Gly Glu Trp
 1               5                  10                  15 ccc tgg caa gtc agc atc cag cgc aac gga agc cac ttc tgc ggg ggc     96
Pro Trp Gln Val Ser Ile Gln Arg Asn Gly Ser His Phe Cys Gly Gly
            20                  25                  30 agc ctc atc gcg gag cag tgg gtc ctg acg gct gcg cac tgc ttc cgc    144
Ser Leu Ile Ala Glu Gln Trp Val Leu Thr Ala Ala His Cys Phe Arg
        35                  40                  45 aac acc tct gag acg tcc ctg tac cag gtc ctg ctg ggg gca agg cag    192
Asn Thr Ser Glu Thr Ser Leu Tyr Gln Val Leu Leu Gly Ala Arg Gln
```

```
Asn Thr Ser Glu Thr Ser Leu Tyr Gln Val Leu Leu Gly Ala Arg Gln
         50                  55                  60 cta gtg cag ccg gga cca cac gct atg tat gcc cgg gtg agg cag gtg      240
Leu Val Gln Pro Gly Pro His Ala Met Tyr Ala Arg Val Arg Gln Val
 65                  70                  75                  80 gag agc aac ccc ctg tac cag ggc acg gcc tcc agc gct gac gtg gcc      288
Glu Ser Asn Pro Leu Tyr Gln Gly Thr Ala Ser Ser Ala Asp Val Ala
                 85                  90                  95 ctg gtg gag ctg gag gca cca gtg ccc ttc acc aat tac atc ctc ccc      336
Leu Val Glu Leu Glu Ala Pro Val Pro Phe Thr Asn Tyr Ile Leu Pro
            100                 105                 110 gtg tgc ctg cct gac ccc tcg gtg atc ttt gag acg ggc atg aac tgc      384
Val Cys Leu Pro Asp Pro Ser Val Ile Phe Glu Thr Gly Met Asn Cys
        115                 120                 125 tgg gtc act ggc tgg ggc agc ccc agt gag gaa gac ctc ctg ccc gaa      432
Trp Val Thr Gly Trp Gly Ser Pro Ser Glu Glu Asp Leu Leu Pro Glu
    130                 135                 140 ccg cgg atc ctg cag aaa ctc gct gtg ccc atc atc gac aca ccc aag      480
Pro Arg Ile Leu Gln Lys Leu Ala Val Pro Ile Ile Asp Thr Pro Lys
145                 150                 155                 160 tgc aac ctg ctc tac agc aaa gac acc gag ttt ggc tac caa ccc aaa      528
Cys Asn Leu Leu Tyr Ser Lys Asp Thr Glu Phe Gly Tyr Gln Pro Lys
                165                 170                 175 acc atc aag aat gac atg ctg tgc gcc ggc ttc gag gag ggc aag aag      576
Thr Ile Lys Asn Asp Met Leu Cys Ala Gly Phe Glu Glu Gly Lys Lys
            180                 185                 190 gat gcc tgc aag ggc gac tcg ggc ggc ccc ctg gtg tgc ctc gtg ggt      624
Asp Ala Cys Lys Gly Asp Ser Gly Gly Pro Leu Val Cys Leu Val Gly
        195                 200                 205 cag tcg tgg ctg cag gcg ggg gtg atc agc tgg ggt gag ggc tgt gcc      672
Gln Ser Trp Leu Gln Ala Gly Val Ile Ser Trp Gly Glu Gly Cys Ala
    210                 215                 220 cgc cag aac cgc cca ggt gtc tac atc cgt gtc acc gcc cac cac aac      720
Arg Gln Asn Arg Pro Gly Val Tyr Ile Arg Val Thr Ala His His Asn
225                 230                 235                 240 tgg atc cat cgg atc atc ccc aaa ctg cag ttc cag cca gcg agg ttg      768
Trp Ile His Arg Ile Ile Pro Lys Leu Gln Phe Gln Pro Ala Arg Leu
                245                 250                 255 ggc ggc cag aag tga                                                  783
Gly Gly Gln Lys  *
            260

<210> SEQ ID NO 23
<211> LENGTH: 271
<212> TYPE: PRT
<213> ORGANISM: Artificial Sequence
<220> FEATURE:
<223> OTHER INFORMATION: Consensus amino acid sequence of trypsin-like
      domain
<220> FEATURE:
<221> NAME/KEY: VARIANT
<222> LOCATION: (21)...(26)
<223> OTHER INFORMATION: Xaa = Any Amino Acid
<220> FEATURE:
<221> NAME/KEY: VARIANT
<222> LOCATION: (44)...(53)
<223> OTHER INFORMATION: Xaa = Any Amino Acid
<220> FEATURE:
<221> NAME/KEY: VARIANT
<222> LOCATION: (96)...(100)
<223> OTHER INFORMATION: Xaa = Any Amino Acid
<220> FEATURE:
<221> NAME/KEY: VARIANT
<222> LOCATION: (184)...(202)
<223> OTHER INFORMATION: Xaa = Any Amino Acid
```

```
<220> FEATURE:
<221> NAME/KEY: VARIANT
<222> LOCATION: (231)...(236)
<223> OTHER INFORMATION: Xaa = Any Amino Acid

<400> SEQUENCE: 23

Arg Ile Val Gly Gly Ser Glu Ala Lys Ile Gly Ser Phe Pro Trp Gln
 1               5                  10                  15

Val Ser Leu Gln Xaa Xaa Xaa Xaa Xaa Cys Gly Gly Ser Leu Ile
            20              25                  30

Ser Pro Arg Trp Val Leu Thr Ala Ala His Cys Xaa Xaa Xaa Xaa
            35              40                  45

Xaa Xaa Xaa Xaa Xaa Arg Val Arg Leu Gly Ser His Asp Leu Ser Ser
 50                  55                  60

Gly Glu Glu Thr Glu Gly Pro Arg Leu Asp Ser Pro Gly Gly Gln
 65              70              75                  80

Val Ile Lys Val Ser Lys Ile Ile Glu Val His Pro Asn Tyr Asn Xaa
            85                  90                  95

Xaa Xaa Xaa Xaa Asn Asp Ile Ala Leu Leu Lys Leu Lys Glu Pro Val
        100                 105                 110

Thr Leu Ser Asp Ser Asn Thr Val Arg Pro Ile Cys Leu Pro Ser Ser
        115                 120                 125

Asn Glu Ile Lys Thr Ser Glu Gly Asn Thr Val Pro Ala Gly Thr Thr
130                 135                 140

Cys Thr Val Ser Gly Trp Gly Arg Thr Ser Glu Gly Pro Glu Ser
145                 150                 155                 160

Gly Gly Gly Ser Leu Pro Asp Val Leu Gln Glu Val Asn Val Pro Ile
                165                 170                 175

Val Ser Asn Glu Thr Cys Arg Xaa Xaa Xaa Xaa Xaa Xaa Xaa Xaa
            180                 185                 190

Xaa Xaa Xaa Xaa Xaa Xaa Xaa Xaa Xaa Xaa Met Leu Cys Ala Gly Tyr
            195                 200                 205

Leu Glu Gly Gly Asn Thr Pro Gly Gly Lys Asp Ala Cys Gln Gly Asp
210                 215                 220

Gly Gly Pro Leu Val Cys Xaa Xaa Xaa Xaa Xaa Val Leu Val Gly
225                 230                 235                 240

Ile Val Ser Trp Gly Ser Ser Ser Leu Tyr Gly Cys Ala Arg Pro Asn
                245                 250                 255

Lys Pro Gly Val Tyr Thr Arg Val Ser Ser Tyr Leu Asp Trp Ile
            260                 265                 270

<210> SEQ ID NO 24
<211> LENGTH: 7
<212> TYPE: PRT
<213> ORGANISM: Artificial Sequence
<220> FEATURE:
<223> OTHER INFORMATION: Consensus amino acid sequence

<400> SEQUENCE: 24

Gly Asp Ser Gly Gly Pro Leu
 1               5

<210> SEQ ID NO 25
<211> LENGTH: 7220
<212> TYPE: DNA
<213> ORGANISM: Homo sapiens
<220> FEATURE:
<221> NAME/KEY: CDS
<222> LOCATION: (129)...(2900)
```

-continued

```
<400> SEQUENCE: 25
agcggcgagc cgcgaaccag gcagtccggg gcatccagac tgcaggccgc gcccaggccg      60
cgcccaggct gcgccgcccg cctgcctccc gcgctgccgc gtcgccagtg ctagcgctcc     120 tctccagc atg ctg cgg cgg ggc agc cag gcg ctc cgg cgc ttc tcc act     170
         Met Leu Arg Arg Gly Ser Gln Ala Leu Arg Arg Phe Ser Thr
           1               5                  10 ggc cgg gtt tat ttc aaa aac aag ctg aag ttg gca cta att ggc cag     218
Gly Arg Val Tyr Phe Lys Asn Lys Leu Lys Leu Ala Leu Ile Gly Gln
 15                  20                  25                  30 agc ctc ttt gga caa gaa gtc tat agc cac ctc cgc aaa gag ggc cac     266
Ser Leu Phe Gly Gln Glu Val Tyr Ser His Leu Arg Lys Glu Gly His
                 35                  40                  45 cga gta gta ggg gtg ttc aca gtt cca gac aag gat gga aaa gct gac     314
Arg Val Val Gly Val Phe Thr Val Pro Asp Lys Asp Gly Lys Ala Asp
             50                  55                  60 cct ctg gct ttg gct gca gag aaa gat ggg acc cct gtg ttc aag ctt     362
Pro Leu Ala Leu Ala Ala Glu Lys Asp Gly Thr Pro Val Phe Lys Leu
         65                  70                  75 cct aaa tgg agg gtc aag ggc aag acc atc aaa gaa gtg gca gaa gcc     410
Pro Lys Trp Arg Val Lys Gly Lys Thr Ile Lys Glu Val Ala Glu Ala
 80                  85                  90 tac aga tcc gtg ggt gca gag cta aat gtg ctc cct ttc tgc act cag     458
Tyr Arg Ser Val Gly Ala Glu Leu Asn Val Leu Pro Phe Cys Thr Gln
 95                 100                 105                 110 ttc att ccc atg gat ata att gat agt cca aag cac ggc tct atc att     506
Phe Ile Pro Met Asp Ile Ile Asp Ser Pro Lys His Gly Ser Ile Ile
                115                 120                 125 tat cac cca tcc atc ctg ccc agg cac aga gga gcc tct gct atc aat     554
Tyr His Pro Ser Ile Leu Pro Arg His Arg Gly Ala Ser Ala Ile Asn
            130                 135                 140 tgg act cta att atg gga gat aag aaa gct ggg ttt tct gtt ttc tgg     602
Trp Thr Leu Ile Met Gly Asp Lys Lys Ala Gly Phe Ser Val Phe Trp
        145                 150                 155 gct gat gat ggc ttg gat aca gga ccc atc ctt ctt cag aga tca tgt     650
Ala Asp Asp Gly Leu Asp Thr Gly Pro Ile Leu Leu Gln Arg Ser Cys
    160                 165                 170 gat gtt gaa ccc aat gat aca gtg gat gca ctt tat aat cgg ttt ctt     698
Asp Val Glu Pro Asn Asp Thr Val Asp Ala Leu Tyr Asn Arg Phe Leu
175                 180                 185                 190 ttt cct gaa gga atc aag gcc atg gta gaa gct gtc caa ctc ata gct     746
Phe Pro Glu Gly Ile Lys Ala Met Val Glu Ala Val Gln Leu Ile Ala
                195                 200                 205 gat gga aaa gct cct cgt ata ccc cag cca gaa gaa ggg gca aca tat     794
Asp Gly Lys Ala Pro Arg Ile Pro Gln Pro Glu Glu Gly Ala Thr Tyr
            210                 215                 220 gaa ggt atc cag aaa aag gaa aat gct gag att tct tgg gac cag tct     842
Glu Gly Ile Gln Lys Lys Glu Asn Ala Glu Ile Ser Trp Asp Gln Ser
        225                 230                 235 gcc gaa gtt tta cat aac tgg att cga ggt cat gat aaa gtc cct gga     890
Ala Glu Val Leu His Asn Trp Ile Arg Gly His Asp Lys Val Pro Gly
    240                 245                 250 gct tgg aca gag ata aat gga cag atg gtc act ttc tat ggc tcg aca     938
Ala Trp Thr Glu Ile Asn Gly Gln Met Val Thr Phe Tyr Gly Ser Thr
255                 260                 265                 270 tta ctg aat agc tct gtg cct cct gga gaa cca ctg gaa att aaa ggt     986
Leu Leu Asn Ser Ser Val Pro Pro Gly Glu Pro Leu Glu Ile Lys Gly
                275                 280                 285
```

```
gcc aag aag cct ggt ctc gtt acc aaa aat gga ctt gtt ctt ttt ggt      1034
Ala Lys Lys Pro Gly Leu Val Thr Lys Asn Gly Leu Val Leu Phe Gly
        290                 295                 300 aac gat gga aaa gca ctg acg gtg aga aat ctg cag ttt gaa gat gga      1082
Asn Asp Gly Lys Ala Leu Thr Val Arg Asn Leu Gln Phe Glu Asp Gly
            305                 310                 315 aaa atg atc cct gcc tct cag tac ttt tca acg ggt gag acg tca gtg     1130
Lys Met Ile Pro Ala Ser Gln Tyr Phe Ser Thr Gly Glu Thr Ser Val
320                 325                 330 gta gaa ctg aca gct gaa gag gtg aaa gtg gca gag acc atc aag gtc     1178
Val Glu Leu Thr Ala Glu Glu Val Lys Val Ala Glu Thr Ile Lys Val
335                 340                 345                 350 atc tgg gct gga att tta agc aat gtc ccc att att gaa gac tca aca     1226
Ile Trp Ala Gly Ile Leu Ser Asn Val Pro Ile Ile Glu Asp Ser Thr
                355                 360                 365 gac ttc ttt aaa tct gga gca agc tca atg gat gtt gcc agg ctg gtt     1274
Asp Phe Phe Lys Ser Gly Ala Ser Ser Met Asp Val Ala Arg Leu Val
            370                 375                 380 gaa gag atc aga cag aaa tgt ggt ggg ctt cag ttg cag aat gaa gat     1322
Glu Glu Ile Arg Gln Lys Cys Gly Gly Leu Gln Leu Gln Asn Glu Asp
        385                 390                 395 gtc tat atg gcc acc aag ttt gaa ggc ttt atc caa aag gtc gtg agg     1370
Val Tyr Met Ala Thr Lys Phe Glu Gly Phe Ile Gln Lys Val Val Arg
    400                 405                 410 aaa ctg aga gga gaa gat caa gag gtg gag ctg gtt gta gat tat att     1418
Lys Leu Arg Gly Glu Asp Gln Glu Val Glu Leu Val Val Asp Tyr Ile
415                 420                 425                 430 tca aag gag gtc aat gaa atc atg gta aaa atg cca tac cag tgt ttc     1466
Ser Lys Glu Val Asn Glu Ile Met Val Lys Met Pro Tyr Gln Cys Phe
                435                 440                 445 ata aat gga cag ttc aca gat gca gac gat gga aag act tac gac act     1514
Ile Asn Gly Gln Phe Thr Asp Ala Asp Asp Gly Lys Thr Tyr Asp Thr
            450                 455                 460 atc aac cca aca gat gga tct aca ata tgc aaa gta tcc tac gct tct     1562
Ile Asn Pro Thr Asp Gly Ser Thr Ile Cys Lys Val Ser Tyr Ala Ser
        465                 470                 475 ttg gcg gat gtt gat aaa gca gta gca gca aaa gat gct ttt gaa        1610
Leu Ala Asp Val Asp Lys Ala Val Ala Ala Lys Asp Ala Phe Glu
    480                 485                 490 aac ggt gaa tgg gga aga atg aat gca aga gaa aga gga aga ttg atg    1658
Asn Gly Glu Trp Gly Arg Met Asn Ala Arg Glu Arg Gly Arg Leu Met
495                 500                 505                 510 tat aga ctt gca gac cta ctg gaa gag aac caa gaa gag ctg gca act    1706
Tyr Arg Leu Ala Asp Leu Leu Glu Glu Asn Gln Glu Glu Leu Ala Thr
                515                 520                 525 att gaa gcc ctt gat tca ggg gct gtc tat acc ttg gcc ctg aag aca    1754
Ile Glu Ala Leu Asp Ser Gly Ala Val Tyr Thr Leu Ala Leu Lys Thr
            530                 535                 540 cac att gga atg tct gtg caa aca ttc aga tat ttt gct ggc tgg tgc    1802
His Ile Gly Met Ser Val Gln Thr Phe Arg Tyr Phe Ala Gly Trp Cys
        545                 550                 555 gac aaa att cag ggt tct act att cca atc aac cag gcc cgt cca aat    1850
Asp Lys Ile Gln Gly Ser Thr Ile Pro Ile Asn Gln Ala Arg Pro Asn
    560                 565                 570 cgc aat ctg acc ttc acc aag aaa gag cca ctc ggt gtc tgt gcc att    1898
Arg Asn Leu Thr Phe Thr Lys Lys Glu Pro Leu Gly Val Cys Ala Ile
575                 580                 585                 590 att att ccc tgg aac tac ccg ctg atg atg ctg gca tgg aag agt gct    1946
Ile Ile Pro Trp Asn Tyr Pro Leu Met Met Leu Ala Trp Lys Ser Ala
                595                 600                 605
```

|     |     |
| --- | --- |
| gcg tgt ttg gca gca ggc aat acc tta gtg ctc aag cca gca cag gtc<br>Ala Cys Leu Ala Ala Gly Asn Thr Leu Val Leu Lys Pro Ala Gln Val<br>          610                   615                620 | 1994 |
| acg ccc ttg act gct ttg aag ttt gca gaa ctg tct gtg aaa gca ggc<br>Thr Pro Leu Thr Ala Leu Lys Phe Ala Glu Leu Ser Val Lys Ala Gly<br>     625                 630                635 | 2042 |
| ttt cca aag ggg gtc atc aac atc att cca ggc tca ggt ggc ata gca<br>Phe Pro Lys Gly Val Ile Asn Ile Ile Pro Gly Ser Gly Gly Ile Ala<br>640                 645                650 | 2090 |
| gga caa cgt ctg tct gaa cat cct gac atc cgc aaa ctt ggt ttc act<br>Gly Gln Arg Leu Ser Glu His Pro Asp Ile Arg Lys Leu Gly Phe Thr<br>655                 660               665            670 | 2138 |
| gga tcc act cct att ggc aaa cag atc atg aag agc tgt gct gtt agc<br>Gly Ser Thr Pro Ile Gly Lys Gln Ile Met Lys Ser Cys Ala Val Ser<br>          675                   680                685 | 2186 |
| aac ttg aag aaa gtt tcc ctt gag ctt ggt ggc aag tct cca ctt ata<br>Asn Leu Lys Lys Val Ser Leu Glu Leu Gly Gly Lys Ser Pro Leu Ile<br>          690                   695               700 | 2234 |
| ata ttt aat gac tgt gaa ctt gac aag gct gtg cga atg ggc atg gga<br>Ile Phe Asn Asp Cys Glu Leu Asp Lys Ala Val Arg Met Gly Met Gly<br>705                 710               715 | 2282 |
| gca gta ttt ttc aac aaa gga gag aac tgt att gct gct ggg cgg ttg<br>Ala Val Phe Phe Asn Lys Gly Glu Asn Cys Ile Ala Ala Gly Arg Leu<br>720                 725               730 | 2330 |
| ttc gtg gaa gaa tcc atc cac gac gaa ttt gtg aca aga gtg gta gaa<br>Phe Val Glu Glu Ser Ile His Asp Glu Phe Val Thr Arg Val Val Glu<br>735                 740               745            750 | 2378 |
| gaa att aaa aag atg aaa att ggt gat cca ctt gac aga tcc act gat<br>Glu Ile Lys Lys Met Lys Ile Gly Asp Pro Leu Asp Arg Ser Thr Asp<br>                   755               760           765 | 2426 |
| cat ggg ccc caa aat cat aag gct cat ctg gaa aag ctg ctg caa tac<br>His Gly Pro Gln Asn His Lys Ala His Leu Glu Lys Leu Leu Gln Tyr<br>          770                   775               780 | 2474 |
| tgt gaa act gga gtg aaa gaa ggg gcc act ttg gtg tac ggg gga aga<br>Cys Glu Thr Gly Val Lys Glu Gly Ala Thr Leu Val Tyr Gly Gly Arg<br>785                 790               795 | 2522 |
| caa gtc caa agg cca ggc ttt ttc atg gag ccg acc gtg ttc aca gat<br>Gln Val Gln Arg Pro Gly Phe Phe Met Glu Pro Thr Val Phe Thr Asp<br>800                 805               810 | 2570 |
| gtg gaa gac tac atg tac ctc gcc aaa gag gaa tcc ttt ggg cct att<br>Val Glu Asp Tyr Met Tyr Leu Ala Lys Glu Glu Ser Phe Gly Pro Ile<br>815                 820               825            830 | 2618 |
| atg gtc att tct aaa ttc caa aat ggg gac atc gat gga gtg ttg cag<br>Met Val Ile Ser Lys Phe Gln Asn Gly Asp Ile Asp Gly Val Leu Gln<br>                   835               840           845 | 2666 |
| cga gca aat agt aca gag tat ggt ttg gcc tca ggg gtt ttt aca aga<br>Arg Ala Asn Ser Thr Glu Tyr Gly Leu Ala Ser Gly Val Phe Thr Arg<br>          850                   855               860 | 2714 |
| gac ata aac aaa gct atg tat gtg agt gaa aaa ctg gaa gca gga act<br>Asp Ile Asn Lys Ala Met Tyr Val Ser Glu Lys Leu Glu Ala Gly Thr<br>865                 870               875 | 2762 |
| gtt ttt att aac aca tac aac aag aca gat gtg gcg gcc cca ttt ggc<br>Val Phe Ile Asn Thr Tyr Asn Lys Thr Asp Val Ala Ala Pro Phe Gly<br>880                 885               890 | 2810 |
| gga gtt aaa caa tct ggc ttt gga aaa gac tta ggt gag gaa gct cta<br>Gly Val Lys Gln Ser Gly Phe Gly Lys Asp Leu Gly Glu Glu Ala Leu<br>895                 900               905           910 | 2858 |
| aat gaa tat ctc aaa acc aag acg gtg aca ctg gaa tat tag<br>Asn Glu Tyr Leu Lys Thr Lys Thr Val Thr Leu Glu Tyr  * | 2900 |

```
                   915         920
agcaacacca tcatcaggaa agccttgaca gacagccctt tacaactctg gacacactta   2960
agaagattgg gtgtgttgag gcaggaggtg tcagccacaa accaaaaaat acacagatgg   3020
accatgaaga gggccaggcc atgttaaagc atttacacat gtgcctgagt attttctaat   3080
acaccttcca gtgatttgga gttgttgcat tttgactatg ttgtatatca tacgtatttc   3140
taaaatacca agctgtttct cccctaccta gacaaatcta ttcatggttc ccatcttgaa   3200
gatgtcagta ccatgcagtt ataatacaca aggtgcattt attggaaact ttgtataata   3260
tgtacaggtt tttaacctct gaactataca taggggggtta ttaaaaagat tttctataag   3320
tcttctaagg aacagtataa cctgtaagga atgtgaaggt agttcttttt tagtatttgg   3380
aaataagata catctttgtg cctttgatat tccattttt  aacccactgt gatgggtgat   3440
caacctagaa acattatctt gagtacctac taggtaccag gtactatatt atgttctgag   3500
gagtatagag aatttaatga tatgatggct ggccccaca  tagtttaaat tttagtaaat   3560
agcttttgaa gcaaatttta catatgatat agtagaaggc tgatccctgg tcgtatcata   3620
ccatcttcct atctatgtaa ctttgggaaa ctctcgcaac tcctctgagc ctctgcttcc   3680
ctatgtgtaa aacagggata gtaaatgcct tcctcaggac ccttaatagg agaattcatt   3740
gcagtaatgt aagtaaagca cctcacatta atgctttgct catggtaagt actcaaattt   3800
aactctgatt tcctccgtca ccattcttaa aagatattga gatagtttaa ttaactagat   3860
gaattcattt cccacaaccc ttttcaatca tcaattccta gatatttttc tcatccattg   3920
ttctgacaca atgcctgata cagcagcact gaaaaatgcc acacaatgaa aaatggcaat   3980
agtacaagga aaagggggtgc ttttctttgg gcagctcgct cgtccttcat gggacatctt   4040
actttccatt tttctaccta ttggttctgc tgttcactgg ctgtgtgatc ttgggcaaga   4100
tagtaatcta atatctcaga gcctaggttg agtatctata aaatgaaaat caaatctcta   4160
tctcagtagg tgttgcaagg attcagtgag ataatataca taatgcactt aacaaggcgt   4220
ttggaccata gcattgaaga aatgaaaact attaacagcc catttcccat tggcagacag   4280
aagtagtcag gtgagtaaat tttcaccatc tatgtgtgac tagaaggcgg caaatttctg   4340
aatcacatga gtctccaaaa gatagccaga agttaaatt  ctattaatcc tcctttaaaa   4400
ataaaatttc agtaaacatt cctttttctt tggctttgaa gaagccttag ggaatatttg   4460
tcatttggga gacttggcag aataacatga ggggattgta gggaatcaat aaaaactaaa   4520
caacaaaatc agagtcagag aacattttca aaaggaagaa taggaggttt gatcccagca   4580
tgataaacag agcgaatttg gcctggaagc acttttgatt atactatagc tcatttacca   4640
tcccagagtt tggcacagct gaaattttaa gttggaatga atattcactg ggcccaaaat   4700
gacagttcat atttgaataa aagtgacaaa agcctttta  taagtaatca cttttaagtg   4760
aaatgtttta actgatttca tgtgatttag aatatgattt aatcaaatta ttttaatgat   4820
agatggaatg gcagacaaaa acatgcctgt ccttctagac tgattttact ttaccctcta   4880
atattcatct cagtagcagt gttttaaata ttctctgggc tgcaaaactc tttgggaatc   4940
tgataaaagc tatgaacact ccctgtgtcc cgcttctacc cccaaaattc atgtgcacac   5000
acacaattct gcaagtatct tcaaagggtt cacagacctc ccaaaggcca tgcttgggcc   5060
ccagattaag aactcctttc tccatagcaa gttttaaaca tttcttacca gcttacattt   5120
ttagatctgg ctgatcagaa tcaaaggctc tgtgtaatac ataaagttac caagtgaact   5180
ggaattggaa catcaccctc cccagcctgc taggtgattt acttaacaca tagagtaata   5240
```

```
aaatcatcgc tgttgctttta gatcacggat tattttgcta ataatgctaa ggatgaagct   5300
gtgatcttat tatcacctga atcgggaggt gtggacactt taagcagttc cactttcctt   5360
ctaattcccc atccccatgc ctttgctaaa gctgtccctt ttgctctaac acccttcctg   5420
gaccttccta ccctagctgg gctaagtgtt tctcctcagc gttcccactt gtttcaaaca   5480
tagcacttac cacttgtact aaaattactt gccttcttaa ttagatatga acaaccctcc   5540
ccaactccag tatgggcctt ctgtcaataa taatacgata tgacagctac catttattaa   5600
gggcctcctg tatgaaagac cttaggctaa gcatgtttta aatgttattt aatcttcaca   5660
atctctgaaa aaatgaaga atcaacgtg cttttcttac tacctctacc cctaagccat      5720
tattactttt ttttttttt tgagacagag ttttgctctt gttgcccagg ctgcagtgca     5780
gtggtgcaat cttggctcac tgcaacctct gcctcttggg ttcaagcgat tgtcatgcct   5840
tagccttcca gtagctggg attacaggtg tgtgccacta cacctggcta agtagagatg    5900
gggtttcgcc atgttggcca ggctggtctt gaactcctga cctcaagtga tccacctgcc   5960
tccgcctccc aaagtgctgg gattacaggc atgaaccact gcacctggcc tgttacctct   6020
ttcctacaat tttgctcaag tctcccaact ggtcttctgg attcctctct tctgcggtcc   6080
tgttcaaagc ttaagtcaga cagtgtcact tcactcgtct gtttaaaacc tttcaatggc   6140
ccccatttca cgtagaccaa agtccaacgt atttacctgg cctactgatc ttgctcctag   6200
ctacctctga cctcatctcc tgtcaatttc cctctcattc tgttccacca tcctgactgc   6260
cttgacttcc tcaacagaac aagcctgctc ctgcctcagg gcctctgtcc ttattcttcc   6320
tcttcccagg ggtgtgctgg taaaatattt aacaaatagt tctccgggac gggggagaaa   6380
accctcattt gtagcatttg caggtatcta tgtgtaaata ctctcatcaa ggctatttt    6440
gagccactaa tttgccttca ctgaatacag agtttgggaa gagatgcatg ccatcagaac   6500
aaatgcaagc cagcaccagc acaccactgc ctcttcctgc aactcttgtc catacacaac   6560
ctcatggctg gctggctcac ttcctgcagg tctctcctca aatatcatct gatgagagac   6620
acattccctg actatgcttt ctaaaatagg ccatatgccc ccacattcat accccatctg   6680
ctgtcattct ttattctttt tataagtgca ttatttcat agcacttatc actacctgtt     6740
gtatattaat caatgatctt ttcccattag aatgtaagtt tcatgaacag gtacttgttt   6800
taatactgta tctccagtcc taatgtgtaa caggagccca ataaatgttt gctttcaaat   6860
ggagaggtta agtaacctgc tcaaatcaca cagctattaa gtggcagaac aggttttcaa   6920
gcaatgcatc tggtggtttt aactaagtcg agatagtttt tattcctaat gcctaaatca   6980
gggcctaggt agtgagctgt gggcacatat taagtattgg ttaaactaaa ataataagc   7040
aaaatggaca ttatctataa aagctttgt ggaaatggct agagctaggg taaggaaaca   7100
aatttggttc cccatacctg cccttcaaga aaataaagct gtcaaggaaa attgggctaa   7160
gagtaggata tgagggatga tggataaggc atgagacatg agaaaataag ggggattaaa   7220
```

<210> SEQ ID NO 26
<211> LENGTH: 923
<212> TYPE: PRT
<213> ORGANISM: Homo sapiens
<400> SEQUENCE: 26

Met Leu Arg Arg Gly Ser Gln Ala Leu Arg Arg Phe Ser Thr Gly Arg
1               5                   10                  15

Val Tyr Phe Lys Asn Lys Leu Lys Leu Ala Leu Ile Gly Gln Ser Leu

```
                    20                  25                  30
Phe Gly Gln Glu Val Tyr Ser His Leu Arg Lys Glu Gly His Arg Val
            35                  40                  45

Val Gly Val Phe Thr Val Pro Asp Lys Asp Gly Lys Ala Asp Pro Leu
    50                  55                  60

Ala Leu Ala Ala Glu Lys Asp Gly Thr Pro Val Phe Lys Leu Pro Lys
65                  70                  75                  80

Trp Arg Val Lys Gly Lys Thr Ile Lys Glu Val Ala Glu Ala Tyr Arg
                85                  90                  95

Ser Val Gly Ala Glu Leu Asn Val Leu Pro Phe Cys Thr Gln Phe Ile
            100                 105                 110

Pro Met Asp Ile Ile Asp Ser Pro Lys His Gly Ser Ile Ile Tyr His
        115                 120                 125

Pro Ser Ile Leu Pro Arg His Arg Gly Ala Ser Ala Ile Asn Trp Thr
    130                 135                 140

Leu Ile Met Gly Asp Lys Lys Ala Gly Phe Ser Val Phe Trp Ala Asp
145                 150                 155                 160

Asp Gly Leu Asp Thr Gly Pro Ile Leu Leu Gln Arg Ser Cys Asp Val
                165                 170                 175

Glu Pro Asn Asp Thr Val Asp Ala Leu Tyr Asn Arg Phe Leu Phe Pro
            180                 185                 190

Glu Gly Ile Lys Ala Met Val Glu Ala Val Gln Leu Ile Ala Asp Gly
        195                 200                 205

Lys Ala Pro Arg Ile Pro Gln Pro Glu Glu Gly Ala Thr Tyr Glu Gly
    210                 215                 220

Ile Gln Lys Lys Glu Asn Ala Glu Ile Ser Trp Asp Gln Ser Ala Glu
225                 230                 235                 240

Val Leu His Asn Trp Ile Arg Gly His Asp Lys Val Pro Gly Ala Trp
                245                 250                 255

Thr Glu Ile Asn Gly Gln Met Val Thr Phe Tyr Gly Ser Thr Leu Leu
            260                 265                 270

Asn Ser Ser Val Pro Pro Gly Glu Pro Leu Glu Ile Lys Gly Ala Lys
        275                 280                 285

Lys Pro Gly Leu Val Thr Lys Asn Gly Leu Val Leu Phe Gly Asn Asp
    290                 295                 300

Gly Lys Ala Leu Thr Val Arg Asn Leu Gln Phe Glu Asp Gly Lys Met
305                 310                 315                 320

Ile Pro Ala Ser Gln Tyr Phe Ser Thr Gly Thr Ser Val Val Glu
                325                 330                 335

Leu Thr Ala Glu Glu Val Lys Val Ala Glu Thr Ile Lys Val Ile Trp
            340                 345                 350

Ala Gly Ile Leu Ser Asn Val Pro Ile Ile Glu Asp Ser Thr Asp Phe
        355                 360                 365

Phe Lys Ser Gly Ala Ser Ser Met Asp Val Ala Arg Leu Val Glu Glu
    370                 375                 380

Ile Arg Gln Lys Cys Gly Gly Leu Gln Leu Gln Asn Glu Asp Val Tyr
385                 390                 395                 400

Met Ala Thr Lys Phe Glu Gly Phe Ile Gln Lys Val Val Arg Lys Leu
                405                 410                 415

Arg Gly Glu Asp Gln Glu Val Glu Leu Val Val Asp Tyr Ile Ser Lys
            420                 425                 430

Glu Val Asn Glu Ile Met Val Lys Met Pro Tyr Gln Cys Phe Ile Asn
        435                 440                 445
```

-continued

Gly Gln Phe Thr Asp Ala Asp Asp Gly Lys Thr Tyr Asp Thr Ile Asn
    450                 455                 460

Pro Thr Asp Gly Ser Thr Ile Cys Lys Val Ser Tyr Ala Ser Leu Ala
465                 470                 475                 480

Asp Val Asp Lys Ala Val Ala Ala Lys Asp Ala Phe Glu Asn Gly
                485                 490                 495

Glu Trp Gly Arg Met Asn Ala Arg Glu Arg Gly Arg Leu Met Tyr Arg
                500                 505                 510

Leu Ala Asp Leu Leu Glu Glu Asn Gln Glu Glu Leu Ala Thr Ile Glu
            515                 520                 525

Ala Leu Asp Ser Gly Ala Val Tyr Thr Leu Ala Leu Lys Thr His Ile
    530                 535                 540

Gly Met Ser Val Gln Thr Phe Arg Tyr Phe Ala Gly Trp Cys Asp Lys
545                 550                 555                 560

Ile Gln Gly Ser Thr Ile Pro Ile Asn Gln Ala Arg Pro Asn Arg Asn
                565                 570                 575

Leu Thr Phe Thr Lys Lys Glu Pro Leu Gly Val Cys Ala Ile Ile Ile
            580                 585                 590

Pro Trp Asn Tyr Pro Leu Met Met Leu Ala Trp Lys Ser Ala Ala Cys
    595                 600                 605

Leu Ala Ala Gly Asn Thr Leu Val Leu Lys Pro Ala Gln Val Thr Pro
    610                 615                 620

Leu Thr Ala Leu Lys Phe Ala Glu Leu Ser Val Lys Ala Gly Phe Pro
625                 630                 635                 640

Lys Gly Val Ile Asn Ile Ile Pro Gly Ser Gly Ile Ala Gly Gln
                645                 650                 655

Arg Leu Ser Glu His Pro Asp Ile Arg Lys Leu Gly Phe Thr Gly Ser
            660                 665                 670

Thr Pro Ile Gly Lys Gln Ile Met Lys Ser Cys Ala Val Ser Asn Leu
            675                 680                 685

Lys Lys Val Ser Leu Glu Leu Gly Gly Lys Ser Pro Leu Ile Ile Phe
    690                 695                 700

Asn Asp Cys Glu Leu Asp Lys Ala Val Arg Met Gly Met Gly Ala Val
705                 710                 715                 720

Phe Phe Asn Lys Gly Glu Asn Cys Ile Ala Ala Gly Arg Leu Phe Val
                725                 730                 735

Glu Glu Ser Ile His Asp Glu Phe Val Thr Arg Val Val Glu Glu Ile
            740                 745                 750

Lys Lys Met Lys Ile Gly Asp Pro Leu Asp Arg Ser Thr Asp His Gly
    755                 760                 765

Pro Gln Asn His Lys Ala His Leu Glu Lys Leu Leu Gln Tyr Cys Glu
    770                 775                 780

Thr Gly Val Lys Glu Gly Ala Thr Leu Val Tyr Gly Gly Arg Gln Val
785                 790                 795                 800

Gln Arg Pro Gly Phe Phe Met Glu Pro Thr Val Phe Thr Asp Val Glu
                805                 810                 815

Asp Tyr Met Tyr Leu Ala Lys Glu Glu Ser Phe Gly Pro Ile Met Val
            820                 825                 830

Ile Ser Lys Phe Gln Asn Gly Asp Ile Asp Gly Val Leu Gln Arg Ala
    835                 840                 845

Asn Ser Thr Glu Tyr Gly Leu Ala Ser Gly Val Phe Thr Arg Asp Ile
    850                 855                 860

```
Asn Lys Ala Met Tyr Val Ser Glu Lys Leu Glu Ala Gly Thr Val Phe
865                 870                 875                 880

Ile Asn Thr Tyr Asn Lys Thr Asp Val Ala Ala Pro Phe Gly Gly Val
                885                 890                 895

Lys Gln Ser Gly Phe Gly Lys Asp Leu Gly Glu Ala Leu Asn Glu
            900                 905                 910

Tyr Leu Lys Thr Lys Thr Val Thr Leu Glu Tyr
        915                 920

<210> SEQ ID NO 27
<211> LENGTH: 2772
<212> TYPE: DNA
<213> ORGANISM: Homo sapiens
<220> FEATURE:
<221> NAME/KEY: CDS
<222> LOCATION: (1)...(2772)

<400> SEQUENCE: 27 atg ctg cgg cgg ggc agc cag gcg ctc cgg cgc ttc tcc act ggc cgg      48
Met Leu Arg Arg Gly Ser Gln Ala Leu Arg Arg Phe Ser Thr Gly Arg
 1               5                  10                  15 gtt tat ttc aaa aac aag ctg aag ttg gca cta att ggc cag agc ctc      96
Val Tyr Phe Lys Asn Lys Leu Lys Leu Ala Leu Ile Gly Gln Ser Leu
                20                  25                  30 ttt gga caa gaa gtc tat agc cac ctc cgc aaa gag ggc cac cga gta     144
Phe Gly Gln Glu Val Tyr Ser His Leu Arg Lys Glu Gly His Arg Val
            35                  40                  45 gta ggg gtg ttc aca gtt cca gac aag gat gga aaa gct gac cct ctg     192
Val Gly Val Phe Thr Val Pro Asp Lys Asp Gly Lys Ala Asp Pro Leu
        50                  55                  60 gct ttg gct gca gag aaa gat ggg acc cct gtg ttc aag ctt cct aaa     240
Ala Leu Ala Ala Glu Lys Asp Gly Thr Pro Val Phe Lys Leu Pro Lys
 65                  70                  75                  80 tgg agg gtc aag ggc aag acc atc aaa gaa gtg gca gaa gcc tac aga     288
Trp Arg Val Lys Gly Lys Thr Ile Lys Glu Val Ala Glu Ala Tyr Arg
                85                  90                  95 tcc gtg ggt gca gag cta aat gtg ctc cct ttc tgc act cag ttc att     336
Ser Val Gly Ala Glu Leu Asn Val Leu Pro Phe Cys Thr Gln Phe Ile
               100                 105                 110 ccc atg gat ata att gat agt cca aag cac ggc tct atc att tat cac     384
Pro Met Asp Ile Ile Asp Ser Pro Lys His Gly Ser Ile Ile Tyr His
            115                 120                 125 cca tcc atc ctg ccc agg cac aga gga gcc tct gct atc aat tgg act     432
Pro Ser Ile Leu Pro Arg His Arg Gly Ala Ser Ala Ile Asn Trp Thr
        130                 135                 140 cta att atg gga gat aag aaa gct ggg ttt tct gtt ttc tgg gct gat     480
Leu Ile Met Gly Asp Lys Lys Ala Gly Phe Ser Val Phe Trp Ala Asp
145                 150                 155                 160 gat ggc ttg gat aca gga ccc atc ctt ctt cag aga tca tgt gat gtt     528
Asp Gly Leu Asp Thr Gly Pro Ile Leu Leu Gln Arg Ser Cys Asp Val
                165                 170                 175 gaa ccc aat gat aca gtg gat gca ctt tat aat cgg ttt ctt ttt cct     576
Glu Pro Asn Asp Thr Val Asp Ala Leu Tyr Asn Arg Phe Leu Phe Pro
            180                 185                 190 gaa gga atc aag gcc atg gta gaa gct gtc caa ctc ata gct gat gga     624
Glu Gly Ile Lys Ala Met Val Glu Ala Val Gln Leu Ile Ala Asp Gly
        195                 200                 205 aaa gct cct cgt ata ccc cag cca gaa gaa ggg gca aca tat gaa ggt     672
Lys Ala Pro Arg Ile Pro Gln Pro Glu Glu Gly Ala Thr Tyr Glu Gly
    210                 215                 220
```

-continued

| | | |
|---|---|---|
| atc cag aaa aag gaa aat gct gag att tct tgg gac cag tct gcc gaa<br>Ile Gln Lys Lys Glu Asn Ala Glu Ile Ser Trp Asp Gln Ser Ala Glu<br>225                     230                     235                   240 | 720 |
| gtt tta cat aac tgg att cga ggt cat gat aaa gtc cct gga gct tgg<br>Val Leu His Asn Trp Ile Arg Gly His Asp Lys Val Pro Gly Ala Trp<br>                     245                     250                   255 | 768 |
| aca gag ata aat gga cag atg gtc act ttc tat ggc tcg aca tta ctg<br>Thr Glu Ile Asn Gly Gln Met Val Thr Phe Tyr Gly Ser Thr Leu Leu<br>             260                     265                   270 | 816 |
| aat agc tct gtg cct cct gga gaa cca ctg gaa att aaa ggt gcc aag<br>Asn Ser Ser Val Pro Pro Gly Glu Pro Leu Glu Ile Lys Gly Ala Lys<br>          275                     280                     285 | 864 |
| aag cct ggt ctc gtt acc aaa aat gga ctt gtt ctt ttt ggt aac gat<br>Lys Pro Gly Leu Val Thr Lys Asn Gly Leu Val Leu Phe Gly Asn Asp<br>290                     295                     300 | 912 |
| gga aaa gca ctg acg gtg aga aat ctg cag ttt gaa gat gga aaa atg<br>Gly Lys Ala Leu Thr Val Arg Asn Leu Gln Phe Glu Asp Gly Lys Met<br>305                     310                     315                   320 | 960 |
| atc cct gcc tct cag tac ttt tca acg ggt gag acg tca gtg gta gaa<br>Ile Pro Ala Ser Gln Tyr Phe Ser Thr Gly Glu Thr Ser Val Val Glu<br>                     325                     330                   335 | 1008 |
| ctg aca gct gaa gag gtg aaa gtg gca gag acc atc aag gtc atc tgg<br>Leu Thr Ala Glu Glu Val Lys Val Ala Glu Thr Ile Lys Val Ile Trp<br>             340                     345                   350 | 1056 |
| gct gga att tta agc aat gtc ccc att att gaa gac tca aca gac ttc<br>Ala Gly Ile Leu Ser Asn Val Pro Ile Ile Glu Asp Ser Thr Asp Phe<br>          355                     360                     365 | 1104 |
| ttt aaa tct gga gca agc tca atg gat gtt gcc agg ctg gtt gaa gag<br>Phe Lys Ser Gly Ala Ser Ser Met Asp Val Ala Arg Leu Val Glu Glu<br>370                     375                     380 | 1152 |
| atc aga cag aaa tgt ggt ggg ctt cag ttg cag aat gaa gat gtc tat<br>Ile Arg Gln Lys Cys Gly Gly Leu Gln Leu Gln Asn Glu Asp Val Tyr<br>385                     390                     395                   400 | 1200 |
| atg gcc acc aag ttt gaa ggc ttt atc caa aag gtc gtg agg aaa ctg<br>Met Ala Thr Lys Phe Glu Gly Phe Ile Gln Lys Val Val Arg Lys Leu<br>                     405                     410                   415 | 1248 |
| aga gga gaa gat caa gag gtg gag ctg gtt gta gat tat att tca aag<br>Arg Gly Glu Asp Gln Glu Val Glu Leu Val Val Asp Tyr Ile Ser Lys<br>             420                     425                   430 | 1296 |
| gag gtc aat gaa atc atg gta aaa atg cca tac cag tgt ttc ata aat<br>Glu Val Asn Glu Ile Met Val Lys Met Pro Tyr Gln Cys Phe Ile Asn<br>          435                     440                     445 | 1344 |
| gga cag ttc aca gat gca gac gat gga aag act tac gac act atc aac<br>Gly Gln Phe Thr Asp Ala Asp Asp Gly Lys Thr Tyr Asp Thr Ile Asn<br>450                     455                     460 | 1392 |
| cca aca gat gga tct aca ata tgc aaa gta tcc tac gct tct ttg gcg<br>Pro Thr Asp Gly Ser Thr Ile Cys Lys Val Ser Tyr Ala Ser Leu Ala<br>465                     470                     475                   480 | 1440 |
| gat gtt gat aaa gca gta gca gca gca aaa gat gct ttt gaa aac ggt<br>Asp Val Asp Lys Ala Val Ala Ala Ala Lys Asp Ala Phe Glu Asn Gly<br>                     485                     490                   495 | 1488 |
| gaa tgg gga aga atg aat gca aga gaa aga gga aga ttg atg tat aga<br>Glu Trp Gly Arg Met Asn Ala Arg Glu Arg Gly Arg Leu Met Tyr Arg<br>             500                     505                   510 | 1536 |
| ctt gca gac cta ctg gaa gag aac caa gaa gag ctg gca act att gaa<br>Leu Ala Asp Leu Leu Glu Glu Asn Gln Glu Glu Leu Ala Thr Ile Glu<br>          515                     520                     525 | 1584 |
| gcc ctt gat tca ggg gct gtc tat acc ttg gcc ctg aag aca cac att<br>Ala Leu Asp Ser Gly Ala Val Tyr Thr Leu Ala Leu Lys Thr His Ile<br>530                     535                     540 | 1632 |

-continued

| | | |
|---|---|---|
| gga atg tct gtg caa aca ttc aga tat ttt gct ggc tgg tgc gac aaa<br>Gly Met Ser Val Gln Thr Phe Arg Tyr Phe Ala Gly Trp Cys Asp Lys<br>545                    550                    555                    560 | 1680 |
| att cag ggt tct act att cca atc aac cag gcc cgt cca aat cgc aat<br>Ile Gln Gly Ser Thr Ile Pro Ile Asn Gln Ala Arg Pro Asn Arg Asn<br>                    565                    570                    575 | 1728 |
| ctg acc ttc acc aag aaa gag cca ctc ggt gtc tgt gcc att att att<br>Leu Thr Phe Thr Lys Lys Glu Pro Leu Gly Val Cys Ala Ile Ile Ile<br>                580                    585                    590 | 1776 |
| ccc tgg aac tac ccg ctg atg atg ctg gca tgg aag agt gct gcg tgt<br>Pro Trp Asn Tyr Pro Leu Met Met Leu Ala Trp Lys Ser Ala Ala Cys<br>          595                    600                    605 | 1824 |
| ttg gca gca ggc aat acc tta gtg ctc aag cca gca cag gtc acg ccc<br>Leu Ala Ala Gly Asn Thr Leu Val Leu Lys Pro Ala Gln Val Thr Pro<br>610                    615                    620 | 1872 |
| ttg act gct ttg aag ttt gca gaa ctg tct gtg aaa gca ggt ttt cca<br>Leu Thr Ala Leu Lys Phe Ala Glu Leu Ser Val Lys Ala Gly Phe Pro<br>625                    630                    635                    640 | 1920 |
| aag ggg gtc atc aac atc att cca ggc tca ggt ggc ata gca gga caa<br>Lys Gly Val Ile Asn Ile Ile Pro Gly Ser Gly Gly Ile Ala Gly Gln<br>                    645                    650                    655 | 1968 |
| cgt ctg tct gaa cat cct gac atc cgc aaa ctt ggt ttc act gga tcc<br>Arg Leu Ser Glu His Pro Asp Ile Arg Lys Leu Gly Phe Thr Gly Ser<br>          660                    665                    670 | 2016 |
| act cct att ggc aaa cag atc atg aag agc tgt gct gtt agc aac ttg<br>Thr Pro Ile Gly Lys Gln Ile Met Lys Ser Cys Ala Val Ser Asn Leu<br>675                    680                    685 | 2064 |
| aag aaa gtt tcc ctt gag ctt ggt ggc aag tct cca ctt ata ata ttt<br>Lys Lys Val Ser Leu Glu Leu Gly Gly Lys Ser Pro Leu Ile Ile Phe<br>          690                    695                    700 | 2112 |
| aat gac tgt gaa ctt gac aag gct gtg cga atg ggc atg gga gca gta<br>Asn Asp Cys Glu Leu Asp Lys Ala Val Arg Met Gly Met Gly Ala Val<br>705                    710                    715                    720 | 2160 |
| ttt ttc aac aaa gga gag aac tgt att gct gct ggg cgg ttg ttc gtg<br>Phe Phe Asn Lys Gly Glu Asn Cys Ile Ala Ala Gly Arg Leu Phe Val<br>                    725                    730                    735 | 2208 |
| gaa gaa tcc atc cac gac gaa ttt gtg aca aga gtg gta gaa gaa att<br>Glu Glu Ser Ile His Asp Glu Phe Val Thr Arg Val Val Glu Glu Ile<br>                    740                    745                    750 | 2256 |
| aaa aag atg aaa att ggt gat cca ctt gac aga tcc act gat cat ggg<br>Lys Lys Met Lys Ile Gly Asp Pro Leu Asp Arg Ser Thr Asp His Gly<br>          755                    760                    765 | 2304 |
| ccc caa aat cat aag gct cat ctg gaa aag ctg ctg caa tac tgt gaa<br>Pro Gln Asn His Lys Ala His Leu Glu Lys Leu Leu Gln Tyr Cys Glu<br>770                    775                    780 | 2352 |
| act gga gtg aaa gaa ggg gcc act ttg gtg tac ggg gga aga caa gtc<br>Thr Gly Val Lys Glu Gly Ala Thr Leu Val Tyr Gly Gly Arg Gln Val<br>785                    790                    795                    800 | 2400 |
| caa agg cca ggc ttt ttc atg gag ccg acc gtg ttc aca gat gtg gaa<br>Gln Arg Pro Gly Phe Phe Met Glu Pro Thr Val Phe Thr Asp Val Glu<br>                    805                    810                    815 | 2448 |
| gac tac atg tac ctc gcc aaa gag gaa tcc ttt ggg cct att atg gtc<br>Asp Tyr Met Tyr Leu Ala Lys Glu Glu Ser Phe Gly Pro Ile Met Val<br>          820                    825                    830 | 2496 |
| att tct aaa ttc caa aat ggg gac atc gat gga gtg ttg cag cga gca<br>Ile Ser Lys Phe Gln Asn Gly Asp Ile Asp Gly Val Leu Gln Arg Ala<br>          835                    840                    845 | 2544 |
| aat agt aca gag tat ggt ttg gcc tca ggg gtt ttt aca aga gac ata<br>Asn Ser Thr Glu Tyr Gly Leu Ala Ser Gly Val Phe Thr Arg Asp Ile | 2592 |

```
                   850                 855                 860
aac aaa gct atg tat gtg agt gaa aaa ctg gaa gca gga act gtt ttt       2640
Asn Lys Ala Met Tyr Val Ser Glu Lys Leu Glu Ala Gly Thr Val Phe
865                 870                 875                 880 att aac aca tac aac aag aca gat gtg gcg gcc cca ttt ggc gga gtt       2688
Ile Asn Thr Tyr Asn Lys Thr Asp Val Ala Ala Pro Phe Gly Gly Val
                885                 890                 895 aaa caa tct ggc ttt gga aaa gac tta ggt gag gaa gct cta aat gaa       2736
Lys Gln Ser Gly Phe Gly Lys Asp Leu Gly Glu Glu Ala Leu Asn Glu
            900                 905                 910 tat ctc aaa acc aag acg gtg aca ctg gaa tat tag                       2772
Tyr Leu Lys Thr Lys Thr Val Thr Leu Glu Tyr  *
            915                 920
```

<210> SEQ ID NO 28
<211> LENGTH: 492
<212> TYPE: PRT
<213> ORGANISM: Artificial Sequence
<220> FEATURE:
<223> OTHER INFORMATION: Aldehyde dehydrogenase Pfam consensus sequence

<400> SEQUENCE: 28

```
Glu Trp Val Asp Ser Ala Ser Gly Lys Thr Phe Glu Val Val Asn Pro
 1               5                  10                  15

Ala Asn Lys Gly Glu Val Ile Gly Arg Val Pro Glu Ala Thr Ala Glu
            20                  25                  30

Asp Val Asp Ala Ala Val Lys Ala Ala Lys Glu Ala Phe Lys Ser Gly
        35                  40                  45

Pro Trp Trp Ala Lys Val Pro Ala Ser Glu Arg Ala Arg Ile Leu Arg
    50                  55                  60

Lys Leu Ala Asp Leu Ile Glu Glu Arg Glu Asp Leu Ala Ala Leu
65                  70                  75                  80

Glu Thr Leu Asp Leu Gly Lys Pro Leu Ala Glu Ala Lys Gly Asp Thr
                85                  90                  95

Glu Val Gly Arg Ala Ile Asp Glu Ile Arg Tyr Tyr Ala Gly Trp Ala
            100                 105                 110

Arg Lys Leu Met Gly Glu Arg Val Ile Pro Ser Leu Ala Thr Asp
        115                 120                 125

Gly Asp Glu Glu Leu Asn Tyr Thr Arg Arg Glu Pro Leu Gly Val Val
    130                 135                 140

Gly Val Ile Ser Pro Trp Asn Phe Pro Leu Leu Leu Ala Leu Trp Lys
145                 150                 155                 160

Leu Ala Pro Ala Leu Ala Ala Gly Asn Thr Val Val Leu Lys Pro Ser
                165                 170                 175

Glu Gln Thr Pro Leu Thr Ala Leu Leu Ala Glu Leu Ile Glu Glu
            180                 185                 190

Ala Gly Ala Asn Asn Leu Pro Lys Gly Val Val Asn Val Val Pro Gly
        195                 200                 205

Phe Gly Ala Glu Val Gly Gln Ala Leu Leu Ser His Pro Asp Ile Asp
    210                 215                 220

Lys Ile Ser Phe Thr Gly Ser Thr Glu Val Gly Lys Leu Ile Met Glu
225                 230                 235                 240

Ala Ala Ala Ala Lys Asn Leu Lys Lys Val Thr Leu Glu Leu Gly Gly
                245                 250                 255

Lys Ser Pro Val Ile Val Phe Asp Asp Ala Asp Leu Asp Lys Ala Val
            260                 265                 270
```

```
Glu Arg Ile Val Phe Gly Ala Phe Gly Asn Ala Gly Gln Val Cys Ile
        275                 280                 285

Ala Pro Ser Arg Leu Leu Val His Glu Ser Ile Tyr Asp Glu Phe Val
        290                 295                 300

Glu Lys Leu Lys Glu Arg Val Lys Leu Lys Leu Ile Gly Asp Pro
305                 310                 315                 320

Leu Asp Ser Asp Thr Asn Ile Tyr Gly Pro Leu Ile Ser Glu Gln Gln
                    325                 330                 335

Phe Asp Arg Val Leu Ser Tyr Ile Glu Asp Gly Lys Glu Glu Gly Ala
                340                 345                 350

Lys Val Leu Cys Gly Gly Glu Arg Asp Glu Ser Lys Glu Tyr Leu Gly
                355                 360                 365

Gly Gly Tyr Tyr Val Gln Pro Thr Ile Phe Thr Asp Val Thr Pro Asp
        370                 375                 380

Met Lys Ile Met Lys Glu Glu Ile Phe Gly Pro Val Leu Pro Ile Ile
385                 390                 395                 400

Lys Phe Lys Asp Leu Asp Glu Ala Ile Glu Leu Ala Asn Asp Thr Glu
                    405                 410                 415

Tyr Gly Leu Ala Ala Tyr Val Phe Thr Lys Asp Ile Leu Ala Arg Ala
                420                 425                 430

Phe Arg Val Ala Lys Ala Leu Glu Ala Gly Ile Val Trp Val Asn Asp
                435                 440                 445

Val Cys Val His Ala Ala Glu Pro Gln Leu Pro Phe Gly Gly Val Lys
        450                 455                 460

Gln Ser Ser Gly Ile Gly Arg Glu His Gly Gly Lys Tyr Gly Leu Glu
465                 470                 475                 480

Glu Tyr Thr Glu Ile Lys Thr Val Thr Ile Arg Leu
                    485                 490

<210> SEQ ID NO 29
<211> LENGTH: 3513
<212> TYPE: DNA
<213> ORGANISM: Homo sapiens
<220> FEATURE:
<221> NAME/KEY: CDS
<222> LOCATION: (82)...(3150)

<400> SEQUENCE: 29
cgcacccagt caccagcgtt cgggagcctg tcgcagcggg accgacggaa tccggagcag      60
gcgacagggc gcagaagcgg g atg tac ttc tgt tgg ggc gcc gac tcc agg     111
                        Met Tyr Phe Cys Trp Gly Ala Asp Ser Arg
                          1               5                  10 gag ctg cag cgc cgg agg acg gcg ggc agc ccc ggg gct gag cta ctg     159
Glu Leu Gln Arg Arg Arg Thr Ala Gly Ser Pro Gly Ala Glu Leu Leu
             15                  20                  25 cag gcg gcc agc ggg gag cgc cac tct ctg ctg ctg ctg acc aac cac     207
Gln Ala Ala Ser Gly Glu Arg His Ser Leu Leu Leu Leu Thr Asn His
         30                  35                  40 agg gtc ctc tcg tgc gga gac aac agc agg ggt cag ctg ggc cgc agg     255
Arg Val Leu Ser Cys Gly Asp Asn Ser Arg Gly Gln Leu Gly Arg Arg
     45                  50                  55 ggc gcg cag cgc ggg gag ctg cca gaa cca att cag gca ttg gaa acc     303
Gly Ala Gln Arg Gly Glu Leu Pro Glu Pro Ile Gln Ala Leu Glu Thr
 60                  65                  70 cta att gtt gat ctc gtg agc tgc ggg aag gag cac tcc ctg gct gtg     351
Leu Ile Val Asp Leu Val Ser Cys Gly Lys Glu His Ser Leu Ala Val
 75                  80                  85                  90
```

```
tgc cac aaa gga agg gtc ttc gca tgg gga gct ggt tct gaa ggg cag     399
Cys His Lys Gly Arg Val Phe Ala Trp Gly Ala Gly Ser Glu Gly Gln
             95                 100                 105 ctg ggg att gga gaa ttc aag gaa ata agt ttc aca cct aag aaa ata     447
Leu Gly Ile Gly Glu Phe Lys Glu Ile Ser Phe Thr Pro Lys Lys Ile
        110                 115                 120 atg act ctg aat gat ata aaa ata ata caa gtt tcc tgt gga cac tac     495
Met Thr Leu Asn Asp Ile Lys Ile Ile Gln Val Ser Cys Gly His Tyr
            125                 130                 135 cac tcc ctg gca tta tca aaa gat agc caa gtg ttt tcg tgg gga aag     543
His Ser Leu Ala Leu Ser Lys Asp Ser Gln Val Phe Ser Trp Gly Lys
        140                 145                 150 aac agc cat ggg cag ctg ggc ttg ggg aag gag ttc ccc tcc caa gcc     591
Asn Ser His Gly Gln Leu Gly Leu Gly Lys Glu Phe Pro Ser Gln Ala
155                 160                 165                 170 agc ccg cag agg gtg agg tcc ctg gag ggg atc cca ctg gct cag gtg     639
Ser Pro Gln Arg Val Arg Ser Leu Glu Gly Ile Pro Leu Ala Gln Val
                175                 180                 185 gct gcc gga ggg gct cac agc ttt gcc ctg tct ctc tgt ggg act tcg     687
Ala Ala Gly Gly Ala His Ser Phe Ala Leu Ser Leu Cys Gly Thr Ser
            190                 195                 200 ttt ggc tgg gga agt aac agt gcc ggg cag ctg gcc ctc agt ggg cgt     735
Phe Gly Trp Gly Ser Asn Ser Ala Gly Gln Leu Ala Leu Ser Gly Arg
        205                 210                 215 aat gtc cca gtg caa agc aac aag cct ctc tca gtc ggt gca ctg aag     783
Asn Val Pro Val Gln Ser Asn Lys Pro Leu Ser Val Gly Ala Leu Lys
            220                 225                 230 aat cta ggt gtg gtt tat atc agc tgt ggt gat gca cac act gcg gtg     831
Asn Leu Gly Val Val Tyr Ile Ser Cys Gly Asp Ala His Thr Ala Val
235                 240                 245                 250 ctt acc cag gac ggg aaa gtg ttc aca ttt gga gac aat cgc tct gga     879
Leu Thr Gln Asp Gly Lys Val Phe Thr Phe Gly Asp Asn Arg Ser Gly
                255                 260                 265 cag ctg gga tac agc ccc act cct gag aag aga ggt cca caa ctt gtg     927
Gln Leu Gly Tyr Ser Pro Thr Pro Glu Lys Arg Gly Pro Gln Leu Val
            270                 275                 280 gaa aga att gat ggc cta gtt tcg cag ata gat tgt gga agt tat cac     975
Glu Arg Ile Asp Gly Leu Val Ser Gln Ile Asp Cys Gly Ser Tyr His
        285                 290                 295 acc ctg gca tat gtg cac acc act ggt cag gta tct ttt ggt cat        1023
Thr Leu Ala Tyr Val His Thr Thr Gly Gln Val Ser Phe Gly His
            300                 305                 310 gga cca agt gac aca agc aag cca act cat ccg gag gcc ctg aca gag    1071
Gly Pro Ser Asp Thr Ser Lys Pro Thr His Pro Glu Ala Leu Thr Glu
315                 320                 325                 330 aac ttt gac att agc tgc ctg att tct gct gaa gac ttc gtg gat gtt    1119
Asn Phe Asp Ile Ser Cys Leu Ile Ser Ala Glu Asp Phe Val Asp Val
                335                 340                 345 caa gtc aaa cac att ttt gct gga aca tat gcc aac ttt gtg aca act    1167
Gln Val Lys His Ile Phe Ala Gly Thr Tyr Ala Asn Phe Val Thr Thr
            350                 355                 360 cat cag gat act agt tcc aca cgt gct ccc ggg aaa acc ctg cca gaa    1215
His Gln Asp Thr Ser Ser Thr Arg Ala Pro Gly Lys Thr Leu Pro Glu
        365                 370                 375 ata agc cga att agc cag tcc atg gca gaa aaa tgg ata gca gtg aaa    1263
Ile Ser Arg Ile Ser Gln Ser Met Ala Glu Lys Trp Ile Ala Val Lys
            380                 385                 390 aga aga agt act gaa cat gaa atg gct aaa agt gaa att aga atg ata    1311
Arg Arg Ser Thr Glu His Glu Met Ala Lys Ser Glu Ile Arg Met Ile
395                 400                 405                 410
```

| | |
|---|---|
| ttt tca tct cct gct tgt ctg act gca agt ttt tta aag aaa aga gga<br>Phe Ser Ser Pro Ala Cys Leu Thr Ala Ser Phe Leu Lys Lys Arg Gly<br>               415                      420                   425 | 1359 |
| act gga gaa acg act tcc att gat gtg gac tta gaa atg gca aga gat<br>Thr Gly Glu Thr Thr Ser Ile Asp Val Asp Leu Glu Met Ala Arg Asp<br>          430                          435                      440 | 1407 |
| acc ttc aag aag tta aca aaa aag gaa tgg att tct tcc atg ata act<br>Thr Phe Lys Lys Leu Thr Lys Lys Glu Trp Ile Ser Ser Met Ile Thr<br>               445                      450                   455 | 1455 |
| acg tgt ctc gag gat gat ctg ctc aga gct ctt cca tgc cat tct cca<br>Thr Cys Leu Glu Asp Asp Leu Leu Arg Ala Leu Pro Cys His Ser Pro<br>460                      465                      470 | 1503 |
| cac caa gaa gct tta tca gtt ttc ctc ctg ctc cca gaa tgt cct gtg<br>His Gln Glu Ala Leu Ser Val Phe Leu Leu Leu Pro Glu Cys Pro Val<br>475                      480                      485                   490 | 1551 |
| atg cat gat tct aag aac tgg aag aac ctg gtg gtt cca ttt gca aag<br>Met His Asp Ser Lys Asn Trp Lys Asn Leu Val Val Pro Phe Ala Lys<br>               495                      500                   505 | 1599 |
| gct gtg tgt gaa atg agt aaa caa tct ttg caa gtc cta aag aag tgt<br>Ala Val Cys Glu Met Ser Lys Gln Ser Leu Gln Val Leu Lys Lys Cys<br>          510                          515                      520 | 1647 |
| tgg gca ttt ttg caa gaa tct tct ctg aat ccg ctg atc cag atg ctt<br>Trp Ala Phe Leu Gln Glu Ser Ser Leu Asn Pro Leu Ile Gln Met Leu<br>               525                      530                   535 | 1695 |
| aaa gca gcc atc atc tct cag ctg ctt cat cag act aaa acc gaa cag<br>Lys Ala Ala Ile Ile Ser Gln Leu Leu His Gln Thr Lys Thr Glu Gln<br>          540                          545                      550 | 1743 |
| gat cac tgt aat gtt aaa gct ctt tta gga atg atg aaa gaa ctg cat<br>Asp His Cys Asn Val Lys Ala Leu Leu Gly Met Met Lys Glu Leu His<br>555                      560                      565                   570 | 1791 |
| aag gta aac aaa gct aac tgt cga cta cca gaa aat act ttc aac ata<br>Lys Val Asn Lys Ala Asn Cys Arg Leu Pro Glu Asn Thr Phe Asn Ile<br>               575                      580                   585 | 1839 |
| aat gaa ctc tcc aac tta tta aac ttt tat ata gat aga gga aga cag<br>Asn Glu Leu Ser Asn Leu Leu Asn Phe Tyr Ile Asp Arg Gly Arg Gln<br>                    590                      595                   600 | 1887 |
| ctc ttt cgg gat aac cac ctg ata cct gca gaa acc ccc agt cct gtt<br>Leu Phe Arg Asp Asn His Leu Ile Pro Ala Glu Thr Pro Ser Pro Val<br>          605                          610                      615 | 1935 |
| att ttc agt gat ttt cca ttt atc ttt aat tcg cta tcc aaa att aaa<br>Ile Phe Ser Asp Phe Pro Phe Ile Phe Asn Ser Leu Ser Lys Ile Lys<br>          620                          625                      630 | 1983 |
| tta ttg caa gct gat tca cat ata aag atg cag atg tca gaa aag aaa<br>Leu Leu Gln Ala Asp Ser His Ile Lys Met Gln Met Ser Glu Lys Lys<br>635                      640                      645                   650 | 2031 |
| gca tac atg ctt atg cat gaa aca att ctg caa aaa aag gat gaa ttt<br>Ala Tyr Met Leu Met His Glu Thr Ile Leu Gln Lys Lys Asp Glu Phe<br>               655                      660                   665 | 2079 |
| cct cca tca ccc aga ttt ata ctt aga gtc aga cga agt cgc ctg gtt<br>Pro Pro Ser Pro Arg Phe Ile Leu Arg Val Arg Arg Ser Arg Leu Val<br>          670                          675                      680 | 2127 |
| aaa gat gct ctg cgt caa tta agt caa gct gaa gct act gac ttc tgc<br>Lys Asp Ala Leu Arg Gln Leu Ser Gln Ala Glu Ala Thr Asp Phe Cys<br>               685                      690                   695 | 2175 |
| aaa gta tta gtg gtt gaa ttt att aat gaa att tgt cct gag tct gga<br>Lys Val Leu Val Val Glu Phe Ile Asn Glu Ile Cys Pro Glu Ser Gly<br>          700                          705                      710 | 2223 |
| ggg gtt agt tca gag ttc ttc cac tgt atg ttt gaa gag atg acc aag<br>Gly Val Ser Ser Glu Phe Phe His Cys Met Phe Glu Glu Met Thr Lys | 2271 |

```
                715                 720                 725                 730
cca gaa tat gga atg ttc atg tat cct gaa atg ggt tcc tgc atg tgg       2319
Pro Glu Tyr Gly Met Phe Met Tyr Pro Glu Met Gly Ser Cys Met Trp
                735                 740                 745 ttt cct gcc aag cct aaa cct gag aag aaa aga tat ttc ctc ttt gga       2367
Phe Pro Ala Lys Pro Lys Pro Glu Lys Lys Arg Tyr Phe Leu Phe Gly
            750                 755                 760 atg ctg tgt gga ctc tcc tta ttc aat tta aat gtt gct aac ctt cct       2415
Met Leu Cys Gly Leu Ser Leu Phe Asn Leu Asn Val Ala Asn Leu Pro
        765                 770                 775 ttc cca ctg gct ctg tat aaa aaa ctt ctg gac caa aag cca tca ttg       2463
Phe Pro Leu Ala Leu Tyr Lys Lys Leu Leu Asp Gln Lys Pro Ser Leu
    780                 785                 790 gaa gat tta aaa gaa ctc agt cct cgg ttg ggg aag agt ttg caa gaa       2511
Glu Asp Leu Lys Glu Leu Ser Pro Arg Leu Gly Lys Ser Leu Gln Glu
795                 800                 805                 810 gtt cta gat gat gct gct gat gac att gga gat gcg ctc tgc ata cgc       2559
Val Leu Asp Asp Ala Ala Asp Asp Ile Gly Asp Ala Leu Cys Ile Arg
                815                 820                 825 ttt tct ata cac tgg gac caa aat gat gtt gac tta att cca aat ggg       2607
Phe Ser Ile His Trp Asp Gln Asn Asp Val Asp Leu Ile Pro Asn Gly
            830                 835                 840 atc tcc ata cct gtg gac caa acc aac aag aga gac tat gtt tct aag       2655
Ile Ser Ile Pro Val Asp Gln Thr Asn Lys Arg Asp Tyr Val Ser Lys
        845                 850                 855 tat att gat tac att ttc aac gtc tct gta aaa gca gtt tat gag gaa       2703
Tyr Ile Asp Tyr Ile Phe Asn Val Ser Val Lys Ala Val Tyr Glu Glu
    860                 865                 870 ttt cag aga gga ttt tat aga gtc tgt gag aag gag ata ctt aga cat       2751
Phe Gln Arg Gly Phe Tyr Arg Val Cys Glu Lys Glu Ile Leu Arg His
875                 880                 885                 890 ttc tac cct gaa gaa cta atg aca gca atc att gga aat act gat tat       2799
Phe Tyr Pro Glu Glu Leu Met Thr Ala Ile Ile Gly Asn Thr Asp Tyr
                895                 900                 905 gac tgg aaa cag ttt gaa cag aat tca aag tat gag caa gga tac caa       2847
Asp Trp Lys Gln Phe Glu Gln Asn Ser Lys Tyr Glu Gln Gly Tyr Gln
            910                 915                 920 aaa tca cat cct act ata cag ttg ttt tgg aag gct ttc cac aaa cta       2895
Lys Ser His Pro Thr Ile Gln Leu Phe Trp Lys Ala Phe His Lys Leu
        925                 930                 935 acc ttg gat gaa aag aaa aaa ttc ctc ttt ttc ctt aca gga cgt gat       2943
Thr Leu Asp Glu Lys Lys Lys Phe Leu Phe Phe Leu Thr Gly Arg Asp
    940                 945                 950 agg ctg cat gca aga ggc ata cag aaa atg gaa ata gta ttt cgc tgt       2991
Arg Leu His Ala Arg Gly Ile Gln Lys Met Glu Ile Val Phe Arg Cys
955                 960                 965                 970 cct gaa act ttc agt gaa aga gat cac cca aca tca ata act tgt cat       3039
Pro Glu Thr Phe Ser Glu Arg Asp His Pro Thr Ser Ile Thr Cys His
                975                 980                 985 aat att ctc tcc ctc cct aag tat tct aca atg gaa aga atg gag gaa       3087
Asn Ile Leu Ser Leu Pro Lys Tyr Ser Thr Met Glu Arg Met Glu Glu
            990                 995                 1000 gca ctt caa gta gcc atc aac aac aac aga gga ttt gtc tca ccc atg       3135
Ala Leu Gln Val Ala Ile Asn Asn Asn Arg Gly Phe Val Ser Pro Met
        1005                1010                1015 ctc aca cag tca taa tcacctctga gagactcagg gtgggctttc tcacacttgg       3190
Leu Thr Gln Ser  *
    1020 atccttctgt tcttccttac acctaaataa tacaagagat taatgaatag tggttagaag    3250
```

-continued

```
tagttgaggg agagattggg ggaatgggga gatgatgatg atggtcaaag ggtgcaaaat    3310
ctcacacaag actgaggcag gagaataggg tacagagata gggatctaag gatgacttgg    3370
acacactccc tggcactgaa gagtctgaac actggcctgt gattggtcca ttccaggacc    3430
ttcatttgca taaggtatca aaccacatca gcctctgatt ggccatgggc cagacctgca    3490
ctctggccaa tgattggttc att                                            3513
```

```
<210> SEQ ID NO 30
<211> LENGTH: 1022
<212> TYPE: PRT
<213> ORGANISM: Homo sapiens

<400> SEQUENCE: 30

Met Tyr Phe Cys Trp Gly Ala Asp Ser Arg Glu Leu Gln Arg Arg
 1               5                  10                  15

Thr Ala Gly Ser Pro Gly Ala Glu Leu Leu Gln Ala Ala Ser Gly Glu
                20                  25                  30

Arg His Ser Leu Leu Leu Thr Asn His Arg Val Leu Ser Cys Gly
                35                  40                  45

Asp Asn Ser Arg Gly Gln Leu Gly Arg Arg Gly Ala Gln Arg Gly Glu
            50                  55                  60

Leu Pro Glu Pro Ile Gln Ala Leu Glu Thr Leu Ile Val Asp Leu Val
65                  70                  75                  80

Ser Cys Gly Lys Glu His Ser Leu Ala Val Cys His Lys Gly Arg Val
                85                  90                  95

Phe Ala Trp Gly Ala Gly Ser Glu Gly Gln Leu Gly Ile Gly Glu Phe
            100                 105                 110

Lys Glu Ile Ser Phe Thr Pro Lys Lys Ile Met Thr Leu Asn Asp Ile
            115                 120                 125

Lys Ile Ile Gln Val Ser Cys Gly His Tyr His Ser Leu Ala Leu Ser
145             130                 135                 140

Lys Asp Ser Gln Val Phe Ser Trp Gly Lys Asn Ser His Gly Gln Leu
145                 150                 155                 160

Gly Leu Gly Lys Glu Phe Pro Ser Gln Ala Ser Pro Gln Arg Val Arg
                165                 170                 175

Ser Leu Glu Gly Ile Pro Leu Ala Gln Val Ala Ala Gly Gly Ala His
            180                 185                 190

Ser Phe Ala Leu Ser Leu Cys Gly Thr Ser Phe Gly Trp Gly Ser Asn
        195                 200                 205

Ser Ala Gly Gln Leu Ala Leu Ser Gly Arg Asn Val Pro Val Gln Ser
    210                 215                 220

Asn Lys Pro Leu Ser Val Gly Ala Leu Lys Asn Leu Gly Val Val Tyr
225                 230                 235                 240

Ile Ser Cys Gly Asp Ala His Thr Ala Val Leu Thr Gln Asp Gly Lys
                245                 250                 255

Val Phe Thr Phe Gly Asp Asn Arg Ser Gly Gln Leu Gly Tyr Ser Pro
            260                 265                 270

Thr Pro Glu Lys Arg Gly Pro Gln Leu Val Glu Arg Ile Asp Gly Leu
        275                 280                 285

Val Ser Gln Ile Asp Cys Gly Ser Tyr His Thr Leu Ala Tyr Val His
    290                 295                 300

Thr Thr Gly Gln Val Val Ser Phe Gly His Gly Pro Ser Asp Thr Ser
305                 310                 315                 320
```

-continued

```
Lys Pro Thr His Pro Glu Ala Leu Thr Glu Asn Phe Asp Ile Ser Cys
            325                 330                 335
Leu Ile Ser Ala Glu Asp Phe Val Asp Val Gln Val Lys His Ile Phe
            340                 345                 350
Ala Gly Thr Tyr Ala Asn Phe Val Thr Thr His Gln Asp Thr Ser Ser
            355                 360                 365
Thr Arg Ala Pro Gly Lys Thr Leu Pro Glu Ile Ser Arg Ile Ser Gln
        370                 375                 380
Ser Met Ala Glu Lys Trp Ile Ala Val Lys Arg Arg Ser Thr Glu His
385                 390                 395                 400
Glu Met Ala Lys Ser Glu Ile Arg Met Ile Phe Ser Ser Pro Ala Cys
                405                 410                 415
Leu Thr Ala Ser Phe Leu Lys Lys Arg Gly Thr Gly Glu Thr Thr Ser
            420                 425                 430
Ile Asp Val Asp Leu Glu Met Ala Arg Asp Thr Phe Lys Lys Leu Thr
        435                 440                 445
Lys Lys Glu Trp Ile Ser Ser Met Ile Thr Thr Cys Leu Glu Asp Asp
450                 455                 460
Leu Leu Arg Ala Leu Pro Cys His Ser Pro His Gln Glu Ala Leu Ser
465                 470                 475                 480
Val Phe Leu Leu Leu Pro Glu Cys Pro Val Met His Asp Ser Lys Asn
                485                 490                 495
Trp Lys Asn Leu Val Val Pro Phe Ala Lys Ala Val Cys Glu Met Ser
            500                 505                 510
Lys Gln Ser Leu Gln Val Leu Lys Lys Cys Trp Ala Phe Leu Gln Glu
        515                 520                 525
Ser Ser Leu Asn Pro Leu Ile Gln Met Leu Lys Ala Ala Ile Ile Ser
    530                 535                 540
Gln Leu Leu His Gln Thr Lys Thr Glu Gln Asp His Cys Asn Val Lys
545                 550                 555                 560
Ala Leu Leu Gly Met Met Lys Glu Leu His Lys Val Asn Lys Ala Asn
                565                 570                 575
Cys Arg Leu Pro Glu Asn Thr Phe Asn Ile Asn Glu Leu Ser Asn Leu
            580                 585                 590
Leu Asn Phe Tyr Ile Asp Arg Gly Arg Gln Leu Phe Arg Asp Asn His
        595                 600                 605
Leu Ile Pro Ala Glu Thr Pro Ser Pro Val Ile Phe Ser Asp Phe Pro
    610                 615                 620
Phe Ile Phe Asn Ser Leu Ser Lys Ile Lys Leu Leu Gln Ala Asp Ser
625                 630                 635                 640
His Ile Lys Met Gln Met Ser Glu Lys Lys Ala Tyr Met Leu Met His
                645                 650                 655
Glu Thr Ile Leu Gln Lys Lys Asp Glu Phe Pro Pro Ser Pro Arg Phe
            660                 665                 670
Ile Leu Arg Val Arg Arg Ser Arg Leu Val Lys Asp Ala Leu Arg Gln
        675                 680                 685
Leu Ser Gln Ala Glu Ala Thr Asp Phe Cys Lys Val Leu Val Val Glu
    690                 695                 700
Phe Ile Asn Glu Ile Cys Pro Glu Ser Gly Gly Val Ser Ser Glu Phe
705                 710                 715                 720
Phe His Cys Met Phe Glu Glu Met Thr Lys Pro Glu Tyr Gly Met Phe
                725                 730                 735
Met Tyr Pro Glu Met Gly Ser Cys Met Trp Phe Pro Ala Lys Pro Lys
```

-continued

```
                740                 745                 750
Pro Glu Lys Lys Arg Tyr Phe Leu Phe Gly Met Leu Cys Gly Leu Ser
        755                 760                 765

Leu Phe Asn Leu Asn Val Ala Asn Leu Pro Phe Pro Leu Ala Leu Tyr
        770                 775                 780

Lys Lys Leu Leu Asp Gln Lys Pro Ser Leu Glu Asp Leu Lys Glu Leu
785                 790                 795                 800

Ser Pro Arg Leu Gly Lys Ser Leu Gln Glu Val Leu Asp Asp Ala Ala
                805                 810                 815

Asp Asp Ile Gly Asp Ala Leu Cys Ile Arg Phe Ser Ile His Trp Asp
                820                 825                 830

Gln Asn Asp Val Asp Leu Ile Pro Asn Gly Ile Ser Ile Pro Val Asp
                835                 840                 845

Gln Thr Asn Lys Arg Asp Tyr Val Ser Lys Tyr Ile Asp Tyr Ile Phe
        850                 855                 860

Asn Val Ser Val Lys Ala Val Tyr Glu Glu Phe Gln Arg Gly Phe Tyr
865                 870                 875                 880

Arg Val Cys Glu Lys Glu Ile Leu Arg His Phe Tyr Pro Glu Glu Leu
                885                 890                 895

Met Thr Ala Ile Ile Gly Asn Thr Asp Tyr Asp Trp Lys Gln Phe Glu
                900                 905                 910

Gln Asn Ser Lys Tyr Glu Gly Tyr Gln Lys Ser His Pro Thr Ile
        915                 920                 925

Gln Leu Phe Trp Lys Ala Phe His Lys Leu Thr Leu Asp Glu Lys Lys
        930                 935                 940

Lys Phe Leu Phe Phe Leu Thr Gly Arg Asp Arg Leu His Ala Arg Gly
945                 950                 955                 960

Ile Gln Lys Met Glu Ile Val Phe Arg Cys Pro Glu Thr Phe Ser Glu
                965                 970                 975

Arg Asp His Pro Thr Ser Ile Thr Cys His Asn Ile Leu Ser Leu Pro
                980                 985                 990

Lys Tyr Ser Thr Met Glu Arg Met Glu Glu Ala Leu Gln Val Ala Ile
        995                 1000                1005

Asn Asn Asn Arg Gly Phe Val Ser Pro Met Leu Thr Gln Ser
        1010                1015                1020

<210> SEQ ID NO 31
<211> LENGTH: 3069
<212> TYPE: DNA
<213> ORGANISM: Homo sapiens
<220> FEATURE:
<221> NAME/KEY: CDS
<222> LOCATION: (1)...(3069)

<400> SEQUENCE: 31 atg tac ttc tgt tgg ggc gcc gac tcc agg gag ctg cag cgc cgg agg      48
Met Tyr Phe Cys Trp Gly Ala Asp Ser Arg Glu Leu Gln Arg Arg Arg
 1               5                  10                  15 acg gcg ggc agc ccc ggg gct gag cta ctg cag gcg gcc agc ggg gag      96
Thr Ala Gly Ser Pro Gly Ala Glu Leu Leu Gln Ala Ala Ser Gly Glu
             20                  25                  30 cgc cac tct ctg ctg ctg ctg acc aac cac agg gtc ctc tcg tgc gga     144
Arg His Ser Leu Leu Leu Leu Thr Asn His Arg Val Leu Ser Cys Gly
         35                  40                  45 gac aac agc agg ggt cag ctg ggc cgc agg ggc gcg cag cgc ggg gag     192
Asp Asn Ser Arg Gly Gln Leu Gly Arg Arg Gly Ala Gln Arg Gly Glu
     50                  55                  60
```

```
ctg cca gaa cca att cag gca ttg gaa acc cta att gtt gat ctc gtg     240
Leu Pro Glu Pro Ile Gln Ala Leu Glu Thr Leu Ile Val Asp Leu Val
 65                  70                  75                  80 agc tgc ggg aag gag cac tcc ctg gct gtg tgc cac aaa gga agg gtc     288
Ser Cys Gly Lys Glu His Ser Leu Ala Val Cys His Lys Gly Arg Val
                 85                  90                  95 ttc gca tgg gga gct ggt tct gaa ggg cag ctg ggg att gga gaa ttc     336
Phe Ala Trp Gly Ala Gly Ser Glu Gly Gln Leu Gly Ile Gly Glu Phe
            100                 105                 110 aag gaa ata agt ttc aca cct aag aaa ata atg act ctg aat gat ata     384
Lys Glu Ile Ser Phe Thr Pro Lys Lys Ile Met Thr Leu Asn Asp Ile
        115                 120                 125 aaa ata ata caa gtt tcc tgt gga cac tac cac tcc ctg gca tta tca     432
Lys Ile Ile Gln Val Ser Cys Gly His Tyr His Ser Leu Ala Leu Ser
130                 135                 140 aaa gat agc caa gtg ttt tcg tgg gga aag aac agc cat ggg cag ctg     480
Lys Asp Ser Gln Val Phe Ser Trp Gly Lys Asn Ser His Gly Gln Leu
145                 150                 155                 160 ggc ttg ggg aag gag ttc ccc tcc caa gcc agc ccg cag agg gtg agg     528
Gly Leu Gly Lys Glu Phe Pro Ser Gln Ala Ser Pro Gln Arg Val Arg
                165                 170                 175 tcc ctg gag ggg atc cca ctg gct cag gtg gct gcc gga ggg gct cac     576
Ser Leu Glu Gly Ile Pro Leu Ala Gln Val Ala Ala Gly Gly Ala His
            180                 185                 190 agc ttt gcc ctg tct ctc tgt ggg act tcg ttt ggc tgg gga agt aac     624
Ser Phe Ala Leu Ser Leu Cys Gly Thr Ser Phe Gly Trp Gly Ser Asn
        195                 200                 205 agt gcc ggg cag ctg gcc ctc agt ggg cgt aat gtc cca gtg caa agc     672
Ser Ala Gly Gln Leu Ala Leu Ser Gly Arg Asn Val Pro Val Gln Ser
210                 215                 220 aac aag cct ctc tca gtc ggt gca ctg aag aat cta ggt gtg gtt tat     720
Asn Lys Pro Leu Ser Val Gly Ala Leu Lys Asn Leu Gly Val Val Tyr
225                 230                 235                 240 atc agc tgt ggt gat gca cac act gcg gtg ctt acc cag gac ggg aaa     768
Ile Ser Cys Gly Asp Ala His Thr Ala Val Leu Thr Gln Asp Gly Lys
                245                 250                 255 gtg ttc aca ttt gga gac aat cgc tct gga cag ctg gga tac agc ccc     816
Val Phe Thr Phe Gly Asp Asn Arg Ser Gly Gln Leu Gly Tyr Ser Pro
            260                 265                 270 act cct gag aag aga ggt cca caa ctt gtg gaa aga att gat ggc cta     864
Thr Pro Glu Lys Arg Gly Pro Gln Leu Val Glu Arg Ile Asp Gly Leu
        275                 280                 285 gtt tcg cag ata gat tgt gga agt tat cac acc ctg gca tat gtg cac     912
Val Ser Gln Ile Asp Cys Gly Ser Tyr His Thr Leu Ala Tyr Val His
290                 295                 300 acc act ggt cag gtg gta tct ttt ggt cat gga cca agt gac aca agc     960
Thr Thr Gly Gln Val Val Ser Phe Gly His Gly Pro Ser Asp Thr Ser
305                 310                 315                 320 aag cca act cat ccg gag gcc ctg aca gag aac ttt gac att agc tgc    1008
Lys Pro Thr His Pro Glu Ala Leu Thr Glu Asn Phe Asp Ile Ser Cys
                325                 330                 335 ctg att tct gct gaa gac ttc gtg gat gtt caa gtc aaa cac att ttt    1056
Leu Ile Ser Ala Glu Asp Phe Val Asp Val Gln Val Lys His Ile Phe
            340                 345                 350 gct gga aca tat gcc aac ttt gtg aca act cat cag gat act agt tcc    1104
Ala Gly Thr Tyr Ala Asn Phe Val Thr Thr His Gln Asp Thr Ser Ser
        355                 360                 365 aca cgt gct ccc ggg aaa acc ctg cca gaa ata agc cga att agc cag    1152
Thr Arg Ala Pro Gly Lys Thr Leu Pro Glu Ile Ser Arg Ile Ser Gln
```

-continued

```
          370                 375                 380
tcc atg gca gaa aaa tgg ata gca gtg aaa aga aga agt act gaa cat       1200
Ser Met Ala Glu Lys Trp Ile Ala Val Lys Arg Arg Ser Thr Glu His
385                 390                 395                 400 gaa atg gct aaa agt gaa att aga atg ata ttt tca tct cct gct tgt       1248
Glu Met Ala Lys Ser Glu Ile Arg Met Ile Phe Ser Ser Pro Ala Cys
                405                 410                 415 ctg act gca agt ttt tta aag aaa aga gga act gga gaa acg act tcc       1296
Leu Thr Ala Ser Phe Leu Lys Lys Arg Gly Thr Gly Glu Thr Thr Ser
            420                 425                 430 att gat gtg gac tta gaa atg gca aga gat acc ttc aag aag tta aca       1344
Ile Asp Val Asp Leu Glu Met Ala Arg Asp Thr Phe Lys Lys Leu Thr
                435                 440                 445 aaa aag gaa tgg att tct tcc atg ata act acg tgt ctc gag gat gat       1392
Lys Lys Glu Trp Ile Ser Ser Met Ile Thr Thr Cys Leu Glu Asp Asp
450                 455                 460 ctg ctc aga gct ctt cca tgc cat tct cca cac caa gaa gct tta tca       1440
Leu Leu Arg Ala Leu Pro Cys His Ser Pro His Gln Glu Ala Leu Ser
465                 470                 475                 480 gtt ttc ctc ctg ctc cca gaa tgt cct gtg atg cat gat tct aag aac       1488
Val Phe Leu Leu Leu Pro Glu Cys Pro Val Met His Asp Ser Lys Asn
                485                 490                 495 tgg aag aac ctg gtg gtt cca ttt gca aag gct gtg tgt gaa atg agt       1536
Trp Lys Asn Leu Val Val Pro Phe Ala Lys Ala Val Cys Glu Met Ser
            500                 505                 510 aaa caa tct ttg caa gtc cta aag aag tgt tgg gca ttt ttg caa gaa       1584
Lys Gln Ser Leu Gln Val Leu Lys Lys Cys Trp Ala Phe Leu Gln Glu
        515                 520                 525 tct tct ctg aat ccg ctg atc cag atg ctt aaa gca gcc atc atc tct       1632
Ser Ser Leu Asn Pro Leu Ile Gln Met Leu Lys Ala Ala Ile Ile Ser
530                 535                 540 cag ctg ctt cat cag act aaa acc gaa cag gat cac tgt aat gtt aaa       1680
Gln Leu Leu His Gln Thr Lys Thr Glu Gln Asp His Cys Asn Val Lys
545                 550                 555                 560 gct ctt tta gga atg atg aaa gaa ctg cat aag gta aac aaa gct aac       1728
Ala Leu Leu Gly Met Met Lys Glu Leu His Lys Val Asn Lys Ala Asn
                565                 570                 575 tgt cga cta cca gaa aat act ttc aac ata aat gaa ctc tcc aac tta       1776
Cys Arg Leu Pro Glu Asn Thr Phe Asn Ile Asn Glu Leu Ser Asn Leu
            580                 585                 590 tta aac ttt tat ata gat aga gga aga cag ctc ttt cgg gat aac cac       1824
Leu Asn Phe Tyr Ile Asp Arg Gly Arg Gln Leu Phe Arg Asp Asn His
        595                 600                 605 ctg ata cct gca gaa acc ccc agt cct gtt att ttc agt gat ttt cca       1872
Leu Ile Pro Ala Glu Thr Pro Ser Pro Val Ile Phe Ser Asp Phe Pro
610                 615                 620 ttt atc ttt aat tcg cta tcc aaa att aaa tta ttg caa gct gat tca       1920
Phe Ile Phe Asn Ser Leu Ser Lys Ile Lys Leu Leu Gln Ala Asp Ser
625                 630                 635                 640 cat ata aag atg cag atg tca gaa aag aaa gca tac atg ctt atg cat       1968
His Ile Lys Met Gln Met Ser Glu Lys Lys Ala Tyr Met Leu Met His
                645                 650                 655 gaa aca att ctg caa aaa aag gat gaa ttt cct cca tca ccc aga ttt       2016
Glu Thr Ile Leu Gln Lys Lys Asp Glu Phe Pro Pro Ser Pro Arg Phe
            660                 665                 670 ata ctt aga gtc aga cga agt cgc ctg gtt aaa gat gct ctg cgt caa       2064
Ile Leu Arg Val Arg Arg Ser Arg Leu Val Lys Asp Ala Leu Arg Gln
        675                 680                 685 tta agt caa gct gaa gct act gac ttc tgc aaa gta tta gtg gtt gaa       2112
Leu Ser Gln Ala Glu Ala Thr Asp Phe Cys Lys Val Leu Val Val Glu
```

```
                Leu Ser Gln Ala Glu Ala Thr Asp Phe Cys Lys Val Leu Val Val Glu
                             690                 695                 700 ttt att aat gaa att tgt cct gag tct gga ggg gtt agt tca gag ttc       2160
Phe Ile Asn Glu Ile Cys Pro Glu Ser Gly Gly Val Ser Ser Glu Phe
705                 710                 715                 720 ttc cac tgt atg ttt gaa gag atg acc aag cca gaa tat gga atg ttc       2208
Phe His Cys Met Phe Glu Glu Met Thr Lys Pro Glu Tyr Gly Met Phe
                725                 730                 735 atg tat cct gaa atg ggt tcc tgc atg tgg ttt cct gcc aag cct aaa       2256
Met Tyr Pro Glu Met Gly Ser Cys Met Trp Phe Pro Ala Lys Pro Lys
            740                 745                 750 cct gag aag aaa aga tat ttc ctc ttt gga atg ctg tgt gga ctc tcc       2304
Pro Glu Lys Lys Arg Tyr Phe Leu Phe Gly Met Leu Cys Gly Leu Ser
        755                 760                 765 tta ttc aat tta aat gtt gct aac ctt cct ttc cca ctg gct ctg tat       2352
Leu Phe Asn Leu Asn Val Ala Asn Leu Pro Phe Pro Leu Ala Leu Tyr
    770                 775                 780 aaa aaa ctt ctg gac caa aag cca tca ttg gaa gat tta aaa gaa ctc       2400
Lys Lys Leu Leu Asp Gln Lys Pro Ser Leu Glu Asp Leu Lys Glu Leu
785                 790                 795                 800 agt cct cgg ttg ggg aag agt ttg caa gaa gtt cta gat gat gct gct       2448
Ser Pro Arg Leu Gly Lys Ser Leu Gln Glu Val Leu Asp Asp Ala Ala
                805                 810                 815 gat gac att gga gat gcg ctc tgc ata cgc ttt tct ata cac tgg gac       2496
Asp Asp Ile Gly Asp Ala Leu Cys Ile Arg Phe Ser Ile His Trp Asp
                820                 825                 830 caa aat gat gtt gac tta att cca aat ggg atc tcc ata cct gtg gac       2544
Gln Asn Asp Val Asp Leu Ile Pro Asn Gly Ile Ser Ile Pro Val Asp
            835                 840                 845 caa acc aac aag aga gac tat gtt tct aag tat att gat tac att ttc       2592
Gln Thr Asn Lys Arg Asp Tyr Val Ser Lys Tyr Ile Asp Tyr Ile Phe
        850                 855                 860 aac gtc tct gta aaa gca gtt tat gag gaa ttt cag aga gga ttt tat       2640
Asn Val Ser Val Lys Ala Val Tyr Glu Glu Phe Gln Arg Gly Phe Tyr
    865                 870                 875                 880 aga gtc tgt gag aag gag ata ctt aga cat ttc tac cct gaa gaa cta       2688
Arg Val Cys Glu Lys Glu Ile Leu Arg His Phe Tyr Pro Glu Glu Leu
                885                 890                 895 atg aca gca atc att gga aat act gat tat gac tgg aaa cag ttt gaa       2736
Met Thr Ala Ile Ile Gly Asn Thr Asp Tyr Asp Trp Lys Gln Phe Glu
                900                 905                 910 cag aat tca aag tat gag caa gga tac caa aaa tca cat cct act ata       2784
Gln Asn Ser Lys Tyr Glu Gln Gly Tyr Gln Lys Ser His Pro Thr Ile
            915                 920                 925 cag ttg ttt tgg aag gct ttc cac aaa cta acc ttg gat gaa aag aaa       2832
Gln Leu Phe Trp Lys Ala Phe His Lys Leu Thr Leu Asp Glu Lys Lys
        930                 935                 940 aaa ttc ctc ttt ttc ctt aca gga cgt gat agg ctg cat gca aga ggc       2880
Lys Phe Leu Phe Phe Leu Thr Gly Arg Asp Arg Leu His Ala Arg Gly
945                 950                 955                 960 ata cag aaa atg gaa ata gta ttt cgc tgt cct gaa act ttc agt gaa       2928
Ile Gln Lys Met Glu Ile Val Phe Arg Cys Pro Glu Thr Phe Ser Glu
                965                 970                 975 aga gat cac cca aca tca ata act tgt cat aat att ctc tcc ctc cct       2976
Arg Asp His Pro Thr Ser Ile Thr Cys His Asn Ile Leu Ser Leu Pro
            980                 985                 990 aag tat tct aca atg gaa aga atg gag gaa gca ctt caa gta gcc atc       3024
Lys Tyr Ser Thr Met Glu Arg Met Glu Glu Ala Leu Gln Val Ala Ile
        995                 1000                1005
```

```
aac aac aac aga gga ttt gtc tca ccc atg ctc aca cag tca taa    3069
Asn Asn Asn Arg Gly Phe Val Ser Pro Met Leu Thr Gln Ser  *
    1010                1015                1020
```

<210> SEQ ID NO 32
<211> LENGTH: 70
<212> TYPE: PRT
<213> ORGANISM: Artificial Sequence
<220> FEATURE:
<223> OTHER INFORMATION: Consensus sequence

<400> SEQUENCE: 32

```
Asp Gly Arg Val Tyr Ser Leu Gly Cys Phe Arg Gly Glu Asn Gly Gln
1               5                   10                  15

Leu Gly Leu Gly Glu Glu Val Glu Glu Ser Lys Gly Gly Arg Gln Gly
            20                  25                  30

Leu Glu Arg Leu Leu Val Pro Val Leu Val Met Leu Lys Ser Thr Ser
        35                  40                  45

Ser Ser Leu Ser Glu Lys Val Val Ser Val Ala Ser Gly Gly Gln His
    50                  55                  60

Thr Val Ala Leu Thr Lys
65                  70
```

<210> SEQ ID NO 33
<211> LENGTH: 358
<212> TYPE: PRT
<213> ORGANISM: Artificial Sequence
<220> FEATURE:
<223> OTHER INFORMATION: Consensus sequence

<400> SEQUENCE: 33

```
Phe Leu Val Ser Lys Glu Met Phe Asn Pro Met Tyr Gly Leu Phe Phe
1               5                   10                  15

Tyr Ser Pro Glu Ser Asp Arg Tyr Thr Leu Tyr Ile Asp Pro Asn Ser
            20                  25                  30

Asp Asp Lys Thr Thr Leu Leu Phe Pro Glu Pro Leu Asn Pro Phe Lys
        35                  40                  45

Ala Asn Glu Glu His Leu Glu Tyr Phe Lys Phe Ile Gly Arg Val Val
    50                  55                  60

Gly Leu Ala Leu Leu His Asn Arg Leu Leu Asp Leu Phe Phe Ala Arg
65                  70                  75                  80

Ala Phe Tyr Lys Lys Leu Leu Arg Lys Ser Ile Lys Phe Val Thr Thr
                85                  90                  95

Val Pro Ser Asp Val Glu Thr Ser Phe His Asp Leu Glu Ser Val Asp
            100                 105                 110

Pro Glu Leu Tyr Asn Ser Leu Ile Lys Ile Leu Glu Asn Thr Glu Asp
        115                 120                 125

Lys Glu Phe Glu Glu Val Ile Asn Leu Thr Asp Leu Thr Phe Ser Ile
    130                 135                 140

Asp Leu Glu Glu Phe Gly Asn Asp Glu Lys Val Ser Lys Glu Tyr Val
145                 150                 155                 160

Thr Val Glu Leu Ile Pro Asn Gly Arg Asn Ile Val Val Thr Lys Ser
                165                 170                 175

Asn Lys Lys Glu Tyr Val His Leu Val Ile Gln Trp Arg Leu Val Lys
            180                 185                 190

Arg Ile Glu Lys Gln Leu Lys Ala Phe Lys Glu Gly Phe Ser Glu Val
        195                 200                 205

Ile Pro Glu Cys Asn Leu Ile Lys Ile Phe Asn Glu Glu Glu Leu Glu
```

```
                210                 215                 220
Leu Leu Ile Gly Gly Val Glu Glu Gly Asp Ile Asp Val Asp Asp
225                 230                 235                 240

Leu Lys Ser Asn Thr Glu Tyr Glu Asp Glu Ser Ser Glu Gly Tyr Ser
                245                 250                 255

Glu Asp Ser Gln Val Ile Gln Trp Phe Trp Glu Ile Val Glu Glu Phe
            260                 265                 270

Asp Lys Glu Glu Arg Ala Lys Leu Leu Gln Phe Val Thr Gly Ser Pro
        275                 280                 285

Arg Leu Pro Leu Gln Gly Phe Lys Ser Leu Gly Ser Asn Gly Ile
    290                 295                 300

Pro Lys Phe Thr Ile Glu Lys Ala Gly Thr Glu Asp Glu Arg Leu Pro
305                 310                 315                 320

Thr Ala His Thr Cys Phe Asn Arg Leu Asp Leu Pro Lys Tyr Ser Ser
                325                 330                 335

Lys Glu Ile Leu Arg Ser Lys Leu Leu Leu Ala Ile Glu Glu Cys Gly
            340                 345                 350

Glu Gly Phe Gly Leu Val
        355

<210> SEQ ID NO 34
<211> LENGTH: 11
<212> TYPE: PRT
<213> ORGANISM: Artificial Sequence
<220> FEATURE:
<223> OTHER INFORMATION: Conserved RCC1_2 pattern
<220> FEATURE:
<221> NAME/KEY: VARIANT
<222> LOCATION: (1)...(1)
<223> OTHER INFORMATION: Xaa at position 1 can be L, I, V, M, F or A
<220> FEATURE:
<221> NAME/KEY: VARIANT
<222> LOCATION: (2)...(3)
<223> OTHER INFORMATION: Xaa at positions 2 and 3 can be S, T, A, G or C
<220> FEATURE:
<221> NAME/KEY: VARIANT
<222> LOCATION: (5)...(6)
<223> OTHER INFORMATION: Xaa = any amino acid
<220> FEATURE:
<221> NAME/KEY: VARIANT
<222> LOCATION: (8)...(8)
<223> OTHER INFORMATION: Xaa at position 8 can be S, T, A, G, L or I
<220> FEATURE:
<221> NAME/KEY: VARIANT
<222> LOCATION: (9)...(9)
<223> OTHER INFORMATION: Xaa at position 9 can be L, I, V, M, F or A
<220> FEATURE:
<221> NAME/KEY: VARIANT
<222> LOCATION: (10)...(10)
<223> OTHER INFORMATION: Xaa = any amino acid
<220> FEATURE:
<221> NAME/KEY: VARIANT
<222> LOCATION: (11)...(11)
<223> OTHER INFORMATION: Xaa at position 11 can be L, I, V or M

<400> SEQUENCE: 34

Xaa Xaa Xaa Gly Xaa Xaa His Xaa Xaa Xaa Xaa
 1               5                  10

<210> SEQ ID NO 35
<211> LENGTH: 3633
<212> TYPE: DNA
<213> ORGANISM: Homo sapiens
<220> FEATURE:
<221> NAME/KEY: CDS
<222> LOCATION: (23)...(3415)
```

<400> SEQUENCE: 35

```
cgcaagcggg acactgtggt gg atg caa ttc ccc tcg cct cca gcc gcg agg        52
                         Met Gln Phe Pro Ser Pro Pro Ala Ala Arg
                          1               5                  10 agc tcc ccg gcg ccg cag gca gcg tcc tcc gaa gca gct gca cct            100
Ser Ser Pro Ala Pro Gln Ala Ala Ser Ser Glu Ala Ala Ala Pro
             15                  20                  25 gca act ggg cag cct gga ccc tcg tgc cct gtt ccc ggg acc tcg cgc        148
Ala Thr Gly Gln Pro Gly Pro Ser Cys Pro Val Pro Gly Thr Ser Arg
                 30                  35                  40 agg ggg cgc ccc ggg aca ccc cct gcg ggc cgg gtg gag gag gaa gag        196
Arg Gly Arg Pro Gly Thr Pro Pro Ala Gly Arg Val Glu Glu Glu Glu
                 45                  50                  55 gag gag gag gaa gaa gac gtg gac aag gac ccc cat cct acc cag aac        244
Glu Glu Glu Glu Glu Asp Val Asp Lys Asp Pro His Pro Thr Gln Asn
     60                  65                  70 acc tgc ctg cgc tgc cgc cac ttc tct tta agg gag agg aaa aga gag        292
Thr Cys Leu Arg Cys Arg His Phe Ser Leu Arg Glu Arg Lys Arg Glu
 75                  80                  85                  90 cct agg aga acc atg ggg ggc tgc gaa gtc cgg gaa ttt ctt ttg caa        340
Pro Arg Arg Thr Met Gly Gly Cys Glu Val Arg Glu Phe Leu Leu Gln
                 95                 100                 105 ttt ggt ttc ttc ttg cct ctg ctg aca gcg tgg cca ggc gac tgc agt        388
Phe Gly Phe Phe Leu Pro Leu Leu Thr Ala Trp Pro Gly Asp Cys Ser
            110                 115                 120 cac gtc tcc aac aac caa gtt gtg ttg ctt gat aca aca act gta ctg        436
His Val Ser Asn Asn Gln Val Val Leu Leu Asp Thr Thr Thr Val Leu
            125                 130                 135 gga gag cta gga tgg aaa aca tat cca tta aat ggg tgg gat gcc atc        484
Gly Glu Leu Gly Trp Lys Thr Tyr Pro Leu Asn Gly Trp Asp Ala Ile
    140                 145                 150 act gaa atg gat gaa cat aat agg ccc att cac aca tac cag gta tgt        532
Thr Glu Met Asp Glu His Asn Arg Pro Ile His Thr Tyr Gln Val Cys
155                 160                 165                 170 aat gta atg gaa cca aac caa aac aac tgg ctt cgt aca aac tgg atc        580
Asn Val Met Glu Pro Asn Gln Asn Asn Trp Leu Arg Thr Asn Trp Ile
                175                 180                 185 tcc cgt gat gca gct cag aaa att tat gtg gaa atg aaa ttc aca cta        628
Ser Arg Asp Ala Ala Gln Lys Ile Tyr Val Glu Met Lys Phe Thr Leu
            190                 195                 200 agg gat tgt aac agc atc cca tgg gtc ttg ggg act tgc aaa gaa aca        676
Arg Asp Cys Asn Ser Ile Pro Trp Val Leu Gly Thr Cys Lys Glu Thr
            205                 210                 215 ttt aat ctg ttt tat atg gaa tca gat gag tcc cac gga att aaa ttc        724
Phe Asn Leu Phe Tyr Met Glu Ser Asp Glu Ser His Gly Ile Lys Phe
220                 225                 230 aag cca aac cag tat aca aag atc gac aca att gct gct gat gag agt        772
Lys Pro Asn Gln Tyr Thr Lys Ile Asp Thr Ile Ala Ala Asp Glu Ser
235                 240                 245                 250 ttt acc cag atg gat ttg ggt gat cgc atc ctc aaa ctc aac act gaa        820
Phe Thr Gln Met Asp Leu Gly Asp Arg Ile Leu Lys Leu Asn Thr Glu
                255                 260                 265 att cgt gag gtg ggg cct ata gaa agg aaa gga ttt tat ctg gct ttt        868
Ile Arg Glu Val Gly Pro Ile Glu Arg Lys Gly Phe Tyr Leu Ala Phe
            270                 275                 280 caa gac att ggg gcg tgc att gcc ctg gtt tca gtc gtt ttc tac            916
Gln Asp Ile Gly Ala Cys Ile Ala Leu Val Ser Val Val Phe Tyr
            285                 290                 295 aag aaa tgc ccc ttc act gtt cgt aac ttg gcc atg ttt cct gat acc        964
Lys Lys Cys Pro Phe Thr Val Arg Asn Leu Ala Met Phe Pro Asp Thr
```

```
                Lys Lys Cys Pro Phe Thr Val Arg Asn Leu Ala Met Phe Pro Asp Thr
                300                 305                 310 att cca agg gtt gat tcc tcc tct ttg gtt gaa gta cgg ggt tct tgt          1012
Ile Pro Arg Val Asp Ser Ser Ser Leu Val Glu Val Arg Gly Ser Cys
315                 320                 325                 330 gtg aag agt gct gaa gag cgt gac act cct aaa ctg tat tgt gga gct          1060
Val Lys Ser Ala Glu Glu Arg Asp Thr Pro Lys Leu Tyr Cys Gly Ala
                335                 340                 345 gat gga gat tgg ctg gtt cct ctt gga agg tgc atc tgc agt aca gga          1108
Asp Gly Asp Trp Leu Val Pro Leu Gly Arg Cys Ile Cys Ser Thr Gly
            350                 355                 360 tat gaa gaa att gag ggt tct tgc cat gct tgc aga cca gga ttc tat          1156
Tyr Glu Glu Ile Glu Gly Ser Cys His Ala Cys Arg Pro Gly Phe Tyr
        365                 370                 375 aaa gct ttt gct ggg aac aca aaa tgt tct aaa tgt cct cca cac agt          1204
Lys Ala Phe Ala Gly Asn Thr Lys Cys Ser Lys Cys Pro Pro His Ser
    380                 385                 390 tta aca tac atg gaa gca act tct gtc tgt cag tgt gaa aag ggt tat          1252
Leu Thr Tyr Met Glu Ala Thr Ser Val Cys Gln Cys Glu Lys Gly Tyr
395                 400                 405                 410 ttc cga gct gaa aaa gac cca cct tct atg gca tgt acc agg cca cct          1300
Phe Arg Ala Glu Lys Asp Pro Pro Ser Met Ala Cys Thr Arg Pro Pro
                415                 420                 425 tca gct cct agg aat gtg gtt ttt aac atc aat gaa aca gcc ctt att          1348
Ser Ala Pro Arg Asn Val Val Phe Asn Ile Asn Glu Thr Ala Leu Ile
            430                 435                 440 ttg gaa tgg agc cca cca agt gac aca gga ggg aga aaa gat ctc aca          1396
Leu Glu Trp Ser Pro Pro Ser Asp Thr Gly Gly Arg Lys Asp Leu Thr
        445                 450                 455 tac agt gta atc tgt aag aaa tgt ggc tta gac acc agc cag tgt gag          1444
Tyr Ser Val Ile Cys Lys Lys Cys Gly Leu Asp Thr Ser Gln Cys Glu
    460                 465                 470 gac tgt ggt gga gga ctc cgc ttc atc cca aga cat aca ggc ctg atc          1492
Asp Cys Gly Gly Gly Leu Arg Phe Ile Pro Arg His Thr Gly Leu Ile
475                 480                 485                 490 aac aat tcc gtg ata gta ctt gac ttt gtg tct cac gtg aat tac acc          1540
Asn Asn Ser Val Ile Val Leu Asp Phe Val Ser His Val Asn Tyr Thr
                495                 500                 505 ttt gaa ata gaa gca atg aat gga gtt tct gag ttg agt ttt tct ccc          1588
Phe Glu Ile Glu Ala Met Asn Gly Val Ser Glu Leu Ser Phe Ser Pro
            510                 515                 520 aag cca ttc aca gct att aca gtg acc acg gat caa gat gca cct tcc          1636
Lys Pro Phe Thr Ala Ile Thr Val Thr Thr Asp Gln Asp Ala Pro Ser
        525                 530                 535 ctg ata ggt gtg gta agg aag gac tgg gca tcc caa aat agc att gcc          1684
Leu Ile Gly Val Val Arg Lys Asp Trp Ala Ser Gln Asn Ser Ile Ala
    540                 545                 550 cta tca tgg caa gca cct gct ttt ccc aat gga gcc att ctg gac tac          1732
Leu Ser Trp Gln Ala Pro Ala Phe Pro Asn Gly Ala Ile Leu Asp Tyr
555                 560                 565                 570 gag atc aag tac tat gag aag gaa cat gag cag ctg acc tac tct tcc          1780
Glu Ile Lys Tyr Tyr Glu Lys Glu His Glu Gln Leu Thr Tyr Ser Ser
                575                 580                 585 aca agg tcc aaa gcc ccc agt gtc atc atc aca ggt ctt aag cca gcc          1828
Thr Arg Ser Lys Ala Pro Ser Val Ile Ile Thr Gly Leu Lys Pro Ala
            590                 595                 600 acc aaa tat gta ttt cac atc cga gtg aga act gcg aca gga tac agt          1876
Thr Lys Tyr Val Phe His Ile Arg Val Arg Thr Ala Thr Gly Tyr Ser
        605                 610                 615
```

-continued

| | | |
|---|---|---|
| ggc tac agt cag aaa ttt gaa ttt gaa aca gga gat gaa act tct gac<br>Gly Tyr Ser Gln Lys Phe Glu Phe Glu Thr Gly Asp Glu Thr Ser Asp<br>620                       625                      630 | | 1924 |
| atg gca gca gaa caa gga cag att ctc gtg ata gcc acc gcc gct gtt<br>Met Ala Ala Glu Gln Gly Gln Ile Leu Val Ile Ala Thr Ala Ala Val<br>635                       640                      645                   650 | | 1972 |
| ggc gga ttc act ctc ctc gtc atc ctc act tta ttc ttc ttg atc act<br>Gly Gly Phe Thr Leu Leu Val Ile Leu Thr Leu Phe Phe Leu Ile Thr<br>                   655                            660                   665 | | 2020 |
| ggg aga tgt cag tgg tac ata aaa gcc aag atg aag tca gaa gag aag<br>Gly Arg Cys Gln Trp Tyr Ile Lys Ala Lys Met Lys Ser Glu Glu Lys<br>                 670                         675                   680 | | 2068 |
| aga aga aac cac tta cag aat ggg cat ttg cgc ttc ccg gga att aaa<br>Arg Arg Asn His Leu Gln Asn Gly His Leu Arg Phe Pro Gly Ile Lys<br>          685                       690                      695 | | 2116 |
| act tac att gat cca gat aca tat gaa gac cca tcc cta gca gtc cat<br>Thr Tyr Ile Asp Pro Asp Thr Tyr Glu Asp Pro Ser Leu Ala Val His<br>700                       705                      710 | | 2164 |
| gaa ttt gca aag gag att gat ccc tca aga att cgt att gag aga gtc<br>Glu Phe Ala Lys Glu Ile Asp Pro Ser Arg Ile Arg Ile Glu Arg Val<br>715                       720                      725                   730 | | 2212 |
| att ggg gca ggt gaa ttt gga gaa gtc tgt agt ggg cgt ttg aag aca<br>Ile Gly Ala Gly Glu Phe Gly Glu Val Cys Ser Gly Arg Leu Lys Thr<br>                   735                            740                   745 | | 2260 |
| cca ggg aaa aga gag atc cca gtt gcc att aaa act ttg aaa ggt ggc<br>Pro Gly Lys Arg Glu Ile Pro Val Ala Ile Lys Thr Leu Lys Gly Gly<br>                   750                       755                   760 | | 2308 |
| cac atg gat cgg caa aga aga gat ttt cta aga gaa gct agt atc atg<br>His Met Asp Arg Gln Arg Arg Asp Phe Leu Arg Glu Ala Ser Ile Met<br>               765                       770                   775 | | 2356 |
| ggc cag ttt gac cat cca aac atc att cgc cta gaa ggg gtt gtc acc<br>Gly Gln Phe Asp His Pro Asn Ile Ile Arg Leu Glu Gly Val Val Thr<br>780                       785                      790 | | 2404 |
| aaa aga tcc ttc ccg gcc att ggg gtg gag gcg ttt tgc ccc agc ttc<br>Lys Arg Ser Phe Pro Ala Ile Gly Val Glu Ala Phe Cys Pro Ser Phe<br>795                       800                      805                   810 | | 2452 |
| ctg agg gca ggg ttt tta aat agc atc cag gcc ccg cat cca gtg cca<br>Leu Arg Ala Gly Phe Leu Asn Ser Ile Gln Ala Pro His Pro Val Pro<br>                   815                        820                   825 | | 2500 |
| ggg gga gga tct ttg ccc ccc agg att cct gct ggc aga cca gta atg<br>Gly Gly Gly Ser Leu Pro Pro Arg Ile Pro Ala Gly Arg Pro Val Met<br>                   830                       835                   840 | | 2548 |
| att gtg gtg gaa tat atg gag aat gga tcc cta gac tcc ttt ttg cgg<br>Ile Val Val Glu Tyr Met Glu Asn Gly Ser Leu Asp Ser Phe Leu Arg<br>          845                       850                      855 | | 2596 |
| aag cat gat ggc cac ttc aca gtc atc cag ttg gtc gga atg ctc cga<br>Lys His Asp Gly His Phe Thr Val Ile Gln Leu Val Gly Met Leu Arg<br>860                       865                      870 | | 2644 |
| ggc att gca tca ggc atg aag tat ctt tct gat atg ggt tat gtt cat<br>Gly Ile Ala Ser Gly Met Lys Tyr Leu Ser Asp Met Gly Tyr Val His<br>875                       880                      885                   890 | | 2692 |
| cga gac cta gcg gct cgg aat ata ctg gtc aat agc aac tta gta tgc<br>Arg Asp Leu Ala Ala Arg Asn Ile Leu Val Asn Ser Asn Leu Val Cys<br>                   895                       900                   905 | | 2740 |
| aaa gtt tct gat ttt ggt ctc tcc aga gtg ctg gaa gat gat cca gaa<br>Lys Val Ser Asp Phe Gly Leu Ser Arg Val Leu Glu Asp Asp Pro Glu<br>                   910                       915                   920 | | 2788 |
| gct gct tat aca aca act ggt gga aaa atc ccc ata agg tgg aca gcc<br>Ala Ala Tyr Thr Thr Thr Gly Gly Lys Ile Pro Ile Arg Trp Thr Ala<br>925                       930                      935 | | 2836 |

```
cca gaa gcc atc gcc tac aga aaa ttc tcc tca gca agc gat gca tgg      2884
Pro Glu Ala Ile Ala Tyr Arg Lys Phe Ser Ser Ala Ser Asp Ala Trp
        940                 945                 950 agc tat ggc att gtc atg tgg gag gtc atg tcc tat gga gag aga cct      2932
Ser Tyr Gly Ile Val Met Trp Glu Val Met Ser Tyr Gly Glu Arg Pro
955                 960                 965                 970 tat tgg gaa atg tct aac caa gat gtc att ctg tcc att gaa gaa ggg      2980
Tyr Trp Glu Met Ser Asn Gln Asp Val Ile Leu Ser Ile Glu Glu Gly
                    975                 980                 985 tac aga ctt cca gct ccc atg ggc tgt cca gca tct cta cac cag ctg      3028
Tyr Arg Leu Pro Ala Pro Met Gly Cys Pro Ala Ser Leu His Gln Leu
                990                 995                 1000 atg ctc cac tgc tgg cag aag gag aga aat cac aga cca aaa ttt act      3076
Met Leu His Cys Trp Gln Lys Glu Arg Asn His Arg Pro Lys Phe Thr
            1005                1010                1015 gac att gtc agc ttc ctt gac aaa ctg atc cga aat ccc agt gcc ctt      3124
Asp Ile Val Ser Phe Leu Asp Lys Leu Ile Arg Asn Pro Ser Ala Leu
        1020                1025                1030 cac acc ctg gtg gag gac atc ctt gta atg cca gag tcc cct ggt gaa      3172
His Thr Leu Val Glu Asp Ile Leu Val Met Pro Glu Ser Pro Gly Glu
1035                1040                1045                1050 gtt ccg gaa tat cct ttg ttt gtc aca gtt ggt gac tgg cta gat tct      3220
Val Pro Glu Tyr Pro Leu Phe Val Thr Val Gly Asp Trp Leu Asp Ser
                1055                1060                1065 ata aag atg ggg caa tac aag aat aac ttc gtg gca gca ggg ttt aca      3268
Ile Lys Met Gly Gln Tyr Lys Asn Asn Phe Val Ala Ala Gly Phe Thr
                    1070                1075                1080 aca ttt gac ctg att tca aga atg agc att gat gac att aga aga att      3316
Thr Phe Asp Leu Ile Ser Arg Met Ser Ile Asp Asp Ile Arg Arg Ile
                1085                1090                1095 gga gtc ata ctt att gga cac cag aga cga ata gtc agc agc ata cag      3364
Gly Val Ile Leu Ile Gly His Gln Arg Arg Ile Val Ser Ser Ile Gln
1100                1105                1110 act tta cgt tta cac atg atg cac ata cag gag aag gga ttt cat gta      3412
Thr Leu Arg Leu His Met Met His Ile Gln Glu Lys Gly Phe His Val
1115                1120                1125                1130 tga aagtaccaca agcacctgtg ttttgtgcct cagcatttct aaaatgaacg          3465
* atatcctctc tactactctc tcttctgatt ctccaaacat cacttcacaa actgcagtct    3525
tctgttcaga ctataggcac acaccttatg tttatgcttc caaccaggat tttaaaatca    3585
tgctacataa atccgttctg aataacctgc aactaaaaaa aaaaaaaa               3633

<210> SEQ ID NO 36
<211> LENGTH: 1130
<212> TYPE: PRT
<213> ORGANISM: Homo sapiens

<400> SEQUENCE: 36

Met Gln Phe Pro Ser Pro Pro Ala Ala Arg Ser Ser Pro Ala Pro Gln
 1               5                  10                  15

Ala Ala Ser Ser Ser Glu Ala Ala Pro Ala Thr Gly Gln Pro Gly
            20                  25                  30

Pro Ser Cys Pro Val Pro Gly Thr Ser Arg Arg Gly Arg Pro Gly Thr
        35                  40                  45

Pro Pro Ala Gly Arg Val Glu Glu Glu Glu Glu Glu Glu Glu Glu Asp
    50                  55                  60

Val Asp Lys Asp Pro His Pro Thr Gln Asn Thr Cys Leu Arg Cys Arg
```

-continued

```
             65                   70                   75                   80
His Phe Ser Leu Arg Glu Arg Lys Arg Glu Pro Arg Arg Thr Met Gly
                    85                   90                   95
Gly Cys Glu Val Arg Glu Phe Leu Leu Gln Phe Gly Phe Phe Leu Pro
                  100                  105                  110
Leu Leu Thr Ala Trp Pro Gly Asp Cys Ser His Val Ser Asn Asn Gln
                  115                  120                  125
Val Val Leu Leu Asp Thr Thr Thr Val Leu Gly Glu Leu Gly Trp Lys
                  130                  135                  140
Thr Tyr Pro Leu Asn Gly Trp Asp Ala Ile Thr Glu Met Asp Glu His
145                  150                  155                  160
Asn Arg Pro Ile His Thr Tyr Gln Val Cys Asn Val Met Glu Pro Asn
                  165                  170                  175
Gln Asn Asn Trp Leu Arg Thr Asn Trp Ile Ser Arg Asp Ala Ala Gln
                  180                  185                  190
Lys Ile Tyr Val Glu Met Lys Phe Thr Leu Arg Asp Cys Asn Ser Ile
                  195                  200                  205
Pro Trp Val Leu Gly Thr Cys Lys Glu Thr Phe Asn Leu Phe Tyr Met
                  210                  215                  220
Glu Ser Asp Glu Ser His Gly Ile Lys Phe Lys Pro Asn Gln Tyr Thr
225                  230                  235                  240
Lys Ile Asp Thr Ile Ala Ala Asp Glu Ser Phe Thr Gln Met Asp Leu
                  245                  250                  255
Gly Asp Arg Ile Leu Lys Leu Asn Thr Glu Ile Arg Glu Val Gly Pro
                  260                  265                  270
Ile Glu Arg Lys Gly Phe Tyr Leu Ala Phe Gln Asp Ile Gly Ala Cys
                  275                  280                  285
Ile Ala Leu Val Ser Val Arg Val Phe Tyr Lys Lys Cys Pro Phe Thr
                  290                  295                  300
Val Arg Asn Leu Ala Met Phe Pro Asp Thr Ile Pro Arg Val Asp Ser
305                  310                  315                  320
Ser Ser Leu Val Glu Val Arg Gly Ser Cys Val Lys Ser Ala Glu Glu
                  325                  330                  335
Arg Asp Thr Pro Lys Leu Tyr Cys Gly Ala Asp Gly Asp Trp Leu Val
                  340                  345                  350
Pro Leu Gly Arg Cys Ile Cys Ser Thr Gly Tyr Glu Glu Ile Glu Gly
                  355                  360                  365
Ser Cys His Ala Cys Arg Pro Gly Phe Tyr Lys Ala Phe Ala Gly Asn
                  370                  375                  380
Thr Lys Cys Ser Lys Cys Pro Pro His Ser Leu Thr Tyr Met Glu Ala
385                  390                  395                  400
Thr Ser Val Cys Gln Cys Glu Lys Gly Tyr Phe Arg Ala Glu Lys Asp
                  405                  410                  415
Pro Pro Ser Met Ala Cys Thr Arg Pro Ser Ala Pro Arg Asn Val
                  420                  425                  430
Val Phe Asn Ile Asn Glu Thr Ala Leu Ile Leu Glu Trp Ser Pro Pro
                  435                  440                  445
Ser Asp Thr Gly Gly Arg Lys Asp Leu Thr Tyr Ser Val Ile Cys Lys
                  450                  455                  460
Lys Cys Gly Leu Asp Thr Ser Gln Cys Glu Asp Cys Gly Gly Gly Leu
465                  470                  475                  480
Arg Phe Ile Pro Arg His Thr Gly Leu Ile Asn Asn Ser Val Ile Val
                  485                  490                  495
```

-continued

```
Leu Asp Phe Val Ser His Val Asn Tyr Thr Phe Glu Ile Glu Ala Met
        500                 505                 510
Asn Gly Val Ser Glu Leu Ser Phe Ser Pro Lys Pro Phe Thr Ala Ile
        515                 520                 525
Thr Val Thr Thr Asp Gln Asp Ala Pro Ser Leu Ile Gly Val Val Arg
        530                 535                 540
Lys Asp Trp Ala Ser Gln Asn Ser Ile Ala Leu Ser Trp Gln Ala Pro
545                 550                 555                 560
Ala Phe Ser Asn Gly Ala Ile Leu Asp Tyr Glu Ile Lys Tyr Tyr Glu
                565                 570                 575
Lys Glu His Glu Gln Leu Thr Tyr Ser Ser Thr Arg Ser Lys Ala Pro
            580                 585                 590
Ser Val Ile Ile Thr Gly Leu Lys Pro Ala Thr Lys Tyr Val Phe His
            595                 600                 605
Ile Arg Val Arg Thr Ala Thr Gly Tyr Ser Gly Tyr Ser Gln Lys Phe
        610                 615                 620
Glu Phe Glu Thr Gly Asp Glu Thr Ser Asp Met Ala Ala Glu Gln Gly
625                 630                 635                 640
Gln Ile Leu Val Ile Ala Thr Ala Ala Val Gly Gly Phe Thr Leu Leu
                645                 650                 655
Val Ile Leu Thr Leu Phe Phe Leu Ile Thr Gly Arg Cys Gln Trp Tyr
            660                 665                 670
Ile Lys Ala Lys Met Lys Ser Glu Glu Lys Arg Arg Asn His Leu Gln
            675                 680                 685
Asn Gly His Leu Arg Phe Pro Gly Ile Lys Thr Tyr Ile Asp Pro Asp
        690                 695                 700
Thr Tyr Glu Asp Pro Ser Leu Ala Val His Glu Phe Ala Lys Glu Ile
705                 710                 715                 720
Asp Pro Ser Arg Ile Arg Ile Glu Arg Val Ile Gly Ala Gly Glu Phe
                725                 730                 735
Gly Glu Val Cys Ser Gly Arg Leu Lys Thr Pro Gly Lys Arg Glu Ile
            740                 745                 750
Pro Val Ala Ile Lys Thr Leu Lys Gly Gly His Met Asp Arg Gln Arg
            755                 760                 765
Arg Asp Phe Leu Arg Glu Ala Ser Ile Met Gly Gln Phe Asp His Pro
        770                 775                 780
Asn Ile Ile Arg Leu Glu Gly Val Val Thr Lys Arg Ser Phe Pro Ala
785                 790                 795                 800
Ile Gly Val Glu Ala Phe Cys Pro Ser Phe Leu Arg Ala Gly Phe Leu
                805                 810                 815
Asn Ser Ile Gln Ala Pro His Pro Val Pro Gly Gly Ser Leu Pro
            820                 825                 830
Pro Arg Ile Pro Ala Gly Arg Pro Val Met Ile Val Glu Tyr Met
            835                 840                 845
Glu Asn Gly Ser Leu Asp Ser Phe Leu Arg Lys His Asp Gly His Phe
        850                 855                 860
Thr Val Ile Gln Leu Val Gly Met Leu Arg Gly Ile Ala Ser Gly Met
865                 870                 875                 880
Lys Tyr Leu Ser Asp Met Gly Tyr Val His Arg Asp Leu Ala Ala Arg
                885                 890                 895
Asn Ile Leu Val Asn Ser Asn Leu Val Cys Lys Val Ser Asp Phe Gly
            900                 905                 910
```

```
Leu Ser Arg Val Leu Glu Asp Asp Pro Glu Ala Ala Tyr Thr Thr Thr
        915                 920                 925
Gly Gly Lys Ile Pro Ile Arg Trp Thr Ala Pro Glu Ala Ile Ala Tyr
            930                 935                 940
Arg Lys Phe Ser Ser Ala Ser Asp Ala Trp Ser Tyr Gly Ile Val Met
945                 950                 955                 960
Trp Glu Val Met Ser Tyr Gly Glu Arg Pro Tyr Trp Glu Met Ser Asn
                965                 970                 975
Gln Asp Val Ile Leu Ser Ile Glu Glu Gly Tyr Arg Leu Pro Ala Pro
                980                 985                 990
Met Gly Cys Pro Ala Ser Leu His Gln Leu Met Leu His Cys Trp Gln
            995                 1000                1005
Lys Glu Arg Asn His Arg Pro Lys Phe Thr Asp Ile Val Ser Phe Leu
        1010                1015                1020
Asp Lys Leu Ile Arg Asn Pro Ser Ala Leu His Thr Leu Val Glu Asp
1025                1030                1035                1040
Ile Leu Val Met Pro Glu Ser Pro Gly Glu Val Pro Glu Tyr Pro Leu
                1045                1050                1055
Phe Val Thr Val Gly Asp Trp Leu Asp Ser Ile Lys Met Gly Gln Tyr
            1060                1065                1070
Lys Asn Asn Phe Val Ala Ala Gly Phe Thr Thr Phe Asp Leu Ile Ser
        1075                1080                1085
Arg Met Ser Ile Asp Asp Ile Arg Arg Ile Gly Val Ile Leu Ile Gly
        1090                1095                1100
His Gln Arg Arg Ile Val Ser Ser Ile Gln Thr Leu Arg Leu His Met
1105                1110                1115                1120
Met His Ile Gln Glu Lys Gly Phe His Val
                1125                1130

<210> SEQ ID NO 37
<211> LENGTH: 3393
<212> TYPE: DNA
<213> ORGANISM: Homo sapiens
<220> FEATURE:
<221> NAME/KEY: CDS
<222> LOCATION: (1)...(3393)

<400> SEQUENCE: 37 atg caa ttc ccc tcg cct cca gcc gcg agg agc tcc ccg gcg ccg cag      48
Met Gln Phe Pro Ser Pro Pro Ala Ala Arg Ser Ser Pro Ala Pro Gln
1               5                   10                  15 gca gcg tcc tcc tcc gaa gca gct gca cct gca act ggg cag cct gga      96
Ala Ala Ser Ser Ser Glu Ala Ala Ala Pro Ala Thr Gly Gln Pro Gly
                20                  25                  30 ccc tcg tgc cct gtt ccc ggg acc tcg cgc agg ggg cgc ccc ggg aca     144
Pro Ser Cys Pro Val Pro Gly Thr Ser Arg Arg Gly Arg Pro Gly Thr
            35                  40                  45 ccc cct gcg ggc cgg gtg gag gag gaa gag gag gag gag gaa gaa gac     192
Pro Pro Ala Gly Arg Val Glu Glu Glu Glu Glu Glu Glu Glu Glu Asp
        50                  55                  60 gtg gac aag gac ccc cat cct acc cag aac acc tgc ctg cgc tgc cgc     240
Val Asp Lys Asp Pro His Pro Thr Gln Asn Thr Cys Leu Arg Cys Arg
65                  70                  75                  80 cac ttc tct tta agg gag agg aaa aga gag cct agg aga acc atg ggc     288
His Phe Ser Leu Arg Glu Arg Lys Arg Glu Pro Arg Arg Thr Met Gly
                85                  90                  95 ggc tgc gaa gtc cgg gaa ttt ctt ttg caa ttt ggt ttc ttc ttg cct     336
Gly Cys Glu Val Arg Glu Phe Leu Leu Gln Phe Gly Phe Phe Leu Pro
```

-continued

```
                    100                 105                 110
ctg ctg aca gcg tgg cca ggc gac tgc agt cac gtc tcc aac aac caa        384
Leu Leu Thr Ala Trp Pro Gly Asp Cys Ser His Val Ser Asn Asn Gln
            115                 120                 125 gtt gtg ttg ctt gat aca aca act gta ctg gga gag cta gga tgg aaa        432
Val Val Leu Leu Asp Thr Thr Thr Val Leu Gly Glu Leu Gly Trp Lys
130                 135                 140 aca tat cca tta aat ggg tgg gat gcc atc act gaa atg gat gaa cat        480
Thr Tyr Pro Leu Asn Gly Trp Asp Ala Ile Thr Glu Met Asp Glu His
145                 150                 155                 160 aat agg ccc att cac aca tac cag gta tgt aat gta atg gaa cca aac        528
Asn Arg Pro Ile His Thr Tyr Gln Val Cys Asn Val Met Glu Pro Asn
                165                 170                 175 caa aac aac tgg ctt cgt aca aac tgg atc tcc cgt gat gca gct cag        576
Gln Asn Asn Trp Leu Arg Thr Asn Trp Ile Ser Arg Asp Ala Ala Gln
            180                 185                 190 aaa att tat gtg gaa atg aaa ttc aca cta agg gat tgt aac agc atc        624
Lys Ile Tyr Val Glu Met Lys Phe Thr Leu Arg Asp Cys Asn Ser Ile
        195                 200                 205 cca tgg gtc ttg ggg act tgc aaa gaa aca ttt aat ctg ttt tat atg        672
Pro Trp Val Leu Gly Thr Cys Lys Glu Thr Phe Asn Leu Phe Tyr Met
210                 215                 220 gaa tca gat gag tcc cac gga att aaa ttc aag cca aac cag tat aca        720
Glu Ser Asp Glu Ser His Gly Ile Lys Phe Lys Pro Asn Gln Tyr Thr
225                 230                 235                 240 aag atc gac aca att gct gct gat gag agt ttt acc cag atg gat ttg        768
Lys Ile Asp Thr Ile Ala Ala Asp Glu Ser Phe Thr Gln Met Asp Leu
                245                 250                 255 ggt gat cgc atc ctc aaa ctc aac act gaa att cgt gag gtg ggg cct        816
Gly Asp Arg Ile Leu Lys Leu Asn Thr Glu Ile Arg Glu Val Gly Pro
            260                 265                 270 ata gaa agg aaa gga ttt tat ctg gct ttt caa gac att ggg gcg tgc        864
Ile Glu Arg Lys Gly Phe Tyr Leu Ala Phe Gln Asp Ile Gly Ala Cys
        275                 280                 285 att gcc ctg gtt tca gtc cgt gtt ttc tac aag aaa tgc ccc ttc act        912
Ile Ala Leu Val Ser Val Arg Val Phe Tyr Lys Lys Cys Pro Phe Thr
290                 295                 300 gtt cgt aac ttg gcc atg ttt cct gat acc att cca agg gtt gat tcc        960
Val Arg Asn Leu Ala Met Phe Pro Asp Thr Ile Pro Arg Val Asp Ser
305                 310                 315                 320 tcc tct ttg gtt gaa gta cgg ggt tct tgt gtg aag agt gct gaa gag       1008
Ser Ser Leu Val Glu Val Arg Gly Ser Cys Val Lys Ser Ala Glu Glu
                325                 330                 335 cgt gac act cct aaa ctg tat tgt gga gct gat gga gat tgg ctg gtt       1056
Arg Asp Thr Pro Lys Leu Tyr Cys Gly Ala Asp Gly Asp Trp Leu Val
            340                 345                 350 cct ctt gga agg tgc atc tgc agt aca gga tat gaa gaa att gag ggt       1104
Pro Leu Gly Arg Cys Ile Cys Ser Thr Gly Tyr Glu Glu Ile Glu Gly
        355                 360                 365 tct tgc cat gct tgc aga cca gga ttc tat aaa gct ttt gct ggg aac       1152
Ser Cys His Ala Cys Arg Pro Gly Phe Tyr Lys Ala Phe Ala Gly Asn
370                 375                 380 aca aaa tgt tct aaa tgt cct cca cac agt tta aca tac atg gaa gca       1200
Thr Lys Cys Ser Lys Cys Pro Pro His Ser Leu Thr Tyr Met Glu Ala
385                 390                 395                 400 act tct gtc tgt cag tgt gaa aag ggt tat ttc cga gct gaa aaa gac       1248
Thr Ser Val Cys Gln Cys Glu Lys Gly Tyr Phe Arg Ala Glu Lys Asp
                405                 410                 415 cca cct tct atg gca tgt acc agg cca cct tca gct cct agg aat gtg       1296
```

```
                    -continued

Pro Pro Ser Met Ala Cys Thr Arg Pro Pro Ser Ala Pro Arg Asn Val
            420                 425                 430 gtt ttt aac atc aat gaa aca gcc ctt att ttg gaa tgg agc cca cca        1344
Val Phe Asn Ile Asn Glu Thr Ala Leu Ile Leu Glu Trp Ser Pro Pro
        435                 440                 445 agt gac aca gga ggg aga aaa gat ctc aca tac agt gta atc tgt aag        1392
Ser Asp Thr Gly Gly Arg Lys Asp Leu Thr Tyr Ser Val Ile Cys Lys
    450                 455                 460 aaa tgt ggc tta gac acc agc cag tgt gag gac tgt ggt gga gga ctc        1440
Lys Cys Gly Leu Asp Thr Ser Gln Cys Glu Asp Cys Gly Gly Gly Leu
465                 470                 475                 480 cgc ttc atc cca aga cat aca ggc ctg atc aac aat tcc gtg ata gta        1488
Arg Phe Ile Pro Arg His Thr Gly Leu Ile Asn Asn Ser Val Ile Val
                485                 490                 495 ctt gac ttt gtg tct cac gtg aat tac acc ttt gaa ata gaa gca atg        1536
Leu Asp Phe Val Ser His Val Asn Tyr Thr Phe Glu Ile Glu Ala Met
            500                 505                 510 aat gga gtt tct gag ttg agt ttt tct ccc aag cca ttc aca gct att        1584
Asn Gly Val Ser Glu Leu Ser Phe Ser Pro Lys Pro Phe Thr Ala Ile
        515                 520                 525 aca gtg acc acg gat caa gat gca cct tcc ctg ata ggt gtg gta agg        1632
Thr Val Thr Thr Asp Gln Asp Ala Pro Ser Leu Ile Gly Val Val Arg
    530                 535                 540 aag gac tgg gca tcc caa aat agc att gcc cta tca tgg caa gca cct        1680
Lys Asp Trp Ala Ser Gln Asn Ser Ile Ala Leu Ser Trp Gln Ala Pro
545                 550                 555                 560 gct ttt tcc aat gga gcc att ctg gac tac gag atc aag tac tat gag        1728
Ala Phe Ser Asn Gly Ala Ile Leu Asp Tyr Glu Ile Lys Tyr Tyr Glu
                565                 570                 575 aag gaa cat gag cag ctg acc tac tct tcc aca agg tcc aaa gcc ccc        1776
Lys Glu His Glu Gln Leu Thr Tyr Ser Ser Thr Arg Ser Lys Ala Pro
            580                 585                 590 agt gtc atc atc aca ggt ctt aag cca gcc acc aaa tat gta ttt cac        1824
Ser Val Ile Ile Thr Gly Leu Lys Pro Ala Thr Lys Tyr Val Phe His
        595                 600                 605 atc cga gtg aga act gcg aca gga tac agt ggc tac agt cag aaa ttt        1872
Ile Arg Val Arg Thr Ala Thr Gly Tyr Ser Gly Tyr Ser Gln Lys Phe
    610                 615                 620 gaa ttt gaa aca gga gat gaa act tct gac atg gca gca gaa caa gga        1920
Glu Phe Glu Thr Gly Asp Glu Thr Ser Asp Met Ala Ala Glu Gln Gly
625                 630                 635                 640 cag att ctc gtg ata gcc acc gcc gct gtt ggc gga ttc act ctc ctc        1968
Gln Ile Leu Val Ile Ala Thr Ala Ala Val Gly Gly Phe Thr Leu Leu
                645                 650                 655 gtc atc ctc act tta ttc ttc ttg atc act ggg aga tgt cag tgg tac        2016
Val Ile Leu Thr Leu Phe Phe Leu Ile Thr Gly Arg Cys Gln Trp Tyr
            660                 665                 670 ata aaa gcc aag atg aag tca gaa gag aag aga aga aac cac tta cag        2064
Ile Lys Ala Lys Met Lys Ser Glu Glu Lys Arg Arg Asn His Leu Gln
        675                 680                 685 aat ggg cat ttg cgc ttc ccg gga att aaa act tac att gat cca gat        2112
Asn Gly His Leu Arg Phe Pro Gly Ile Lys Thr Tyr Ile Asp Pro Asp
    690                 695                 700 aca tat gaa gac cca tcc cta gca gtc cat gaa ttt gca aag gag att        2160
Thr Tyr Glu Asp Pro Ser Leu Ala Val His Glu Phe Ala Lys Glu Ile
705                 710                 715                 720 gat ccc tca aga att cgt att gag aga gtc att ggg gca ggt gaa ttt        2208
Asp Pro Ser Arg Ile Arg Ile Glu Arg Val Ile Gly Ala Gly Glu Phe
                725                 730                 735
```

```
gga gaa gtc tgt agt ggg cgt ttg aag aca cca ggg aaa aga gag atc        2256
Gly Glu Val Cys Ser Gly Arg Leu Lys Thr Pro Gly Lys Arg Glu Ile
        740                 745                 750 cca gtt gcc att aaa act ttg aaa ggt ggc cac atg gat cgg caa aga        2304
Pro Val Ala Ile Lys Thr Leu Lys Gly Gly His Met Asp Arg Gln Arg
            755                 760                 765 aga gat ttt cta aga gaa gct agt atc atg ggc cag ttt gac cat cca        2352
Arg Asp Phe Leu Arg Glu Ala Ser Ile Met Gly Gln Phe Asp His Pro
770                 775                 780 aac atc att cgc cta gaa ggg gtt gtc acc aaa aga tcc ttc ccg gcc        2400
Asn Ile Ile Arg Leu Glu Gly Val Val Thr Lys Arg Ser Phe Pro Ala
785                 790                 795                 800 att ggg gtg gag gcg ttt tgc ccc agc ttc ctg agg gca ggg ttt tta        2448
Ile Gly Val Glu Ala Phe Cys Pro Ser Phe Leu Arg Ala Gly Phe Leu
                805                 810                 815 aat agc atc cag gcc ccg cat cca gtg cca ggg gga gga tct ttg ccc        2496
Asn Ser Ile Gln Ala Pro His Pro Val Pro Gly Gly Gly Ser Leu Pro
            820                 825                 830 ccc agg att cct gct ggc aga cca gta atg att gtg gtg gaa tat atg        2544
Pro Arg Ile Pro Ala Gly Arg Pro Val Met Ile Val Val Glu Tyr Met
        835                 840                 845 gag aat gga tcc cta gac tcc ttt ttg cgg aag cat gat ggc cac ttc        2592
Glu Asn Gly Ser Leu Asp Ser Phe Leu Arg Lys His Asp Gly His Phe
850                 855                 860 aca gtc atc cag ttg gtc gga atg ctc cga ggc att gca tca ggc atg        2640
Thr Val Ile Gln Leu Val Gly Met Leu Arg Gly Ile Ala Ser Gly Met
865                 870                 875                 880 aag tat ctt tct gat atg ggt tat gtt cat cga gac cta gcg gct cgg        2688
Lys Tyr Leu Ser Asp Met Gly Tyr Val His Arg Asp Leu Ala Ala Arg
                885                 890                 895 aat ata ctg gtc aat agc aac tta gta tgc aaa gtt tct gat ttt ggt        2736
Asn Ile Leu Val Asn Ser Asn Leu Val Cys Lys Val Ser Asp Phe Gly
            900                 905                 910 ctc tcc aga gtg ctg gaa gat gat cca gaa gct gct tat aca aca act        2784
Leu Ser Arg Val Leu Glu Asp Asp Pro Glu Ala Ala Tyr Thr Thr Thr
        915                 920                 925 ggt gga aaa atc ccc ata agg tgg aca gcc cca gaa gcc atc gcc tac        2832
Gly Gly Lys Ile Pro Ile Arg Trp Thr Ala Pro Glu Ala Ile Ala Tyr
930                 935                 940 aga aaa ttc tcc tca gca agc gat gca tgg agc tat ggc att gtc atg        2880
Arg Lys Phe Ser Ser Ala Ser Asp Ala Trp Ser Tyr Gly Ile Val Met
945                 950                 955                 960 tgg gag gtc atg tcc tat gga gag aga cct tat tgg gaa atg tct aac        2928
Trp Glu Val Met Ser Tyr Gly Glu Arg Pro Tyr Trp Glu Met Ser Asn
                965                 970                 975 caa gat gtc att ctg tcc att gaa gaa ggg tac aga ctt cca gct ccc        2976
Gln Asp Val Ile Leu Ser Ile Glu Glu Gly Tyr Arg Leu Pro Ala Pro
            980                 985                 990 atg ggc tgt cca gca tct cta cac cag ctg atg ctc cac tgc tgg cag        3024
Met Gly Cys Pro Ala Ser Leu His Gln Leu Met Leu His Cys Trp Gln
        995                 1000                1005 aag gag aga aat cac aga cca aaa ttt act gac att gtc agc ttc ctt        3072
Lys Glu Arg Asn His Arg Pro Lys Phe Thr Asp Ile Val Ser Phe Leu
    1010                1015                1020 gac aaa ctg atc cga aat ccc agt gcc ctt cac acc ctg gtg gag gac        3120
Asp Lys Leu Ile Arg Asn Pro Ser Ala Leu His Thr Leu Val Glu Asp
1025                1030                1035                1040 atc ctt gta atg cca gag tcc cct ggt gaa gtt ccg gaa tat cct ttg        3168
Ile Leu Val Met Pro Glu Ser Pro Gly Glu Val Pro Glu Tyr Pro Leu
                1045                1050                1055
```

```
ttt gtc aca gtt ggt gac tgg cta gat tct ata aag atg ggg caa tac      3216
Phe Val Thr Val Gly Asp Trp Leu Asp Ser Ile Lys Met Gly Gln Tyr
        1060                1065                1070 aag aat aac ttc gtg gca gca ggg ttt aca aca ttt gac ctg att tca      3264
Lys Asn Asn Phe Val Ala Ala Gly Phe Thr Thr Phe Asp Leu Ile Ser
    1075                1080                1085 aga atg agc att gat gac att aga aga att gga gtc ata ctt att gga      3312
Arg Met Ser Ile Asp Asp Ile Arg Arg Ile Gly Val Ile Leu Ile Gly
1090                1095                1100 cac cag aga cga ata gtc agc agc ata cag act tta cgt tta cac atg      3360
His Gln Arg Arg Ile Val Ser Ser Ile Gln Thr Leu Arg Leu His Met
1105                1110                1115                1120 atg cac ata cag gag aag gga ttt cat gta tga                          3393
Met His Ile Gln Glu Lys Gly Phe His Val *
            1125                1130
```

<210> SEQ ID NO 38
<211> LENGTH: 2466
<212> TYPE: DNA
<213> ORGANISM: Homo sapiens
<220> FEATURE:
<221> NAME/KEY: CDS
<222> LOCATION: (437)...(1981)
<220> FEATURE:
<221> NAME/KEY: misc_feature
<222> LOCATION: (1)...(2466)
<223> OTHER INFORMATION: n = A,T,C or G

<400> SEQUENCE: 38

```
gtccttctct aaggcgagct gcccttgggc gcgcctgggg ctgcacctgg gtcacgtggg     60
cgccgttgtg catgccggca cctcccggnc aaccccgcgg cttggagaag gggctttgca   120
cccgccgccg ctgtttgtcc tcgcgcggcc cccgtccact gccctgcggt tgctctgcgg   180
gctgaaaagt ttctcccggt gcagaattcc gggctcagcg acagcctgcg ccagtgtgc   240 gcacctgtcg gagacccgcc agtccgccgg ccgcgctctc acgtgtgaat atgtgtctag   300
tgcatcctta acctgaggac ttcaccagtt cgaaattaca gttttcacca tcaactacct   360
tatccttttt ggtctggttt tcttcctcaa acagtggaaa catttttaaa gttgcttttg   420
ttgcagagtt aaacaa atg gct gat agt ggc tta gat aaa aaa tcc aca aaa   472
              Met Ala Asp Ser Gly Leu Asp Lys Lys Ser Thr Lys
                1               5                   10 tgc ccc gac tgt tca tct gct tct cag aaa gat gta ctt tgt gta tgt   520
Cys Pro Asp Cys Ser Ser Ala Ser Gln Lys Asp Val Leu Cys Val Cys
        15                  20                  25 tcc agc aaa aca agg gtt cct cca gtt ttg gtg gtg gaa atg tca cag   568
Ser Ser Lys Thr Arg Val Pro Pro Val Leu Val Val Glu Met Ser Gln
    30                  35                  40 aca tca agc att ggt agt gca gaa tct tta att tca ctg gag aga aaa   616
Thr Ser Ser Ile Gly Ser Ala Glu Ser Leu Ile Ser Leu Glu Arg Lys
45                  50                  55                  60 aaa gaa aaa aat atc aac aga gat ata acc tcc agg aaa gat ttg ccc   664
Lys Glu Lys Asn Ile Asn Arg Asp Ile Thr Ser Arg Lys Asp Leu Pro
                65                  70                  75 tca aga acc tca aat gta gag aga aaa gca tct cag caa caa tgg ggt   712
Ser Arg Thr Ser Asn Val Glu Arg Lys Ala Ser Gln Gln Gln Trp Gly
        80                  85                  90 cgg ggc aac ttt aca gaa gga aaa gtt cct cac ata agg att gag aat   760
Arg Gly Asn Phe Thr Glu Gly Lys Val Pro His Ile Arg Ile Glu Asn
    95                  100                 105 gga gct gct att gag gaa atc tat acc ttt gga aga ata ttg gga aaa   808
```

```
Gly Ala Ala Ile Glu Glu Ile Tyr Thr Phe Gly Arg Ile Leu Gly Lys
        110                 115                 120 ggg agc ttt gga ata gtc att gaa gcg aca gac aag gaa aca gaa acg      856
Gly Ser Phe Gly Ile Val Ile Glu Ala Thr Asp Lys Glu Thr Glu Thr
125                 130                 135                 140 aag tgg gca att aaa aaa gtg aac aaa gaa aag gct gga agc tct gct      904
Lys Trp Ala Ile Lys Lys Val Asn Lys Glu Lys Ala Gly Ser Ser Ala
                145                 150                 155 gtg aag tta ctt gaa cga gag gtg aac att ctg aaa agt gta aaa cat      952
Val Lys Leu Leu Glu Arg Glu Val Asn Ile Leu Lys Ser Val Lys His
160                 165                 170 gaa cac atc ata cat ctg gaa caa gta ttt gaa acg cca aag aaa atg     1000
Glu His Ile Ile His Leu Glu Gln Val Phe Glu Thr Pro Lys Lys Met
        175                 180                 185 tac ctt gtg atg gag ctt tgt gag gat gga gaa ctc aaa gaa att ctg     1048
Tyr Leu Val Met Glu Leu Cys Glu Asp Gly Glu Leu Lys Glu Ile Leu
        190                 195                 200 gat agg aaa ggg cat ttc tca gag aat gag aca agg tgg atc att caa     1096
Asp Arg Lys Gly His Phe Ser Glu Asn Glu Thr Arg Trp Ile Ile Gln
205                 210                 215                 220 agt ctc gca tca gct ata gca tat ctt cac aat aat gat att gta cat     1144
Ser Leu Ala Ser Ala Ile Ala Tyr Leu His Asn Asn Asp Ile Val His
                225                 230                 235 aga gat ctg aaa ctg gaa aat ata atg gtt aaa agc agt ctt att gat     1192
Arg Asp Leu Lys Leu Glu Asn Ile Met Val Lys Ser Ser Leu Ile Asp
                240                 245                 250 gat aac aat gaa ata aac tta aac ata aag gtg act gat ttt ggc tta     1240
Asp Asn Asn Glu Ile Asn Leu Asn Ile Lys Val Thr Asp Phe Gly Leu
        255                 260                 265 gcg gtg aag aag caa agt agg agt gaa gcc atg ctg cag gcc aca tgt     1288
Ala Val Lys Lys Gln Ser Arg Ser Glu Ala Met Leu Gln Ala Thr Cys
270                 275                 280 ggg act cct atc tat atg gcc cct gaa gtt atc agt gcc cac gac tat     1336
Gly Thr Pro Ile Tyr Met Ala Pro Glu Val Ile Ser Ala His Asp Tyr
285                 290                 295                 300 agc cag cag tgt gac att tgg agc ata ggc gtc gta atg tac atg tta     1384
Ser Gln Gln Cys Asp Ile Trp Ser Ile Gly Val Val Met Tyr Met Leu
                305                 310                 315 tta cgt gga gaa cca ccc ttt ttg gca agc tca gaa gag aag ctt ttt     1432
Leu Arg Gly Glu Pro Pro Phe Leu Ala Ser Ser Glu Glu Lys Leu Phe
                320                 325                 330 gag tta ata aga aaa gga gaa cta cat ttt gaa aat gca gtc tgg aat     1480
Glu Leu Ile Arg Lys Gly Glu Leu His Phe Glu Asn Ala Val Trp Asn
        335                 340                 345 tcc ata agt gac tgt gct aaa agt gtt ttg aaa caa ctt atg aaa gta     1528
Ser Ile Ser Asp Cys Ala Lys Ser Val Leu Lys Gln Leu Met Lys Val
        350                 355                 360 gat cct gct cac aga atc aca gct aag gaa cta cta gat aac cag tgg     1576
Asp Pro Ala His Arg Ile Thr Ala Lys Glu Leu Leu Asp Asn Gln Trp
365                 370                 375                 380 tta aca ggc aat aaa ctt tct tcg gtg aga cca acc aat gta tta gag     1624
Leu Thr Gly Asn Lys Leu Ser Ser Val Arg Pro Thr Asn Val Leu Glu
                385                 390                 395 atg atg aag gaa tgg aaa aat aac cca gaa agt gtt gag gaa aac aca     1672
Met Met Lys Glu Trp Lys Asn Asn Pro Glu Ser Val Glu Glu Asn Thr
                400                 405                 410 aca gaa gag aag aat aag ccg tcc act gaa gaa aag ttg aaa agt tac     1720
Thr Glu Glu Lys Asn Lys Pro Ser Thr Glu Glu Lys Leu Lys Ser Tyr
        415                 420                 425
```

```
caa ccc tgg gga aat gtc cct gat gcc aat tac act tca gat gaa gag    1768
Gln Pro Trp Gly Asn Val Pro Asp Ala Asn Tyr Thr Ser Asp Glu Glu
    430                 435                 440 gag gaa aaa cag tct act gct tat gaa aag caa ttt cct gca acc agt    1816
Glu Glu Lys Gln Ser Thr Ala Tyr Glu Lys Gln Phe Pro Ala Thr Ser
445                 450                 455                 460 aag gac aac ttt gat atg tgc agt tca agt ttc aca tct agc aaa ctc    1864
Lys Asp Asn Phe Asp Met Cys Ser Ser Ser Phe Thr Ser Ser Lys Leu
                465                 470                 475 ctt cca gct gaa atc aag gga gaa atg gag aaa acc cct gtg act cca    1912
Leu Pro Ala Glu Ile Lys Gly Glu Met Glu Lys Thr Pro Val Thr Pro
            480                 485                 490 agc caa gga aca gca acc aag tac cct gct aaa tcc ggc gcc ctg tcc    1960
Ser Gln Gly Thr Ala Thr Lys Tyr Pro Ala Lys Ser Gly Ala Leu Ser
        495                 500                 505 aga acc aaa aag aaa ctc taa ggttccctcc agtgttggac agtacaaaaa       2011
Arg Thr Lys Lys Lys Leu  *
    510 caaagctgct cttgttagca cttttgatgag ggggtaggag gggaagaaga cagccctatg  2071 ctgagcttgt agcctttttag ctccacagag ccccgccatg tgtttgcacc agcttaaaat  2131 tgaagctgct tatctccaaa gcagcataag ctgcacatgg cattaaagga cagccaccag   2191 taggcttggc agtgggctgc agtggaaatc aactcaagat gtacgcgaag gtttttttagg  2251 ggggcagata ccttcaattt aaggctgtgg gcacacttgc tcattttttac ttcaaattct  2311 tatgtttagg cacagctatt tataggggaa acaagaggc caaatatagt aatggaggtg    2371 ccaaataatt atgtgcactt tgcactagaa gactttgtta gaaaattact aataaacttg   2431 ccatacgtat tacaaaaaaa aaaaaaaaaa aaaaa                              2466

<210> SEQ ID NO 39
<211> LENGTH: 514
<212> TYPE: PRT
<213> ORGANISM: Homo sapiens

<400> SEQUENCE: 39

Met Ala Asp Ser Gly Leu Asp Lys Lys Ser Thr Lys Cys Pro Asp Cys
 1               5                   10                  15

Ser Ser Ala Ser Gln Lys Asp Val Leu Cys Val Cys Ser Ser Lys Thr
            20                  25                  30

Arg Val Pro Pro Val Leu Val Val Glu Met Ser Gln Thr Ser Ser Ile
        35                  40                  45

Gly Ser Ala Glu Ser Leu Ile Ser Leu Glu Arg Lys Lys Glu Lys Asn
    50                  55                  60

Ile Asn Arg Asp Ile Thr Ser Arg Lys Asp Leu Pro Ser Arg Thr Ser
65                  70                  75                  80

Asn Val Glu Arg Lys Ala Ser Gln Gln Gln Trp Gly Arg Gly Asn Phe
                85                  90                  95

Thr Glu Gly Lys Val Pro His Ile Arg Ile Glu Asn Gly Ala Ala Ile
            100                 105                 110

Glu Glu Ile Tyr Thr Phe Gly Arg Ile Leu Gly Lys Gly Ser Phe Gly
        115                 120                 125

Ile Val Ile Glu Ala Thr Asp Lys Glu Thr Gly Thr Lys Trp Ala Ile
    130                 135                 140

Lys Lys Val Asn Lys Glu Lys Ala Gly Ser Ser Ala Val Lys Leu Leu
145                 150                 155                 160

Glu Arg Glu Val Asn Ile Leu Lys Ser Val Lys His Glu His Ile Ile
```

```
                        165                 170                 175
His Leu Glu Gln Val Phe Glu Thr Pro Lys Lys Met Tyr Leu Val Met
            180                 185                 190
Glu Leu Cys Glu Asp Gly Glu Leu Lys Glu Ile Leu Asp Arg Lys Gly
        195                 200                 205
His Phe Ser Glu Asn Glu Thr Arg Trp Ile Ile Gln Ser Leu Ala Ser
    210                 215                 220
Ala Ile Ala Tyr Leu His Asn Asn Asp Ile Val His Arg Asp Leu Lys
225                 230                 235                 240
Leu Glu Asn Ile Met Val Lys Ser Ser Leu Ile Asp Asp Asn Asn Glu
                245                 250                 255
Ile Asn Leu Asn Ile Lys Val Thr Asp Phe Gly Leu Ala Val Lys Lys
            260                 265                 270
Gln Ser Arg Ser Glu Ala Met Leu Gln Ala Thr Cys Gly Thr Pro Ile
        275                 280                 285
Tyr Met Ala Pro Glu Val Ile Ser Ala His Asp Tyr Ser Gln Gln Cys
    290                 295                 300
Asp Ile Trp Ser Ile Gly Val Val Met Tyr Met Leu Leu Arg Gly Glu
305                 310                 315                 320
Pro Pro Phe Leu Ala Ser Ser Glu Glu Lys Leu Phe Glu Leu Ile Arg
                325                 330                 335
Lys Gly Glu Leu His Phe Glu Asn Ala Val Trp Asn Ser Ile Ser Asp
            340                 345                 350
Cys Ala Lys Ser Val Leu Lys Gln Leu Met Lys Val Asp Pro Ala His
        355                 360                 365
Arg Ile Thr Ala Lys Glu Leu Leu Asp Asn Gln Trp Leu Thr Gly Asn
    370                 375                 380
Lys Leu Ser Ser Val Arg Pro Thr Asn Val Leu Glu Met Met Lys Glu
385                 390                 395                 400
Trp Lys Asn Asn Pro Glu Ser Val Glu Glu Asn Thr Thr Glu Glu Lys
                405                 410                 415
Asn Lys Pro Ser Thr Glu Glu Lys Leu Lys Ser Tyr Gln Pro Trp Gly
            420                 425                 430
Asn Val Pro Asp Ala Asn Tyr Thr Ser Asp Glu Glu Glu Lys Gln
        435                 440                 445
Ser Thr Ala Tyr Glu Lys Gln Phe Pro Ala Thr Ser Lys Asp Asn Phe
    450                 455                 460
Asp Met Cys Ser Ser Ser Phe Thr Ser Ser Lys Leu Leu Pro Ala Glu
465                 470                 475                 480
Ile Lys Gly Glu Met Glu Lys Thr Pro Val Thr Pro Ser Gln Gly Thr
                485                 490                 495
Ala Thr Lys Tyr Pro Ala Lys Ser Gly Ala Leu Ser Arg Thr Lys Lys
            500                 505                 510
Lys Leu

<210> SEQ ID NO 40
<211> LENGTH: 1545
<212> TYPE: DNA
<213> ORGANISM: Homo sapiens
<220> FEATURE:
<221> NAME/KEY: CDS
<222> LOCATION: (1)...(1545)

<400> SEQUENCE: 40 atg gct gat agt ggc tta gat aaa aaa tcc aca aaa tgc ccc gac tgt      48
```

```
Met Ala Asp Ser Gly Leu Asp Lys Lys Ser Thr Lys Cys Pro Asp Cys
 1               5                  10                  15 tca tct gct tct cag aaa gat gta ctt tgt gta tgt tcc agc aaa aca      96
Ser Ser Ala Ser Gln Lys Asp Val Leu Cys Val Cys Ser Ser Lys Thr
             20                  25                  30 agg gtt cct cca gtt ttg gtg gtg gaa atg tca cag aca tca agc att     144
Arg Val Pro Pro Val Leu Val Val Glu Met Ser Gln Thr Ser Ser Ile
         35                  40                  45 ggt agt gca gaa tct tta att tca ctg gag aga aaa aaa gaa aaa aat     192
Gly Ser Ala Glu Ser Leu Ile Ser Leu Glu Arg Lys Lys Glu Lys Asn
 50                  55                  60 atc aac aga gat ata acc tcc agg aaa gat ttg ccc tca aga acc tca     240
Ile Asn Arg Asp Ile Thr Ser Arg Lys Asp Leu Pro Ser Arg Thr Ser
 65                  70                  75                  80 aat gta gag aga aaa gca tct cag caa caa tgg ggt cgg ggc aac ttt     288
Asn Val Glu Arg Lys Ala Ser Gln Gln Gln Trp Gly Arg Gly Asn Phe
             85                  90                  95 aca gaa gga aaa gtt cct cac ata agg att gag aat gga gct gct att     336
Thr Glu Gly Lys Val Pro His Ile Arg Ile Glu Asn Gly Ala Ala Ile
        100                 105                 110 gag gaa atc tat acc ttt gga aga ata ttg gga aaa ggg agc ttt gga     384
Glu Glu Ile Tyr Thr Phe Gly Arg Ile Leu Gly Lys Gly Ser Phe Gly
        115                 120                 125 ata gtc att gaa gcg aca gac aag gaa aca gaa acg aag tgg gca att     432
Ile Val Ile Glu Ala Thr Asp Lys Glu Thr Glu Thr Lys Trp Ala Ile
130                 135                 140 aaa aaa gtg aac aaa gaa aag gct gga agc tct gct gtg aag tta ctt     480
Lys Lys Val Asn Lys Glu Lys Ala Gly Ser Ser Ala Val Lys Leu Leu
145                 150                 155                 160 gaa cga gag gtg aac att ctg aaa agt gta aaa cat gaa cac atc ata     528
Glu Arg Glu Val Asn Ile Leu Lys Ser Val Lys His Glu His Ile Ile
                165                 170                 175 cat ctg gaa caa gta ttt gaa acg cca aag aaa atg tac ctt gtg atg     576
His Leu Glu Gln Val Phe Glu Thr Pro Lys Lys Met Tyr Leu Val Met
                180                 185                 190 gag ctt tgt gag gat gga gaa ctc aaa gaa att ctg gat agg aaa ggg     624
Glu Leu Cys Glu Asp Gly Glu Leu Lys Glu Ile Leu Asp Arg Lys Gly
            195                 200                 205 cat ttc tca gag aat gag aca agg tgg atc att caa agt ctc gca tca     672
His Phe Ser Glu Asn Glu Thr Arg Trp Ile Ile Gln Ser Leu Ala Ser
        210                 215                 220 gct ata gca tat ctt cac aat aat gat att gta cat aga gat ctg aaa     720
Ala Ile Ala Tyr Leu His Asn Asn Asp Ile Val His Arg Asp Leu Lys
225                 230                 235                 240 ctg gaa aat ata atg gtt aaa agc agt ctt att gat gat aac aat gaa     768
Leu Glu Asn Ile Met Val Lys Ser Ser Leu Ile Asp Asp Asn Asn Glu
                245                 250                 255 ata aac tta aac ata aag gtg act gat ttt ggc tta gcg gtg aag aag     816
Ile Asn Leu Asn Ile Lys Val Thr Asp Phe Gly Leu Ala Val Lys Lys
            260                 265                 270 caa agt agg agt gaa gcc atg ctg cag gcc aca tgt ggg act cct atc     864
Gln Ser Arg Ser Glu Ala Met Leu Gln Ala Thr Cys Gly Thr Pro Ile
        275                 280                 285 tat atg gcc cct gaa gtt atc agt gcc cac gac tat agc cag cag tgt     912
Tyr Met Ala Pro Glu Val Ile Ser Ala His Asp Tyr Ser Gln Gln Cys
290                 295                 300 gac att tgg agc ata ggc gtc gta atg tac atg tta tta cgt gga gaa     960
Asp Ile Trp Ser Ile Gly Val Val Met Tyr Met Leu Leu Arg Gly Glu
305                 310                 315                 320
```

```
cca ccc ttt ttg gca agc tca gaa gag aag ctt ttt gag tta ata aga      1008
Pro Pro Phe Leu Ala Ser Ser Glu Glu Lys Leu Phe Glu Leu Ile Arg
                325                 330                 335 aaa gga gaa cta cat ttt gaa aat gca gtc tgg aat tcc ata agt gac      1056
Lys Gly Glu Leu His Phe Glu Asn Ala Val Trp Asn Ser Ile Ser Asp
            340                 345                 350 tgt gct aaa agt gtt ttg aaa caa ctt atg aaa gta gat cct gct cac      1104
Cys Ala Lys Ser Val Leu Lys Gln Leu Met Lys Val Asp Pro Ala His
        355                 360                 365 aga atc aca gct aag gaa cta cta gat aac cag tgg tta aca ggc aat      1152
Arg Ile Thr Ala Lys Glu Leu Leu Asp Asn Gln Trp Leu Thr Gly Asn
    370                 375                 380 aaa ctt tct tcg gtg aga cca acc aat gta tta gag atg atg aag gaa      1200
Lys Leu Ser Ser Val Arg Pro Thr Asn Val Leu Glu Met Met Lys Glu
385                 390                 395                 400 tgg aaa aat aac cca gaa agt gtt gag gaa aac aca aca gaa gag aag      1248
Trp Lys Asn Asn Pro Glu Ser Val Glu Glu Asn Thr Thr Glu Glu Lys
                405                 410                 415 aat aag ccg tcc act gaa gaa aag ttg aaa agt tac caa ccc tgg gga      1296
Asn Lys Pro Ser Thr Glu Glu Lys Leu Lys Ser Tyr Gln Pro Trp Gly
            420                 425                 430 aat gtc cct gat gcc aat tac act tca gat gaa gag gag aaa cag          1344
Asn Val Pro Asp Ala Asn Tyr Thr Ser Asp Glu Glu Glu Lys Gln
        435                 440                 445 tct act gct tat gaa aag caa ttt cct gca acc agt aag gac aac ttt      1392
Ser Thr Ala Tyr Glu Lys Gln Phe Pro Ala Thr Ser Lys Asp Asn Phe
    450                 455                 460 gat atg tgc agt tca agt ttc aca tct agc aaa ctc ctt cca gct gaa      1440
Asp Met Cys Ser Ser Ser Phe Thr Ser Ser Lys Leu Leu Pro Ala Glu
465                 470                 475                 480 atc aag gga gaa atg gag aaa acc cct gtg act cca agc caa gga aca      1488
Ile Lys Gly Glu Met Glu Lys Thr Pro Val Thr Pro Ser Gln Gly Thr
                485                 490                 495 gca acc aag tac cct gct aaa tcc ggc gcc ctg tcc aga acc aaa aag      1536
Ala Thr Lys Tyr Pro Ala Lys Ser Gly Ala Leu Ser Arg Thr Lys Lys
            500                 505                 510 aaa ctc taa                                                          1545
Lys Leu *

<210> SEQ ID NO 41
<211> LENGTH: 2711
<212> TYPE: DNA
<213> ORGANISM: Homo sapiens
<220> FEATURE:
<221> NAME/KEY: CDS
<222> LOCATION: (198)...(1883)
<220> FEATURE:
<221> NAME/KEY: misc_feature
<222> LOCATION: (1)...(2711)
<223> OTHER INFORMATION: n = A,T,C or G

<400> SEQUENCE: 41
cgcgtccgaa aaaaaaaaa aaaaaaaaaa aangggctgn gctcsrcgmt yccggcccca        60
gcgaggcggt ggggcgggc ggggcggggc gggcgcgca gcaggagcga gtggggccgc       120
cgccgggccg cggacactgt cgcccggcgc ccaggttccc aacaaggcta cgcagaagaa      180 ccccccttgac tgaagca atg gag ggg ggt cca gct gtc tgc tgc cag gat        230
                    Met Glu Gly Gly Pro Ala Val Cys Cys Gln Asp
                     1               5                  10 cct cgg gca gag ctg gta gaa cgg gtg gca gcc atc gat gtg act cac        278
Pro Arg Ala Glu Leu Val Glu Arg Val Ala Ala Ile Asp Val Thr His
        15                  20                  25
```

-continued

| | |
|---|---|
| ttg gag gag gca gat ggt ggc cca gag cct act aga aac ggt gtg gac<br>Leu Glu Glu Ala Asp Gly Gly Pro Glu Pro Thr Arg Asn Gly Val Asp<br>30                           35                      40 | 326 |
| ccc cca cca cgg gcc aga gct gcc tct gtg atc cct ggc agt act tca<br>Pro Pro Pro Arg Ala Arg Ala Ala Ser Val Ile Pro Gly Ser Thr Ser<br>45                       50                        55 | 374 |
| aga ctg ctc cca gcc cgg cct agc ctc tca gcc agg aag ctt tcc cta<br>Arg Leu Leu Pro Ala Arg Pro Ser Leu Ser Ala Arg Lys Leu Ser Leu<br>60                         65                     70                     75 | 422 |
| cag gag cgg cca gca gga agc tat ctg gag gcg cag gct ggg cct tat<br>Gln Glu Arg Pro Ala Gly Ser Tyr Leu Glu Ala Gln Ala Gly Pro Tyr<br>                 80                     85                     90 | 470 |
| gcc acg ggg cct gcc agc cac atc tcc ccc cgg gcc tgg cgg agg ccc<br>Ala Thr Gly Pro Ala Ser His Ile Ser Pro Arg Ala Trp Arg Arg Pro<br>                    95                     100                 105 | 518 |
| acc atc gag tcc cac cac gtg gcc atc tca gat gca gag gac tgc gtg<br>Thr Ile Glu Ser His His Val Ala Ile Ser Asp Ala Glu Asp Cys Val<br>           110                         115                     120 | 566 |
| cag ctg aac cag tac aag ctg cag agt gag att ggc aag ggt gcc tac<br>Gln Leu Asn Gln Tyr Lys Leu Gln Ser Glu Ile Gly Lys Gly Ala Tyr<br>125                       130                     135 | 614 |
| ggt gtg gtg agg ctg gcc tac aac gaa agt gaa gac aga cac tat gca<br>Gly Val Val Arg Leu Ala Tyr Asn Glu Ser Glu Asp Arg His Tyr Ala<br>140                       145                     150                 155 | 662 |
| atg aaa gtc ctt tcc aaa aag aag tta ctg aag cag tat ggc ttt cca<br>Met Lys Val Leu Ser Lys Lys Lys Leu Leu Lys Gln Tyr Gly Phe Pro<br>                    160                        165                 170 | 710 |
| cgt cgc cct ccc cca aga ggg tcc cag gct gcc cag gga gga cca gcc<br>Arg Arg Pro Pro Pro Arg Gly Ser Gln Ala Ala Gln Gly Gly Pro Ala<br>                   175                        180                 185 | 758 |
| aag cag ctg ctg ccc ctg gag cgg gtg tac cag gag att gcc atc ctg<br>Lys Gln Leu Leu Pro Leu Glu Arg Val Tyr Gln Glu Ile Ala Ile Leu<br>           190                         195                     200 | 806 |
| aag aag ctg gac cac gtg aat gtg gtc aaa ctg atc gag gtc ctg gat<br>Lys Lys Leu Asp His Val Asn Val Val Lys Leu Ile Glu Val Leu Asp<br>205                       210                     215 | 854 |
| gac cca gct gag gac aac ctc tat ttg gtg ttt gac ctc ctg aga aag<br>Asp Pro Ala Glu Asp Asn Leu Tyr Leu Val Phe Asp Leu Leu Arg Lys<br>220                       225                     230                 235 | 902 |
| ggg ccc gtc atg gaa gtg ccc tgt gac aag ccc ttc tcg gag gag caa<br>Gly Pro Val Met Glu Val Pro Cys Asp Lys Pro Phe Ser Glu Glu Gln<br>                   240                        245                 250 | 950 |
| gct cgc ctc tac ctg cgg gac gtc atc ctg ggc ctc gag tac ttg cac<br>Ala Arg Leu Tyr Leu Arg Asp Val Ile Leu Gly Leu Glu Tyr Leu His<br>                   255                        260                 265 | 998 |
| tgc cag aag atc gtc cac agg gac atc aag cca tcc aac ctg ctc ctg<br>Cys Gln Lys Ile Val His Arg Asp Ile Lys Pro Ser Asn Leu Leu Leu<br>           270                         275                     280 | 1046 |
| ggg gat gat ggg cac gtg aag atc gcc gac ttt ggc gtc agc aac cag<br>Gly Asp Asp Gly His Val Lys Ile Ala Asp Phe Gly Val Ser Asn Gln<br>285                       290                     295 | 1094 |
| ttt gag ggg aac gac gct cag ctg tcc agc acg gcg gga acc cca gca<br>Phe Glu Gly Asn Asp Ala Gln Leu Ser Ser Thr Ala Gly Thr Pro Ala<br>300                       305                     310                 315 | 1142 |
| ttc atg gcc ccc gag gcc att tct gat tcc ggc cag agc ttc agt ggg<br>Phe Met Ala Pro Glu Ala Ile Ser Asp Ser Gly Gln Ser Phe Ser Gly<br>                   320                        325                 330 | 1190 |
| aag gcc ttg gat gta tgg gcc act ggc gtc acg ttg tac tgc ttt gtc<br>Lys Ala Leu Asp Val Trp Ala Thr Gly Val Thr Leu Tyr Cys Phe Val | 1238 |

-continued

```
                335                  340                  345
tat ggg aag tgc ccg ttc atc gac gat ttc atc ctg gcc ctc cac agg      1286
Tyr Gly Lys Cys Pro Phe Ile Asp Asp Phe Ile Leu Ala Leu His Arg
            350                  355                  360 aag atc aag aat gag ccc gtg gtg ttt cct gag ggg cca gaa atc agc      1334
Lys Ile Lys Asn Glu Pro Val Val Phe Pro Glu Gly Pro Glu Ile Ser
365                  370                  375 gag gag ctc aag gac ctg atc ctg aag atg tta gac aag aat ccc gag      1382
Glu Glu Leu Lys Asp Leu Ile Leu Lys Met Leu Asp Lys Asn Pro Glu
380                  385                  390                  395 acg aga att ggg gtg cca gac atc aag ttg cac cct tgg gtg acc aag      1430
Thr Arg Ile Gly Val Pro Asp Ile Lys Leu His Pro Trp Val Thr Lys
            400                  405                  410 aac ggg gag gag ccc ctt cct tcg gag gag gag cac tgc agc gtg gtg      1478
Asn Gly Glu Glu Pro Leu Pro Ser Glu Glu Glu His Cys Ser Val Val
            415                  420                  425 gag gtg aca gag gag gag gtt aag aac tca gtc agg ctc atc ccc agc      1526
Glu Val Thr Glu Glu Glu Val Lys Asn Ser Val Arg Leu Ile Pro Ser
            430                  435                  440 tgg acc acg gtg atc ctg gtg aag tcc atg ctg agg aag cgt tcc ttt      1574
Trp Thr Thr Val Ile Leu Val Lys Ser Met Leu Arg Lys Arg Ser Phe
            445                  450                  455 ggg aac ccg ttt gag ccc caa gca cgg agg gaa gag cga tcc atg tct      1622
Gly Asn Pro Phe Glu Pro Gln Ala Arg Arg Glu Glu Arg Ser Met Ser
460                  465                  470                  475 gct cca gga aac cta ctg gtg aaa gaa ggg ttt ggt gaa ggg ggc aag      1670
Ala Pro Gly Asn Leu Leu Val Lys Glu Gly Phe Gly Glu Gly Gly Lys
            480                  485                  490 agc cca gag ctc ccc ggc gtc cag gct tac cac aac gga aga gac ctc      1718
Ser Pro Glu Leu Pro Gly Val Gln Ala Tyr His Asn Gly Arg Asp Leu
            495                  500                  505 ccg ctg ggg ccg ggc agg cct ggc tca gct gcc aca ggc ata tgg tgg      1766
Pro Leu Gly Pro Gly Arg Pro Gly Ser Ala Ala Thr Gly Ile Trp Trp
            510                  515                  520 aga ggg ggg tac cct gcc cac ctt ggg gtg gtg gca cca gag ctc ttg      1814
Arg Gly Gly Tyr Pro Ala His Leu Gly Val Val Ala Pro Glu Leu Leu
525                  530                  535 tct att cag acg ctg gta tgg ggg ctc gga ccc ctc act ggg gac agg      1862
Ser Ile Gln Thr Leu Val Trp Gly Leu Gly Pro Leu Thr Gly Asp Arg
540                  545                  550                  555 gcc agt gtt gga gaa ttc tga ttccttttt gttgtctttt acttttgttt          1913
Ala Ser Val Gly Glu Phe  *
                560 ttaacctggg ggttcgggga gaggccctgc ttgggaacat ctcacgagct ttcctacatc    1973 ttccgtggtt cccagcacag cccaagatta tttggcagcc aagtggatgg aactaacttt    2033 cctggactgt gtttcgcatt cggcgttatc tggaaagtgg actgaacgga atcaagctct    2093 gagcagaggc ctgaagcgga agcaccacat cgtccctgcc catctcactc tctcccttga    2153 tgatgcccct agagctgagg ctggagaaga caccagggct gactttgacc gagggccatg    2213 gacgcgacag gcctgtggcc ctgcgcatgc tgaaataact ggaacccagc ctctcctcct    2273 acaccggcct acccatctgg gcccaagagc tgcactcaca ctcctacaac gaaggacaaa    2333 ctgtccaggt cggagggatc acgagacaca gaacctggag gggtgtgcac gctggcaggt    2393 ggcctctgcg gcaattgcct caccctgagg acatcagcag tcagcctgct tcagaagcgg    2453 nggtgctgga gcgccgtgca gacacaagct ttttcggagc aggccttcac cttctctntg    2513 ggatcaagtg tcccggctgg cccgacgtgg catttgctga cccgaatgct tatagaggtt    2573
```

```
gacccccaac agggtcaccg cangactcgg gacactgccc tggaaaacat ggatggacaa    2633
ggggcttttg gccacaggtg tgggtgtcct gttggaggan ggctttgttt ggagaangga    2693
ggcttgctgg gggagaaa                                                  2711
```

<210> SEQ ID NO 42
<211> LENGTH: 561
<212> TYPE: PRT
<213> ORGANISM: Homo sapiens

<400> SEQUENCE: 42

```
Met Glu Gly Gly Pro Ala Val Cys Cys Gln Asp Pro Arg Ala Glu Leu
 1               5                  10                  15

Val Glu Arg Val Ala Ala Ile Asp Val Thr His Leu Glu Glu Ala Asp
            20                  25                  30

Gly Gly Pro Glu Pro Thr Arg Asn Gly Val Asp Pro Pro Arg Ala
        35                  40                  45

Arg Ala Ser Val Ile Pro Gly Ser Thr Ser Arg Leu Leu Pro Ala
 50                  55                  60

Arg Pro Ser Leu Ser Ala Arg Lys Leu Ser Leu Gln Glu Arg Pro Ala
 65                  70                  75                  80

Gly Ser Tyr Leu Glu Ala Gln Ala Gly Pro Tyr Ala Thr Gly Pro Ala
                85                  90                  95

Ser His Ile Ser Pro Arg Ala Trp Arg Arg Pro Thr Ile Glu Ser His
            100                 105                 110

His Val Ala Ile Ser Asp Ala Glu Asp Cys Val Gln Leu Asn Gln Tyr
        115                 120                 125

Lys Leu Gln Ser Glu Ile Gly Lys Gly Ala Tyr Gly Val Val Arg Leu
    130                 135                 140

Ala Tyr Asn Glu Ser Glu Asp Arg His Tyr Ala Met Lys Val Leu Ser
145                 150                 155                 160

Lys Lys Lys Leu Leu Lys Gln Tyr Gly Phe Pro Arg Arg Pro Pro Pro
                165                 170                 175

Arg Gly Ser Gln Ala Ala Gln Gly Gly Pro Ala Lys Gln Leu Leu Pro
            180                 185                 190

Leu Glu Arg Val Tyr Gln Glu Ile Ala Ile Leu Lys Lys Leu Asp His
        195                 200                 205

Val Asn Val Val Lys Leu Ile Glu Val Leu Asp Asp Pro Ala Glu Asp
    210                 215                 220

Asn Leu Tyr Leu Val Phe Asp Leu Leu Arg Lys Gly Pro Val Met Glu
225                 230                 235                 240

Val Pro Cys Asp Lys Pro Phe Ser Glu Glu Gln Ala Arg Leu Tyr Leu
                245                 250                 255

Arg Asp Val Ile Leu Gly Leu Glu Tyr Leu His Cys Gln Lys Ile Val
            260                 265                 270

His Arg Asp Ile Lys Pro Ser Asn Leu Leu Leu Gly Asp Asp Gly His
        275                 280                 285

Val Lys Ile Ala Asp Phe Gly Val Ser Asn Gln Phe Glu Gly Asn Asp
    290                 295                 300

Ala Gln Leu Ser Ser Thr Ala Gly Thr Pro Ala Phe Met Ala Pro Glu
305                 310                 315                 320

Ala Ile Ser Asp Ser Gly Gln Ser Phe Ser Gly Lys Ala Leu Asp Val
                325                 330                 335

Trp Ala Thr Gly Val Thr Leu Tyr Cys Phe Val Tyr Gly Lys Cys Pro
```

```
                     340                 345                 350
Phe Ile Asp Asp Phe Ile Leu Ala Leu His Arg Lys Ile Lys Asn Glu
                355                 360                 365
Pro Val Val Phe Pro Glu Gly Pro Glu Ile Ser Glu Glu Leu Lys Asp
            370                 375                 380
Leu Ile Leu Lys Met Leu Asp Lys Asn Pro Glu Thr Arg Ile Gly Val
385                 390                 395                 400
Pro Asp Ile Lys Leu His Pro Trp Val Thr Lys Asn Gly Glu Glu Pro
                405                 410                 415
Leu Pro Ser Glu Glu His Cys Ser Val Glu Val Thr Glu Glu
                420                 425                 430
Glu Val Lys Asn Ser Val Arg Leu Ile Pro Ser Trp Thr Thr Val Ile
                435                 440                 445
Leu Val Lys Ser Met Leu Arg Lys Arg Ser Phe Gly Asn Pro Phe Glu
            450                 455                 460
Pro Gln Ala Arg Arg Glu Glu Arg Ser Met Ser Ala Pro Gly Asn Leu
465                 470                 475                 480
Leu Val Lys Glu Gly Phe Gly Glu Gly Lys Ser Pro Glu Leu Pro
                485                 490                 495
Gly Val Gln Ala Tyr His Asn Gly Arg Asp Leu Pro Leu Gly Pro Gly
                500                 505                 510
Arg Pro Gly Ser Ala Ala Thr Gly Ile Trp Trp Arg Gly Gly Tyr Pro
            515                 520                 525
Ala His Leu Gly Val Val Ala Pro Glu Leu Leu Ser Ile Gln Thr Leu
            530                 535                 540
Val Trp Gly Leu Gly Pro Leu Thr Gly Asp Arg Ala Ser Val Gly Glu
545                 550                 555                 560
Phe

<210> SEQ ID NO 43
<211> LENGTH: 1686
<212> TYPE: DNA
<213> ORGANISM: Homo sapiens
<220> FEATURE:
<221> NAME/KEY: CDS
<222> LOCATION: (1)...(1686)

<400> SEQUENCE: 43 atg gag ggg ggt cca gct gtc tgc tgc cag gat cct cgg gca gag ctg      48
Met Glu Gly Gly Pro Ala Val Cys Cys Gln Asp Pro Arg Ala Glu Leu
 1               5                  10                  15 gta gaa cgg gtg gca gcc atc gat gtg act cac ttg gag gag gca gat      96
Val Glu Arg Val Ala Ala Ile Asp Val Thr His Leu Glu Glu Ala Asp
             20                  25                  30 ggt ggc cca gag cct act aga aac ggt gtg gac ccc cca cca cgg gcc     144
Gly Gly Pro Glu Pro Thr Arg Asn Gly Val Asp Pro Pro Pro Arg Ala
         35                  40                  45 aga gct gcc tct gtg atc cct ggc agt act tca aga ctg ctc cca gcc     192
Arg Ala Ala Ser Val Ile Pro Gly Ser Thr Ser Arg Leu Leu Pro Ala
     50                  55                  60 cgg cct agc ctc tca gcc agg aag ctt tcc cta cag gag cgg cca gca     240
Arg Pro Ser Leu Ser Ala Arg Lys Leu Ser Leu Gln Glu Arg Pro Ala
 65                  70                  75                  80 gga agc tat ctg gag gcg cag gct ggg cct tat gcc acg ggg cct gcc     288
Gly Ser Tyr Leu Glu Ala Gln Ala Gly Pro Tyr Ala Thr Gly Pro Ala
                 85                  90                  95 agc cac atc tcc ccc cgg gcc tgg cgg agg ccc acc atc gag tcc cac     336
```

```
                Ser His Ile Ser Pro Arg Ala Trp Arg Arg Pro Thr Ile Glu Ser His
                            100                 105                 110 cac gtg gcc atc tca gat gca gag gac tgc gtg cag ctg aac cag tac        384
His Val Ala Ile Ser Asp Ala Glu Asp Cys Val Gln Leu Asn Gln Tyr
            115                 120                 125 aag ctg cag agt gag att ggc aag ggt gcc tac ggt gtg gtg agg ctg        432
Lys Leu Gln Ser Glu Ile Gly Lys Gly Ala Tyr Gly Val Val Arg Leu
130                 135                 140 gcc tac aac gaa agt gaa gac aga cac tat gca atg aaa gtc ctt tcc        480
Ala Tyr Asn Glu Ser Glu Asp Arg His Tyr Ala Met Lys Val Leu Ser
145                 150                 155                 160 aaa aag aag tta ctg aag cag tat ggc ttt cca cgt cgc cct ccc cca        528
Lys Lys Lys Leu Leu Lys Gln Tyr Gly Phe Pro Arg Arg Pro Pro Pro
                165                 170                 175 aga ggg tcc cag gct gcc cag gga gga cca gcc aag cag ctg ctg ccc        576
Arg Gly Ser Gln Ala Ala Gln Gly Gly Pro Ala Lys Gln Leu Leu Pro
            180                 185                 190 ctg gag cgg gtg tac cag gag att gcc atc ctg aag aag ctg gac cac        624
Leu Glu Arg Val Tyr Gln Glu Ile Ala Ile Leu Lys Lys Leu Asp His
        195                 200                 205 gtg aat gtg gtc aaa ctg atc gag gtc ctg gat gac cca gct gag gac        672
Val Asn Val Val Lys Leu Ile Glu Val Leu Asp Asp Pro Ala Glu Asp
210                 215                 220 aac ctc tat ttg gtg ttt gac ctc ctg aga aag ggg ccc gtc atg gaa        720
Asn Leu Tyr Leu Val Phe Asp Leu Leu Arg Lys Gly Pro Val Met Glu
225                 230                 235                 240 gtg ccc tgt gac aag ccc ttc tcg gag gag caa gct cgc ctc tac ctg        768
Val Pro Cys Asp Lys Pro Phe Ser Glu Glu Gln Ala Arg Leu Tyr Leu
                245                 250                 255 cgg gac gtc atc ctg ggc ctc gag tac ttg cac tgc cag aag atc gtc        816
Arg Asp Val Ile Leu Gly Leu Glu Tyr Leu His Cys Gln Lys Ile Val
            260                 265                 270 cac agg gac atc aag cca tcc aac ctg ctc ctg ggg gat gat ggg cac        864
His Arg Asp Ile Lys Pro Ser Asn Leu Leu Leu Gly Asp Asp Gly His
        275                 280                 285 gtg aag atc gcc gac ttt ggc gtc agc aac cag ttt gag ggg aac gac        912
Val Lys Ile Ala Asp Phe Gly Val Ser Asn Gln Phe Glu Gly Asn Asp
290                 295                 300 gct cag ctg tcc agc acg gcg gga acc cca gca ttc atg gcc ccc gag        960
Ala Gln Leu Ser Ser Thr Ala Gly Thr Pro Ala Phe Met Ala Pro Glu
305                 310                 315                 320 gcc att tct gat tcc ggc cag agc ttc agt ggg aag gcc ttg gat gta       1008
Ala Ile Ser Asp Ser Gly Gln Ser Phe Ser Gly Lys Ala Leu Asp Val
                325                 330                 335 tgg gcc act ggc gtc acg ttg tac tgc ttt gtc tat ggg aag tgc ccg       1056
Trp Ala Thr Gly Val Thr Leu Tyr Cys Phe Val Tyr Gly Lys Cys Pro
            340                 345                 350 ttc atc gac gat ttc atc ctg gcc ctc cac agg aag atc aag aat gag       1104
Phe Ile Asp Asp Phe Ile Leu Ala Leu His Arg Lys Ile Lys Asn Glu
        355                 360                 365 ccc gtg gtg ttt cct gag ggg cca gaa atc agc gag gag ctc aag gac       1152
Pro Val Val Phe Pro Glu Gly Pro Glu Ile Ser Glu Glu Leu Lys Asp
370                 375                 380 ctg atc ctg aag atg tta gac aag aat ccc gag acg aga att ggg gtg       1200
Leu Ile Leu Lys Met Leu Asp Lys Asn Pro Glu Thr Arg Ile Gly Val
385                 390                 395                 400 cca gac atc aag ttg cac cct tgg gtg acc aag aac ggg gag gag ccc       1248
Pro Asp Ile Lys Leu His Pro Trp Val Thr Lys Asn Gly Glu Glu Pro
                405                 410                 415
```

```
ctt cct tcg gag gag gag cac tgc agc gtg gtg gag gtg aca gag gag      1296
Leu Pro Ser Glu Glu Glu His Cys Ser Val Val Glu Val Thr Glu Glu
        420                 425                 430 gag gtt aag aac tca gtc agg ctc atc ccc agc tgg acc acg gtg atc      1344
Glu Val Lys Asn Ser Val Arg Leu Ile Pro Ser Trp Thr Thr Val Ile
435                 440                 445 ctg gtg aag tcc atg ctg agg aag cgt tcc ttt ggg aac ccg ttt gag      1392
Leu Val Lys Ser Met Leu Arg Lys Arg Ser Phe Gly Asn Pro Phe Glu
    450                 455                 460 ccc caa gca cgg agg gaa gag cga tcc atg tct gct cca gga aac cta      1440
Pro Gln Ala Arg Arg Glu Glu Arg Ser Met Ser Ala Pro Gly Asn Leu
465                 470                 475                 480 ctg gtg aaa gaa ggg ttt ggt gaa ggg ggc aag agc cca gag ctc ccc      1488
Leu Val Lys Glu Gly Phe Gly Glu Gly Gly Lys Ser Pro Glu Leu Pro
                485                 490                 495 ggc gtc cag gct tac cac aac gga aga gac ctc ccg ctg ggg ccg ggc      1536
Gly Val Gln Ala Tyr His Asn Gly Arg Asp Leu Pro Leu Gly Pro Gly
            500                 505                 510 agg cct ggc tca gct gcc aca ggc ata tgg tgg aga ggg ggg tac cct      1584
Arg Pro Gly Ser Ala Ala Thr Gly Ile Trp Trp Arg Gly Gly Tyr Pro
        515                 520                 525 gcc cac ctt ggg gtg gtg gca cca gag ctc ttg tct att cag acg ctg      1632
Ala His Leu Gly Val Val Ala Pro Glu Leu Leu Ser Ile Gln Thr Leu
530                 535                 540 gta tgg ggg ctc gga ccc ctc act ggg gac agg gcc agt gtt gga gaa      1680
Val Trp Gly Leu Gly Pro Leu Thr Gly Asp Arg Ala Ser Val Gly Glu
545                 550                 555                 560 ttc tga                                                              1686
Phe  *

<210> SEQ ID NO 44
<211> LENGTH: 178
<212> TYPE: PRT
<213> ORGANISM: Artificial Sequence
<220> FEATURE:
<223> OTHER INFORMATION: Consensus amino acid sequence

<400> SEQUENCE: 44

Glu Val Thr Leu Leu Asp Thr Lys Thr Ala Thr Gly Glu Leu Gly Trp
1               5                   10                  15

Leu Thr Tyr Pro Val Pro Ser Gly Trp Glu Glu Val Ser Gly Leu Asp
            20                  25                  30

Glu Asn Asn Arg Pro Ile Arg Thr Tyr Gln Val Cys Asn Val Met Glu
        35                  40                  45

Pro Asn Gln Asn Asn Trp Leu Arg Thr Asn Trp Ile Glu Arg Arg Gly
    50                  55                  60

Ala Gln Arg Val Tyr Val Glu Leu Lys Phe Thr Val Arg Asp Cys Asn
65                  70                  75                  80

Ser Leu Pro Gly Val Leu Gly Thr Cys Lys Glu Thr Phe Asn Leu Tyr
                85                  90                  95

Tyr Tyr Glu Ser Asp Glu Asp Val Gly Thr Ala Leu Pro Ala Trp Arg
            100                 105                 110

Glu Asn Gln Tyr Ile Lys Val Asp Thr Ile Ala Ala Asp Glu Ser Phe
        115                 120                 125

Thr Gln Val Asp Leu Gly Asp Arg Val Leu Lys Leu Asn Thr Glu Val
    130                 135                 140

Arg Ser Val Gly Pro Leu Ser Lys Lys Gly Phe Tyr Leu Ala Phe Gln
145                 150                 155                 160
```

```
Asp Val Gly Ala Cys Ile Ala Leu Val Ser Val Arg Val Phe Tyr Lys
                165                 170                 175

Lys Cys

<210> SEQ ID NO 45
<211> LENGTH: 273
<212> TYPE: PRT
<213> ORGANISM: Artificial Sequence
<220> FEATURE:
<223> OTHER INFORMATION: Consensus amino acid sequence

<400> SEQUENCE: 45

Tyr Glu Leu Leu Glu Lys Leu Gly Glu Gly Ser Phe Gly Lys Val Tyr
  1               5                  10                  15

Lys Ala Lys His Lys Thr Gly Lys Ile Val Ala Val Lys Ile Leu Lys
                 20                  25                  30

Lys Glu Ser Leu Ser Leu Arg Glu Ile Gln Ile Leu Lys Arg Leu Ser
             35                  40                  45

His Pro Asn Ile Val Arg Leu Leu Gly Val Phe Glu Asp Thr Asp Asp
         50                  55                  60

His Leu Tyr Leu Val Met Glu Tyr Met Glu Gly Gly Asp Leu Phe Asp
 65                  70                  75                  80

Tyr Leu Arg Arg Asn Gly Pro Leu Ser Glu Lys Glu Ala Lys Lys Ile
                 85                  90                  95

Ala Leu Gln Ile Leu Arg Gly Leu Glu Tyr Leu His Ser Asn Gly Ile
                100                 105                 110

Val His Arg Asp Leu Lys Pro Glu Asn Ile Leu Leu Asp Glu Asn Gly
            115                 120                 125

Thr Val Lys Ile Ala Asp Phe Gly Leu Ala Arg Leu Leu Glu Lys Leu
        130                 135                 140

Thr Thr Phe Val Gly Thr Pro Trp Tyr Met Met Ala Pro Glu Val Ile
145                 150                 155                 160

Leu Glu Gly Arg Gly Tyr Ser Ser Lys Val Asp Val Trp Ser Leu Gly
                165                 170                 175

Val Ile Leu Tyr Glu Leu Leu Thr Gly Gly Pro Leu Phe Pro Gly Ala
                180                 185                 190

Asp Leu Pro Ala Phe Thr Gly Gly Asp Glu Val Asp Gln Leu Ile Ile
            195                 200                 205

Phe Val Leu Lys Leu Pro Phe Ser Asp Glu Leu Pro Lys Thr Arg Ile
        210                 215                 220

Asp Pro Leu Glu Glu Leu Phe Arg Ile Lys Lys Arg Arg Leu Pro Leu
225                 230                 235                 240

Pro Ser Asn Cys Ser Glu Glu Leu Lys Asp Leu Leu Lys Lys Cys Leu
                245                 250                 255

Asn Lys Asp Pro Ser Lys Arg Pro Gly Ser Ala Thr Ala Lys Glu Ile
            260                 265                 270

Leu

<210> SEQ ID NO 46
<211> LENGTH: 180
<212> TYPE: PRT
<213> ORGANISM: Artificial Sequence
<220> FEATURE:
<223> OTHER INFORMATION: Consensus amino acid sequence

<400> SEQUENCE: 46

Glu Val Thr Leu Leu Asp Thr Lys Thr Val Gln Gly Glu Leu Gly Trp
```

-continued

```
                1               5                  10                 15
Ile Thr Tyr Pro Pro Gln Asn Gly Gly Trp Glu Glu Val Ser Gly Met
                20                 25                 30

Asp Glu Asn Asn Thr Pro Ile Arg Thr Tyr Gln Val Cys Asn Val Met
                35                 40                 45

Glu Pro His Asn Gln Asn Asn Trp Leu Arg Thr Asn Trp Ile Pro Arg
 50                 55                 60

Arg Gly Ala Gln Arg Ile Tyr Val Glu Leu Lys Phe Thr Val Arg Asp
 65                 70                 75                 80

Cys Asn Ser Leu Pro Gly Val Ala Gly Thr Cys Lys Glu Thr Phe Asn
                85                 90                 95

Leu Tyr Tyr Tyr Glu Ser Asp Glu Asp Thr Gly Thr Ala Thr Ser Pro
                100                105                110

Asn Trp Arg Glu Asn Gln Tyr Val Lys Ile Asp Thr Ile Ala Ala Asp
                115                120                125

Glu Ser Phe Thr Gln Met Asp Leu Gly Asp Arg Val Met Lys Leu Asn
                130                135                140

Thr Glu Val Arg Ser Ile Gly Pro Leu Ser Lys Lys Gly Phe Tyr Leu
145                 150                155                160

Ala Phe Gln Asp Val Gly Ala Cys Ile Ala Leu Ile Ser Val Arg Val
                165                170                175

Tyr Tyr Lys Lys
                180

<210> SEQ ID NO 47
<211> LENGTH: 127
<212> TYPE: PRT
<213> ORGANISM: Artificial Sequence
<220> FEATURE:
<223> OTHER INFORMATION: Consensus amino acid sequence

<400> SEQUENCE: 47

Tyr Arg Ala Pro Ser Asp Pro Pro Ser Met Pro Cys Thr Arg Pro Pro
 1               5                  10                 15

Ser Ala Pro Arg Asn Leu Ile Ser Asn Phe Val Asn Glu Thr Ser Val
                20                 25                 30

Met Leu Glu Trp Ser Pro Pro Ala Asp Thr Gly Gly Arg Ser Asp Ile
                35                 40                 45

Thr Tyr Asn Val Ile Cys Lys Lys Cys Arg Ser Trp Gly Asp Lys Gly
 50                 55                 60

Lys Cys Asn Pro Cys Gly Asp Asn Val His Phe Ser Pro Arg Gln Thr
 65                 70                 75                 80

Gly Leu Thr Glu Thr Arg Val Thr Val Thr Asp Leu Glu Pro His Thr
                85                 90                 95

Asn Tyr Thr Phe Glu Val Glu Ala Val Asn Gly Val Ser Asp Leu Ser
                100                105                110

Pro Ser Pro Pro Gln Tyr Ala Ser Val Asn Val Thr Thr Asn Gln
                115                120                125

<210> SEQ ID NO 48
<211> LENGTH: 50
<212> TYPE: PRT
<213> ORGANISM: Artificial Sequence
<220> FEATURE:
<223> OTHER INFORMATION: Consensus amino acid sequence

<400> SEQUENCE: 48
```

```
Glu Gly Val Val Thr Lys Arg Ser Phe Pro Ala Ile Gly Val Glu Ala
 1               5                  10                  15

Phe Cys Pro Ser Phe Leu Arg Ala Gly Phe Leu Asn Gly Ile Gln Ala
                20                  25                  30

Pro His Pro Val Pro Gly Gly Gly Ser Leu Pro Pro Arg Ile Pro Ala
                35                  40                  45

Gly Arg
    50

<210> SEQ ID NO 49
<211> LENGTH: 59
<212> TYPE: PRT
<213> ORGANISM: Artificial Sequence
<220> FEATURE:
<223> OTHER INFORMATION: Consensus amino acid sequence

<400> SEQUENCE: 49

Leu Gly Lys Cys Lys Cys Lys Ala Gly Tyr Glu Pro Asn Glu Asn Asn
 1               5                  10                  15

Lys Thr Cys Gln Ala Cys Pro Pro Gly Thr Tyr Lys Ala Glu Ala Gly
                20                  25                  30

Asp Ser Ser Cys Ser Pro Cys Pro Pro His Ser Thr Thr Thr Ser Glu
                35                  40                  45

Gly Ser Thr Thr Cys Thr Cys Glu Cys Gly Tyr
    50                  55

<210> SEQ ID NO 50
<211> LENGTH: 178
<212> TYPE: PRT
<213> ORGANISM: Artificial Sequence
<220> FEATURE:
<223> OTHER INFORMATION: Consensus amino acid sequence

<400> SEQUENCE: 50

Met Val Gln Glu Tyr Val Arg Tyr Gly Pro Leu Asp Leu Phe Leu His
 1               5                  10                  15

Lys Asn Lys Pro Asn Val Thr Leu His Trp Lys Leu Asp Val Ala Lys
                20                  25                  30

Gln Leu Ala Arg Ala Met His Tyr Leu Glu Asp Lys Lys Leu Val His
                35                  40                  45

Gly Asn Val Cys Cys Lys Asn Ile Leu Val Thr Arg Glu Gly Pro Glu
    50                  55                  60

Lys Asn Ser Tyr Pro Pro Phe Ile Lys Leu Ser Asp Pro Gly Ile Pro
65                  70                  75                  80

Ile Thr Val Leu Thr Arg Glu Tyr Arg Val Glu Arg Ile Pro Trp Ile
                85                  90                  95

Pro Pro Glu Cys Ile Glu Asn Pro Gln Asn Leu Lys Thr Asp Gln Phe
                100                 105                 110

Ala Asp Lys Trp Ser Phe Gly Thr Thr Leu Trp Glu Ile Cys Ser Asn
                115                 120                 125

Gly Glu Glu Pro Leu Ser Thr Leu Arg Gln Glu Glu Leu Lys Glu Arg
                130                 135                 140

Phe Tyr Glu Asp Arg His Gln Leu Pro Ala Pro Lys Trp Lys Glu Leu
145                 150                 155                 160

Ala Asn Leu Ile Asn His Cys Met Asp Tyr Asp Pro Thr Gln Arg Pro
                165                 170                 175

Phe Phe
```

```
<210> SEQ ID NO 51
<211> LENGTH: 55
<212> TYPE: PRT
<213> ORGANISM: Artificial Sequence
<220> FEATURE:
<223> OTHER INFORMATION: Consensus amino acid sequence

<400> SEQUENCE: 51

Arg Arg Lys Gly Tyr Ser Lys Ala Glu Gln Glu Tyr Asp Glu Lys Lys
 1               5                   10                  15

Gln His Tyr His Asn Gly His Leu Lys Ala Pro Gly Val Lys Thr Tyr
            20                  25                  30

Ile Asp Pro Phe Thr Tyr Glu Asp Pro Asn Gln Ala Val Arg Glu Phe
        35                  40                  45

Ala Lys Glu Ile Asp Val Ser
    50                  55

<210> SEQ ID NO 52
<211> LENGTH: 278
<212> TYPE: PRT
<213> ORGANISM: Artificial Sequence
<220> FEATURE:
<223> OTHER INFORMATION: Consensus amino acid sequence

<400> SEQUENCE: 52

Tyr Glu Leu Leu Glu Lys Leu Gly Glu Gly Ser Phe Gly Lys Val Tyr
 1               5                   10                  15

Lys Ala Lys His Lys Thr Gly Lys Ile Val Ala Val Lys Ile Leu Lys
            20                  25                  30

Lys Glu Ser Leu Ser Leu Arg Glu Ile Gln Ile Leu Lys Arg Leu Ser
            35                  40                  45

His Pro Asn Ile Val Arg Leu Leu Gly Val Phe Glu Asp Thr Asp Asp
        50                  55                  60

His Leu Tyr Leu Val Met Glu Tyr Met Glu Gly Gly Asp Leu Phe Asp
65                  70                  75                  80

Tyr Leu Arg Arg Asn Gly Pro Leu Ser Glu Lys Glu Ala Lys Lys Ile
                85                  90                  95

Ala Leu Gln Ile Leu Arg Gly Leu Glu Tyr Leu His Ser Asn Gly Ile
            100                 105                 110

Val His Arg Asp Leu Lys Pro Glu Asn Ile Leu Leu Asp Glu Asn Gly
        115                 120                 125

Thr Val Lys Ile Ala Asp Phe Gly Leu Ala Arg Leu Leu Glu Lys Leu
    130                 135                 140

Thr Thr Phe Val Gly Thr Pro Trp Tyr Met Met Ala Pro Glu Val Ile
145                 150                 155                 160

Leu Glu Gly Arg Gly Tyr Ser Ser Lys Val Asp Val Trp Ser Leu Gly
                165                 170                 175

Val Ile Leu Tyr Glu Leu Leu Thr Gly Gly Pro Leu Phe Pro Gly Ala
            180                 185                 190

Asp Leu Pro Ala Phe Thr Gly Gly Asp Glu Val Asp Gln Leu Ile Ile
        195                 200                 205

Phe Val Leu Lys Leu Pro Phe Ser Asp Glu Leu Pro Lys Thr Arg Ile
    210                 215                 220

Asp Pro Leu Glu Glu Leu Phe Arg Ile Lys Lys Arg Arg Leu Pro Leu
225                 230                 235                 240

Pro Ser Asn Cys Ser Glu Glu Leu Lys Asp Leu Leu Lys Lys Cys Leu
                245                 250                 255
```

```
Asn Lys Asp Pro Ser Lys Arg Pro Gly Ser Ala Thr Ala Lys Glu Ile
            260                 265                 270

Leu Asn His Pro Trp Phe
        275

<210> SEQ ID NO 53
<211> LENGTH: 48
<212> TYPE: PRT
<213> ORGANISM: Artificial Sequence
<220> FEATURE:
<223> OTHER INFORMATION: Consensus amino acid sequence

<400> SEQUENCE: 53

Gly Thr Arg Trp Tyr Met Ala Pro Glu Val Leu Met Gly Ser Ser Tyr
1               5                   10                  15

Gly Gln Tyr Ser Glu Lys Ser Asp Val Trp Ser Phe Gly Val Ile Leu
            20                  25                  30

Tyr Glu Leu Leu Thr Gly Lys Pro Pro Phe Phe Pro Gly Ser Ser Glu
        35                  40                  45

<210> SEQ ID NO 54
<211> LENGTH: 100
<212> TYPE: PRT
<213> ORGANISM: Artificial Sequence
<220> FEATURE:
<223> OTHER INFORMATION: Consensus amino acid sequence

<400> SEQUENCE: 54

Glu Met Met Glu Lys Leu Gln Lys Gln Ser Met Ser Glu Lys Lys Met
1               5                   10                  15

Glu Glu Met Ser Trp Val Ser Gln Leu Met Lys Ile Ala Tyr Gln Ile
            20                  25                  30

Ala Lys Gly Leu Glu Tyr Leu His Ser Lys Ser Asn Lys Gln Asn Ile
            35                  40                  45

Ile His Arg Asp Leu Lys Pro Glu Asn Ile Leu Leu Asp Asn Asn Met
    50                  55                  60

Val Ala Lys Gly Asp Ser Glu Ile Lys Val Val Lys Ile Ala Asp Phe
65                  70                  75                  80

Gly Leu Ala Arg Met Ile Glu Glu Ser Ser Glu Glu Ser Ser Ser Ser
                85                  90                  95

Ser Ser Ser Thr
            100

<210> SEQ ID NO 55
<211> LENGTH: 134
<212> TYPE: PRT
<213> ORGANISM: Artificial Sequence
<220> FEATURE:
<223> OTHER INFORMATION: Consensus amino acid sequence

<400> SEQUENCE: 55

Lys Ala Ala Thr Lys Val Ala Val Lys Lys Lys Met Lys Glu Glu Glu
1               5                   10                  15

Lys Lys Glu Ser Lys Thr Ser Met Arg Glu Glu Met Gln Met Met
            20                  25                  30

Met Glu Ile Glu Thr His Pro Asn Ile Met Ile Ile Arg His Val Asn
            35                  40                  45

Leu Val Val Val Met Gly Tyr Cys Thr Tyr Glu Glu Ser Glu Glu Glu
        50                  55                  60
```

-continued

Asp Glu Asn Lys Leu Tyr Ile Val Met Glu Tyr Met Asn Gly Gly Ser
65                  70                  75                  80

Leu Glu Asp Tyr Leu Glu Met Met Glu Lys Leu Gln Lys Gln Ser Met
            85                  90                  95

Ser Glu Lys Lys Met Glu Glu Met Ser Trp Val Ser Gln Leu Met Lys
            100                 105                 110

Ile Ala Tyr Gln Ile Ala Lys Gly Leu Glu Tyr Leu His Ser Lys Ser
            115                 120                 125

Asn Lys Gln Asn Ile Ile
        130

<210> SEQ ID NO 56
<211> LENGTH: 40
<212> TYPE: PRT
<213> ORGANISM: Artificial Sequence
<220> FEATURE:
<223> OTHER INFORMATION: Consensus amino acid sequence

<400> SEQUENCE: 56

Glu Glu Leu Ser Ala His Glu Ile Lys Gln His Pro Trp Phe Arg Lys
1               5                   10                  15

Arg Asp Ser Phe Ser Asp Met His Ser Val Gly Tyr Met Met Tyr Glu
            20                  25                  30

Met Met Ser Gly Gln Pro Pro Phe
        35                  40

<210> SEQ ID NO 57
<211> LENGTH: 80
<212> TYPE: PRT
<213> ORGANISM: Artificial Sequence
<220> FEATURE:
<223> OTHER INFORMATION: Consensus amino acid sequence

<400> SEQUENCE: 57

Tyr Glu Leu Leu Lys Lys Leu Gly Glu Gly Ser Phe Gly Lys Val Tyr
1               5                   10                  15

Lys Ala Arg His Lys Val Val Tyr Lys Ala Lys Asp Lys Ser Lys Glu
            20                  25                  30

Thr Tyr Ala Ala Lys Val Val Ala Lys Leu Lys Val Leu Lys Ala Ala
            35                  40                  45

Thr Lys Val Ala Val Lys Lys Met Lys Glu Glu Lys Lys Glu
    50                  55                  60

Ser Lys Thr Ser Met Arg Glu Glu Glu Met Gln Met Met Met Glu Ile
65                  70                  75                  80

<210> SEQ ID NO 58
<211> LENGTH: 27
<212> TYPE: PRT
<213> ORGANISM: Artificial Sequence
<220> FEATURE:
<223> OTHER INFORMATION: Consensus amino acid sequence

<400> SEQUENCE: 58

Ser Glu Ala Val Lys Asp Leu Ile Lys Lys Cys Trp Gln Lys Asp Pro
1               5                   10                  15

Glu Lys Arg Pro Thr Phe Ala Gln Val Val Glu
            20                  25

<210> SEQ ID NO 59
<211> LENGTH: 162
<212> TYPE: PRT

```
<213> ORGANISM: Artificial Sequence
<220> FEATURE:
<223> OTHER INFORMATION: Consensus amino acid sequence

<400> SEQUENCE: 59

Ser Leu Gly Val Cys Ile Phe Val Met Ala Thr Gly Ser Cys Pro Phe
  1               5                  10                  15

Ile Leu Glu Ser Arg Asn Thr Met Met Glu Ser Ile Gln Ala Gly Ile
                 20                  25                  30

Leu Gly Ser Pro Val Leu Ala Ser Asp Lys Ile Gln Ser Leu Val Glu
             35                  40                  45

Gln Leu Ile His Val Asn Pro Ser Glu Arg Met Ser Leu Lys Ser Leu
 50                  55                  60

Ile Glu Asp Asp Trp Met Thr Ser Asp Leu Val Trp Asn Tyr Phe Ile
 65                  70                  75                  80

Ser Cys His Glu Asp Leu Ile Arg Glu Leu Pro Val Val Asp Arg Phe
                 85                  90                  95

Ile Pro Ala Glu Ser Leu Glu Lys Ser Thr Val Gln Arg Asp Gly Ser
                100                 105                 110

Glu Ile Ser Ile Glu Thr Leu Asp Glu Gly Tyr Lys Ser Val Ala Ser
            115                 120                 125

Asp His Pro Glu Glu Pro Ala Val Ser Gly Gln Gln Val Leu Thr
130                 135                 140

Glu Pro Val Pro Lys Lys Tyr His Lys Lys Phe Ala Val Phe Ala Met
145                 150                 155                 160

Glu Asn

<210> SEQ ID NO 60
<211> LENGTH: 141
<212> TYPE: PRT
<213> ORGANISM: Artificial Sequence
<220> FEATURE:
<223> OTHER INFORMATION: Consensus amino acid sequence

<400> SEQUENCE: 60

Ile Ala Ser Gly Arg Phe Gly Thr Val Phe Leu Gly Thr Ile Thr Asp
  1               5                  10                  15

Ser Met Leu Gln Val Ala Ile Lys Glu Tyr His Glu Thr Phe His Asp
                 20                  25                  30

Ala Val Leu Thr Ala His Asp Glu Gly Ser Thr Leu Gln Lys Ile Ile
             35                  40                  45

Ser Ile Glu His Pro Ala Ile Val Gln Thr Phe Ser Val Ser His Phe
 50                  55                  60

Gln Asp Ile Val Tyr Lys Val Met Glu Phe His Ser Trp Thr Leu His
 65                  70                  75                  80

Glu Lys Arg Val Tyr Phe Glu Lys Ile Asp Arg Thr Asn Asn Asp Ile
                 85                  90                  95

Leu Asp Lys Gly Lys Tyr Asp Glu Ser Gln Thr Lys Leu Val Leu Val
                100                 105                 110

Gln Ala Thr Arg Ala Leu Glu Tyr Leu His Ala Gln Asn Leu Cys His
            115                 120                 125

Gly Thr Leu His Thr Lys Asn Ile Phe Leu Gln Glu Asn
            130                 135                 140

<210> SEQ ID NO 61
<211> LENGTH: 278
<212> TYPE: PRT
```

<213> ORGANISM: Artificial Sequence
<220> FEATURE:
<223> OTHER INFORMATION: Consensus amino acid sequence

<400> SEQUENCE: 61

Tyr Glu Leu Leu Glu Lys Leu Gly Glu Gly Ser Phe Gly Lys Val Tyr
1               5                   10                  15

Lys Ala Lys His Lys Thr Gly Lys Ile Val Ala Val Lys Ile Leu Lys
            20                  25                  30

Lys Glu Ser Leu Ser Leu Arg Glu Ile Gln Ile Leu Lys Arg Leu Ser
        35                  40                  45

His Pro Asn Ile Val Arg Leu Leu Gly Val Phe Glu Asp Thr Asp Asp
    50                  55                  60

His Leu Tyr Leu Val Met Glu Tyr Met Glu Gly Gly Asp Leu Phe Asp
65                  70                  75                  80

Tyr Leu Arg Arg Asn Gly Pro Leu Ser Glu Lys Glu Ala Lys Lys Ile
                85                  90                  95

Ala Leu Gln Ile Leu Arg Gly Leu Glu Tyr Leu His Ser Asn Gly Ile
            100                 105                 110

Val His Arg Asp Leu Lys Pro Glu Asn Ile Leu Leu Asp Glu Asn Gly
        115                 120                 125

Thr Val Lys Ile Ala Asp Phe Gly Leu Ala Arg Leu Leu Glu Lys Leu
    130                 135                 140

Thr Thr Phe Val Gly Thr Pro Trp Tyr Met Met Ala Pro Glu Val Ile
145                 150                 155                 160

Leu Glu Gly Arg Gly Tyr Ser Ser Lys Val Asp Val Trp Ser Leu Gly
                165                 170                 175

Val Ile Leu Tyr Glu Leu Leu Thr Gly Gly Pro Leu Phe Pro Gly Ala
            180                 185                 190

Asp Leu Pro Ala Phe Thr Gly Gly Asp Glu Val Asp Gln Leu Ile Ile
        195                 200                 205

Phe Val Leu Lys Leu Pro Phe Ser Asp Glu Leu Pro Lys Thr Arg Ile
    210                 215                 220

Asp Pro Leu Glu Glu Leu Phe Arg Ile Lys Lys Arg Leu Pro Leu
225                 230                 235                 240

Pro Ser Asn Cys Ser Glu Glu Leu Lys Asp Leu Leu Lys Lys Cys Leu
                245                 250                 255

Asn Lys Asp Pro Ser Lys Arg Pro Gly Ser Ala Thr Ala Lys Glu Ile
            260                 265                 270

Leu Asn His Pro Trp Phe
        275

<210> SEQ ID NO 62
<211> LENGTH: 80
<212> TYPE: PRT
<213> ORGANISM: Artificial Sequence
<220> FEATURE:
<223> OTHER INFORMATION: Consensus amino acid sequence

<400> SEQUENCE: 62

Met Glu Arg Ser Pro Ala Val Cys Cys Gln Asp Pro Arg Ala Glu Leu
1               5                   10                  15

Val Glu Arg Val Ala Ala Ile Ser Val Ala His Leu Glu Glu Ala Glu
            20                  25                  30

Glu Gly Pro Glu Pro Ala Ser Asn Gly Val Asp Pro Pro Arg Ala
        35                  40                  45

Arg Ala Ala Ser Val Ile Pro Gly Ser Ala Ser Arg Pro Thr Pro Val
    50                  55                  60

Arg Pro Ser Leu Ser Ala Arg Lys Phe Ser Leu Gln Glu Arg Pro Ala
65                  70                  75                  80

<210> SEQ ID NO 63
<211> LENGTH: 61
<212> TYPE: PRT
<213> ORGANISM: Artificial Sequence
<220> FEATURE:
<223> OTHER INFORMATION: Consensus amino acid sequence

<400> SEQUENCE: 63

Leu Lys Thr His Lys Trp Val Thr Arg His Gly Glu Pro Leu Pro
 1               5                   10                  15

Ser Glu Glu Asn Cys Thr Leu Val Glu Val Thr Glu Glu Val
                20                  25                  30

Glu Asn Ser Val Lys His Ile Pro Ser Leu Thr Thr Val Ile Leu Val
            35                  40                  45

Lys Thr Met Leu Arg Lys Arg Ser Phe Gly Asn Pro Phe
    50                  55                  60

<210> SEQ ID NO 64
<211> LENGTH: 47
<212> TYPE: PRT
<213> ORGANISM: Artificial Sequence
<220> FEATURE:
<223> OTHER INFORMATION: Consensus amino acid sequence
<220> FEATURE:
<221> NAME/KEY: VARIANT
<222> LOCATION: (1)...(47)
<223> OTHER INFORMATION: Xaa = Any Amino Acid

<400> SEQUENCE: 64

Gly Xaa Cys Leu Gly Ala Gln Val Gly Pro Tyr Ser Thr Gly Pro Ala
 1               5                   10                  15

Ser His Met Cys Pro Arg Ser Trp Arg Arg Pro Thr Ile Glu Ser His
                20                  25                  30

Arg Val Ala Ile Ser Asp Thr Glu Asp Cys Val Gln Leu Asn Gln
            35                  40                  45

<210> SEQ ID NO 65
<211> LENGTH: 36
<212> TYPE: PRT
<213> ORGANISM: Artificial Sequence
<220> FEATURE:
<223> OTHER INFORMATION: Consensus amino acid sequence

<400> SEQUENCE: 65

Glu Pro Gln Ala Arg Arg Glu Glu Arg Ser Met Ser Ala Pro Gly Asn
 1               5                   10                  15

Leu Leu Leu Lys Glu Gly Cys Gly Glu Gly Lys Ser Pro Glu Leu
                20                  25                  30

Pro Gly Val Gln
        35

<210> SEQ ID NO 66
<211> LENGTH: 17
<212> TYPE: PRT
<213> ORGANISM: Artificial Sequence
<220> FEATURE:
<223> OTHER INFORMATION: Consensus amino acid sequence
<220> FEATURE:
<221> NAME/KEY: VARIANT

```
<222> LOCATION: (1)...(1)
<223> OTHER INFORMATION: Xaa at position 1 can be L, I or V
<220> FEATURE:
<221> NAME/KEY: VARIANT
<222> LOCATION: (3)...(3)
<223> OTHER INFORMATION: Xaa at position 3 can be any amino acid
      except P
<220> FEATURE:
<221> NAME/KEY: VARIANT
<222> LOCATION: (5)...(5)
<223> OTHER INFORMATION: Xaa at position 5 can be any amino acid
      except P
<220> FEATURE:
<221> NAME/KEY: VARIANT
<222> LOCATION: (6)...(6)
<223> OTHER INFORMATION: Xaa at position 6 can be F, Y, W, M, G, S, T,
      N or H
<220> FEATURE:
<221> NAME/KEY: VARIANT
<222> LOCATION: (7)...(7)
<223> OTHER INFORMATION: Xaa at position 7 can be S, G or A
<220> FEATURE:
<221> NAME/KEY: VARIANT
<222> LOCATION: (8)...(8)
<223> OTHER INFORMATION: Xaa at position 8 can be any amino acid
      except P or W
<220> FEATURE:
<221> NAME/KEY: VARIANT
<222> LOCATION: (9)...(9)
<223> OTHER INFORMATION: Xaa at position 9 can be L, I, V, C, A or T
<220> FEATURE:
<221> NAME/KEY: VARIANT
<222> LOCATION: (10)...(10)
<223> OTHER INFORMATION: Xaa at position 10 can be any amino acid
      except P or D
<220> FEATURE:
<221> NAME/KEY: VARIANT
<222> LOCATION: (11)...(11)
<223> OTHER INFORMATION: Xaa = Any Amino Acid
<220> FEATURE:
<221> NAME/KEY: VARIANT
<222> LOCATION: (12)...(12)
<223> OTHER INFORMATION: Xaa at position 12 can be G, S, T, A, C, L,
      I, V,M, F or Y
<220> FEATURE:
<221> NAME/KEY: VARIANT
<222> LOCATION: (13)...(13)
<223> OTHER INFORMATION: Xaa at position 13 can be 5 to 18 of any amino
      acid
<220> FEATURE:
<221> NAME/KEY: VARIANT
<222> LOCATION: (14)...(14)
<223> OTHER INFORMATION: Xaa at position 14 can be L, I, V, M, F, Y,
      W, C,S, T, A or R
<220> FEATURE:
<221> NAME/KEY: VARIANT
<222> LOCATION: (15)...(15)
<223> OTHER INFORMATION: Xaa at position 15 can be A, I, V or P
<220> FEATURE:
<221> NAME/KEY: VARIANT
<222> LOCATION: (16)...(16)
<223> OTHER INFORMATION: Xaa at position 9 can be L, I, V, M, F, A, G,
      C, K or R

<400> SEQUENCE: 66

Xaa Gly Xaa Gly Xaa Xaa Xaa Xaa Xaa Xaa Xaa Xaa Xaa Xaa Xaa Xaa
1               5                   10                  15

Lys

<210> SEQ ID NO 67
<211> LENGTH: 13
<212> TYPE: PRT
<213> ORGANISM: Artificial Sequence
<220> FEATURE:
<223> OTHER INFORMATION: Consensus amino acid sequence
<220> FEATURE:
```

```
<221> NAME/KEY: VARIANT
<222> LOCATION: (1)...(1)
<223> OTHER INFORMATION: Xaa at position 1 can be L, I, V, M, F, Y or C
<220> FEATURE:
<221> NAME/KEY: VARIANT
<222> LOCATION: (2)...(2)
<223> OTHER INFORMATION: Xaa = Any Amino Acid
<220> FEATURE:
<221> NAME/KEY: VARIANT
<222> LOCATION: (3)...(3)
<223> OTHER INFORMATION: Xaa at position 3 can be H or Y
<220> FEATURE:
<221> NAME/KEY: VARIANT
<222> LOCATION: (4)...(4)
<223> OTHER INFORMATION: Xaa = Any Amino Acid
<220> FEATURE:
<221> NAME/KEY: VARIANT
<222> LOCATION: (6)...(6)
<223> OTHER INFORMATION: Xaa at position 6 can be L, I, V, M, F or Y
<220> FEATURE:
<221> NAME/KEY: VARIANT
<222> LOCATION: (7)...(7)
<223> OTHER INFORMATION: Xaa at position 7 can be R, S, T, A or C
<220> FEATURE:
<221> NAME/KEY: VARIANT
<222> LOCATION: (8)...(9)
<223> OTHER INFORMATION: Xaa = Any Amino Acid
<220> FEATURE:
<221> NAME/KEY: VARIANT
<222> LOCATION: (11)...(13)
<223> OTHER INFORMATION: Xaa at positions 11 to 13 can be L, I, V, M,
      F, Y or C

<400> SEQUENCE: 67

Xaa Xaa Xaa Xaa Asp Xaa Xaa Xaa Xaa Asn Xaa Xaa Xaa
 1               5                   10

<210> SEQ ID NO 68
<211> LENGTH: 13
<212> TYPE: PRT
<213> ORGANISM: Artificial Sequence
<220> FEATURE:
<223> OTHER INFORMATION: Consensus amino acid sequence
<220> FEATURE:
<221> NAME/KEY: VARIANT
<222> LOCATION: (1)...(1)
<223> OTHER INFORMATION: Xaa at position 1 can be L, I, V, M, F, Y or C
<220> FEATURE:
<221> NAME/KEY: VARIANT
<222> LOCATION: (2)...(2)
<223> OTHER INFORMATION: Xaa = Any Amino Acid
<220> FEATURE:
<221> NAME/KEY: VARIANT
<222> LOCATION: (3)...(3)
<223> OTHER INFORMATION: Xaa at position 3 can be H or Y,
<220> FEATURE:
<221> NAME/KEY: VARIANT
<222> LOCATION: (4)...(4)
<223> OTHER INFORMATION: Xaa = Any Amino Acid
<220> FEATURE:
<221> NAME/KEY: VARIANT
<222> LOCATION: (6)...(6)
<223> OTHER INFORMATION: Xaa at position 6 can be L, I, V, M, F or Y
<220> FEATURE:
<221> NAME/KEY: VARIANT
<222> LOCATION: (80)...(9)
<223> OTHER INFORMATION: Xaa = Any Amino Acid
<220> FEATURE:
<221> NAME/KEY: VARIANT
<222> LOCATION: (11)...(13)
<223> OTHER INFORMATION: Xaa at positions 11 to 13 can be L, I, V, M,
      F, Y,C or T

<400> SEQUENCE: 68

Xaa Xaa Xaa Xaa Asp Xaa Lys Xaa Xaa Asn Xaa Xaa Xaa
 1               5                   10
```

```
<210> SEQ ID NO 69
<211> LENGTH: 21
<212> TYPE: PRT
<213> ORGANISM: Artificial Sequence
<220> FEATURE:
<223> OTHER INFORMATION: Consensus amino acid sequence
<220> FEATURE:
<221> NAME/KEY: VARIANT
<222> LOCATION: (2)...(2)
<223> OTHER INFORMATION: Xaa = Any Amino Acid
<220> FEATURE:
<221> NAME/KEY: VARIANT
<222> LOCATION: (3)...(3)
<223> OTHER INFORMATION: Xaa at position 3 can be D or N
<220> FEATURE:
<221> NAME/KEY: VARIANT
<222> LOCATION: (4)...(4)
<223> OTHER INFORMATION: Xaa = Any Amino Acid
<220> FEATURE:
<221> NAME/KEY: VARIANT
<222> LOCATION: (5)...(5)
<223> OTHER INFORMATION: Xaa at position 5 can be G, A or W
<220> FEATURE:
<221> NAME/KEY: VARIANT
<222> LOCATION: (6)...(6)
<223> OTHER INFORMATION: Xaa at position 6 can be G or A
<220> FEATURE:
<221> NAME/KEY: VARIANT
<222> LOCATION: (8)...(8)
<223> OTHER INFORMATION: Xaa at position 8 can be L, I, V or M
<220> FEATURE:
<221> NAME/KEY: VARIANT
<222> LOCATION: (9)...(9)
<223> OTHER INFORMATION: Xaa at position 9 can be S or A
<220> FEATURE:
<221> NAME/KEY: VARIANT
<222> LOCATION: (10)...(11)
<223> OTHER INFORMATION: Xaa at positions 10 to 11 can be L, I, V or M
<220> FEATURE:
<221> NAME/KEY: VARIANT
<222> LOCATION: (12)...(12)
<223> OTHER INFORMATION: Xaa at position 12 can be S or A
<220> FEATURE:
<221> NAME/KEY: VARIANT
<222> LOCATION: (13)...(13)
<223> OTHER INFORMATION: Xaa at position 13 can be L or V
<220> FEATURE:
<221> NAME/KEY: VARIANT
<222> LOCATION: (14)...(14)
<223> OTHER INFORMATION: Xaa at position 14 can be K, R, H or Q
<220> FEATURE:
<221> NAME/KEY: VARIANT
<222> LOCATION: (15)...(15)
<223> OTHER INFORMATION: Xaa at position 15 can be L, I, V or A
<220> FEATURE:
<221> NAME/KEY: VARIANT
<222> LOCATION: (16)...(18)
<223> OTHER INFORMATION: Xaa = Any Amino Acid
<220> FEATURE:
<221> NAME/KEY: VARIANT
<222> LOCATION: (19)...(19)
<223> OTHER INFORMATION: Xaa at position 19 can be K or R
<220> FEATURE:
<221> NAME/KEY: VARIANT
<222> LOCATION: (21)...(21)
<223> OTHER INFORMATION: Xaa at position 21 can be P, S, A or W

<400> SEQUENCE: 69

Phe Xaa Xaa Xaa Xaa Xaa Cys Xaa Xaa Xaa Xaa Xaa Xaa Xaa Xaa
 1               5                  10                  15

Xaa Xaa Xaa Cys Xaa
            20

<210> SEQ ID NO 70
```

```
<211> LENGTH: 20
<212> TYPE: PRT
<213> ORGANISM: Artificial Sequence
<220> FEATURE:
<223> OTHER INFORMATION: Consensus amino acid sequence
<220> FEATURE:
<221> NAME/KEY: VARIANT
<222> LOCATION: (2)...(3)
<223> OTHER INFORMATION: Xaa = Any Amino Acid
<220> FEATURE:
<221> NAME/KEY: VARIANT
<222> LOCATION: (4)...(4)
<223> OTHER INFORMATION: Xaa at position 4 can be D or E
<220> FEATURE:
<221> NAME/KEY: VARIANT
<222> LOCATION: (6)...(6)
<223> OTHER INFORMATION: Xaa at position 6 can be D, E or Q
<220> FEATURE:
<221> NAME/KEY: VARIANT
<222> LOCATION: (8)...(8)
<223> OTHER INFORMATION: Xaa at position 8 can be 2 to 3 residues of any
      amino acid
<220> FEATURE:
<221> NAME/KEY: VARIANT
<222> LOCATION: (9)...(9)
<223> OTHER INFORMATION: Xaa at position 9 can be P, A or Q
<220> FEATURE:
<221> NAME/KEY: VARIANT
<222> LOCATION: (10)...(10)
<223> OTHER INFORMATION: Xaa at position 10 can be L, I, V, M or T
<220> FEATURE:
<221> NAME/KEY: VARIANT
<222> LOCATION: (11)...(11)
<223> OTHER INFORMATION: Xaa at position 11 can be G or T
<220> FEATURE:
<221> NAME/KEY: VARIANT
<222> LOCATION: (12)...(12)
<223> OTHER INFORMATION: Xaa = Any Amino Acid
<220> FEATURE:
<221> NAME/KEY: VARIANT
<222> LOCATION: (14)...(14)
<223> OTHER INFORMATION: Xaa = Any Amino Acid
<220> FEATURE:
<221> NAME/KEY: VARIANT
<222> LOCATION: (16)...(17)
<223> OTHER INFORMATION: Xaa = Any Amino Acid
<220> FEATURE:
<221> NAME/KEY: VARIANT
<222> LOCATION: (19)...(19)
<223> OTHER INFORMATION: Xaa at position 19 can be H, F or Y
<220> FEATURE:
<221> NAME/KEY: VARIANT
<222> LOCATION: (20)...(20)
<223> OTHER INFORMATION: Xaa at position 20 can be E or Q

<400> SEQUENCE: 70

Cys Xaa Xaa Xaa Gly Xaa Trp Xaa Xaa Xaa Xaa Cys Xaa Cys Xaa
1               5                   10                  15

Xaa Gly Xaa Xaa
            20

<210> SEQ ID NO 71
<211> LENGTH: 9
<212> TYPE: PRT
<213> ORGANISM: Artificial Sequence
<220> FEATURE:
<223> OTHER INFORMATION: Consensus amino acid sequence
<220> FEATURE:
<221> NAME/KEY: VARIANT
<222> LOCATION: (2)...(2)
<223> OTHER INFORMATION: Xaa = Any Amino Acid
<220> FEATURE:
<221> NAME/KEY: VARIANT
<222> LOCATION: (4)...(5)
<223> OTHER INFORMATION: Xaa = Any Amino Acid
<220> FEATURE:
```

```
<221> NAME/KEY: VARIANT
<222> LOCATION: (6)...(6)
<223> OTHER INFORMATION: Xaa at position 6 can be G or P
<220> FEATURE:
<221> NAME/KEY: VARIANT
<222> LOCATION: (7)...(7)
<223> OTHER INFORMATION: Xaa at position 7 can be F, Y or W
<220> FEATURE:
<221> NAME/KEY: VARIANT
<222> LOCATION: (8)...(8)
<223> OTHER INFORMATION: Xaa at position 8 can be 4 to 8 residues of any
      amino acid

<400> SEQUENCE: 71

Cys Xaa Cys Xaa Xaa Xaa Xaa Xaa Cys
 1               5

<210> SEQ ID NO 72
<211> LENGTH: 8
<212> TYPE: PRT
<213> ORGANISM: Artificial Sequence
<220> FEATURE:
<223> OTHER INFORMATION: Consensus amino acid sequence
<220> FEATURE:
<221> NAME/KEY: VARIANT
<222> LOCATION: (1)...(1)
<223> OTHER INFORMATION: Xaa at position 1 can be A or G
<220> FEATURE:
<221> NAME/KEY: VARIANT
<222> LOCATION: (2)...(5)
<223> OTHER INFORMATION: Xaa = Any Amino Acid
<220> FEATURE:
<221> NAME/KEY: VARIANT
<222> LOCATION: (8)...(8)
<223> OTHER INFORMATION: Xaa at position 8 can be S or T

<400> SEQUENCE: 72

Xaa Xaa Xaa Xaa Xaa Gly Lys Xaa
 1               5

<210> SEQ ID NO 73
<211> LENGTH: 1154
<212> TYPE: DNA
<213> ORGANISM: Homo sapiens
<220> FEATURE:
<221> NAME/KEY: CDS
<222> LOCATION: (22)...(870)

<400> SEQUENCE: 73
cggacgcgtg ggtccgtgac c atg aag gtc aag gtc atc ccc gtg ctc gag       51
                         Met Lys Val Lys Val Ile Pro Val Leu Glu
                          1               5                  10 gac aac tac atg tac ctg gtc atc gag gag ctc acg cgc gag gcg gtg       99
Asp Asn Tyr Met Tyr Leu Val Ile Glu Glu Leu Thr Arg Glu Ala Val
             15                  20                  25 gcc gtg gac gtg gct gtg ccc aag agg ctg ctg gag atc gtg ggc cgg      147
Ala Val Asp Val Ala Val Pro Lys Arg Leu Leu Glu Ile Val Gly Arg
         30                  35                  40 gag ggg gtg tct ctg acc gct gtg ctg acc acc cac cat cac tgg gac      195
Glu Gly Val Ser Leu Thr Ala Val Leu Thr Thr His His His Trp Asp
     45                  50                  55 cac gcg cgg gga aac ccg gag ctg gcg cgg ctt cgt ccc ggg ctg gcg      243
His Ala Arg Gly Asn Pro Glu Leu Ala Arg Leu Arg Pro Gly Leu Ala
 60                  65                  70 gtg ctg ggc gcg gac gag cgc atc ttc tcg ctg acg cgc agg ctg gcg      291
Val Leu Gly Ala Asp Glu Arg Ile Phe Ser Leu Thr Arg Arg Leu Ala
 75                  80                  85                  90 cac ggc gag gag ctg cgg ttc ggg gcc atc cac gtg cgt tgc ctc ctg      339
```

-continued

```
                His Gly Glu Glu Leu Arg Phe Gly Ala Ile His Val Arg Cys Leu Leu
                             95                  100                 105 acg ccc ggc cac acc gcc ggc cac atg agc tac ttc ctg tgg gag gac              387
Thr Pro Gly His Thr Ala Gly His Met Ser Tyr Phe Leu Trp Glu Asp
            110                 115                 120 gat tgc ccg gac cca ccc gcc ctg ttc tcg ggc gac gcg ctg tcg gtg              435
Asp Cys Pro Asp Pro Pro Ala Leu Phe Ser Gly Asp Ala Leu Ser Val
        125                 130                 135 gcc ggc tgc ggc tcg tgc ctg gag ggc agc gcc cag cag atg tac cag              483
Ala Gly Cys Gly Ser Cys Leu Glu Gly Ser Ala Gln Gln Met Tyr Gln
    140                 145                 150 agc ctg gcc gag ctg ggt acc ctg ccc ccc gag acg aag gtg ttc tgc              531
Ser Leu Ala Glu Leu Gly Thr Leu Pro Pro Glu Thr Lys Val Phe Cys
155                 160                 165                 170 ggc cac gag cac acg ctt agc aac ctg gag ttt gcc cag aaa gtg gag              579
Gly His Glu His Thr Leu Ser Asn Leu Glu Phe Ala Gln Lys Val Glu
                175                 180                 185 ccc tgc aac gac cac gtg aga gcc aag ctg tcc tgg gct aag aag agg              627
Pro Cys Asn Asp His Val Arg Ala Lys Leu Ser Trp Ala Lys Lys Arg
            190                 195                 200 gat gag gat gac gtg ccc act gtg ccg tcg act ctg ggc gag gag cgc              675
Asp Glu Asp Asp Val Pro Thr Val Pro Ser Thr Leu Gly Glu Glu Arg
        205                 210                 215 ctc tac aac ccc ttc ctg cgg gtg gca gag gag ccg gtg cgc aag ttc              723
Leu Tyr Asn Pro Phe Leu Arg Val Ala Glu Glu Pro Val Arg Lys Phe
    220                 225                 230 acg ggc aag gcg gtc ccc gcc gac gtc ctg gag gcg cta tgc aag gag              771
Thr Gly Lys Ala Val Pro Ala Asp Val Leu Glu Ala Leu Cys Lys Glu
235                 240                 245                 250 cgg gcg cgc ttc gaa cag gcg ggc gag ccg cgg cag cca cag gcg cgg              819
Arg Ala Arg Phe Glu Gln Ala Gly Glu Pro Arg Gln Pro Gln Ala Arg
                255                 260                 265 gcc ctc ctt gcg ctg cag tgg ggg ctc ctg agt gca gcc cca cac gac              867
Ala Leu Leu Ala Leu Gln Trp Gly Leu Leu Ser Ala Ala Pro His Asp
            270                 275                 280 tga gccacccaga ccctcacagg gctggggcct gcgtccctcc tcgtgacctc                   920
* ggccagctgg acccacatga gggccaccctc tggaaccttc ttcgaggccc tggccagcca           980
tctgcccagc ctcggagggt gggcaacctg gtgcttcccg ggtggacaca caggaccact           1040
cagtggggcc tgtgtgggcg ccagacctg ggtgtctggg aagtggggca cggggcct             1100 ccgaactatg aataaagctt tgaaagccgt tgtcaaaaaa aaaaaaaaa aaaa                  1154
```

<210> SEQ ID NO 74
<211> LENGTH: 282
<212> TYPE: PRT
<213> ORGANISM: Homo sapiens

<400> SEQUENCE: 74

```
Met Lys Val Lys Val Ile Pro Val Leu Glu Asp Asn Tyr Met Tyr Leu
  1               5                  10                  15

Val Ile Glu Glu Leu Thr Arg Glu Ala Val Ala Val Asp Val Ala Val
             20                  25                  30

Pro Lys Arg Leu Leu Glu Ile Val Gly Arg Glu Gly Val Ser Leu Thr
         35                  40                  45

Ala Val Leu Thr Thr His His His Trp Asp His Ala Arg Gly Asn Pro
     50                  55                  60

Glu Leu Ala Arg Leu Arg Pro Gly Leu Ala Val Leu Gly Ala Asp Glu
```

```
                65                  70                  75                  80
Arg Ile Phe Ser Leu Thr Arg Arg Leu Ala His Gly Glu Glu Leu Arg
                    85                  90                  95

Phe Gly Ala Ile His Val Arg Cys Leu Leu Thr Pro Gly His Thr Ala
                    100                 105                 110

Gly His Met Ser Tyr Phe Leu Trp Glu Asp Asp Cys Pro Asp Pro Pro
                    115                 120                 125

Ala Leu Phe Ser Gly Asp Ala Leu Ser Val Ala Gly Cys Gly Ser Cys
            130                 135                 140

Leu Glu Gly Ser Ala Gln Gln Met Tyr Gln Ser Leu Ala Glu Leu Gly
145                 150                 155                 160

Thr Leu Pro Pro Glu Thr Lys Val Phe Cys Gly His Glu His Thr Leu
                165                 170                 175

Ser Asn Leu Glu Phe Ala Gln Lys Val Glu Pro Cys Asn Asp His Val
                180                 185                 190

Arg Ala Lys Leu Ser Trp Ala Lys Lys Arg Asp Glu Asp Asp Val Pro
                195                 200                 205

Thr Val Pro Ser Thr Leu Gly Glu Arg Leu Tyr Asn Pro Phe Leu
            210                 215                 220

Arg Val Ala Glu Glu Pro Val Arg Lys Phe Thr Gly Lys Ala Val Pro
225                 230                 235                 240

Ala Asp Val Leu Glu Ala Leu Cys Lys Glu Arg Ala Arg Phe Glu Gln
                    245                 250                 255

Ala Gly Glu Pro Arg Gln Pro Gln Ala Arg Ala Leu Leu Ala Leu Gln
                260                 265                 270

Trp Gly Leu Leu Ser Ala Ala Pro His Asp
            275                 280

<210> SEQ ID NO 75
<211> LENGTH: 849
<212> TYPE: DNA
<213> ORGANISM: Homo sapiens
<220> FEATURE:
<221> NAME/KEY: CDS
<222> LOCATION: (1)...(849)

<400> SEQUENCE: 75 atg aag gtc aag gtc atc ccc gtg ctc gag gac aac tac atg tac ctg     48
Met Lys Val Lys Val Ile Pro Val Leu Glu Asp Asn Tyr Met Tyr Leu
 1               5                  10                  15 gtc atc gag gag ctc acg cgc gag gcg gtg gcc gtg gac gtg gct gtg     96
Val Ile Glu Glu Leu Thr Arg Glu Ala Val Ala Val Asp Val Ala Val
                20                  25                  30 ccc aag agg ctg ctg gag atc gtg ggc cgg gag ggg gtg tct ctg acc    144
Pro Lys Arg Leu Leu Glu Ile Val Gly Arg Glu Gly Val Ser Leu Thr
            35                  40                  45 gct gtg ctg acc acc cac cat cac tgg gac cac gcg cgg gga aac ccg    192
Ala Val Leu Thr Thr His His His Trp Asp His Ala Arg Gly Asn Pro
        50                  55                  60 gag ctg gcg cgg ctt cgt ccc ggg ctg gcg gtg ctg ggc gcg gac gag    240
Glu Leu Ala Arg Leu Arg Pro Gly Leu Ala Val Leu Gly Ala Asp Glu
65                  70                  75                  80 cgc atc ttc tcg ctg acg cgc agg ctg gcg cac ggc gag gag ctg cgg    288
Arg Ile Phe Ser Leu Thr Arg Arg Leu Ala His Gly Glu Glu Leu Arg
                85                  90                  95 ttc ggg gcc atc cac gtg cgt tgc ctc ctg acg ccc ggc cac acc gcc    336
Phe Gly Ala Ile His Val Arg Cys Leu Leu Thr Pro Gly His Thr Ala
                100                 105                 110
```

```
ggc cac atg agc tac ttc ctg tgg gag gac gat tgc ccg gac cca ccc    384
Gly His Met Ser Tyr Phe Leu Trp Glu Asp Asp Cys Pro Asp Pro Pro
        115                 120                 125 gcc ctg ttc tcg ggc gac gcg ctg tcg gtg gcc ggc tgc ggc tcg tgc    432
Ala Leu Phe Ser Gly Asp Ala Leu Ser Val Ala Gly Cys Gly Ser Cys
130                 135                 140 ctg gag ggc agc gcc cag cag atg tac cag agc ctg gcc gag ctg ggt    480
Leu Glu Gly Ser Ala Gln Gln Met Tyr Gln Ser Leu Ala Glu Leu Gly
145                 150                 155                 160 acc ctg ccc ccc gag acg aag gtg ttc tgc ggc cac gag cac acg ctt    528
Thr Leu Pro Pro Glu Thr Lys Val Phe Cys Gly His Glu His Thr Leu
            165                 170                 175 agc aac ctg gag ttt gcc cag aaa gtg gag ccc tgc aac gac cac gtg    576
Ser Asn Leu Glu Phe Ala Gln Lys Val Glu Pro Cys Asn Asp His Val
        180                 185                 190 aga gcc aag ctg tcc tgg gct aag aag agg gat gag gat gac gtg ccc    624
Arg Ala Lys Leu Ser Trp Ala Lys Lys Arg Asp Glu Asp Asp Val Pro
    195                 200                 205 act gtg ccg tcg act ctg ggc gag gag cgc ctc tac aac ccc ttc ctg    672
Thr Val Pro Ser Thr Leu Gly Glu Glu Arg Leu Tyr Asn Pro Phe Leu
210                 215                 220 cgg gtg gca gag gag ccg gtg cgc aag ttc acg ggc aag gcg gtc ccc    720
Arg Val Ala Glu Glu Pro Val Arg Lys Phe Thr Gly Lys Ala Val Pro
225                 230                 235                 240 gcc gac gtc ctg gag gcg cta tgc aag gag cgg gcg cgc ttc gaa cag    768
Ala Asp Val Leu Glu Ala Leu Cys Lys Glu Arg Ala Arg Phe Glu Gln
            245                 250                 255 gcg ggc gag ccg cgg cag cca cag gcg cgg gcc ctc ctt gcg ctg cag    816
Ala Gly Glu Pro Arg Gln Pro Gln Ala Arg Ala Leu Leu Ala Leu Gln
        260                 265                 270 tgg ggg ctc ctg agt gca gcc cca cac gac tga                        849
Trp Gly Leu Leu Ser Ala Ala Pro His Asp *
            275                 280

<210> SEQ ID NO 76
<211> LENGTH: 2853
<212> TYPE: DNA
<213> ORGANISM: Homo sapiens
<220> FEATURE:
<221> NAME/KEY: CDS
<222> LOCATION: (1)...(2853)

<400> SEQUENCE: 76 atg ctt ctg ctg ggc atc cta acc ctg gct ttc gcc ggg cga acc gct    48
Met Leu Leu Leu Gly Ile Leu Thr Leu Ala Phe Ala Gly Arg Thr Ala
1               5                   10                  15 gga ggc tct gag cca gag cgg gag gta gtc gtt ccc atc gac tg gac     96
Gly Gly Ser Glu Pro Glu Arg Glu Val Val Val Pro Ile Arg Leu Asp
            20                  25                  30 ccg gac att aac ggc cgc gc tac tac tgg cgg ggt ccc gag gac tcc    144
Pro Asp Ile Asn Gly Arg Arg Tyr Tyr Trp Arg Gly Pro Glu Asp Ser
        35                  40                  45 ggg gat cag gga ctc att ttt cag atc aca gca ttt cag gag gac ttt    192
Gly Asp Gln Gly Leu Ile Phe Gln Ile Thr Ala Phe Gln Glu Asp Phe
    50                  55                  60 tac cta cac ctg acg ccg gat gct cag ttc ttg gct ccc gcc ttc tcc    240
Tyr Leu His Leu Thr Pro Asp Ala Gln Phe Leu Ala Pro Ala Phe Ser
65                  70                  75                  80 act gag cat ctg ggc gtc ccc ctc cag ggg ctc acc ggg ggc tct tca    288
Thr Glu His Leu Gly Val Pro Leu Gln Gly Leu Thr Gly Gly Ser Ser
            85                  90                  95
```

-continued

| | |
|---|---|
| gac ctg cga cgc tgc ttc tat tct ggg gac gtg aac gcc gag ccg gac<br>Asp Leu Arg Arg Cys Phe Tyr Ser Gly Asp Val Asn Ala Glu Pro Asp<br>100                           105                       110 | 336 |
| tcg ttc gct gct gtg agc ctg tgc ggg ggg ctc cgc gga gcc ttt ggc<br>Ser Phe Ala Ala Val Ser Leu Cys Gly Gly Leu Arg Gly Ala Phe Gly<br>        115                       120                     125 | 384 |
| tac cga ggc gcc gag tat gtc att agc ccg ctg ccc aat gct agc gcg<br>Tyr Arg Gly Ala Glu Tyr Val Ile Ser Pro Leu Pro Asn Ala Ser Ala<br>130                           135                       140 | 432 |
| ccg gcg gcg cag cgc aac agc cag ggc gca cac ctt ctc cag cgc cgg<br>Pro Ala Ala Gln Arg Asn Ser Gln Gly Ala His Leu Leu Gln Arg Arg<br>145                         150                     155                 160 | 480 |
| ggt gtt ccg ggc ggg cct tcc gga gac ccc acc tct cgc tgc ggg gtg<br>Gly Val Pro Gly Gly Pro Ser Gly Asp Pro Thr Ser Arg Cys Gly Val<br>                  165                     170                     175 | 528 |
| gcc tcg ggc tgg aac ccc gcc atc cta cgg gcc ctg gac cct tac aag<br>Ala Ser Gly Trp Asn Pro Ala Ile Leu Arg Ala Leu Asp Pro Tyr Lys<br>180                         185                       190 | 576 |
| ccg cgg cgg gcg ggc ttc ggg gag agt cgt agc cgg cgc agg tct ggg<br>Pro Arg Arg Ala Gly Phe Gly Glu Ser Arg Ser Arg Arg Ser Gly<br>                 195                     200                     205 | 624 |
| cgc gcc aag cgt ttc gtg tct atc ccg cgg tac gtg gag acg ctg gtg<br>Arg Ala Lys Arg Phe Val Ser Ile Pro Arg Tyr Val Glu Thr Leu Val<br>210                           215                       220 | 672 |
| gtc gcg gac gag tca atg gtc aag ttc cac ggc gcg gac ctg gaa cat<br>Val Ala Asp Glu Ser Met Val Lys Phe His Gly Ala Asp Leu Glu His<br>225                         230                     235                 240 | 720 |
| tat ctg ctg acg ctg ctg gca acg gcg gcg cga ctc tac cgc cat ccc<br>Tyr Leu Leu Thr Leu Leu Ala Thr Ala Ala Arg Leu Tyr Arg His Pro<br>                 245                     250                     255 | 768 |
| agc atc ctc aac ccc atc aac atc gtt gtg gtc aag gtg ctg ctt ctt<br>Ser Ile Leu Asn Pro Ile Asn Ile Val Val Val Lys Val Leu Leu Leu<br>                 260                     265                     270 | 816 |
| aga gat cgt gac tcc ggg ccc aag gtc acc ggc aat gcg gcc ctg acg<br>Arg Asp Arg Asp Ser Gly Pro Lys Val Thr Gly Asn Ala Ala Leu Thr<br>             275                     280                     285 | 864 |
| ctg cgc aac ttc tgt gcc tgg cag aag aag ctg aac aaa gtg agt gac<br>Leu Arg Asn Phe Cys Ala Trp Gln Lys Lys Leu Asn Lys Val Ser Asp<br>290                         295                     300 | 912 |
| aag cac ccc gag tac tgg gac act gcc atc ctc ttc acc agg cag gac<br>Lys His Pro Glu Tyr Trp Asp Thr Ala Ile Leu Phe Thr Arg Gln Asp<br>305                         310                     315                 320 | 960 |
| ctg tgt gga gcc acc acc tgt gac acc ctg ggc atg gct gat gtg ggt<br>Leu Cys Gly Ala Thr Thr Cys Asp Thr Leu Gly Met Ala Asp Val Gly<br>                 325                     330                     335 | 1008 |
| acc atg tgt gac ccc aag aga agc tgc tct gtc att gag gac gat ggg<br>Thr Met Cys Asp Pro Lys Arg Ser Cys Ser Val Ile Glu Asp Asp Gly<br>                 340                     345                     350 | 1056 |
| ctt cca tca gcc ttc acc act gcc cac gag ctg ggc cac gtg ttc aac<br>Leu Pro Ser Ala Phe Thr Thr Ala His Glu Leu Gly His Val Phe Asn<br>                 355                     360                     365 | 1104 |
| atg ccc cat gac aat gtg aaa gtc tgt gag gag gtg ttt ggg aag ctc<br>Met Pro His Asp Asn Val Lys Val Cys Glu Glu Val Phe Gly Lys Leu<br>370                         375                     380 | 1152 |
| cga gcc aac cac atg atg tcc ccg acc ctc atc cag atc gac cgt gcc<br>Arg Ala Asn His Met Met Ser Pro Thr Leu Ile Gln Ile Asp Arg Ala<br>385                         390                     395                 400 | 1200 |
| aac ccc tgg tca gcc tgc agt gct gcc atc atc acc gac ttc ctg gac<br>Asn Pro Trp Ser Ala Cys Ser Ala Ala Ile Ile Thr Asp Phe Leu Asp | 1248 |

|                                                                                                    |      |
|----------------------------------------------------------------------------------------------------|------|
| agc ggg cac ggt gac tgc ctc ctg gac caa ccc agc aag ccc atc tcc<br>Ser Gly His Gly Asp Cys Leu Leu Asp Gln Pro Ser Lys Pro Ile Ser<br>420                        425                      430 | 1296 |
| ctg ccc gag gat ctg ccg ggc gcc agc tac acc ctg agc cag cag tgc<br>Leu Pro Glu Asp Leu Pro Gly Ala Ser Tyr Thr Leu Ser Gln Gln Cys<br>                 435                        440                      445 | 1344 |
| gag ctg gct ttt ggc gtg ggc tcc aag ccc tgt cct tac atg cag tac<br>Glu Leu Ala Phe Gly Val Gly Ser Lys Pro Cys Pro Tyr Met Gln Tyr<br>450                        455                      460 | 1392 |
| tgc acc aag ctg tgg tgc acc ggg aag gcc aag gga cag atg gtg tgc<br>Cys Thr Lys Leu Trp Cys Thr Gly Lys Ala Lys Gly Gln Met Val Cys<br>465                        470                      475                      480 | 1440 |
| cag acc cgc cac ttc ccc tgg gcc gat ggc acc agc tgt ggc gag ggc<br>Gln Thr Arg His Phe Pro Trp Ala Asp Gly Thr Ser Cys Gly Glu Gly<br>                 485                        490                      495 | 1488 |
| aag ctc tgc ctc aaa ggg gcc tgc gtg gag aga cac aac ctc aac aag<br>Lys Leu Cys Leu Lys Gly Ala Cys Val Glu Arg His Asn Leu Asn Lys<br>                 500                        505                      510 | 1536 |
| cac agg gtg gat ggt tcc tgg gcc aaa tgg gat ccc tat ggc ccc tgc<br>His Arg Val Asp Gly Ser Trp Ala Lys Trp Asp Pro Tyr Gly Pro Cys<br>515                        520                      525 | 1584 |
| tcg cgc aca tgt ggt ggg ggc gtg cag ctg gcc agg agg cag tgc acc<br>Ser Arg Thr Cys Gly Gly Gly Val Gln Leu Ala Arg Arg Gln Cys Thr<br>530                        535                      540 | 1632 |
| aac ccc acc cct gcc aac ggg ggc aag tac tgc gag gga gtg agg gtg<br>Asn Pro Thr Pro Ala Asn Gly Gly Lys Tyr Cys Glu Gly Val Arg Val<br>545                        550                      555                      560 | 1680 |
| aaa tac cga tcc tgc aat ctg gag ccc tgc ccc agc tca gcc tcc gga<br>Lys Tyr Arg Ser Cys Asn Leu Glu Pro Cys Pro Ser Ser Ala Ser Gly<br>                 565                        570                      575 | 1728 |
| aag agc ttc cgg gag gag cag tgt gag gct ttc aac ggc tac aac cac<br>Lys Ser Phe Arg Glu Glu Gln Cys Glu Ala Phe Asn Gly Tyr Asn His<br>                 580                        585                      590 | 1776 |
| agc acc aac cgg ctc act ctc gcc gtg gca tgg gtg ccc aag tac tcc<br>Ser Thr Asn Arg Leu Thr Leu Ala Val Ala Trp Val Pro Lys Tyr Ser<br>595                        600                      605 | 1824 |
| ggc gtg tct ccc cgg gac aag tgc aag ctc atc tgc cga gcc aat ggc<br>Gly Val Ser Pro Arg Asp Lys Cys Lys Leu Ile Cys Arg Ala Asn Gly<br>610                        615                      620 | 1872 |
| act ggc tac ttc tat gtg ctg gca ccc aag gtg gtg gac ggc acg ctg<br>Thr Gly Tyr Phe Tyr Val Leu Ala Pro Lys Val Val Asp Gly Thr Leu<br>625                        630                      635                      640 | 1920 |
| tgc tct cct gac tcc acc tcc gtc tgt gtc caa ggc aag tgc atc aag<br>Cys Ser Pro Asp Ser Thr Ser Val Cys Val Gln Gly Lys Cys Ile Lys<br>                 645                        650                      655 | 1968 |
| gct ggc tgt gat ggg aac ctg ggc tcc aag aag aga ttc gac aag tgt<br>Ala Gly Cys Asp Gly Asn Leu Gly Ser Lys Lys Arg Phe Asp Lys Cys<br>                 660                        665                      670 | 2016 |
| ggg gtg tgt ggg gga gac aat aag agc tgc aag aag gtg act gga ctc<br>Gly Val Cys Gly Gly Asp Asn Lys Ser Cys Lys Lys Val Thr Gly Leu<br>675                        680                      685 | 2064 |
| ttc acc aag ccc atg cat ggc tac aat ttc gtg gtg gcc atc ccc gca<br>Phe Thr Lys Pro Met His Gly Tyr Asn Phe Val Val Ala Ile Pro Ala<br>                 690                        695                      700 | 2112 |
| ggc gcc tca agc atc gac atc cgc cag cgc ggt tac aaa ggg ctg atc<br>Gly Ala Ser Ser Ile Asp Ile Arg Gln Arg Gly Tyr Lys Gly Leu Ile<br>705                        710                      715                      720 | 2160 |
| ggg gat gac aac tac ctg gct ctg aag aac agc caa ggc aag tac ctg | 2208 |

```
Gly Asp Asp Asn Tyr Leu Ala Leu Lys Asn Ser Gln Gly Lys Tyr Leu
                725                 730                 735 ctc aac ggg cat ttc gtg gtg tcg gcg gtg gag cgg gac ctg gtg gtg    2256
Leu Asn Gly His Phe Val Val Ser Ala Val Glu Arg Asp Leu Val Val
            740                 745                 750 aag ggc agt ctg ctg cgg tac agc ggc acg ggc aca gcg gtg gag agc    2304
Lys Gly Ser Leu Leu Arg Tyr Ser Gly Thr Gly Thr Ala Val Glu Ser
        755                 760                 765 ctg cag gct tcc cgg ccc atc ctg gag ccg ctg acc gtg gag gtc ctc    2352
Leu Gln Ala Ser Arg Pro Ile Leu Glu Pro Leu Thr Val Glu Val Leu
    770                 775                 780 tcc gtg ggg aag atg aca ccg ccc cgg gtc cgc tac tcc ttc tat ctg    2400
Ser Val Gly Lys Met Thr Pro Pro Arg Val Arg Tyr Ser Phe Tyr Leu
785                 790                 795                 800 ccc aaa gag cct cgg gag gac aag tcc tct cat ccc aag gac ccc cgg    2448
Pro Lys Glu Pro Arg Glu Asp Lys Ser Ser His Pro Lys Asp Pro Arg
                805                 810                 815 gga ccc tct gtc ttg cac aac agc gtc ctc agc ctc tcc aac cag gtg    2496
Gly Pro Ser Val Leu His Asn Ser Val Leu Ser Leu Ser Asn Gln Val
            820                 825                 830 gag cag ccg gac gac agg ccc cct gca cgc tgg gtg gct ggc agc tgg    2544
Glu Gln Pro Asp Asp Arg Pro Pro Ala Arg Trp Val Ala Gly Ser Trp
        835                 840                 845 ggg ccg tgc tcc gcg agc tgc ggc agt ggc ctg cag aag cgg gcg gtg    2592
Gly Pro Cys Ser Ala Ser Cys Gly Ser Gly Leu Gln Lys Arg Ala Val
    850                 855                 860 gac tgc cgg ggc tcc gcc ggg cag cgc acg gtc cct gcc tgt gat gca    2640
Asp Cys Arg Gly Ser Ala Gly Gln Arg Thr Val Pro Ala Cys Asp Ala
865                 870                 875                 880 gcc cat cgg ccc gtg gag aca caa gcc tgc ggg gag ccc tgc ccc acc    2688
Ala His Arg Pro Val Glu Thr Gln Ala Cys Gly Glu Pro Cys Pro Thr
                885                 890                 895 tgg gag ctc agc gcc tgg tca ccc tgc tcc aag agc tgc ggc cgg gga    2736
Trp Glu Leu Ser Ala Trp Ser Pro Cys Ser Lys Ser Cys Gly Arg Gly
            900                 905                 910 ttt cag agg cgc tca ctc aag tgt gtg ggc cac gga ggc cgg ctg ctg    2784
Phe Gln Arg Arg Ser Leu Lys Cys Val Gly His Gly Gly Arg Leu Leu
        915                 920                 925 gcc cgg gac cag tgc aac ttg cac cgc aag ccc cag gag ctg gac ttc    2832
Ala Arg Asp Gln Cys Asn Leu His Arg Lys Pro Gln Glu Leu Asp Phe
    930                 935                 940 tgc gtc ctg agg ccg tgc tga                                        2853
Cys Val Leu Arg Pro Cys *
945                 950

<210> SEQ ID NO 77
<211> LENGTH: 950
<212> TYPE: PRT
<213> ORGANISM: Homo sapiens

<400> SEQUENCE: 77

Met Leu Leu Leu Gly Ile Leu Thr Leu Ala Phe Ala Gly Arg Thr Ala
1               5                   10                  15

Gly Gly Ser Glu Pro Glu Arg Glu Val Val Pro Ile Arg Leu Asp
            20                  25                  30

Pro Asp Ile Asn Gly Arg Arg Tyr Tyr Trp Arg Gly Pro Glu Asp Ser
            35                  40                  45

Gly Asp Gln Gly Leu Ile Phe Gln Ile Thr Ala Phe Gln Glu Asp Phe
    50                  55                  60
```

-continued

```
Tyr Leu His Leu Thr Pro Asp Ala Gln Phe Leu Ala Pro Ala Phe Ser
 65                  70                  75                  80

Thr Glu His Leu Gly Val Pro Leu Gln Gly Leu Thr Gly Gly Ser Ser
             85                  90                  95

Asp Leu Arg Arg Cys Phe Tyr Ser Gly Asp Val Asn Ala Glu Pro Asp
            100                 105                 110

Ser Phe Ala Ala Val Ser Leu Cys Gly Gly Leu Arg Gly Ala Phe Gly
            115                 120                 125

Tyr Arg Gly Ala Glu Tyr Val Ile Ser Pro Leu Pro Asn Ala Ser Ala
            130                 135                 140

Pro Ala Ala Gln Arg Asn Ser Gln Gly Ala His Leu Leu Gln Arg Arg
145                 150                 155                 160

Gly Val Pro Gly Gly Pro Ser Gly Asp Pro Thr Ser Arg Cys Gly Val
                165                 170                 175

Ala Ser Gly Trp Asn Pro Ala Ile Leu Arg Ala Leu Asp Pro Tyr Lys
                180                 185                 190

Pro Arg Arg Ala Gly Phe Gly Glu Ser Arg Ser Arg Arg Ser Gly
            195                 200                 205

Arg Ala Lys Arg Phe Val Ser Ile Pro Arg Tyr Val Glu Thr Leu Val
            210                 215                 220

Val Ala Asp Glu Ser Met Val Lys Phe His Gly Ala Asp Leu Glu His
225                 230                 235                 240

Tyr Leu Leu Thr Leu Leu Ala Thr Ala Ala Arg Leu Tyr Arg His Pro
                245                 250                 255

Ser Ile Leu Asn Pro Ile Asn Ile Val Val Lys Val Leu Leu Leu
                260                 265                 270

Arg Asp Arg Asp Ser Gly Pro Lys Val Thr Gly Asn Ala Ala Leu Thr
            275                 280                 285

Leu Arg Asn Phe Cys Ala Trp Gln Lys Lys Leu Asn Lys Val Ser Asp
            290                 295                 300

Lys His Pro Glu Tyr Trp Asp Thr Ala Ile Leu Phe Thr Arg Gln Asp
305                 310                 315                 320

Leu Cys Gly Ala Thr Thr Cys Asp Thr Leu Gly Met Ala Asp Val Gly
                325                 330                 335

Thr Met Cys Asp Pro Lys Arg Ser Cys Ser Val Ile Glu Asp Asp Gly
            340                 345                 350

Leu Pro Ser Ala Phe Thr Thr Ala His Glu Leu Gly His Val Phe Asn
            355                 360                 365

Met Pro His Asp Asn Val Lys Val Cys Glu Glu Val Phe Gly Lys Leu
            370                 375                 380

Arg Ala Asn His Met Met Ser Pro Thr Leu Ile Gln Ile Asp Arg Ala
385                 390                 395                 400

Asn Pro Trp Ser Ala Cys Ser Ala Ala Ile Ile Thr Asp Phe Leu Asp
                405                 410                 415

Ser Gly His Gly Asp Cys Leu Leu Asp Gln Pro Ser Lys Pro Ile Ser
            420                 425                 430

Leu Pro Glu Asp Leu Pro Gly Ala Ser Tyr Thr Leu Ser Gln Gln Cys
            435                 440                 445

Glu Leu Ala Phe Gly Val Gly Ser Lys Pro Cys Pro Tyr Met Gln Tyr
            450                 455                 460

Cys Thr Lys Leu Trp Cys Thr Gly Lys Ala Lys Gly Gln Met Val Cys
465                 470                 475                 480

Gln Thr Arg His Phe Pro Trp Ala Asp Gly Thr Ser Cys Gly Glu Gly
```

```
                    485                 490                 495
Lys Leu Cys Leu Lys Gly Ala Cys Val Glu Arg His Asn Leu Asn Lys
                500                 505                 510

His Arg Val Asp Gly Ser Trp Ala Lys Trp Asp Pro Tyr Gly Pro Cys
                515                 520                 525

Ser Arg Thr Cys Gly Gly Val Gln Leu Ala Arg Arg Gln Cys Thr
                530                 535                 540

Asn Pro Thr Pro Ala Asn Gly Gly Lys Tyr Cys Glu Gly Val Arg Val
545                 550                 555                 560

Lys Tyr Arg Ser Cys Asn Leu Glu Pro Cys Pro Ser Ser Ala Ser Gly
                565                 570                 575

Lys Ser Phe Arg Glu Glu Gln Cys Glu Ala Phe Asn Gly Tyr Asn His
                580                 585                 590

Ser Thr Asn Arg Leu Thr Leu Ala Val Ala Trp Val Pro Lys Tyr Ser
                595                 600                 605

Gly Val Ser Pro Arg Asp Lys Cys Lys Leu Ile Cys Arg Ala Asn Gly
                610                 615                 620

Thr Gly Tyr Phe Tyr Val Leu Ala Pro Lys Val Val Asp Gly Thr Leu
625                 630                 635                 640

Cys Ser Pro Asp Ser Thr Ser Val Cys Val Gln Gly Lys Cys Ile Lys
                645                 650                 655

Ala Gly Cys Asp Gly Asn Leu Gly Ser Lys Lys Arg Phe Asp Lys Cys
                660                 665                 670

Gly Val Cys Gly Gly Asp Asn Lys Ser Cys Lys Val Thr Gly Leu
                675                 680                 685

Phe Thr Lys Pro Met His Gly Tyr Asn Phe Val Val Ala Ile Pro Ala
690                 695                 700

Gly Ala Ser Ser Ile Asp Ile Arg Gln Arg Gly Tyr Lys Gly Leu Ile
705                 710                 715                 720

Gly Asp Asp Asn Tyr Leu Ala Leu Lys Asn Ser Gln Gly Lys Tyr Leu
                725                 730                 735

Leu Asn Gly His Phe Val Val Ser Ala Val Glu Arg Asp Leu Val Val
                740                 745                 750

Lys Gly Ser Leu Leu Arg Tyr Ser Gly Thr Gly Thr Ala Val Glu Ser
                755                 760                 765

Leu Gln Ala Ser Arg Pro Ile Leu Glu Pro Leu Thr Val Glu Val Leu
                770                 775                 780

Ser Val Gly Lys Met Thr Pro Arg Val Arg Tyr Ser Phe Tyr Leu
785                 790                 795                 800

Pro Lys Glu Pro Arg Glu Asp Lys Ser Ser His Pro Lys Asp Pro Arg
                805                 810                 815

Gly Pro Ser Val Leu His Asn Ser Val Leu Ser Leu Ser Asn Gln Val
                820                 825                 830

Glu Gln Pro Asp Asp Arg Pro Pro Ala Arg Trp Val Ala Gly Ser Trp
                835                 840                 845

Gly Pro Cys Ser Ala Ser Cys Gly Ser Gly Leu Gln Lys Arg Ala Val
                850                 855                 860

Asp Cys Arg Gly Ser Ala Gly Gln Arg Thr Val Pro Ala Cys Asp Ala
865                 870                 875                 880

Ala His Arg Pro Val Glu Thr Gln Ala Cys Gly Glu Pro Cys Pro Thr
                885                 890                 895

Trp Glu Leu Ser Ala Trp Ser Pro Cys Ser Lys Ser Cys Gly Arg Gly
                900                 905                 910
```

```
Phe Gln Arg Arg Ser Leu Lys Cys Val Gly His Gly Gly Arg Leu Leu
            915                 920                 925

Ala Arg Asp Gln Cys Asn Leu His Arg Lys Pro Gln Glu Leu Asp Phe
            930                 935                 940

Cys Val Leu Arg Pro Cys
945                 950

<210> SEQ ID NO 78
<211> LENGTH: 2853
<212> TYPE: DNA
<213> ORGANISM: Homo sapiens
<220> FEATURE:
<221> NAME/KEY: CDS
<222> LOCATION: (1)...(2853)

<400> SEQUENCE: 78 atg ctt ctg ctg ggc atc cta acc ctg gct ttc gcc ggg cga acc gct    48
Met Leu Leu Leu Gly Ile Leu Thr Leu Ala Phe Ala Gly Arg Thr Ala
1               5                   10                  15 gga ggc tct gag cca gag cgg gag gta gtc gtt ccc atc cga ctg gac    96
Gly Gly Ser Glu Pro Glu Arg Glu Val Val Val Pro Ile Arg Leu Asp
            20                  25                  30 ccg gac att aac ggc cgc cgc tac tac tgg cgg ggt ccc gag gac tcc   144
Pro Asp Ile Asn Gly Arg Arg Tyr Tyr Trp Arg Gly Pro Glu Asp Ser
        35                  40                  45 ggg gat cag gga ctc att ttt cag atc aca gca ttt cag gag gac ttt   192
Gly Asp Gln Gly Leu Ile Phe Gln Ile Thr Ala Phe Gln Glu Asp Phe
    50                  55                  60 tac cta cac ctg acg ccg gat gct cag ttc ttg gct ccc gcc ttc tcc   240
Tyr Leu His Leu Thr Pro Asp Ala Gln Phe Leu Ala Pro Ala Phe Ser
65                  70                  75                  80 act gag cat ctg ggc gtc ccc ctc cag ggg ctc acc ggg ggc tct tca   288
Thr Glu His Leu Gly Val Pro Leu Gln Gly Leu Thr Gly Gly Ser Ser
                85                  90                  95 gac ctg cga cgc tgc ttc tat tct ggg gac gtg aac gcc gag ccg gac   336
Asp Leu Arg Arg Cys Phe Tyr Ser Gly Asp Val Asn Ala Glu Pro Asp
            100                 105                 110 tcg ttc gct gct gtg agc ctg tgc ggg ggg ctc cgc gga gcc ttt ggc   384
Ser Phe Ala Ala Val Ser Leu Cys Gly Gly Leu Arg Gly Ala Phe Gly
        115                 120                 125 tac cga ggc gcc gag tat gtc att agc ccg ctg ccc aat gct agc gcg   432
Tyr Arg Gly Ala Glu Tyr Val Ile Ser Pro Leu Pro Asn Ala Ser Ala
    130                 135                 140 ccg gcg gcg cag cgc aac agc cag ggc gca cac ctt ctc cag cgc cgg   480
Pro Ala Ala Gln Arg Asn Ser Gln Gly Ala His Leu Leu Gln Arg Arg
145                 150                 155                 160 ggt gtt ccg ggc ggg cct tcc gga gac ccc acc tct cgc tgc ggg gtg   528
Gly Val Pro Gly Gly Pro Ser Gly Asp Pro Thr Ser Arg Cys Gly Val
                165                 170                 175 gcc tcg ggc tgg aac ccc gcc atc cta cgg gcc ctg gac cct tac aag   576
Ala Ser Gly Trp Asn Pro Ala Ile Leu Arg Ala Leu Asp Pro Tyr Lys
            180                 185                 190 ccg cgg cgg gcg ggc ttc ggg gag agt cgt agc cgg cgc agg tct ggg   624
Pro Arg Arg Ala Gly Phe Gly Glu Ser Arg Ser Arg Arg Ser Gly
        195                 200                 205 cgc gcc aag cgt ttc gtg tct atc ccg cgg tac gtg gag acg ctg gtg   672
Arg Ala Lys Arg Phe Val Ser Ile Pro Arg Tyr Val Glu Thr Leu Val
    210                 215                 220 gtc gcg gac gag tca atg gtc aag ttc cac ggc gcg gac ctg gaa cat   720
Val Ala Asp Glu Ser Met Val Lys Phe His Gly Ala Asp Leu Glu His
```

```
                       -continued 225               230               235               240
tat ctg ctg acg ctg ctg gca acg gcg gcg cga ctc tac cgc cat ccc      768
Tyr Leu Leu Thr Leu Leu Ala Thr Ala Ala Arg Leu Tyr Arg His Pro
            245               250               255 agc atc ctc aac ccc atc aac atc gtt gtg gtc aag gtg ctg ctt ctt      816
Ser Ile Leu Asn Pro Ile Asn Ile Val Val Val Lys Val Leu Leu Leu
        260               265               270 aga gat cgt gac tcc ggg ccc aag gtc acc ggc aat gcg gcc ctg acg      864
Arg Asp Arg Asp Ser Gly Pro Lys Val Thr Gly Asn Ala Ala Leu Thr
    275               280               285 ctg cgc aac ttc tgt gcc tgg cag aag aag ctg aac aaa gtg agt gac      912
Leu Arg Asn Phe Cys Ala Trp Gln Lys Lys Leu Asn Lys Val Ser Asp
290               295               300 aag cac ccc gag tac tgg gac act gcc atc ctc ttc acc agg cag gac      960
Lys His Pro Glu Tyr Trp Asp Thr Ala Ile Leu Phe Thr Arg Gln Asp
305               310               315               320 ctg tgt gga gcc acc acc tgt gac acc ctg ggc atg gct gat gtg ggt     1008
Leu Cys Gly Ala Thr Thr Cys Asp Thr Leu Gly Met Ala Asp Val Gly
            325               330               335 acc atg tgt gac ccc aag aga agc tgc tct gtc att gag gac gat ggg     1056
Thr Met Cys Asp Pro Lys Arg Ser Cys Ser Val Ile Glu Asp Asp Gly
        340               345               350 ctt cca tca gcc ttc acc act gcc cac gag ctg ggc cac gtg ttc aac     1104
Leu Pro Ser Ala Phe Thr Thr Ala His Glu Leu Gly His Val Phe Asn
    355               360               365 atg ccc cat gac aat gtg aaa gtc tgt gag gag gtg ttt ggg aag ctc     1152
Met Pro His Asp Asn Val Lys Val Cys Glu Glu Val Phe Gly Lys Leu
370               375               380 cga gcc aac cac atg atg tcc ccg acc ctc atc cag atc gac cgt gcc     1200
Arg Ala Asn His Met Met Ser Pro Thr Leu Ile Gln Ile Asp Arg Ala
385               390               395               400 aac ccc tgg tca gcc tgc agt gct gcc atc atc acc gac ttc ctg gac     1248
Asn Pro Trp Ser Ala Cys Ser Ala Ala Ile Ile Thr Asp Phe Leu Asp
            405               410               415 agc ggg cac ggt gac tgc ctc ctg gac caa ccc agc aag ccc atc tcc     1296
Ser Gly His Gly Asp Cys Leu Leu Asp Gln Pro Ser Lys Pro Ile Ser
        420               425               430 ctg ccc gag gat ctg ccg ggc gcc agc tac acc ctg agc cag cag tgc     1344
Leu Pro Glu Asp Leu Pro Gly Ala Ser Tyr Thr Leu Ser Gln Gln Cys
    435               440               445 gag ctg gct ttt ggc gtg ggc tcc aag ccc tgt cct tac atg cag tac     1392
Glu Leu Ala Phe Gly Val Gly Ser Lys Pro Cys Pro Tyr Met Gln Tyr
450               455               460 tgc acc aag ctg tgg tgc acc ggg aag gcc aag gga cag atg gtg tgc     1440
Cys Thr Lys Leu Trp Cys Thr Gly Lys Ala Lys Gly Gln Met Val Cys
465               470               475               480 cag acc cgc cac ttc ccc tgg gcc gat ggc acc agc tgt ggc gag ggc     1488
Gln Thr Arg His Phe Pro Trp Ala Asp Gly Thr Ser Cys Gly Glu Gly
            485               490               495 aag ctc tgc ctc aaa ggg gcc tgc gtg gag aga cac aac ctc aac aag     1536
Lys Leu Cys Leu Lys Gly Ala Cys Val Glu Arg His Asn Leu Asn Lys
        500               505               510 cac agg gtg gat ggt tcc tgg gcc aaa tgg gat ccc tat ggc ccc tgc     1584
His Arg Val Asp Gly Ser Trp Ala Lys Trp Asp Pro Tyr Gly Pro Cys
    515               520               525 tcg cgc aca tgt ggt ggg ggc gtg cag ctg gcc agg agg cag tgc acc     1632
Ser Arg Thr Cys Gly Gly Gly Val Gln Leu Ala Arg Arg Gln Cys Thr
530               535               540 aac ccc acc cct gcc aac ggg ggc aag tac tgc gag gga gtg agg gtg     1680
```

```
                Asn Pro Thr Pro Ala Asn Gly Gly Lys Tyr Cys Glu Gly Val Arg Val
                545                 550                 555                 560 aaa tac cga tcc tgc aat ctg gag ccc tgc ccc agc tca gcc tcc gga          1728
Lys Tyr Arg Ser Cys Asn Leu Glu Pro Cys Pro Ser Ser Ala Ser Gly
                565                 570                 575 aag agc ttc cgg gag gag cag tgt gag gct ttc aac ggc tac aac cac          1776
Lys Ser Phe Arg Glu Glu Gln Cys Glu Ala Phe Asn Gly Tyr Asn His
                580                 585                 590 agc acc aac cgg ctc act ctc gcc gtg gca tgg gtg ccc aag tac tcc          1824
Ser Thr Asn Arg Leu Thr Leu Ala Val Ala Trp Val Pro Lys Tyr Ser
            595                 600                 605 ggc gtg tct ccc cgg gac aag tgc aag ctc atc tgc cga gcc aat ggc          1872
Gly Val Ser Pro Arg Asp Lys Cys Lys Leu Ile Cys Arg Ala Asn Gly
            610                 615                 620 act ggc tac ttc tat gtg ctg gca ccc aag gtg gtg gac ggc acg ctg          1920
Thr Gly Tyr Phe Tyr Val Leu Ala Pro Lys Val Val Asp Gly Thr Leu
625                 630                 635                 640 tgc tct cct gac tcc acc tcc gtc tgt gtc caa ggc aag tgc atc aag          1968
Cys Ser Pro Asp Ser Thr Ser Val Cys Val Gln Gly Lys Cys Ile Lys
                645                 650                 655 gct ggc tgt gat ggg aac ctg ggc tcc aag aag aga ttc gac aag tgt          2016
Ala Gly Cys Asp Gly Asn Leu Gly Ser Lys Lys Arg Phe Asp Lys Cys
                660                 665                 670 ggg gtg tgt ggg gga gac aat aag agc tgc aag aag gtg act gga ctc          2064
Gly Val Cys Gly Gly Asp Asn Lys Ser Cys Lys Lys Val Thr Gly Leu
            675                 680                 685 ttc acc aag ccc atg cat ggc tac aat ttc gtg gtg gcc atc ccc gca          2112
Phe Thr Lys Pro Met His Gly Tyr Asn Phe Val Val Ala Ile Pro Ala
690                 695                 700 ggc gcc tca agc atc gac atc cgc cag cgc ggt tac aaa ggg ctg atc          2160
Gly Ala Ser Ser Ile Asp Ile Arg Gln Arg Gly Tyr Lys Gly Leu Ile
705                 710                 715                 720 ggg gat gac aac tac ctg gct ctg aag aac agc caa ggc aag tac ctg          2208
Gly Asp Asp Asn Tyr Leu Ala Leu Lys Asn Ser Gln Gly Lys Tyr Leu
                725                 730                 735 ctc aac ggg cat ttc gtg gtg tcg gcg gtg gag cgg gac ctg gtg gtg          2256
Leu Asn Gly His Phe Val Val Ser Ala Val Glu Arg Asp Leu Val Val
                740                 745                 750 aag ggc agt ctg ctg cgg tac agc ggc acg ggc aca gcg gtg gag agc          2304
Lys Gly Ser Leu Leu Arg Tyr Ser Gly Thr Gly Thr Ala Val Glu Ser
            755                 760                 765 ctg cag gct tcc cgg ccc atc ctg gag ccg ctg acc gtg gag gtc ctc          2352
Leu Gln Ala Ser Arg Pro Ile Leu Glu Pro Leu Thr Val Glu Val Leu
            770                 775                 780 tcc gtg ggg aag atg aca ccg ccc cgg gtc cgc tac tcc ttc tat ctg          2400
Ser Val Gly Lys Met Thr Pro Pro Arg Val Arg Tyr Ser Phe Tyr Leu
785                 790                 795                 800 ccc aaa gag cct cgg gag gac aag tcc tct cat ccc aag gac ccc cgg          2448
Pro Lys Glu Pro Arg Glu Asp Lys Ser Ser His Pro Lys Asp Pro Arg
                805                 810                 815 gga ccc tct gtc ttg cac aac agc gtc ctc agc ctc tcc aac cag gtg          2496
Gly Pro Ser Val Leu His Asn Ser Val Leu Ser Leu Ser Asn Gln Val
                820                 825                 830 gag cag ccg gac gac agg ccc cct gca cgc tgg gtg gct ggc agc tgg          2544
Glu Gln Pro Asp Asp Arg Pro Pro Ala Arg Trp Val Ala Gly Ser Trp
            835                 840                 845 ggg ccg tgc tcc gcg agc tgc ggc agt ggc ctg cag aag cgg gcg gtg          2592
Gly Pro Cys Ser Ala Ser Cys Gly Ser Gly Leu Gln Lys Arg Ala Val
            850                 855                 860
```

```
gac tgc cgg ggc tcc gcc ggg cag cgc acg gtc cct gcc tgt gat gca    2640
Asp Cys Arg Gly Ser Ala Gly Gln Arg Thr Val Pro Ala Cys Asp Ala
865                 870                 875                 880 gcc cat cgg ccc gtg gag aca caa gcc tgc ggg gag ccc tgc ccc acc    2688
Ala His Arg Pro Val Glu Thr Gln Ala Cys Gly Glu Pro Cys Pro Thr
                885                 890                 895 tgg gag ctc agc gcc tgg tca ccc tgc tcc aag agc tgc ggc cgg gga    2736
Trp Glu Leu Ser Ala Trp Ser Pro Cys Ser Lys Ser Cys Gly Arg Gly
            900                 905                 910 ttt cag agg cgc tca ctc aag tgt gtg ggc cac gga ggc cgg ctg ctg    2784
Phe Gln Arg Arg Ser Leu Lys Cys Val Gly His Gly Gly Arg Leu Leu
        915                 920                 925 gcc cgg gac cag tgc aac ttg cac cgc aag ccc cag gag ctg gac ttc    2832
Ala Arg Asp Gln Cys Asn Leu His Arg Lys Pro Gln Glu Leu Asp Phe
930                 935                 940 tgc gtc ctg agg ccg tgc tga                                        2853
Cys Val Leu Arg Pro Cys *
945                 950
```

<210> SEQ ID NO 79
<211> LENGTH: 119
<212> TYPE: PRT
<213> ORGANISM: Artificial Sequence
<220> FEATURE:
<223> OTHER INFORMATION: Consensus amino acid sequence

<400> SEQUENCE: 79

```
His Leu Glu Lys Asn Arg Ser Leu Leu Ala Pro Asp Phe Thr Val Thr
1               5                   10                  15

Thr Tyr Asp Glu Asp Gly Thr Leu Val Thr Glu Glu Pro Leu Ile Gln
            20                  25                  30

Asp Asp His Cys Tyr Tyr Gln Gly Tyr Val Glu Gly Tyr Pro Asn Ser
        35                  40                  45

Ala Val Ser Leu Ser Thr Cys Ser Gly Gly Leu Arg Gly Ile Leu Gln
    50                  55                  60

Leu Glu Asn Leu Ser Tyr Gly Ile Glu Pro Leu Glu Ser Ser Asp Gly
65                  70                  75                  80

Phe Glu His Ile Ile Tyr Gln Ile Glu Asn Asp Lys Thr Glu Pro Ser
                85                  90                  95

Pro Cys Gly Glu Cys Gly Ser Leu Ser Thr Ser Thr Asp Ser Ser Tyr
            100                 105                 110

Gly Ile Arg Ser Ala Ser Pro
        115
```

<210> SEQ ID NO 80
<211> LENGTH: 203
<212> TYPE: PRT
<213> ORGANISM: Artificial Sequence
<220> FEATURE:
<223> OTHER INFORMATION: Consensus amino acid sequence

<400> SEQUENCE: 80

```
Arg Tyr Ile Glu Leu Val Ile Val Val Asp His Gly Met Tyr Thr Lys
1               5                   10                  15

Tyr Gly Ser Asp Leu Asn Lys Ile Arg Gln Arg Val His Gln Ile Val
            20                  25                  30

Asn Leu Val Asn Glu Ile Tyr Arg Pro Leu Asn Ile Arg Val Val
        35                  40                  45

Leu Val Gly Leu Glu Ile Trp Ser Asp Gly Asp Lys Ile Asn Val Gln
    50                  55                  60
```

```
Ser Asp Ala Asn Asp Thr Leu His Ser Phe Gly Glu Trp Arg Glu Thr
 65                  70                  75                  80

Asp Leu Leu Lys Arg Lys Ser His Asp Asn Ala Gln Leu Leu Thr Gly
                 85                  90                  95

Ile Asp Phe Asp Gly Asn Thr Ile Gly Ala Ala Tyr Val Gly Gly Met
            100                 105                 110

Cys Ser Pro Lys Arg Ser Val Gly Val Val Gln Asp His Ser Pro Ile
        115                 120                 125

Val Leu Leu Val Ala Val Thr Met Ala His Glu Leu Gly His Asn Leu
130                 135                 140

Gly Met Thr His Asp Asp Lys Asn Lys Asp Gly Cys Thr Cys Pro Gly
145                 150                 155                 160

Gly Gly Ser Cys Ile Met Asn Pro Val Ala Ser Ser Pro Ser Lys
            165                 170                 175

Lys Lys Phe Ser Asn Cys Ser Lys Asp Asp Tyr Gln Lys Phe Leu Thr
        180                 185                 190

Lys Gln Lys Pro Gln Cys Leu Leu Asn Lys Pro
        195                 200

<210> SEQ ID NO 81
<211> LENGTH: 54
<212> TYPE: PRT
<213> ORGANISM: Artificial Sequence
<220> FEATURE:
<223> OTHER INFORMATION: Consensus amino acid sequence

<400> SEQUENCE: 81

Ser Pro Trp Ser Glu Trp Ser Pro Cys Ser Val Thr Cys Gly Lys Gly
 1               5                  10                  15

Ile Arg Thr Arg Gln Arg Thr Cys Asn Ser Pro Ala Pro Gln Lys Lys
            20                  25                  30

Gly Gly Lys Pro Cys Thr Gly Asp Ala Gln Glu Glu Thr Glu Ala Cys
        35                  40                  45

Asp Met Met Asp Lys Cys
    50

<210> SEQ ID NO 82
<211> LENGTH: 968
<212> TYPE: PRT
<213> ORGANISM: Mus musculus

<400> SEQUENCE: 82

Met Gln Pro Lys Val Pro Leu Gly Ser Arg Lys Gln Lys Pro Cys Ser
 1               5                  10                  15

Asp Met Gly Asp Val Gln Arg Ala Ala Arg Ser Arg Gly Ser Leu Ser
            20                  25                  30

Ala His Met Leu Leu Leu Leu Ala Ser Ile Thr Met Leu Leu Cys
        35                  40                  45

Ala Arg Gly Ala His Gly Arg Pro Thr Glu Glu Asp Glu Glu Leu Val
 50                  55                  60

Leu Pro Ser Leu Glu Arg Ala Pro Gly His Asp Ser Thr Thr Thr Arg
 65                  70                  75                  80

Leu Arg Leu Asp Ala Phe Gly Gln Gln Leu His Leu Lys Leu Gln Pro
                 85                  90                  95

Asp Ser Gly Phe Leu Ala Pro Gly Phe Thr Leu Gln Thr Val Gly Arg
            100                 105                 110
```

```
Ser Pro Gly Ser Glu Ala Gln His Leu Asp Pro Thr Gly Asp Leu Ala
        115                 120                 125
His Cys Phe Tyr Ser Gly Thr Val Asn Gly Asp Pro Gly Ser Ala Ala
130                 135                 140
Ala Leu Ser Leu Cys Glu Gly Val Arg Gly Ala Phe Tyr Leu Gln Gly
145                 150                 155                 160
Glu Glu Phe Phe Ile Gln Pro Ala Pro Gly Val Ala Thr Glu Arg Leu
                165                 170                 175
Ala Pro Ala Val Pro Glu Glu Ser Ser Ala Arg Pro Gln Phe His
            180                 185                 190
Ile Leu Arg Arg Arg Arg Gly Ser Gly Ala Lys Cys Gly Val
        195                 200                 205
Met Asp Asp Glu Thr Leu Pro Thr Ser Asp Ser Arg Pro Glu Ser Gln
210                 215                 220
Asn Thr Arg Asn Gln Trp Pro Val Arg Asp Pro Thr Pro Gln Asp Ala
225                 230                 235                 240
Gly Lys Pro Ser Gly Pro Gly Ser Ile Arg Lys Lys Arg Phe Val Ser
                245                 250                 255
Ser Pro Arg Tyr Val Glu Thr Met Leu Val Ala Asp Gln Ser Met Ala
            260                 265                 270
Asp Phe His Gly Ser Gly Leu Lys His Tyr Leu Leu Thr Leu Phe Ser
        275                 280                 285
Val Ala Ala Arg Phe Tyr Lys His Pro Ser Ile Arg Asn Ser Ile Ser
        290                 295                 300
Leu Val Val Val Lys Ile Leu Val Ile Tyr Glu Glu Gln Lys Gly Pro
305                 310                 315                 320
Glu Val Thr Ser Asn Ala Ala Leu Thr Leu Arg Asn Phe Cys Asn Trp
                325                 330                 335
Gln Lys Gln His Asn Ser Pro Ser Asp Arg Asp Pro Glu His Tyr Asp
            340                 345                 350
Thr Ala Ile Leu Phe Thr Arg Gln Asp Leu Cys Gly Ser His Thr Cys
        355                 360                 365
Asp Thr Leu Gly Met Ala Asp Val Gly Thr Val Cys Asp Pro Ser Arg
        370                 375                 380
Ser Cys Ser Val Ile Glu Asp Asp Gly Leu Gln Ala Ala Phe Thr Thr
385                 390                 395                 400
Ala His Glu Leu Gly His Val Phe Asn Met Pro His Asp Asp Ala Lys
                405                 410                 415
His Cys Ala Ser Leu Asn Gly Val Thr Gly Asp Ser His Leu Met Ala
            420                 425                 430
Ser Met Leu Ser Ser Leu Asp His Ser Gln Pro Trp Ser Pro Cys Ser
        435                 440                 445
Ala Tyr Met Val Thr Ser Phe Leu Asp Asn Gly His Gly Glu Cys Leu
        450                 455                 460
Met Asp Lys Pro Gln Asn Pro Ile Lys Leu Pro Ser Asp Leu Pro Gly
465                 470                 475                 480
Thr Leu Tyr Asp Ala Asn Arg Gln Cys Gln Phe Thr Phe Gly Glu Glu
                485                 490                 495
Ser Lys His Cys Pro Asp Ala Ala Ser Thr Cys Thr Thr Leu Trp Cys
            500                 505                 510
Thr Gly Thr Ser Gly Gly Leu Leu Val Cys Gln Thr Lys His Phe Pro
        515                 520                 525
Trp Ala Asp Gly Thr Ser Cys Gly Glu Gly Lys Trp Cys Val Ser Gly
```

-continued

```
            530                 535                 540
Lys Cys Val Asn Lys Thr Asp Met Lys His Phe Ala Thr Pro Val His
545                 550                 555                 560

Gly Ser Trp Gly Pro Trp Gly Pro Trp Gly Asp Cys Ser Arg Thr Cys
                565                 570                 575

Gly Gly Gly Val Gln Tyr Thr Met Arg Glu Cys Asp Asn Pro Val Pro
                580                 585                 590

Lys Asn Gly Gly Lys Tyr Cys Glu Gly Lys Arg Val Arg Tyr Arg Ser
                595                 600                 605

Cys Asn Ile Glu Asp Cys Pro Asp Asn Asn Gly Lys Thr Phe Arg Glu
                610                 615                 620

Glu Gln Cys Glu Ala His Asn Glu Phe Ser Lys Ala Ser Phe Gly Asn
625                 630                 635                 640

Glu Pro Thr Val Glu Trp Thr Pro Lys Tyr Ala Gly Val Ser Pro Lys
                645                 650                 655

Asp Arg Cys Lys Leu Thr Cys Glu Ala Lys Gly Ile Gly Tyr Phe Phe
                660                 665                 670

Val Leu Gln Pro Lys Val Val Asp Gly Thr Pro Cys Ser Pro Asp Ser
                675                 680                 685

Thr Ser Val Cys Val Gln Gly Gln Cys Val Lys Ala Gly Cys Asp Arg
690                 695                 700

Ile Ile Asp Ser Lys Lys Lys Phe Asp Lys Cys Gly Val Cys Gly Gly
705                 710                 715                 720

Asn Gly Ser Thr Cys Lys Lys Met Ser Gly Ile Val Thr Ser Thr Arg
                725                 730                 735

Pro Gly Tyr His Asp Ile Val Thr Ile Pro Ala Gly Ala Thr Asn Ile
                740                 745                 750

Glu Val Lys His Arg Asn Gln Arg Gly Ser Arg Asn Asn Gly Ser Phe
                755                 760                 765

Leu Ala Ile Arg Ala Ala Asp Gly Thr Tyr Ile Leu Asn Gly Asn Phe
                770                 775                 780

Thr Leu Ser Thr Leu Glu Gln Asp Leu Thr Tyr Lys Gly Thr Val Leu
785                 790                 795                 800

Arg Tyr Ser Gly Ser Ser Ala Ala Leu Glu Arg Ile Arg Ser Phe Ser
                805                 810                 815

Pro Leu Lys Glu Pro Leu Thr Ile Gln Val Leu Met Val Gly His Ala
                820                 825                 830

Leu Arg Pro Lys Ile Lys Phe Thr Tyr Phe Met Lys Lys Lys Thr Glu
                835                 840                 845

Ser Phe Asn Ala Ile Pro Thr Phe Ser Glu Trp Val Ile Glu Glu Trp
850                 855                 860

Gly Glu Cys Ser Lys Thr Cys Gly Ser Gly Trp Gln Arg Arg Val Val
865                 870                 875                 880

Gln Cys Arg Asp Ile Asn Gly His Pro Ala Ser Glu Cys Ala Lys Glu
                885                 890                 895

Val Lys Pro Ala Ser Thr Arg Pro Cys Ala Asp Leu Pro Cys Pro His
                900                 905                 910

Trp Gln Val Gly Asp Trp Ser Pro Cys Ser Lys Thr Cys Gly Lys Gly
                915                 920                 925

Tyr Lys Lys Arg Thr Leu Lys Cys Val Ser His Asp Gly Gly Val Leu
                930                 935                 940

Ser Asn Glu Ser Cys Asp Pro Leu Lys Lys Pro Lys His Tyr Ile Asp
945                 950                 955                 960
```

```
Phe Cys Thr Leu Thr Gln Cys Ser
                965

<210> SEQ ID NO 83
<211> LENGTH: 10
<212> TYPE: PRT
<213> ORGANISM: Homo sapiens
<220> FEATURE:
<221> NAME/KEY: VARIANT
<222> LOCATION: (1)...(1)
<223> OTHER INFORMATION: Xaa position one can be G or S or T or A or L
      or I or V or N
<220> FEATURE:
<221> NAME/KEY: VARIANT
<222> LOCATION: (2)...(3)
<223> OTHER INFORMATION: Xaa = Any Amino Acid
<220> FEATURE:
<221> NAME/KEY: VARIANT
<222> LOCATION: (6)...(6)
<223> OTHER INFORMATION: Xaa at position 6 can be L or I or V or M or
      F or Y or W
<220> FEATURE:
<221> NAME/KEY: VARIANT
<222> LOCATION: (7)...(7)
<223> OTHER INFORMATION: Xaa at position 7 can be A, Q, N, L, G, S,
      V, T,I, M, F, Y, C, or W
<220> FEATURE:
<221> NAME/KEY: VARIANT
<222> LOCATION: (9)...(9)
<223> OTHER INFORMATION: Xaa = Any Amino Acid
<220> FEATURE:
<221> NAME/KEY: VARIANT
<222> LOCATION: (10)...(10)
<223> OTHER INFORMATION: Xaa at position 10 can be L or I or V or M or
      F or Y or W or G or S or P or Q

<400> SEQUENCE: 83

Xaa Xaa Xaa His Glu Xaa Xaa His Xaa Xaa
 1               5                  10

<210> SEQ ID NO 84
<211> LENGTH: 5
<212> TYPE: PRT
<213> ORGANISM: Artificial Sequence
<220> FEATURE:
<223> OTHER INFORMATION: Consensus amino acid sequence
<220> FEATURE:
<221> NAME/KEY: VARIANT
<222> LOCATION: (3)...(4)
<223> OTHER INFORMATION: Xaa = Any Amino Acid

<400> SEQUENCE: 84

His Glu Xaa Xaa His
 1               5

<210> SEQ ID NO 85
<211> LENGTH: 22
<212> TYPE: PRT
<213> ORGANISM: Artificial Sequence
<220> FEATURE:
<223> OTHER INFORMATION: Consensus amino acid sequence
<220> FEATURE:
<221> NAME/KEY: VARIANT
<222> LOCATION: (2)...(7)
<223> OTHER INFORMATION: Xaa = Any Amino Acid
<220> FEATURE:
<221> NAME/KEY: VARIANT
<222> LOCATION: (9)...(14)
<223> OTHER INFORMATION: Xaa = Any Amino Acid
<220> FEATURE:
<221> NAME/KEY: VARIANT
<222> LOCATION: (16)...(21)
<223> OTHER INFORMATION: Xaa = Any Amino Acid
```

<400> SEQUENCE: 85

Leu Xaa Xaa Xaa Xaa Xaa Leu Xaa Xaa Xaa Xaa Xaa Leu Xaa
1               5                   10                  15

Xaa Xaa Xaa Xaa Xaa Leu
            20

<210> SEQ ID NO 86
<211> LENGTH: 3445
<212> TYPE: DNA
<213> ORGANISM: Homo sapiens
<220> FEATURE:
<221> NAME/KEY: CDS
<222> LOCATION: (83)...(3328)

<400> SEQUENCE: 86

```
cggccgcgga aagaatgcgc gccgcccgtg cgctccgcct gccgcgtctg gccacccgca         60
gccgccgcgt ccgcacctga cc atg gag tgc gcc ctc ctg ctc gcg tgt gcc        112
                        Met Glu Cys Ala Leu Leu Leu Ala Cys Ala
                          1               5                  10 ttc ccg gct gcg ggt tcg ggc ccg ccg agg ggc ctg gcg gga ctg ggg         160
Phe Pro Ala Ala Gly Ser Gly Pro Pro Arg Gly Leu Ala Gly Leu Gly
                15                  20                  25 cgc gtg gcc aag gcg ctc cag ctg tgc tgc ctc tgc tgt gcg tcg gtc         208
Arg Val Ala Lys Ala Leu Gln Leu Cys Cys Leu Cys Cys Ala Ser Val
        30                  35                  40 gcc gcg gcc tta gcc agt gac agc agc agc ggc gcc agc gga tta aat         256
Ala Ala Ala Leu Ala Ser Asp Ser Ser Ser Gly Ala Ser Gly Leu Asn
    45                  50                  55 gat gat tac gtc ttt gtc acg cca gta gaa gta gac tca gcc ggg tca         304
Asp Asp Tyr Val Phe Val Thr Pro Val Glu Val Asp Ser Ala Gly Ser
60                  65                  70 tat att tca cac gac att ttg cac aac ggc agg aaa aag cga tcg gcg         352
Tyr Ile Ser His Asp Ile Leu His Asn Gly Arg Lys Lys Arg Ser Ala
        75                  80                  85                  90 cag aat gcc aga agc tcc ctg cac tac cga ttt tca gca ttt gga cag         400
Gln Asn Ala Arg Ser Ser Leu His Tyr Arg Phe Ser Ala Phe Gly Gln
                95                  100                 105 gaa ctg cac tta gaa ctt aag ccc tcg gcg att ttg agc agt cac ttt         448
Glu Leu His Leu Glu Leu Lys Pro Ser Ala Ile Leu Ser Ser His Phe
            110                 115                 120 att gtc cag gta ctt gga aaa gat ggt gct tca gag act cag aaa ccc         496
Ile Val Gln Val Leu Gly Lys Asp Gly Ala Ser Glu Thr Gln Lys Pro
        125                 130                 135 gag gtg cag caa tgc ttc tat cag gga ttt atc aga aat gac agc tcc         544
Glu Val Gln Gln Cys Phe Tyr Gln Gly Phe Ile Arg Asn Asp Ser Ser
    140                 145                 150 tcc tct gtc gct gtg tct acg tgt gct ggc ttg tca ggt tta ata agg         592
Ser Ser Val Ala Val Ser Thr Cys Ala Gly Leu Ser Gly Leu Ile Arg
155                 160                 165                 170 aca cga aaa aat gaa ttc ctc atc tcg cca tta cct cag ctt ctg gcc         640
Thr Arg Lys Asn Glu Phe Leu Ile Ser Pro Leu Pro Gln Leu Leu Ala
                175                 180                 185 cag gaa cac aac tac agc tcc cct gcg ggt cac cat cct cac gta ctg         688
Gln Glu His Asn Tyr Ser Ser Pro Ala Gly His His Pro His Val Leu
            190                 195                 200 tac aaa agg aca gca gag gag aag atc cag cgg tac cgt ggc tac ccc         736
Tyr Lys Arg Thr Ala Glu Glu Lys Ile Gln Arg Tyr Arg Gly Tyr Pro
        205                 210                 215 ggc tct ggc cgg aat tat cct ggt tac tcc cca agt cac att ccc cat         784
```

```
                 Gly Ser Gly Arg Asn Tyr Pro Gly Tyr Ser Pro Ser His Ile Pro His
                     220                 225                 230 gca tct cag agt cga gag aca gag tat cac cat cga agg ttg caa aag       832
Ala Ser Gln Ser Arg Glu Thr Glu Tyr His His Arg Arg Leu Gln Lys
235                 240                 245                 250 cag cat ttt tgt gga cga cgc aag aaa tat gct ccc aag cct ccc aca       880
Gln His Phe Cys Gly Arg Arg Lys Lys Tyr Ala Pro Lys Pro Pro Thr
                255                 260                 265 gag gac acc tat cta agg ttt gat gaa tat ggg agc tct ggg cga ccc       928
Glu Asp Thr Tyr Leu Arg Phe Asp Glu Tyr Gly Ser Ser Gly Arg Pro
            270                 275                 280 aga aga tca gct gga aaa tca caa aag ggc ctc aat gtg gaa acc ctc       976
Arg Arg Ser Ala Gly Lys Ser Gln Lys Gly Leu Asn Val Glu Thr Leu
        285                 290                 295 gtg gtg gca gac aag aaa atg gtg gaa aag cat ggc aag gga aat gtc      1024
Val Val Ala Asp Lys Lys Met Val Glu Lys His Gly Lys Gly Asn Val
    300                 305                 310 acc aca tac att ctc aca gta atg aag gtt tct ggc cta ttt aaa gat      1072
Thr Thr Tyr Ile Leu Thr Val Met Lys Val Ser Gly Leu Phe Lys Asp
315                 320                 325                 330 ggg act att gga agt gac ata aac gtg gtt gtg gtg agc cta att ctt      1120
Gly Thr Ile Gly Ser Asp Ile Asn Val Val Val Val Ser Leu Ile Leu
                335                 340                 345 ctg gaa caa gaa cct gga gga tta ttg atc aac cat cat gca gac cag      1168
Leu Glu Gln Glu Pro Gly Gly Leu Leu Ile Asn His His Ala Asp Gln
                350                 355                 360 tct ctg aat agt ttt tgt caa tgg cag tct gcc ctc att gga aag aat      1216
Ser Leu Asn Ser Phe Cys Gln Trp Gln Ser Ala Leu Ile Gly Lys Asn
            365                 370                 375 ggc aag aga cat gat cat gcc atc tta cta aca gga ttt gat att tgt      1264
Gly Lys Arg His Asp His Ala Ile Leu Leu Thr Gly Phe Asp Ile Cys
        380                 385                 390 tct tgg aag aat gaa cca tgt gac act cta ggg ttt gcc ccc acc agt      1312
Ser Trp Lys Asn Glu Pro Cys Asp Thr Leu Gly Phe Ala Pro Thr Ser
395                 400                 405                 410 gga atg tgc tct aag tac cga agt tgt acc atc aat gag gac aca gga      1360
Gly Met Cys Ser Lys Tyr Arg Ser Cys Thr Ile Asn Glu Asp Thr Gly
                415                 420                 425 ctt ggc ctt gcc ttc acc atc gct cat gag tca ggg cac aac ttt ggt      1408
Leu Gly Leu Ala Phe Thr Ile Ala His Glu Ser Gly His Asn Phe Gly
                430                 435                 440 atg att cac gac gga gaa ggg aat ccc tgc aga aag gct gaa ggc aat      1456
Met Ile His Asp Gly Glu Gly Asn Pro Cys Arg Lys Ala Glu Gly Asn
            445                 450                 455 atc atg tct ccc aca ctg acc gga aac aat gga gtg ttt tca tgg tct      1504
Ile Met Ser Pro Thr Leu Thr Gly Asn Asn Gly Val Phe Ser Trp Ser
        460                 465                 470 tcc tgc agc cgc cag tat ctc aag aaa ttc ctc agc aca cct cag gcg      1552
Ser Cys Ser Arg Gln Tyr Leu Lys Lys Phe Leu Ser Thr Pro Gln Ala
475                 480                 485                 490 ggg tgt cta gtg gat gag ccc aag caa gca gga cag tat aaa tat ccg      1600
Gly Cys Leu Val Asp Glu Pro Lys Gln Ala Gly Gln Tyr Lys Tyr Pro
                495                 500                 505 gac aaa cta cca gga cag att tat gat gct gac aca cag tgt aaa tgg      1648
Asp Lys Leu Pro Gly Gln Ile Tyr Asp Ala Asp Thr Gln Cys Lys Trp
                510                 515                 520 caa ttt gga gca aaa gcc aag tta tgc agc ctt ggt ttt gtg aag gat      1696
Gln Phe Gly Ala Lys Ala Lys Leu Cys Ser Leu Gly Phe Val Lys Asp
            525                 530                 535
```

-continued

```
att tgc aaa tca ctt tgg tgc cac cga gta ggc cac agg tgt gag acc     1744
Ile Cys Lys Ser Leu Trp Cys His Arg Val Gly His Arg Cys Glu Thr
540                 545                 550 aag ttt atg ccc gca gca gaa ggg acc gtt tgt ggc ttg agt atg tgg     1792
Lys Phe Met Pro Ala Ala Glu Gly Thr Val Cys Gly Leu Ser Met Trp
555                 560                 565                 570 tgt cgg caa ggc cag tgc gta aag ttt ggg gag ctc ggg ccc cgg ccc     1840
Cys Arg Gln Gly Gln Cys Val Lys Phe Gly Glu Leu Gly Pro Arg Pro
            575                 580                 585 atc cac ggc cag tgg tcc gcc tgg tcg aag tgg tca gaa tgt tcc cgg     1888
Ile His Gly Gln Trp Ser Ala Trp Ser Lys Trp Ser Glu Cys Ser Arg
        590                 595                 600 aca tgt ggt gga gga gtc aag ttc cag gag aga cac tgc aat aac ccc     1936
Thr Cys Gly Gly Gly Val Lys Phe Gln Glu Arg His Cys Asn Asn Pro
    605                 610                 615 aag cct cag tat ggt ggc ata ttc tgt cca ggt tct agc cgt att tat     1984
Lys Pro Gln Tyr Gly Gly Ile Phe Cys Pro Gly Ser Ser Arg Ile Tyr
620                 625                 630 cag ctg tgc aat att aac cct tgc aat gaa aat agc ttg gat ttt cgg     2032
Gln Leu Cys Asn Ile Asn Pro Cys Asn Glu Asn Ser Leu Asp Phe Arg
635                 640                 645                 650 gct caa cag tgt gca gaa tat aac agc aaa cct ttc cgt gga tgg ttc     2080
Ala Gln Gln Cys Ala Glu Tyr Asn Ser Lys Pro Phe Arg Gly Trp Phe
            655                 660                 665 tac cag tgg aaa ccc tat aca aaa gtg gaa gag gaa gat cga tgc aaa     2128
Tyr Gln Trp Lys Pro Tyr Thr Lys Val Glu Glu Glu Asp Arg Cys Lys
        670                 675                 680 ctg tac tgc aag gct gag aac ttt gaa ttt ttt ttt gca atg tcc ggc     2176
Leu Tyr Cys Lys Ala Glu Asn Phe Glu Phe Phe Phe Ala Met Ser Gly
    685                 690                 695 aaa gtg aaa gat gga act ccc tgc tcc cca aac aaa aat gat gtt tgt     2224
Lys Val Lys Asp Gly Thr Pro Cys Ser Pro Asn Lys Asn Asp Val Cys
700                 705                 710 att gac ggg gtt tgt gaa cta gtg gga tgt gat cat gaa cta ggc tct     2272
Ile Asp Gly Val Cys Glu Leu Val Gly Cys Asp His Glu Leu Gly Ser
715                 720                 725                 730 aaa gca gtt tca gat gct tgt ggc gtt tgc aaa ggt gat aat tca act     2320
Lys Ala Val Ser Asp Ala Cys Gly Val Cys Lys Gly Asp Asn Ser Thr
            735                 740                 745 tgc aag ttt tat aaa ggc ctg tac ctc aac cag cat aaa gca aat gaa     2368
Cys Lys Phe Tyr Lys Gly Leu Tyr Leu Asn Gln His Lys Ala Asn Glu
        750                 755                 760 tat tat ccg gtg gtc ctc att cca gct ggc gcc cga agc atc gaa atc     2416
Tyr Tyr Pro Val Val Leu Ile Pro Ala Gly Ala Arg Ser Ile Glu Ile
    765                 770                 775 cag gag ctg cag gtt tcc tcc agt tac ctc gca gtt cga agc ctc agt     2464
Gln Glu Leu Gln Val Ser Ser Ser Tyr Leu Ala Val Arg Ser Leu Ser
780                 785                 790 caa aag tat tac ctc acc ggg ggc tgg agc atc gac tgg cct ggg gag     2512
Gln Lys Tyr Tyr Leu Thr Gly Gly Trp Ser Ile Asp Trp Pro Gly Glu
795                 800                 805                 810 ttc ccc ttc gct ggg acc acg ttt gaa tac cag cgc tct ttc aac cgc     2560
Phe Pro Phe Ala Gly Thr Thr Phe Glu Tyr Gln Arg Ser Phe Asn Arg
            815                 820                 825 ccg gaa cgt ctg tac gcg cca ggg ccc aca aat gag acg ctg gtc ttt     2608
Pro Glu Arg Leu Tyr Ala Pro Gly Pro Thr Asn Glu Thr Leu Val Phe
        830                 835                 840 gaa att ctg atg caa ggc aaa aat cca ggg ata gct tgg aag tat gca     2656
Glu Ile Leu Met Gln Gly Lys Asn Pro Gly Ile Ala Trp Lys Tyr Ala
    845                 850                 855
```

-continued

| | | |
|---|---|---|
| ctt ccc aag gtc atg aat gga act cca cca gcc aca aaa aga cct gcc<br>Leu Pro Lys Val Met Asn Gly Thr Pro Pro Ala Thr Lys Arg Pro Ala<br>860                        865                          870 | 2704 |
| tat acc tgg agt atc gtg cag tca gag tgc tcc gtc tcc tgt ggt gga<br>Tyr Thr Trp Ser Ile Val Gln Ser Glu Cys Ser Val Ser Cys Gly Gly<br>875                        880                          885                      890 | 2752 |
| ggt tac ata aat gta aag gcc att tgc ttg cga gat caa aat act caa<br>Gly Tyr Ile Asn Val Lys Ala Ile Cys Leu Arg Asp Gln Asn Thr Gln<br>                        895                          900                          905 | 2800 |
| gtc aat tcc tca ttc tgc agt gca aaa acc aag cca gta act gag ccc<br>Val Asn Ser Ser Phe Cys Ser Ala Lys Thr Lys Pro Val Thr Glu Pro<br>910                        915                          920 | 2848 |
| aaa atc tgc aac gct ttc tcc tgc ccg gct tac tgg atg cca ggt gaa<br>Lys Ile Cys Asn Ala Phe Ser Cys Pro Ala Tyr Trp Met Pro Gly Glu<br>925                        930                          935 | 2896 |
| tgg agt aca tgc agc aag tcc tgt gct gga ggc cag cag agc cga aag<br>Trp Ser Thr Cys Ser Lys Ser Cys Ala Gly Gly Gln Gln Ser Arg Lys<br>940                        945                          950 | 2944 |
| atc cag tgt gtg caa aag aag ccc ttc caa aag gag gaa gca gtg ttg<br>Ile Gln Cys Val Gln Lys Lys Pro Phe Gln Lys Glu Glu Ala Val Leu<br>955                        960                          965                      970 | 2992 |
| cat tct ctc tgt cca gta agc aca ccc act cag gtc caa gcc tgc aac<br>His Ser Leu Cys Pro Val Ser Thr Pro Thr Gln Val Gln Ala Cys Asn<br>                        975                          980                          985 | 3040 |
| agc cat gcc tgc cct cca caa tgg agc ctt gga ccc tgg tct cag tgt<br>Ser His Ala Cys Pro Pro Gln Trp Ser Leu Gly Pro Trp Ser Gln Cys<br>990                        995                          1000 | 3088 |
| tcc aag acc tgt gga cga ggg gtg agg aag cgt gaa ctc ctc tgc aag<br>Ser Lys Thr Cys Gly Arg Gly Val Arg Lys Arg Glu Leu Leu Cys Lys<br>                        1005                      1010                      1015 | 3136 |
| ggc tct gcc gca gaa acc ctc ccc gag agc cag tgt acc agt ctc ccc<br>Gly Ser Ala Ala Glu Thr Leu Pro Glu Ser Gln Cys Thr Ser Leu Pro<br>1020                      1025                      1030 | 3184 |
| aga cct gag ctg cag gag ggc tgt gtg ctt gga cga tgt ccc aag aac<br>Arg Pro Glu Leu Gln Glu Gly Cys Val Leu Gly Arg Cys Pro Lys Asn<br>1035                      1040                      1045                      1050 | 3232 |
| agc cgg cta cag tgg gtc gct tct tcg tgg agc gag gta tgg att aga<br>Ser Arg Leu Gln Trp Val Ala Ser Ser Trp Ser Glu Val Trp Ile Arg<br>                        1055                      1060                      1065 | 3280 |
| agt cac tgc tgg gtc agg aga ttg aga cca tcc tgg cta aca cag tga<br>Ser His Cys Trp Val Arg Arg Leu Arg Pro Ser Trp Leu Thr Gln *<br>1070                      1075                      1080 | 3328 |
| aaccctgtct ctactaaaaa tacaaaaaat tagccaggca aggtggcagg cgcctgtagt | 3388 |
| ctgatctact ggggctgtag tctgatctac tggggctgtt cttgggacat cgtcggg | 3445 |

<210> SEQ ID NO 87
<211> LENGTH: 1081
<212> TYPE: PRT
<213> ORGANISM: Homo sapiens

<400> SEQUENCE: 87

Met Glu Cys Ala Leu Leu Leu Ala Cys Ala Phe Pro Ala Ala Gly Ser
 1               5                   10                 15

Gly Pro Pro Arg Gly Leu Ala Gly Leu Gly Arg Val Ala Lys Ala Leu
              20                 25                 30

Gln Leu Cys Cys Leu Cys Cys Ala Ser Val Ala Ala Ala Leu Ala Ser
        35                   40                 45

Asp Ser Ser Ser Gly Ala Ser Gly Leu Asn Asp Asp Tyr Val Phe Val

-continued

```
              50                  55                  60
Thr Pro Val Glu Val Asp Ser Ala Gly Ser Tyr Ile Ser His Asp Ile
 65                  70                  75                  80

Leu His Asn Gly Arg Lys Lys Arg Ser Ala Gln Asn Ala Arg Ser Ser
                 85                  90                  95

Leu His Tyr Arg Phe Ser Ala Phe Gly Gln Glu Leu His Leu Glu Leu
                100                 105                 110

Lys Pro Ser Ala Ile Leu Ser Ser His Phe Ile Val Gln Val Leu Gly
                115                 120                 125

Lys Asp Gly Ala Ser Glu Thr Gln Lys Pro Gly Val Gln Gln Cys Phe
130                 135                 140

Tyr Gln Gly Phe Ile Arg Asn Asp Ser Ser Ser Val Ala Val Ser
145                 150                 155                 160

Thr Cys Ala Gly Leu Ser Gly Leu Ile Arg Thr Arg Lys Asn Glu Phe
                165                 170                 175

Leu Ile Ser Pro Leu Pro Gln Leu Leu Ala Gln Glu His Asn Tyr Ser
                180                 185                 190

Ser Pro Ala Gly His His Pro His Val Leu Tyr Lys Arg Thr Ala Glu
                195                 200                 205

Glu Lys Ile Gln Arg Tyr Arg Gly Tyr Pro Gly Ser Gly Arg Asn Tyr
210                 215                 220

Pro Gly Tyr Ser Pro Ser His Ile Pro His Ala Ser Gln Ser Arg Glu
225                 230                 235                 240

Thr Glu Tyr His His Arg Arg Leu Gln Lys Gln His Phe Cys Gly Arg
                245                 250                 255

Arg Lys Lys Tyr Ala Pro Lys Pro Pro Thr Glu Asp Thr Tyr Leu Arg
                260                 265                 270

Phe Asp Glu Tyr Gly Ser Ser Gly Arg Pro Arg Arg Ser Ala Gly Lys
                275                 280                 285

Ser Gln Lys Gly Leu Asn Val Glu Thr Leu Val Val Ala Asp Lys Lys
                290                 295                 300

Met Val Glu Lys His Gly Lys Gly Asn Val Thr Thr Tyr Ile Leu Thr
305                 310                 315                 320

Val Met Lys Val Ser Gly Leu Phe Lys Asp Gly Thr Ile Gly Ser Asp
                325                 330                 335

Ile Asn Val Val Val Ser Leu Ile Leu Leu Glu Gln Glu Pro Gly
                340                 345                 350

Gly Leu Leu Ile Asn His His Ala Asp Gln Ser Leu Asn Ser Phe Cys
                355                 360                 365

Gln Trp Gln Ser Ala Leu Ile Gly Lys Asn Gly Lys Arg His Asp His
370                 375                 380

Ala Ile Leu Leu Thr Gly Phe Asp Ile Cys Ser Trp Lys Asn Glu Pro
385                 390                 395                 400

Cys Asp Thr Leu Gly Phe Ala Pro Thr Ser Gly Met Cys Ser Lys Tyr
                405                 410                 415

Arg Ser Cys Thr Ile Asn Glu Asp Thr Gly Leu Gly Leu Ala Phe Thr
                420                 425                 430

Ile Ala His Glu Ser Gly His Asn Phe Gly Met Ile His Asp Gly Glu
                435                 440                 445

Gly Asn Pro Cys Arg Lys Ala Glu Gly Asn Ile Met Ser Pro Thr Leu
                450                 455                 460

Thr Gly Asn Asn Gly Val Phe Ser Trp Ser Ser Cys Ser Arg Gln Tyr
465                 470                 475                 480
```

-continued

```
Leu Lys Lys Phe Leu Ser Thr Pro Gln Ala Gly Cys Leu Val Asp Glu
            485                 490                 495
Pro Lys Gln Ala Gly Gln Tyr Lys Tyr Pro Asp Lys Leu Pro Gly Gln
        500                 505                 510
Ile Tyr Asp Ala Asp Thr Gln Cys Lys Trp Gln Phe Gly Ala Lys Ala
        515                 520                 525
Lys Leu Cys Ser Leu Gly Phe Val Lys Asp Ile Cys Lys Ser Leu Trp
    530                 535                 540
Cys His Arg Val Gly His Arg Cys Glu Thr Lys Phe Met Pro Ala Ala
545                 550                 555                 560
Glu Gly Thr Val Cys Gly Leu Ser Met Trp Cys Arg Gln Gly Gln Cys
                565                 570                 575
Val Lys Phe Gly Glu Leu Gly Pro Pro Ile His Gly Gln Trp Ser
            580                 585                 590
Ala Trp Ser Lys Trp Ser Glu Cys Ser Arg Thr Cys Gly Gly Gly Val
        595                 600                 605
Lys Phe Gln Glu Arg His Cys Asn Asn Pro Lys Pro Gln Tyr Gly Gly
    610                 615                 620
Ile Phe Cys Pro Gly Ser Ser Arg Ile Tyr Gln Leu Cys Asn Ile Asn
625                 630                 635                 640
Pro Cys Asn Glu Asn Ser Leu Asp Phe Arg Ala Gln Gln Cys Ala Glu
                645                 650                 655
Tyr Asn Ser Lys Pro Phe Arg Gly Trp Phe Tyr Gln Trp Lys Pro Tyr
            660                 665                 670
Thr Lys Val Glu Glu Glu Asp Arg Cys Lys Leu Tyr Cys Lys Ala Glu
        675                 680                 685
Asn Phe Glu Phe Phe Phe Ala Met Ser Gly Lys Val Lys Asp Gly Thr
    690                 695                 700
Pro Cys Ser Pro Asn Lys Asn Asp Val Cys Ile Asp Gly Val Cys Glu
705                 710                 715                 720
Leu Val Gly Cys Asp His Glu Leu Gly Ser Lys Ala Val Ser Asp Ala
                725                 730                 735
Cys Gly Val Cys Lys Gly Asp Asn Ser Thr Cys Lys Phe Tyr Lys Gly
            740                 745                 750
Leu Tyr Leu Asn Gln His Lys Ala Asn Glu Tyr Tyr Pro Val Val Leu
        755                 760                 765
Ile Pro Ala Gly Ala Arg Ser Ile Glu Ile Gln Glu Leu Gln Val Ser
    770                 775                 780
Ser Ser Tyr Leu Ala Val Arg Ser Leu Ser Gln Lys Tyr Tyr Leu Thr
785                 790                 795                 800
Gly Gly Trp Ser Ile Asp Trp Pro Gly Glu Phe Pro Phe Ala Gly Thr
                805                 810                 815
Thr Phe Glu Tyr Gln Arg Ser Phe Asn Arg Pro Glu Arg Leu Tyr Ala
            820                 825                 830
Pro Gly Pro Thr Asn Glu Thr Leu Val Phe Glu Ile Leu Met Gln Gly
        835                 840                 845
Lys Asn Pro Gly Ile Ala Trp Lys Tyr Ala Leu Pro Lys Val Met Asn
    850                 855                 860
Gly Thr Pro Pro Ala Thr Lys Arg Pro Ala Tyr Thr Trp Ser Ile Val
865                 870                 875                 880
Gln Ser Glu Cys Ser Val Ser Cys Gly Gly Gly Tyr Ile Asn Val Lys
                885                 890                 895
```

-continued

```
Ala Ile Cys Leu Arg Asp Gln Asn Thr Gln Val Asn Ser Ser Phe Cys
            900                 905                 910

Ser Ala Lys Thr Lys Pro Val Thr Glu Pro Lys Ile Cys Asn Ala Phe
            915                 920                 925

Ser Cys Pro Ala Tyr Trp Met Pro Gly Glu Trp Ser Thr Cys Ser Lys
            930                 935                 940

Ser Cys Ala Gly Gly Gln Gln Ser Arg Lys Ile Gln Cys Val Gln Lys
945                 950                 955                 960

Lys Pro Phe Gln Lys Glu Glu Ala Val Leu His Ser Leu Cys Pro Val
                965                 970                 975

Ser Thr Pro Thr Gln Val Gln Ala Cys Asn Ser His Ala Cys Pro Pro
            980                 985                 990

Gln Trp Ser Leu Gly Pro Trp Ser Gln Cys Ser Lys Thr Cys Gly Arg
            995                 1000                1005

Gly Val Arg Lys Arg Glu Leu Leu Cys Lys Gly Ser Ala Ala Glu Thr
            1010                1015                1020

Leu Pro Glu Ser Gln Cys Thr Ser Leu Pro Arg Pro Glu Leu Gln Glu
1025                1030                1035                1040

Gly Cys Val Leu Gly Arg Cys Pro Lys Asn Ser Arg Leu Gln Trp Val
                1045                1050                1055

Ala Ser Ser Trp Ser Glu Val Trp Ile Arg Ser His Cys Trp Val Arg
                1060                1065                1070

Arg Leu Arg Pro Ser Trp Leu Thr Gln
            1075                1080

<210> SEQ ID NO 88
<211> LENGTH: 3246
<212> TYPE: DNA
<213> ORGANISM: Homo sapiens
<220> FEATURE:
<221> NAME/KEY: CDS
<222> LOCATION: (1)...(3246)

<400> SEQUENCE: 88 atg gag tgc gcc ctc ctg ctc gcg tgt gcc ttc ccg gct gcg ggt tcg      48
Met Glu Cys Ala Leu Leu Leu Ala Cys Ala Phe Pro Ala Ala Gly Ser
1               5                   10                  15 ggc ccg ccg agg ggc ctg gcg gga ctg ggg cgc gtg gcc aag gcg ctc      96
Gly Pro Pro Arg Gly Leu Ala Gly Leu Gly Arg Val Ala Lys Ala Leu
            20                  25                  30 cag ctg tgc tgc ctc tgc tgt gcg tcg gtc gcc gcg gcc tta gcc agt     144
Gln Leu Cys Cys Leu Cys Cys Ala Ser Val Ala Ala Ala Leu Ala Ser
        35                  40                  45 gac agc agc agc ggc gcc agc gga tta aat gat gat tac gtc ttt gtc     192
Asp Ser Ser Ser Gly Ala Ser Gly Leu Asn Asp Asp Tyr Val Phe Val
    50                  55                  60 acg cca gta gaa gta gac tca gcc ggg tca tat att tca cac gac att     240
Thr Pro Val Glu Val Asp Ser Ala Gly Ser Tyr Ile Ser His Asp Ile
65                  70                  75                  80 ttg cac aac ggc agg aaa aag cga tcg gcg cag aat gcc aga agc tcc     288
Leu His Asn Gly Arg Lys Lys Arg Ser Ala Gln Asn Ala Arg Ser Ser
                85                  90                  95 ctg cac tac cga ttt tca gca ttt gga cag gaa ctg cac tta gaa ctt     336
Leu His Tyr Arg Phe Ser Ala Phe Gly Gln Glu Leu His Leu Glu Leu
            100                 105                 110 aag ccc tcg gcg att ttg agc agt cac ttt att gtc cag gta ctt gga     384
Lys Pro Ser Ala Ile Leu Ser Ser His Phe Ile Val Gln Val Leu Gly
        115                 120                 125
```

-continued

| | | |
|---|---|---|
| aaa gat ggt gct tca gag act cag aaa ccc gag gtg cag caa tgc ttc<br>Lys Asp Gly Ala Ser Glu Thr Gln Lys Pro Glu Val Gln Gln Cys Phe<br>130                        135                    140 | | 432 |
| tat cag gga ttt atc aga aat gac agc tcc tct gtc gct gtg tct<br>Tyr Gln Gly Phe Ile Arg Asn Asp Ser Ser Ser Val Ala Val Ser<br>145                    150                    155                    160 | | 480 |
| acg tgt gct ggc ttg tca ggt tta ata agg aca cga aaa aat gaa ttc<br>Thr Cys Ala Gly Leu Ser Gly Leu Ile Arg Thr Arg Lys Asn Glu Phe<br>                165                    170                    175 | | 528 |
| ctc atc tcg cca tta cct cag ctt ctg gcc cag gaa cac aac tac agc<br>Leu Ile Ser Pro Leu Pro Gln Leu Leu Ala Gln Glu His Asn Tyr Ser<br>                180                    185                    190 | | 576 |
| tcc cct gcg ggt cac cat cct cac gta ctg tac aaa agg aca gca gag<br>Ser Pro Ala Gly His His Pro His Val Leu Tyr Lys Arg Thr Ala Glu<br>                195                    200                    205 | | 624 |
| gag aag atc cag cgg tac cgt ggc tac ccc ggc tct ggc cgg aat tat<br>Glu Lys Ile Gln Arg Tyr Arg Gly Tyr Pro Gly Ser Gly Arg Asn Tyr<br>          210                    215                    220 | | 672 |
| cct ggt tac tcc cca agt cac att ccc cat gca tct cag agt cga gag<br>Pro Gly Tyr Ser Pro Ser His Ile Pro His Ala Ser Gln Ser Arg Glu<br>225                        230                    235                    240 | | 720 |
| aca gag tat cac cat cga agg ttg caa aag cag cat ttt tgt gga cga<br>Thr Glu Tyr His His Arg Arg Leu Gln Lys Gln His Phe Cys Gly Arg<br>                        245                    250                    255 | | 768 |
| cgc aag aaa tat gct ccc aag cct ccc aca gag gac acc tat cta agg<br>Arg Lys Lys Tyr Ala Pro Lys Pro Pro Thr Glu Asp Thr Tyr Leu Arg<br>                260                    265                    270 | | 816 |
| ttt gat gaa tat ggg agc tct ggg cga ccc aga aga tca gct gga aaa<br>Phe Asp Glu Tyr Gly Ser Ser Gly Arg Pro Arg Arg Ser Ala Gly Lys<br>              275                    280                    285 | | 864 |
| tca caa aag ggc ctc aat gtg gaa acc ctc gtg gtg gca gac aag aaa<br>Ser Gln Lys Gly Leu Asn Val Glu Thr Leu Val Val Ala Asp Lys Lys<br>290                        295                    300 | | 912 |
| atg gtg gaa aag cat ggc aag gga aat gtc acc aca tac att ctc aca<br>Met Val Glu Lys His Gly Lys Gly Asn Val Thr Thr Tyr Ile Leu Thr<br>305                        310                    315                    320 | | 960 |
| gta atg aag gtt tct ggc cta ttt aaa gat ggg act att gga agt gac<br>Val Met Lys Val Ser Gly Leu Phe Lys Asp Gly Thr Ile Gly Ser Asp<br>                        325                    330                    335 | | 1008 |
| ata aac gtg gtt gtg gtg agc cta att ctt ctg gaa caa gaa cct gga<br>Ile Asn Val Val Val Val Ser Leu Ile Leu Leu Glu Gln Glu Pro Gly<br>                        340                    345                    350 | | 1056 |
| gga tta ttg atc aac cat cat gca gac cag tct ctg aat agt ttt tgt<br>Gly Leu Leu Ile Asn His His Ala Asp Gln Ser Leu Asn Ser Phe Cys<br>          355                    360                    365 | | 1104 |
| caa tgg cag tct gcc ctc att gga aag aat ggc aag aga cat gat cat<br>Gln Trp Gln Ser Ala Leu Ile Gly Lys Asn Gly Lys Arg His Asp His<br>          370                    375                    380 | | 1152 |
| gcc atc tta cta aca gga ttt gat att tgt tct tgg aag aat gaa cca<br>Ala Ile Leu Leu Thr Gly Phe Asp Ile Cys Ser Trp Lys Asn Glu Pro<br>385                        390                    395                    400 | | 1200 |
| tgt gac act cta ggg ttt gcc ccc acc agt gga atg tgc tct aag tac<br>Cys Asp Thr Leu Gly Phe Ala Pro Thr Ser Gly Met Cys Ser Lys Tyr<br>                        405                    410                    415 | | 1248 |
| cga agt tgt acc atc aat gag gac aca gga ctt ggc ctt gcc ttc acc<br>Arg Ser Cys Thr Ile Asn Glu Asp Thr Gly Leu Gly Leu Ala Phe Thr<br>                    420                    425                    430 | | 1296 |
| atc gct cat gag tca ggg cac aac ttt ggt atg att cac gac gga gaa<br>Ile Ala His Glu Ser Gly His Asn Phe Gly Met Ile His Asp Gly Glu<br>                    435                    440                    445 | | 1344 |

```
ggg aat ccc tgc aga aag gct gaa ggc aat atc atg tct ccc aca ctg      1392
Gly Asn Pro Cys Arg Lys Ala Glu Gly Asn Ile Met Ser Pro Thr Leu
    450                 455                 460 acc gga aac aat gga gtg ttt tca tgg tct tcc tgc agc cgc cag tat      1440
Thr Gly Asn Asn Gly Val Phe Ser Trp Ser Ser Cys Ser Arg Gln Tyr
465                 470                 475                 480 ctc aag aaa ttc ctc agc aca cct cag gcg ggg tgt cta gtg gat gag      1488
Leu Lys Lys Phe Leu Ser Thr Pro Gln Ala Gly Cys Leu Val Asp Glu
                485                 490                 495 ccc aag caa gca gga cag tat aaa tat ccg gac aaa cta cca gga cag      1536
Pro Lys Gln Ala Gly Gln Tyr Lys Tyr Pro Asp Lys Leu Pro Gly Gln
            500                 505                 510 att tat gat gct gac aca cag tgt aaa tgg caa ttt gga gca aaa gcc      1584
Ile Tyr Asp Ala Asp Thr Gln Cys Lys Trp Gln Phe Gly Ala Lys Ala
        515                 520                 525 aag tta tgc agc ctt ggt ttt gtg aag gat att tgc aaa tca ctt tgg      1632
Lys Leu Cys Ser Leu Gly Phe Val Lys Asp Ile Cys Lys Ser Leu Trp
    530                 535                 540 tgc cac cga gta ggc cac agg tgt gag acc aag ttt atg ccc gca gca      1680
Cys His Arg Val Gly His Arg Cys Glu Thr Lys Phe Met Pro Ala Ala
545                 550                 555                 560 gaa ggg acc gtt tgt ggc ttg agt atg tgg tgt cgg caa ggc cag tgc      1728
Glu Gly Thr Val Cys Gly Leu Ser Met Trp Cys Arg Gln Gly Gln Cys
                565                 570                 575 gta aag ttt ggg gag ctc ggg ccc cgg ccc atc cac ggc cag tgg tcc      1776
Val Lys Phe Gly Glu Leu Gly Pro Arg Pro Ile His Gly Gln Trp Ser
            580                 585                 590 gcc tgg tcg aag tgg tca gaa tgt tcc cgg aca tgt ggt gga gga gtc      1824
Ala Trp Ser Lys Trp Ser Glu Cys Ser Arg Thr Cys Gly Gly Gly Val
        595                 600                 605 aag ttc cag gag aga cac tgc aat aac ccc aag cct cag tat ggt ggc      1872
Lys Phe Gln Glu Arg His Cys Asn Asn Pro Lys Pro Gln Tyr Gly Gly
    610                 615                 620 ata ttc tgt cca ggt tct agc cgt att tat cag ctg tgc aat att aac      1920
Ile Phe Cys Pro Gly Ser Ser Arg Ile Tyr Gln Leu Cys Asn Ile Asn
625                 630                 635                 640 cct tgc aat gaa aat agc ttg gat ttt cgg gct caa cag tgt gca gaa      1968
Pro Cys Asn Glu Asn Ser Leu Asp Phe Arg Ala Gln Gln Cys Ala Glu
                645                 650                 655 tat aac agc aaa cct ttc cgt gga tgg ttc tac cag tgg aaa ccc tat      2016
Tyr Asn Ser Lys Pro Phe Arg Gly Trp Phe Tyr Gln Trp Lys Pro Tyr
            660                 665                 670 aca aaa gtg gaa gag gaa gat cga tgc aaa ctg tac tgc aag gct gag      2064
Thr Lys Val Glu Glu Glu Asp Arg Cys Lys Leu Tyr Cys Lys Ala Glu
        675                 680                 685 aac ttt gaa ttt ttt ttt gca atg tcc ggc aaa gtg aaa gat gga act      2112
Asn Phe Glu Phe Phe Phe Ala Met Ser Gly Lys Val Lys Asp Gly Thr
    690                 695                 700 ccc tgc tcc cca aac aaa aat gat gtt tgt att gac ggg gtt tgt gaa      2160
Pro Cys Ser Pro Asn Lys Asn Asp Val Cys Ile Asp Gly Val Cys Glu
705                 710                 715                 720 cta gtg gga tgt gat cat gaa cta ggc tct aaa gca gtt tca gat gct      2208
Leu Val Gly Cys Asp His Glu Leu Gly Ser Lys Ala Val Ser Asp Ala
                725                 730                 735 tgt ggc gtt tgc aaa ggt gat aat tca act tgc aag ttt tat aaa ggc      2256
Cys Gly Val Cys Lys Gly Asp Asn Ser Thr Cys Lys Phe Tyr Lys Gly
            740                 745                 750 ctg tac ctc aac cag cat aaa gca aat gaa tat tat ccg gtg gtc ctc      2304
Leu Tyr Leu Asn Gln His Lys Ala Asn Glu Tyr Tyr Pro Val Val Leu
```

-continued

```
            755                 760                 765
att cca gct ggc gcc cga agc atc gaa atc cag gag ctg cag gtt tcc    2352
Ile Pro Ala Gly Ala Arg Ser Ile Glu Ile Gln Glu Leu Gln Val Ser
    770                 775                 780 tcc agt tac ctc gca gtt cga agc ctc agt caa aag tat tac ctc acc    2400
Ser Ser Tyr Leu Ala Val Arg Ser Leu Ser Gln Lys Tyr Tyr Leu Thr
785                 790                 795                 800 ggg ggc tgg agc atc gac tgg cct ggg gag ttc ccc ttc gct ggg acc    2448
Gly Gly Trp Ser Ile Asp Trp Pro Gly Glu Phe Pro Phe Ala Gly Thr
                805                 810                 815 acg ttt gaa tac cag cgc tct ttc aac cgc ccg gaa cgt ctg tac gcg    2496
Thr Phe Glu Tyr Gln Arg Ser Phe Asn Arg Pro Glu Arg Leu Tyr Ala
            820                 825                 830 cca ggg ccc aca aat gag acg ctg gtc ttt gaa att ctg atg caa ggc    2544
Pro Gly Pro Thr Asn Glu Thr Leu Val Phe Glu Ile Leu Met Gln Gly
        835                 840                 845 aaa aat cca ggg ata gct tgg aag tat gca ctt ccc aag gtc atg aat    2592
Lys Asn Pro Gly Ile Ala Trp Lys Tyr Ala Leu Pro Lys Val Met Asn
850                 855                 860 gga act cca cca gcc aca aaa aga cct gcc tat acc tgg agt atc gtg    2640
Gly Thr Pro Pro Ala Thr Lys Arg Pro Ala Tyr Thr Trp Ser Ile Val
865                 870                 875                 880 cag tca gag tgc tcc gtc tcc tgt ggt gga ggt tac ata aat gta aag    2688
Gln Ser Glu Cys Ser Val Ser Cys Gly Gly Gly Tyr Ile Asn Val Lys
                885                 890                 895 gcc att tgc ttg cga gat caa aat act caa gtc aat tcc tca ttc tgc    2736
Ala Ile Cys Leu Arg Asp Gln Asn Thr Gln Val Asn Ser Ser Phe Cys
            900                 905                 910 agt gca aaa acc aag cca gta act gag ccc aaa atc tgc aac gct ttc    2784
Ser Ala Lys Thr Lys Pro Val Thr Glu Pro Lys Ile Cys Asn Ala Phe
        915                 920                 925 tcc tgc ccg gct tac tgg atg cca ggt gaa tgg agt aca tgc agc aag    2832
Ser Cys Pro Ala Tyr Trp Met Pro Gly Glu Trp Ser Thr Cys Ser Lys
930                 935                 940 tcc tgt gct gga ggc cag cag agc cga aag atc cag tgt gtg caa aag    2880
Ser Cys Ala Gly Gly Gln Gln Ser Arg Lys Ile Gln Cys Val Gln Lys
945                 950                 955                 960 aag ccc ttc caa aag gag gaa gca gtg ttg cat tct ctc tgt cca gta    2928
Lys Pro Phe Gln Lys Glu Glu Ala Val Leu His Ser Leu Cys Pro Val
                965                 970                 975 agc aca ccc act cag gtc caa gcc tgc aac agc cat gcc tgc cct cca    2976
Ser Thr Pro Thr Gln Val Gln Ala Cys Asn Ser His Ala Cys Pro Pro
            980                 985                 990 caa tgg agc ctt gga ccc tgg tct cag tgt tcc aag acc tgt gga cga    3024
Gln Trp Ser Leu Gly Pro Trp Ser Gln Cys Ser Lys Thr Cys Gly Arg
        995                 1000                1005 ggg gtg agg aag cgt gaa ctc ctc tgc aag ggc tct gcc gca gaa acc    3072
Gly Val Arg Lys Arg Glu Leu Leu Cys Lys Gly Ser Ala Ala Glu Thr
1010                1015                1020 ctc ccc gag agc cag tgt acc agt ctc ccc aga cct gag ctg cag gag    3120
Leu Pro Glu Ser Gln Cys Thr Ser Leu Pro Arg Pro Glu Leu Gln Glu
1025                1030                1035                1040 ggc tgt gtg ctt gga cga tgt ccc aag aac agc cgg cta cag tgg gtc    3168
Gly Cys Val Leu Gly Arg Cys Pro Lys Asn Ser Arg Leu Gln Trp Val
                1045                1050                1055 gct tct tcg tgg agc gag gta tgg att aga agt cac tgc tgg gtc agg    3216
Ala Ser Ser Trp Ser Glu Val Trp Ile Arg Ser His Cys Trp Val Arg
            1060                1065                1070 aga ttg aga cca tcc tgg cta aca cag tga                            3246
```

Arg Leu Arg Pro Ser Trp Leu Thr Gln *
        1075                1080

<210> SEQ ID NO 89
<211> LENGTH: 119
<212> TYPE: PRT
<213> ORGANISM: Artificial Sequence
<220> FEATURE:
<223> OTHER INFORMATION: Consensus amino acid sequence

<400> SEQUENCE: 89

His Leu Glu Lys Asn Arg Ser Leu Leu Ala Pro Asp Phe Thr Val Thr
 1               5                  10                  15

Thr Tyr Asp Glu Asp Gly Thr Leu Val Thr Glu Glu Pro Leu Ile Gln
            20                  25                  30

Asp Asp His Cys Tyr Tyr Gln Gly Tyr Val Glu Gly Tyr Pro Asn Ser
        35                  40                  45

Ala Val Ser Leu Ser Thr Cys Ser Gly Gly Leu Arg Gly Ile Leu Gln
    50                  55                  60

Leu Glu Asn Leu Ser Tyr Gly Ile Glu Pro Leu Glu Ser Ser Asp Gly
65                  70                  75                  80

Phe Glu His Ile Ile Tyr Gln Ile Glu Asn Asp Lys Thr Glu Pro Ser
                85                  90                  95

Pro Cys Gly Glu Cys Gly Ser Leu Ser Thr Ser Thr Asp Ser Ser Tyr
            100                 105                 110

Gly Ile Arg Ser Ala Ser Pro
        115

<210> SEQ ID NO 90
<211> LENGTH: 187
<212> TYPE: PRT
<213> ORGANISM: Artificial Sequence
<220> FEATURE:
<223> OTHER INFORMATION: Consensus amino acid sequence

<400> SEQUENCE: 90

Tyr Gly Ser Asp Leu Asn Lys Ile Arg Gln Arg Val His Gln Ile Val
 1               5                  10                  15

Asn Leu Val Asn Glu Ile Tyr Arg Pro Gln Leu Asn Ile Arg Val Val
            20                  25                  30

Leu Val Gly Leu Glu Ile Trp Ser Asp Gly Asp Lys Ile Asn Val Gln
        35                  40                  45

Ser Asp Ala Asn Asp Thr Leu His Ser Phe Gly Glu Trp Arg Glu Thr
    50                  55                  60

Asp Leu Leu Lys Arg Lys Ser His Asp Asn Ala Gln Leu Leu Thr Gly
65                  70                  75                  80

Ile Asp Phe Asp Gly Asn Thr Ile Gly Ala Ala Tyr Val Gly Gly Met
                85                  90                  95

Cys Ser Pro Lys Arg Ser Val Gly Val Gln Asp His Ser Pro Ile
            100                 105                 110

Val Leu Leu Val Ala Val Thr Met Ala His Glu Leu Gly His Asn Leu
        115                 120                 125

Gly Met Thr His Asp Asp Lys Asn Lys Asp Gly Cys Thr Cys Glu Gly
    130                 135                 140

Gly Gly Ser Cys Ile Met Asn Pro Val Ala Ser Ser Pro Ser Lys
145                 150                 155                 160

Lys Lys Phe Ser Asn Cys Ser Lys Asp Asp Tyr Gln Lys Phe Leu Thr
                165                 170                 175

Lys Gln Lys Pro Gln Cys Leu Leu Asn Lys Pro
            180                 185

<210> SEQ ID NO 91
<211> LENGTH: 1311
<212> TYPE: PRT
<213> ORGANISM: Homo sapiens

<400> SEQUENCE: 91

Met Arg Leu Leu Leu Val Pro Leu Leu Ala Pro Ala Pro Gly
 1               5                  10                  15

Ser Ser Ala Pro Lys Val Arg Arg Gln Ser Asp Thr Trp Pro Trp
            20                  25                  30

Ser Gln Trp Ser Pro Cys Ser Arg Thr Cys Gly Gly Gly Val Ser Phe
            35                  40                  45

Arg Glu Arg Pro Cys Tyr Ser Gln Arg Arg Asp Gly Gly Ser Ser Cys
        50                  55                  60

Val Gly Pro Ala Arg Ser His Arg Ser Cys Arg Thr Glu Ser Cys Pro
65                  70                  75                  80

Asp Gly Ala Arg Asp Phe Arg Ala Glu Gln Cys Ala Glu Phe Asp Gly
                85                  90                  95

Ala Glu Phe Gln Gly Arg Arg Tyr Arg Trp Leu Pro Tyr Tyr Ser Ala
                100                 105                 110

Pro Asn Lys Cys Glu Leu Asn Cys Ile Pro Lys Gly Glu Asn Phe Tyr
            115                 120                 125

Tyr Lys His Arg Glu Ala Val Val Asp Gly Thr Pro Cys Glu Pro Gly
            130                 135                 140

Lys Arg Asp Val Cys Val Asp Gly Ser Cys Arg Val Val Gly Cys Asp
145                 150                 155                 160

His Glu Leu Asp Ser Ser Lys Gln Glu Asp Lys Cys Leu Arg Cys Gly
                165                 170                 175

Gly Asp Gly Thr Cys Tyr Pro Val Ala Gly Thr Phe Asp Ala Asn Asp
            180                 185                 190

Leu Ser Arg Gly Tyr Asn Gln Ile Leu Ile Val Pro Met Gly Ala Thr
            195                 200                 205

Ser Ile Leu Ile Asp Glu Ala Ala Ala Ser Arg Asn Phe Leu Ala Val
        210                 215                 220

Lys Asn Val Arg Gly Glu Tyr Tyr Leu Asn Gly His Trp Thr Ile Glu
225                 230                 235                 240

Ala Ala Arg Ala Leu Pro Ala Ala Ser Thr Ile Leu His Tyr Glu Arg
                245                 250                 255

Gly Ala Glu Gly Asp Leu Ala Pro Glu Arg Leu His Ala Arg Gly Pro
            260                 265                 270

Thr Ser Glu Pro Leu Val Ile Glu Leu Ile Ser Gln Glu Pro Asn Pro
            275                 280                 285

Gly Val His Tyr Glu Tyr His Leu Pro Leu Arg Arg Pro Ser Pro Gly
        290                 295                 300

Phe Ser Trp Ser His Gly Ser Trp Ser Asp Cys Ser Ala Glu Cys Gly
305                 310                 315                 320

Gly Gly His Gln Ser Arg Leu Val Phe Cys Thr Ile Asp His Glu Ala
                325                 330                 335

Tyr Pro Asp His Met Cys Gln Arg Gln Pro Arg Pro Ala Asp Arg Arg
            340                 345                 350

Ser Cys Asn Leu His Pro Cys Pro Glu Thr Lys Arg Thr Ser Tyr Leu

-continued

```
               355                 360                 365
His Arg Pro Gly Ala Trp Arg Leu Ala Gly Ala Gln Arg Val Cys Gly
370                 375                 380

Asn Ser Trp Lys Ala Gly Pro Trp Ala Pro Cys Ser Ala Ser Cys Gly
385                 390                 395                 400

Gly Gly Ser Gln Ser Arg Ser Val Tyr Cys Ile Ser Ser Asp Gly Ala
                405                 410                 415

Gly Ile Gln Glu Ala Val Glu Ala Glu Cys Ala Gly Leu Pro Gly
                420                 425                 430

Lys Pro Pro Ala Ile Gln Ala Cys Asn Leu Gln Arg Cys Ala Ala Trp
                435                 440                 445

Ser Pro Glu Pro Trp Gly Glu Cys Ser Val Ser Cys Gly Val Gly Val
450                 455                 460

Arg Lys Arg Ser Val Thr Cys Arg Gly Glu Arg Gly Ser Leu Leu His
465                 470                 475                 480

Thr Ala Ala Cys Ser Leu Glu Asp Arg Pro Leu Thr Glu Pro Cys
                485                 490                 495

Val His Glu Asp Cys Pro Leu Leu Ser Asp Gln Ala Trp His Val Gly
                500                 505                 510

Thr Trp Gly Leu Cys Ser Lys Ser Cys Ser Ser Gly Thr Arg Arg Arg
                515                 520                 525

Gln Val Ile Cys Ala Ile Gly Pro Ser His Cys Gly Ser Leu Gln
                530                 535                 540

His Ser Lys Pro Val Asp Val Glu Pro Cys Asn Thr Gln Pro Cys His
545                 550                 555                 560

Leu Pro Gln Glu Val Pro Ser Met Gln Asp Val His Thr Pro Ala Ser
                565                 570                 575

Asn Pro Trp Met Pro Leu Gly Pro Gln Glu Ser Pro Ala Ser Ala Ala
                580                 585                 590

Pro Ile Pro Ala Thr Pro Ala Val Gly Leu Arg Ala Pro Arg Leu Gln
                595                 600                 605

Thr Gln Ser Ser Arg Val Leu Pro Arg Trp Pro His Gly Ile Ser Arg
610                 615                 620

Ala Ser Val Ala Arg Leu Pro Trp Gly Pro Leu Ser Ala Glu Gln Val
625                 630                 635                 640

His Asn Thr His Gln Pro Gln Ala Gln Gln Asn Glu Pro Ser Glu Cys
                645                 650                 655

Arg Gly Asp Thr Tyr Leu Arg Phe Asp Glu Tyr Gly Ser Ser Gly Arg
                660                 665                 670

Pro Arg Arg Ser Ala Gly Lys Ser Gln Lys Gly Leu Asn Val Glu Thr
                675                 680                 685

Leu Val Val Ala Asp Lys Lys Met Val Glu Lys His Gly Lys Gly Ser
690                 695                 700

Gln Phe Gly Cys Cys Tyr Asp Asn Val Ala Thr Ala Ala Gly Pro Leu
705                 710                 715                 720

Gly Glu Gly Cys Val Gly Gln Pro Ser His Ala Tyr Pro Val Arg Cys
                725                 730                 735

Leu Leu Pro Ser Ala His Gly Ser Cys Ala Asp Trp Ala Ala Arg Trp
                740                 745                 750

Tyr Phe Val Ala Ser Val Gly Gln Cys Asn Arg Phe Trp Tyr Gly Gly
                755                 760                 765

Cys His Gly Asn Ala Asn Asn Phe Ala Ser Glu Gln Glu Cys Met Ser
770                 775                 780
```

```
Ser Cys Gln Gly Ser Leu His Gly Pro Arg Arg Pro Gln Pro Gly Ala
785                 790                 795                 800

Ser Gly Arg Ser Thr His Thr Asp Gly Gly Ser Ser Pro Ala Gly
            805                 810                 815

Glu Gln Glu Pro Ser Gln His Arg Thr Gly Ala Ala Val Gln Arg Lys
                820                 825                 830

Pro Trp Pro Ser Gly Gly Leu Trp Arg Gln Asp Gln Pro Gly Pro
            835                 840                 845

Gly Glu Ala Pro His Thr Gln Ala Phe Gly Glu Trp Pro Trp Gly Gln
850                 855                 860

Glu Leu Gly Ser Arg Ala Pro Gly Leu Gly Gly Asp Ala Arg Ser Pro
865                 870                 875                 880

Ala Pro Pro Lys Asn Gly Lys Arg His Asp His Ala Ile Leu Leu Thr
                885                 890                 895

Gly Phe Asp Ile Cys Ser Trp Lys Asn Glu Pro Cys Asp Thr Leu Gly
                900                 905                 910

Phe Ala Pro Phe His Ser Ser Tyr Arg Ile Ser Leu Ala Gly Val
            915                 920                 925

Glu Pro Ser Leu Val Gln Ala Ala Leu Gly Gln Leu Val Arg Leu Ser
930                 935                 940

Cys Ser Asp Asp Thr Ala Pro Glu Ser Gln Ala Ala Trp Gln Lys Asp
945                 950                 955                 960

Gly Gln Pro Ile Ser Ser Asp Arg His Arg Leu Gln Phe Asp Gly Ser
                965                 970                 975

Leu Ile Ile His Pro Leu Gln Ala Glu Asp Ala Gly Thr Tyr Ser Cys
                980                 985                 990

Gly Ser Thr Arg Pro Gly Arg Asp Ser Gln Lys Ile Gln Leu Arg Ile
                995                 1000                1005

Ile Gly Leu Cys Pro His Pro Ile His His Ser His Leu Val Ser Pro
            1010                1015                1020

Gly Leu Met Thr Gly Gly Asp Met Ala Val Leu Ser Glu Ala Glu Leu
1025                1030                1035                1040

Ser Arg Phe Pro Gln Pro Arg Asp Pro Ala Gln Asp Phe Gly Gln Ala
                1045                1050                1055

Gly Ala Ala Gly Pro Leu Gly Ala Ile Pro Ser Ser His Pro Gln Pro
                1060                1065                1070

Ala Asn Arg Leu Arg Leu Asp Gln Asn Gln Pro Arg Val Val Asp Ala
            1075                1080                1085

Ser Pro Gly Gln Arg Ile Arg Met Thr Cys Arg Ala Glu Gly Phe Pro
            1090                1095                1100

Pro Pro Ala Ile Glu Trp Gln Arg Asp Gly Gln Pro Val Ser Ser Pro
1105                1110                1115                1120

Arg His Gln Leu Gln Pro Asp Gly Ser Leu Val Ile Ser Arg Val Ala
                1125                1130                1135

Val Glu Asp Gly Gly Phe Tyr Thr Cys Val Ala Phe Asn Gly Gln Asp
            1140                1145                1150

Arg Asp Gln Arg Trp Val Gln Leu Arg Val Leu Gly Glu Leu Thr Ile
            1155                1160                1165

Ser Gly Leu Pro Pro Thr Val Thr Val Pro Glu Gly Asp Thr Ala Arg
            1170                1175                1180

Leu Leu Cys Val Val Ala Gly Glu Ser Val Asn Ile Arg Trp Ser Arg
1185                1190                1195                1200
```

-continued

```
Asn Gly Leu Pro Val Gln Ala Asp Gly His Arg Val His Gln Ser Pro
            1205                1210                1215

Asp Gly Thr Leu Leu Ile Tyr Asn Leu Arg Ala Arg Asp Glu Gly Ser
        1220                1225                1230

Tyr Thr Cys Ser Ala Tyr Gln Gly Ser Gln Ala Val Ser Arg Ser Thr
    1235                1240                1245

Glu Val Lys Val Val Ser Pro Ala Pro Thr Ala Gln Pro Arg Asp Pro
1250                1255                1260

Gly Arg Asp Cys Val Asp Gln Pro Glu Leu Ala Asn Cys Asp Leu Ile
1265                1270                1275                1280

Leu Gln Ala Gln Leu Cys Gly Asn Glu Tyr Tyr Ser Phe Cys Cys
                1285                1290                1295

Ala Ser Cys Ser Arg Phe Gln Pro His Ala Gln Pro Ile Trp Gln
            1300                1305                1310

<210> SEQ ID NO 92
<211> LENGTH: 10
<212> TYPE: PRT
<213> ORGANISM: Artificial Sequence
<220> FEATURE:
<223> OTHER INFORMATION: Consensus amino acid sequence
<220> FEATURE:
<221> NAME/KEY: VARIANT
<222> LOCATION: (1)...(1)
<223> OTHER INFORMATION: Xaa at position 1 can be G or S or T or A or
      L or I or V or N
<220> FEATURE:
<221> NAME/KEY: VARIANT
<222> LOCATION: (2)...(3)
<223> OTHER INFORMATION: Xaa = any amino acid
<220> FEATURE:
<221> NAME/KEY: VARIANT
<222> LOCATION: (6)...(6)
<223> OTHER INFORMATION: Xaa at position 6 can be L or I or V or M or
      F or Y or W
<220> FEATURE:
<221> NAME/KEY: VARIANT
<222> LOCATION: (7)...(7)
<223> OTHER INFORMATION: Xaa at position 7 can be A, Q, N, L, G, S, V,
      T, I, M, F, Y, C, or W
<220> FEATURE:
<221> NAME/KEY: VARIANT
<222> LOCATION: (9)...(9)
<223> OTHER INFORMATION: Xaa = any amino acid
<220> FEATURE:
<221> NAME/KEY: VARIANT
<222> LOCATION: (10)...(10)
<223> OTHER INFORMATION: Xaa at position 10 can be L, I, V, M, F, Y,
      W, G,S, P or Q

<400> SEQUENCE: 92

Xaa Xaa Xaa His Glu Xaa Xaa His Xaa Xaa
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Consensus amino acid sequence

<400> SEQUENCE: 93

His Glu Leu Gly His Asn Leu Gly Met Lys His
1               5                   10
```

US 7,611,879 B2

27877, 18080, 14081, 32140, 50352, 16658, 14223, 16002, 50566, 65552 AND 65577 MOLECULES AND USES THEREFOR

RELATED APPLICATIONS

The present application is a divisional of U.S. patent application Ser. No. 11/429,599, filed May 5, 2006 (now U.S. Pat. No. 7,351,566), which is a divisional of U.S. patent application Ser. No. 10/391,364, filed Mar. 18, 2003, now U.S. Pat. No. 7,094,587, which is a continuation-in-part of: (i) U.S. patent application Ser. No. 09/950,370, filed Sep. 10, 2001, (abandoned) which claims the benefit of U.S. Provisional Application Ser. No. 60/231,084, filed Sep. 8, 2000; (abandoned)(ii) U.S. patent application Ser. No. 10/294,039, filed Nov. 13, 2002 (abandoned), which claims the benefit of U.S. Provisional Application Ser. No. 60/338,587, filed Nov. 13, 2001 (abandoned); (iii) U.S. patent application Ser. No. 10/266,035, filed Oct. 7, 2002 (abandoned), which claims the benefit of U.S. Provisional Application Ser. No. 60/328,198, filed Oct. 9, 2001 (abandoned); (iv) U.S. patent application Ser. No. 09/717,926, filed Nov. 21, 2000 (now U.S. Pat. No. 6,569,657), which claims the benefit of U.S. Provisional Application Ser. No. 60/214,707, filed Jun. 27, 2000 (abandoned); (v) U.S. patent application Ser. No. 10/268,036, filed Oct. 9, 2002 (abandoned), which claims the benefit of U.S. Provisional Application Ser. No. 60/327,820, filed Oct. 9, 2001 (abandoned); (vi) U.S. patent application Ser. No. 09/922,138, filed Aug. 3, 2001 (abandoned), which claims the benefit of U.S. Provisional Application Ser. No. 60/229,299, filed Sep. 1, 2000 (abandoned); (vii) U.S. patent application Ser. No. 09/945,327, filed Aug. 31, 2001 (abandoned), which claims the benefit of U.S. Provisional Application Ser. No. 60/229,425, filed Aug. 31, 2000 (abandoned); (viii) U.S. patent application Ser. No. 10/163,316, filed Jun. 5, 2002 (abandoned), which claims the benefit of U.S. Provisional Application Ser. No. 60/297,863, filed Jun. 13, 2001 (abandoned); and (ix) U.S. patent application Ser. No. 10/103,377, filed Mar. 21, 2002 (abandoned), which claims the benefit of U.S. Provisional Application Ser. No. 60/278,347, filed Mar. 23, 2001 (abandoned). The entire contents of each of the above-referenced patent applications are incorporated herein by this reference.

BACKGROUND OF THE INVENTION

The enormous variety of biochemical reactions that comprise life are nearly all mediated by a series of biological catalysts known as enzymes. Enzymes are proteins which possess specific catalytic activities that enable them to catalyze a series of reactions, hence enabling metabolic pathways to degrade and to reconstruct products needed to maintain organisms. By the binding of substrates through geometrically and physically complementary reactions, enzymes are stereospecific in binding substrates as well as in catalyzing reactions. The stringency for this stereospecificity varies as some enzymes are more specific to the identity of their substrates, while others are capable of binding multiple substrates and can catalyze numerous types of reactions.

Examples of enzymes include, for example, phospholipases, serine carboxypeptidases, trypsin-like serine proteases, aldehyde dehydrogenases, ubiquitin-protein ligases, protein kinases, hydrolases and matrix metalloproteinases. Such enzymes have the ability to, for example: to reversibly phosphorylate proteins in order to regulate protein activity in eukaryotic cells; to catalyze the hydrolysis of an acyl or phosphoacyl bond of a phospholipids; to modulate removal of COOH-terminal residues, i.e., having carboxypeptidase activity; to modulate the transfer of an acyl group from a donor to an acceptor molecule, i.e., having acyltransferase activity; to degrade proteins; to phosphorylate carbohydrates; to oxidate an aldehyde; to modulate ubiquitination of a substrate, e.g., a protein targeted for degradation; to modulate substrate specificity for ubiquitination; to reversibly phosphorylate proteins in order to regulate protein activity in eukaryotic cells; to interact with cytotoxins and metabolites (e.g., lactoylglutathione, a glutathione-conjugated metabolite, a hydroxycarboxylic acid, and the like); to catalyze the metabolism of a cytotoxin or metabolite; to hydrolyze a thioester containing compound (e.g., lactoylglutathione, and the like); to catalyze the formation of a thioester conjugation on a substrate (e.g., lactate or a hydroxycarboxylic acid); to cleave or modulate the degradation of proteins or peptides of the extracellular matrix; to catalyze or modulate catalysis of cleavage of covalent bonds within or between amino acid residues (e.g., in extracellular matrix, cell-surface, and extracellular proteins); as well as many others. Accordingly, there exists a need to identify additional human enzymes, for example, for use as disease markers and as targets for identifying various therapeutic modulators.

SUMMARY OF THE INVENTION

The present invention is based, at least in part, on the discovery of novel nucleic acid molecules and proteins encoded by such nucleic acid molecules, referred to herein as "27877, 18080, 14081, 32140, 50352, 16658, 14223, 16002, 50566, 65552 or 65577". The 27877, 18080, 14081, 32140, 50352, 16658, 14223, 16002, 50566, 65552 or 65577 nucleic acid and protein molecules of the present invention are useful as modulating agents in regulating a variety of cellular processes, e.g., including, but not limited to cell proliferation, differentiation, growth and division. In particular, these nucleic acid molecules will be advantageous in the regulation of any cellular function, uncontrolled proliferation and differentiation, such as in cases of cancer. Accordingly, in one aspect, this invention provides isolated nucleic acid molecules encoding 27877, 18080, 14081, 32140, 50352, 16658, 14223, 16002, 50566, 65552 or 65577 proteins or biologically active portions thereof, as well as nucleic acid fragments suitable as primers or hybridization probes for the detection of 27877, 18080, 14081, 32140, 50352, 16658, 14223, 16002, 50566, 65552 or 65577-encoding nucleic acids.

The nucleotide sequence of the cDNA encoding 27877, 18080, 14081, 32140, 50352, 16658, 14223, 16002, 50566, 65552 or 65577, and the amino acid sequence of 27877, 18080, 14081, 32140, 50352, 16658, 14223, 16002, 50566, 65552 or 65577 polypeptides are depicted in Table 1.

TABLE 1

Sequences of the invention

| Gene Name | cDNA | Protein | Coding Region | ATCC accession number |
|---|---|---|---|---|
| 27877 | SEQ ID NO:1 and 4 | SEQ ID NO:2 and 5 | SEQ ID NO:3 and 6 | PTA-3217 |
| 18080 | SEQ ID NO:11 | SEQ ID NO:12 | SEQ ID NO:13 | N/A |
| 14081 | SEQ ID NO:20 | SEQ ID NO:21 | SEQ ID NO:22 | N/A |
| 32140 | SEQ ID NO:25 | SEQ ID NO:26 | SEQ ID NO:27 | PTA-3424 |
| 50352 | SEQ ID NO:29 | SEQ ID NO:30 | SEQ ID NO:31 | N/A |
| 16658 | SEQ ID NO:35 | SEQ ID NO:36 | SEQ ID NO:37 | N/A |
| 14223 | SEQ ID NO:38 | SEQ ID NO:39 | SEQ ID NO:40 | N/A |
| 16002 | SEQ ID NO:41 | SEQ ID NO:42 | SEQ ID NO:43 | N/A |
| 50566 | SEQ ID NO:73 | SEQ ID NO:74 | SEQ ID NO:75 | N/A |
| 65552 | SEQ ID NO:76 | SEQ ID NO:77 | SEQ ID NO:78 | N/A |
| 65577 | SEQ ID NO:86 | SEQ ID NO:87 | SEQ ID NO:88 | N/A |

Accordingly, in one aspect, the invention features a nucleic acid molecule which encodes a 27877, 18080, 14081, 32140, 50352, 16658, 14223, 16002, 50566, 65552 or 65577 protein or polypeptide, e.g., a biologically active portion of the 27877, 18080, 14081, 32140, 50352, 16658, 14223, 16002, 50566, 65552 or 65577 protein. In a preferred embodiment, the isolated nucleic acid molecule encodes a polypeptide having the amino acid sequence of SEQ ID NO:2, 5, 12, 21, 26, 30, 36, 39, 42, 74, 77 or 87. In other embodiments, the invention provides isolated 27877, 18080, 14081, 32140, 50352, 16658, 14223, 16002, 50566, 65552 or 65577 nucleic acid molecules having the nucleotide sequence shown in SEQ ID NO:1, 3, 4, 6, 11, 13, 20, 22, 25, 27, 29, 31, 35, 37, 38, 40, 41, 43, 73, 75, 76, 78, 86 or 88 or the nucleotide sequence of the DNA insert of the plasmid deposited with ATCC Accession Number PTA-3217 or PTA-3424. In still other embodiments, the invention provides nucleic acid molecules that are substantially identical (e.g., naturally occurring allelic variants) to the nucleotide sequence shown in SEQ ID NO:1, 3, 4, 6, 11, 13, 20, 22, 25, 27, 29, 31, 35, 37, 38, 40, 41, 43, 73, 75, 76, 78, 86 or 88 or the nucleotide sequence of the DNA insert of the plasmid deposited with ATCC Accession Number PTA-3217 or PTA-3424. In other embodiments, the invention provides a nucleic acid molecule which hybridizes under a stringent hybridization condition as described herein to a nucleic acid molecule comprising the nucleotide sequence of SEQ ID NO:1, 3, 4, 6, 11, 13, 20, 22, 25, 27, 29, 31, 35, 37, 38, 40, 41, 43, 73, 75, 76, 78, 86 or 88 or the nucleotide sequence of the DNA insert of the plasmid deposited with ATCC Accession Number PTA-3217 or PTA-3424, wherein the nucleic acid encodes a full length 27877, 18080, 14081, 32140, 50352, 16658, 14223, 16002, 50566, 65552 or 65577 protein or an active fragment thereof.

In a related aspect, the invention further provides nucleic acid constructs which include a 27877, 18080, 14081, 32140, 50352, 16658, 14223, 16002, 50566, 65552 or 65577 nucleic acid molecule described herein. In certain embodiments, the nucleic acid molecules of the invention are operatively linked to native or heterologous regulatory sequences. Also included are vectors and host cells containing the 27877, 18080, 14081, 32140, 50352, 16658, 14223, 16002, 50566, 65552 or 65577 nucleic acid molecules of the invention e.g., vectors and host cells suitable for producing polypeptides.

In another related aspect, the invention provides nucleic acid fragments suitable as primers or hybridization probes for the detection of 27877, 18080, 14081, 32140, 50352, 16658, 14223, 16002, 50566, 65552 or 65577-encoding nucleic acids.

In still another related aspect, isolated nucleic acid molecules that are antisense to a 27877, 18080, 14081, 32140, 50352, 16658, 14223, 16002, 50566, 65552 or 65577 encoding nucleic acid molecule are provided.

In another aspect, the invention features 27877, 18080, 14081, 32140, 50352, 16658, 14223, 16002, 50566, 65552 or 65577 polypeptides, and biologically active or antigenic fragments thereof that are useful, e.g., as reagents or targets in assays applicable to treatment and diagnosis of 27877, 18080, 14081, 32140, 50352, 16658, 14223, 16002, 50566, 65552 or 65577-associated disorders. In another embodiment, the invention provides 27877, 18080, 14081, 32140, 50352, 16658, 14223, 16002, 50566, 65552 or 65577 polypeptides having a 27877, 18080, 14081, 32140, 50352, 16658, 14223, 16002, 50566, 65552 or 65577 activity.

In other embodiments, the invention provides 27877, 18080, 14081, 32140, 50352, 16658, 14223, 16002, 50566, 65552 or 65577 polypeptides, e.g., a 27877, 18080, 14081, 32140, 50352, 16658, 14223, 16002, 50566, 65552 or 65577 polypeptide having the amino acid sequence shown in SEQ ID NO:2, 5, 12, 21, 26, 30, 36, 39, 42, 74, 77 or 87 or the amino acid sequence encoded by the cDNA insert of the plasmid deposited with ATCC Accession Number PTA-3217 or PTA-3424; an amino acid sequence that is substantially identical to the amino acid sequence shown in SEQ ID NO:2, 5, 12, 21, 26, 30, 36, 39, 42, 74, 77 or 87 or the amino acid sequence encoded by the cDNA insert of the plasmid deposited with ATCC Accession Number PTA-3217 or PTA-3424; or an amino acid sequence encoded by a nucleic acid molecule having a nucleotide sequence which hybridizes under a stringent hybridization condition as described herein to a nucleic acid molecule comprising the nucleotide sequence of SEQ ID NO:1, 3, 4, 6, 11, 13, 20, 22, 25, 27, 29, 31, 35, 37, 38, 40, 41, 43, 73, 75, 76, 78, 86 or 88 or the nucleotide sequence of the insert of the plasmid deposited with ATCC Accession Number PTA-3217 or PTA-3424, wherein the nucleic acid encodes a full length 27877, 18080, 14081, 32140, 50352, 16658, 14223, 16002, 50566, 65552 or 65577 protein or an active fragment thereof.

In a related aspect, the invention further provides nucleic acid constructs which include a 27877, 18080, 14081, 32140, 50352, 16658, 14223, 16002, 50566, 65552 or 65577 nucleic acid molecule described herein.

In a related aspect, the invention provides 27877, 18080, 14081, 32140, 50352, 16658, 14223, 16002, 50566, 65552 or 65577 polypeptides or fragments operatively linked to non-27877, 18080, 14081, 32140, 50352, 16658, 14223, 16002, 50566, 65552 or 65577 polypeptides to form fusion proteins.

In another aspect, the invention features antibodies and antigen-binding fragments thereof, that react with, or more preferably specifically or selectively bind 27877, 18080, 14081, 32140, 50352, 16658, 14223, 16002, 50566, 65552 or 65577 polypeptides.

In another aspect, the invention provides methods of screening for compounds that modulate the expression or activity of the 27877, 18080, 14081, 32140, 50352, 16658, 14223, 16002, 50566, 65552 or 65577 polypeptides or nucleic acids.

In still another aspect, the invention provides a process for modulating 27877, 18080, 14081, 32140, 50352, 16658, 14223, 16002, 50566, 65552 or 65577 polypeptide or nucleic acid expression or activity, e.g., using the compounds identified in the screens described herein. In certain embodiments, the methods involve treatment of conditions related to aberrant activity or expression of the 27877, 18080, 14081, 32140, 50352, 16658, 14223, 16002, 50566, 65552 or 65577 polypeptides or nucleic acids, such as conditions or disorders involving aberrant or deficient 27877, 18080, 14081, 32140, 50352, 16658, 14223, 16002, 50566, 65552 or 65577 expression. Examples of such disorders include, but are not limited to cellular proliferative and/or differentiative disorders, brain disorders, blood vessel disorders, platelet disorders, breast disorders, colon disorders, kidney disorders, lung disorders, ovarian disorders, prostate disorders, hematopoeitic disorders, pancreatic disorders, skeletal muscle disorders, testicular disorders, skin disorders, hormonal disorders, disorders associated with bone metabolism, immune e.g., inflammatory, disorders, cardiovascular disorders, endothelial cell disorders, liver disorders, viral diseases, pain, metabolic disorders, anemias, angiogenesis, neoplastic disorders, endocrine disorders, neurological disorders and heart disorders.

The invention also provides assays for determining the activity of or the presence or absence of 27877, 18080, 14081, 32140, 50352, 16658, 14223, 16002, 50566, 65552 or 65577 polypeptides or nucleic acid molecules in a biological sample, including for disease diagnosis.

In a further aspect, the invention provides assays for determining the presence or absence of a genetic alteration in a 27877, 18080, 14081, 32140, 50352, 16658, 14223, 16002, 50566, 65552 or 65577 polypeptide or nucleic acid molecule, including for disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 27877, 18080, 14081, 32140, 50352, 16658, 14223, 16002, 50566, 65552 or 65577 molecule. In one embodiment, the capture probe is a nucleic acid, e.g., a probe complementary to a 27877, 18080, 14081, 32140, 50352, 16658, 14223, 16002, 50566, 65552 or 65577 nucleic acid sequence. In another embodiment, the capture probe is a polypeptide, e.g., an antibody specific for 27877, 18080, 14081, 32140, 50352, 16658, 14223, 16002, 50566, 65552 or 65577 polypeptides. Also featured is a method of analyzing a sample by contacting the sample to the aforementioned array and detecting binding of the sample to the array.

Other features and advantages of the invention will be apparent from the following detailed description, and from the claims.

DETAILED DESCRIPTION OF THE INVENTION

Human 27877

The invention relates to a novel phospholipase protein that can exist in at least two forms, herein designated the 'short' and 'long' forms. The phospholipase (i.e., in either form) is referred to herein as "27877," and can exhibit phospholipase A1 activity. Phosphatidic acids are preferred substrates for the catalytic activity of 27877, although non-phosphatidic acid phospholipids can also act as substrates for the enzyme.

The human short form of 27877 sequence (SEQ ID NO:1), which is approximately 2981 nucleotides long including untranslated regions, contains a predicted methionine-initiated coding sequence of about 2622 nucleotides (nucleotides 202-2823 of SEQ ID NO:1; nucleotides 1-2622 of SEQ ID NO:3), not including the terminal codon. The coding sequence encodes a 874 amino acid protein (SEQ ID NO:2).

The long form human 27877 cDNA sequence (SEQ ID NO:4), which is approximately 3065 nucleotide residues long including non-translated regions, contains a predicted methionine-initiated coding sequence of about 2706 nucleotide residues, excluding termination codon (i.e., nucleotide residues 202-2907 of SEQ ID NO:4; nucleotides 1-2706 SEQ ID NO:6). The coding sequence encodes a 902 amino acid protein (SEQ ID NO:5).

Human 27877 proteins contain a predicted transmembrane domain at about amino acid residues 620-636 of SEQ ID NOs:2 and 5. 27877 proteins can thus exist in a membrane bound form comprising two extra-membrane domains (the first corresponding to about amino acid residues 1-619 of each of SEQ ID NOs:2 and 5, and the second corresponding to about amino acid residues 637 through the carboxyl terminus of each of these sequences) separated by a transmembrane domain. In one embodiment, a 27877 protein can exist in a form in which the region corresponding to about amino acid residues 1-619 of each of SEQ ID NOs:2 and 5 is oriented on the non-lumenal side of a membrane (e.g., a cell membrane or a nuclear or other organellar membrane) and the region corresponding to about amino acid residues 637 through the carboxyl terminus of each of SEQ ID NOs:2 and 5 is oriented on the lumenal side of the membrane. In another embodiment, the regions have the opposite orientations. In still another embodiment, the 27877 protein exists in a soluble form (i.e., not inserted in a membrane).

The human 27877 protein has predicted N-glycosylation sites (Pfam accession number PS00001) at about amino acid residues 486-489 and 690-693 of each of SEQ ID NOs:2 and 5; a predicted cAMP-/cGMP-dependent protein kinase phosphorylation site (Pfam accession number PS00004) at about amino acid residues 145-148 of each of SEQ ID NOs:2 and 5; predicted protein kinase C phosphorylation sites (Pfam accession number PS00005) at about amino acid residues 8-10, 99-101, 180-182, 189-191, 343-345, 367-369, 375-377, 588-590, 733-735, and 778-780 of each of SEQ ID NOs:2 and 5; predicted casein kinase H phosphorylation sites (Pfam accession number PS00006) located at about amino acid residues 92-95, 104-107, 141-144, 226-229, 244-247, 271-274, 271-274, 355-358, 399-402, 450-453, 488-491, 575-578, 713-716, 778-781, 782-785, 813-816, and 846-849 of SEQ ID NO:2 (about amino acid residues 92-95, 104-107, 141-144, 226-229, 244-247, 271-274, 271-274, 355-358, 399-402, 450-453, 488-491, 575-578, 713-716, 778-781, 782-785, and 874-877 of SEQ ID NO:5); a predicted tyrosine kinase phosphorylation site (Pfam accession number PS00007) at about amino acid residues 579-586 of each of SEQ ID NOs:2 and 5; and predicted N-myristoylation sites (Pfam accession number PS00008) at about amino acid residues 18-23, 35-40, 109-114, 133-138, 139-144, 151-156, 530-535, 541-546, 601-606, 624-629, 635-640, 761-766, and 828-833 of SEQ ID NO:2 (about amino acid residues 18-23, 35-40, 109-114, 133-138, 139-144, 151-156, 530-535, 541-546, 601-606, 624-629, 635-640, 761-766, and 856-861 of SEQ ID NO:5).

For general information regarding PFAM identifiers, PS prefix and PF prefix domain identification numbers, refer to Sonnhammer et al. (1997, Protein 28:405-420).

A plasmid containing the nucleotide sequence encoding the short form of human 27877 was deposited with American Type Culture Collection (ATCC®), 10801 University Boulevard, Manassas, Va. 20110-2209, on Mar. 23, 2001 and assigned accession number PTA-3217. A plasmid containing the nucleotide sequence encoding the short form of human 27877 was deposited with ATCC® on Mar. 23, 2001 and assigned accession number PTA-3217. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required pursuant to 35 U.S.C. § 112.

Phospholipids (sometimes designated 'phosphatides') are mixed esters of fatty acids and phosphoric acid with an alcohol such as glycerol or sphingosine. Glycerol-based phospholipids have a phosphoryl moiety esterified with a hydroxyl moiety at one end of the glycerol moiety and at least one fatty acyl moiety esterified with the remaining glyceroyl hydroxyl moieties. The phosphoryl moiety can be esterified with an additional moiety (e.g., choline, ethanolamine, serine, inositol or an inositol phosphate), some of which (e.g., choline or inositol-4-phosphate) can have a charged moiety. Phospholipids are the primary lipid component of most animal cellular membranes. Most membrane phospholipids comprise two fatty acyl moieties, often including both a saturated fatty acyl moiety and an unsaturated fatty acyl moiety.

Phospholipases are a ubiquitous class of enzymes that catalyze hydrolysis of phospholipids. Multiple classes of phospholipases are known, and phospholipases can be classified based on the phospholipid bond of which the enzyme catalyzes hydrolysis. For example, phospholipase A1 enzymes cleave the acyl moiety esterified at the glyceroyl hydroxyl moiety most distal from the phosphoryl moiety in a phospholipid. One known phospholipase A1 enzyme is designated phosphatidic acid-preferring phospholipase A1 and was isolated from bovine testis (Higgs et al., 1998, J. Biol. Chem. 273:5468-5477). Phospholipase A2 enzymes more specifically cleave the acyl moiety at the glyceroyl hydroxyl moiety adjacent the phosphoryl moiety of a phospholipid. Phospholipase B enzymes can cleave acyl moieties from either of these positions. Phospholipase C enzymes cleave the phosphoryl moiety from the glycerol backbone of a glycerophosphatide, and phospholipase D enzymes can cleave phosphatidic acid from a moiety bound with the phosphoryl moiety.

Because hydrolyzed phospholipids and products generated therefrom (e.g., arachidonic acid and lipoxygenase- and cyclooxygenase-catalyzed reaction products such as prostaglandins) can act as second messengers in cellular signaling systems, expression of many phospholipases is highly regulated in cells. Many and complex array of regulatory mechanisms have been described for regulating phospholipase expression, some involving cytoplasmic proteins, notably G-proteins, as well as different effector lipids (e.g., phosphatidylinositol-4,5-biphosphate) or $Ca^{2+}$. Phospholipase expression can be modulated by numerous signal transduction pathways, and phospholipases can also participate in numerous signal transduction pathways.

Numerous phospholipases have been described. However, in view of the widespread and critical nature of phospholipase activities in normal and pathological physiological processes, a need exists for identification of further members of this protein family. The present invention satisfies this need by providing a novel human phospholipase.

The 27877 protein contains a significant number of structural characteristics in common with members of the phospholipase family. One characteristic of the lipase family of enzymes is the presence of five amino acids that have the consensus sequence $Xaa_1$-$Xaa_2$-Ser-$Xaa_3$-Gly (SEQ ID NO:10), wherein $Xaa_1$ is Gly or Ser and each of $Xaa_2$ and $Xaa_3$ can be any amino acid residue. This sequence is highly conserved among lipases and contains the active serine nucleophile present in most lipases. This sequence is present in the 27877 amino acid sequence as Ser-His-Ser-Leu-Gly (SEQ ID NO:9), with the first amino acid of this consensus sequence present in the 27877 sequence being a serine rather than a glycine. The predicted active serine nucleophile is located at amino acid position 539 of both the short form and the long form of the human 27877 protein. Higgs et al. describe a bovine phosphatidic acid-preferring phospholipase A1 (PA-PLA1) which comprises an identical version of the consensus sequence (i.e., Ser-His-Ser-Leu-Gly, SEQ ID NO:9) wherein the active serine nucleophile is located at amino acid position 540 (1998, J. Biol. Chem. 273:5468-5477). These characteristics indicate that human 27877 protein is an active phospholipase molecule.

In another embodiment, a 27877 protein includes at least one transmembrane domain. As used herein, the term "transmembrane domain" includes an amino acid sequence of about 5 amino acid residues in length that spans the plasma membrane. More preferably, a transmembrane domain includes about at least 10, 15, or 17 amino acid residues and spans a membrane. Transmembrane domains are rich in hydrophobic residues, and typically have an alpha-helical structure. In a preferred embodiment, at least 50%, 60%, 70%, 80%, 90%, or 95% or more of the amino acids of a transmembrane domain are hydrophobic, e.g., leucines, isoleucines, tyrosines, or tryptophans. Transmembrane domains are described in, for example, Zagotta W. N. et al. (1996, Annu. Rev. Neurosci. 19: 235-263), the contents of which are incorporated herein by reference. Amino acid residues 1 to about 620-636 of SEQ ID NOs:2 and 5 comprise a transmembrane domain in a 27877 protein.

The 27877 molecules of the present invention can further include one or more of the N-glycosylation, cAMP-/cGMP-dependent protein kinase phosphorylation, protein kinase C phosphorylation, casein kinase II phosphorylation, tyrosine kinase, and N-myristoylation sites described herein, and preferably comprises most or all of them.

In an alignment of the nucleotide sequences of cDNAs encoding the long form of the human 27877 protein and the bovine PA-PLA1 (SEQ ID NO:7) (made using the ALIGN software, using default parameters, including gap opening penalty=12, and gap extension penalty=2), the nucleic acid sequences of the cDNAs are 87.6% identical. An alignment (made using the ALIGN software, using default parameters, including gap opening penalty=12, and gap extension penalty=2) of the amino acid sequences of the long form of the 27877 protein and the bovine PA-(SEQ ID NO:8), the amino acid sequences of the proteins are 88.5% identical. The similarity of the sequences of human 27877 protein and bovine PA-PLA1 indicates that the two proteins exhibit common activities.

A hydropathy plot of the short and long forms of human 27877 was performed. Polypeptides of the invention include fragments which include: all or part of a hydrophobic sequence e.g., the sequence of about residues 620-636 of either of SEQ ID NOs:2 and 5; all or part of a hydrophilic sequence, e.g., the sequence of residues 200-215 of either of SEQ ID NOs:2 and 5; a sequence which includes a cysteine residue, or a glycosylation site.

Because the 27877 polypeptides of the invention can modulate 27877-mediated activities, they can be used to develop novel diagnostic and therapeutic agents for 27877-mediated or related disorders, as described below.

As used herein, a "27877 activity," "biological activity of 27877," or "functional activity of 27877," refers to an activity exerted by a 27877 protein, polypeptide or nucleic acid molecule on, for example, a 27877-responsive cell or on a 27877 substrate (e.g., a protein substrate) as determined in vivo or in vitro. In one embodiment, a 27877 activity is a direct activity, such as association with a 27877 target molecule. A "target molecule" or "binding partner" of a 27877 protein is a molecule with which the 27877 protein binds or interacts in nature. In an exemplary embodiment, such a target molecule is a 27877 receptor. A 27877 activity can also be an indirect activity, such as a cellular signaling activity mediated by interaction of the 27877 protein with a 27877 receptor.

The 27877 molecules of the present invention are predicted to have similar biological activities as phospholipase family members. For example, the 27877 proteins of the present invention can have one or more of the following activities: catalyzing hydrolysis of an acyl or phosphoacyl bond of a phospholipid; catalyzing production of arachidonic acid; modulating generation of a prostaglandin; modulating generation of a lipoxygenase reaction product formed from arachidonic acid; modulating tumor cell invasion or metastasis; modulating tumorigenesis; modulating a response to infection; modulating inflammation; modulating a cellular response to inflammation; modulating pain impulse generation; modulating pain impulse transmission; modulating pain sensation modulating apoptosis; modulating growth of erythroid lineage precursor cells; modulating differentiation of erythroid lineage precursor cells; and modulating production of erythrocytes. Thus, 27877 molecules described herein can act as novel diagnostic targets and therapeutic agents for prognosticating, diagnosing, preventing, inhibiting, alleviating, or curing phospholipase-, lipoxygenase-, and cyclooxygenase-related disorders.

Other activities, as described below, include the ability to modulate function, survival, morphology, proliferation and/or differentiation of cells of tissues in which 27877 molecules are expressed. Thus, the 27877 molecules can act as novel diagnostic targets and therapeutic agents for controlling disorders involving aberrant activities of these cells. 27877 molecules can also act as novel diagnostic targets and therapeutic agents for controlling cellular proliferative and/or differentiative disorders (e.g., hematopoietic neoplastic disorders, carcinoma, sarcoma, metastatic disorders or hematopoietic neoplastic disorders, e.g., leukemias. A metastatic tumor can arise from a multitude of primary tumor types, including but not limited to those of prostate, colon, lung, breast, and liver origin.

Based on data generated by reverse-transcriptase PCR sequence detection (i.e., "TAQMAN®") techniques using a panel of tissues obtained from selected human tissues, a high level of 27877 expression was observed in normal brain cortex. Brain cortex is the tissue location of numerous physiological activities, in each of which 27877 proteins can have a role. By way of example, interconnections that are formed in normal brain cortex tissue can mediate muscular and intellectual learning, and can facilitate 'neuronal learning' processes whereby physical stimuli can more easily evoke a sensation of pain over time. Because 27877 protein is involved in cell signaling and differentiation processes, 27877 molecules can be used to modulate muscular, intellectual, and neuronal learning processes in humans.

Various neurodegenerative disorders are known to involve aberrant functioning of cell signaling mechanisms. For example, Alzheimer's disease is often characterized by generation and accumulation of neurofibrillary tangles containing large quantities of abnormally phosphorylated tau protein. Although the intracellular signaling mechanisms that affect tau phosphorylation have not been fully elucidated, it is known that numerous signaling proteins (including those which affect intracellular phosphate pools, such as kinase, phosphatases, and phospholipases) can affect the phosphorylation state of tau protein. 27877 protein can influence the phosphorylation state of tau protein, and molecules that affect expression, activity, or cellular level of 27877 protein can be used to modulate phosphate-mediated cellular signaling. Thus, these molecules can be used to treat patients afflicted with neurodegenerative disorders such as Alzheimer's disease.

Because 27877 protein is involved in cell differentiation processes and is expressed in normal brain cortex, modulating expression, activity, or cellular level of 27877 protein can improve recovery of brain tissue following ischemic traumas, such as those associated with stroke and traumatic brain injuries.

Expression of 27877 was also detected in normal brain hypothalamus tissue, astrocytes, and ovary tissue. Each of these cell or tissue types is characterized by growth or proliferation during at least certain portions of the adult lifespan. Involvement of 27877 protein in cell differentiation processes indicates that 27877 molecules can influence growth and proliferation of cells in these tissues, such as differentiation of precursor cells (e.g., neuronal stem cells or partially differentiated brain or ovarian cell types) in a process that leads to formation of the fully-differentiated tissue.

TAQMAN® analysis performed on a panel of selected human hematological tissues indicated high levels of 27877 expression in fetal liver, bone marrow erythrocytes, in vitro generated erythroid lineage progenitor cells at day 6 through day 12, in vitro generated burst forming unit-erythroid (BFU-E), and BFU-E exposed to erythropoietin for 3 days. Each of these tissues and cell types is involved in differentiation of blood cells and blood cell precursors. 27877 was most highly expressed in cells of the myeloid line, particularly in differentiating erythroid lineage progenitor cells (including burst-forming units of erythroid lineage; "BFU-E") and bone marrow erythrocytes (i.e., GPA+ cells of bone marrow). BFU-E that were exposed to erythropoietin for 3 days expressed 27877 at an even greater level. Expression of 27877 was also observed in bone marrow tissue (including erythroid progenitor cells which expressed GPA at a low level), mobilized peripheral blood, and cord blood CD34+ cells.

These expression data indicate that 27877 has a role in differentiation of erythroid cells, such as in terminal differentiation of these cells to form erythrocytes. An increase in intracellular 27877 activity can lead to increased intracellular production of phosphatidic acid (PA). PA accumulation leads to cessation of cell growth, and this may be a mechanism by which the activity of 27877 protein can modulate the rate or extent of erythroid cell differentiation. PA is also known to act as an intracellular second messenger, and can regulate growth and differentiation of cells in which it is expressed. Involvement of 27877 protein in regulation of intracellular PA indicates that 27877 molecules can be used to modulate erythroid cell growth and differentiation, both in normal tissues and tissues affected by a disorder, particularly disorders which affect erythroid cell growth or differentiation.

27877 molecules can be used to enhance growth and differentiation of erythroid precursor cells to induce formation of erythrocytes and alleviate the severity of the anemia. Naturally, 27877 molecules can also be used to inhibit or prevent anemia in situations in which anemia is anticipated (e.g., in advance of administering a hemolytic medication).

27877 molecules can be used in non-diseased humans in order to increase erythrocyte production. Enhanced erythrocyte production can be beneficial, for example, during or prior to periods of intense physical exertion or exposure to a relatively oxygen-poor altitude (e.g., at high altitudes). These molecules can also be used to enhance oxygen absorption by humans whose oxygen intake may be hampered by environmental contaminants (e.g., carbon monoxide or tobacco smoke) or by physical infirmity (e.g., diaphragm weakness associated with traumatic injury or pneumonia).

Other disorders associated with aberrant growth and proliferation of erythrocytes include polycythemias, which are associated with an overabundance of erythrocytes or hemoglobin. Examples of polycythemias that can be treated using 27877 molecules include polycythemia vera, secondary polycythemia, and relative polycythemia.

Gene Expression of 27877

Expression of 27877 was assessed in a variety of cell and tissue types using a standard TAQMAN™ PCR-based sequence detection procedure. The data collected from these experiments are summarized in Tables 2-6.

TABLE 2

| Tissue or Cell Type | Relative Expression |
|---|---|
| Normal Artery | 0.2 |
| Normal Vein | 0.8 |
| Early Aortic Smooth Muscle Cells | 7.2 |
| Coronary Smooth Muscle Cells | 14.3 |
| Static Human Umbilical Vascular Epithelial Cells | 8.3 |
| Shear Human Umbilical Vascular Epithelial Cells | 8.4 |
| Normal Heart | 2.2 |
| Heart Congestive Heart Failure | 3.4 |
| Kidney | 6.4 |
| Skeletal Muscle | 1.7 |
| Normal Adipose | 0.4 |
| Pancreas | 3.2 |
| Primary Osteoblasts | 1.4 |
| Differentiated Osteoclasts | 0.2 |
| Normal Skin | 3.2 |
| Normal Spinal cord | 4.9 |
| Normal Brain Cortex | 128 |
| Normal Brain Hypothalamus | 32.0 |
| Nerve | 3.9 |
| Dorsal Root Ganglion | 9.3 |
| Glial Cells (Astrocytes) | 31.9 |
| Glioblastoma | 2.5 |
| Normal Breast | 1.2 |
| Breast Tumor | 5.3 |
| Normal Ovary | 21.9 |
| Ovary Tumor | 2.9 |
| Normal Prostate | 2.0 |
| Prostate Tumor | 2.7 |
| Prostate Epithelial Cells | 6.8 |
| Normal Colon | 0.6 |
| Colon Tumor | 3.8 |
| Normal Lung | 0.7 |
| Lung Tumor | 5.2 |
| Chronic Obstructive Pulmonary Disease Lung | 1.7 |
| Inflammatory Bowel Disease Colon | 0.8 |
| Normal Liver | 1.4 |

TABLE 2-continued

| Tissue or Cell Type | Relative Expression |
|---|---|
| Liver fibrosis | 4.3 |
| Dermal Cells-fibroblasts | 4.3 |
| Normal Spleen | 2.7 |
| Normal Tonsil | 3.9 |
| Lymph node | 9.5 |
| Resting Peripheral Blood Mononuclear Cells | 1.0 |
| Skin-Decubitus | 5.9 |
| Synovium | 1.8 |
| Bone marrow mononuclear cells | 2.8 |
| Activated Peripheral Blood Mononuclear Cells | 3.0 |

TABLE 3

| Tissue or Cell Type | Relative Expression |
|---|---|
| Lung MPI 188 | 1 |
| Kidney | 9 |
| Spleen | 3 |
| Fetal Liver MPI BMW54 | 17 |
| Grans #9 | 3 |
| NHDF Mock | 1 |
| NHLF Mock | 4 |
| NHLF TGF | 5 |
| NC Heps | 2 |
| Pass Stell | 2 |
| Liver LF NDR 200 | 0 |
| Liver LF NDR 191 | 1 |
| Lymph Nodes | 11 |
| Tonsils | 3 |
| TH0 046 6 hr | 3 |
| TH1 046 6 hr | 5 |
| TH2 046 6 hr | 3 |
| CD8 | 6 |
| CD14 | 0 |
| CD19 | 2 |
| CD3 Resting | 3 |
| MBM MNC LP139 | 1 |
| mPB CD34+ LP152 | 1 |
| Bone Marrow CD34+ LP154 | 1 |
| Cord Blood CD34+ LP121 | 2 |
| Erythroid | 32 |
| Meg | 3 |
| Neut d14 | 1 |
| Bone Marrow CD15+ CD14– LP32 | 0 |
| mBM CD15+ CD11b– | 0 |
| Bone Marrow GPA+ | 14 |
| K562 | 7 |
| HL60 | 6 |
| Molt4 | 22 |
| Normal Hep3b | 3 |
| Hep3b Hyp | 8 |

TABLE 4

| Tissue or Cell Type | Relative Expression |
|---|---|
| Brain | 8.7 |
| Brain Cortex | 18.2 |
| Breast | 0.7 |
| Colon Tumor | 0.5 |
| Heart | 2.0 |
| Kidney | 1.3 |
| Normal Liver | 0.4 |
| Liver fib | 0.5 |
| Lung Tumor | 1.2 |
| Ovary | 2.4 |
| mBM CD34+ LP92 | 1.3 |
| mBM CD34+ LP143 | 1.2 |
| mPB CD34+ LF70 | 1.2 |
| mPB CD34+ LF162 | 1.1 |
| Bone Marrow CD34+ LF93 | 0.4 |

TABLE 4-continued

| Tissue or Cell Type | Relative Expression |
| --- | --- |
| Bone Marrow CD34+ LP154 | 2.0 |
| Cord Blood CD34+ LP121 | 1.7 |
| Cord Blood CD34+ LF101 | 2.1 |
| GPA+ High LP34-1 | 9.8 |
| GPA+ High | 9.5 |
| GPA+ High 69 | 5.6 |
| GPA+ High 74 | 3.2 |
| GPA+ Low LP69 | 5.4 |
| GPA+ Low LP82 | 3.6 |
| In Vitro Erythroid 24 hours LF102 | 3.9 |
| In Vitro Erythroid 48 hours LF87 | 2.7 |
| In Vitro Erythroid 48 hours LF102 | 4.0 |
| In Vitro Erythroid 48 hours LF72 | 7.6 |
| In Vitro Erythroid day 6 LP31-1 | 7.8 |
| In Vitro Erythroid day 6 LF113 | 21.1 |
| In Vitro Erythroid day 7 LF24-5 | 13.6 |
| In Vitro Erythroid day 8 LF113 | 24.2 |
| In Vitro Erythroid day 10 LP24-4 | 16.0 |
| In Vitro Erythroid day 12 LF23-8 | 13.1 |
| In Vitro Erythroid day 12 LF24-10 | 13.0 |
| In Vitro Erythroid day 12 LF113 | 13.5 |
| In Vitro Erythroid day 14 GPA+ LP31-4 | 3.7 |
| In Vitro Burst-Forming Unit day 7 LP79 | 10.6 |
| In Vitro Burst-Forming Unit day 7 LP95 | 10.9 |
| In Vitro Burst-Forming Unit day 7 + 3 days Erythropoietin LP81 | 10.9 |
| In Vitro Burst-Forming Unit day 7 + 3 days Erythropoietin LP104 | 15.6 |

TABLE 5

| Tissue or Cell Type | Relative Expression |
| --- | --- |
| Lung | 2 |
| Colon MPI 60 | 2 |
| Spleen MPI 380 | 4 |
| Kidney MPI 58 | 2 |
| Liver NDR 200 | 0 |
| Fetal Liver MPI 133 | 31 |
| Sk Muscle MPI 167 | 2 |
| mBM MNC LP140 | 2 |
| mBM MNC LP7 | 0 |
| mBM CD34+ LP92 | 4 |
| mBM CD34+ LP143 | 2 |
| mPB CD34+ LF70 | 1 |
| mPB CD34+ LP162 | 1 |
| Bone Marrow CD34+ LF93 | 1 |
| Bone Marrow CD34+ LP154 | 2 |
| Cord Blood CD34+ LP163 | 3 |
| Cord Blood CD34+ LP101 | 2 |
| Bone Marrow GPA+ LF74 | 4 |
| Bone Marrow GPA+ LP34-1 | 18 |
| Bone Marrow GPA$^{Low}$ LP69 | 5 |
| Bone Marrow GPA$^{Low}$ LP82 | 6 |
| mPB CD41+ CD14− LP119 | 0 |
| Bone Marrow CD41+ CD14− LP132 | 1 |
| mBM CD15+ LP15 | 0 |
| mBM CD15+ CD11b− LF120 | 0 |
| mBM CD15+ CD11b+ LP15-2 | 0 |
| Bone Marrow CD15+ CD11b− LF80-4 | 1 |
| Bone Marrow CD15+ CD11b− LP23-2 | 0 |
| Bone Marrow CD15+ CD11b− LF128 | 1 |
| Bone Marrow CD15+ CD11b+ LF128 | 0 |
| Bone Marrow CD15+ CD34− LP27-2 | 0 |
| Bone Marrow CD15+ CD34− LP41-1 | 0 |

TABLE 6

| Tissue or Cell Type | Relative Expression |
| --- | --- |
| In Vitro Erythroid 24 hours LF102 | 2 |
| In Vitro Erythroid 48 hours LF73 | 4 |
| In Vitro Erythroid 48 hours LF87 | 2 |
| In Vitro Erythroid 48 hours LF90 | 2 |
| In Vitro Erythroid 48 hours LF102 | 3 |
| In Vitro Erythroid day 6 LP31-1 | 7 |
| In Vitro Erythroid day 6 LF113 | 16 |
| In Vitro Erythroid day 7 LF24-5 | 10 |
| In Vitro Erythroid day 8 LF113 | 20 |
| In Vitro Erythroid day 10 LP24-4 | 9 |
| In Vitro Erythroid day 12 LF23-8 | 13 |
| In Vitro Erythroid day 12 LF24-10 | 15 |
| In Vitro Erythroid day 12 LF113 | 9 |
| In Vitro Erythroid day 14 GPA+ LP31-4 | 2 |
| Megs 24 hr LF102 | 3 |
| Megs 48 hr LF102 | 3 |
| Meg d6 LF110 | 2 |
| Meg d7 LP31-2 | 2 |
| Meg d10 LF110 | 2 |
| Meg d12 LF102 | 1 |
| Meg d12 LF35 | 1 |
| Meg d14 LP31-5 | 2 |
| Neutrophils d4 LF71 | 2 |
| Neutrophils d4 LF78 | 1 |
| Neutrophils d6 LF26 | 1 |
| Neutrophils d6 LP71 | 1 |
| Neutrophils d6 LP78 | 2 |
| Neutrophils d7 LP41-3 | 1 |
| Neutrophils d8 LF78 | 1 |
| Neutrophils d11 LF78 | 3 |
| Neutrophils d12 LP26B | 1 |
| Neutrophils d13 LF78 | 3 |
| Neutrophils d14 LF71 | 1 |
| Neutrophils d14 LF78 | 1 |
| Neutrophils d14 LP31-6 | 0 |
| Platelets | 0 |
| Mast cells LP71 | 3 |
| Mast Cells LP118 | 4 |
| Burst-Forming Units day 7 LP79 | 12 |
| Burst-Forming Units day 7 LP95 | 12 |
| Burst-Forming Units day 7 + 3 days Erythropoietin LP81 | 15 |
| Burst-Forming Units day 7 + 3 days Erythropoietin LP104 | 18 |

Human 18080

Nucleotide and corresponding amino acid sequences for a serine carboxypeptidase family member, referred to herein as "18080" are disclosed. 18080 protein is identical in sequence to Genbank Accession No. AF282618_1. Applicants have shown expression of 18080 mRNA in human hematopoietic cells, e.g., erythroid cells, as well as, adrenal glands and endothelial cells. Accordingly, modulators of 18080 polypeptide activity or expression may be used to treat or prevent hematopoietic and angiogenic disorders.

The human 18080 sequence (SEQ ID NO:11), which is approximately 1921 nucleotides long including untranslated regions, contains a predicted methionine-initiated coding sequence of about 1356 nucleotides (nucleotides 33-1388 of SEQ ID NO:11; 1-1356 of SEQ ID NO:13), not including the terminal codon. The coding sequence encodes a 452 amino acid protein (SEQ ID NO:12).

The human 18080 protein of SEQ ID NO:12 includes an amino-terminal hydrophobic amino acid sequence, consistent with a signal sequence, of about 27 amino acids (from amino acid 1 to about amino acid 27 of SEQ ID NO:12), which upon cleavage results in the production of a mature protein form. This mature protein form is approximately 425 amino acid residues in length (from about amino acid 28 to amino acid 452 of SEQ ID NO:12).

The serine carboxypeptidase domain of human 18080 was aligned with a consensus amino acid sequence derived from a hidden Markov model (HMM) from PFAM. The algorithm identified two local alignments between the consensus amino acid sequence and human 18080. Two consensus amino acid sequences (SEQ ID NOs:14 and 15), aligned to amino acids 42 to 236 and 337 to 451 of SEQ ID NO:12.

Human 18080 contains the following regions or other structural features: a serine carboxypeptidase domain (PROSITE Accession Number PDOC00122) including a serine carboxypeptidase-serine active site (PS00131) and a serine carboxypeptidase-histidine active site (PS00560) located at about amino acid residues 42 to 236 and 337 to 451 of SEQ ID NO:12, respectively; three predicted N-glycosylation sites (PS00001) located at about amino acids 64 to 67, 126 to 129, and 362 to 365 of SEQ ID NO: 12; one predicted cAMP/cGMP-dependent protein kinase phosphorylation sites (PS00004) located at about amino acids 101 to 104 of SEQ ID NO:12; four predicted Protein Kinase C phosphorylation sites (PS00005) located at about amino acids 44 to 46, 61 to 63, 188 to 190, and 417 to 419 of SEQ ID NO:12; six predicted Casein Kinase II phosphorylation sites (PS00006) located at about amino acids 204 to 207, 220 to 223, 280 to 283, 284 to 287, 351 to 354, and 449 to 452 of SEQ ID NO:12; and eight predicted N-myristylation sites (PS00008) located at about amino acids 22 to 27, 76 to 81, 119 to 124, 169 to 174, 187 to 192, 195 to 200, 331 to 336, and 360 to 365 of SEQ ID NO:12.

For general information regarding PFAM identifiers, PS prefix and PF prefix domain identification numbers, refer to Sonnhammer et al. (1997) *Protein* 28:405-420.

Proteolytic enzymes that exploit serine in their catalytic activity are ubiquitous, being found in viruses, bacteria, and eukaryotes. See, e.g., Rawlings & Barrett (1994) *Methods Enzymol.* 244: 19-61. Over 20 families of serine peptidase have been identified, these being grouped into 6 clans on the basis of structural similarity and other functional evidence. Structures are known for 4 of the clans: these appear to be totally unrelated, suggesting at least four evolutionary origins of serine peptidases. Their different evolutionary origins notwithstanding, there are similarities in the reaction mechanisms of several peptidases. Carboxypeptidase C family, like chymotrypsin and subtilisin, has a catalytic triad of serine (S), aspartate (D), and histidine (H): serine acts as a nucleophile, aspartate as an electrophile, and histidine as a base. See, e.g., Rawlings & Barrett (1994) *Biochem. J.* 290: 205-218.

Carboxypeptidase C includes a number of serine carboxypeptidases, which are unusual in that their optimum activity occurs in acidic conditions. In higher organisms, serine carboxypeptidases are glycoproteins (for reviews, see Breddam (1986) *Carlsberg Res. Commun.* 51: 83-128), and hydrolyze COOH-terminal peptide bonds. In humans, a highly specific serine carboxypeptidase cleaves the COOH-terminal residue of angiotensin II and III, and may be involved in the regulation of blood pressure. See, e.g., Odya et al. (1978) *J. Biol. Chem.* 253: 5927-5931 and Odya & Erdos (1981) *Methods Enzymol.* 80: 460-466. In addition, serine carboxypeptidases may be involved in degrading growth factors or extracellular matrix.

The 18080 protein contains a significant number of structural characteristics in common with members of the serine carboxypeptidase family. Serine carboxypeptidase family members are characterized by a common catalytic mechanism which is provided by a charge relay system involving an aspartic acid residue hydrogen-bonded to a histidine, which is itself hydrogen-bonded to a serine. The catalytic triad catalyzes a hydrolysis reaction involving a COOH-terminal peptide bond. A serine carboxypeptidase family of proteins has two signature motifs—one motif includes the residues of [LIVM]-x-[GTA]-E-S-Y-[AG]-[GS] (SEQ ID NO:16), which contains the catalytic serine (S); and one motif spans the region encoded by [LIVF]-x(2)-[LIVSTA]-x-[IVPST]-x-[GSDNQL]-[SAGV]-[SG]-H-x-[IVAQ]-P-x(3)-[PSA] (SEQ ID NO:17), which contains the catalytic histidine (H). Residues corresponding to catalytic serine and histidine residues are located at amino acids 167 and 431 of SEQ ID NO:12, respectively. The amino acid sequence of 18080 is identical to the sequence of a serine carboxypeptidase I precursor protein having Genbank's accession number AAG16692 (AF282618).

As used herein, the term "serine carboxypeptidase domain" includes an amino acid sequence of about 50 to 500 amino acid residues in length, more preferably about 70 to 400 amino acid residues, or about 100 to 350 amino acids and has a bit score for the alignment of the sequence to the serine carboxypeptidase domain (HMM) of at least 70 or greater. Preferably, the domain includes one motif: IFSESYGG (SEQ ID NO:18) located at about amino acids 163 to 170 of SEQ ID NO:12, which includes the catalytic serine (located at amino acid 167 of SEQ ID NO:12), and another motif: LAFYWILKAGHMVP (SEQ ID NO:19) located at about amino acids 421 to 434 of SEQ ID NO:12, which includes the catalytic histidine (located at amino acid 431 of SEQ ID NO:12). The serine carboxypeptidase motif including a catalytic serine (HMM) has been assigned the PFAM Accession Number PF00131, and the serine carboxypeptidase motif including a catalytic histidine (HMM) has been assigned the PFAM Accession Number PF00560. The serine carboxypeptidase domain (amino acids 42 to 236 and 337 to 451 of SEQ ID NO:12) of human 18080 aligns with a consensus amino acid sequence derived from a hidden Markov model derived from PFAM.

In a preferred embodiment 18080 polypeptide or protein has a "serine carboxypeptidase domain" or a region which includes at least about 50 to 500 more preferably about 70 to 400, or 100 to 350 amino acid residues and has at least about 50%, 60%, 70% 80% 90% 95%, 99%, or 100% homology with a "serine carboxypeptidase domain," e.g., the serine carboxypeptidase domain of human 18080 (e.g., residues 42 to 236 and 337 to 451 of SEQ ID NO:12).

In a hydropathy plot of human 18080, polypeptides of the invention include fragments which include: all or part of a hydrophobic sequence, e.g., the sequence from about amino acid 135 to 152 of SEQ ID NO:12; and all or part of a hydrophilic sequence, e.g., the sequence of from about amino acid 93 to 108 of SEQ ID NO:12.

To identify the presence of a "serine carboxypeptidase" domain in a 18080 protein sequence, and make the determination that a polypeptide or protein of interest has a particular profile, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3): 405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of two "serine carboxypeptidase" domains in the amino acid sequence of human 18080 at about residues 42 to 236 and 337 to 451 of SEQ ID NO:12.

A 18080 protein can further include a signal peptide, and is predicted to be a secreted protein. As used herein, a "signal peptide" or "signal sequence" refers to a peptide of about 10 to 40, preferably about 15 to 30, more preferably, about 27 amino acid residues in length which occurs at the N-terminus of secretory and integral membrane proteins and which contains a majority of hydrophobic amino acid residues. For example, a signal sequence contains at least about 10 to 40, preferably about 15 to 30, more preferably, 27 amino acid residues, and has at least about 40-70%, preferably about 50-65%, and more preferably about 55-60% hydrophobic amino acid residues (e.g., alanine, valine, leucine, isoleucine, phenylalanine, tyrosine, tryptophan, or proline). Such a "signal sequence", also referred to in the art as a "signal peptide," serves to direct a protein containing such a sequence to a lipid bilayer. For example, in one embodiment, a 18080 protein contains a signal sequence of about amino acids 1 to 27 of SEQ ID NO:12. The "signal sequence" is cleaved during processing of the mature protein. The mature 18080 protein corresponds to amino acids 28 to 452 of SEQ ID NO:12.

A 18080 family member can include a "serine carboxypeptidase domain" or regions homologous with a "serine carboxypeptidase domain." A 18080 polypeptide can optionally further include at least one, two, preferably three N-glycosylation sites (PS0001); at least one cAMP- and cGMP-dependent protein kinase phosphorylation site (PS0004); at least one, two, three, preferably four protein kinase C phosphorylation sites (PS0005); at least one, two, three, four, five, preferably six casein kinase II phosphorylation sites (PS0006); and at least one, two, three, four, five, six, seven, preferably eight N-myristylation sites (PS0008).

Based on the above-described sequence similarities and the tissue distribution described below, the 18080 molecules of the present invention are predicted to have similar biological activities as serine carboxypeptidase family members. Thus, in accordance with the invention, a 18080 serine carboxypeptidase or subsequence or variant polypeptide may have one or more domains and, therefore, one or more activities or functions characteristic of a serine carboxypeptidase family member, including, but not limited to: (1) modulating removal of COOH-terminal residues, i.e., having carboxypeptidase activity; (2) modulating the transfer of an acyl group from a donor to an acceptor molecule, i.e., having acyltransferase activity; (3) modulating (e.g., stimulating) cell differentiation, e.g., differentiation of hematopoietic cells (e.g., differentiation of blood cells (e.g., erythroid progenitor cells, such as CD34+ erythroid progenitors)); (4) modulating hematopoiesis, e.g., erythropoiesis; (5) modulating cell proliferation, e.g., proliferation of hematopoietic cells (e.g., erythroid progenitor cells); (6) modulating apoptosis, of a cell, e.g., increase apoptosis of a cancer cell, e.g., a leukemic cell, (e.g., an erythroleukemia cell); or suppress apoptosis of a blood or erythroid cell; or (7) modulating erythroid progenitors by allowing greater interaction with growth factors or extracellular matrix.

As the 18080 polypeptides of the invention may modulate 18080-mediated activities, they may be useful as of for developing novel diagnostic and therapeutic agents for 18080-mediated or related disorders, as described below.

As used herein, a "18080 activity", "biological activity of 18080" or "functional activity of 18080", refers to an activity exerted by a 18080 protein, polypeptide or nucleic acid molecule. For example, a 18080 activity can be an activity exerted by 18080 in a physiological milieu on, e.g., a 18080-responsive cell or on a 18080 substrate, e.g., a protein substrate. A 18080 activity can be determined in vivo or in vitro. In one embodiment, a 18080 activity is a direct activity, such as an association with a 32229 target molecule. A "target molecule" or "binding partner" is a molecule with which a 18080 protein binds or interacts in nature. In an exemplary embodiment, 18080 is an enzyme for peptide or protein substrate. In other embodiments, an 18080 has acyltransferase activity.

18080 mRNA is found primarily in hematopoietic progenitor cells (Tables 7-11). High levels of 18080 mRNA expression were observed in erythroid cells. Its expression is further enhanced in the erythroid lineage and increases as bone marrow/blood cell differentiation proceeds. High levels of 18080 mRNA expression were also detected in adrenal glands and human umbilical vein endothelial cells (HUVECS). Tables 8-11 show TaqMan assays on mRNA most derived from human hematological samples, e.g., bone marrow (BM), erythroid cells (Eryth), megakaryocytes (Meg), neutrophils (Neut), or a negative reference sample (NTC). In Table 8, 18080 mRNA was highly expressed in BM glycophorin A (GPA) positive cells, followed by mBM CD34+ cells and Eryth cells. In Table 9, 18080 mRNA expression was observed in GPA Hi/Lo LF 156 Eryth cells, GPA Hi/Lo LF154 Eryth cells, and Kidney cells. In Table 10, mRNA expression was detected at the indicated times in culture (e.g., 24 hrs, 48 hrs, 6 days (D6), 12 days (D12). High levels of 18080 expressions were observed in one sample of Eryth LF127 cells and in one sample of Eryth LF139 cells, especially day 6 and day 12, respectively. In Table 11, mRNA expression was detected at the indicated times in culture (e.g., 24 hrs., 48 hrs., days in culture). Moderate level of 18080 mRNA expressions were observed in Meg LF 157 cells and Neut LF141 cells, especially day 10 and day 6, respectively.

Significant expression of 18080 mRNA is found in the bone marrow, cord blood, fetal liver, and in particular, in glycophorin A-expressing (GPA) cells or CD34-expressing populations of cells from those tissues, such as mobilized peripheral blood GPA+/CD34+ cells, normal adult bone marrow GPA+/CD34+ cells, cord blood GPA+/CD34+ cells, normal adult bone marrow GPA+/CD34+ cells, and fetal liver GPA+/CD34+ cells; as well as erythroid progenitor cells, e.g., erythropoietin treated erythroid burst forming units (BFUs), erythrocytes, in vitro generated erythroblasts, and megakaryocytes (Tables 7-8). Thus, diagnostic and therapeutic methods using the molecules of the invention (or agents that modulate the activity or expression of the 18080 molecules) to treat/diagnose disorders involving the cells/tissues expressing 18080 molecules are contemplated by the present invention. Inhibition of the 18080 molecules will likely stimulate erythroid progenitors by allowing greater interaction with growth factors or extracellular matrix.

As used herein, a "glycophorin A-positive cell" or a "glycophorin A-expressing cell-cell" refers to a cell that expresses detectable levels of the glycophorin A antigen, preferably human glycophorin A antigen. Glycophorin A is a 31 kD erythrocyte membrane glycoprotein, and is typically present on immature hematopoietic precursor cells and hematopoietic colony-forming cells in the bone marrow.

As used herein, a "CD34-positive cell" or a "CD34-expressing cell" refers to a cell that expresses detectable levels of the CD34 antigen, preferably human CD34 antigen. The sequence for human CD34 is provided in SwissProt Accession Number P28906. The CD34 antigen is typically present on immature hematopoietic precursor cells and hematopoietic colony-forming cells in the bone marrow, including unipotent (CFU-GM, BFU-E) and pluripotent progenitors (CFU-GEMM, CFU-Mix and CFU-blast). The CD34 is also expressed on stromal cell precursors. Terminal deoxynucleotidyl transferase (TdT)-positive B- and T-lymphoid precursors in normal bone also are CD34+. The CD34 antigen is typically present on early myeloid cells that express the CD33 antigen, but lack the CD14 and CD15 antigens and on early erythroid cells that express the CD71 antigen and dimly express the CD45 antigen. The CD34 antigen is also found on capillary endothelial cells and approximately 1% of human thymocytes. Normal peripheral blood lymphocytes, monocytes, granulocytes and platelets do not express the CD34 antigen. CD34 antigen density is highest on early hematopoietic progenitor cells and decreases as the cells mature. The antigen is undetectably on fully differentiated hematopoietic cells. Approximately 60% of acute B-lymphoid leukemia's and acute myeloid leukemia express the CD34 antigen. The antigen is not expressed on chronic lymphoid leukemia (B or T lineage) or lymphomas.

As the 18080 polypeptides of the invention may modulate 18080-mediated activities, they may be useful as of for developing novel diagnostic and therapeutic agents for 18080-mediated or related disorders, e.g., hematopoeitic disorder (e.g., blood cell- (e.g., erythroid-) associated disorders), endothelial cell disorders, cardiovascular disorders, as well as angiogenic disorders (e.g., cancerous disorders and/or disorders involving aberrant tumor growth).

Agents that modulate 18080 polypeptide or nucleic acid activity or expression can be used to treat anemias, in particular, drug-induced anemias or anemias associated with cancer chemotherapy, chronic renal failure, malignancies, adult and juvenile rheumatoid arthritis, disorders of hemoglobin synthesis, prematurity, and zidovudine treatment of HIV infection. A subject receiving the treatment can be additionally treated with a second agent, e.g., erythropoietin, to further ameliorate the condition.

As used herein, the term "erythropoietin" or "EPO" refers to a glycoprotein produced in the kidney, which is the principal hormone responsible for stimulating red blood cell production (erythrogenesis). EPO stimulates the division and differentiation of committed erythroid progenitors in the bone marrow. Normal plasma erythropoietin levels range from 0.01 to 0.03 Units/mL, and can increase up to 100 to 1.000-fold during hypoxia or anemia. Graber and Krantz, *Ann. Rev. Med.* 29:51 (1978); Eschbach and Adamson, *Kidney Intl.* 28:1 (1985). Recombinant human erythropoietin (rHuEpo or epoietin alpha) is commercially available as EPOGEN.™. (epoietin alpha, recombinant human erythropoietin) (Amgen Inc., Thousand Oaks, Calif.) and as PROCRIT.™. (epoietin alpha, recombinant human erythropoietin) (Ortho Biotech Inc., Raritan, N.J.).

Another example of an erythroid-associated disorder is erythrocytosis. Erythrocytosis, a disorder of red blood cell overproduction caused by excessive and/or ectopic erythropoietin production, can be caused by cancers, e.g., a renal cell cancer, a hepatocarcinoma, and a central nervous system cancer. Diseases associated with erythrocytosis include polycythemias, e.g., polycythemia vera, secondary polycythemia, and relative polycythemia.

Since 18080 mRNA is expressed in endothelial cells, molecules of the incention can be used as therapeutic and diagnostic target to treat enodothelial cell related disorders, e.g., cardiovascular (e.g., blood vessel or hematological disorders), and angiogenic disorders, e.g., cancers or disorders involving tumor growth.

Aberrant expression or activity of the 18080 molecules may be involved in neoplastic disorders. Accordingly, treatment, prevention and diagnosis of cancer or neoplastic disorders related to hematopoietic cells and, in particular, cells of the erythroid lineage are also included in the present invention. Such neoplastic disorders are exemplified by erythroid leukemias, or leukemias of erythroid precursor cells, e.g., poorly differentiated acute leukemias such as erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97). In particular, AML can include the uncontrolled proliferation of CD34+ cells such as AML subtypes M1 and M2, myeloblastic leukemias with and without maturation, and AML subtype M6, erythroleukemia (Di Guglielmo's disease). Additional neoplastic disorders include a myelodysplastic syndrome or preleukemic disorder, e.g., oligoblastic leukemia, smoldering leukemia. Additional cancers of the erythroid lineage include erythroblastosis, and other relevant diseases of the bone marrow.

The molecules of the invention may also modulate the activity of neoplastic, non-hematopoietic tissues. Accordingly, the 18080 molecules can act as novel diagnostic targets and therapeutic agents for controlling one or more of cellular proliferative and/or differentiative disorders. Examples of such cellular proliferative and/or differentiative disorders include cancer, e.g., carcinoma, sarcoma, or metastatic disorders. A metastatic tumor can arise from a multitude of primary tumor types, including but not limited to those of lung, prostate, colon, breast, and liver origin.

Gene Expression of 18080

Table 7 depicts relative 18080 mRNA expression as determined by TaqMan assays in a panel of human tissues, including artery normal, aorta diseased, vein normal, coronary SMC, Human Umbilical Vein Endothelial Cells (HUVEC), heart, pancreas, skin, spinal cord, brain, adrenal glands, dorsal root gland (DRG), nerve, breast, ovary, colon, lung, liver, megakaryocytes, and erythroid. The highest 18080 mRNA expression was observed in erythroid, followed by adrenal glands and HUVEC cells. Moderate 18080 mRNA expression was observed in most of the other tissues Tables 8-11 depicts relative 18080 mRNA expression as determined by TaqMan assays on mRNA most derived from human hematological samples, e.g., bone marrow (BM), erythroid cells (Eryth), megakaryocytes (Meg), neutrophils (Neut), or a negative reference sample (NTC). In Table 8, 18080 mRNA was highly expressed in BM glycophorin A (GPA) positive cells, followed by mBM CD34+ cells and erythroid cells. In Table 9, 18080 mRNA expression was observed in GPA Hi/Lo LF 156 Eryth cells, GPA Hi/Lo LF154 erythroid cells, and kidney cells. In Table 10, mRNA expression was detected at the indicated times in culture (e.g., 24 hrs, 48 hrs, 6 days (D6), 12 days (D12). High levels of 18080 expressions were observed in one sample of Eryth LF127 cells and in one sample of Eryth LF139 cells, especially day 6 and day 12, respectively. In Table 11, 18080 mRNA expression was detected at the indicated times in culture (e.g., 24 hrs., 48 hrs., days in culture). Moderate levels of 18080 mRNA expressions were observed in Meg LF 157 cells and Neut LF141 cells, especially day 10 and day 6, respectively. The relative tissue distribution of 18080 mRNA is depicted in tabular form in Tables 8-11.

TABLE 7

| Tissue Type | β2 Mean | Mean | ∂∂ Ct | Expression |
|---|---|---|---|---|
| Artery normal | 27 | 21 | 6 | 18 |
| Aorta diseased | 29 | 23 | 6 | 16 |
| Vein normal | 27 | 20 | 7 | 10 |
| Coronary SMC | 28 | 21 | 6 | 12 |
| HUVEC | 26 | 21 | 5 | 33 |
| Hemangioma | 29 | 21 | 8 | 3 |
| Heart normal | 27 | 21 | 7 | 11 |
| Heart CHF | 28 | 21 | 6 | 12 |
| Kidney | 27 | 21 | 6 | 15 |
| Skeletal Muscle | 30 | 23 | 7 | 7 |
| Liver normal | 30 | 20 | 10 | 1 |
| Small intestine normal | 31 | 21 | 10 | 1 |
| Adipose normal | 28 | 20 | 8 | 5 |
| Pancreas | 31 | 23 | 9 | 3 |
| primary osteoblasts | 28 | 20 | 8 | 4 |
| Bladder-Female normal | 28 | 20 | 8 | 5 |
| Adrenal Gland normal | 25 | 20 | 5 | 30 |
| Pituitary Gland normal | 28 | 21 | 8 | 5 |
| Brain Cortex normal | 30 | 23 | 6 | 13 |
| Brain Hypothalamus normal | 29 | 22 | 7 | 6 |
| Nerve | 29 | 21 | 7 | 6 |
| DRG (Dorsal Root Ganglion) | 29 | 22 | 8 | 5 |
| Breast normal | 27 | 21 | 6 | 17 |
| Breast tumor/IDC | 29 | 20 | 8 | 3 |
| Ovary normal | 28 | 21 | 8 | 5 |
| Ovary Tumor | 27 | 21 | 6 | 11 |
| Prostate BPH | 27 | 20 | 7 | 11 |
| Prostate Adenocarcinoma | 28 | 21 | 7 | 7 |
| Colon normal | 28 | 20 | 8 | 4 |
| Colon Adenocarcinoma | 30 | 22 | 8 | 5 |
| Lung normal | 27 | 19 | 8 | 4 |
| Lung tumor | 28 | 22 | 6 | 13 |
| Lung COPD | 26 | 19 | 7 | 6 |
| Colon IBD | 32 | 21 | 11 | 1 |
| Synovium | 29 | 20 | 9 | 2 |
| Tonsil normal | 28 | 19 | 8 | 3 |
| Lymph node normal | 29 | 21 | 8 | 3 |
| Liver fibrosis | 31 | 22 | 9 | 2 |
| Spleen normal | 29 | 19 | 10 | 1 |
| Macrophages | 25 | 18 | 7 | 7 |
| Progenitors (erythroid, megakaryocyte, neutrophil) | 29 | 20 | 8 | 3 |
| Megakaryocytes | 28 | 20 | 7 | 6 |
| Activated PBMC | 30 | 17 | 13 | 0 |
| Neutrophils | 30 | 19 | 11 | 1 |
| Erythroid | 27 | 22 | 5 | 32 |
| positive control | 28 | 22 | 6 | 12 |

TABLE 8

|  | 18080 | B2 | relative exp. |
|---|---|---|---|
| lung | 24 | 18 | 24 |
| kidney | 23 | 19 | 53 |
| spleen | 26 | 20 | 14 |
| fetal liver | 29 | 24 | 31 |
| grans. | 28 | 21 | 9 |
| NHDF mock | 24 | 18 | 22 |
| NHDF TGF | 24 | 19 | 31 |
| NHLF mock | 24 | 19 | 22 |
| NHLF TGF | 24 | 18 | 23 |
| NC Heps | 27 | 20 | 6 |
| Pass. Stel. | 24 | 18 | 21 |
| liver | 27 | 20 | 8 |
| NDR200 | 29 | 22 | 7 |
| NDR191 | 27 | 21 | 14 |
| NDR079 | 25 | 20 | 30 |
| lymph node | 25 | 18 | 10 |
| tonsil | 24 | 19 | 22 |
| Th0 | 27 | 17 | 1 |
| Th1 | 27 | 17 | 1 |
| Th2 | 27 | 17 | 1 |
| CD4 | 29 | 21 | 3 |
| CD8 | 26 | 18 | 4 |
| CD14 | 22 | 17 | 32 |
| CD19 | 27 | 20 | 8 |
| CD3 | 27 | 18 | 2 |
| mBM CD34+ | 23 | 18 | 42 |
| mPB CD34+ | 27 | 19 | 3 |
| BM CD34+ | 26 | 20 | 15 |
| Cord Blood | 27 | 19 | 4 |
| Ery. | 22 | 18 | 42 |
| Megs. | 27 | 21 | 19 |
| neut. | 26 | 19 | 5 |
| CD15+ 14− | 22 | 17 | 20 |
| mBM CD15+ 11b− | 23 | 18 | 22 |
| BM GPA+ | 25 | 22 | 132 |
| K562 | 25 | 20 | 26 |
| HL60 | 23 | 18 | 36 |
| molt | 25 | 20 | 18 |
| Hep36norm | 25 | 20 | 37 |
| Hep36 Hyp | 25 | 21 | 45 |
| NTC | 40 | 40 |  |

TABLE 9

|  | 18080 | Beta | Rel exp |
|---|---|---|---|
| Lung CHT 330 | 28 | 22 | 12 |
| Heart PT 262 | 29 | 22 | 9 |
| Spleen 380 | 27 | 20 | 5 |
| Kidney 27 | 25 | 21 | 58 |
| Liver NDR 379 | 30 | 22 | 3 |
| Fetal Liver BWH 54 | 29 | 22 | 7 |
| Brain MCL 400 | 27 | 21 | 16 |
| Colon PIT 259 | 28 | 21 | 7 |
| Muscle PIT 284 | 30 | 23 | 7 |
| mBM MNC LP7 | 25 | 19 | 13 |
| mBM CD34+ LP92 | 28 | 20 | 5 |
| mPB CD34+ LP350 | 30 | 20 | 1 |
| mPB CD34+ LF53 | 26 | 20 | 16 |
| BM CD34+ LF89 | 27 | 19 | 6 |
| BM CD34+ LF75 | 26 | 19 | 12 |
| Cord Blood CD34+ MF1 | 29 | 22 | 5 |
| Cord Blood CD34+ LF101 | 27 | 19 | 3 |
| GPA Hi LF154 | 27 | 22 | 39 |
| GPA Hi LF156 | 26 | 21 | 20 |
| GPA Lo LF154 | 26 | 21 | 31 |
| GPA Lo LF156 | 27 | 21 | 25 |
| MF11 Stromal D32 post irrad | 25 | 19 | 13 |
| MF12 Stromal cntl | 24 | 18 | 12 |
| MF13 Stromal D2 post irrad | 24 | 17 | 8 |

TABLE 10

|  | 18080 | Beta | Rel exp |
|---|---|---|---|
| mBM CD61+ LP196 | 26 | 21 | 26 |
| Platelets LP57 | 39 | 22 | 0 |
| mBM CD14−/11b−/15+ LF120 | 25 | 19 | 21 |
| BM CD14−/11b−/15+ LF54 | 25 | 20 | 25 |
| BM CD14−/11b−/15+ LF128 | 26 | 19 | 6 |
| BM CD14−/11b−/15+ LF145 | 25 | 20 | 16 |
| mBM CD14−/11b+/15+ LF120 | 26 | 20 | 11 |
| BM CD14−/11b+/15+ LF106 | 25 | 19 | 23 |
| BM CD11b+/15+ LF128 | 26 | 20 | 19 |
| BM-1 CD15+ ench LP41 | 26 | 20 | 16 |
| Eryth D0 LF127 | 30 | 20 | 2 |
| Eryth 48 hr LF127 | 31 | 24 | 5 |
| Eryth D6 LF127 | 26 | 22 | 97 |
| Eryth D12 LF127 | 27 | 21 | 21 |
| Eryth D0 LF139 | 31 | 22 | 1 |
| Eryth 24 hr LF139 | 32 | 23 | 1 |
| Eryth 48 hr LF139 | 30 | 21 | 2 |

TABLE 10-continued

|  | 18080 | Beta | Rel exp |
|---|---|---|---|
| Eryth D6 LF139 | 27 | 22 | 26 |
| Eryth D12 LF139 | 26 | 22 | 47 |
| BFU Eryth D7 LP79 | 27 | 21 | 17 |
| BFU Eryth D7 LP95 | 28 | 21 | 14 |
| BFU Eryth D7 +3epo LP81 | 28 | 21 | 11 |
| BFU Eryth D7 +3epo LP104 | 27 | 22 | 17 |
| Mast Cell LP118 | 27 | 21 | 20 |

TABLE 11

|  | 18080 | Beta | Rel exp |
|---|---|---|---|
| Meg D0 LF140 | 28 | 20 | 4 |
| Meg 48 hr LF140 | 29 | 20 | 2 |
| Meg D6 LF140 | 27 | 20 | 7 |
| Meg D12 LF140 | 26 | 20 | 9 |
| Meg 24 hr LF102 | 30 | 20 | 1 |
| Meg 48 hr LF102 | 29 | 20 | 2 |
| Meg 48 hr LF110 | 31 | 21 | 1 |
| Meg D9 LP127 | 27 | 20 | 6 |
| Meg D10 LF110 | 27 | 19 | 6 |
| Meg D12 LF26 | 27 | 21 | 10 |
| Meg 24 hr LF157 | 30 | 20 | 2 |
| Meg 48 hr LF157 | 29 | 20 | 2 |
| Meg D6 LF157 | 27 | 19 | 6 |
| Meg D10 LF157 | 26 | 20 | 14 |
| Meg D0 LF166 | 29 | 19 | 1 |
| Meg 24 hr LF166 | 30 | 19 | 1 |
| Meg 48 hr LF166 | 30 | 20 | 1 |
| Meg D6 LF166 | 28 | 20 | 4 |
| Meg D10 LF166 | 27 | 20 | 6 |
| Neut D0 LF141 | 27 | 19 | 4 |
| Neut 48 hr LF141 | 27 | 19 | 5 |
| Neut D6 LF141 | 26 | 19 | 10 |
| Neut D12 LF141 | 25 | 18 | 7 |
| Neut D0 LF144 | 29 | 22 | 7 |
| Neut 48 hr LF144 | 26 | 19 | 11 |
| Neut D6 LF144 | 28 | 21 | 5 |
| Neut D12 LF144 | 28 | 21 | 8 |
| NTC | 40 | 40 |  |

Human 14081

The present invention is based, in part, on the discovery of a serine protease, referred to herein as "14081". The transporter molecule of the invention shares characteristics with members of the trypsin-like family of serine proteases.

The human 14081 sequence (SEQ ID NO:20), which is approximately 980 nucleotides long including untranslated regions, contains a predicted methionine-initiated coding sequence of about 780 nucleotides, not including the termination codon (nucleotides 18-797 of SEQ ID NO:20; 1-780 of SEQ ID NO:22). The coding sequence encodes a 260 amino acid protein (SEQ ID NO:21).

Human 14081 contains the following regions or other structural features (for general information regarding PFAM identifiers, PS prefix and PF prefix domain identification numbers, refer to Sonnhammer et al. (1997) *Protein* 28:405-420 and a trypsin-like domain located at about amino acid nucleotides 4 to 242 of SEQ ID NO:21; two transmembrane domains (predicted 106 to 122 and 203 to 219 of SEQ ID NO:21; two protein kinase C phosphorylation sites (Prosite PS00005) located at about amino acids 158 to 160, and 177 to 179 of SEQ ID NO:21; three casein kinase II phosphorylation sites (Prosite PS00006) located at about amino acids 91 to 94, 135 to 138, and 218 to 221 of SEQ ID NO:21; two N-glycosylation sites (Prosite PS00001) located at about amino acids 25 to 28 and 49 to 52 of SEQ ID NO:21; and four N-myristoylation sites (Prosite PS00008) located at about amino acids 7 to 12, 26 to 31, 32 to 37, and 88 to 93 of SEQ ID NO:21.

A hydropathy plot of human 14081 was performed. Polypeptides of the invention include fragments which include: all or part of a hydrophobic sequence, e.g., the sequence from about amino acid 25 to 45 (a sequence that includes a glycosylation site at position 24 to 28), from about 52 to 62, from about 91 to 122, and from about 203 to 219 of SEQ ID NO:21; all or part of a hydrophilic sequence, e.g., the sequence from about amino acid 6 to 32, from about 131 to 146, from about 166 to 181, and from about 222 to 232 of SEQ ID NO:21.

Proteases are enzymes that cleave proteins at single, specific peptide bonds. Proteases can be classified into four generic classes; serine, thiol or cysteinyl, acid or aspartyl, and metalloproteases (Cuypers et al., *J. Biol. Chem.* 257:7086 (1982)). Proteases are essential to a variety of biological activities, such as digestion, formation and dissolution of blood clots, reproduction, cell growth, and the mounting of an immune reaction to foreign cells and organisms. Aberrant proteolysis is associated with a number of disease states in man and other mammals.

The serine proteases include enzymes such as elastase (human leukocyte), cathepsin G, plasmin, C-1 esterase, C-3 convertase, urokinase, plasminogen activator, acrosin, and kallikreins. The trypsin-like subclass of serine proteases include chymotrypsin, trypsin, thrombin, plasmin, Factor Xa. Certain trypsin-like proteases such as thrombin, plasmin, and Factor Xa, occupy a central role in hemostasis and thrombosis.

Homeostasis, the control of bleeding, is regulated by the physiological properties of vasoconstriction and coagulation. Under normal hemostatic circumstances, the body maintains an acute balance between clot formation and clot removal (fibrinolysis). The blood coagulation cascade involves the conversion of a variety of inactive enzymes (zymogens) into active enzymes which ultimately convert the soluble plasma protein fibrinogen into an insoluble matrix of highly cross-linked fibrin, Davie, E. J. et al., "The Coagulation Cascade: Initiation, Maintenance and Regulation," Biochemistry, 30, 10363-10370 (1991). The coagulation cascade is initiated with the activation of Factor X by activated Factor VII and Tissue Factor. Factor Xa and Factor VIIa are both trypsin-like serine proteases, which are involved in platelet activation and thrombus formation. In certain diseases of the cardiovascular system, deviations from normal hemostasis push the balance of clot formation and clot dissolution towards life-threatening thrombus formation when thrombi occlude blood flow in coronary vessels (myocardial infarctions) or limb and pulmonary veins (venous thrombosis).

Proteases are a major target for drug action and development. Accordingly, it is valuable to the field of pharmaceutical development to identify and characterize protease enzymes. The present invention advances the state of the art by providing a human serine protease. The invention further provides the opportunity to identify inhibitors and/or activators of a serine proteolytic enzyme, which may be useful in treating thrombosis-related and other serine protease-related disorders.

The 14081 protein contains a number of structural characteristics in common with members of the serine protease family. Among these characteristics are domains required for substrate binding, specificity, and catalysis. In particular serine proteases have a critical serine residue in the active site or catalytic domain of the enzyme that is required for catalysis. Typically, the catalytic domain has the consensus sequence -G-D-S-G-G-P-L- (SEQ ID NO:24) surrounding the active Ser residue.

As used herein, the term "serine protease" includes a protein or polypeptide that is capable of degrading protein, which has a serine residue at its catalytic center. A specific class of serine proteases, the trypsin-like serine proteases, share homology with the protease trypsin. Some trypsin-like serine proteases (e.g., trypsin, chymotrypsin, and elastase) are digestive enzymes that catalyze the breakdown of protein in food. Other trypsin-like serine proteases (e.g., thrombin, plasmin, factor Xa) participate in the regulation of the coagulation cascade to regulate homeostasis. Trypsin-like and other serine proteases differ in their protein specificity that is, each is active only against the peptide bonds in protein molecules that have carboxyl groups donated by certain amino acids. For the enzyme trypsin, these amino acids are arginine and lysine, for chymotrypsin they are tyrosine, phenylalanine, tryptophan, methionine, and leucine. Trypsin is the most discriminating of all the proteolytic enzymes in terms of the restricted number of chemical bonds that it will attack. Trypsin cleaves very specifically at R—X and K—X bonds. If X=P, no cleavage occurs.

Members of a serine protease family of proteins share a common catalytic mechanism characterized structurally by the possession of a reactive serine (Ser) residue that is essential for their enzymatic activity. Conserved histidine (His) (e.g., located anywhere from residues 41-46 of SEQ ID NO:21) and arginine (Arg) residues, which with Ser (located anywhere from residues 193-204 of SEQ ID NO:21) make up what is known as the catalytic triad, are also catalytically essential. The His and Ser residues are located at the substrate-binding site together with the conserved Asp, which is commonly buried in a solvent inaccessible pocket in a folded serine protease protein. Alignment among family members of the trypsin-like proteases (e.g., trypsin, chyrmotrypsin, bovine trypsin, and pocine elastase) shows that these enzymes are about 40% identical in their internal sequences, and their internal sequences are even more alike (Voet & Voet, Biochemistry, John Wiley & Sons, New York, N.Y. p. 373-382 (1990)).

A 14081 polypeptide can include a "serine protease domain" or regions homologous with a "serine protease domain". A 14081 polypeptide can further include a "trypsin-like serine protease domain" or regions homologous with a "trypsin-like serine protease domain." and at least one catalytic triad.

As used herein, the term "trypsin-like domain" includes an amino acid sequence of about 4 to 242 amino acid residues in length and having a bit score for the alignment of the sequence to the trypsin-like domain (HMM) of at least 280. Preferably a trypsin-like domain mediates proteolytic degradation of proteins and polypeptides. Preferably, a trypsin-like domain includes at least about 5 to 10 amino acids, more preferably about 10 to 100 amino acid residues, more preferably 100 to 200, or about 200 to 250 amino acids and has a bit score for the alignment of the sequence to the trypsin-like domain (HMM) of at least 50, more preferably 100, most preferably 200 or greater.

As mentioned above, the trypsin-like domain can include a trypsin-like catalytic domain having a catalytic triad. In the above conserved signature sequence, and other motifs or signature sequences described herein, the standard IUPAC one-letter code for the amino acids is used. Each element in the pattern is separated by a dash (-); square brackets ([ ]) indicate the particular residues that are accepted at that position; x indicates that any residue is accepted at that position;

and numbers in parentheses (( )) indicate the number of residues represented by the accompanying amino acid. The consensus sequence surrounding the active site of trypsin is -G-D-S-G-G-P-L- (SEQ ID NO:24) located about amino acids 197 to 203 of SEQ ID NO:21 of human 14081 polypeptide. The trypsin-like domain (amino acids 4 to 242 of SEQ ID NO:21) of human 14081 aligns with the trypsin consensus amino acid sequence (SEQ ID NO:23) derived from a hidden Markov model.

In a preferred embodiment, a 14081 polypeptide or protein has a "trypsin-like domain" or a region which includes at least about 5 to 10 more preferably about 100 to 200 or 200 to 250 amino acid residues and has at least about 60%, 70% 80% 90% 95%, 99%, or 100% homology with a "trypsin-like domain," e.g., the trypsin-like domain of human 14081 (e.g., residues 4 to 242 of SEQ ID NO:21).

To identify the presence of a "trypsin-like" domain in a 14081 protein sequence, and make the determination that a polypeptide or protein of interest has a particular profile, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28:405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of a "trypsin-like domain" domain in the amino acid sequence of human 14081 at about residues 4 to 242 of SEQ ID NO:21.

A 14081 polypeptide can include at least one, preferably two "transmembrane domains" or regions homologous with a "transmembrane domain". As used herein, the term "transmembrane domain" includes an amino acid sequence of about 10 to 40 amino acid residues in length and spans the plasma membrane. Transmembrane domains are rich in hydrophobic residues, e.g., at least 40%, 50%, 60%, 70%, 80%, 90%, 95% or more of the amino acids of a transmembrane domain are hydrophobic, e.g., leucines, isoleucines, tyrosines, or tryptophans. Transmembrane domains typically have alpha-helical structures and are described in, for example, Zagotta et al., (1996) *Annual Rev. Neurosci.* 19:235-263, the contents of which are incorporated herein by reference. The transmembrane domains of human 14081 are located at about residues 106 to 122 and about residues 203 to 219 of SEQ ID NO:21.

To identify the presence of a "transmembrane" domain in a 14081 protein sequence, and make the determination that a polypeptide or protein of interest has a particular profile, the amino acid sequence of the protein can be analyzed by a transmembrane prediction method that predicts the secondary structure and topology of integral membrane proteins based on the recognition of topological models (MEMSAT, Jones et al., (1994) *Biochemistry* 33:3038-3049).

A 14081 polypeptide can include at least one, preferably three "non-transmembrane regions." As used herein, the term "non-transmembrane region" includes an amino acid sequence not identified as a transmembrane domain. The non-transmembrane regions in 14081 are located at about amino acids 1 to 105, 123 to 202, and 220 to 260 of SEQ ID NO:21. The second non-transmembrane domain (amino acids 123 to 202) is predicted to be intracellular.

The non-transmembrane regions of 14081 include at least one cytoplasmic region. In one embodiment, a 14081 cytoplasmic region includes at least one, cytoplasmic loop. As used herein, the term "loop" includes an amino acid sequence which is not included within a phospholipid membrane, having a length of at least about 4, preferably about 5 to 30, more preferably about 6 to 60, most preferably 6 to 80 or more amino acid residues, and has an amino acid sequence that connects two transmembrane domains within a protein or polypeptide. Accordingly, the N-terminal amino acid of a loop is adjacent to a C-terminal amino acid of a transmembrane domain in a 14081 molecule, and the C-terminal amino acid of a loop is adjacent to an N-terminal amino acid of a transmembrane domain in a 14081 molecule. As used herein, a "cytoplasmic loop" includes a loop located inside of a cell or within the cytoplasm of a cell. For example, a "cytoplasmic loop" can be found at about amino acid residues 123 to 202 of SEQ ID NO:21.

In a preferred embodiment, a 14081 polypeptide or protein has a cytoplasmic loop or a region which includes at least about 4, preferably about 5 to 30, and more preferably about 6 to 60, most preferably 6 to 80 or more amino acid residues and has at least about 60%, 70% 80% 90% 95%, 99%, or 100% homology with a cytoplasmic loop," e.g., a cytoplasmic loop of human 14081 (e.g., residues 123 to 202 of SEQ ID NO:21).

In another embodiment, a 14081 non-transmembrane region includes at least one, two, preferably three non-cytoplasmic loops. As used herein, a "non-cytoplasmic loop" includes a loop located outside of a cell or within an intracellular organelle. Non-cytoplasmic loops include extracellular domains (i.e., outside of the cell) and intracellular domains (i.e., within the cell). When referring to membrane-bound proteins found in intracellular organelles (e.g., mitochondria, endoplasmic reticulum, peroxisomes microsomes, vesicles, endosomes, and lysosomes), non-cytoplasmic loops include those domains of the protein that reside in the lumen of the organelle or the matrix or the intermembrane space. For example, a "non-cytoplasmic loop" can be found at about amino acid residues 123 to 202 of SEQ ID NO:21.

In a preferred embodiment, a 14081 polypeptide or protein has at least one non-cytoplasmic loop or a region which includes at least about 4, preferably about 5 to 30, more preferably about 6 to 60 most preferably 6 to 80 or more amino acid residues and has at least about 60%, 70% 80% 90% 95%, 99%, or 100% homology with a "non-cytoplasmic loop," e.g., at least one non-cytoplasmic loop of human 14081 (e.g., residues 1 to 105, 123 to 202, and 220 to 260 of SEQ ID NO:21).

A human 14081 protein can further include at least one tyrosine kinase phosphorylation site (e.g., at residues 48 to 56 and 167 to 173) or an amidation site (e.g., at residues 189 to 192) or a glycosylation site (e.g., at residues 25 to 28 and 49 to 52) or a myristoylation site (e.g., at residues 7 to 12, 26 to 31, 32 to 37, and 88 to 93).

A 14081 family member can include at least one trypsin-like domains; and optionally a transmembrane or non-transmembrane domain. Furthermore, a 14081 family member can include at least one, preferably two protein kinase C phosphorylation sites (Prosite PS00005); at least one, two, and preferably three casein kinase II phosphorylation sites (Prosite PS00006); at least one, preferably two N-glycosylation sites (Prosite PS00001); and at least one, two, three, and preferably four N-myristoylation sites (Prosite PS00008).

As the 14081 polypeptides of the invention can modulate 14081-mediated activities, they can be useful for developing novel diagnostic and therapeutic agents for trypsin-like serine protease-associated or other 14081-associated disorders, as described below.

As used herein, a "serine protease-associated activity" includes an activity which involves "trypsin-like serine protease activity," which degrade proteins with varying specificity. Members of this family can play a role in diseases involving biological activities such as digestion formation and dissolution of blood clots, reproduction, cell growth, and the immune reaction to foreign cells and organisms. Such diseases include cardiovascular and non-cardiovascular diseases such as atherosclerosis, myocardial infarction, unstable angina, stroke, restenosis, deep vein thrombosis, disseminated intravascular coagulation caused by trauma, reperfusion damage, sepsis or tumor metastasis, hemodialysis, cardiopulmonary bypass surgery, atherectomy, arterial stent placement, adult respiratory distress syndrome, edotoxic shock, rheumatoid arthritis, ulcerative colitis, induration, metastasis, hypercoagulability during chemotherapy, adult respiratory distress syndrome, Alzheimer's disease, Parkinson's disease, Down's syndrome, inflammation such as edema, pancreatitis, and cancer.

As used herein, a "14081 activity", "biological activity of 14081" or "functional activity of 14081", refers to an activity exerted by a 14081 protein, polypeptide or nucleic acid molecule on e.g., a 14081-responsive cell or on a 14081 substrate, e.g., a protein substrate, as determined in vivo or in vitro. In one embodiment, a 14081 activity is a direct activity, such as an association with a 14081 target molecule. A "target molecule" or "binding partner" is a molecule with which a 14081 protein binds or interacts in nature. In an exemplary embodiment, 14081 is a receptor (or transporter or protease), e.g., a trypsin-like protease, and thus binds to or interacts in nature with a molecule (or protein substrate), e.g., an organic ion. (or signal peptide).

In an exemplary embodiment, 14081 is an enzyme for a protein or polypeptide substrate.

A 14081 activity can also be an indirect activity, e.g., a cellular signaling activity mediated by interaction of the 14081 protein with a 14081 receptor. Based on the above-described sequence structures and similarities to molecules of known function, the 14081 molecules of the present invention can have similar biological activities as trypsin-like serine protease family members. For example, the 14081 proteins of the present invention can have one or more of the following activities: (1) the ability to degrade proteins; and (2) the ability to phosphorylate carbohydrates. The ability to degrade proteins is based on the ability to bind, hydrolyze, and release a protein. The catalytic mechanism of serine proteases has been studies extensively. In general, to bind a molecule, the serine protease binds a protein substrate to form a Michaelis complex and the Ser residue nucleophilically attacks the scisslile peptide's carbonyl group to form a tetrahedral intermediate, wherein the Asp remains a carboxylate ion. The tetrahydral intermediate has a well defined, although transient existence. During the hydrolysis step, the tetrahedral intermediate decomposes to an acyl-enzyme intermediate under the driving force of proton domation from the His. The amine leaving group is released from the enzyme and replace by water from the solvent. The acyl-enzyme intermediate is extremely unstable to gydrolytic cleavage because of the enzyme's catalytic properties. Next, a deacylation step proceeds largely through the reversal of the previous steps with the release of the carboylate product (the new C-terminal portion of the cleaved polypeptide chain) and the concomitant regeneration of the enzyme.

The 14081 molecules of the invention can modulate the activities of cells in tissues where they are expressed. For example, TaqMan analysis shows that 14081 mRNA is expressed in hemangioma, kidney, pituitary, spinal cord, prostate tumor, human umbilical vein endothelial cells, hypothalamus, normal breast, bone marrow megakaryocytes, isolated CD61+ cells, brain cortex, tonsil, and platelets from patients with ischemic heart disease. Accordingly, the 14081 molecules of the invention can act as therapeutic or diagnostic agents for renal, hormonal, endocrine, neurological, hyperprolifereative, reproductive, breast, hematological and inflammatory disorders.

As a preferred embodiment, the 14081 molecules can be used to treat coagulation-related disorders in part because the 14081 mRNA is expressed in the platelets of patients with ischemic heart disease. In addition, 14081 levels are increased in samples from patients with coronary artery disease. Thus, the 14081 molecules can act as novel diagnostic targets and therapeutic agents for controlling one or more coagulation or other serine protease or trypsin-like serine protease disorders. As used herein, "serine protease disorders" or "trypsin-like serine protease disorders" are diseases or disorders whose pathogenesis is caused by, is related to, or is associated with aberrant or deficient serine protease or trypsin-like serine protease protein function or expression. Examples of such disorders, e.g., trypsin-like serine protease-associated or other 14081-associated disorders, include but are not limited to, cellular proliferative and/or differentiative disorders, disorders associated with metabolism (e.g., hormonal), immune e.g., inflammatory, disorders, cardiovascular disorders, endothelial cell disorders, renal disorders, neurological disorders, hyperprolifereative disorders, reproductive disorders, breast disorders, and hematological disorders.

The 14081 molecules can be used to treat cellular proliferative and/or differentiative disorders in part because trypsin-like serine protease family members are found in the prostate tumors. Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

The 14081 molecules can be used to treat immune disorders in part because trypsin-like serine protease family members are found in the bone marrow megakaryocytes, CD61+ cells, and platelets. More particularly, the 14081 nucleic acid and protein of the invention can be used to treat and/or diagnose a variety of immune, e.g., inflammatory, (e.g. respiratory inflammatory) disorders, as described herein.

The 14081 molecules can be used to treat cardiovascular disorders in part because trypsin-like serine protease family members are found in the platelets and participate in platelet activation and thrombus formation. In addition, 14081 levels are increased in samples from patients with coronary artery disease. 14081 may cleave and activate channels regulating platelet function. Antagonizing 14081 will block platelet activation.

The 14081 molecules can be used to treat endothelial cell disorders in part because trypsin-like serine protease family members are found in the human umbilical endothelial cells.

The 14081 molecules can be used to treat metabolic disorders in part because trypsin-like serine protease family members are found in the pituitary gland. 14081 can play an important role in the regulation of metabolism or pain disorders.

Human 32140

The present invention is based, in part, on the discovery of a novel human aldehyde dehydrogenase, referred to herein as "32140".

The human 32140 sequence (SEQ ID NO:25), which is approximately 7220 nucleotides long including untranslated regions, contains a predicted methionine-initiated coding sequence of about 2769 nucleotides (nucleotides 129-2897 of SEQ ID NO:25; nucleotides 1-2769 of SEQ ID NO:27), not including the terminal codon. The coding sequence encodes a 923 amino acid protein (SEQ ID NO:26).

Human 32140 contains the following regions: a predicted aldehyde dehydrogenase domain (PFAM Accession PF00171) located at about amino acid residues 450-923 of SEQ ID NO:26, and a predicted formyl transferase (PFAM Accession PF00551) located at about amino acid residues 23-202 of SEQ ID NO:26.

The 32140 protein also includes the following domains: a "10-formyltetrahydrofolate dehydrogenase domain" at about amino acid residues 265-336 of SEQ ID NO:26, and a "formyltransferase/methyltransferase domain" at about amino acid residues 211-328 of SEQ ID NO:26.

For general information regarding PFAM identifiers, PS prefix and PF prefix domain identification numbers, refer to Sonnhammer et al. (1997) *Protein* 28:405-420.

A plasmid containing the nucleotide sequence encoding human 32140 was deposited with American Type Culture Collection (ATCC), 10801 University Boulevard, Manassas, Va. 20110-2209, on Jun. 1, 2001 and assigned Accession Number PTA-3424. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The 32140 protein contains a significant number of structural characteristics in common with members of the aldehyde dehydrogenase family. As used herein, the term "aldehyde dehydrogenase" refers to a protein or polypeptide which is capable of catalyzing an aldehyde oxidation reaction. Aldehyde dehydrogenases can have a specificity for various aldehyde precursors. An aldehyde dehydrogenase polypeptide typically includes a region of sequence similarity that comprises both the NAD+/NADP binding site and the enzyme active site (Vasiliou et al., (1999) *Pharmacogenetics* 9:421-434). This region of sequence similarity is located at about amino acids 669-728 of SEQ ID NO:26. The 32140 polypeptide exhibits sequence identity with the aldehyde dehydrogenase family at four key amino acid residues that have been shown to be important for aldehyde dehydrogenase function, including a glutamate involved in catalytic activity (amino acid 694 of SEQ ID NO:26), a cysteine involved in substrate binding (amino acid 728 of SEQ ID NO:26), and two glycines involved in $NAD^+$ or NADP binding (amino acids 671 and 676 of SEQ ID NO:26).

Typically, aldehyde dehydrogenases play a role in a wide variety of cellular processes. For example, the metabolism of many amino acids, fatty acids, and glycerolipids, as well as ascorbate, aldarate, butanoate, pyruvate, propanoate, and 4-aminobutyric acid (GABA), involves specific oxidation reactions catalyzed by aldehyde dehydrogenases. Aldehyde dehydrogenases also participate in retinoid signaling, catalyzing the oxidation of retinal (which is required for vision) to retinoic acid (which plays an important role as a signaling molecule in embryonic differentiation) (reviewed by Duester, in *Enzymology and Molecular Biology of Carbonyl Metabolism*, Keuwer Academic/Plenum Publishers, 1989). Thus, the molecules of the present invention may be involved in one or more of: 1) the oxidation of an aldehyde; 2) the modulation of amino acid metabolism; 3) the modulation of fatty acid or glycerophospholipid metabolism; 4) the modulation of retinoic acid signaling; 5) the modulation of cell differentiation; 6) the modulation of vision; 7) the modulation of 4-aminobutyric acid (GABA) metabolism; 8) the modulation of the metabolism of drugs or environmental agents; 9) the modulation of alcohol metabolism; 10) the modulation of tumor cell growth and invasion; or 11) the modulation of vitamin metabolism.

A 32140 polypeptide can include an "aldehyde dehydrogenase domain" or regions homologous with an "aldehyde dehydrogenase domain". As used herein, the term "aldehyde dehydrogenase domain" includes an amino acid sequence of about 80-300 amino acid residues in length and having a bit score for the alignment of the sequence to the aldehyde dehydrogenase domain (HMM) of at least 8. Preferably, an aldehyde dehydrogenase domain includes at least about 100-250 amino acids, more preferably about 130-200 amino acid residues, or about 160-200 amino acids and has a bit score for the alignment of the sequence to the aldehyde dehydrogenase domain (HMM) of at least 16 or greater. The aldehyde dehydrogenase domain (HMM) has been assigned the PFAM Accession PF00171. The aldehyde dehydrogenase domain (amino acids 450-923 of SEQ ID NO:26) of human 32140 aligns with a consensus amino acid sequence derived from a hidden Markov model (SEQ ID NO:28).

In a preferred embodiment, 32140 polypeptide or protein has a "aldehyde dehydrogenase domain" or a region which includes at least about 100-250 more preferably about 130-200 or 160-200 amino acid residues and has at least about 60%, 70%, 80%, 90%, 95%, 99%, or 100% homology with an "aldehyde dehydrogenase domain," e.g., the aldehyde dehydrogenase domain of human 32140 (e.g., amino acid residues 450-923 of SEQ ID NO:26).

To identify the presence of an "aldehyde dehydrogenase" domain in a 32140 protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al., (1997) *Proteins* 28(3):405-420 and a detailed description of HMMs can be found, for example, in Gribskov et al., (1990) *Meth. Enzymol.* 183:146-159; Gribskov et al., (1987) *Proc. Natl. Acad. Sci. USA* 84:4355-4358; Krogh et al., (1994) *J. Mol. Biol.* 235:1501-1531; and Stultz et al., (1993) *Protein Sci.* 2:305-314, the contents of which are incorporated herein by reference.

As the 32140 polypeptides of the invention may modulate 32140-mediated activities, they may be useful for developing novel diagnostic and therapeutic agents for 32140-mediated or related disorders, as described below.

As used herein, a "32140 activity", "biological activity of 32140" or "functional activity of 32140", refers to an activity exerted by a 32140 protein, polypeptide or nucleic acid molecule on e.g., a 32140-responsive cell or on a 32140 substrate, e.g., a lipid or protein substrate, as determined in vivo or in vitro. In one embodiment, a 32140 activity is a direct activity, such as an association with a 32140 target molecule. A "target molecule" or "binding partner" is a molecule with which a 32140 protein binds or interacts in nature, e.g., an aldehyde, which the 32140 protein oxidizes. A 32140 activity can also be an indirect activity, e.g., a cellular signaling activity mediated by interaction of the 32140 protein with a 32140 ligand. For example, the 32140 proteins of the present invention can have one or more of the following activities: 1) the oxidation of an aldehyde; 2) the modulation of amino acid metabolism; 3) the modulation of fatty acid or glycerophospholipid metabolism; 4) the modulation of retionic acid signaling; 5) the modulation of cell differentiation; 6) the modulation of vision; 7) the modulation of 4-aminobutyric acid (GABA) metabolism; 8) the modulation of the metabolism of drugs or environmental agents; 9) the modulation of alcohol metabolism; 10) the modulation of tumor cell growth and invasion; or 11) the modulation of vitamin metabolism. 12) the ability to antagonize or inhibit, competitively or non-competitively, any of 1-11.

Accordingly, 32140 protein may mediate various disorders, including cellular proliferative and/or differentiative disorders, lung disorders, liver disorders, brain disorders, heart disorders, kidney disorders, breast disorders, and testis disorders.

The 32140 nucleic acid and protein of the invention can be used to treat and/or diagnose a variety of proliferative disorders.

The 32140 gene appears to have an important role in viral pathogenesis. In particular, Herpes Simples Virus (HSV) induces expression of the novel 10-formyltetrahydrofolate DH encoded by the gene 32140, particularly in infected neurons. Viral panels have shown that 32140 is induced in HSV-infected mouse ganglia both during active and latent phases. It is induced up to 5-fold in HSV-infected neuroblastoma (Ntera2). 32140 appears to be a 10-formyltetrahydrofolate DH isozyme which is expressed in different tissues (e.g. neuronal tissues) compared to the known 10-formyltetrahydrofolate DH. The 32140 aldehyde dehydrogenase is therefore an important host gene for HSV infection and finds use in the treatment of disorders resulting from Herpes Simples Virus (HSV) and hepatitis B infection. Also, gene 32140 is induced during infection by HSV, but not infection with other viruses such as VZV, HBV, and HCV.

Gene Expression Analysis of 32140

TaqMan analysis shows 32140 was expressed in different cells: normal or uninfected liver; uninfected ganglia and ganglia infected with Herpes Simplex Virus; a time course of HSV (strain 17+) infection of human Ntera2 neuroblastoma cells (times are 0, 2.5, 5, and 7 hours post-infection); same infection experiment using HSV strain KOS; a time course of Varicella Zoster virus (VZV) infected human MRC5 (lung fibroblast cells) (times are 0, 18 and 72 hours post-infection); and Ntera2 cells infected with an adenovirus that expresses the HSV ICPO transcription factor.

TaqMan analysis also shows 32140 was expressed in different tissues: "normal" liver, lung and kidney tissue; uninfected ganglia and ganglia infected with Herpes Simplex Virus; HSV (strain 17+) infection of human Ntera2 neuroblastoma cells (times are 0, 2.5, 5, and 7 hours post-infection); a time course of Varicella Zoster virus (VZV) infected human MRC5 (lung fibroblast cells) (times are 0, 18 and 72 hours post-infection); Ntera2 cells infected with an adenovirus that expresses the HSV ICPO transcription factor; hepatitis B virus (HBV) expressing HepG2.2.15 cells compared to the parental HepG2 cell control; and HBV-infected and hepatitis C virus (HCV)-infected liver samples.

Gene 32140 is highly expressed in salivary glands and testes, more moderately expressed in brain, small intestine, stomach, spinal cord, and dorsal root ganglia, and it is expressed at lower levels in the other tissues indicated.

Human 50352

The present invention is based, in part, on the discovery of a novel ubiquitin-protein ligase family member, referred to herein as "50352".

The human 50352 sequence (SEQ ID NO:29), which is approximately 3513 nucleotides long including untranslated regions, contains a predicted methionine-initiated coding sequence of about 3066 nucleotides, not including the termination codon (nucleotides 82-3147 of SEQ ID NO:29; 1-3066 of SEQ ID NO:31). The coding sequence encodes a 1022 amino acid protein (SEQ ID NO:30).

Human 50352 contains the following regions or other structural features (for general information regarding PFAM identifiers, PS prefix and PF prefix domain identification numbers, refer to Sonnhammer et al. (1997) *Protein* 28:405-420:

One, two, three, preferably four and most preferably five or more regulator of chromosome condensation domain(s) (PFAM Accession Number PF00415; SEQ ID NO:32) located at about amino acid residues 43 to 92, from about residues 93 to 145, from about residues 146 to 198, from about residues 200 to 253 and from about residues 254 to 304 of SEQ ID NO:30; a homologous to the E6-AP carboxyl terminus domain (PFAM Accession Number PF00632; SEQ ID NO:33) located at about amino acid residues 726 to 1015 of SEQ ID NO:30; a conjugation ubiquitin cyclin KIAA0032 binding CG9153 cyclin E domain (Propom Accession Number PD136613) located at about amino acids 374 to 645 of SEQ ID NO:30; a ligase ubiquitin conjugation ubiquitin-protein 6.3.2 domain (ProDom Accession Number PD255820) located at about amino acids 758 to 811 of SEQ ID NO:30; a ligase ubiquitin conjugation 6.3.2 domain (ProDom Accession Number PD002225) located at about amino acids 836 to 1013 of SEQ ID NO:30; fourteen protein kinase C phosphorylation sites (Prosite PS00005) located at about amino acids 118 to 120, 216 to 218, 224 to 226, 319 to 321, 368 to 370, 443 to 445, 448 to 450, 647 to 649, 669 to 671, 801 to 803, 850 to 852, 867 to 869, 951 to 953, and 975 to 977 of SEQ ID NO:30; twenty five casein kinase II phosphorylation sites (Prosite PS00006) located at about amino acids 46 to 49, 124 to 127, 242 to 245, 259 to 262, 290 to 293, 323 to 326, 339 to 342, 362 to 365, 375 to 378, 385 to 388, 398 to 401, 431 to 434, 448 to 451, 459 to 462, 550 to 553, 690 to 693, 729 to 732, 793 to 796, 807 to 810, 904 to 907, 915 to 918, 939 to 942, 951 to 954, 973 to 976, and 995 to 998 of SEQ ID NO:30; four cAMP/cGMP-dependent protein kinase phosphorylation sites (Prosite PS00004) located at about amino acids 14 to 17, 394 to 397, 424 to 427, and 445 to 448 of SEQ ID NO:30; two N-glycosylation sites (Prosite PS00001) located at about amino acids 263 to 266 and 865 to 868 of SEQ ID NO:30; thirteen N-myristoylation sites (Prosite PS00008) located at about amino acids 19 to 24, 59 to 64, 180 to 185, 189 to 194, 200 to 205, 206 to 211, 231 to 236, 295 to 300, 307 to 312, 354 to 359, 426 to 431, 714 to 719, and 762 to 767 of SEQ ID NO:30; one tyrosine kinase phosphorylation site (Prosite PS00007) located at about amino acids 750 to 758 of SEQ ID NO:30; one amidation site (Prosite PS00009) located at about amino acids 55 to 58 of SEQ ID NO:30; and one, two, three, preferably four and most preferably five regulator of chromosome condensation signature 2 domain(s) (Prosite PS00626) located at about amino acids 28 to 38, 80 to 90, 133 to 143, 186 to 196, and 241 to 251 of SEQ ID NO:30.

A hydropathy plot of human 50352 was performed. Polypeptides of the invention include fragments which include: all or part of a hydrophobic sequence, e.g., the sequence from about amino acid 71 to 81, from about 411 to 421, from about 475 to 490, from about 500 to 510, from about 532 to 544, from about 615 to 631, from about 695 to 705, and from about 761 to 772 of SEQ ID NO:30; all or part of a hydrophilic sequence, e.g., the sequence from about amino acid 5 to 20, from about 48 to 63, from about 261 to 280, from about 312 to 325, from about 392 to 403, from about 439 to 451, from about 551 to 560, from about 660 to 670, from about 749 to 757, from about 851 to 861, and from about 903 to 928 of SEQ ID NO:30; a sequence which includes a Cys, or a glycosylation site.

The 50352 protein contains a significant number of structural characteristics in common with members of the ubiquitin-protein ligase family.

As used herein, the term "ubiquitin-protein ligase" includes a protein or polypeptide which is capable of conjugating ubiquitin molecules to either substrates or to ubiquitin moieties bound to substrates deemed for degradation. Ubiquitin-protein ligases are responsible for the third and final step of ubiquitin conjugation, they accept ubiquitin from an E2 ubiquitin-conjugated enzyme in the form of a thioester and then transfer the ubiquitin to a target protein by forming an isopeptide bond between glycine residues of ubiquitin and an alpha amino group of a lysine residue of the substrate or of a previously conjugated ubiquitin. Ubiquitin-protein ligases are also responsible in determining the specificity of ubiquitination. Members of the ubiquitin-protein ligase family of proteins share a region of similarity known as the homologous to the E6-AP carboxyl terminus domain. This domain is composed of approximately 350 amino acids and it has a conserved cysteine residue located in the last 32 to 46 amino acids which is necessary for the ubiquitin thioester formation.

In one embodiment of the invention, a 50352 polypeptide includes at least one, two, three, preferably four and most preferably five or more regulator of chromosome condensation domain.

In another embodiment of the invention, a 50352 polypeptide includes at least one "homologous to the E6-AP carboxyl terminus" domain.

A 50352 polypeptide can include a "homologous to the E6-AP carboxyl terminus domain" or regions homologous with a "homologous to the E6-AP carboxyl terminus domain". A 50352 polypeptide can further include one, two, three, preferably four, and most preferably five or more "regulator of chromosome condensation domain(s)" or regions homologous with a "regulator of chromosome condensation domain".

As used herein, the term "homologous to the E6-AP carboxyl terminus domain" includes an amino acid sequence of about 250 to 350 amino acid residues in length and having a bit score for the alignment of the sequence to the homologous to the E6-AP carboxyl terminus domain (HMM) of at least 110.9. Preferably a homologous to the E6-AP carboxyl terminus domain mediates ubiquitin conjugation and specificity of ubiquitin conjugation to substrates or ubiquitin moieties bound to substrates. Preferably, a homologous to the E6-AP carboxyl terminus domain includes at least about 200 to 400 amino acids, more preferably about 225 to 375 amino acid residues, or about 250 to 350 amino acids and has a bit score for the alignment of the sequence to the homologous to the E6-AP carboxyl terminus domain (HMM) of at least 80, 90, 100, 110 or greater.

In a preferred embodiment, a 50352 polypeptide or protein has a "homologous to the E6-AP carboxyl terminus domain" or a region which includes at least about 200 to 400 more preferably about 225 to 375 or 250 to 350 amino acid residues and has at least about 60%, 70% 80% 90% 95%, 99%, or 100% homology with a "homologous to the E6-AP carboxyl terminus domain," e.g., the homologous to the E6-AP carboxyl terminus domain of human 50352 (e.g., residues 726 to 1015 of SEQ ID NO:30).

To identify the presence of a "homologous to the E6-AP carboxyl terminus domain" in a 50352 protein sequence, and make the determination that a polypeptide or protein of interest has a particular profile, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28:405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of a "homologous to the E6-AP carboxyl terminus domain" in the amino acid sequence of human 50352 at about residues 726 to 1015 of SEQ ID NO:30.

A 50352 molecule can further include one, two, three, preferably four, and most preferably five or more "regulator of chromosome condensation domain(s)". As used herein, the term "regulator of chromosome condensation domain" includes amino acid sequence(s) of about 40 to 60 amino acid residues in length and having a bit score for the alignment of the sequence to the regulator of chromosome condensation domain (HMM) of at least 30. Preferably, regulator of chromosome condensation domain(s) include at least about 20 to 80 amino acids, more preferably about 30 to 70 amino acid residues, or about 40 to 60 amino acids and have a bit scores for the alignment of the sequences to the regulator of chromosome condensation domain(s) (HMM) of at least 5, 10, 20, 30 or greater.

Regulator of chromosome condensation domains typically contain a conserved regulator of chromosome condensation signature 2 (RCC1_2) pattern which participates in the catalytic mechanism. The conserved RCC1_2 pattern is as follows: [LIVMFA]-[STAGC](2)-G-X(2)-H-[STAGLI]-[LIVMFA]-X-[LIVM] (SEQ ID NO:34).

In the above conserved signature sequence, and other motifs or signature sequences described herein, the standard IUPAC one-letter code for the amino acids is used. Each element in the pattern is separated by a dash (-); square brackets ([ ]) indicate the particular residues that are accepted at that position; x indicates that any residue is accepted at that position; and numbers in parentheses (( )) indicate the number of residues represented by the accompanying amino acid.

A 50352 protein contains one, two, three, preferably four, and most preferably five or greater RCC1_2 pattern(s) at about amino acid residues 28 to 38, 80 to 90, 133 to 143, 186 to 196, and 241 to 251 of SEQ ID NO:30.

In a preferred embodiment, a 50352 polypeptide or protein has one, two, three, preferably four and most preferably five or greater "regulator of chromosome condensation domain(s)" or one, two, three, preferably four and most preferably five or more region(s) which includes at least about 20 to 80 more preferably about 30 to 40 or 40 to 60 amino acid residues and has at least about 60%, 70% 80% 90% 95%, 99%, or 100% homology with a "regulator of chromosome condensation domain," e.g., the regulator of chromosome condensation domain of human 50352 (e.g., residues 43 to 92, 93 to 145, 146 to 198, 200 to 253, and 254 to 304 of SEQ ID NO:30).

To identify the presence of a "regulator of chromosome condensation domain" in a 50352 protein sequence, and make the determination that a polypeptide or protein of interest has a particular profile, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28:405-420 and a detailed description of HMMs can be found, for example, in Gribskov et al. (1990) *Meth. Enzymol* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of five "regulator of chromosome condensation domains" in the amino acid sequence of human 50352 at about residues 43 to 92, 93 to 145, 146 to 198, 200 to 253, and 254 to 304 of SEQ ID NO:30.

For further identification of domains, and make the determination that a polypeptide or protein of interest has a particular profile, the amino acid sequence of the protein can be searched against a database of domains, e.g., the Propom database (Corpet et al. (1999), *Nucl. Acids Res.* 27:263-267). The Propom protein domain database consists of an automatic compilation of homologous domains. Current versions of Propom are built using recursive PSI-BLAST searches (Altschul et al. (1997) *Nucleic Acids Res.* 25:3389-3402; Gouzy et al. (1999) *Computers and Chemistry* 23:333-340) of the SWISS-PROT 38 and TREMBL protein databases. The database automatically generates a consensus sequence for each domain. A BLAST search was performed against the HMM database resulting in the identification of a "conjugation ubiquitin cyclin KIAA0032 binding CG9153 cyclin E" domain in the amino acid sequence of human 50352 at about residues 374 to 645 of SEQ ID NO:30, and two "ligase ubiquitin conjugation ubiquitin-protein 6.3.2" domains in the amino acid sequence of human 50352 at about residues 758 to 811 and 836 to 1013 of SEQ ID NO:30.

A 50352 family member can include at least one homologous to the E6-AP carboxyl terminus domain and at least one, two, three, preferably four, and most preferably five or greater regulator of chromosome condensation domain(s). Furthermore, a 50352 family member can include at least one, two, three, four, five, six, seven, eight, nine, ten, eleven, twelve, thirteen, and preferably fourteen protein kinase C phosphorylation sites (Prosite PS00005); at least one, two, three, four, five, six, seven, eight, nine, ten, eleven, twelve, thirteen, fourteen, fifteen, sixteen, seventeen, eighteen, nineteen, twenty, twenty one, twenty two, twenty three, twenty four, and preferably twenty five casein kinase II phosphorylation sites (Prosite PS00006); at least one, preferably two N-glycosylation sites (Prosite PS00001); at least one, two, three, and preferably four cAMP/cGMP protein kinase phosphorylation sites (Prosite PS00004); at least one tyrosine kinase phosphorylation site (Prosite PS00007); at least one amidation site (Prosite PS00009); at least one, two, three, four, five, six, seven, eight, nine, ten, eleven, twelve, and preferably thirteen N-myristoylation sites (Prosite PS00008); at least one conjugation ubiquitin cyclin KIAA0032 binding CG9153 cyclin E domain (Propom Accession Number PD136613); at least one ligase ubiquitin conjugation ubiquitin-protein 6.3.2 domain (Propom Accession Number PD255820); and at least one ligase ubiquitin conjugation 6.3.2 domain (Propom Accession Number PD002225).

As the 50352 polypeptides of the invention can modulate 50352-mediated activities, they can be useful for developing novel diagnostic and therapeutic agents for ubiquitin-protein ligase-associated or other 50352-associated disorders, as described below.

Ubiquitin mediated intracellular proteolysis is essential for cell viability. Abnormalities within the ubiquitin pathway, either with ubiquitin-protein ligases or with de-ubiquitinating enzymes, cause problems with substrate recognition or supply of free ubiquitin, respectively. Such abnormalities can lead to or contribute to disease pathogenesis, such as human neurodegenerative diseases. Layfield et al., (2001) *Neuropathol Appl Neurobiol* 27(3):171-179.

As used herein, a "ubiquitin-protein ligase-mediated activity" includes an activity which involves the addition of ubiquitin to either substrates or ubiquitin moieties bound to substrates. This activity involves both the recognition of substrate specificity as well as the creation of an isopeptide bond between glycine residues of ubiquitin and an alpha amino group of a lysine residue of the substrate or of a previously conjugated ubiquitin. Therefore, these enzymes are responsible for recognizing proteins which need to undergo intracellular proteolysis as well as for the attachment of ubiquitin molecules to such proteins deemed for degradation.

As used herein, a "50352 activity", "biological activity of 50352" or "functional activity of 50352", refers to an activity exerted by a 50352 protein, polypeptide or nucleic acid molecule on e.g., a 50352-responsive cell or on a 50352 substrate, e.g., a protein substrate, as determined in vivo or in vitro. In one embodiment, a 50352 activity is a direct activity, such as an association with a 50352 target molecule. A "target molecule" or "binding partner" is a molecule with which a 50352 protein binds or interacts in nature. A 50352 activity can also be an indirect activity, e.g., a cellular signaling activity mediated by interaction of the 50352 protein with a 50352 receptor.

Based on the above-described sequence structures and similarities to molecules of known function, the 50352 molecules of the present invention can have similar biological activities as ubiquitin-protein ligase family members. For example, the 50352 proteins of the present invention can have one or more of the following activities: (1) the ability to modulate ubiquitination of a substrate, e.g., a protein targeted for degradation; (2) the ability to modulate substrate specificity for ubiquitination; (3) the ability to modulate cellular proliferation and/or differentiation; (4) the ability to modulate apoptosis; (5) the ability to modulate transcription and/or cell-cycle progression; (6) the ability to modulate signal-transduction; (7) the ability to modulate antigen processing; (8) the ability to modulate cell-cell adhesion; (9) the ability to modulate receptor-mediated endocytosis; (10) the ability to modulate organelle biogenesis and development; (11) the ability to modulate neuropathological conditions; (12) the ability to modulate oncogenesis, and (13) the ability to modulate protein levels, e.g., cellular protein levels.

The 50352 molecules of the invention can modulate the activities of cells in tissues where they are expressed. For example, 50352 mRNA is expressed in human umbilical vain endothelial cells, in human normal brain cortex, in human colon tumors and in human lung tumors. Accordingly, the 50352 molecules of the invention can act as therapeutic or diagnostic agents for cardiovascular, colon, lung and neurological disorders.

Thus, the 50352 molecules can act as novel diagnostic targets and therapeutic agents for controlling one or more ubiquitin-protein ligase-associated or other 50352-associated disorders. As used herein, "ubiquitin-protein ligase disorders" are diseases or disorders whose pathogenesis is caused by, is related to, or is associated with aberrant or deficient ubiquitin-protein ligase function or expression. The 50352 molecules can be used to treat neurological disorders in part because the 50352 mRNA is expressed in the brain.

The 50352 molecules can also be used to treat cardiovascular disorders in part because the 50352 mRNA is expressed in human umbilical vein endothelial cells.

The 50352 molecules can also be used to treat colon disorders in part because the 50352 mRNA is expressed in human colon tumors.

The 50352 molecules can also be used to treat lung disorders in part because the 50352 mRNA is expressed in human lung tumors.

The 50352 molecules and modulators thereof can act as novel therapeutic agents for controlling one or more of cellular proliferative and/or differentiative disorders, hormonal disorders, immune and inflammatory disorders, neurological disorders, blood vessel disorders, platelet disorders, cardiovascular disorders, endothelial cell disorders, liver disorders, viral diseases, pain or metabolic disorders.

Isolation of 50352

Total RNA was prepared from various human tissues by a single step extraction method using RNA STAT-60 according to the manufacturer's instructions (TelTest, Inc). Each RNA preparation was treated with DNase I (Ambion) at 37° C. for 1 hour. DNAse I treatment was determined to be complete if the sample required at least 38 PCR amplification cycles to reach a threshold level of fluorescence using β-2 microglobulin as an internal amplicon reference. The integrity of the RNA samples following DNase I treatment was confirmed by agarose gel electrophoresis and ethidium bromide staining. After phenol extraction cDNA was prepared from the sample using the SUPERSCRIPT™ Choice System following the manufacturer's instructions (GibcoBRL). A negative control of RNA without reverse transcriptase was mock reverse transcribed for each RNA sample.

Gene Expression of 50352

TaqMan analysis results indicate significant 50352 expression in human umbilical vein endothelial cells, in normal human brain cortex, in lung tumors and in colon tumors.

Human 16658

The present invention is based, in part, on the discovery of a novel human kinase, referred to herein as "16658".

The human 16658 sequence (SEQ ID NO:35), which is approximately 3633 nucleotides long including untranslated regions, contains a predicted methionine-initiated coding sequence of about 3390 nucleotides (nucleotides 23-3412 of SEQ ID NO:35; 1-3390 of SEQ ID NO:37), not including the terminal codon. The coding sequence encodes a 1130 amino acid protein (SEQ ID NO:36).

This mature protein form is approximately 1130 amino acid residues in length (from about amino acid 1 to amino acid 1130 of SEQ ID NO:36). Human 16658 contains the following regions or other structural features: a predicted kinase domain located at about amino acid residues 725-1021 of SEQ ID NO:36; and predicted transmembrane domains which extend from about amino acids 103-119 and 642-665 of SEQ ID NO:36.

A hydropathy plot of human 16658 was performed. Polypeptides of the invention include fragments which include: all or part of a hydrophobic sequence, e.g., the sequence from about amino acid 100 to 120, from about 280 to 290, and from about 985 to 650 of SEQ ID NO:36; all or part of a hydrophilic sequence, the sequence from about amino acid 50 to 80, from about 620 to 640, and from about 680 to 690 of SEQ ID NO:36; a sequence which includes a Cys, or a glycosylation site.

The mature human 16658 protein contains the following structural features: two predicted transmembrane domains located at about amino acids 103-119 and 642-665 of SEQ ID NO:36. Predicted transmembrane domains extend from about amino acid 103 (cytoplasmic end) to about amino acid 119 (extracellular end) of SEQ ID NO:36; and from about amino acid 642 (extracellular end) to about amino acid 665 (cytoplasmic end); one extracellular loop found at about amino acid 120-641 of SEQ ID NO:36; one N-terminal cytoplasmic domain is found at about amino acid residues 1-102 of SEQ ID NO:36; and a C-terminal cytoplasmic domain is found at about amino acid residues 666-1130 of SEQ ID NO:36.

The 16658 protein also includes the following domains: four N-glycosylation sites (PS00001) located at about amino acids 437-440, 491-494, 504-507, and 850-853 of SEQ ID NO:36; one cAMP- and cGMP-dependent protein kinase phosphorylation site (PS00004) located at about amino acids 945-948 of SEQ ID NO:36; sixteen predicted protein kinase C phosphorylation sites (PS00005) located at about amino acids 40-42, 83-85, 201-203, 214-216, 293-295, 304-306, 339-341, 521-523, 586-588, 621-623, 666-668, 741-743, 758-760, 794-796, 1066-1068, and 1115-1117 of SEQ ID NO:36; twenty-seven predicted casein kinase II phosphorylation sites (PS00006) located at about amino 19-22, 83-86, 155-158, 201-204, 214-217, 240-243, 252-255, 322-325, 333-336, 361-364, 396-399, 471-474, 532-535, 628-631, 699-702, 705-708, 937-940, 949-952, 965-968, 975-978, 982-985, 1022-1025, 1036-1039, 1047-1050, 1059-1062, 1082-1085, and 1091-1094 of SEQ ID NO:36; three predicted tyrosine kinase phosphorylation sites (PS00007) located at about amino acids 577-584, 698-706, and 881-888 of SEQ ID NO:36; eleven predicted N-myristoylation sites (PS00008) located at about amino acids 47-52, 286-291, 368-373, 383-388, 467-472, 488-493, 598-603, 851-856, 871-876, 994-999, and 1070-1075 of SEQ ID NO:36; two predicted amidation site (PS00009) located at about amino acids 452-455 and 747-750 of SEQ ID NO:36; one predicted protein kinases ATP-binding region signature site (PS00107) located at about amino acids 731-739 of SEQ ID NO:36; one tyrosine protein kinase specific active-site sign (PS00109) located at about amino acids 888-900 of SEQ ID NO:36; and one receptor tyrosine kinase class V signature 1 site (PS00790) located at about amino acids 286-302 of SEQ ID NO:36.

For general information regarding PFAM identifiers, PS prefix and PF prefix domain identification numbers, refer to Sonnhammer et al. (1997) *Protein* 28:405-420. The ephrin receptor ligand binding domain of human 16658 (amino acids 128 to 301 of SEQ ID NO:36) aligns with a consensus amino acid sequence derived from a hidden Markov model (HMM) from PFAM (SEQ ID NO:44).

The protein kinase domain of human 16658 (amino acids 725 to 1021 of SEQ ID NO:36) aligns with a consensus amino acid sequence derived from a hidden Markov model (HMM) from PFAM (SEQ ID NO:45).

A BLAST alignment of human 16658 with a consensus amino acid sequence derived from a Propomain "receptor kinase tyrosine-protein ephrin precursor transferase ATP-binding phosphorylation type-A transmembrane" (Release 2001.1) shows amino acid residues 1 to 180 of the 181 amino acid consensus sequence (SEQ ID NO:46) aligns with the "receptor kinase tyrosine-protein ephrin precursor transferase ATP-binding phosphorylation type-A transmembrane" domain of human 16658, amino acid residues 128 to 301 of SEQ ID NO:36.

Another BLAST alignment of human 16658 with a consensus amino acid sequence derived from a Propomain "receptor kinase tyrosine-protein precursor ephrin transferase ATP-binding phosphorylation type-A transmembrane" (Release 2001.1) shows amino acid residues 1 to 127 of the 128 amino acid consensus sequence (SEQ ID NO:47) aligns with the "receptor kinase tyrosine-protein precursor ephrin transferase ATP-binding phosphorylation type-A transmembrane" domain of human 16658, amino acid residues 411 to 534 of SEQ ID NO:36.

Another BLAST alignment of human 16658 with a consensus amino acid sequence derived from a Propomain "receptor tyrosine-protein kinase transm precursor ephrin EHK-2 kinase-2 type-A phosphorylation" (Release 2001.1) shows amino acid residues 1 to 50 of the 50 amino acid consensus sequence (SEQ ID NO:48) aligns with the "receptor tyrosine-protein kinase transm precursor ephrin EHK-2 kinase-2 type-A phosphorylation" domain of human 16658, amino acid residues 790 to 839 of SEQ ID NO:36.

A BLAST alignment of human 16658 with a consensus amino acid sequence derived from a Propomain "receptor kinase tyrosine-protein precursor ephrin ATP-binding transferase phosphorylation type-A transmembrane" (Release 2001.1) shows amino acid residues 15 to 73 of the 74 amino acid consensus sequence (SEQ ID NO:49) aligns with the "receptor kinase tyrosine-protein precursor ephrin ATP-binding transferase phosphorylation type-A transmembrane" domain of human 16658, amino acid residues 354 to 410 of SEQ ID NO:36.

A BLAST alignment of human 16658 with a consensus amino acid sequence derived from a Propomain "kinase tyrosine-protein repeat janus domain phosphorylation ATP-binding SH2" (Release 2001.1) shows amino acid residues 1 to 178 of the 179 amino acid consensus sequence (SEQ ID NO:50), aligns with the "kinase tyrosine-protein repeat janus domain phosphorylation ATP-binding SH2e" domain of human 16658, amino acid residues 843 to 1017 of SEQ ID NO:36.

A BLAST alignment of human 16658 with a consensus amino acid sequence derived from a Propomain "receptor kinase tyrosine-protein precursor ephrin transferase ATP-binding phosphorylation transmembrane type-A" (Release 2001.1) shows amino acid residues 28 to 82 of the 83 amino acid consensus sequence (SEQ ID NO:51) aligns with the "receptor kinase tyrosine-protein precursor ephrin transferase ATP-binding phosphorylation transmembrane type-A" domain of human 16658, amino acid residues 668 to 723 of SEQ ID NO:36.

Human 14223

The present invention is based, in part, on the discovery of a novel human kinase, referred to herein as "14223".

The human 14223 sequence (SEQ ID NO:38), which is approximately 2466 nucleotides long including untranslated regions, contains a predicted methionine-initiated coding sequence of about 1542 nucleotides (nucleotides 437-1978 of SEQ ID NO:38; 1-1542 of SEQ ID NO:40), not including the terminal codon. The coding sequence encodes a 514 amino acid protein (SEQ ID NO:39).

This mature protein form is approximately 514 amino acid residues in length (from about amino acid 1 to amino acid 514 of SEQ ID NO:39). Human 14223 contains the following regions or other structural features: a predicted kinase domain located at about amino acid residues 116-381 of SEQ ID NO:39.

A hydropathy plot of human 14223 was performed. Polypeptides of the invention include fragments which include: all or part of a hydrophobic sequence, e.g., the sequence from about amino acid 220 to 230, from about 285 to 295, and from about 310 to 320 of SEQ ID NO:39; all or part of a hydrophilic sequence, e.g., the sequence from about amino acid 60 to 100, from about 205 to 215, and from about 400 to 460 of SEQ ID NO:39; a sequence which includes a Cys, or a glycosylation site.

The 14223 protein also includes the following domains: four N-glycosylation sites (PS00001) located at about amino acids 95-98, 213-216, 411-414, and 438-441 of SEQ ID NO:39; three cAMP- and cGMP-dependent protein kinase phosphorylation site (PS00004) located at about amino acids 8-11, 84-87, and 271-274 of SEQ ID NO:39; twelve predicted protein kinase C phosphorylation sites (PS00005) located at about amino acids 10-12, 20-22, 29-31, 70-72, 134-136, 169-171, 184-186, 371-373, 388-390, 459-461, 473-475, and 510-512 of SEQ ID NO:39; eighteen predicted casein kinase II phosphorylation sites (PS00006) located at about amino 4-7, 20-23, 71-74, 80-83, 134-137, 211-214, 249-252, 274-277, 296-299, 326-329, 349-352, 371-374, 407-410, 412-415, 420-423, 440-443, 450-453, and 459-462 of SEQ ID NO:39; two predicted N-myristoylation sites (PS00008) located at about amino acids 49-54 and 383-388 of SEQ ID NO:39; one predicted protein kinases ATP-binding region signature site (PS00107) located at about amino acids 122-130 of SEQ ID NO:39; one serine/threonine protein kinases active-site sign (PS00108) located at about amino acids 234-246 of SEQ ID NO:39.

For general information regarding PFAM identifiers, PS prefix and PF prefix domain identification numbers, refer to Sonnhammer et al. (1997) *Protein* 28:405-420.

The protein kinase domain of human 14223 (amino acids 116 to 381 of SEQ ID NO:39) aligns with a consensus amino acid sequence derived from a hidden Markov model (HMM) from PFAM (SEQ ID NO:52).

A BLAST alignment of human 14223 with a consensus amino acid sequence derived from a Propomain "kinase serine/threonine-protein transferase receptor ATP-binding 2.7.1.-tyrosine-protein phosphorylation precursor" (Release 2001.1) shows that amino acid residues 254 to 301, 136 to 235, 51 to 184, 370 to 409, 6 to 85, and 344 to 370 of the 424 amino acid consensus sequence (SEQ ID NOs:53-58) align with the "kinase serine/threonine-protein transferase receptor ATP-binding 2.7.1.-tyrosine-protein phosphorylation precursor" domains of human 14223, found from amino acid residues 285 to 329, 199 to 286, 124 to 245, 293 to 323, 116 to 194, and 351 to 377 of SEQ ID NO:39.

A BLAST alignment of human 14223 with a consensus amino acid sequence derived from a Propomain "serine/threonine similar kinase kinases serine/threonine-protein" (Release 2001.1) shows that amino acid residues 353 to 514 and 90 to 230 of the 717 amino acid consensus sequence (SEQ ID NOs:59-60) align with the "serine/threonine similar kinase kinases serine/threonine-protein" domains of human 14223, found from amino acid residues 308 to 463 and 122 to 249 of SEQ ID NO:39.

Human 16002

The present invention is based, in part, on the discovery of a novel human kinase, referred to herein as "16002".

The human 16002 sequence (SEQ ID NO:41), which is approximately 2711 nucleotides long including untranslated regions, contains a predicted methionine-initiated coding sequence of about 1683 nucleotides (nucleotides 198-1880 of SEQ ID NO:41; 1-1683 of SEQ ID NO:43), not including the terminal codon. The coding sequence encodes a 561 amino acid protein (SEQ ID NO:42).

This mature protein form is approximately 561 amino acid residues in length (from about amino acid 1 to amino acid 561 of SEQ ID NO:42). Human 16002 contains the following regions or other structural features: a predicted kinase domain located at about amino acid residues 128-409 of SEQ ID NO:42; and a predicted transmembrane domain which extends from about amino acid residue 336-354 of SEQ ID NO:42.

The 16002 protein also includes the following domains: one N-glycosylation site (PS00001) located at about amino acids 147-150 of SEQ ID NO:42; three cAMP- and cGMP-dependent protein kinase phosphorylation site (PS00004) located at about amino acids 71-74, 105-108, and 455-458 of SEQ ID NO:42; six predicted protein kinase C phosphorylation sites (PS00005) located at about amino acids 58-60, 69-71, 100-102, 160-162, 330-332, and 437-439 of SEQ ID NO:42; eight predicted casein kinase II phosphorylation sites (PS00006) located at about amino 26-29, 74-77, 82-85, 117-120, 419-422, 425-428, 430-433, and 557-560 of SEQ ID NO:42; four predicted N-myristoylation sites (PS00008) located at about amino acids 178-183, 326-331, 515-520, and 525-530 of SEQ ID NO:42; one predicted ATP/GTP-binding site motif A (P-loop) (PS00017) located at about amino acids 485-492; one predicted protein kinases ATP-binding region signature site (PS00107) located at about amino acids 134-142 of SEQ ID NO:42; and one serine/threonine protein kinases active-site sign (PS00108) located at about amino acids 271-283 of SEQ ID NO:42.

For general information regarding PFAM identifiers, PS prefix and PF prefix domain identification numbers, refer to Sonnhammer et al. (1997) *Protein* 28:405-420

Polypeptides of the invention include fragments which include: all or part of a hydrophobic sequence, e.g., the sequence from about amino acid 255 to 265, from about 330 to 350, and from about 530 to 550 of SEQ ID NO:42; all or part of a hydrophilic sequence, e.g., the sequence from about amino acid 30 to 50, from about 170 to 185, and from about 455 to 475 of SEQ ID NO:42; a sequence which includes a Cys, or a glycosylation site.

The protein kinase domain of human 16002 (amino acids 128 to 409 of SEQ ID NO:42) aligns with a consensus amino acid sequence derived from a hidden Markov model (HMM) from PFAM (SEQ ID NO:61).

A BLAST alignment of human 16002 with a consensus amino acid sequence derived from a Propomain "kinase Ca2/calmodulin-dependent phosphorylase serine threonine hydroxyalkyl-protein B calcium/calmodulin alpha glycogen" (Release 2001.1) shows amino acid residues 1 to 80 of the 80 amino acid consensus sequence (SEQ ID NO:62) aligns with the "kinase Ca2/calmodulin-dependent phosphorylase serine threonine hydroxyalkyl-protein B calcium/calmodulin alpha glycogen" domain of human 16002, amino acid residues 1 to 80 of SEQ ID NO:42.

A BLAST alignment of human 16002 with a consensus amino acid sequence derived from a Propomain "kinase Ca2/calmodulin-dependent beta alpha synthase phosphorylase serine threonine calcium/calmodulin" (Release 2001.1) shows amino acid residues 1 to 61 of the 61 amino acid consensus sequence (SEQ ID NO:63) aligns with the "kinase Ca2/calmodulin-dependent beta alpha synthase phosphorylase serine threonine calcium/calmodulin" domain of human 16002, amino acid residues 403 to 463 of SEQ ID NO:42.

A BLAST alignment of human 16002 with a consensus amino acid sequence derived from a Propomain "kinase calcium/calmodulin alpha-dependent" (Release 2001.1). shows amino acid residues 1 to 47 of the 47 amino acid consensus sequence (SEQ ID NO:64), aligns with the "kinase calcium/calmodulin alpha-dependent" domain of human 16002, amino acid residues 81 to 127 of SEQ ID NO:42.

A BLAST alignment of human 16002 with a consensus amino acid sequence derived from a Propomain "kinase Ca2/calmodulin-dependent phosphorylase serinethreonine hydroxyalkyl-protein B calcium/calmodulin alpha glycogen" (Release 2001.1) shows amino acid residues 1 to 36 of the 42 amino acid consensus sequence (SEQ ID NO:65) aligns with the "kinase Ca2/calmodulin-dependent phosphorylase serine threonine hydroxyalkyl-protein B calcium/calmodulin alpha glycogen" domain of human 16002, amino acid residues 464 to 499 of SEQ ID NO:42.

The 16658, 14223, and 16002 proteins contain a significant number of structural characteristics in common with members of the kinase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

The present invention is based, at least in part, on the discovery of novel molecules, referred to herein as "16658, 14223, and 16002" nucleic acid and polypeptide molecules, which play a role in or function in the transduction of signals for cell proliferation, differentiation and apoptosis. In one embodiment, the 16658, 14223, and 16002 molecules modulate the activity of one or more proteins involved in cellular growth or differentiation, e.g., cell growth or differentiation. In another embodiment, the 16658, 14223, and 16002 molecules of the present invention are capable of modulating the phosphorylation state of 16658, 14223, and 16002 molecules or one or more proteins involved in cellular growth or differentiation.

16022 has homology to rat calcium/calmodulin-dependent protein kinase kinase (CaMKK) alpha. As such, without being bound by theory, 16002 is expected to be a CaMKK that mediates responses in different pain states of BDNF, the growth factor of the neurotrophin family that is upregulated in nociceptive neurons after axotomy and CCI and released into the dorsal horn of the spinal cord. CaMKK alpha phosphorylates CaMK I and IV that regulate transcription. Itself is negatively regulated by PKA. In the brain, CaMKK alpha blocks apoptosis-induced by increase of intracellular Ca++ levels after NMDA receptor stimulation. NMDA receptors are very important players in the modulation of pain in the spinal cord. In addition, CaMKIV, a substrate for CaMKK alpha, is phosphorylated after BDNF exposure.

As used herein, the term "protein kinase" includes a protein or polypeptide which is capable of modulating its own phosphorylation state or the phosphorylation state of another protein or polypeptide. Protein kinases can have a specificity for (i.e., a specificity to phosphorylate) serine/threonine residues, tyrosine residues, or both serine/threonine and tyrosine residues, e.g., the dual specificity kinases. As referred to herein, protein kinases preferably include a catalytic domain of about 200-400 amino acid residues in length, preferably about 250-300 amino acid residues in length, or more preferably about 265-296 amino acid residues in length, which includes preferably 5-20, more preferably 5-15, or preferably 11 highly conserved motifs or subdomains separated by sequences of amino acids with reduced or minimal conservation. Specificity of a protein kinase for phosphorylation of either tyrosine or serine/threonine can be predicted by the sequence of two of the subdomains (VIb and VIII) in which different residues are conserved in each class (as described in, for example, Hanks et al. (1988) *Science* 241:42-52) the contents of which are incorporated herein by reference). These subdomains are also described in further detail herein.

Protein kinases play a role in signaling pathways associated with cellular growth. For example, protein kinases are involved in the regulation of signal transmission from cellular receptors, e.g., growth-factor receptors; entry of cells into mitosis; and the regulation of cytoskeleton function, e.g., actin bundling. Thus, the 16658, 14223, and 16002 molecules of the present invention may be involved in: 1) the regulation of transmission of signals from cellular receptors, e.g., growth factor receptors; 2) the modulation of the entry of cells into mitosis; 3) the modulation of cellular differentiation; 4) the modulation of cell death; and 5) the regulation of cytoskeleton function.

Inhibition or over stimulation of the activity of protein kinases involved in signaling pathways associated with cellular growth can lead to perturbed cellular growth, which can in turn lead to cellular growth related disorders. As used herein, a "cellular growth related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy.

The present invention is based, at least in part, on the discovery of novel molecules, referred to herein as 16658, 14223, and 16002 protein and nucleic acid molecules, which comprise a family of molecules having certain conserved structural and functional features.

One embodiment of the invention features 16658, 14223, and 16002 nucleic acid molecules, preferably human 16658, 14223, and 16002 molecules, e.g., 16658, 14223, and 16002. The 16658, 14223, and 16002 nucleic acid and protein molecules of the invention are described in further detail in the following subsections.

A 16658, 14223, and 16002 polypeptide can include a "kinase domain" or regions homologous with a "kinase domain".

As used herein, the term "kinase domain" includes an amino acid sequence of about 100-400 amino acid residues in length and having a bit score for the alignment of the sequence to the kinase domain (HMM) of at least 8. Preferably, a kinase domain includes at least about 100-350 amino acids, more preferably about 250-300 amino acid residues, or about 265-396 amino acids and has a bit score for the alignment of the sequence to the kinase domain (HMM) of at least 16 or greater. The kinase domain (amino acids 725-1021, 116-381, and 128-409 of SEQ ID NO:36, SEQ ID NO:39, and SEQ ID NO:42, respectively) of human 16658, 14223, and 16002 were aligned with a consensus amino acid sequence derived from a hidden Markov model.

In a preferred embodiment 16658, 14223, and 16002 polypeptides or proteins have a "kinase domain" or a region which includes at least about 200-350 more preferably about 250-300 or 265-396 amino acid residues and has at least about 60%, 70%, 80%, 90%, 95%, 99%, or 100% homology with an "kinase domain," e.g., the kinase domain of human 16658, 14223, and 16002 (e.g., amino acid residues 725-1021, 116-381, and 128-409 of SEQ ID NO:36, SEQ ID NO:39, and SEQ ID NO:42, respectively).

To identify the presence of a "kinase domain" in a 16658, 14223 or 16002 protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al., (1997) *Proteins* 28(3):405-420 and a detailed description of HMMs can be found, for example, in Gribskov et al., (1990) *Meth. Enzymol.* 183:146-159; Gribskov et al., (1987) *Proc. Natl. Acad. Sci. USA* 84:4355-4358; Krogh et al., (1994) *J. Mol. Biol.* 235:1501-1531; and Stultz et al., (1993) *Protein Sci.* 2:305-314, the contents of which are incorporated herein by reference. A search was performed against the HMM database resulting in the identification of a "kinase domain" in the amino acid sequence of human 16658 at about residues 725 to 1021 of SEQ ID NO:36; of human 14223 at about residues 116 to 381 of SEQ ID NO:39; or of human 16002 at about residues 128 to 409 of SEQ ID NO:42.

For further identification of domains in a 16658, 14223, and 16002 protein sequence, and make the determination that a polypeptide or protein of interest has a particular profile, the amino acid sequence of the protein can be searched against a database of domains, e.g., the ProDom database (Corpet et al. (1999), Nucl. Acids Res. 27:263-267). The ProDom protein domain database consists of an automatic compilation of homologous domains. Current versions of Propom are built using recursive PSI-BLAST searches (Altschul S F et al. (1997) *Nucleic Acids Res.* 25:3389-3402; Gouzy et al. (1999) 23:333-340) of the SWISS-PROT 38 and TREMBL protein databases. The database automatically generates a consensus sequence for each domain. A BLAST search was performed against the HMM database resulting in the identification of a "kinase" domain(s) in the amino acid sequence of human 16658 at about residues 128 to 301, 411 to 534, 790 to 839, 354 to 410, 843 to 1017, 668 to 723 of SEQ ID NO:36 having 71%, 58%, 98%, 54%, 28% and 60% identity over those residues respectively; of human 14223 at about residues 285 to 329, 199 to 286, 124 to 245, 293 to 323, 116 to 194, and 351 to 377 (six local alignments) of SEQ ID NO:39 having 52%, 29%, 21%, 35%, 31% and 25% identity over those residues respectively; 308 to 463 and 122 to 249 (two local alignments) of SEQ ID NO:39 having 25% identity over those residues; and of human 16002 at about residues 1 to 80, 403 to 463, 81 to 127, or 464 to 499 of SEQ ID NO:42 having 83%, 78%, 78%, and 94%, identity over those residues respectively.

The 16658, 14223, and 16002 proteins include an ATP-binding region signature. Preferably, the ATP-binding region signature includes the following amino acid consensus sequence having Prosite signature as PS00107, or sequences homologous thereto: [LIV]-G-{P}-G-{P}-[FYWMG-STNH]-[SGA]-{PW}-[LIVCAT]-{PD}-x-[GSTA-CLIVMFY]-x(5,18)-[LIVMFYWCSTAR]-[AIVP]-[LIVM-FAGCKR]-K [K binds ATP] (SEQ ID NO:66). In the above conserved motif, and other motifs described herein, the standard IUPAC one-letter code for the amino acids is used. Each element in the pattern is separated by a dash (-); square brackets ([ ]) indicate the particular residues that are accepted at that position; x indicates that any residue is accepted at that position; and numbers in parentheses (( )) indicate the number of residues represented by the accompanying amino acid. The ATP-binding region of 16658 is found in the C-terminal cytoplasmic domain. The ATP-binding region of 16002 is found in the N-terminal cytoplasmic domain A 16658 polypeptide can also include a "tyrosine protein kinase specific active-site signature". Preferably, the tyrosine protein kinase specific active-site signature includes the following amino acid consensus sequence having Prosite signature as PS00109, or sequences homologous thereto: [LIVM-FYC]-x-[HY]-x-D-[LIVMFY]-[RSTAC]-x(2)-N-[LIVMFYC](3) [D is an active site residue] (SEQ ID NO:67). The tyrosine protein kinase specific active-site signature for 16658 is found in the C-terminal cytoplasmic domain.

A 14223 or 16002 polypeptide can also include a "serine/threonine protein kinases active-site signature". Preferably, the serine/threonine protein kinases active-site signature includes the following amino acid consensus sequence having Prosite signature as PS00109, or sequences homologous thereto: [LIVMFYC]-x-[HY]-x-D-[LIVMFY]-K-x(2)-N-[LIVMFYCT](3) [D is an active site residue] (SEQ ID NO:68). The serine/threonine protein kinases active-site signature for 14223 is found in a hydrophilic region of the polypeptide. The serine/threonine protein kinases active-site signature for the 16002 polypeptide is found in N-terminal cytoplasmic domain.

A 16658 polypeptide can also include a "receptor tyrosine kinase class V signature 1". Preferably, the receptor tyrosine kinase class V signature 1 includes the following amino acid consensus sequence having Prosite signature as PS00790, or sequences homologous thereto: F-x-[DN]-x-[GAW]-[GA]-C-[LIVM]-[SA]-[LIVM](2)-[SA]-[LV]-[KRHQ]-[LIVA]-x(3)-[KR]-C-[PSAW] (SEQ ID NO:69). A 16658 polypeptide can also include a "receptor tyrosine kinase class V signature 2". Preferably, the receptor tyrosine kinase class V signature 2 includes the following amino acid consensus sequence having Prosite signature as PS00791, or sequences homologous thereto: C-x(2)-[DE]-G-[DEQ]-W-x(2,3)-[PAQ]-[LIVMT]-[GT]-x-C-x-C-x(2)-G-[HFY]-[EQ] (SEQ ID NO:70). The receptor tyrosine kinase class V signatures 1 and 2 for 16658 are found in the extracellular loop.

A 16658 polypeptide can also include a "EGF-like domain signature 2". Preferably, the EGF-like domain signature 2 includes the following amino acid consensus sequence having Prosite signature as PS01186, or sequences homologous thereto: C-x-C-x(2)-[GP]-[FYW]-x(4,8)-C (SEQ ID NO:71). The EGF-like domain signature 2 for 16658 is found in the extracellular loop.

A 16002 polypeptide can also include an "ATP/GTP-binding site motif A (P-loop)". Preferably, the ATP/GTP-binding site motif A (P-loop) includes the following amino acid consensus sequence having Prosite signature as PS00017, or sequences homologous thereto: [AG]-x(4)-G-K-[ST] (SEQ ID NO:72). The ATP/GTP-binding site motif A (P-loop) for 16002 is found in the extracellular loop.

In one embodiment, a 16658 protein includes at least one and preferably two transmembrane domains and a 16002 protein includes at least one transmembrane domain. As used herein, the term "transmembrane domain" includes an amino acid sequence of about 10 to 40 amino acid residues in length and spans the plasma membrane. Transmembrane domains are rich in hydrophobic residues, e.g., at least 50%, 60%, 70%, 80%, 90%, 95% or more of the amino acids of a transmembrane domain are hydrophobic, e.g., leucines, isoleucines, tyrosines, or tryptophans. Transmembrane domains typically have alpha-helical structures and are described in, for example, Zagotta, W. N. et al., (1996) *Annual Rev. Neurosci.* 19:235-263, the contents of which are incorporated herein by reference.

In a preferred embodiment, a 16658 protein includes at least one and preferably two transmembrane domains and a 16002 protein includes at least one transmembrane domain or a region which includes at least or regions which include at least about 12 to 35 more preferably about 14 to 30 or 15 to 25 amino acid residues or 16, 18, 20, 22, 23, 24, 25, or 30 amino acid residues and has at least about 60%, 70% 80% 90% 95%, 99%, or 100% homology with a "transmembrane domain," e.g., at least one transmembrane domain of human 16658 or 16002 (e.g., amino acid residues 103-119 and 642-665 of SEQ ID NO:36, or amino acid residues 336-354 of SEQ ID NO:42). The transmembrane domain of human 16658 and 16002 can be visualized in a hydropathy plot as regions of about 15 to 25 amino acids where the hydropathy trace is mostly above the horizontal line.

To identify the presence of a "transmembrane" domain in a 16658 or 16002 protein sequence, and make the determination that a polypeptide or protein of interest has a particular profile, the amino acid sequence of the protein can be analyzed by a transmembrane prediction method that predicts the secondary structure and topology of integral membrane proteins based on the recognition of topological models (MEMSAT, Jones et al., (1994) *Biochemistry* 33:3038-3049).

A mature 16658 protein includes at least one, two, preferably three "non-transmembrane regions" and a mature 16002 protein includes at least one, and preferably two "non-transmembrane regions." As used herein, the term "non-transmembrane region" includes an amino acid sequence not identified as a transmembrane domain. The non-transmembrane regions in 16658 or 16002 are located at about amino acids residues 1-102, 120-641, and 666-1130 of SEQ ID NO:36 or 1-335 and 356-561 of SEQ ID NO:42.

The non-transmembrane regions of 16658 include at least one preferably two cytoplasmic regions, and non-transmembrane regions of 16002 include at least one cytoplasmic region. When located at the N-terminus, the cytoplasmic region is referred to herein as the "N-terminal cytoplasmic domain." As used herein, an "N-terminal cytoplasmic domain" includes an amino acid sequence having about 1-400, preferably about 30-75, more preferably about 50-350, or even more preferably about 102-335 amino acid residues in length and is located inside of a cell or within the cytoplasm of a cell. The C-terminal amino acid residue of an "N-terminal cytoplasmic domain" is adjacent to an N-terminal amino acid residue of a transmembrane domain in a 16658 or 16002 protein. For example, an N-terminal non-transmembrane domain is located at about amino acid residues 1-102 of SEQ ID NO:36.

In a preferred embodiment, a polypeptide or protein has an N-terminal cytoplasmic domain or a region which includes at least about 5, preferably about 1 to 400, and more preferably about 1 to 350 amino acid residues and has at least about 60%, 70% 80% 90% 95%, 99%, or 100% homology with an "N-terminal cytoplasmic domain," e.g., the N-terminal cytoplasmic domain of human 16658 (e.g., residues 1 to 102 of SEQ ID NO:36).

In another embodiment, a cytoplasmic region of a 16658 protein can include the C-terminus and can be a "C-terminal cytoplasmic domain," also referred to herein as a "C-terminal cytoplasmic tail." As used herein, a "C-terminal cytoplasmic domain" includes an amino acid sequence having a length of at least about 10, preferably about 1-500, preferably about 100-490, preferably about 150-480, more preferably about 200-464 amino acid residues and is located inside of a cell or within the cytoplasm of a cell. The N-terminal amino acid residue of a "C-terminal cytoplasmic domain" is adjacent to a C-terminal amino acid residue of a transmembrane domain in a 16658 protein. For example, a C-terminal cytoplasmic domain is located at about amino acid residues 666-1130 of SEQ ID NO:36.

In a preferred embodiment, a 16658 polypeptide or protein has a C-terminal cytoplasmic domain or a region which includes at least about 5, preferably about 10 to 200, and more preferably about 150 to 200 amino acid residues and has at least about 60%, 70% 80% 90% 95%, 99%, or 100% homology with a C-terminal cytoplasmic domain," e.g., the C-terminal cytoplasmic domain of human 16658 (e.g., residues 666-1130 of SEQ ID NO:36).

In another embodiment, a 16658 protein includes at least one non-cytoplasmic loop. As used herein, a "non-cytoplasmic loop" includes an amino acid sequence located outside of a cell or within an intracellular organelle. Non-cytoplasmic loops include extracellular domains (i.e., outside of the cell) and intracellular domains (i.e., within the cell). When referring to membrane-bound proteins found in intracellular organelles (e.g., mitochondria, endoplasmic reticulum, peroxisomes microsomes, vesicles, endosomes, and lysosomes), non-cytoplasmic loops include those domains of the protein that reside in the lumen of the organelle or the matrix or the intermembrane space. For example, a "non-cytoplasmic loop" can be found at about amino acid residues 120-641 of SEQ ID NO:36.

In a preferred embodiment, a 16658 polypeptide or protein has at least one non-cytoplasmic loop or a region which includes at least about 4, preferably about 5 to 600, more preferably about 6 to 550 amino acid residues and has at least about 60%, 70% 80% 90% 95%, 99%, or 100% homology with a "non-cytoplasmic loop," e.g., at least one non-cytoplasmic loop of human 16658 (e.g., residues 120-641 of SEQ ID NO:36).

As the 16658, 14223, and 16002 polypeptides of the invention may modulate 16658-, 14223-, and 16002-mediated activities, they may be useful for developing novel diagnostic and therapeutic agents for 16658-, 14223-, and 16002-mediated or related disorders. Accordingly, 16658, 14223, and 16002 proteins may mediate various disorders, including cellular proliferative and/or differentiative disorders, brain disorders, pain or metabolic disorders.

The 16658, 14223, and 16002 nucleic acid and protein of the invention can be used to treat and/or diagnose a variety of proliferative disorders, e.g., such disorders include hematopoietic neoplastic disorders.

Gene Expression of 16658 and 16002

TaqMan real-time quantitative RT-PCR is used to detect the presence of RNA transcript corresponding to human 16658 or 16002 relative to a no template control in a panel of human tissues or cells.

It was found that the highest expression of 16658 orthologs are expressed in normal ovary cell lines in an oncology phase II plate as shown in the following Table 12.

TABLE 12

16658 Expression in Oncology Phase II plate

| Tissue Type | Mean 16658 | β 2 Mean | ∂∂ Ct | Expression |
|---|---|---|---|---|
| PIT 400 Breast N | 40 | 19.47 | 20.53 | 0 |
| PIT 372 Breast N | 40 | 20.18 | 19.82 | 0 |
| CHT 558 Breast N | 40 | 19.05 | 20.95 | 0 |
| CLN 168 Breast T: IDC | 40 | 19.61 | 20.39 | 0 |
| MDA 304 Breast T: MD-IDC | 39.36 | 18.51 | 20.85 | 0 |
| NDR 57 Breast T: IDC-PD | 40 | 19.03 | 20.97 | 0 |
| NDR 132 Breast T: IDC/ILC | 40 | 20.78 | 19.22 | 0 |
| CHT 562 Breast T: IDC | 39.31 | 18.8 | 20.5 | 0 |
| NDR 12 Breast T | 36 | 21.84 | 14.16 | 0 |
| PIT 208 Ovary N | 27.6 | 18.53 | 9.07 | 1.86 |
| CHT 620 Ovary N | 32.58 | 19.47 | 13.11 | 0.11 |
| CLN 03 Ovary T | 35.49 | 19.43 | 16.07 | 0 |
| CLN 17 Ovary T | 39.73 | 19.95 | 19.78 | 0 |
| MDA 25 Ovary T | 40 | 21.82 | 18.18 | 0 |
| MDA 216 Ovary T | 37.59 | 20.09 | 17.5 | 0 |
| CLN 012 Ovary T | 38.48 | 21.16 | 17.32 | 0 |
| MDA 185 Lung N | 40 | 19.57 | 20.43 | 0 |
| CLN 930 Lung N | 40 | 18.89 | 21.11 | 0 |
| MDA 183 Lung N | 40 | 18.06 | 21.95 | 0 |
| MPI 215 Lung T-SmC | 39.92 | 19.05 | 20.88 | 0 |
| MDA 259 Lung T-PDNSCCL | 40 | 19.95 | 20.05 | 0 |
| CHT 832 Lung T-PDNSCCL | 40 | 18.98 | 21.02 | 0 |
| CHT 911 Lung T-SCC | 37.59 | 19.32 | 18.27 | 0 |
| MDA 262 Lung T-SCC | 37.15 | 22.34 | 14.81 | 0 |
| CHT 211 Lung T-AC | 40 | 19.17 | 20.83 | 0 |
| MDA 253 Lung T-PDNSCCL | 40 | 18.36 | 21.64 | 0 |
| NHBE | 39.42 | 21.09 | 18.34 | 0 |
| CHT 396 Colon N | 40 | 23.82 | 16.18 | 0 |
| CHT 523 Colon N | 36.09 | 18.77 | 17.32 | 0 |
| CHT 452 Colon N | 40 | 17.4 | 22.6 | 0 |
| CHT 382 Colon T: MD | 40 | 18.19 | 21.81 | 0 |
| CHT 528 Colon T: MD | 40 | 17.99 | 22.01 | 0 |
| CLN 609 Colon T | 39.51 | 18.77 | 20.73 | 0 |
| CHT 372 Colon T: MD-PD | 40 | 19.41 | 20.59 | 0 |
| NDR 217 Colon-Liver Met | 39.8 | 18.61 | 21.19 | 0 |
| NDR 100 Colon-Liver Met | 40 | 18.06 | 21.94 | 0 |
| PIT 260 Liver N (female) | 40 | 17.02 | 22.98 | 0 |
| ONC 102 Hemangioma | 40 | 19.22 | 20.78 | 0 |
| A24 HMVEC-Arr | 37.68 | 18.96 | 18.72 | 0 |
| C48 HMVEC-Prol | 38.31 | 20.68 | 17.62 | 0 |

As seen by these results, 16658 molecules have been found to be underexpressed in some tumor cells, where the molecules may be inappropriately propagating either cell proliferation or cell survival signals. As such, activators of the 16658 molecules are useful for the treatment of cancer, preferably ovarian cancer, and useful as a diagnostic.

It was found that the highest expression of 16658 orthologs in phase 1.5.1 expression of 16658 w/β2 is found in normal brain cortex and also in brain hypothalamus as shown in the following Table 13.

TABLE 13

Phase 1.5.1 Expression of 16658 w/β2

| Tissue Type | Mean | β 2 Mean | ∂∂ Ct | Expression |
|---|---|---|---|---|
| Artery normal | 37.62 | 21.77 | 15.85 | 0 |
| Aorta diseased | 39.01 | 21.77 | 17.23 | 0 |
| Vein normal | 40 | 19.7 | 20.31 | 0 |
| Coronary SMC | 38.19 | 22.4 | 15.79 | 0 |
| HUVEC | 36.99 | 20.75 | 16.25 | 0 |
| Hemangioma | 37.32 | 19.04 | 18.29 | 0 |
| Heart normal | 38.34 | 29.85 | 8.49 | 0 |
| Heart CHF | 38.87 | 19.26 | 19.61 | 0 |

TABLE 13-continued

Phase 1.5.1 Expression of 16658 w/β2

| Tissue Type | Mean | β 2 Mean | ∂∂ Ct | Expression |
|---|---|---|---|---|
| Kidney | 34.42 | 20.2 | 14.22 | 0.0524 |
| Skeletal Muscle | 40 | 22 | 18 | 0 |
| Adipose normal | 39.63 | 20.18 | 19.45 | 0 |
| Pancreas | 39.73 | 21.28 | 18.45 | 0 |
| primary osteoblasts | 40 | 20.22 | 19.79 | 0 |
| Osteoclasts (diff) | 40 | 17.22 | 22.78 | 0 |
| Skin normal | 40 | 21.95 | 18.05 | 0 |
| Spinal cord normal | 35.52 | 20.14 | 15.39 | 0 |
| Brain Hypothalamus normal | 30.54 | 21.7 | 8.83 | 2.1974 |
| Nerve | 39.85 | 21.81 | 18.05 | 0 |
| Breast normal | 40 | 20.03 | 19.97 | 0 |
| Breast tumor | 40 | 20.3 | 19.7 | 0 |
| Ovary Tumor | 34.32 | 19.86 | 14.46 | 0.0444 |
| Prostate Normal | 37.01 | 19.34 | 17.66 | 0 |
| Prostate Tumor | 33.24 | 20.34 | 12.9 | 0.1313 |
| Salivary glands | 38.98 | 19.57 | 19.41 | 0 |
| Colon normal | 34.03 | 17.91 | 16.13 | 0.0139 |
| Colon Tumor | 39.34 | 18.36 | 20.98 | 0 |
| Lung normal | 38.15 | 17.58 | 20.57 | 0 |
| Lung tumor | 39.68 | 19.72 | 19.97 | 0 |
| Lung COPD | 39.65 | 28.95 | 10.69 | 0 |
| Colon IBD | 40 | 18.16 | 21.84 | 0 |
| Liver normal | 40 | 19.55 | 20.45 | 0 |
| Liver fibrosis | 38.11 | 21.5 | 16.61 | 0 |
| Spleen normal | 39.62 | 18.73 | 20.88 | 0 |
| Tonsil normal | 39.63 | 16.91 | 22.72 | 0 |
| Lymph node normal | 40 | 18.34 | 21.66 | 0 |
| Small intestine normal | 38.42 | 30.05 | 8.37 | 0 |
| Skin-Decubitus | 40 | 20.39 | 19.61 | 0 |
| Synovium | 37.49 | 18.91 | 18.57 | 0 |
| BM-MNC | 40 | 18.04 | 21.96 | 0 |
| Activated PBMC | 40 | 17.5 | 22.5 | 0 |
| Neutrophils | 40 | 18.4 | 21.61 | 0 |
| Megakaryocytes | 40 | 18.09 | 21.91 | 0 |
| Erythroid | 40 | 21 | 19 | 0 |
| Brain Cortex normal | 28.31 | 23.11 | 5.19 | 27.3939 |
| DRG (Dorsal Root Ganglion) | 33.59 | 21.65 | 11.94 | 0.2554 |
| Ovary normal | 31.93 | 19.76 | 12.17 | 0.217 |

The highest levels of expression of 16658 orthologs in expression of 16658 w/β2 (Table 14) and in pain human panel phase I (Table 15) was found in brain. 16002 was also expressed at much lower levels in spinal cord, DRG, thymus, salivary gland and trachea.

TABLE 14

Expression of 16002 w/β2

| Tissue Type | Mean | β 2 Mean | ∂∂ Ct | Expression |
|---|---|---|---|---|
| Artery normal | 38.79 | 21.54 | 7.25 | 0 |
| Vein normal | 32.73 | 19.97 | 12.76 | 0.1442 |
| Aortic SMC EARLY | 28.18 | 20.94 | 7.24 | 6.6152 |
| Coronary SMC | 28.45 | 21.41 | 7.04 | 7.5726 |
| Static HUVEC | 28.9 | 20.44 | 8.46 | 2.8398 |
| Shear HUVEC | 27.92 | 20.37 | 7.55 | 5.3361 |
| Heart normal | 28.25 | 18.66 | 9.59 | 1.2975 |
| Heart CHF | 29.3 | 18.34 | 10.96 | 0.502 |
| Kidney | 27.47 | 19.12 | 8.35 | 3.0754 |
| Skeletal Muscle | 31.7 | 21.29 | 10.41 | 0.7324 |
| Adipose normal | 32.27 | 19.48 | 12.79 | 0.1417 |
| Pancreas | 30.33 | 20.44 | 9.89 | 1.0539 |
| primary osteoblasts | 30.16 | 19.1 | 11.06 | 0.47 |
| Osteoclasts (diff) | 29.45 | 16.77 | 12.68 | 0.1529 |
| Skin normal | 30.22 | 20.68 | 9.54 | 1.3433 |
| Spinal cord normal | 29.13 | 19.47 | 9.66 | 1.2361 |
| Brain Cortex normal | 23.04 | 20.75 | 2.28 | 205.8978 |
| Brain Hypothalamus normal | 27.03 | 21.25 | 5.78 | 18.2621 |
| Nerve | 34.86 | 24.16 | 10.7 | 0.6011 |
| DRG (Dorsal Root Ganglion) | 27.07 | 21.12 | 5.95 | 16.176 |
| Glial Cells (Astrocytes) | 28.18 | 21.9 | 6.29 | 12.8241 |

TABLE 14-continued

Expression of 16002 w/β2

| Tissue Type | Mean | β 2 Mean | ∂∂ Ct | Expression |
|---|---|---|---|---|
| Glioblastoma | 27.87 | 17.25 | 10.62 | 0.6354 |
| Breast normal | 29.34 | 19.52 | 9.82 | 1.1063 |
| Breast tumor | 26.34 | 17.91 | 8.43 | 2.8995 |
| Ovary normal | 29.27 | 19.8 | 9.46 | 1.415 |
| Ovary Tumor | 30.86 | 19.22 | 11.64 | 0.3133 |
| Prostate Normal | 27.75 | 18.95 | 8.79 | 2.2513 |
| Prostate Tumor | 25.32 | 16.34 | 8.97 | 1.9873 |
| Epithelial Cells (Prostate) | 29.62 | 20.36 | 9.26 | 1.631 |
| Colon normal | 28.68 | 17.66 | 11.02 | 0.4816 |
| Colon Tumor | 25.57 | 18.23 | 7.34 | 6.1936 |
| Lung normal | 30.5 | 17.28 | 13.23 | 0.1044 |
| Lung tumor | 26.75 | 17.41 | 9.34 | 1.5484 |
| Lung COPD | 28.23 | 17.9 | 10.33 | 0.7769 |
| Colon IBD | 29.56 | 16.81 | 12.75 | 0.1452 |
| Liver normal | 32.91 | 19.06 | 13.85 | 0.0677 |
| Liver fibrosis | 31.59 | 20.67 | 10.91 | 0.5179 |
| Dermal Cells-fibroblasts | 28.26 | 19.29 | 8.97 | 1.9942 |
| Spleen normal | 29.64 | 19.12 | 10.52 | 0.681 |
| Tonsil normal | 27.81 | 16.56 | 11.25 | 0.4106 |
| Lymph node | 29.51 | 18.22 | 11.3 | 0.398 |
| Resting PBMC | 30.27 | 19.47 | 10.8 | 0.5628 |
| Skin-Decubitus | 28.75 | 20.12 | 8.63 | 2.5329 |
| Synovium | 28.93 | 18.57 | 10.36 | 0.7635 |
| BM-MNC (Bone marrow mononuclear cells) | 26.46 | 16.51 | 9.95 | 1.011 |
| Activated PBMC | 28.18 | 15.37 | 12.82 | 0.1388 |

TABLE 15

16002 Human Panel Phase I

| Tissue Type | 16002 | β2.803 | ∂Ct | Expression |
|---|---|---|---|---|
| Adrenal Gland | 25.91 | 17.60 | 8.31 | 3.15 |
| Brain | 23.20 | 19.95 | 3.26 | 104.75 |
| Heart | 28.94 | 18.08 | 10.86 | 0.54 |
| Kidney | 27.86 | 17.86 | 10.00 | 0.98 |
| Liver | 29.25 | 18.08 | 11.17 | 0.44 |
| Lung | 28.16 | 16.28 | 11.88 | 0.27 |
| Mammary Gland | 27.38 | 17.24 | 10.14 | 0.89 |
| Pancreas | 28.21 | 20.37 | 7.85 | 4.35 |
| Placenta | 33.31 | 18.18 | 15.13 | 0.03 |
| Prostate | 30.26 | 16.90 | 13.36 | 0.10 |
| Salivary Gland | 26.38 | 18.49 | 7.89 | 4.22 |
| Muscle | 29.10 | 19.92 | 9.18 | 1.72 |
| Sm. Intestine | 27.59 | 18.05 | 9.54 | 1.35 |
| Spleen | 30.06 | 15.99 | 14.07 | 0.06 |
| Stomach | 28.18 | 17.64 | 10.55 | 0.67 |
| Teste | 25.67 | 19.68 | 5.99 | 15.79 |
| Thymus | 26.28 | 17.56 | 8.72 | 2.37 |
| Trachea | 27.28 | 18.41 | 8.88 | 2.13 |
| Uterus | 27.08 | 18.54 | 8.54 | 2.69 |
| Spinal Cord | 28.49 | 18.69 | 9.80 | 1.12 |
| DRG | 28.20 | 19.24 | 8.96 | 2.01 |
| Skin | 28.03 | 18.08 | 9.95 | 1.01 |

The following Table 16 showing the results of a TaqMan experiment with rat panel phase I, showed a similar pattern of expression as that of the human 16002 gene. This gene is also expressed in the SCG.

TABLE 16

12818 Rat Panel Phase I

| Tissue | r12818 | 18S | ∂Ct | Expression |
|---|---|---|---|---|
| Brain | 23.92 | 12.85 | 11.07 | 0.47 |
| Spinal Cord | 23.77 | 12.86 | 10.91 | 0.52 |

TABLE 16-continued

12818 Rat Panel Phase I

| Tissue | r12818 | 18S | ∂Ct | Expression |
|---|---|---|---|---|
| DRG | 25.27 | 13.69 | 11.59 | 0.33 |
| SCG | 26.10 | 13.58 | 12.52 | 0.17 |
| Hairy Skin | 26.98 | 13.91 | 13.07 | 0.12 |
| Gastro Muscle | 28.88 | 14.24 | 14.64 | 0.04 |
| Heart | 29.76 | 13.68 | 16.08 | 0.01 |
| Kidney | 28.67 | 13.43 | 15.25 | 0.03 |
| Liver | 30.95 | 12.95 | 18.00 | 0.00 |
| Lung | 25.91 | 12.71 | 13.20 | 0.11 |
| Spleen | 27.52 | 13.78 | 13.75 | 0.07 |
| Aorta | 28.78 | 14.20 | 14.58 | 0.04 |
| Adrenal Gland | 25.46 | 13.35 | 12.12 | 0.23 |
| Salivary Gland | 27.47 | 13.15 | 14.33 | 0.05 |
| Thyroid | 26.47 | 14.37 | 12.10 | 0.23 |
| Prostate | 28.93 | 13.50 | 15.43 | 0.02 |
| Thymus | 26.64 | 13.56 | 13.08 | 0.12 |
| Trachea | 28.04 | 14.37 | 13.67 | 0.08 |
| Esophagus | 27.12 | 14.16 | 12.96 | 0.13 |
| Duodenum | 31.70 | 14.48 | 17.22 | 0.01 |
| Diaphragm | 29.63 | 13.98 | 15.65 | 0.02 |

The following table, Table 17, shows the results of a TaqMan experiment with rat phase II and II panels. There is little or no regulation of this gene in animal models.

TABLE 17

12818 Rat Panel Phase II and III

| Tissue | r12818 | 18S | ∂Ct | Expression |
|---|---|---|---|---|
| Naïve DRG | 24.77 | 12.27 | 12.50 | 0.17 |
| I DRG CCI 3 | 24.51 | 12.52 | 11.99 | 0.25 |
| I DRG CCI 7 | 25.22 | 12.03 | 13.20 | 0.11 |
| I DRG CCI 10 | 25.25 | 12.09 | 13.16 | 0.11 |
| I DRG CCI 14 | 25.07 | 11.98 | 13.09 | 0.11 |
| I DRG CCI 28 | 25.33 | 11.99 | 13.34 | 0.10 |
| Naïve DRG | 25.17 | 12.34 | 12.83 | 0.14 |
| I DRG CFA 1 | 24.92 | 12.08 | 12.84 | 0.14 |
| I DRG CFA 3 | 25.17 | 12.23 | 12.94 | 0.13 |
| I DRG CFA 7 | 25.05 | 12.16 | 12.89 | 0.13 |
| I DRG CFA 10 | 24.88 | 12.34 | 12.54 | 0.17 |
| I DRG CFA 14 | 24.57 | 11.84 | 12.73 | 0.15 |
| I DRG CFA 28 | 24.69 | 12.14 | 12.55 | 0.17 |
| Naïve DRG | 24.99 | 11.82 | 13.18 | 0.11 |
| I DRG AXT 1 | 24.95 | 12.11 | 12.84 | 0.14 |
| I DRG AXT 3 | 25.24 | 12.30 | 12.94 | 0.13 |
| I DRG AXT 7 | 25.57 | 12.15 | 13.43 | 0.09 |
| I DRG AXT 14 | 25.27 | 11.99 | 13.29 | 0.10 |
| Naïve SC | 22.31 | 12.34 | 9.97 | 1.00 |
| I SC CCI 3 | 22.80 | 12.63 | 10.17 | 0.87 |
| I SC CCI 7 | 22.71 | 12.79 | 9.92 | 1.03 |
| I SC CCI 10 | 22.42 | 13.14 | 9.28 | 1.61 |
| I SC CCI 14 | 22.33 | 12.12 | 10.22 | 0.84 |
| I SC CCI 28 | 22.47 | 13.07 | 9.40 | 1.48 |
| Naïve SC | 22.67 | 12.85 | 9.82 | 1.11 |
| I SC CFA 1 | 22.96 | 12.77 | 10.19 | 0.86 |
| I SC CFA 3 | 22.75 | 12.45 | 10.31 | 0.79 |
| I SC CFA 7 | 23.30 | 12.37 | 10.93 | 0.51 |
| I SC CFA 10 | 23.09 | 12.86 | 10.23 | 0.83 |
| I SC CFA 14 | 23.14 | 13.30 | 9.84 | 1.09 |
| I SC CFA 28 | 23.03 | 12.97 | 10.06 | 0.94 |
| Naïve SC | 22.75 | 12.71 | 10.04 | 0.95 |
| I SC AXT 1 | 22.65 | 12.81 | 9.85 | 1.09 |
| I SC AXT 3 | 23.26 | 12.51 | 10.75 | 0.58 |
| I SC AXT 7 | 23.36 | 12.42 | 10.94 | 0.51 |
| I SC AXT 14 | 22.41 | 13.34 | 9.07 | 1.86 |
| mAorta | 38.01 | 14.41 | 23.60 | 0.00 |
| mL4/5 DRG | 34.11 | 13.69 | 20.42 | 0.00 |
| mCerv DRG | 34.00 | 14.01 | 19.99 | 0.00 |
| mL4/5 SC | 28.77 | 12.79 | 15.98 | 0.02 |
| mCerv. SC | 28.95 | 12.95 | 16.00 | 0.02 |
| mSciatic | 39.37 | 14.58 | 24.80 | 0.00 |
| mPancreas | 40.00 | 28.96 | 11.04 | 0.47 |

TABLE 17-continued

| | 12818 Rat Panel Phase II and III | | | |
|---|---|---|---|---|
| Tissue | r12818 | 18S | ∂Ct | Expression |
| SNS WT | 32.44 | 13.23 | 19.21 | 0.00 |
| SNS WT | 31.22 | 12.66 | 18.56 | 0.00 |
| rDRG | 26.62 | 13.64 | 12.99 | 0.12 |
| rSC | 28.40 | 15.21 | 13.19 | 0.11 |

In Situ Hybridization of 16002

ISH experiment using a human probe showed that the 16002 gene is expressed in human, monkey and rat cortex as well as in monkey and rat spinal cord and DRG. In the rat brain this gene is also expressed at high levels in the hippocampus and at lower levels in the thalamus and in the basal ganglia. In the spinal cord, 16002 is expressed in lamina II of the dorsal horn as well as in laminae V-X. In the DRG, neurons mainly of intermediate size are expressing this gene.

Human 50566 (G2RF)

The present invention is based, at least in part, on the discovery of novel molecules, referred to herein as "Glyoxalase II Related Factor" or "G2RF" or "50566" nucleic acid and polypeptide molecules, which are novel members of the glyoxalase system enzyme family. These novel molecules are capable of metabolizing toxic compounds (e.g., cytotoxin or other metabolites) in a cell, e.g., a heart, placenta, lung, liver, skeletal muscle, thymus, kidney, pancreas, testis, ovary, prostate, colon, or brain cell. By doing so, these molecules help maintain a proper equilibrium of toxic compounds in a cell, thus preventing the occurrence of cellular damage.

As used herein, a "glyoxalase II related factor" includes a protein or polypeptide which is involved in the metabolism of cytotoxins and other metabolites, as well as in the regulation of their cellular levels. As used herein, the terms "cytotoxins" and "metabolites" include compounds which can be harmful or detrimental to a cell when present in sufficient concentrations or quantities. Cytotoxins and metabolites include those which arise from endogenous sources, e.g., the normal metabolic processes of the cell such as the energetic metabolic pathways. Cytotoxins and metabolites may also enter the cell from the extracellular milieu. Cytotoxins and metabolites which enter the cell include those which originate from outside the organism (xenobiotic compounds). Examples of cytotoxins and metabolites include oxaloaldehydes, hydrocarboxylic acids, pharmacological compounds (e.g., chemotherapeutic compounds and anti-cancer drugs), oxidative compounds, glutathione-conjugates, energy metabolites, methylglyoxal, and the like.

As used herein, the phrase "regulation of cellular levels" includes cellular mechanisms involved in regulating and influencing the levels (e.g., intracellular and/or extracellular levels) of cytotoxins and metabolites (e.g., oxaloaldehydes and hydrocarboxylic acids or glutathione-conjugates). Such mechanisms include the conversion of potentially cytotoxic compounds into non-toxic or less toxic compounds, e.g., conversion of oxaloaldehydes (such as methylglyoxal or glutathione conjugates) into hydrocarboxylic acids (such as lactate) in response to biological cues, such as formation of nucleotide adjunct, modification of amino acids, and oxidative stress. The maintenance of regulation of cytotoxin and metabolite levels is particularly important for a cell's ability to function properly. Thus, the G2RF or 50566 molecules, by participating in the regulation of cytotoxin and metabolite levels, may provide novel diagnostic targets and therapeutic agents for controlling cytotoxin- and metabolite-associated disorders (e.g., glyoxalase-associated disorders, oxaloaldehyde- and methylglyoxal-associated disorders).

As used herein, the terms "cytotoxin-associated disorders" and "metabolite-associated disorders" include disorders, diseases, or conditions which are characterized by aberrant, e.g., upregulated, downregulated, or misregulated, cytotoxin and/or metabolite levels (e.g., oxaloacetate, hydroxycarboxylic acid, thioester compound, or glutathione-conjugated compound levels). Examples of such disorders may include cardiovascular disorders, e.g., arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, or arrhythmia.

Other examples of cytotoxin- and metabolite-associated disorders include disorders of the central nervous system, e.g., cystic fibrosis, type 1 neurofibromatosis, cognitive and neurodegenerative disorders, examples of which include, but are not limited to, Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further cytotoxin- and metabolite-associated disorders include, for example, those listed in the American Psychiatric Association's Diagnostic and Statistical manual of Mental Disorders (DSM), the most current version of which is incorporated herein by reference in its entirety.

Still other examples of cytotoxin- and metabolite-associated disorders include cellular proliferation, growth, differentiation, or migration disorders. Cellular proliferation, growth, differentiation, or migration disorders include those disorders that affect cell proliferation, growth, differentiation, or migration processes. As used herein, a "cellular proliferation, growth, differentiation, or migration process" is a process by which a cell increases in number, size or content, by which a cell develops a specialized set of characteristics which differ from that of other cells (e.g., spermatogenesis), or by which a cell moves closer to or further from a particular location or stimulus. Such disorders include cancer, e.g., carcinoma, sarcoma, or leukemia; tumor angiogenesis and metastasis; skeletal dysplasia; hepatic disorders; and hematopoietic and/or myeloproliferative disorders.

Still other examples of cytotoxin- and metabolite-associated disorders include disorders of the immune system, such as the immune response during starvation, Wiskott-Aldrich syndrome, viral infection, autoimmune disorders or immune deficiency disorders, e.g., congenital X-linked infantile hypogammaglobulinemia, transient hypogammaglobulinemia, common variable immunodeficiency, selective IgA deficiency, chronic mucocutaneous candidiasis, or severe combined immunodeficiency. Other examples of cytotoxin- and metabolite-associated disorders include congenital malformities, including facio-genital dysplasia; and skin disorders, including microphthalmia with linear skin defects syndrome.

The term "family" when referring to the polypeptide and nucleic acid molecules of the invention is intended to mean two or more polypeptides or nucleic acid molecules having a common structural domain or motif and having sufficient amino acid or nucleotide sequence homology as defined herein. For example, the family of G2RF polypeptides comprise at least one "transmembrane domain." As used herein, the term "transmembrane domain" includes an amino acid sequence of about 20-45 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, alanines, valines, phenylalanines, prolines or methionines. Transmembrane domains are described in, for example, Zagotta W. N. et al., (1996) *Annual Rev. Neurosci.* 19: 235-263, the contents of which are incorporated herein by reference. Amino acid residues 129-145 of the human G2RF polypeptide (SEQ ID NO:74) comprise a transmembrane domain. Accordingly, G2RF or 50566 polypeptides having at least 50-60% homology, preferably about 60-70%, more preferably about 70-80%, or about 80-90% homology with a transmembrane domain of human G2RF or 50566 are within the scope of the invention.

To identify the presence of a transmembrane domain in a G2RF or 50566 protein, and make the determination that a protein of interest has a particular profile, the amino acid sequence of the protein may be subjected to MEMSAT analysis. A MEMSAT analysis resulted in the identification of a transmembrane domain in the amino acid sequence of human G2RF or 50566 (SEQ ID NO:74) at about residues 129-145.

In another embodiment, a G2RF or 50566 molecule of the present invention is identified based on the presence of at least one "metallo-beta-lactamase superfamily domain", also referred to interchangeably herein as a "lactamase-B domain." As used herein, the term "metallo-beta-lactamase superfamily domain" or "lactamase-B domain" includes a protein domain having an amino acid sequence of about 80-250 amino acid residues and has a bit score of at least 80 when compared against a metallo-beta-lactamase superfamily domain Hidden Markov Model (HMM). Preferably, a "metallo-beta-lactamase superfamily domain" has an amino acid sequence of about 90-240, 100-220, 120-200, 140-180, or more preferably, about 165 amino acid residues, and a bit score of at least 90, 100, 110, 120, or more preferably about 133.3. In a preferred embodiment, a "metallo-beta-lactamase superfamily domain" includes a domain which has an amino acid sequence of about 80-250 amino acid residues, and serves to catalyze the hydrolysis of a thioester (e.g. the thioester in a lactoylglutathione compound). Metallo-beta lactamase superfamily domains are described in, for example, Carfi et al., (1995) EMBO *Journal* 14:4914-4921, the contents of which are incorporated herein by reference. To identify the presence of a metallo-beta-lactamase superfamily domain in a G2RF protein, and make the determination that a protein of interest has a particular profile, the amino acid sequence of the protein may be searched against a database of known protein domains (e.g., the HMM database). The metallo-beta-lactamase superfamily domain has been assigned the PFAM Accession No. PF00753 and InterPro Accession No. IPR001279. A search was performed against the HMM database resulting in the identification of a metallo-beta-lactamase superfamily domain in the amino acid sequence of human G2RF or 50566 (SEQ ID NO:74) at about residues 7-172 of SEQ ID NO:74.

A description of the Pfam database can be found in Sonhammer et al. (1997) *Proteins* 28:405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference.

In a preferred embodiment, the G2RF or 50566 molecules of the invention include at least one transmembrane domain and/or at least one a metallo-beta-lactamase superfamily domain.

Isolated G2RF or 50566 polypeptides of the present invention, have an amino acid sequence sufficiently identical to the amino acid sequence of SEQ ID NO:74 or are encoded by a nucleotide sequence sufficiently identical to SEQ ID NO:73 or 75. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains having at least 50%, 55%, 60%, 65%, 70%, 75%, 80%, 85%, 85%, 90%, 95%, 96%, 97%, 98%, 99% or more homology or identity across the amino acid sequences of the domains and contain at least one and preferably two structural domains or motifs, are defined herein as sufficiently identical. Furthermore, amino acid or nucleotide sequences which share at least 50%, 52%, 53%, 54%, 55%, 60%, 65%, 70%, 75%, 80%, 85%, 85%, 90%, 95%, 96%, 97%, 98%, 99% or more homology or identity and share a common functional activity are defined herein as sufficiently identical.

In a preferred embodiment, a G2RF or 50566 polypeptide includes at least one or more of the following domains: a transmembrane domain and/or a metallo-beta-lactamase superfamily domain, and has an amino acid sequence at least about 50%, 53%, 54%, 55%, 60%, 65%, 70%, 75%, 80%, 85%, 85%, 90%, 95%, 96%, 97%, 98%, 99% or more homologous or identical to the amino acid sequence of SEQ ID NO:74. In yet another preferred embodiment, a G2RF polypeptide includes at least one or more of the following domains: a transmembrane domain and/or a metallo-beta-lactamase superfamily domain, and is encoded by a nucleic acid molecule having a nucleotide sequence which hybridizes under stringent hybridization conditions to a complement of a nucleic acid molecule comprising the nucleotide sequence of SEQ ID NO:73 or SEQ ID NO:75. In another preferred embodiment, a G2RF polypeptide includes at least one or more of the following domains: a transmembrane domain and/or a metallo-beta-lactamase superfamily domain, and has a G2RF activity.

As used interchangeably herein, "G2RF or 50566 activity", "biological activity of G2RF or 50566" or "functional activity of G2RF or 50566", includes an activity exerted by a G2RF polypeptide or nucleic acid molecule on a G2RF responsive cell or tissue, or on a G2RF polypeptide substrate, as determined in vivo, or in vitro, according to standard techniques. In one embodiment, a G2RF activity is a direct activity, such as an association with a G2RF-target molecule. As used herein, a "target molecule" or "binding partner" is a molecule with which a G2RF polypeptide binds or interacts in nature, such that G2RF-mediated function is achieved. A G2RF target molecule can be a non-G2RF molecule, for example, a non-G2RF polypeptide. In an exemplary embodiment, a G2RF target molecule is a G2RF ligand, e.g., a cytotoxin, a metabolite, glutathione, a gluathione-conjugated compound such as lactoylglutathione, or a thioester-containing compound. For example, a G2RF target molecule can have one or more of the following activities: (1) it may interact with cytotoxins and metabolites (e.g., lactoylglutathione, a glutathione-conjugated metabolite, a hydroxycarboxylic acid, and the like), (2) it may catalyze the mebobolism of a cytotoxin or metabolite (e.g., lactoylglutathione, a glutathione-conjugated metabolite, a hydroxycarboxylic acid, and the like), (3) it may hydrolyze a thioester containing compound (e.g., lactoylglutathione, and the like), (4) it may catalyze the formation of a thioester conjugation on a substrate (e.g., lactate or a hydroxycarboxylic acid). Moreover, a G2RF activity is an indirect activity, such as a cellular signaling activity mediated by interaction of the G2RF polypeptide with a G2RF ligand. The biological activities of G2RF are described herein. For example, the G2RF polypeptides of the present invention can have one or more of the following activities: (1) modulation of signal transduction in a cell, (2) modulation of cytotoxin and/or metabolite levels (e.g., detoxification), (3) maintenance of equilibrium of cytotoxins and/or metabolites, (4) modulation of cancer or tumor progression, (5) modulation of cellular proliferation, (6) modulation of tissue development (e.g. embryogenesis), (7) modulation of differentiation, (8) modulation of apoptosis, and (9) modulation of energy metabolism.

The human G2RF or 50566 cDNA sequence (SEQ ID NO:73), which is approximately 1154 nucleotide residues long including un-translated regions, contains a predicted methionine-initiated coding sequence of about 846 nucleotide residues, (nucleotide residues 22-867 of SEQ ID NO:73; 1-846 SEQ ID NO:75), not including the terminal codon. The coding sequence encodes a 282 amino acid protein having the amino acid sequence SEQ ID NO:74.

Analysis of the Human G2RF or 50566 Molecules

A search using the polypeptide sequence of SEQ ID NO:74 was performed against the HMM database in PFAM resulting in the identification of a metallo-beta-lactamase superfamily domain in the amino acid sequence of human G2RF or 50566 at about residues 7-172 of SEQ ID NO:74 (score=133.3).

A search using the polypeptide sequence of SEQ ID NO:74 was also performed against the Memsat database, resulting in the identification of a potential transmembrane domain in the amino acid sequence of human G2RF or 50566 (SEQ ID NO:74) at about residues 129-145, and the identification of a potential signal peptide in the amino acid sequence of human G2RF at about residues 1-54 of SEQ ID NO:74.

Further domain motifs were identified by using the amino acid sequence of 50566 (SEQ ID NO:74) to search the Propom database. Numerous matches against protein domains described as "Hydrolase II Hydroxyacylglutathione Glyoxalase Glx Zinc Cytoplasmic Plasmid Peptide Multigene", Hydrolase Similar Flavoprotein Rv2260 Tuberculosis Mycobacterium PH1213", "Hydrolase II Hydroxyacylglutathione Zinc Glyoxalase Glx Precursor Family", "II Hydrolase Glyoxalase Glx Hydroxyacylglutathione Zinc Precursor Specific MNCB-5687 Peptide" and the like were identified.

A search was also performed against the Prosite database, which resulted in the identification of a potential "cAMP- and cGMP-dependent protein kinase phosphorylation site" at residues 232-235 of SEQ ID NO:74 (Prosite accession number PS00004), two potential "Protein kinase C phosphorylation sites" at residues 86-88 and 235-237 of SEQ ID NO:74 (Prosite accession number PS00005), multiple potential "Casein kinase II phosphorylation sites" at residues 143-146, 155-158, 177-180 and 213-216 of SEQ ID NO:74 (Prosite accession number PS00006), and multiple potential N-myristoylation sites at residues 44-49, 140-145 and 274-279 of SEQ ID NO:74 (Prosite accession number PS00008).

The amino acid sequence of human G2RF or 50566 was analyzed using the program PSORT to predict the localization of the proteins within the cell. This program assesses the presence of different targeting and localization amino acid sequences within the query sequence. The results of the analyses show that human G2RF may be localized to the cytoplasm, nucleus, mitochondria, or golgi.

Tissue Expression Analysis of G2RF mRNA Using Taqman Analysis

The following describes the tissue distribution of human G2RF mRNA in a variety of cells and tissues, as determined using the TaqMan™ procedure.

An array of human tissues were tested. Expression was greatest in the brain cortex and hypothalamus, normal skin, heart with coronary heart failure (CHF) and erythroid cells. Expression was also high in the kidney, coronary smooth muscle cells (SMC), human umbilical vein epithelial cells (HUVEC), normal spinal cord tissue, dorsal root ganglions and colon tumor.

Human 65552

The present invention is based, in part, on the discovery of a novel gene encoding an MMP ("MMP" is used interchangeably herein with "matrix metalloprotease", "matrix metalloprotease-ADAMTS" and "matrix metalloproteinase"), the gene referred to herein as "65552".

The human 65552 cDNA sequence (SEQ ID NO:76), which is approximately 2853 nucleotide residues long including un-translated regions, contains a predicted methionine-initiated coding sequence of about 2850 nucleotide residues, (i.e., nucleotide residues 1-2850 of SEQ ID NO:76; also shown in SEQ ID NO:78). The coding sequence encodes a 950 amino acid protein having the amino acid sequence SEQ ID NO:77.

A hydropathy plot of human 65552 was performed. Polypeptides of the invention include fragments which include: all or part of a hydrophobic sequence, e.g., the sequence from about amino acid 408 to 424 of SEQ ID NO:77; a sequence which includes a Cys, or a glycosylation site.

The 65552 protein contains a significant number of structural characteristics in common with members of the matrix metalloproteinase (MMP) family. The 65552 protein contains a significant number of structural characteristics in common with members of the adamalysins (reprolysin) family. For example, the 65552 molecule may contain a peptidase M12B propeptide domain, a reprolysin domain, and a thrombospondin domain.

Matrix metalloproteinase adamalysin molecules require a metal for catalyzing the cleavage of peptides or proteins. Typically, these proteases require zinc for the catalysis, ligands for which can be histidine residues. Many of these proteins have collagenase-like catalytic activity. For example, collagens are extracellular matrix proteins responsible for the architecture and structural integrity of most tissues and stromelysin, which degrade the extracellular matrix.

Metalloproteases (also referred to herein as "metallopeptidases" or "metalloproteinases" or "MMPs") are a group of highly diverse, widely distributed proteolytic enzymes that depend on bound $Ca^{2+}$ or $Zn^{2+}$ for activity. Certain metalloproteases can readily utilize $Mn^{2+}$ and $Mg^{2+}$ as well. About 30 families of metalloproteases are recognized, about half of which comprise enzymes containing the HEXXH motif (SEQ ID NO:84) (Rawlings et al. (1995) *Meth Enzymol* 248:183-228). The most thoroughly characterized of the metalloproteases is thermolysin, a member of the M4 metalloprotease family.

Another metalloprotease family, the M12 family, contains the reprolysin (M12B) subfamily, which contains the snake venom metalloproteases and adamalysins family. The reprolysin subfamily also includes BRCA1, a human breast cancer-associated protein, and mammalian fertilin.

The ADAM subfamily of reprolysins comprises a broad family of multifunctional proteins, members of which may include, but are not limited to, a disintegrin and/or a metalloprotease domain (Wolfsberg et al. (1995) *Developmental Biol* 169:378-383; Wolfsberg et al. (1995) *J Cell Biol* 131:275-278; Hurskainen et al. (1999) *J Biol Chem* 274:25555-25563).

The ADAMs are expressed by a wide variety of cell types, and are involved in functions as diverse as sperm-egg binding, myotube formation, neurogenesis, and proteolytic processing of cell surface proteins. Their functions involve proteolysis on the cell surface: the formation and inactivation of regulatory peptides and growth factors, as well as modification of cell surface proteins. Most members of this family are snake venom endopeptidases, but there are also some mammalian proteins such as fertilin and TACE. (Fertilin is involved in sperm-egg binding, and TACE is a member of the ADAM family that cleaves membrane-bound TNF-alpha to generate soluble TNF-alpha). The active enzymes degrade components of the extracellular matrix, playing a role in the initial steps of tissue remodeling during morphogenesis, wound healing, angiogenesis and tumor invasion.

The ADAMTSs ("a disintegrin and metalloprotease with thrombosponding type I motifs") subfamily of ADAMs are similar in domain organization (though different from other ADAM family members), having one or more of the following domains: a signal peptide, peptidase M12B propeptide domain, a zinc binding region signature a domain, a cysteine-rich domain, a thrombospondin type-1 domain, and in many cases a membrane-spanning region and a cytoplasmic domain with signaling potential. For example, ADAMTS-1 differs from other ADAM family members due to a lack of the cysteine rich, EGF and transmembrane domains and the addition of thrombospondin type I motifs (Kuno et al. (1997) *J Biol Chem* 272: 556-562).

Reprolysin (M12B) is a zinc metalloprotease family member with no disintegrin-like domain, but with one propeptide for members of the peptidase family M12, and one thrombospondin type I motif. These proteins have collagenase-like catalytic activity. For example, collagens are extracellular matrix proteins responsible for the architecture and structural integrity of most tissues. They are synthesized as procollagens and go through a series of post-translational modifications both inside and outside the cell before they are fully functional (Duance and Bailey (1981) *Handbook of Inflammation. Vol. 3 Tissue Regeneration and Repair*, ed. Glynn, L E Elsevier, Amsterdam, 51-109). Included in collagen maturation are the steps of removing the extension peptides from the N- and C-termini. The failure of this process results in many connective tissue disorders, for example, Ehlers-Danlos syndrome type VIIC, characterized by the retention of the N-terminal propeptide of collagen I (Lenaers et al. (1971) *Eur J Biochem* 23: 533-543) by a metalloprotease, procollagen I N-protease (Colige et al. (1999) *Am. J. Hum. Genet.* 65: 308-317).

The known members of the reprolysin subfamily mostly lack essential peptidase active sites, but can contain one of the following domains: a C-terminal disintegrin-like domain, an epidermal growth factor (EGF)-like domain, and transmembrane domains (Rawlings et al. (1995) *Meth Enzymol* 248: 183-228). In addition, members of the reprolysin (M12B) subfamily of zinc metalloproteases contain a reprolysin propeptide region. Many MMPs are expressed as latent proenzymes that are activated by proteolytic cleavage. Cleavage of the M12B propeptide triggers a conformational change in the propeptide, thereby converting an M12B family type metalloprotease to its active strate. Coordination of Zn2+ in the active site of the catalytic domain of the M12B propeptide by a cysteine residue in the prodomain is critical for inhibition of the protease. (Overgaard et al. (1999), *J Biol. Chem.,* 7:274 (19):13427-33).

The reprolysin domain is characteristic of extracellular metalloproteinases, such as collagenase and stromelysin, which degrade the extracellular matrix. The members of this family are enzymes that cleave peptides. These proteases require zinc for catalysis, ligands for which can be histidine residues. Members of this family are also known as adamalysins. There are two subfamilies of adamalysins: the snake venom metalloproteases (SVMPs) and the ADAMs ("a disintegrin and metalloprotease"). At least 23 ADAMs have been identified to date. Members of the ADAMs family of proteins include, but are not limited to, MDC (ADAM1), ADAMTS-1, fertilin (ADAM2), cryitestin (ADAM3), epididymal apical protein I, meltrin, MS2, TNF-a converting enzyme, Kuzbanian and metargidin.

The thrombospondin type I (TSP I) motifs in ADAMTS-1 enable it to bind to the extracellular matrix (Kuno and Matsushima (1998) *J Biol Chem* 273: 13912-13917). TSP I motifs are conserved domains in thrombospondin 1 and 2, multifunctional secretory glycoproteins involved in blood clotting, inhibiting angiogenesis and regulating the proliferation, adhesion and migration of normal and tumor cells. The biological activities of thrombospondin 1 and 2 are mediated by the binding of the TSP type I motifs to extracellular matrix molecules, such as heparan sulfate, proteoglycans, fibronectin, laminin and collagen. Thrombospondin-1 is a platelet-derived glycoprotein that is released from platelet alpha granules in response to thrombin stimulation. It is involved in cell adhesion and modulates cell movement, cell proliferation, neurite outgrowth and angiogenesis. In general, the biological functions of metalloproteases include protein maturation, degradation of proteins, such as extracellular matrix proteins (ECM proteins), tumor growth, metastasis and angiogenesis, among others. Thus, metalloproteases are likely to play important roles in a wide range of diseases including, but not limited to, cancer, arthritis, Alzheimer's disease, and a variety of inflammatory conditions. Other normal and pathological processes in which MMP-catalyzed changes in ECM protein structures have been implicated are described, for example, in Nagase et al. (1999) *J. Biol. Chem.* 274:21491-21494. Accordingly, metalloproteases are an important target for drug action and development. Therefore, it is valuable to the field of pharmaceutical development to identify and characterize previously unknown metalloproteases.

A human 65552 polypeptide can include a reprolysin domain.

In a preferred embodiment, the reprolysin domain is characteristic of extracellular metalloproteinases.

As used herein, the term "reprolysin domain" refers to a protein domain having an amino acid sequence of about 100-300 amino acid residues in length, and having an E value of about 2.5e-8. Preferably, the reprolysin domain has a length of about 100-300 amino acid residues in length, preferably about 150-250 amino acid residues in length, more preferably about 175-225 amino acid residues in length, and even more preferably about 205-220 amino acids residues in length, and has an E-value of about 2.5 e-9 or less, more preferably about 2.5 e-10 or less, and most preferably about 2.5e-11 or less. The reprolysin domain has been assigned the PFAM Accession number PF01421.

The consensus sequence for a reprolysin domain was derived from a hidden Markov model (HMM) within Pfam (version 5.5) (PFAM Accession number PF01421). An alignment of the 65552 protein with a consensus reprolysin amino acid sequence (SEQ ID NO:80) has a predicted bit score of 9.3, and an E-value of 2.5e-11. Preferably, the reprolysin domain has the ability to cleave a protein or peptide in the presence of a metal (i.e., $Zn^{++}$).

A reprolysin domain of a 65552 protein can also include a neutral zinc metallopeptidases, zinc-binding region having the following signature sequence: [GSTALIVN]-x(2)-H-E-[LIVMFYW]-{DEHRKP}-H-x-[LIVMFYWGSPQ] (SEQ ID NO:83). In this signature sequence pattern, each element in the pattern is separated by a dash (-); square [ ] brackets indicate the particular residues that are accepted at that position; elaborate { } brackets indicate the residues that are not accepted at that position; x indicates any residue is accepted at that position; a whole number in parenthesis following an x indicates any amino acid repetition of a particular element is accepted for that specified number of residues i.e., x(4), and the standard IUPAC one-letter code for the amino acids is used. The two H's are zinc ligands and E is the active site residue.

This signature sequence can be found from about residues 358 to 367 of the 65552 protein (SEQ ID NO:77). For example, the conserved histidines can be found at about amino acid residues 361 and 365 of SEQ ID NO:77. These histidine residues are believed to interact with zinc ions.

In a preferred embodiment, 65552 polypeptide or protein has a reprolysin domain or a region which includes at least about 100 to 300, more preferably about 150 to 250, 175 to 225, 205 to 220 amino acid residues and has at least about 60%, 70%, 80%, 90%, 95%, 99%, or 100% identity with a reprolysin domain, e.g., the domain of human 65552 (e.g., residues 218 to 427 of SEQ ID NO:77) (SEQ ID NO:80). Preferably a 65552 polypeptide or protein contains the typical neutral zinc metallopeptidases, zinc binding region signature sequence described above. This sequence is located at about amino acid residues 357 to 367 of SEQ ID NO:77.

A 65552 polypeptide can also include one or more peptidase M12B propeptide domains. As used herein, the term "peptidase M12B propeptide domain" refers to a protein domain having an amino acid sequence of about 40 to 160 amino acid residues in length, and having an E value of about 4.3 e-3. The peptidase M12B propeptide domain has a length of about 40 to 160 amino acid residues, preferably between about 60 to 150 amino acids residues in length, more preferably between about 80 to 130 amino acid residues in length, and even more preferably between about 100 to 120 amino acid residues in length, and has an E-value of about 4.3e-4 or less, more preferably 4.3-5 or less, and most preferably about 4.3e-6 or less.

The peptidase M12B propeptide domain of the 65552 polypeptide shows homology to the peptidase M12B propeptide domain corresponding to PFAM Accession PF06562 derived from a hidden Markov model (HMM) within Pfam (version 5.5) (PFAM Accession number PF01562) (SEQ ID NO:79). An alignment of the 65552 protein (residues 67-181 of SEQ ID NO:77) with a consensus peptidase M12B propeptide amino acid sequence derived from a hidden Markov model as predicted by PFAM has a bit score of 25.7, and an E-value of 24.3e-6.

In a preferred embodiment, a 65552 polypeptide or protein has a peptidase M12B propeptide domain or a region which includes at least about 40-160 amino acids, preferably about 60-150 amino acids, more preferably about 80-130 amino acids, even more preferably about 100-120 amino acid residues and has at least about 60%, 70%, 80%, 90%, 95%, 99%, or 100% identity with a peptidase M12B propeptide domain (e.g., the peptidase M12B propeptide domains of human 65552 (e.g., residues 67-181 of SEQ ID NO:77).

The peptidase M12B propeptide domain may be involved in maintaining the protease in a latent form. The propeptide contains a sequence motif similar to the "cysteine switch" of matrixins. The function of the domain can be explained by the cysteine switch model, in which coordination of Zn2+ in the active site of the catalytic domain by a cysteine residue in the prodomain is critical for inhibition of the protease.

A 65552 polypeptide can also include one or more thrombospondin type 1 domains. As used herein, the term "thrombospondin type 1 domain" also referred to herein as "TSP-1 domain" refers to a protein domain having an amino acid sequence of about 10 to 100 amino acid residues in length, and an E-value of about 1.5e-4. Preferably, the TSP-1 domain is between 10 to 100 amino acid residues in length, preferably between about 20 to 80 amino acids residues in length, more preferably between about 40 to 60 amino acid residues in length, and even more preferably between about 45 to 55 amino acids in length, and has an E-value of about 1.5e-5 or less, more preferably about 1.5e-5 or less, and most preferably about 1.5e-7 or less. The thrombospondin type 1 domain has been assigned the PFAM Accession number PF00090. An alignment of the 65552 protein, (amino acid residues 520-570 of SEQ ID NO:77) with a consensus thrombospondin type 1 amino acid sequence (SEQ ID NO:81) derived from a hidden Markov model within Pfam (version 5.5) (PFAM Accession number PF00090) (SEQ ID NO:81) has a bit score of 38.5, and an E-value of 1.5e-07.

In a preferred embodiment, a 65552 polypeptide or protein has a thrombospondin type 1 domain or a region which includes at least about 10-100 amino acids, preferably about 20-80 amino acids, more preferably about 40-60 amino acids, even more preferably about 45-55 amino acid residues and has at least about 60%, 70%, 80%, 90%, 95%, 99%, or 100% identity with a thrombospondin type 1 domain, e.g., the thrombospondin type 1 domains of human 65552 (e.g., 520-570 of SEQ ID NO:77).

Preferably, the thrombospondin type 1 domain has the ability to suppress tumor growth by its ability to inhibit neovascularization (angiogenesis) and proliferation. Preferably as well, the thrombospondin type 1 domain has the ability to modulate cell-cell interaction (i.e., modulating endothelial cell growth, adhesion, and motility and apoptosis).

To identify the presence of a reprolysin domain profile, a peptidase M12B propeptide domain profile, and a thrombospondin type 1 domain profile in a 65552 polypeptide, the amino acid sequence of the protein is searched against a database of HMMs (e.g., the Pfam database, release 2.1) using the default parameters. For example, the hmmsf program, which is available as part of the HMMER package of search programs, is a family specific default program for PF01421, PF01562, and PF00090 and score of 15 is the default threshold score for determining a hit. Using the hmmsf program, the following domains were identified: a reprolysin domain profile was identified in the amino acid sequence of SEQ ID NO:77 (e.g., amino acids 218-427 of SEQ ID NO:77 (SEQ ID NO:80)); a peptidase M12B propeptide was identified in the amino acid sequence of SEQ ID NO:77 (e.g., amino acids 67-181 of SEQ ID NO:77 (SEQ ID NO:79)), and a thrombospondin type 1 domain profile was identified in the amino acid sequence of SEQ ID NO:77 (e.g., amino acids 520-570 of SEQ ID NO:77 (SEQ ID NO:81)). Accordingly, a 65552 protein, or a domain thereof having at least about 60-70%, more preferably about 70-80%, or still more preferably about 80-90% homology with the reprolysin domain profile, and the peptidase M12B propeptide domain profile, and the thrombospondin type I domain profile of human 65552 are within the scope of the invention.

For further identification of polypeptides, and demonstration of shared characteristics with other metalloproteases, the 65552 polypeptide molecule is aligned to that of other metalloproteases. An alignment of human 65552 protein (SEQ ID NO:77) with a murine metalloproteinase (Swissprot Accession #: O54768: SEQ ID NO:82) demonstrates that these sequences are 43.4% identical, and have a glogal alignment score of 2516.

The human 65552 polypeptide can also contains a leucine zipper pattern, or regions homologous with a leucine zipper pattern.

Metalloproteases, fragments or variants thereof can have a leucine zipper motif or regions homologous with a leucine zipper motif. Leucine zippers typically contain a repeat of leucine positioned every seven amino acids (L-x(6)-L-x(6)-L-x(6)-L) (SEQ ID NO:85), over a distance of eight helical turns. The segments containing these periodic arrays of leucines appear to exist in an alpha-helical conformation in which leucine side chains extending from one alpha-helix interact with those from a similar alpha helix of a second polypeptide, facilitating dimerization. These interactions are frequently required for the activity of the protein complex, e.g., transcriptional activation of a nucleic acid via binding to a gene regulatory sequence and subsequent formation of a transcription initiation complex. Leucine zippers therefore mediate protein-protein interactions in vivo and in particular, interactions between multi-subunit transcription factors (homodimers, heterodimers, etc.).

Thus, in another embodiment, a 65552 metalloprotease or fragment or variant can have one or more activities of a leucine zipper motif, such as binding to another polypeptide that has a leucine zipper, for example, forming a dimer with a 65552 metalloprotease or fragment or variant containing a leucine zipper. The presence of a leucine zipper motif indicates that 65552 metalloprotease can participate in different pathways due to an ability to interact with different proteins via the leucine zipper motif. For example, the leucine zipper motif can allow 65552 metalloprotease binding to a protein substrate which 65552 may then cleave. Thus, the leucine zipper motif modulates or is involved in one or more activities or functions of 65552 metalloprotease through its ability to confer binding of 65552 metalloprotease to a target molecule or binding partner. The term "leucine zipper activity," when used in reference to a protein, means a protein having one or more activities associated with leucine-zipper function as described herein or otherwise known in the art.

65552 proteins of the invention can have signal sequences. As used herein, a "signal sequence" includes a peptide of at least about 15 or 20 amino acid residues in length which occurs at the N-terminus of secretory and membrane-bound proteins and which contains at least about 70% hydrophobic amino acid residues such as alanine, leucine, isoleucine, phenylalanine, proline, tyrosine, tryptophan, or valine. In a preferred embodiment, a signal sequence contains at least about 10 to 40 amino acid residues, preferably about 15-30 amino acid residues, more preferably about 17 amino acid residues, and has at least about 60-80%, more preferably 65-75%, and more preferably at least about 70% hydrophobic residues. A signal sequence serves to direct a protein containing such a sequence to a lipid bilayer. Thus, in one embodiment, a 65552 protein contains a signal sequence at about amino acids 1 to 17 of SEQ ID NO:77. The signal sequence is cleaved during processing of the mature protein.

In one embodiment, a 65552 protein exists in a mature form which does not include a signal sequence. In this embodiment, the 65552 protein can have a length of about 934 (e.g., 927, 928, 929, 930, 931, 932, 933, 934, 935, 936, or 937) amino acid residues, corresponding to a protein having an amino terminus at about residue 18 (e.g., at residues 15, 16, 17, 18, 19 or 20) and having a carboxyl terminus at about residue 950 of SEQ ID NO:77. In this embodiment, the protein is preferably not membrane-bound, and is also preferably extracellular.

The human 65552 protein has four predicted N-glycosylation sites (Pfam Accession number PS00001) at about amino acid residues 141-144, 591-594, 623-626 and 679-682 of SEQ ID NO:77; two glycosaminoglycan attachment sites (PFAM Accession Number PS00002) at about amino acid residues 417-420 and 760-763; two cAMP and cGMP-dependent protein kinase phosphorylation sites (PFAM Accession Number PS00004) at about amino acid residues 204-207 and 683-686 of SEQ ID NO:77; fourteen predicted protein kinase C phosphorylation sites (PFAM Accession Number PS00005) at about amino acid residues 171-173, 203-205, 207-209, 288-290, 303-305, 471-473, 575-577, 578-580, 594-596, 617-619, 611-613, 665-667, 681-683, and 917-919 of SEQ ID NO:77; fourteen predicted casein kinase II phosphorylation sites (PFAM Accession Number PS00006) located at about amino acid residues 19-22, 317-320, 325-328, 337-340, 346-349, 359-362, 432-435, 492-495, 578-581, 611-614, 707-710, 730-733, 744-747, and 764-767 SEQ ID NO:77; fifteen predicted N-myristoylation sites (PFAM Accession Number PS00008) at about amino acid residues 90-95, 105-110, 121-126, 164-169, 175-180, 323-328, 352-357, 439-444, 476-481, 490-495, 535-540, 551-556, 658-663, 673-678, and 761-766 of SEQ ID NO:77; one predicted amidation site (PFAM Accession Number PS00009) at about amino acid residues 36-39 of SEQ ID NO:77; one predicted leucine zipper pattern (PFAM Accession Number PS00029) at about amino acid residues 238-259 of SEQ ID NO:77; one zinc binding signature (PFAM Accession Number PS00142) at about amino acid residues 358-367 of SEQ ID NO:77; and one P-II protein urydylation site at about amino acid residues 129-134 of SEQ ID NO:77.

Information regarding PFAM identifiers, PS prefix and PF prefix domain identification numbers can be found at Sonnhammer et al. (1997) *Protein* 28:405-420.

In one embodiment of the invention, a 65552 polypeptide includes at least one reprolysin domain. In another embodiment, the 65552 polypeptide comprises at least one reprolysin domain and at least one peptidase M12B propeptide domain.

In still another embodiment, the 65552 polypeptide contains at least one reprolysin domain, at least one peptidase M12B propeptide domain, and at least one thrombospondin type-1 domain.

The 65552 molecules of the present invention can further include one or more of the N-glycosylation, glycosaminoglycan attachment, cAMP and cGMP-dependent protein kinase phosphorylation, protein kinase C phosphorylation, casein kinase II phosphorylation, N-myristoylation, amidation, leucine zipper, zinc binding signature, and P-II protein urydylation sites sites described herein.

Because the 65552 polypeptides of the invention can modulate 65552-mediated activities, they can be used to develop novel diagnostic and therapeutic agents for 65552-mediated or related disorders, as described herein.

As used herein, a "65552 activity," "biological activity of 65552," or "functional activity of 65552," refers to an activity exerted (directly or indirectly) by a 65552 protein, polypeptide or nucleic acid molecule on, for example, a 65552-responsive cell or on a 65552 substrate (e.g., a protein substrate) as determined in vivo or in vitro. In one embodiment, a 65552 activity is a direct activity, such as association with a 65552 target molecule. A "target molecule" or "binding partner" of a 65552 protein is a molecule with which the 65552 protein binds or interacts in nature. In an exemplary embodiment, such a target molecule is a 65552 receptor. A 65552 activity can also be an indirect activity, such as a cellular signaling activity mediated by interaction of the 65552 protein with a 65552 receptor.

The 65552 molecules of the present invention can have similar biological activities as other MMP family members. For example, the 65552 proteins of the present invention can modulate (directly or indirectly) any one or more of the following activities: 1) smooth muscle cell function (i.e., the muscular component of visceral structures (i.e., blood vessels, the gastrointestinal tract, the uterus, or the urinary bladder)); 2) function of muscular arterial cells. (i.e., cells of radial arteries, (i.e., cells of the tunica intima or the tunica adventicia; 3) catalyzed cleavage of covalent bonds within or between amino acid residues in, for example, ECM, cell-surface, and extracellular proteins; 4) degradation of ECM; 5) angiogenesis; 6) neurite growth; 7 tumor cell invasion or metastasis; 8) the ability to modulate tissue or organ integrity; 9) wound healing; 10) endometrial cycling; 11) hair follicle cycling; 12) bone remodeling; 13) ovulation; 14 embryonic development; or 15) apoptosis.

Other activities, as described herein, include the ability to modulate function, survival, morphology, proliferation and/or differentiation of cells of tissues in which 65552 molecules are expressed. Thus, the 65552 molecules can act as novel diagnostic targets and therapeutic agents for controlling disorders involving aberrant activities of these cells.

As used herein, the term "metalloprotease activity," or "protease activity" when used in reference to a protein, means a protein having the ability to cleave a protein substrate by hydrolysis of an amide bond. Typically, the ability to cleave a protein substrate depends upon the presence of a metal ion, such as zinc. Thus, a 65552 metalloproteinase or fragment or variant having metalloproteinase activity is capable of cleaving one or more protein substrates in the presence of a metal, e.g., zinc. Thus, a 65552 metalloproteinase or fragment or variant having metalloproteinase activity is capable of cleaving one or more protein substrates in the presence of zinc.

Activity assays for the metalloproteinase family members, such as 65552 polypeptides, involve any of the known metalloproteinase, reprolysin, or thrombospondin-like activity or functions, as well as activities/functions that may not typically be found in other metalloproteinases. These assays include, but are not limited to: 1) binding extracellular matrix; 2) binding collagen or gelatin; 3) binding integrin; 4) binding zinc or other metals; 5) binding a2-macroglobulin; 6) cleaving specific peptide substrates to produce fragments, affecting cell adhesion; 7) binding heparin or other sulfated glycosaminoglycan, such as heparan sulfate; 8) modulation of vascularization or vascular endothelial growth; 9) breaking down cartilage; 10) induction of apoptosis of endothelial cells; 11) suppressing tumor growth; 12) modulating angiogenesis; 13) affecting cellular chemotaxis; 14) affecting cell-cell adhesion or cell-matrix interaction; 15) binding integrin; 16) and any of the other biological or functional properties of these proteins, including, but not limited to, those disclosed herein, and in the references cited herein. Further, assays can relate to changes in the protein, per se, and on the effects of these changes, for example, cleavage of the substrate, activation of the protein following cleavage, etc. Such assays are described in Tang et al. (1999) *FEBS Letters* 445:223-225 (for example, induction by interleukin I in vitro and by intravenous administration of lipopolysaccharide in vivo, as well as effects on cell adhesion, motility, and growth); Abbaszade et al., (*J Biol Chem.* 2000 Aug. 18; 275(33):25791-7). (for example, products resulting from cleavage at the Glu-Ala site in cartilage explants and chondrocyte cultures treated with interleukin I and retinoic acid, determination of aggrecan cleaving activity with and without hydroxamate inhibitors); (Kuno and Matsushima (1998) *J Biol Chem* 273: 13912-13917) (binding to the extracellular matrix, binding to sulfated glycosaminoglycans, binding to heparan sulfate); Kuno et al. *J* (1999) *Biol. Chem.* June 25; 274(26):18821-6. (protease trapping of a2-macroglobulin, furin processing); Tortorella et al. (1999) *Science.* 284(5420):1664-6. (detection of aggrecan fragments, especially by neoepitope antibodies, inhibition of cleavage by ADAM-TS inhibitors, inhibition of pro-MMP activation); Vasquez et al., *J Appl Physiol.* (1998) October; 85(4):1421-8. (suppression of fibroblast growth factor-2-induced vascularization in the cornea pocket assay and inhibition of vascular endothelial growth factor-induced angiogenesis in the chorioallantoic membrane assay, inhibition of endothelial cell proliferation, competitive inhibition with endostatin, proliferation of human dermal endothelial cells, use of the antiangiogenic region of the TSP-1 motif as bait); (Kuno et al. (1997) *J Biol Chem* 272: 556-562); Wolfsberg et al., *Dev Biol.* 1995 May; 169(1):378-83; Guilpin et al. (1988) *J. Biol. Chem.* 273:157-166 (α2-macroglobulin trapping, cleavage of prodomain at the furin site to generate active metalloproteinase); Rosendahl et al., (1997) (*J. Biol. Chem.* 272:24588-24593)) (TNF α processing). Recombinant assay systems include, but are not limited to, those described in Abbaszade et al., supra; Kuno et al. (1998), supra; Kuno et al. (1999), supra; Tortorella et al., supra; Vasquez et al., supra, and Kuno et al. (1997), supra.

As used herein, the term "TSP activity" or "TSP function," when used in reference to a protein, means a protein that has one or more activities associated with a TSP e.g., a TSP-1 domain as described herein or otherwise known in the art. For example, TSP domains are involved in cell adhesion, migration, proliferation, outgrowth or angiogenesis. Thus, a 65552 metalloproteinase or fragment or variant having a TSP activity can mediate or modulate cell-cell adhesion (e.g., due to the presence of 65552 metalloproteinase in extracellular matrix), motility/migration, proliferation, outgrowth or angiogenesis, for example. TSP domains also have been implicated in inflammatory conditions and, therefore, a 65552 metalloproteinase or fragment or variant with a TSP domain can participate in a pathway that affects an inflammatory response.

The 65552 metalloproteinase molecules find use in modulating 65552 metalloproteinase function, activity, or expression, or related responses to metalloproteinase function, activity or expression. As used herein, the term "modulate" or grammatical variations thereof means increasing or decreasing an activity, function, signal or response. That is, the 65552 metalloproteinase molecules of the invention affect the targeted activity in either a positive or negative fashion (e.g., increase or decrease activity, function, or signal). Accordingly, the 65552 molecules can act as novel diagnostic targets and therapeutic agents for controlling metalloproteinase disorders.

Thus, 65552 molecules described herein can act as novel diagnostic targets and therapeutic agents for prognosticating, modulating, diagnosing, preventing, inhibiting, alleviating, or treating metalloproteinase-associated disorders.

As used herein, a "metalloproteinase-associated disorder" (MMP-associated disorder) includes a disorder, disease or condition which is characterized by a misregulation of a metalloproteinase mediated activity or by an abnormal metalloproteinase mediated activity. Metalloproteinase-associated disorders can detrimentally affect cell proliferation, cell adhesion, cell motility and migration, tissue structural integrity (e.g., connective tissue formation and maintenance), inflammatory response, erythroid cell activity, gene expression, or angiogenesis and vascularization, among others. Thus, examples of metalloproteinase associated disorders in which the 65552 molecules of the invention can be directly or indirectly involved include cellular proliferative and/or differentiative disorders; disorders associated with undesirable or deficient vascularization/angiogenesis; disorders associated with undesirable or deficient cell adhesion, motility or migration, including, e.g., metastasis; disorders associated with undesirable or deficient tissue structural integrity; disorders associated with undesirable extracellular matrix accumulation, e.g., characterized by fibrosis or a scar; inflammatory disorders, erythroid cell associated disorders; gene expression disorders; and bleeding/clotting disorders.

The 65552 metalloproteinase molecules also find use in diagnosis of disorders involving an increase or decrease in 65552 metalloproteinase expression relative to normal expression, such as a proliferative disorder, a differentiative disorder (e.g., cancer), an immune disorder, an erythroid cell-associated disorder; a motility disorder, a vascular disorder, a bleeding or clotting disorder, or a developmental disorder. Thus, where expression or activity of 65552 metalloproteinase is greater or less than normal, this may indicate the presence of or a predisposition towards a 65552 metalloproteinase disorder. The presence of 65552 metalloproteinase RNA or protein, e.g., by hybridization of a 65552 specific probe or with a 65552 specific antibody, can be used to identify the amount of 65552 present in a particular cell or tissue, or other biological sample. 65552 activity (protease activity assays, adhesion assays, binding assays, motility/migration assays, vascularization assays, etc.) can be assessed using the various techniques described herein or otherwise known in the art. Thus, in another embodiment, the invention provides methods and compositions for detection of 65552 metalloproteinase in tissues that normally or do not normally express 65552 metalloproteinase.

The 65552 molecules and modulators thereof can act as novel therapeutic agents for controlling one or more of cellular proliferative and/or differentiative disorders, cardiovascular disorders, blood vessel disorders as described herein.

Tissue Distribution of 65552 mRNA

TaqMan analysis indicates the highest levels of 65552 expression are in aortic smooth muscle cells, and muscular artery cells. 65552 is also expressed in adipose tissue, human umbilical vein epithelial cells, diseased aorta cells, and cells of the vein Human 65577

The present invention is based, in part, on the discovery of a novel gene, referenced to herein as 65577, which encodes a matrix metalloprotease (also referred to herein as a matrix metalloproteinase, or an MMP), which is a member of the reprolysin (M12B) subfamily of the M12 family of metalloproteinase.

The human 65577 cDNA sequence which is approximately 3445 nucleotide residues long including un-translated regions, contains a predicted methionine-initiated coding sequence of about 3243 nucleotide residues, excluding termination codon (i.e., nucleotide residues 83-3325 of SEQ ID NO:86; 1-3243 of SEQ ID NO:88). The coding sequence encodes a 1081 amino acid protein having the amino acid sequence SEQ ID NO:87.

The 65577 protein contains a significant number of structural characteristics in common with members of the reprolysin (M12B) subfamily of MMPs. Like other members of this subfamily of MMPs, the 65577 proteins of the invention can include a peptidase M12B-propeptide domain having a sequence motif similar to the cysteine switch motif of the matrixins, and a reprolysin-like domain containing a zinc binding site (e.g., HEXXH; SEQ ID NO:84). Unlike the other members of the reprolysin (M12B) subfamily of MMPs, the 65577 proteins of the invention do not include an EGF-like domain, or a disintigrin domain.

The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., matrix metalloprotease proteins for any species described in the art (e.g., Steiner et al. (1995) *Mol. Microbiol.* 16:825-834, and references cited therein). Members of a family can also have common functional characteristics.

Metalloproteases are a group of highly diverse, widely distributed proteolytic enzymes that depend on bound $Ca^{2+}$ or $Zn^{2+}$ for activity. Certain metalloproteases can readily utilize $Mn^{2+}$ and $Mg^{2+}$ as well. About 30 families of metalloproteases are recognized, about half of which comprise enzymes containing the HEXXH motif (Rawlings et al. (1995) *Meth Enzymol* 248:183-228) (SEQ ID NO:84). The most thoroughly characterized of the metalloproteases is thermolysin, a member of the M4 metalloprotease family.

Another metalloprotease family, the M12 family, contains the reprolysin (M12B) subfamily, which contains the snake venom metalloproteases and adamalysins family. The known members of the reprolysin subfamily mostly lack essential peptidase active sites, but typically contain a putative zinc-chelating sequence HELGHNLGMKH (SEQ ID NO:93), characteristic for the reprolysin family of zinc-metalloproteinases. The reprolysin family also contains six cysteine residues in standard positions for this group of proteins suggesting disulfide bonding (Leonardi A J et al. (1999) *Chro-*

*matogrphy;* 852 (1):237-43). These include BRCA1, a human breast cancer-associated protein, and mammalian fertilin.

In addition, there is a propeptide region for members of the peptidase family M12B. The propeptide contains a sequence motif similar to the "cysteine switch" of the matrixins. Matrix metalloproteinases" are expressed as latent proenzymes that are activated by proteolytic cleavage that triggers a conformational change in the propeptide (cysteine switch) model, in which coordination of $Zn^{2+}$ in the active site of the catalytic domain by a cysteine residue in the prodomain is critical for inhibition of the protease. (Overgaard et al. (1999) *J Biol. Chem,* 7:274(19):13427-33).

In general, the biological functions of metalloproteases include protein maturation, degradation of proteins, such as extracellular matrix proteins, tumor growth, metastasis and angiogenesis, among others. Thus, metalloproteases are likely to play important roles in a wide range of diseases including, but not limited to, cancer, arthritis, Alzheimer's disease, and a variety of inflammatory conditions other normal and pathological processes in which matrix metalloproteinase-catalyzed changes in extracellular matrix protein structures have been implicated are described, for example in Nagase et al. (1999) *J. Biol. Chem.* 274:21491-21494. Accordingly, metalloproteases are an important target for drug action and development. Therefore, it is valuable to the field of pharmaceutical development to identify and characterize previously unknown metalloproteases.

65577 proteins of the invention can have signal sequences. As used herein, a "signal sequence" includes a peptide of at least about 40 or 50 amino acid residues in length which occurs at the N-terminus of secretory and membrane-bound proteins and which contains at least about 70% hydrophobic amino acid residues such as alanine, leucine, isoleucine, phenylalanine, proline, tyrosine, tryptophan, or valine. In a preferred embodiment, a signal sequence contains at least about 20 to 60 amino acid residues, preferably about 30-50 amino acid residues, more preferably about 47 amino acid residues, and has at least about 60-80%, more preferably 65-75%, and more preferably at least about 70% hydrophobic residues. A signal sequence serves to direct a protein containing such a sequence to a lipid bilayer. Thus, in one embodiment, a 65577 protein contains a signal sequence at about amino acids 1 to 47 of SEQ ID NO:87. The signal sequence is cleaved during processing of the mature protein.

In one embodiment, a 65577 protein exists in a mature form which does not include a signal sequence (e.g., in a form which does not include residues I to about 47 of SEQ ID NO:87). In this embodiment, the 65577 protein can have a length of about 1035 (e.g., 1027, 1028, 1029, 1030, 1031, 1032, 1033, 1034, 1035, 1036, 1037) amino acid residues, corresponding to a protein having an amino terminus at about residue 48 and having a carboxyl terminus at about residue 1081 of SEQ ID NO:87.

In another embodiment, rather than a signal sequence at about residues 1 to 47 of SEQ ID NO:87, a 65577 protein may include at least one transmembrane domain at about amino acid residues 31 to 47 of SEQ ID NO:87. As used herein, the term "transmembrane domain" includes an amino acid sequence of about 5 amino acid residues in length that spans the plasma membrane. More preferably, a transmembrane domain includes about at least 10, 15, 20 or 22 amino acid residues and spans a membrane. Transmembrane domains are rich in hydrophobic residues, and typically have an alpha-helical structure. In a preferred embodiment, at least, 60%, 70%, 80%, 90%, 95%, 99% or 100% or more of the amino acids of a transmembrane domain are hydrophobic, e.g., leucines, isoleucines, tyrosines, or tryptophans. Transmembrane domains are described in, for example, Zagotta W. N. et al. (1996) *Annu. Rev. Neurosci.* 19: 235-263, the contents of which are incorporated herein by reference. Thus, amino acid residues 31 to 47, 153-169 and 331-347 of SEQ ID NO:87 can alternatively comprise transmembrane domains in a 65577 protein.

A human 65577 polypeptide can also include various other domains or regions. A 65577 polypeptide can also include a peptidase M12B propeptide domain. As used herein, the term "peptidase M12B propeptide domain" refers to a protein domain having an amino acid sequence of about 40-160 amino acid residues in length, preferably between about 60-150 amino acid residues, more preferably between about 80-130 amino acid residues, and even more preferably between about 100-120 amino acid residues, and a bit score of about 30 or greater, preferably 40 or greater, and most preferably 50 or greater, and an E-value of about 2.3e-10 or less, more preferably about 2.3e-11 or less, and most preferably about 2.3e-12 or less when aligned with a M12B peptidase propeptide domain (SEQ ID NO:89) derived from a hidden Markov model (HMM) with PFAM (PFAM Accession No. PF01562. The M12B propeptide domain in 65577 has a bit score of 57.8, and an e-value of 2.3e-13 when aligned to this consensus sequence. An alignment of the 65577 protein with consensus peptidase M12B propeptide amino acid sequence (SEQ ID NO:89) (PFAM Accession No. PF01562) derived from a hidden Markov model shows that a peptidase M12B propeptide domain of 65577 appears at about residues 109-234 of SEQ ID NO:87.

In a preferred embodiment, a 65577 polypeptide or protein has a peptidase M12B propeptide domain or a region which includes at least about 50-175 amino acids, preferably about 75-150 amino acids, more preferably about 100-125 amino acids, even more preferably about 110-120 amino acid residues and has at least about 60%, 70%, 80%, 90%, 95%, 99%, or 100% identity with a peptidase M12B propeptide domain, e.g., the peptidase M12B propeptide domain of human 65577 (e.g., residues 109-234 of SEQ ID NO:87).

The peptidase M12B propeptide domain contains conserved cysteines, any one of which can be involved in the "cysteine switch" mechanism of action of these family members. It is believed that metalloproteinases exist in a latent form. Evidence suggests that this latency is the result of formation of an intramolecular complex between the single cysteine residue in its propeptide domain (referred to herein as the peptidase M12B propeptide domain) and the essential zinc atom in the catalytic domain (referred to herein as a reprolysin-like domain), a complex that blocks the active site. Latent metalloproteinase in the presence of matrix degrading enzyme (i.e. collagenase) can be activated by multiple means, all of which effect the dissociation of the cysteine residue from the complex. This is referred to as the "cysteine-switch" mechanism of activation. The reprolysin-like domain contains the typical HEXXH motif (SEQ ID NO:84), characteristic of enzymes that cleave peptides. The histidines are positioned close together and act as zinc ligands, that are required for catalysis. The propeptide domain that contains the critical cysteine residue, and the catalytic domain that contains the zinc-binding site are the only two domains common to all of the MMPs. The amino acid sequences surrounding both the critical cysteine residue and a region of the protein chains containing two of the putative histidine zinc-binding ligands are highly conserved in all of the MMPs. (Van Wart et al., (1990) *Proc Natl Acad Sci USA;* 87(14):5578-82).

To identify the presence of a peptidase M12B propeptide domain profiles in a 65577 protein, the amino acid sequence of the protein is searched against a database of HMMs (e.g., the Pfam database, release 2.1) using the default parameters. For example, the hmmsf program, which is available as part of the HMMER package of search programs, is a family specific default program for MILPAT0063 and score of 15 is the default threshold score for determining a hit.

For further characterization of 65577 molecule of the invention as a matrix metalloprotease, the peptide sequence is searched against a database of proteins. An alignment of amino acid residues 1-1081 of human 65577 (SEQ ID NO:87) with amino acid residues 1-1235 of a human metalloproteinase (SEQ ID NO:91) (TrEMBL:O95428) demonstrates that these sequences are 19.0% identical using a BLOSUM 50 scoring matrix and gap penalties of −12/2.

A 65577 protein can also include a reprolysin-like domain, which is the catalytic domain of the protein. As used herein, the term "reprolysin-like domain" refers to a protein domain having an amino acid sequence of about 100-300 amino acid residues in length, preferably about 150-250 amino acid residues, more preferably about 175-225 amino acid residues, and even more preferably about 205-220 amino acid residues, and has a bit score of −50 or greater, preferably −40 or greater, and most preferably −30 or greater, and an E-value of about 1.8 e-3 or less, more preferably about 1.8 e-4 or less, and most preferably about 1.8-5 or less when aligned with a consensus reprolysin amino acid sequence (SEQ ID NO:90) from a hidden Markov model (HMM) within PFAM (PFAM Accession No. PF01421). The reprolysin-like domain in 65577 as predicted by PFAM has a bit score of −28.2, and E value of 1.8e-6. An alignment of the 65577 protein with the consensus reprolysin amino acid sequence (SEQ ID NO:90) within PFAM (PFAM Accession No. PF01421) shows that a reprolysin-like domain of 65577 appears at residues 295 to 497 of SEQ ID NO:87.

The reprolysin-like domain typically includes the following consensus sequence:

```
                                           (SEQ ID NO:92)
[GSTALIVN]-x(2)-H-E-[LIVMFYW]-{DEHRKP}-H-x-
[LIVMFYWGSPQ]

(PROSITE Pattern PDOC00129).
```

In this consensus sequence pattern, each element in the pattern is separated by a dash (-); square [ ] brackets indicate the particular residues that are accepted at that position; x indicates any residue is accepted at that position; a whole number in parenthesis following an x indicates any amino acid repetition of a particular element is accepted for that specified number of residues i.e. x(2); { } brackets indicate that the particular amino acid in that position can be any except those enclosed in the bracket.

The 65577 polypeptide of the invention contains a reprolysin-like consensus sequence at amino acid residues 432 to 441 of SEQ ID NO:87 which represents 90% of the reprolysin consensus pattern described in PROSITE pattern PDOC00129. The reprolysin consensus sequence of the 65577 polypeptide differs at amino acid residue 437 of SEQ ID NO:87, wherein an "S" is substituted for any of the "LIVMFY or W" residues characteristic of this sequence. The two histidines in this consensus sequence bind zinc and are part of the conserved HEXXH motif (SEQ ID NO:84). The HEXXH motif is located at about amino acid residues 435 to 439 of SEQ ID NO:87.

In a preferred embodiment, a 65577 polypeptide or protein has a reprolysin-like domain or a region which includes at least about 90-270 amino acids, preferably about 135-225 amino acids, more preferably about 155-200 amino acids, even more preferably about 175-185 amino acid residues and has at least about 60%, 70%, 80%, 90%, 95%, 99%, or 100% identity with a reprolysin domain, e.g., the reprolysin-like domain of human 65577 (e.g., residues 295 to 497 of SEQ ID NO:87).

The reprolysin domain is characteristic of extracellular metalloproteases, such as collagenase and stromelysin, which degrade the extracellular matrix. The members of this family are enzymes that cleave peptides. These proteases require zinc for catalysis, ligands for which can be histidine residues. Members of this family containing the reprolysin domain are also known as adamalysins.

To identify the presence of a reprolysin-like domain profile in a 65577 protein, the amino acid sequence of the protein is searched against a database of HMMs (e.g., the Pfam database, release 2.1) using the default parameters. For example, the hmmsf program, which is available as part of the HMMER package of search programs, is a family specific default program for MILPAT0063 and score of 15 is the default threshold score for determining a hit.

The human 65577 protein has six predicted N-glycosylation sites (Pfam Accession number PS00001) at about amino acid residues 151-154, 190-193, 313-316, 744-747, 837-840, and 908-911 of SEQ ID NO:87; one cAMP and cGMP-dependent protein kinase phosphorylation sites (PFAM Accession Number PS00004) at about amino acid residues 86-89 of SEQ ID NO:87; fourteen predicted protein kinase C phosphorylation sites (PFAM Accession Number PS00005) at about amino acid residues 135-137, 171-173, 220-222, 279-281, 289-291, 395-397, 453-455, 630-623, 697-699, 746-748, 794-796, 870-872, 913-915 and 952-954 of SEQ ID NO:87; nine predicted casein kinase II phosphorylation sites (PFAM Accession Number PS00006) located at about amino acid residues 65-68, 206-209, 389-392, 420-423, 676-676, 816-819, 1020-1023, 1024-1027 and 1059-1062 of SEQ ID NO:87; one tyrosine kinase phosphorylation site (PFAM Accession Number PS00007) at about amino acid residues 263-270 of SEQ ID NO:87; sixteen predicted N-myristoylation sites (PFAM Accession Number PS00008) at about amino acid residues 73-78, 131-136, 167-172, 219-224, 312-317, 331-336, 353-358, 426-431, 562-567, 589-584, 738-743, 752-757, 865-870, 890-895, 948-953 and 1041-1046 of SEQ ID NO:87; and three predicted amidation sites (PFAM Accession Number PS00009) at about amino acid residues 83-86, 254-257 and 378-381 of SEQ ID NO:87.

General information regarding PFAM identifiers, PS prefix and PF prefix domain identification numbers can be found at Sonnhammer et al. (1997) *Protein* 28:405-420.

In one embodiment of the invention, a 65577 polypeptide includes at least one reprolysin-like domain. In another embodiment, the 65577 polypeptide includes at least one reprolysin-like domain and at least one peptidase M12B propeptide domain. In still another embodiment, the 65577 polypeptide contains at least one reprolysin-like domain, at least one peptidase M12B propeptide domain, and at least one transmembrane domain.

The 65577 molecules of the present invention can further include one or more of the N-glycosylation, cAMP and cGMP-dependent protein kinase phosphorylation, protein kinase C phosphorylation, casein kinase II phosphorylation, tyrosine kinase phosphorylation, N-myristoylation, and amidation sites described herein.

Because the 65577 polypeptides of the invention can modulate 65577 activities, they can be used to develop novel diagnostic and therapeutic agents for 65577-mediated or related disorders, as described herein.

As used herein, a "65577 activity," "biological activity of 65577," or "functional activity of 65577," refers to an activity exerted (directly or indirectly) by a 65577 protein, polypeptide or nucleic acid molecule on, for example, a 65577-responsive cell or on a 65577 substrate (e.g., a protein substrate) as determined in vivo or in vitro. In one embodiment, a 65577 activity is a direct activity, such as association with a 65577 target molecule. A "target molecule" or "binding partner" of a 65577 protein is a molecule with which the 65577 protein binds or interacts in nature. In an exemplary embodiment, such a target molecule is a 65577 receptor (e.g. an ECM protein). A 65577 activity can also be an indirect activity, such as a cellular signaling activity mediated by interaction of the 65577 protein with a 65577 receptor.

The 65577 molecules of the present invention have similar biological activities as other MMP family members. For example, the 65577 proteins of the present invention can have (directly or indirectly) any one or more of the following activities: (1) the ability to cleave or modulate the degradation of proteins or peptides of the extracellular matrix in cells of the cardiovascular system. Examples of such cells in which the 65577 molecule can act include arterial cells (e.g., arterial smooth muscle cells (e.g., coronary arterial smooth muscle cells)), and venous cells (e.g., venous smooth muscle cells); (2) the ability to cleave or modulate the degradation of peptides in cells of the central nervous system (e.g., brain cortex, spinal cord (e.g., schwann cells, neuronal cells, and glial cells (e.g., astrocytes)); (3) the ability to catalyze or modulate catalysis of cleavage of covalent bonds within or between amino acid residues, e.g., in ECM, cell-surface, and extracellular proteins; (4) the ability to degrade ECM; (5) the ability to modulate angiogenesis; (6) the ability to modulate neurite growth; (7) the ability to modulate tumor cell invasion or metastasis; (8) the ability to modulate tissue or organ integrity; (9) the ability to modulate wound healing; (10) the ability to modulate endometrial cycling; (11) the ability to modulate hair follicle cycling; (12) the ability to modulate bone remodeling; (13) the ability to modulate ovulation; (14) the ability to modulate embryonic development; and (15) the ability to modulate apoptosis.

Other activities of the 65577 molecules of the invention include the ability to modulate function, survival, morphology, proliferation and/or differentiation of cells of tissues in which 65577 molecules are expressed. Thus, the 65577 molecules can act as novel diagnostic targets and therapeutic agents for controlling disorders involving aberrant activities of these cells.

Still other activities of the 65577 molecules of the invention include the ability to cleave a protein substrate by hydrolysis of an amide bond. Typically, this ability of the molecules of the invention to cleave a protein substrate depends upon the presence of a metal ion, such as zinc. Thus, a 65577 molecule or subsequence or variant having metalloproteinase activity is capable of cleaving one or more protein substrates in the presence of a metal, e.g., zinc. Thus, a 65577 metalloprotease or subsequence or variant can cleave one or more protein substrates in the presence of zinc.

Activity assays for the metalloproteinase family members, such as 65577 polypeptides, involve any of the known metalloproteinase, reprolysin, or peptidase M12B propeptide activity or functions, as well as activities/functions that may not typically be found in other metalloproteinases. These assays include assays which test the ability to modulate (directly or indirectly) any one or more of the following MMP functions: (1) the ability to cleave or modulate the degradation proteins or peptides of the extracellular matrix in cells of the cardiovascular system. Examples of such cells in which the 65577 molecule can act include arterial cells (e.g., arterial smooth muscle cells (e.g., coronary arterial smooth muscle cells)), and venous cells (e.g., venous smooth muscle cells); (2) the ability to cleave or modulate the degradation of peptides in cells of the central nervous system (e.g., brain cortex, spinal cord (e.g., schwann cells, neuronal cells, and glial cells (e.g. astrocytes)); (3) binding ECM; (4) binding collagen or gelatin; (5) binding integrin; (6) binding zinc or other metals; (7) binding a2-macroglobulin; (8) cleaving specific peptide substrates to produce fragments, affecting cell adhesion; (9) binding heparin or other sulfated glycosaminoglycan, such as heparan sulfate; (10) modulating vascularization or vascular endothelial growth; (11 breaking down cartilage; (12) induceing apoptosis of endothelial cells; (13) suppressing tumor growth; (14) modulating angiogenesis; (15) affecting cellular chemotaxis; (16) affecting cell-cell adhesion or cell-matrix interaction; (17) and any of the other biological or functional properties of these proteins, including, but not limited to, those disclosed herein, and in the references cited herein. Further, assays can relate to changes in the protein, per se, and on the effects of these changes, for example, cleavage of the substrate, activation of the protein following cleavage, etc. Such assays are described in Tang et al. (1999) *FEBS Letters* 445:223-225 (for example, induction by interleukin I in vitro and by intravenous administration of lipopolysaccharide in vivo, as well as effects on cell adhesion, motility, and growth); (Abbaszade et al., (2000) *J Biol Chem.* 18; 275(33):25791-7) (for example, products resulting from cleavage at the Glu-Ala site in cartilage explants and chondrocyte cultures treated with interleukin I and retinoic acid, determination of aggrecan cleaving activity with and without hydroxamate inhibitors); (Kuno and Matsushima (1998) *J Biol Chem* 273: 13912-13917) (binding to the extracellular matrix, binding to sulfated glycosaminoglycans, binding to heparan sulfate); Kuno et al. (1999) *J Biol Chem.* June 25; 274(26):18821-6 (protease trapping of a2-macroglobulin, furin processing); Tortorella et al. (1999) *Science;* 284(5420):1664-6 (detection of aggrecan fragments, especially by neoepitope antibodies, inhibition of cleavage by ADAM-TS inhibitors, inhibition of pro-MMP activation); Vasquez et al., (1998) *J Appl Physiol.* October; 85(4):1421-8 (suppression of fibroblast growth factor-2-induced vascularization in the cornea pocket assay and inhibition of vascular endothelial growth factor-induced angiogenesis in the chorioallantoic membrane assay, inhibition of endothelial cell proliferation, competitive inhibition with endostatin, proliferation of human dermal endothelial cells, use of the antiangiogenic region of the TSP-1 motif as bait); (Kuno et al. (1997) *J Biol Chem* 272: 556-562); Wolfsberg et al., *Dev Biol.* (1995) May; 169(1):378-83; Guilpin et al. (1988) *J. Biol. Chem.* 273:157-166 ($\alpha$2-macroglobulin trapping, cleavage of prodomain at the furin site to generate active metalloproteinase); Rosendahl et al., (*J. Biol. Chem.* (1997) 272:24588-24593) (TNF $\alpha$ processing). Recombinant assay systems include, but are not limited to, those described in Abbaszade et al., supra; Kuno et al. (1998), supra; Kuno et al. (1999), supra; Tortorella et al., supra; Vasquez et al., supra, and Kuno et al. (1997), supra.

The 65577 molecules find use in modulating the 65577 activities described herein. As used herein, the term "modulate" or grammatical variations thereof means increasing or decreasing an activity, function, signal or response. That is, the 65577 molecules of the invention affect the targeted activity in either a positive or negative fashion (e.g., increase or decrease activity, function, or signal). Accordingly, the 65577 molecules can act as novel diagnostic targets and therapeutic agents for controlling disorders involving such activities (e.g., metalloproteinase activities).

Thus, 65577 molecules described herein can act as novel diagnostic targets and therapeutic agents for prognosticating, modulating, diagnosing, preventing, inhibiting, alleviating, or treating metalloproteinase-associated disorders As used herein, a "metalloproteinase-associated disorder" (MMP-associated disorder) includes a disorder, disease or condition which is characterized by a misregulation of a metalloproteinase mediated activity or by an abnormal metalloproteinase mediated activity. As used herein, a metalloproteinase mediated activity, is an activity mediated or involving a molecule which can cleave a protein or peptide substrate in the presence of a metal. (e.g., $Ca^{2+}$, $Zn^{2+}$, $Mn^{2+}$, $Mg^{2+}$). Metalloproteinase-associated disorders can detrimentally affect cell proliferation, cell adhesion, cell motility and migration, tissue structural integrity (e.g., connective tissue formation and maintenance), inflammatory response, erythroid cell activity, gene expression; or angiogenesis and vascularization, among others. Thus, examples of metalloproteinase-associated disorders in which the 65577 molecules of the invention can be directly or indirectly involved include cellular proliferative and/or differentiative disorders; disorders associated with undesirable or deficient vascularization/angiogenesis; disorders associated with undesirable or deficient cell adhesion, motility or migration, including, e.g., metastasis; disorders associated with undesirable or deficient tissue structural integrity; disorders associated with undesirable extracellular matrix accumulation, e.g., characterized by fibrosis or a scar; inflammatory disorders, erythroid cell associated disorders; gene expression disorders; and bleeding/clotting disorders.

The 65577 molecules also find use in diagnosis of disorders involving an increase or decrease in 65577 expression relative to normal expression, such as a proliferative disorder, a differentiative disorder (e.g., cancer), an immune disorder, an erythroid cell-associated disorder; a motility disorder, a vascular disorder, a bleeding or clotting disorder, or a developmental disorder. Thus, where expression or activity of 65577 is greater or less than normal, this may indicate the presence of or a predisposition towards a 65577 disorder. The presence of 65577 RNA or protein, e.g., by hybridization of a 65577 specific probe or with a 65577 specific antibody, can be used to identify the amount of 65577 present in a particular cell or tissue, or other biological sample. 65577 activity (protease activity assays, adhesion assays, binding assays, motility/migration assays, vascularization assays, etc.) can be assessed using the various techniques described herein or otherwise known in the art. Thus, in another embodiment, the invention provides methods and compositions for detection of 65577 in tissues that normally or do not normally express 65577.

The 65577 molecules and modulators thereof can act as novel therapeutic agents for controlling one or more of cardiovascular disorders, or neurological disorders as described herein.

Tissue Distribution of 65577 mRNA

TaqMan analysis indicates the highest levels of 65577 expression are in normal artery cells, normal vein cells, aortic and coronary smooth muscle cells, and human umbilical vein cells. Furthermore, the results indicate high levels of expression in brain cortex, and spinal cord. 65577 is also expressed at lower levels in in glial cells, normal ovary cells, and skin cells

DEFINITIONS

The 27877, 18080, 14081, 32140, 50352, 16658, 14223, 16002, 50566, 65552 or 65577 protein, fragments thereof, and derivatives and other variants of the sequence in SEQ ID NO:2, 5, 12, 21, 26, 30, 36, 39, 42, 74, 77 or 87 thereof are collectively referred to as "polypeptides or proteins of the invention" or "27877, 18080, 14081, 32140, 50352, 16658, 14223, 16002, 50566, 65552 or 65577 polypeptides or proteins". Nucleic acid molecules encoding such polypeptides or proteins are collectively referred to as "nucleic acids of the invention" or "27877, 18080, 14081, 32140, 50352, 16658, 14223, 16002, 50566, 65552 or 65577 nucleic acids."

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology* (1989) John Wiley & Sons, N.Y., 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 27877, 18080, 14081, 32140, 50352, 16658, 14223, 16002, 50566, 65552 or 65577 protein, preferably a mammalian 27877, 18080, 14081, 32140, 50352, 16658, 14223, 16002, 50566, 65552 or 65577 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 27877, 18080, 14081, 32140, 50352, 16658, 14223, 16002, 50566, 65552 or 65577 protein having less than about 30%, 20%, 10% and more preferably 5% (by dry weight), of non-27877, 18080, 14081, 32140, 50352, 16658, 14223, 16002, 50566, 65552 or 65577 protein (also referred to herein as a "contaminating protein"), or of chemical precursors or non-27877, 18080, 14081, 32140, 50352, 16658, 14223, 16002, 50566, 65552 or 65577 chemicals. When the 27877, 18080, 14081, 32140, 50352, 16658, 14223, 16002, 50566, 65552 or 65577 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 27877, 18080, 14081, 32140, 50352, 16658, 14223, 16002, 50566, 65552 or 65577 (e.g., the sequence of SEQ ID NO:1, 3, 4, 6, 11, 13, 20, 22, 25, 27, 29, 31, 35, 37, 38, 40, 41, 43, 73, 75, 76, 78, 86 or 88) without abolishing or more preferably, without substantially altering a biological activity, whereas an "essential" amino acid residue results in such a change. For example, amino acid residues that are conserved among the polypeptides of the present invention, e.g., those present in the conserved domains, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 27877, 18080, 14081, 32140, 50352, 16658, 14223, 16002, 50566, 65552 or 65577 protein is preferably replaced with another amino acid residue from the same side chain family. Alternatively, in another embodiment, mutations can be introduced randomly along all or part of a 27877, 18080, 14081, 32140, 50352, 16658, 14223, 16002, 50566, 65552 or 65577 coding sequence, such as by saturation mutagenesis, and the resultant mutants can be screened for 27877, 18080, 14081, 32140, 50352, 16658, 14223, 16002, 50566, 65552 or 65577 biological activity to identify mutants that retain activity. Following mutagenesis of SEQ ID NO: 1, 3, 4, 6, 11, 13, 20, 22, 25, 27, 29, 31, 35, 37, 38, 40, 41, 43, 73, 75, 76, 78, 86 or 88, the encoded protein can be expressed recombinantly and the activity of the protein can be determined.

As used herein, a "biologically active portion" of a 27877, 18080, 14081, 32140, 50352, 16658, 14223, 16002, 50566, 65552 or 65577 protein includes a fragment of a 27877, 18080, 14081, 32140, 50352, 16658, 14223, 16002, 50566, 65552 or 65577 protein which participates in an interaction between a 27877, 18080, 14081, 32140, 50352, 16658, 14223, 16002, 50566, 65552 or 65577 molecule and a non-27877, 18080, 14081, 32140, 50352, 16658, 14223, 16002, 50566, 65552 or 65577 molecule. Biologically active portions of a 27877, 18080, 14081, 32140, 50352, 16658, 14223, 16002, 50566, 65552 or 65577 protein include peptides comprising amino acid sequences sufficiently homologous to or derived from the amino acid sequence of the 27877, 18080, 14081, 32140, 50352, 16658, 14223, 16002, 50566, 65552 or 65577 protein, e.g., the amino acid sequence shown in SEQ ID NO:2, 5, 12, 21, 26, 30, 36, 39, 42, 74, 77 or 87, which include fewer amino acids than the full length 27877, 18080, 14081, 32140, 50352, 16658, 14223, 16002, 50566, 65552 or 65577 protein, and exhibit at least one activity of a 27877, 18080, 14081, 32140, 50352, 16658, 14223, 16002, 50566, 65552 or 65577 protein. Typically, biologically active portions comprise a domain or motif with at least one activity of the 27877, 18080, 14081, 32140, 50352, 16658, 14223, 16002, 50566, 65552 or 65577 protein. A biologically active portion of a 27877, 18080, 14081, 32140, 50352, 16658, 14223, 16002, 50566, 65552 or 65577 protein can be a polypeptide which is, for example, 10, 25, 50, 100, 200 or more amino acids in length. Biologically active portions of a 27877, 18080, 14081, 32140, 50352, 16658, 14223, 16002, 50566, 65552 or 65577 protein can be used as targets for developing agents which modulate a 27877, 18080, 14081, 32140, 50352, 16658, 14223, 16002, 50566, 65552 or 65577 mediated activity.

Calculations of homology or sequence identity (the terms "homology" and "identity" are used interchangeably herein) between sequences are performed as follows:

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) *J. Mol. Biol.* 48:444-453 algorithm which has been incorporated into the GAP program in the GCG software package using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of Meyers and Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to 27877, 18080, 14081, 32140, 50352, 16658, 14223, 16002, 50566, 65552 or 65577 nucleic acid molecules of the invention. BLAST protein searches can be performed with the XBLAST program, score=50, wordlength=3 to obtain amino acid sequences homologous to 27877, 18080, 14081, 32140, 50352, 16658, 14223, 16002, 50566, 65552 or 65577 protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used.

Particular 27877, 18080, 14081, 32140, 50352, 16658, 14223, 16002, 50566, 65552 or 65577 polypeptides of the present invention have an amino acid sequence substantially identical to the amino acid sequence of SEQ ID NO:2, 5, 12, 21, 26, 30, 36, 39, 42, 74, 77 or 87. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%, 91%, 92%, 93%, 94%, 95%, 96%, 97%, 98% or 99% identity to SEQ ID NO:2, 5, 12, 21, 26, 30, 36, 39, 42, 74, 77 or 87 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%, 91%, 92%, 93%, 94%, 95%, 96%, 97%, 98% or 99% identity to SEQ ID NO:1, 3, 4, 6, 11, 13, 20, 22, 25, 27, 29, 31, 35, 37, 38, 40, 41, 43, 73, 75, 76, 78, 86 or 88 are termed substantially identical.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

As used herein, cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the term "cancer" (also used interchangeably with the terms, "hyperproliferative" and "neoplastic") refers to cells having the capacity for autonomous growth, i.e., an abnormal state or condition characterized by rapidly proliferating cell growth. Cancerous disease states may be categorized as pathologic, i.e., characterizing or constituting a disease state, e.g., malignant tumor growth, or may be categorized as non-pathologic, i.e., a deviation from normal but not associated with a disease state, e.g., cell proliferation associated with wound repair. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

Examples of cellular proliferative and/or differentiative disorders of the lung include, but are not limited to, tumors such as bronchogenic carcinoma, including paraneoplastic syndromes, bronchioloalveolar carcinoma, neuroendocrine tumors, such as bronchial carcinoid, miscellaneous tumors, metastatic tumors, and pleural tumors, including solitary fibrous tumors (pleural fibroma) and malignant mesothelioma.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders involving the colon include, but are not limited to, tumors of the colon, such as non-neoplastic polyps, adenomas, familial syndromes, colorectal carcinogenesis, colorectal carcinoma, and carcinoid tumors.

Examples of cancers or neoplastic conditions, in addition to the ones described above, include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemiaAymphoma (ATL), cutaneous T-cell lymphoma (CTCL), large granular lymphocytic leukemia (LGF), Hodgkin's disease and Reed-Sternberg disease.

As used herein, an "angiogenesis disorder" includes a disease or disorder which affects or is caused by aberrant or deficient angiogenesis. Disorders involving angiogenesis include, but are not limited to, aberrant or excess angiogenesis in tumors such as hemangiomas and Kaposi's sarcoma, von Hippel-Lindau disease, as well as the angiogenesis associated with tumor growth; aberrant or excess angiogenesis in diseases such as a Castleman's disease or fibrodysplasia ossificans progressiva; aberrant or deficient angiogenesis associated with aging, complications of healing certain wounds and complications of diseases such as diabetes and rheumatoid arthritis; or aberrant or deficient angiogenesis associated with hereditary hemorrhagic telangiectasia, autosomal dominant polycystic kidney disease, myelodysplastic syndrome or Klippel-Trenaunay-Weber syndrome.

As used herein, disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

As used herein, disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

As used herein, disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Examples of disorders of the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

As used herein, disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

As used herein, disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

As used herein, hormonal disorders and diseases include type I and type II diabetes mellitus, pituitary disorders (e.g., growth disorders), thyroid disorders (e.g., hypothyroidism or hyperthyroidism), and reproductive or fertility disorders (e.g., disorders which affect the organs of the reproductive system, e.g., the prostate gland, the uterus, or the vagina; disorders which involve an imbalance in the levels of a reproductive hormone in a subject; disorders affecting the ability of a subject to reproduce; and disorders affecting secondary sex characteristic development, e.g., adrenal hyperplasia).

Aberrant expression and/or activity of the molecules of the invention can mediate disorders associated with bone metabolism. "Bone metabolism" refers to direct or indirect effects in the formation or degeneration of bone structures, e.g., bone formation, bone resorption, etc., which can ultimately affect the concentrations in serum of calcium and phosphate. This term also includes activities mediated by the molecules of the invention in bone cells, e.g. osteoclasts and osteoblasts, that can in turn result in bone formation and degeneration. For example, molecules of the invention can support different activities of bone resorbing osteoclasts such as the stimulation of differentiation of monocytes and mononuclear phagocytes into osteoclasts. Accordingly, molecules of the invention that modulate the production of bone cells can influence bone formation and degeneration, and thus can be used to treat bone disorders. Examples of such disorders include, but are not limited to, osteoporosis, osteodystrophy, osteomalacia, rickets, osteitis fibrosa cystica, renal osteodystrophy, osteoscierosis, anti-convulsant treatment, osteopenia, fibrogenesis-imperfecta ossium, secondary hyperparathyroidism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

As used herein, "a prostate disorder" refers to an abnormal condition occurring in the male pelvic region characterized by, e.g., male sexual dysfunction and/or urinary symptoms. This disorder may be manifested in the form of genitourinary inflammation (e.g., inflammation of smooth muscle cells) as in several common diseases of the prostate including prostatitis, benign prostatic hyperplasia and cancer, e.g., adenocarcinoma or carcinoma, of the prostate.

Examples of immune, e.g., inflammatory, (e.g. respiratory inflammatory) disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, inflammatory bowel disease, e.g. Crohn's disease and ulcerative colitis, aphthous ulcer, iritis, conjunctivitis, keratoconjunctivitis, asthma, allergic asthma, chronic obstructive pulmonary disease, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

As used herein, disorders involving the heart, or "cardiovascular disease" or a "cardiovascular disorder" includes a disease or disorder which affects the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. A cardiovascular disorder includes, but is not limited to disorders such as arteriosclerosis, atherosclerosis, cardiac hypertrophy, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, valvular disease, including but not limited to, valvular degeneration caused by calcification, rheumatic heart disease, endocarditis, or complications of artificial valves; atrial fibrillation, long-QT syndrome, congestive heart failure, sinus node dysfunction, angina, heart failure, hypertension, atrial fibrillation, atrial flutter, pericardial disease, including but not limited to, pericardial effusion and pericarditis; cardiomyopathies, e.g., dilated cardiomyopathy or idiopathic cardiomyopathy, myocardial infarction, coronary artery disease, coronary artery spasm, ischemic disease, arrhythmia, sudden cardiac death, and cardiovascular developmental disorders (e.g., arteriovenous malformations, arteriovenous fistulae, raynaud's syndrome, neurogenic thoracic outlet syndrome, causalgia/reflex sympathetic dystrophy, hemangioma, aneurysm, cavernous angioma, aortic valve stenosis, atrial septal defects, atrioventricular canal, coarctation of the aorta, ebsteins anomaly, hypoplastic left heart syndrome, interruption of the aortic arch, mitral valve prolapse, ductus arteriosus, patent foramen ovale, partial anomalous pulmonary venous return, pulmonary atresia with ventricular septal defect, pulmonary atresia without ventricular septal defect, persistance of the fetal circulation, pulmonary valve stenosis, single ventricle, total anomalous pulmonary venous return, transposition of the great vessels, tricuspid atresia, truncus arteriosus, ventricular septal defects). A cardiovascular disease or disorder also can include an endothelial cell disorder.

"Procedural vascular trauma" includes the effects of surgical/medical-mechanical interventions into mammalian vasculature, but does not include vascular trauma due to the organic vascular pathologies listed hereinabove, or to unintended traumas, such as due to an accident. Thus, procedural vascular traumas within the scope of the present treatment method include (1) organ grafting or transplantation, such as transplantation and grafting of heart, kidney, liver and the like, e.g., involving vessel anastomosis; (2) vascular surgery, such as coronary bypass surgery, biopsy, heart valve replacement, atheroectomy, thrombectomy, and the like; (3) transcatheter vascular therapies (TVT) including angioplasty, e.g., laser angioplasty and PTCA procedures discussed hereinbelow, employing balloon catheters, or indwelling catheters; (4) vascular grafting using natural or synthetic materials, such as in saphenous vein coronary bypass grafts, dacron and venous grafts used for peripheral arterial reconstruction, etc.; (5) placement of a mechanical shunt, such as a PTFE hemodialysis shunt used for arteriovenous communications; and (6) placement of an intravascular stent, which may be metallic, plastic or a biodegradable polymer. See U.S. patent application Ser. No. 08/389,712, filed Feb. 15, 1995, which is incorporated by reference herein. For a general discussion of implantable devices and biomaterials from which they can be formed, see H. Kambic et al., "Biomaterials in Artificial Organs", Chem. Eng. News, 30 (Apr. 14, 1986), the disclosure of which is incorporated by reference herein.

Small vessel disease includes, but is not limited to, vascular insufficiency in the limbs, peripheral neuropathy and retinopathy, e.g., diabetic retinopathy.

As used herein, disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicella-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telangiectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

As used herein, disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

As used herein, disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor choriocarcinoma, teratoma, and mixed tumors, tumore of sex cord-gonadal stroma including, but not limited to, Leydig (interstitial) cell tumors and sertoli cell tumors (androblastoma), and testicular lymphoma, and miscellaneous lesions of tunica vaginalis.

As used herein, skeletal muscle disorders include, but are not limited to, muscular dystrophy (e.g., Duchenne muscular dystrophy, Becker muscular dystrophy, Emery-Dreifuss muscular dystrophy, limb-girdle muscular dystrophy, facioscapulohumeral muscular dystrophy, myotonic dystrophy, oculopharyngeal muscular dystrophy, distal muscular dystrophy, and congenital muscular dystrophy), motor neuron diseases (e.g., amyotrophic lateral sclerosis, infantile progressive spinal muscular atrophy, intermediate spinal muscular atrophy, spinal bulbar muscular atrophy, and adult spinal muscular atrophy), myopathies (e.g., inflammatory myopathies (e.g., dermatomyositis and polymyositis), myotonia congenita, paramyotonia congenita, central core disease, nemaline myopathy, myotubular myopathy, and periodic paralysis), tumors such as rhabdomyosarcoma, and metabolic diseases of muscle (e.g., phosphorylase deficiency, acid maltase deficiency, phosphofructokinase deficiency, debrancher enzyme deficiency, mitochondrial myopathy, carnitine deficiency, carnitine palmityl transferase deficiency, phosphoglycerate kinase deficiency, phosphoglycerate mutase deficiency, lactate dehydrogenase deficiency, and myoadenylate deaminase deficiency).

As used herein, an "endothelial cell disorder" includes a disorder characterized by aberrant, unregulated, or unwanted endothelial cell activity, e.g., proliferation, migration, angiogenesis, or vascularization; or aberrant expression of cell surface adhesion molecules or genes associated with angiogenesis, e.g., TIE-2, FLT and FLK. Endothelial cell disorders include tumorigenesis, tumor metastasis, psoriasis, diabetic retinopathy, endometriosis, Grave's disease, ischemic disease (e.g., atherosclerosis), and chronic inflammatory diseases (e.g., rheumatoid arthritis).

Disorders which can be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inbom errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein can be used for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, the molecules of the invention can play an important role in the etiology of certain viral diseases, including but not limited to Hepatitis B, Hepatitis C and Herpes Simplex Virus (HSV). Modulators of the activity of the molecules of the invention could be used to control viral diseases. The modulators can be used in the treatment and/or diagnosis of viral infected tissue or virus-associated tissue fibrosis, especially liver and liver fibrosis. Also, such modulators can be used in the treatment and/or diagnosis of virus-associated carcinoma, especially hepatocellular cancer.

As used herein, a "viral pathogen" or "viral pathogen disorder" includes respiratory viral pathogens and their associated disorders include, for example, adenovirus, resulting in upper and lower respiratory tract infections; conjuctivitis and diarrhea; echovirus, resulting in upper respiratory tract infections, pharyngitis and rash; rhinovirus, resulting in upper respiratory tract infections; cosackievirus, resulting in Pleurodynia, herpangia, hand-foot-mouth disease; coronavirus, resulting in upper respiratory tract infections; influenza A and B viruses, resulting in influenza; parainfluenza virus 1-4, resulting in upper and lower respiratory tract infections and croup; respiratory syncytial virus, resulting in bronchiolitis and pneumonia. Digestive viral pathogens and their associated disorders include, for example, mumps virus, resulting in mumps, pancreatitis, and orchitis; rotavirus, resulting in childhood diarrhea; Norwalk Agent, resulting in gastroenteritis; hepatitis A virus, resulting in acute viral hepatitis; hepatitis B virus, hepatitis D virus and hepatitis C virus, resulting in acute or chronic hepatitis; hepatitis E virus, resulting in enterically transmitted hepatitis. Systemic viral pathogens associated with disorders involving skin eruptions include, for example, measles virus, resulting in measles (rubeola); rubella virus, resulting in German measles (rubella); parvovirus, resulting in erythema infectiosum and aplastic anemia; varicella-zoster virus, resulting in chicken pox and shingles; herpes simplex virus 1-associated, resulting in cold sores; and herpes simplex virus 2, resulting in genital herpes. Systemic viral pathogens associated with hematopoietic disorders include, for example, cytomegalovirus, resulting in cytomegalic inclusion disease; Epstein-Barr virus, resulting in mononucleosis; HTLV-1, resulting in adult T-cell leukemia and tropical spastic paraparesis; HTLV-II; and HIV 1 and HIV 2, resulting in AIDS. Arboviral pathogens associated with hemorrhagic fevers include, for example, dengue virus 1-4, resulting in dengue and hemorrhagic fever; yellow fever virus, resulting in yellow fever; Colorado tick fever virus, resulting in Colorado tick fever; and regional hemorrhagic fever viruses, resulting in Bolivian, Argentinian, Lassa fever. Viral pathogens associated with warty growths and other hyperplasias include, for example, papillomavirus, resulting in condyloma and cervical carcinoma; and molluscum virus, resulting in molluscum contagiosum. Viral pathogens associated with central nervous system disorders include, for example, poliovirus, resulting in poliomyelitis; rabiesvirus, associated with rabies; JC virus, associated with progressive multifocal leukoencephalopathy; and arboviral encephalitis viruses, resulting in Eastern, Western, Venezuelan, St. Louis, or California group encephalitis. Viral pathogens associated with cancer include, for example, human papillomaviruses, implicated in the genesis of several cancers including squamous cell carcinoma of the cervix and anogenital region, oral cancer and laryngeal cancers; Epstein-Barr virus, implicated in pathogenesis of the African form of Burkitt lymphoma, B-cell lymphomas, Hodgkin disease, and nasopharyngeal carcinomas; hepatitis B virus, implicated in liver cancer; human T-cell leukemia virus type 1 (HTLV-1), associated with T-cell leukemia/lymphoma; and the Kaposi sarcoma herpesvirus (KSHV).

Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

As used herein, neurological disorders include disorders of the central nervous system (CNS) and the peripheral nervous system, e.g., cognitive and neurodegenerative disorders, Examples of neurological disorders include, but are not limited to, autonomic function disorders such as hypertension and sleep disorders, and neuropsychiatric disorders, such as depression, schizophrenia, schizoaffective disorder, Korsakoff's psychosis, alcoholism, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Such neurological disorders include, for example, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicella-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer's disease and Pick's disease, degenerative diseases of basal ganglia and brain stem, including Parkinsonism, idiopathic Parkinson's disease (paralysis agitans) and other Lewy diffuse body diseases, progressive supranuclear palsy, corticobasal degenration, multiple system atrophy, including striatonigral degenration, Shy-Drager syndrome, and olivopontocerebellar atrophy, and Huntington's disease, senile dementia, Gilles de la Tourette's syndrome, epilepsy, and Jakob-Creutzfieldt disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inbom errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease. Further CNS-related disorders include, for example, those listed in the American Psychiatric Association's Diagnostic and Statistical manual of Mental Disorders (DSM), the most current version of which is incorporated herein by reference in its entirety.

As used herein, diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

Additionally, molecules of the invention can play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields (1987) *Pain*, New York: McGraw-Hill); pain associated with musculoskeletal disorders, e.g., joint pain; tooth pain; headaches; pain associated with surgery; pain related to irritable bowel syndrome; or chest pain.

As used herein, a "hematological disorder" includes a disease, disorder, or condition which affects a hematopoietic cell or tissue. Hematological disorders include diseases, disorders, or conditions associated with aberrant hematological content or function. Hematological disorders can be characterized by a misregulation (e.g., downregulation or upregulation) of activity. Examples of hematological disorders include disorders resulting from bone marrow irradiation or chemotherapy treatments for cancer, disorders such as Pernicious Anemia, Hemorrhagic Anemia, Hemolytic Anemia, Aplastic Anemia, Sickle Cell Anemia, Sideroblastic Anemia, Anemia associated with chronic infections such as Malaria, Trypanosomiasis, HIV, Hepatitis virus or other viruses, Myelophthisic Anemias caused by marrow deficiencies, renal failure resulting from Anemia, Anemia, Polycethemia, Infectious Mononucleosis (IM), Acute Non-Lymphocytic Leukemia (ANLL), Acute Myeloid Leukemia (AML), Acute Promyelocytic Leukemia (APL), Acute Myelomonocytic Leukemia (AMMoL), Polycethemia Vera, Lymphoma, Acute Lymphocytic Leukemia (ALL), Chronic Lymphocytic Leukemia, Wilm's Tumor, Ewing's Sarcoma, Retinoblastoma, Hemophilia, disorders associated with an increased risk of Thrombosis, Herpes, Thalessemia, antibody-mediated disorders such as transfusion reactions and Erythroblastosis, mechanical trauma to red blood cells such as micro-angiopathic hemolytic anemias, Thrombotic Thrombocytopenic Purpura and disseminated intravascular coagulation, infections by parasites such as Plasmodium, chemical injuries from, e.g., lead poisoning, and Hypersplenism.

As used herein, the term "hematopoietic cell" includes yolk sac stem cells, primitive erythroid cells, fetal liver cells, fetal spleen cells, fetal bone marrow cells, non-fetal bone marrow cells, megakaryocytes, stem cells, lymphoid stem cells, myeloid stem cells, progenitor cells, progenitor lymphocytes, progenitor T lymphocytes, progenitor B lymphocytes, progenitor erythrocytes, progenitor neutrophils, progenitor eosinophils, progenitor basophils, progenitor monocytes, progenitor mast cells, progenitor platelets, committed lymphocytes, committed T lymphocytes, committed B lymphocytes, committed erythrocytes, committed neutrophils, committed eosinophils, committed basophils, committed monocytes, committed mast cells, committed platelets, differentiated lymphocytes, differentiated T lymphocytes, differentiated B lymphocytes, differentiated erythrocytes, differentiated neutrophils, differentiated eosinophils, differentiated basophils, differentiated monocytes, differentiated mast cells, differentiated platelets, mature lymphocytes, mature T lymphocytes, mature B lymphocytes, mature erythrocytes, mature neutrophils, mature eosinophils, mature basophils, mature monocytes, mature mast cells, and mature platelets.

As used herein, the term "progenitor cell" includes any somatic cell which has the capacity to generate fully differentiated, functional progeny by differentiation and proliferation. Progenitor cells include progenitors from any tissue or organ system, including, but not limited to, blood, nerve, muscle, skin, gut, bone, kidney, liver, pancreas, thymus, and the like. Progenitor cells are distinguished from "committed cells" and "differentiated cells," which are defined as those cells which may or may not have the capacity to proliferate, i.e., self-replicate, but which are unable to undergo further differentiation to a different cell type under normal physiological conditions. Moreover, progenitor cells are further distinguished from abnormal cells such as cancer cells, especially leukemia cells, which proliferate (self-replicate) but which generally do not further differentiate, despite appearing to be immature or undifferentiated.

Progenitor cells include all the cells in a lineage of differentiation and proliferation prior to the most differentiated or the fully mature cell. Thus, for example, progenitors include the skin progenitor in the mature individual, which is capable of differentiation to only one type of cell, but which is itself not fully mature or fully differentiated. Production of mature, functional blood cells results from proliferation and differentiation of "unipotential progenitors," i.e., those progenitors which have the capacity to make only one type of one type of blood cell. For red blood cell production, a progenitor called a "CFU-E" (colony forming unit-erythroid) has the capacity to generate two to 32 progeny cells.

Various other hematopoietic progenitors have been characterized. For example, hematopoietic progenitor cells include those cells which are capable of successive cycles of differentiating and proliferating to yield up to eight different mature hematopoietic cell lineages. At the most primitive or undifferentiated end of the hematopoietic spectrum, hematopoietic progenitor cells include the hematopoietic "stem cells." These rare cells, which represent 1 in 10,000 to 1 in 100,000 of cells in the bone marrow, each have the capacity to generate a billion mature blood cells of all lineages and are responsible for sustaining blood cell production over the life of an animal. They reside in the marrow primarily in a quiescent state and may form identical daughter cells through a process called self-renewal. Accordingly, such an uncommitted progenitor can be described as being "totipotent," i.e., both necessary and sufficient for generating all types of mature blood cells. Progenitor cells which retain a capacity to generate all blood cell lineages but which can not self-renew are termed "pluripotent." Cells which can produce some but not all blood lineages and can not self-renew are termed "multipotent."

As used herein, "hematopoietic cell activity" includes an activity exerted by a hematopoietic cell, or an activity that takes place in a hematopoietic cell. For example, such activities include cellular processes that contribute to the physiological role of hematopoietic cells, such as hematopoiesis, but are not limited to, cell proliferation, differentiation, growth, migration and programmed cell death.

As used herein, the term "erythroid associated disorders" include disorders involving aberrant (increased or deficient) erythroblast proliferation, e.g., an erythroleukemia, and aberrant (increased or deficient) erythroblast differentiation, e.g., an anemia. Erythrocyte-associated disorders include anemias such as, for example, drug- (chemotherapy-) induced anemias, hemolytic anemias due to hereditary cell membrane abnormalities, such as hereditary spherocytosis, hereditary elliptocytosis, and hereditary pyropoikilocytosis; hemolytic anemias due to acquired cell membrane defects, such as paroxysmal nocturnal hemoglobinuria and spur cell anemia; hemolytic anemias caused by antibody reactions, for example to the RBC antigens, or antigens of the ABO system, Lewis system, Ii system, Rh system, Kidd system, Duffy system, and Kell system; methemoglobinemia; a failure of erythropoiesis, for example, as a result of aplastic anemia, pure red cell aplasia, myelodysplastic syndromes, sideroblastic anemias, and congenital dyserythropoietic anemia; secondary anemia in non-hematolic disorders, for example, as a result of chemotherapy, alcoholism, or liver disease; anemia of chronic disease, such as chronic renal failure; and endocrine deficiency diseases.

Anemias are an important class of disorders which affect erythroid cell growth or differentiation. Anemias include a variety of disorders in which the content of erythrocytes or hemoglobin in the blood is insufficient to fully provide transportation of oxygen for all of the body's needs. Examples of anemias include hemolytic anemias attributable to hereditary cell membrane abnormalities (e.g., hereditary spherocytosis, hereditary elliptocytosis, and hereditary pyropoikilocytosis), hemolytic anemias attributable to acquired cell membrane defects (e.g., paroxysmal nocturnal hemoglobinuria and spur cell anemia), hemolytic anemias attributable to antibody reactions (e.g., reactions to RBC antigens or antigens of the ABO system, Lewis system, Ii system, Rh system, Kidd system, Duffy system, and Kell system), methemoglobinemia, anemias attributable to a failure of erythropoiesis (e.g., as a result of aplastic anemia, pure red cell aplasia, myelodysplastic syndromes, sideroblastic anemias, or congenital dyserythropoietic anemia), secondary anemia in non-hematological disorders (e.g., anemia attributable to chemotherapy, alcoholism, or liver disease), anemia associated with a chronic disease (e.g., anemia associated with chronic renal failure), anemias attributable to bleeding, and anemia associated with endocrine deficiency diseases. Some of these disorders are known to affect growth or differentiation of erythroid cells.

As used herein, the term "modulate" includes alteration of, e.g., by increasing or decreasing the particular parameter being described.

As used herein, the term "apoptosis" includes programmed cell death which can be characterized using techniques which are known in the art. Apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage.

As used herein, the term "endocrine disorder" includes, but is not limited to, disorders of the pancreas, e.g., diabetes mellitus; islet cell tumors, including but not limited to, insulinomas, gastrinomas, and other rare islet cell tumors, the pituitary, or the hypothalamus.

Various aspects of the invention are described in further detail below.

Isolated Nucleic Acid Molecules

In one aspect, the invention provides, an isolated or purified, nucleic acid molecule that encodes a 27877, 18080, 14081, 32140, 50352, 16658, 14223, 16002, 50566, 65552 or 65577 polypeptide described herein, e.g., a full length 27877, 18080, 14081, 32140, 50352, 16658, 14223, 16002, 50566, 65552 or 65577 protein or a fragment thereof, e.g., a biologically active portion of 27877, 18080, 14081, 32140, 50352, 16658, 14223, 16002, 50566, 65552 or 65577 protein. Also included is a nucleic acid fragment suitable for use as a hybridization probe, which can be used, e.g., to identify a nucleic acid molecule encoding a polypeptide of the invention, 27877, 18080, 14081, 32140, 50352, 16658, 14223, 16002, 50566, 65552 or 65577 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO: 1, 3, 4, 6, 11, 13, 20, 22, 25, 27, 29, 31, 35, 37, 38, 40, 41, 43, 73, 75, 76, 78, 86 or 88, or a portion of any of this nucleotide sequence. In one embodiment, the nucleic acid molecule includes sequences encoding the human 27877, 18080, 14081, 32140, 50352, 16658, 14223, 16002, 50566, 65552 or 65577 protein (i.e., "the coding region" of SEQ ID NO: 1, 4, 11, 20, 25, 29, 35, 38, 41, 73, 76 or 86, as shown in SEQ ID NO: 3, 6, 13, 22, 27, 31, 37, 40, 43, 75, 78 or 88, respectively), as well as 5' untranslated sequences and 3' untranslated sequences. Alternatively, the nucleic acid molecule can include only the coding region of SEQ ID NO: 1, 4, 11, 20, 25, 29, 35, 38, 41, 73, 76 or 86 (e.g., SEQ ID NO: 3, 6, 13, 22, 27, 31, 37, 40, 43, 75, 78 or 88) and, e.g., no flanking sequences which normally accompany the subject sequence. In another embodiment, the nucleic acid molecule encodes a sequence corresponding to a fragment of the protein corresponding to conserved domains identified within SEQ ID NO:2, 5, 12, 21, 26, 30, 36, 39, 42, 74, 77 or 87.

In another embodiment, an isolated nucleic acid molecule of the invention includes a nucleic acid molecule which is a complement of the nucleotide sequence shown in SEQ ID NO: 1, 3, 4, 6, 11, 13, 20, 22, 25, 27, 29, 31, 35, 37, 38, 40, 41, 43, 73, 75, 76, 78, 86 or 88, or a portion of any of these nucleotide sequences. In other embodiments, the nucleic acid molecule of the invention is sufficiently complementary to the nucleotide sequence shown in SEQ ID NO:1, 3, 4, 6, 11, 13, 20, 22, 25, 27, 29, 31, 35, 37, 38, 40, 41, 43, 73, 75, 76, 78, 86 or 88 such that it can hybridize to the nucleotide sequence shown in SEQ ID NO: 1, 3, 4, 6, 11, 13, 20, 22, 25, 27, 29, 31, 35, 37, 38, 40, 41, 43, 73, 75, 76, 78, 86 or 88, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO: 1, 3, 4, 6, 11, 13, 20, 22, 25, 27, 29, 31, 35, 37, 38, 40, 41, 43, 73, 75, 76, 78, 86 or 88, or a portion, preferably of the same length, of any of these nucleotide sequences.

27877, 18080, 14081, 32140, 50352, 16658, 14223, 16002, 50566, 65552 or 65577 Nucleic Acid Fragments A nucleic acid molecule of the invention can include only a portion of the nucleic acid sequence of SEQ ID NO:1, 3, 4, 6, 11, 13, 20, 22, 25, 27, 29, 31, 35, 37, 38, 40, 41, 43, 73, 75, 76, 78, 86 or 88. For example, such a nucleic acid molecule can include a fragment which can be used as a probe or primer or a fragment encoding a portion of a 27877, 18080, 14081, 32140, 50352, 16658, 14223, 16002, 50566, 65552 or 65577 protein, e.g., an immunogenic or biologically active portion of a 27877, 18080, 14081, 32140, 50352, 16658, 14223, 16002, 50566, 65552 or 65577 protein. A fragment can comprise those nucleotides of SEQ ID NO:1, 3, 4, 6, 11, 13, 20, 22, 25, 27, 29, 31, 35, 37, 38, 40, 41, 43, 73, 75, 76, 78, 86 or 88, which encode a domain of human 27877, 18080, 14081, 32140, 50352, 16658, 14223, 16002, 50566, 65552 or 65577. The nucleotide sequence determined from the cloning of the 27877, 18080, 14081, 32140, 50352, 16658, 14223, 16002, 50566, 65552 or 65577 gene allows for the generation of probes and primers designed for use in identifying and/or cloning other 27877, 18080, 14081, 32140, 50352, 16658, 14223, 16002, 50566, 65552 or 65577 family members, or fragments thereof, as well as 27877, 18080, 14081, 32140, 50352, 16658, 14223, 16002, 50566, 65552 or 65577 homologs, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 100 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 27877, 18080, 14081, 32140, 50352, 16658, 14223, 16002, 50566, 65552 or 65577 nucleic acid fragment can include a sequence corresponding to a domain of 27877, 18080, 14081, 32140, 50352, 16658, 14223, 16002, 50566, 65552 or 65577, as described herein.

27877, 18080, 14081, 32140, 50352, 16658, 14223, 16002, 50566, 65552 or 65577 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1, 3, 4, 6, 11, 13, 20, 22, 25, 27, 29, 31, 35, 37, 38, 40, 41, 43, 73, 75, 76, 78, 86 or 88, or of a naturally occurring allelic variant or mutant of SEQ ID NO:1, 3, 4, 6, 11, 13, 20, 22, 25, 27, 29, 31, 35, 37, 38, 40, 41, 43, 73, 75, 76, 78, 86 or 88.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or antisense strand of a nucleic acid which encodes a domain identified in the 27877, 18080, 14081, 32140, 50352, 16658, 14223, 16002, 50566, 65552 or 65577 sequences.

In another embodiment a set of primers is provided, e.g., primers suitable for use in a PCR, which can be used to amplify a selected region of a 27877, 18080, 14081, 32140, 50352, 16658, 14223, 16002, 50566, 65552 or 65577 sequence, e.g., a domain, region, site or other sequence described herein. The primers should be at least 5, 10, or 50 base pairs in length and less than 100, or less than 200, base pairs in length. The primers should be identical, or differ by one base from a sequence disclosed herein or from a naturally occurring variant.

A nucleic acid fragment can encode an epitope bearing region of a polypeptide described herein.

A nucleic acid fragment encoding a "biologically active portion of a 27877, 18080, 14081, 32140, 50352, 16658, 14223, 16002, 50566, 65552 or 65577 polypeptide" can be prepared by isolating a portion of the nucleotide sequence of SEQ ID NO:1, 3, 4, 6, 11, 13, 20, 22, 25, 27, 29, 31, 35, 37, 38, 40, 41, 43, 73, 75, 76, 78, 86 or 88, which encodes a polypeptide having a 27877, 18080, 14081, 32140, 50352, 16658, 14223, 16002, 50566, 65552 or 65577 biological activity (e.g., the biological activities of the 27877, 18080, 14081, 32140, 50352, 16658, 14223, 16002, 50566, 65552 or 65577 proteins are described herein), expressing the encoded portion of the 27877, 18080, 14081, 32140, 50352, 16658, 14223, 16002, 50566, 65552 or 65577 protein (e.g., by recombinant expression in vitro) and assessing the activity of the encoded portion of the 27877, 18080, 14081, 32140, 50352, 16658, 14223, 16002, 50566, 65552 or 65577 protein. A nucleic acid fragment encoding a biologically active portion of a 27877, 18080, 14081, 32140, 50352, 16658, 14223, 16002, 50566, 65552 or 65577 polypeptide, can comprise a nucleotide sequence which is greater than 300 or more nucleotides in length.

In preferred embodiments, a nucleic acid includes a nucleotide sequence which is about 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, or more nucleotides in length and hybridizes under stringent hybridization conditions to a nucleic acid molecule of SEQ ID NO:1, 3, 4, 6, 11, 13, 20, 22, 25, 27, 29, 31, 35, 37, 38, 40, 41, 43, 73, 75, 76, 78, 86 or 88.

27877, 18080, 14081, 32140, 50352, 16658, 14223, 16002, 50566, 65552 or 65577 Nucleic Acid Variants The invention further encompasses nucleic acid molecules that differ from the nucleotide sequence shown in SEQ ID NO:1, 3, 4, 6, 11, 13, 20, 22, 25, 27, 29, 31, 35, 37, 38, 40, 41, 43, 73, 75, 76, 78, 86 or 88. Such differences can be due to degeneracy of the genetic code (and result in a nucleic acid which encodes the same 27877, 18080, 14081, 32140, 50352, 16658, 14223, 16002, 50566, 65552 or 65577 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2, 5, 12, 21, 26, 30, 36, 39, 42, 74, 77 or 87. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1, 3, 4, 6, 11, 13, 20, 22, 25, 27, 29, 31, 35, 37, 38, 40, 41, 43, 73, 75, 76, 78, 86 or 88, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the nucleotide sequence shown in SEQ ID NO:2, 5, 12, 21, 26, 30, 36, 39, 42, 74, 77 or 87 or a fragment of this sequence. Such nucleic acid molecules can readily be identified as being able to hybridize under stringent conditions, to the nucleotide sequence shown in SEQ ID NO:2, 5, 12, 21, 26, 30, 36, 39, 42, 74, 77 or 87 or a fragment of the sequence. Nucleic acid molecules corresponding to orthologs, homologs, and allelic variants of the 27877, 18080, 14081, 32140, 50352, 16658, 14223, 16002, 50566, 65552 or 65577 cDNAs of the invention can further be isolated by mapping to the same chromosome or locus as the 27877, 18080, 14081, 32140, 50352, 16658, 14223, 16002, 50566, 65552 or 65577 gene.

Preferred variants include those that are correlated with activities specific to the molecules of the invention, i.e. phospholipase activity, serine carboxypeptidase activity, trypsin-like serine protease activity, aldehyde dehydrogenase activity, ubiquitin-protein ligase activity, protein kinase activity, hydrolase activity or matrix metalloproteinase activity.

Allelic variants of 27877, 18080, 14081, 32140, 50352, 16658, 14223, 16002, 50566, 65552 or 65577, e.g., human 27877, 18080, 14081, 32140, 50352, 16658, 14223, 16002, 50566, 65552 or 65577, include both functional and non-functional proteins. Functional allelic variants are naturally occurring amino acid sequence variants of the 27877, 18080, 14081, 32140, 50352, 16658, 14223, 16002, 50566, 65552 or 65577 protein within a population that maintain the ability to bind a 27877, 18080, 14081, 32140, 50352, 16658, 14223, 16002, 50566, 65552 or 65577 ligand or substrate and/or modulate phospholipase activity, serine carboxypeptidase activity, trypsin-like serine protease activity, aldehyde dehydrogenase activity, ubiquitin-protein ligase activity, protein kinase activity, hydrolase activity or matrix metalloproteinase activity. Functional allelic variants will typically contain only conservative substitution of one or more amino acids of SEQ ID NO:2, 5, 12, 21, 26, 30, 36, 39, 42, 74, 77 or 87, or substitution, deletion or insertion of non-critical residues in non-critical regions of the protein. Non-functional allelic variants are naturally-occurring amino acid sequence variants of the 27877, 18080, 14081, 32140, 50352, 16658, 14223, 16002, 50566, 65552 or 65577, e.g., human 27877, 18080, 14081, 32140, 50352, 16658, 14223, 16002, 50566, 65552 or 65577, protein within a population that do not have the ability to bind a 27877, 18080, 14081, 32140, 50352, 16658, 14223, 16002, 50566, 65552 or 65577 ligand or substrate and/or phospholipase activity, serine carboxypeptidase activity, trypsin-like serine protease activity, aldehyde dehydrogenase activity, ubiquitin-protein ligase activity, protein kinase activity, hydrolase activity or matrix metalloproteinase activity. Non-functional allelic variants will typically contain a non-conservative substitution, a deletion, or insertion, or premature truncation of the amino acid sequence of SEQ ID NO:2, 5, 12, 21, 26, 30, 36, 39, 42, 74, 77 or 87, or a substitution, insertion, or deletion in critical residues or critical regions of the protein.

Moreover, nucleic acid molecules encoding other 27877, 18080, 14081, 32140, 50352, 16658, 14223, 16002, 50566, 65552 or 65577 family members and, thus, which have a nucleotide sequence which differs from the 27877, 18080, 14081, 32140, 50352, 16658, 14223, 16002, 50566, 65552 or 65577 sequences of SEQ ID NO:1, 3, 4, 6, 11, 13, 20, 22, 25, 27, 29, 31, 35, 37, 38, 40, 41, 43, 73, 75, 76, 78, 86 or 88 are intended to be within the scope of the invention.

Antisense Nucleic Acid Molecules, Ribozymes and Modified 27877, 18080, 14081, 32140, 50352, 16658, 14223, 16002, 50566, 65552 or 65577 Nucleic Acid Molecules In another aspect, the invention features, an isolated nucleic acid molecule which is antisense to 27877, 18080, 14081, 32140, 50352, 16658, 14223, 16002, 50566, 65552 or 65577. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 27877, 18080, 14081, 32140, 50352, 16658, 14223, 16002, 50566, 65552 or 65577 coding strand, or to only a portion thereof (e.g., the coding region of human 27877, 18080, 14081, 32140, 50352, 16658, 14223, 16002, 50566, 65552 or 65577 corresponding to SEQ ID NO:3, 6, 13, 22, 27, 31, 37, 40, 43, 75, 78, 88, respectively). In another embodiment, the antisense nucleic acid molecule is antisense to a "noncoding region" of the coding strand of a nucleotide sequence encoding 27877, 18080, 14081, 32140, 50352, 16658, 14223, 16002, 50566, 65552 or 65577 (e.g., the 5' and 3' untranslated regions).

An antisense nucleic acid can be designed such that it is complementary to the entire coding region of 27877, 18080, 14081, 32140, 50352, 16658, 14223, 16002, 50566, 65552 or 65577 mRNA, but more preferably is an oligonucleotide which is antisense to only a portion of the coding or noncoding region of 27877, 18080, 14081, 32140, 50352, 16658, 14223, 16002, 50566, 65552 or 65577 mRNA. For example, the antisense oligonucleotide can be complementary to the region surrounding the translation start site of 27877, 18080, 14081, 32140, 50352, 16658, 14223, 16002, 50566, 65552 or 65577 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 27877, 18080, 14081, 32140, 50352, 16658, 14223, 16002, 50566, 65552 or 65577 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically or selectively bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. A ribozyme having specificity for a 27877, 18080, 14081, 32140, 50352, 16658, 14223, 16002, 50566, 65552 or 65577-encoding nucleic acid can include one or more sequences complementary to the nucleotide sequence of a 27877, 18080, 14081, 32140, 50352, 16658, 14223, 16002, 50566, 65552 or 65577 cDNA disclosed herein (i.e., SEQ ID NO: 1, 3, 4, 6, 11, 13, 20, 22, 25, 27, 29, 31, 35, 37, 38, 40, 41, 43, 73, 75, 76, 78, 86 or 88), and a sequence having known catalytic sequence responsible for mRNA cleavage (see U.S. Pat. No. 5,093,246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a 27877, 18080, 14081, 32140, 50352, 16658, 14223, 16002, 50566, 65552 or 65577-encoding mRNA. See, e.g., Cech et al. U.S. Pat. No. 4,987,071; and Cech et al. U.S. Pat. No. 5,116,742. Alternatively, 27877, 18080, 14081, 32140, 50352, 16658, 14223, 16002, 50566, 65552 or 65577 mRNA can be used to select a catalytic RNA having a specific ribonuclease activity from a pool of RNA molecules. See, e.g., Bartel and Szostak (1993) *Science* 261:1411-1418.

27877, 18080, 14081, 32140, 50352, 16658, 14223, 16002, 50566, 65552 or 65577 gene expression can be inhibited by targeting nucleotide sequences complementary to the regulatory region of the 27877, 18080, 14081, 32140, 50352, 16658, 14223, 16002, 50566, 65552 or 65577 (e.g., the 27877, 18080, 14081, 32140, 50352, 16658, 14223, 16002, 50566, 65552 or 65577 promoter and/or enhancers) to form triple helical structures that prevent transcription of the 27877, 18080, 14081, 32140, 50352, 16658, 14223, 16002, 50566, 65552 or 65577 gene in target cells. See generally, Helene (1991) *Anticancer Drug Des.* 6:569-84; Helene (1992) *Ann. N.Y. Acad. Sci.* 660:27-36; and Maher (1992) *Bioassays* 14:807-15. The potential sequences that can be targeted for triple helix formation can be increased by creating a so-called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 27877, 18080, 14081, 32140, 50352, 16658, 14223, 16002, 50566, 65552 or 65577 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup et al. (1996) *Bioorganic & Medicinal Chemistry* 4: 5-23).

As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) *Proc. Natl. Acad. Sci.* 93: 14670-675.

PNAs of 27877, 18080, 14081, 32140, 50352, 16658, 14223, 16002, 50566, 65552 or 65577 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 27877, 18080, 14081, 32140, 50352, 16658, 14223, 16002, 50566, 65552 or 65577 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup et al. (1996) supra)); or as probes or primers for DNA sequencing or hybridization (Hyrup et al. (1996) supra; Perry-O'Keefe supra).

In other embodiments, the oligonucleotide can include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO88/09810) or the blodd-brain barrier (see, e.g., PCT Publication No. WO89/10134). In addition, oligonucleotides can be modified with hybridization-triggered cleavage agents (see, e.g., Krol et al. (1988) *Bio-Techniques* 6:958-976) or intercalating agents. (see, e.g., Zon (1988) *Pharm. Res.* 5:539-549). To this end, the oligonucleotide can be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 27877, 18080, 14081, 32140, 50352, 16658, 14223, 16002, 50566, 65552 or 65577 nucleic acid of the invention, two complementary regions one having a fluorophore and one a quencher such that the molecular beacon is useful for quantitating the presence of the 27877, 18080, 14081, 32140, 50352, 16658, 14223, 16002, 50566, 65552 or 65577 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 27877, 18080, 14081, 32140, 50352, 16658, 14223, 16002, 50566, 65552 or 65577 Polypeptides In another aspect, the invention features, an isolated 27877, 18080, 14081, 32140, 50352, 16658, 14223, 16002, 50566, 65552 or 65577 protein, or fragment, e.g., a biologically active portion, for use as immunogens or antigens to raise or test (or more generally to bind) anti-27877, 18080, 14081, 32140, 50352, 16658, 14223, 16002, 50566, 65552 or 65577 antibodies. 27877, 18080, 14081, 32140, 50352, 16658, 14223, 16002, 50566, 65552 or 65577 protein can be isolated from cells or tissue sources using standard protein purification techniques. 27877, 18080, 14081, 32140, 50352, 16658, 14223, 16002, 50566, 65552 or 65577 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when the polypeptide is expressed in a native cell, or in systems which result in the alteration or omission of post-translational modifications, e.g., glycosylation or cleavage, present in a native cell.

In a preferred embodiment, a 27877, 18080, 14081, 32140, 50352, 16658, 14223, 16002, 50566, 65552 or 65577 polypeptide has one or more of the following characteristics:

it has the ability to catalyze the hydrolysis of an acyl or phosphoacyl bond of a phospholipids; to modulate removal of COOH-terminal residues; (ii) it has the ability to modulate the transfer of an acyl group from a donor to an acceptor molecule; (iii) it has the ability to phosphorylate carbohydrates; (iv) it has the ability to oxidate an aldehyde; (v) it has the ability to modulate ubiquitination of a substrate; (vi) it has the ability to reversibly phosphorylate proteins in order to regulate protein activity in eukaryotic cells; (vii) it has the ability to interact with cytotoxins and metabolites; (viii) it has the ability to catalyze the metobolism of a cytotoxin or metabolite; (ix) it has the ability to hydrolyze a thioester containing compound; (x) it has the ability to catalyze the formation of a thioester conjugation on a substrate; (xi) it has the ability to cleave or modulate the degredation of proteins or peptides of the extracellular matrix; (xii) it has the ability to catalyze or modulate catalysis of cleavage of covalent bonds within or between amino acid residues; (xiii) it has a molecular weight, e.g., a deduced molecular weight, preferably ignoring any contribution of post translational modifications, amino acid composition or other physical characteristic of a 27877, 18080, 14081, 32140, 50352, 16658, 14223, 16002, 50566, 65552 or 65577 polypeptide, e.g., a polypeptide of SEQ ID NO:2, 5, 12, 21, 26, 30, 36, 39, 42, 74, 77 or 87; (xiv) it has an overall sequence similarity of at least 60%, preferably at least 70%, more preferably at least 80, 90, or 95%, with a polypeptide of SEQ ID NO:2, 5, 12, 21, 26, 30, 36, 39, 42, 74, 77 or 87; (xv) it is expressed in a multitude of human tissues and cell lines (refer to section for each molecule of the invention); and it has specific domains which are preferably about 70%, 80%, 90% or 95% identical to the identified amino acid residues of SEQ ID NO:2, 5, 12, 21, 26, 30, 36, 39, 42, 74, 77 or 87 (refer to section for each molecule of the invention for domain names and locations within amino acid sequence).

In a preferred embodiment the 27877, 18080, 14081, 32140, 50352, 16658, 14223, 16002, 50566, 65552 or 65577 protein, or fragment thereof, differs from the corresponding sequence in SEQ ID NO:2, 5, 12, 21, 26, 30, 36, 39, 42, 74, 77 or 87. In one embodiment it differs by at least one but by less than 15, 10 or 5 amino acid residues. In another it differs from the corresponding sequence in SEQ ID NO:2, 5, 12, 21, 26, 30, 36, 39, 42, 74, 77 or 87 by at least one residue but less than 20%, 15%, 10% or 5% of the residues in it differ from the corresponding sequence in SEQ ID NO:2, 5, 12, 21, 26, 30, 36, 39, 42, 74, 77 or 87. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the identified or conserved domain(s) within SEQ ID NO:2, 5, 12, 21, 26, 30, 36, 39, 42, 74, 77 or 87. In another embodiment one or more differences are in the cidentified or conserved domain(s) within SEQ ID NO:2, 5, 12, 21, 26, 30, 36, 39, 42, 74, 77 or 87.

Other embodiments include a protein that contains one or more changes in amino acid sequence, e.g., a change in an amino acid residue which is not essential for activity. Such 27877, 18080, 14081, 32140, 50352, 16658, 14223, 16002, 50566, 65552 or 65577 proteins differ in amino acid sequence from SEQ ID NO:2, 5, 12, 21, 26, 30, 36, 39, 42, 74, 77 or 87, yet retain biological activity.

In one embodiment, the protein includes an amino acid sequence at least about 60%, 65%, 70%, 75%, 80%, 85%, 90%, 95%, 98% or more homologous to SEQ ID NO:2, 5, 12, 21, 26, 30, 36, 39, 42, 74, 77 or 87.

A 27877, 18080, 14081, 32140, 50352, 16658, 14223, 16002, 50566, 65552 or 65577 protein or fragment is provided which varies from the sequence of SEQ ID NO:2, 5, 12, 21, 26, 30, 36, 39, 42, 74, 77 or 87 in regions defined by amino acids that are not within identified or conserved domains or regions by at least one but by less than 15, 10 or 5 amino acid residues in the protein or fragment but which does not differ from SEQ ID NO:2, 5, 12, 21, 26, 30, 36, 39, 42, 74, 77 or 87 in regions defined by amino acids that are within identified or conserved domains or regions. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 27877, 18080, 14081, 32140, 50352, 16658, 14223, 16002, 50566, 65552 or 65577 protein includes an identified domain (refer to section for each molecule of the invention). Moreover, other biologically active portions, in which other regions of the protein are deleted, can be prepared by recombinant techniques and evaluated for one or more of the functional activities of a native 27877, 18080, 14081, 32140, 50352, 16658, 14223, 16002, 50566, 65552 or 65577 protein.

In a preferred embodiment, the 27877, 18080, 14081, 32140, 50352, 16658, 14223, 16002, 50566, 65552 or 65577 protein has an amino acid sequence shown in SEQ ID NO:2, 5, 12, 21, 26, 30, 36, 39, 42, 74, 77 or 87. In other embodiments, the 27877, 18080, 14081, 32140, 50352, 16658, 14223, 16002, 50566, 65552 or 65577 protein is sufficiently or substantially identical to SEQ ID NO:2, 5, 12, 21, 26, 30, 36, 39, 42, 74, 77 or 87. In yet another embodiment, the 27877, 18080, 14081, 32140, 50352, 16658, 14223, 16002, 50566, 65552 or 65577 protein is sufficiently or substantially identical to SEQ ID NO:2, 5, 12, 21, 26, 30, 36, 39, 42, 74, 77 or 87 and retains the functional activity of the protein of SEQ ID NO:2, 5, 12, 21, 26, 30, 36, 39, 42, 74, 77 or 87, as described in detail in the subsections above.

27877, 18080, 14081, 32140, 50352, 16658, 14223, 16002, 50566, 65552 or 65577 Chimeric or Fusion Proteins In another aspect, the invention provides 27877, 18080, 14081, 32140, 50352, 16658, 14223, 16002, 50566, 65552 or 65577 chimeric or fusion proteins. As used herein, a 27877, 18080, 14081, 32140, 50352, 16658, 14223, 16002, 50566, 65552 or 65577 "chimeric protein" or "fusion protein" includes a 27877, 18080, 14081, 32140, 50352, 16658, 14223, 16002, 50566, 65552 or 65577 polypeptide linked to a non-27877, 18080, 14081, 32140, 50352, 16658, 14223, 16002, 50566, 65552 or 65577 polypeptide. A "non-27877, 18080, 14081, 32140, 50352, 16658, 14223, 16002, 50566, 65552 or 65577 polypeptide" refers to a polypeptide having an amino acid sequence corresponding to a protein which is not substantially homologous to the 27877, 18080, 14081, 32140, 50352, 16658, 14223, 16002, 50566, 65552 or 65577 protein, e.g., a protein which is different from the 27877, 18080, 14081, 32140, 50352, 16658, 14223, 16002, 50566, 65552 or 65577 protein and which is derived from the same or a different organism. The 27877, 18080, 14081, 32140, 50352, 16658, 14223, 16002, 50566, 65552 or 65577 polypeptide of the fusion protein can correspond to all or a portion e.g., a fragment described herein of a 27877, 18080, 14081, 32140, 50352, 16658, 14223, 16002, 50566, 65552 or 65577 amino acid sequence. In a preferred embodiment, a 27877, 18080, 14081, 32140, 50352, 16658, 14223, 16002, 50566, 65552 or 65577 fusion protein includes at least one (or two) biologically active portion of a 27877, 18080, 14081, 32140, 50352, 16658, 14223, 16002, 50566, 65552 or 65577 protein. The non-27877, 18080, 14081, 32140, 50352, 16658, 14223, 16002, 50566, 65552 or 65577 polypeptide can be fused to the N-terminus or C-terminus of the 27877, 18080, 14081, 32140, 50352, 16658, 14223, 16002, 50566, 65552 or 65577 polypeptide.

The fusion protein can include a moiety which has a high affinity for a ligand. For example, the fusion protein can be a GST-27877, 18080, 14081, 32140, 50352, 16658, 14223, 16002, 50566, 65552 or 65577 fusion protein in which the 27877, 18080, 14081, 32140, 50352, 16658, 14223, 16002, 50566, 65552 or 65577 sequences are fused to the C-terminus of the GST sequences. Such fusion proteins can facilitate the purification of recombinant 27877, 18080, 14081, 32140, 50352, 16658, 14223, 16002, 50566, 65552 or 65577. Alternatively, the fusion protein can be a 27877, 18080, 14081, 32140, 50352, 16658, 14223, 16002, 50566, 65552 or 65577 protein containing a heterologous signal sequence at its N-terminus. In certain host cells (e.g., mammalian host cells), expression and/or secretion of 27877, 18080, 14081, 32140, 50352, 16658, 14223, 16002, 50566, 65552 or 65577 can be increased through use of a heterologous signal sequence.

Fusion proteins can include all or a part of a serum protein, e.g., a portion of an immunoglobulin (e.g., IgG, IgA, or IgE), e.g., an Fc region and/or the hinge C1 and C2 sequences of an immunoglobulin or human serum albumin.

The 27877, 18080, 14081, 32140, 50352, 16658, 14223, 16002, 50566, 65552 or 65577 fusion proteins of the invention can be incorporated into pharmaceutical compositions and administered to a subject in vivo. The 27877, 18080, 14081, 32140, 50352, 16658, 14223, 16002, 50566, 65552 or 65577 fusion proteins can be used to affect the bioavailability of a 27877, 18080, 14081, 32140, 50352, 16658, 14223, 16002, 50566, 65552 or 65577 substrate. 27877, 18080, 14081, 32140, 50352, 16658, 14223, 16002, 50566, 65552 or 65577 fusion proteins can be useful therapeutically for the treatment of disorders caused by, for example, (i) aberrant modification or mutation of a gene encoding a 27877, 18080, 14081, 32140, 50352, 16658, 14223, 16002, 50566, 65552 or 65577 protein; (ii) mis-regulation of the 27877, 18080, 14081, 32140, 50352, 16658, 14223, 16002, 50566, 65552 or 65577 gene; and (iii) aberrant post-translational modification of a 27877, 18080, 14081, 32140, 50352, 16658, 14223, 16002, 50566, 65552 or 65577 protein.

Moreover, the 27877, 18080, 14081, 32140, 50352, 16658, 14223, 16002, 50566, 65552 or 65577-fusion proteins of the invention can be used as immunogens to produce anti-27877, 18080, 14081, 32140, 50352, 16658, 14223, 16002, 50566, 65552 or 65577 antibodies in a subject, to purify 27877, 18080, 14081, 32140, 50352, 16658, 14223, 16002, 50566, 65552 or 65577 ligands and in screening assays to identify molecules which inhibit the interaction of 27877, 18080, 14081, 32140, 50352, 16658, 14223, 16002, 50566, 65552 or 65577 with a 27877, 18080, 14081, 32140, 50352, 16658, 14223, 16002, 50566, 65552 or 65577 substrate.

Expression vectors are commercially available that already encode a fusion moiety (e.g., a GST polypeptide). A 27877, 18080, 14081, 32140, 50352, 16658, 14223, 16002, 50566, 65552 or 65577-encoding nucleic acid can be cloned into such an expression vector such that the fusion moiety is linked in-frame to the 27877, 18080, 14081, 32140, 50352, 16658, 14223, 16002, 50566, 65552 or 65577 protein.

Variants of 27877, 18080, 14081, 32140, 50352, 16658, 14223, 16002, 50566, 65552 or 65577 Proteins In another aspect, the invention also features a variant of a 27877, 18080, 14081, 32140, 50352, 16658, 14223, 16002, 50566, 65552 or 65577 polypeptide, e.g., which functions as an agonist (mimetics) or as an antagonist. Variants of the 27877, 18080, 14081, 32140, 50352, 16658, 14223, 16002, 50566, 65552 or 65577 proteins can be generated by mutagenesis, e.g., discrete point mutation, the insertion or deletion of sequences or the truncation of a 27877, 18080, 14081, 32140, 50352, 16658, 14223, 16002, 50566, 65552 or 65577 protein. An agonist of the 27877, 18080, 14081, 32140, 50352, 16658, 14223, 16002, 50566, 65552 or 65577 proteins can retain substantially the same, or a subset, of the biological activities of the naturally occurring form of a 27877, 18080, 14081, 32140, 50352, 16658, 14223, 16002, 50566, 65552 or 65577 protein. An antagonist of a 27877, 18080, 14081, 32140, 50352, 16658, 14223, 16002, 50566, 65552 or 65577 protein can inhibit one or more of the activities of the naturally occurring form of the 27877, 18080, 14081, 32140, 50352, 16658, 14223, 16002, 50566, 65552 or 65577 protein by, for example, competitively modulating a 27877, 18080, 14081, 32140, 50352, 16658, 14223, 16002, 50566, 65552 or 65577-mediated activity of a 27877, 18080, 14081, 32140, 50352, 16658, 14223, 16002, 50566, 65552 or 65577 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 27877, 18080, 14081, 32140, 50352, 16658, 14223, 16002, 50566, 65552 or 65577 protein.

Variants of a 27877, 18080, 14081, 32140, 50352, 16658, 14223, 16002, 50566, 65552 or 65577 protein can be identified by screening combinatorial libraries of mutants, e.g., truncation mutants, of a 27877, 18080, 14081, 32140, 50352, 16658, 14223, 16002, 50566, 65552 or 65577 protein for agonist or antagonist activity.

Libraries of fragments e.g., N terminal, C terminal, or internal fragments, of a 27877, 18080, 14081, 32140, 50352, 16658, 14223, 16002, 50566, 65552 or 65577 protein coding sequence can be used to generate a variegated population of fragments for screening and subsequent selection of variants of a 27877, 18080, 14081, 32140, 50352, 16658, 14223, 16002, 50566, 65552 or 65577 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Recursive ensemble mutagenesis (REM), a new technique which enhances the frequency of functional mutants in the libraries, can be used in combination with the screening assays to identify 27877, 18080, 14081, 32140, 50352, 16658, 14223, 16002, 50566, 65552 or 65577 variants (Arkin and Yourvan (1992) *Proc. Natl. Acad. Sci. USA* 89:7811-7815; Delgrave et al. (1993) *Protein Engineering* 6:327-331).

Cell based assays can be exploited to analyze a variegated 27877, 18080, 14081, 32140, 50352, 16658, 14223, 16002, 50566, 65552 or 65577 library. For example, a library of expression vectors can be transfected into a cell line, e.g., a cell line, which ordinarily responds to 27877, 18080, 14081, 32140, 50352, 16658, 14223, 16002, 50566, 65552 or 65577 in a substrate-dependent manner. The transfected cells are then contacted with 27877, 18080, 14081, 32140, 50352, 16658, 14223, 16002, 50566, 65552 or 65577 and the effect of the expression of the mutant on signaling by the 27877, 18080, 14081, 32140, 50352, 16658, 14223, 16002, 50566, 65552 or 65577 substrate can be detected, e.g., by measuring either phospholipase activity, serine carboxypeptidase activity, trypsin-like serine protease activity, aldehyde dehydrogenase activity, ubiquitin-protein ligase activity, protein kinase activity, hydrolase activity, matrix metalloproteinase activity, or other activity. Plasmid DNA can then be recovered from the cells which score for inhibition, or alternatively, potentiation of signaling by the 27877, 18080, 14081, 32140, 50352, 16658, 14223, 16002, 50566, 65552 or 65577 substrate, and the individual clones further characterized.

In another aspect, the invention features a method of making a 27877, 18080, 14081, 32140, 50352, 16658, 14223, 16002, 50566, 65552 or 65577 polypeptide, e.g., a peptide having a non-wild type activity, e.g., an antagonist, agonist, or super agonist of a naturally occurring 27877, 18080, 14081, 32140, 50352, 16658, 14223, 16002, 50566, 65552 or 65577 polypeptide, e.g., a naturally occurring 27877, 18080, 14081, 32140, 50352, 16658, 14223, 16002, 50566, 65552 or 65577 polypeptide. The method includes altering the sequence of a 27877, 18080, 14081, 32140, 50352, 16658, 14223, 16002, 50566, 65552 or 65577 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 27877, 18080, 14081, 32140, 50352, 16658, 14223, 16002, 50566, 65552 or 65577 polypeptide a biological activity of a naturally occurring 27877, 18080, 14081, 32140, 50352, 16658, 14223, 16002, 50566, 65552 or 65577 polypeptide. The method includes altering the sequence, e.g., by substitution or deletion of one or more residues, of a 27877, 18080, 14081, 32140, 50352, 16658, 14223, 16002, 50566, 65552 or 65577 polypeptide, e.g., altering the sequence of a non-conserved region, or a domain or residue described herein, and testing the altered polypeptide for the desired activity.

Anti-27877, 18080, 14081, 32140, 50352, 16658, 14223, 16002, 50566, 65552 or 65577 Antibodies In another aspect, the invention provides an anti-27877, 18080, 14081, 32140, 50352, 16658, 14223, 16002, 50566, 65552 or 65577 antibody. The term "antibody" as used herein refers to an immunoglobulin molecule or immunologically active portion thereof, i.e., an antigen-binding portion. Examples of immunologically active portions of immunoglobulin molecules include scFV and dcFV fragments, Fab and F(ab')$_2$ fragments which can be generated by treating the antibody with an enzyme such as papain or pepsin, respectively.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length 27877, 18080, 14081, 32140, 50352, 16658, 14223, 16002, 50566, 65552 or 65577 protein or, antigenic peptide fragment of 27877, 18080, 14081, 32140, 50352, 16658, 14223, 16002, 50566, 65552 or 65577 can be used as an immunogen or can be used to identify anti-27877, 18080, 14081, 32140, 50352, 16658, 14223, 16002, 50566, 65552 or 65577 antibodies made with other immunogens, e.g., cells, membrane preparations, and the like. The antigenic peptide of 27877, 18080, 14081, 32140, 50352, 16658, 14223, 16002, 50566, 65552 or 65577 should include at least 8 amino acid residues of the amino acid sequence shown in SEQ ID NO:2, 5, 12, 21, 26, 30, 36, 39, 42, 74, 77 or 87 and encompasses an epitope of 27877, 18080, 14081, 32140, 50352, 16658, 14223, 16002, 50566, 65552 or 65577. Preferably, the antigenic peptide includes at least 10 amino acid residues, more preferably at least 15 amino acid residues, even more preferably at least 20 amino acid residues, and most preferably at least 30 amino acid residues.

Fragments of 27877, 18080, 14081, 32140, 50352, 16658, 14223, 16002, 50566, 65552 or 65577 which include hydrophilic regions of SEQ ID NO:2, 5, 12, 21, 26, 30, 36, 39, 42, 74, 77 or 87 can be used to make, e.g., used as immunogens or used to characterize the specificity of an antibody, antibodies against hydrophilic regions of the 27877, 18080, 14081, 32140, 50352, 16658, 14223, 16002, 50566, 65552 or 65577 protein. Similarly, fragments of 27877, 18080, 14081, 32140, 50352, 16658, 14223, 16002, 50566, 65552 or 65577 which include hydrophobic regions of SEQ ID NO:2, 5, 12, 21, 26, 30, 36, 39, 42, 74, 77 or 87 can be used to make an antibody against a hydrophobic region of the 27877, 18080, 14081, 32140, 50352, 16658, 14223, 16002, 50566, 65552 or 65577 protein; fragments of 27877, 18080, 14081, 32140, 50352, 16658, 14223, 16002, 50566, 65552 or 65577 which include residues within extra cellular domain(s) of SEQ ID NO:2, 5, 12, 21, 26, 30, 36, 39, 42, 74, 77 or 87 can be used to make an antibody against an extracellular or non-cytoplasmic region of the 27877, 18080, 14081, 32140, 50352, 16658, 14223, 16002, 50566, 65552 or 65577 protein; fragments of 27877, 18080, 14081, 32140, 50352, 16658, 14223, 16002, 50566, 65552 or 65577 which include residues within intracellular regions of SEQ ID NO:2, 5, 12, 21, 26, 30, 36, 39, 42, 74, 77 or 87 can be used to make an antibody against an intracellular region of the 27877, 18080, 14081, 32140, 50352, 16658, 14223, 16002, 50566, 65552 or 65577 protein; a fragment of 27877, 18080, 14081, 32140, 50352, 16658, 14223, 16002, 50566, 65552 or 65577 which include residues within identified or conserved domains of SEQ ID NO:2, 5, 12, 21, 26, 30, 36, 39, 42, 74, 77 or 87 can be used to make an antibody against the identified or conserved domain of the 27877, 18080, 14081, 32140, 50352, 16658, 14223, 16002, 50566, 65552 or 65577 protein.

Antibodies reactive with, or specific or selective for, any of these regions, or other regions or domains described herein are provided.

Preferred epitopes encompassed by the antigenic peptide are regions of 27877, 18080, 14081, 32140, 50352, 16658, 14223, 16002, 50566, 65552 or 65577 located on the surface of the protein, e.g., hydrophilic regions, as well as regions with high antigenicity. For example, an Emini surface probability analysis of the human 27877, 18080, 14081, 32140, 50352, 16658, 14223, 16002, 50566, 65552 or 65577 protein sequence can be used to indicate the regions that have a particularly high probability of being localized to the surface of the 27877, 18080, 14081, 32140, 50352, 16658, 14223, 16002, 50566, 65552 or 65577 protein and are thus likely to constitute surface residues useful for targeting antibody production.

In a preferred embodiment the antibody can bind to the extracellular portion of the 27877, 18080, 14081, 32140, 50352, 16658, 14223, 16002, 50566, 65552 or 65577 protein, e.g., it can bind to a whole cell which expresses the 27877, 18080, 14081, 32140, 50352, 16658, 14223, 16002, 50566, 65552 or 65577 protein. In another embodiment, the antibody binds an intracellular portion of the 27877, 18080, 14081, 32140, 50352, 16658, 14223, 16002, 50566, 65552 or 65577 protein.

In a preferred embodiment the antibody binds an epitope on any domain or region on 27877, 18080, 14081, 32140, 50352, 16658, 14223, 16002, 50566, 65552 or 65577 proteins described herein.

Additionally, chimeric, humanized, and completely human antibodies are also within the scope of the invention. Chimeric, humanized, but most preferably, completely human antibodies are desirable for applications which include repeated administration, e.g., therapeutic treatment of human patients, and some diagnostic applications.

Chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Canc. Res. 47:999-1005; Wood et al. (1985) Nature 314:446-449; and Shaw et al. (1988) J. Natl. Cancer Inst. 80:1553-1559).

A humanized or complementarity determining region (CDR)-grafted antibody will have at least one or two, but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 27877, 18080, 14081, 32140, 50352, 16658, 14223, 16002, 50566, 65552 or 65577 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, (1987) From Genes to Clones (Verlagsgesellschaft, Weinheim, Germany). In a family of proteins; each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison (1985) Science 229:1202-1207, by Oi et al. (1986) BioTechniques 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 27877, 18080, 14081, 32140, 50352, 16658, 14223, 16002, 50566, 65552 or 65577 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. (1986) Nature 321:552-525; Verhoeyan et al. (1988) Science 239:1534; Beidler et al. (1988) J. Immunol. 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) Int. Rev. Immunol. 13:65-93); and U.S. Pat. Nos. 5,625,126; 5,633,425; 5,569,825; 5,661,016; and 5,545,806. In addition, companies such as Abgenix, Inc. (Fremont, Calif.) and Medarex, Inc. (Princeton, N.J.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) Bio/Technology 12:899-903).

The anti-27877, 18080, 14081, 32140, 50352, 16658, 14223, 16002, 50566, 65552 or 65577 antibody can be a single chain antibody. A single-chain antibody (scFV) can be engineered as described in, for example, Colcher et al. (1999) Ann. NY Acad. Sci. 880:263-80; and Reiter (1996) Clin. Cancer Res. 2:245-52. The single chain antibody can be dimerized or multimerized to generate multivalent antibodies having specificities for different epitopes of the same target 27877, 18080, 14081, 32140, 50352, 16658, 14223, 16002, 50566, 65552 or 65577 protein.

In a preferred embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

Radioactive ions include, but are not limited to iodine, yttrium and praseodymium.

The conjugates of the invention can be used for modifying a given biological response, the therapeutic moiety is not to be construed as limited to classical chemical therapeutic agents. For example, the therapeutic moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

An anti-27877, 18080, 14081, 32140, 50352, 16658, 14223, 16002, 50566, 65552 or 65577 antibody (e.g., monoclonal antibody) can be used to isolate 27877, 18080, 14081, 32140, 50352, 16658, 14223, 16002, 50566, 65552 or 65577 by standard techniques, such as affinity chromatography or immunoprecipitation. Moreover, an anti-27877, 18080, 14081, 32140, 50352, 16658, 14223, 16002, 50566, 65552 or 65577 antibody can be used to detect 27877, 18080, 14081, 32140, 50352, 16658, 14223, 16002, 50566, 65552 or 65577 protein (e.g., in a cellular lysate or cell supernatant) in order to evaluate the abundance and pattern of expression of the protein. Anti-27877, 18080, 14081, 32140, 50352, 16658, 14223, 16002, 50566, 65552 or 65577 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

In preferred embodiments, an antibody can be made by immunizing with a purified 27877, 18080, 14081, 32140, 50352, 16658, 14223, 16002, 50566, 65552 or 65577 antigen, or a fragment thereof, e.g., a fragment described herein, a membrane associated antigen, tissues, e.g., crude tissue preparations, whole cells, preferably living cells, lysed cells, or cell fractions, e.g., membrane fractions.

Antibodies which bind only a native 27877, 18080, 14081, 32140, 50352, 16658, 14223, 16002, 50566, 65552 or 65577 protein, only denatured or otherwise non-native 27877, 18080, 14081, 32140, 50352, 16658, 14223, 16002, 50566, 65552 or 65577 protein, or which bind both, are within the invention. Antibodies with linear or conformational epitopes are within the invention. Conformational epitopes sometimes can be identified by identifying antibodies which bind to native but not denatured 27877, 18080, 14081, 32140, 50352, 16658, 14223, 16002, 50566, 65552 or 65577 protein.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 27877, 18080, 14081, 32140, 50352, 16658, 14223, 16002, 50566, 65552 or 65577 nucleic acid in a form suitable for expression of the nucleic acid in a host cell.

Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 27877, 18080, 14081, 32140, 50352, 16658, 14223, 16002, 50566, 65552 or 65577 proteins, mutant forms of 27877, 18080, 14081, 32140, 50352, 16658, 14223, 16002, 50566, 65552 or 65577 proteins, fusion proteins, and the like).

The recombinant expression vectors of the invention can be designed for expression of 27877, 18080, 14081, 32140, 50352, 16658, 14223, 16002, 50566, 65552 or 65577 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 27877, 18080, 14081, 32140, 50352, 16658, 14223, 16002, 50566, 65552 or 65577 activity assays, (e.g., direct assays or competitive assays described in detail below), or to generate antibodies specific or selective for 27877, 18080, 14081, 32140, 50352, 16658, 14223, 16002, 50566, 65552 or 65577 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The 27877, 18080, 14081, 32140, 50352, 16658, 14223, 16002, 50566, 65552 or 65577 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub et al., (1986) *Reviews—Trends in Genetics* 1:1.

Another aspect the invention provides a host cell which includes a nucleic acid molecule described herein, e.g., a 27877, 18080, 14081, 32140, 50352, 16658, 14223, 16002, 50566, 65552 or 65577 nucleic acid molecule within a recombinant expression vector or a 27877, 18080, 14081, 32140, 50352, 16658, 14223, 16002, 50566, 65552 or 65577 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications can occur in succeeding generations due to either mutation or environmental influences, such progeny may not, in fact, be identical to the parent cell, but are still included within the scope of the term as used herein.

A host cell can be any prokaryotic or eukaryotic cell. For example, a 27877, 18080, 14081, 32140, 50352, 16658, 14223, 16002, 50566, 65552 or 65577 protein can be expressed in bacterial cells such as *E. coli*, insect cells, yeast or mammalian cells (such as Chinese hamster ovary (CHO) cells or CV-1 origin, SV-40 (COS) cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 27877, 18080, 14081, 32140, 50352, 16658, 14223, 16002, 50566, 65552 or 65577 protein. Accordingly, the invention further provides methods for producing a 27877, 18080, 14081, 32140, 50352, 16658, 14223, 16002, 50566, 65552 or 65577 protein using the host cells of the invention. In one embodiment, the method includes culturing the host cell of the invention (into which a recombinant expression vector encoding a 27877, 18080, 14081, 32140, 50352, 16658, 14223, 16002, 50566, 65552 or 65577 protein has been introduced) in a suitable medium such that a 27877, 18080, 14081, 32140, 50352, 16658, 14223, 16002, 50566, 65552 or 65577 protein is produced. In another embodiment, the method further includes isolating a 27877, 18080, 14081, 32140, 50352, 16658, 14223, 16002, 50566, 65552 or 65577 protein from the medium or the host cell.

In another aspect, the invention features, a cell or purified preparation of cells which include a 27877, 18080, 14081, 32140, 50352, 16658, 14223, 16002, 50566, 65552 or 65577 transgene, or which otherwise misexpress 27877, 18080, 14081, 32140, 50352, 16658, 14223, 16002, 50566, 65552 or 65577. The cell preparation can consist of human or non-human cells, e.g., rodent cells, e.g., mouse or rat cells, rabbit cells, or pig cells. In preferred embodiments, the cell or cells include a 27877, 18080, 14081, 32140, 50352, 16658, 14223, 16002, 50566, 65552 or 65577 transgene, e.g., a heterologous form of a 27877, 18080, 14081, 32140, 50352, 16658, 14223, 16002, 50566, 65552 or 65577, e.g., a gene derived from humans (in the case of a non-human cell). The 27877, 18080, 14081, 32140, 50352, 16658, 14223, 16002, 50566, 65552 or 65577 transgene can be misexpressed, e.g., overexpressed or underexpressed. In other preferred embodiments, the cell or cells include a gene which misexpresses an endogenous 27877, 18080, 14081, 32140, 50352, 16658, 14223, 16002, 50566, 65552 or 65577, e.g., a gene the expression of which is disrupted, e.g., a knockout. Such cells can serve as a model for studying disorders which are related to mutated or mis-expressed 27877, 18080, 14081, 32140, 50352, 16658, 14223, 16002, 50566, 65552 or 65577 alleles or for use in drug screening.

In another aspect, the invention features, a human cell, e.g., a hematopoietic stem cell, transformed with nucleic acid which encodes a subject 27877, 18080, 14081, 32140, 50352, 16658, 14223, 16002, 50566, 65552 or 65577 polypeptide.

Also provided are cells, preferably human cells, e.g., human hematopoietic or fibroblast cells, in which an endogenous 27877, 18080, 14081, 32140, 50352, 16658, 14223, 16002, 50566, 65552 or 65577 is under the control of a regulatory sequence that does not normally control the expression of the endogenous 27877, 18080, 14081, 32140, 50352, 16658, 14223, 16002, 50566, 65552 or 65577 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 27877, 18080, 14081, 32140, 50352, 16658, 14223, 16002, 50566, 65552 or 65577 gene. For example, an endogenous 27877, 18080, 14081, 32140, 50352, 16658, 14223, 16002, 50566, 65552 or 65577 gene which is "transcriptionally silent," e.g., not normally expressed, or expressed only at very low levels, can be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

Transgenic Animals

The invention provides non-human transgenic animals. Such animals are useful for studying the function and/or activity of a 27877, 18080, 14081, 32140, 50352, 16658, 14223, 16002, 50566, 65552 or 65577 protein and for identifying and/or evaluating modulators of 27877, 18080, 14081, 32140, 50352, 16658, 14223, 16002, 50566, 65552 or 65577 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 27877, 18080, 14081, 32140, 50352, 16658, 14223, 16002, 50566, 65552 or 65577 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 27877, 18080, 14081, 32140, 50352, 16658, 14223, 16002, 50566, 65552 or 65577 protein to particular cells. A transgenic founder animal can be identified based upon the presence of a 27877, 18080, 14081, 32140, 50352, 16658, 14223, 16002, 50566, 65552 or 65577 transgene in its genome and/or expression of 27877, 18080, 14081, 32140, 50352, 16658, 14223, 16002, 50566, 65552 or 65577 mRNA in tissues or cells of the animals. A transgenic founder animal can then be used to breed additional animals carrying the transgene. Moreover, transgenic animals carrying a transgene encoding a 27877, 18080, 14081, 32140, 50352, 16658, 14223, 16002, 50566, 65552 or 65577 protein can further be bred to other transgenic animals carrying other transgenes.

27877, 18080, 14081, 32140, 50352, 16658, 14223, 16002, 50566, 65552 or 65577 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologs, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 27877, 18080, 14081, 32140, 50352, 16658, 14223, 16002, 50566, 65552 or 65577 protein (e.g., via a recombinant expression vector in a host cell in gene therapy applications), to detect a 27877, 18080, 14081, 32140, 50352, 16658, 14223, 16002, 50566, 65552 or 65577 mRNA (e.g., in a biological sample) or a genetic alteration in a 27877, 18080, 14081, 32140, 50352, 16658, 14223, 16002, 50566, 65552 or 65577 gene, and to modulate 27877, 18080, 14081, 32140, 50352, 16658, 14223, 16002, 50566, 65552 or 65577 activity, as described further below. The 27877, 18080, 14081, 32140, 50352, 16658, 14223, 16002, 50566, 65552 or 65577 proteins can be used to treat disorders characterized by insufficient or excessive production of a 27877, 18080, 14081, 32140, 50352, 16658, 14223, 16002, 50566, 65552 or 65577 substrate or production of 27877, 18080, 14081, 32140, 50352, 16658, 14223, 16002, 50566, 65552 or 65577 inhibitors. In addition, the 27877, 18080, 14081, 32140, 50352, 16658, 14223, 16002, 50566, 65552 or 65577 proteins can be used to screen for naturally occurring 27877, 18080, 14081, 32140, 50352, 16658, 14223, 16002, 50566, 65552 or 65577 substrates, to screen for drugs or compounds which modulate 27877, 18080, 14081, 32140, 50352, 16658, 14223, 16002, 50566, 65552 or 65577 activity, as well as to treat disorders characterized by insufficient or excessive production of 27877, 18080, 14081, 32140, 50352, 16658, 14223, 16002, 50566, 65552 or 65577 protein or production of 27877, 18080, 14081, 32140, 50352, 16658, 14223, 16002, 50566, 65552 or 65577 protein forms which have decreased, aberrant or unwanted activity compared to 27877, 18080, 14081, 32140, 50352, 16658, 14223, 16002, 50566, 65552 or 65577 wild type protein (e.g., aberrant or deficient phospholipase activity, serine carboxypeptidase activity, trypsin-like serine protease activity, aldehyde dehydrogenase activity, ubiquitin-protein ligase activity, protein kinase activity, hydrolase activity, matrix metalloproteinase activity, or other activity). Moreover, the anti-27877, 18080, 14081, 32140, 50352, 16658, 14223, 16002, 50566, 65552 or 65577 antibodies of the invention can be used to detect and isolate 27877, 18080, 14081, 32140, 50352, 16658, 14223, 16002, 50566, 65552 or 65577 proteins, regulate the bioavailability of 27877, 18080, 14081, 32140, 50352, 16658, 14223, 16002, 50566, 65552 or 65577 proteins, and modulate 27877, 18080, 14081, 32140, 50352, 16658, 14223, 16002, 50566, 65552 or 65577 activity.

A method of evaluating a compound for the ability to interact with, e.g., bind, a subject 27877, 18080, 14081, 32140, 50352, 16658, 14223, 16002, 50566, 65552 or 65577 polypeptide is provided. The method includes: contacting the compound with the subject 27877, 18080, 14081, 32140, 50352, 16658, 14223, 16002, 50566, 65552 or 65577 polypeptide; and evaluating ability of the compound to interact with, e.g., to bind or form a complex with the subject 27877, 18080, 14081, 32140, 50352, 16658, 14223, 16002, 50566, 65552 or 65577 polypeptide. This method can be performed in vitro, e.g., in a cell free system, or in vivo, e.g., in a two-hybrid interaction trap assay. This method can be used to identify naturally occurring molecules which interact with subject 27877, 18080, 14081, 32140, 50352, 16658, 14223, 16002, 50566, 65552 or 65577 polypeptide. It can also be used to find natural or synthetic inhibitors of subject 27877, 18080, 14081, 32140, 50352, 16658, 14223, 16002, 50566, 65552 or 65577 polypeptide. Screening methods are discussed in more detail below.

Screening Assays:

The invention provides methods (also referred to herein as "screening assays") for identifying modulators, i.e., candidate or test compounds or agents (e.g., proteins, peptides, peptidomimetics, peptoids, small molecules or other drugs) which bind to 27877, 18080, 14081, 32140, 50352, 16658, 14223, 16002, 50566, 65552 or 65577 proteins, have a stimulatory or inhibitory effect on, for example, 27877, 18080, 14081, 32140, 50352, 16658, 14223, 16002, 50566, 65552 or 65577 expression or 27877, 18080, 14081, 32140, 50352, 16658, 14223, 16002, 50566, 65552 or 65577 activity, or have a stimulatory or inhibitory effect on, for example, the expression or activity of a 27877, 18080, 14081, 32140, 50352, 16658, 14223, 16002, 50566, 65552 or 65577 substrate. Compounds thus identified can be used to modulate the activity of target gene products (e.g., 27877, 18080, 14081, 32140, 50352, 16658, 14223, 16002, 50566, 65552 or 65577 genes) in a therapeutic protocol, to elaborate the biological function of the target gene product, or to identify compounds that disrupt normal target gene interactions.

In one embodiment, the invention provides assays for screening candidate or test compounds which are substrates of a 27877, 18080, 14081, 32140, 50352, 16658, 14223, 16002, 50566, 65552 or 65577 protein or polypeptide or a biologically active portion thereof. In another embodiment, the invention provides assays for screening candidate or test compounds which bind to or modulate the activity of a 27877, 18080, 14081, 32140, 50352, 16658, 14223, 16002, 50566, 65552 or 65577 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909-13; Erb et al. (1994) *Proc. Natl. Acad. Sci. USA* 91:11422-426; Zuckermann et al. (1994). *J. Med. Chem.* 37:2678-85; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233-51.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

In one embodiment, an assay is a cell-based assay in which a cell which expresses a 27877, 18080, 14081, 32140, 50352, 16658, 14223, 16002, 50566, 65552 or 65577 protein or biologically active portion thereof is contacted with a test compound, and the ability of the test compound to modulate 27877, 18080, 14081, 32140, 50352, 16658, 14223, 16002, 50566, 65552 or 65577 activity is determined. Determining the ability of the test compound to modulate 27877, 18080, 14081, 32140, 50352, 16658, 14223, 16002, 50566, 65552 or 65577 activity can be accomplished by monitoring, for example, phospholipase activity, serine carboxypeptidase activity, trypsin-like serine protease activity, aldehyde dehydrogenase activity, ubiquitin-protein ligase activity, protein kinase activity, hydrolase activity, matrix metalloproteinase activity, or other activity. The cell, for example, can be of mammalian origin, e.g., human.

The ability of the test compound to modulate 27877, 18080, 14081, 32140, 50352, 16658, 14223, 16002, 50566, 65552 or 65577 binding to a compound, e.g., a 27877, 18080, 14081, 32140, 50352, 16658, 14223, 16002, 50566, 65552 or 65577 substrate, or to bind to 27877, 18080, 14081, 32140, 50352, 16658, 14223, 16002, 50566, 65552 or 65577 can also be evaluated. This can be accomplished, for example, by coupling the compound, e.g., the substrate, with a radioisotope or enzymatic label such that binding of the compound, e.g., the substrate, to 27877, 18080, 14081, 32140, 50352, 16658, 14223, 16002, 50566, 65552 or 65577 can be determined by detecting the labeled compound, e.g., substrate, in a complex. Alternatively, 27877, 18080, 14081, 32140, 50352, 16658, 14223, 16002, 50566, 65552 or 65577 could be coupled with a radioisotope or enzymatic label to monitor the ability of a test compound to modulate 27877, 18080, 14081, 32140, 50352, 16658, 14223, 16002, 50566, 65552 or 65577 binding to a 27877, 18080, 14081, 32140, 50352, 16658, 14223, 16002, 50566, 65552 or 65577 substrate in a complex. For example, compounds (e.g., 27877, 18080, 14081, 32140, 50352, 16658, 14223, 16002, 50566, 65552 or 65577 substrates) can be labeled with $^{125}I$, $^{14}C$, $^{35}S$ or $^3H$., either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 27877, 18080, 14081, 32140, 50352, 16658, 14223, 16002, 50566, 65552 or 65577 substrate) to interact with 27877, 18080, 14081, 32140, 50352, 16658, 14223, 16002, 50566, 65552 or 65577 with or without the labeling of any of the interactants can be evaluated. For example, a microphysiometer can be used to detect the interaction of a compound with 27877, 18080, 14081, 32140, 50352, 16658, 14223, 16002, 50566, 65552 or 65577 without the labeling of either the compound or the 27877, 18080, 14081, 32140, 50352, 16658, 14223, 16002, 50566, 65552 or 65577. McConnell et al. (1992) Science 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 27877, 18080, 14081, 32140, 50352, 16658, 14223, 16002, 50566, 65552 or 65577.

In yet another embodiment, a cell-free assay is provided in which a 27877, 18080, 14081, 32140, 50352, 16658, 14223, 16002, 50566, 65552 or 65577 protein or biologically active portion thereof is contacted with a test compound and the ability of the test compound to bind to the 27877, 18080, 14081, 32140, 50352, 16658, 14223, 16002, 50566, 65552 or 65577 protein or biologically active portion thereof is evaluated. Preferred biologically active portions of the 27877, 18080, 14081, 32140, 50352, 16658, 14223, 16002, 50566, 65552 or 65577 proteins to be used in assays of the present invention include fragments which participate in interactions with non-27877, 18080, 14081, 32140, 50352, 16658, 14223, 16002, 50566, 65552 or 65577 molecules, e.g., fragments with high surface probability scores.

Soluble and/or membrane-bound forms of isolated proteins (e.g., 27877, 18080, 14081, 32140, 50352, 16658, 14223, 16002, 50566, 65552 or 65577 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 27877, 18080, 14081, 32140, 50352, 16658, 14223, 16002, 50566, 65552 or 65577 protein to bind to a target molecule can be accomplished using real-time Biomolecular Interaction Analysis (BIA) (see, e.g., Sjolander and Urbaniczky (1991) Anal. Chem. 63:2338-2345 and Szabo et al. (1995) Curr. Opin. Struct. Biol. 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 27877, 18080, 14081, 32140, 50352, 16658, 14223, 16002, 50566, 65552 or 65577, an anti-27877, 18080, 14081, 32140, 50352, 16658, 14223, 16002, 50566, 65552 or 65577 antibody or its target molecule to facilitate separation of complexed from uncomplexed forms of one or both of the proteins, as well as to accommodate automation of the assay. Binding of a test compound to a 27877, 18080, 14081, 32140, 50352, 16658, 14223, 16002, 50566, 65552 or 65577 protein, or interaction of a 27877, 18080, 14081, 32140, 50352, 16658, 14223, 16002, 50566, 65552 or 65577 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/27877, 18080, 14081, 32140, 50352, 16658, 14223, 16002, 50566, 65552 or 65577 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 27877, 18080, 14081, 32140, 50352, 16658, 14223, 16002, 50566, 65552 or 65577 protein, and the mixture incubated under conditions conducive to complex formation (e.g., at physiological conditions for salt and pH).

Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 27877, 18080, 14081, 32140, 50352, 16658, 14223, 16002, 50566, 65552 or 65577 binding or activity determined using standard techniques.

Other techniques for immobilizing either a 27877, 18080, 14081, 32140, 50352, 16658, 14223, 16002, 50566, 65552 or 65577 protein or a target molecule on matrices include using conjugation of biotin and streptavidin. Biotinylated 27877, 18080, 14081, 32140, 50352, 16658, 14223, 16002, 50566, 65552 or 65577 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific or selective for the immobilized component (the antibody, in turn, can be directly labeled or indirectly labeled with, e.g., a labeled anti-Ig antibody).

In one embodiment, this assay is performed utilizing antibodies reactive with 27877, 18080, 14081, 32140, 50352, 16658, 14223, 16002, 50566, 65552 or 65577 protein or target molecules but which do not interfere with binding of the 27877, 18080, 14081, 32140, 50352, 16658, 14223, 16002, 50566, 65552 or 65577 protein to its target molecule. Such antibodies can be derivatized to the wells of the plate, and unbound target or 27877, 18080, 14081, 32140, 50352, 16658, 14223, 16002, 50566, 65552 or 65577 protein trapped in the wells by antibody conjugation. Methods for detecting such complexes, in addition to those described above for the GST-immobilized complexes, include immunodetection of complexes using antibodies reactive with the 27877, 18080, 14081, 32140, 50352, 16658, 14223, 16002, 50566, 65552 or 65577 protein or target molecule, as well as enzyme-linked assays which rely on detecting an enzymatic activity associated with the 27877, 18080, 14081, 32140, 50352, 16658, 14223, 16002, 50566, 65552 or 65577 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas and Minton (1993) *Trends Biochem Sci* 18:284-7); chromatography (gel filtration chromatography, ion-exchange chromatography); electrophoresis (see, e.g., Ausubel et al., eds. (1999) *Current Protocols in Molecular Biology*, J. Wiley, New York.); and immunoprecipitation (see, for example, Ausubel et al., eds. (1999) *Current Protocols in Molecular Biology*, J. Wiley, New York). Such resins and chromatographic techniques are known to one skilled in the art (see, e.g., Heegaard (1998) *J Mol Recognit* 11:141-8; Hage and Tweed (1997) *J Chromatogr B Biomed Sci Appl.* 699:499-525). Further, fluorescence energy transfer can also be conveniently utilized, as described herein, to detect binding without further purification of the complex from solution.

In a preferred embodiment, the assay includes contacting the 27877, 18080, 14081, 32140, 50352, 16658, 14223, 16002, 50566, 65552 or 65577 protein or biologically active portion thereof with a known compound which binds 27877, 18080, 14081, 32140, 50352, 16658, 14223, 16002, 50566, 65552 or 65577 to form an assay mixture, contacting the assay mixture with a test compound, and determining the ability of the test compound to interact with a 27877, 18080, 14081, 32140, 50352, 16658, 14223, 16002, 50566, 65552 or 65577 protein, wherein determining the ability of the test compound to interact with a 27877, 18080, 14081, 32140, 50352, 16658, 14223, 16002, 50566, 65552 or 65577 protein includes determining the ability of the test compound to preferentially bind to 27877, 18080, 14081, 32140, 50352, 16658, 14223, 16002, 50566, 65552 or 65577 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 27877, 18080, 14081, 32140, 50352, 16658, 14223, 16002, 50566, 65552 or 65577 genes herein identified. In an alternative embodiment, the invention provides methods for determining the ability of the test compound to modulate the activity of a 27877, 18080, 14081, 32140, 50352, 16658, 14223, 16002, 50566, 65552 or 65577 protein through modulation of the activity of a downstream effector of a 27877, 18080, 14081, 32140, 50352, 16658, 14223, 16002, 50566, 65552, 65577 or 56919 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner.

Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific or selective for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific or selective for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific or selective for one of the binding components to anchor any complexes formed in solution, and a labeled antibody specific or selective for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 27877, 18080, 14081, 32140, 50352, 16658, 14223, 16002, 50566, 65552 or 65577 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 27877, 18080, 14081, 32140, 50352, 16658, 14223, 16002, 50566, 65552 or 65577 ("27877, 18080, 14081, 32140, 50352, 16658, 14223, 16002, 50566, 65552 or 65577-binding proteins" or "27877, 18080, 14081, 32140, 50352, 16658, 14223, 16002, 50566, 65552 or 65577-bp") and are involved in 27877, 18080, 14081, 32140, 50352, 16658, 14223, 16002, 50566, 65552 or 65577 activity. Such 27877, 18080, 14081, 32140, 50352, 16658, 14223, 16002, 50566, 65552 or 65577-bps can be activators or inhibitors of signals by the 27877, 18080, 14081, 32140, 50352, 16658, 14223, 16002, 50566, 65552 or 65577 proteins or 27877, 18080, 14081, 32140, 50352, 16658, 14223, 16002, 50566, 65552, 65577 or 56919 targets as, for example, downstream elements of a 27877, 18080, 14081, 32140, 50352, 16658, 14223, 16002, 50566, 65552 or 65577-mediated signaling pathway.

The two-hybrid system is based on the modular nature of most transcription factors, which consist of separable DNA-binding and activation domains. Briefly, the assay utilizes two different DNA constructs. In one construct, the gene that codes for a 27877, 18080, 14081, 32140, 50352, 16658, 14223, 16002, 50566, 65552 or 65577 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 27877, 18080, 14081, 32140, 50352, 16658, 14223, 16002, 50566, 65552 or 65577 protein can be the fused to the activator domain.) If the "bait" and the "prey" proteins are able to interact, in vivo, forming a 27877, 18080, 14081, 32140, 50352, 16658, 14223, 16002, 50566, 65552 or 65577-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 27877, 18080, 14081, 32140, 50352, 16658, 14223, 16002, 50566, 65552 or 65577 protein.

In another embodiment, modulators of 27877, 18080, 14081, 32140, 50352, 16658, 14223, 16002, 50566, 65552 or 65577 expression are identified. For example, a cell or cell free mixture is contacted with a candidate compound and the expression of 27877, 18080, 14081, 32140, 50352, 16658, 14223, 16002, 50566, 65552 or 65577 mRNA or protein evaluated relative to the level of expression of 27877, 18080, 14081, 32140, 50352, 16658, 14223, 16002, 50566, 65552 or 65577 mRNA or protein in the absence of the candidate compound. When expression of 27877, 18080, 14081, 32140, 50352, 16658, 14223, 16002, 50566, 65552 or 65577 mRNA or protein is greater in the presence of the candidate compound than in its absence, the candidate compound is identified as a stimulator of 27877, 18080, 14081, 32140, 50352, 16658, 14223, 16002, 50566, 65552 or 65577 mRNA or protein expression. Alternatively, when expression of 27877, 18080, 14081, 32140, 50352, 16658, 14223, 16002, 50566, 65552 or 65577 mRNA or protein is less (statistically significantly less) in the presence of the candidate compound than in its absence, the candidate compound is identified as an inhibitor of 27877, 18080, 14081, 32140, 50352, 16658, 14223, 16002, 50566, 65552 or 65577 mRNA or protein expression. The level of 27877, 18080, 14081, 32140, 50352, 16658, 14223, 16002, 50566, 65552 or 65577 mRNA or protein expression can be determined by methods described herein for detecting 27877, 18080, 14081, 32140, 50352, 16658, 14223, 16002, 50566, 65552 or 65577 mRNA or protein.

In another aspect, the invention pertains to a combination of two or more of the assays described herein. For example, a modulating agent can be identified using a cell-based or a cell free assay, and the ability of the agent to modulate the activity of a 27877, 18080, 14081, 32140, 50352, 16658, 14223, 16002, 50566, 65552 or 65577 protein can be confirmed in vivo, e.g., in an animal such as an animal model for aberrant or deficient phospholipase activity, serine carboxypeptidase activity, trypsin-like serine protease activity, aldehyde dehydrogenase activity, ubiquitin-protein ligase activity, protein kinase activity, hydrolase activity or matrix metalloproteinase activity.

This invention further pertains to novel agents identified by the above-described screening assays. Accordingly, it is within the scope of this invention to further use an agent identified as described herein (e.g., a 27877, 18080, 14081, 32140, 50352, 16658, 14223, 16002, 50566, 65552 or 65577 modulating agent, an antisense 27877, 18080, 14081, 32140, 50352, 16658, 14223, 16002, 50566, 65552 or 65577 nucleic acid molecule, a 27877, 18080, 14081, 32140, 50352, 16658, 14223, 16002, 50566, 65552 or 65577-specific antibody, or a 27877, 18080, 14081, 32140, 50352, 16658, 14223, 16002, 50566, 65552 or 65577-binding partner) in an appropriate animal model to determine the efficacy, toxicity, side effects, or mechanism of action, of treatment with such an agent.

Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 27877, 18080, 14081, 32140, 50352, 16658, 14223, 16002, 50566, 65552 or 65577 with a disease; (ii) identify an individual from a minute biological sample (tissue typing); and (iii) aid in forensic identification of a biological sample. These applications are described in the subsections below.

Chromosome Mapping

The 27877, 18080, 14081, 32140, 50352, 16658, 14223, 16002, 50566, 65552 or 65577 nucleotide sequences or portions thereof can be used to map the location of the 27877, 18080, 14081, 32140, 50352, 16658, 14223, 16002, 50566, 65552 or 65577 genes on a chromosome. This process is called chromosome mapping. Chromosome mapping is useful in correlating the 27877, 18080, 14081, 32140, 50352, 16658, 14223, 16002, 50566, 65552 or 65577 sequences with genes associated with disease.

Briefly, 27877, 18080, 14081, 32140, 50352, 16658, 14223, 16002, 50566, 65552 or 65577 genes can be mapped to chromosomes by preparing PCR primers (preferably 15-25 bp in length) from the 27877, 18080, 14081, 32140, 50352, 16658, 14223, 16002, 50566, 65552 or 65577 nucleotide sequences. These primers can then be used for PCR screening of somatic cell hybrids containing individual human chromosomes. Only those hybrids containing the human gene corresponding to the 27877, 18080, 14081, 32140, 50352, 16658, 14223, 16002, 50566, 65552 or 65577 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio et al. (1983) *Science* 220:919-924).

Other mapping strategies e.g., in situ hybridization (described in Fan et al. (1990) *Proc. Natl. Acad. Sci. USA*, 87:6223-27), pre-screening with labeled flow-sorted chromosomes, and pre-selection by hybridization to chromosome specific cDNA libraries can be used to map 27877, 18080, 14081, 32140, 50352, 16658, 14223, 16002, 50566, 65552 or 65577 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al. (1988) *Human Chromosomes: A Manual of Basic Techniques*, Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in McKusick, *Mendelian Inheritance in Man*, available on-line through Johns Hopkins University Welch Medical Library). The relationship between a gene and a disease, mapped to the same chromosomal region, can then be identified through linkage analysis (co-inheritance of physically adjacent genes), described in, for example, Egeland et al. (1987) *Nature,* 325:783-787.

Moreover, differences in the DNA sequences between individuals affected and unaffected with a disease associated with the 27877, 18080, 14081, 32140, 50352, 16658, 14223, 16002, 50566, 65552 or 65577 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 27877, 18080, 14081, 32140, 50352, 16658, 14223, 16002, 50566, 65552 or 65577 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 27877, 18080, 14081, 32140, 50352, 16658, 14223, 16002, 50566, 65552 or 65577 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, 4, 11, 20, 25, 29, 35, 38, 41, 73, 76 or 86 can provide positive individual identification with a panel of perhaps 10 to 1,000 primers which each yield a noncoding amplified sequence of 100 bases. If predicted coding sequences, such as those in SEQ ID NO: 3, 6, 13, 22, 27, 31, 37, 40, 43, 75, 78 or 88 are used, a more appropriate number of primers for positive individual identification would be 500-2,000.

If a panel of reagents from 27877, 18080, 14081, 32140, 50352, 16658, 14223, 16002, 50566, 65552 or 65577 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 27877, 18080, 14081, 32140, 50352, 16658, 14223, 16002, 50566, 65552 or 65577 Sequences in Forensic Biology DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, 4, 11, 20, 25, 29, 35, 38, 41, 73, 76 or 86 (e.g., fragments derived from the noncoding regions of SEQ ID NO: 1, 4, 11, 20, 25, 29, 35, 38, 41, 73, 76 or 86 having a length of at least 20 bases, preferably at least 30 bases) are particularly appropriate for this use.

The 27877, 18080, 14081, 32140, 50352, 16658, 14223, 16002, 50566, 65552 or 65577 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 27877, 18080, 14081, 32140, 50352, 16658, 14223, 16002, 50566, 65552 or 65577 probes can be used to identify tissue by species and/or by organ type.

In a similar fashion, these reagents, e.g., 27877, 18080, 14081, 32140, 50352, 16658, 14223, 16002, 50566, 65552 or 65577 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 27877, 18080, 14081, 32140, 50352, 16658, 14223, 16002, 50566, 65552 or 65577.

Such disorders include, e.g., a disorder associated with the misexpression of 27877, 18080, 14081, 32140, 50352, 16658, 14223, 16002, 50566, 65552 or 65577 gene; a cellular proliferative and/or differentiative disorder, brain, blood vessel, platelet, breast, colon, kidney, lung, ovarian, prostate, hematopoeitic, pancreatic, skeletal muscle, testicular, skin, hormonal, associated with bone metabolism, immune e.g., inflammatory, cardiovascular, endothelial cell, liver, viral diseases, pain, metabolic, anemias, angiogenesis, neoplastic, endocrine, neurological or heart disorder.

The method includes one or more of the following: detecting, in a tissue of the subject, the presence or absence of a mutation which affects the expression of the 27877, 18080, 14081, 32140, 50352, 16658, 14223, 16002, 50566, 65552 or 65577 gene, or detecting the presence or absence of a mutation in a region which controls the expression of the gene, e.g., a mutation in the 5' control region; detecting, in a tissue of the subject, the presence or absence of a mutation which alters the structure of the 27877, 18080, 14081, 32140, 50352, 16658, 14223, 16002, 50566, 65552 or 65577 gene; detecting, in a tissue of the subject, the misexpression of the 27877, 18080, 14081, 32140, 50352, 16658, 14223, 16002, 50566, 65552 or 65577 gene, at the mRNA level, e.g., detecting a non-wild type level of an mRNA; or detecting, in a tissue of the subject, the misexpression of the gene, at the protein level, e.g., detecting a non-wild type level of a 27877, 18080, 14081, 32140, 50352, 16658, 14223, 16002, 50566, 65552 or 65577 polypeptide.

In preferred embodiments the method includes: ascertaining the existence of at least one of: a deletion of one or more nucleotides from the 27877, 18080, 14081, 32140, 50352, 16658, 14223, 16002, 50566, 65552 or 65577 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, 4, 11, 20, 25, 29, 35, 38, 41, 73, 76 or 86, or naturally occurring mutants thereof or 5' or 3' flanking sequences naturally associated with the 27877, 18080, 14081, 32140, 50352, 16658, 14223, 16002, 50566, 65552 or 65577 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 27877, 18080, 14081, 32140, 50352, 16658, 14223, 16002, 50566, 65552 or 65577 gene; the presence of a non-wild type splicing pattern of a messenger RNA transcript of the gene; or a non-wild type level of 27877, 18080, 14081, 32140, 50352, 16658, 14223, 16002, 50566, 65552 or 65577.

Methods of the invention can be used prenatally or to determine if a subject's offspring will be at risk for a disorder.

In preferred embodiments the method includes determining the structure of a 27877, 18080, 14081, 32140, 50352, 16658, 14223, 16002, 50566, 65552 or 65577 gene, an abnormal structure being indicative of risk for the disorder.

In preferred embodiments the method includes contacting a sample from the subject with an antibody to the 27877, 18080, 14081, 32140, 50352, 16658, 14223, 16002, 50566, 65552 or 65577 protein or a nucleic acid, which hybridizes specifically with the gene. These and other embodiments are discussed below.

Diagnostic and Prognostic Assays

The presence, level, or absence of 27877, 18080, 14081, 32140, 50352, 16658, 14223, 16002, 50566, 65552 or 65577 protein or nucleic acid in a biological sample can be evaluated by obtaining a biological sample from a test subject and contacting the biological sample with a compound or an agent capable of detecting 27877, 18080, 14081, 32140, 50352, 16658, 14223, 16002, 50566, 65552 or 65577 protein or nucleic acid (e.g., mRNA, genomic DNA) that encodes 27877, 18080, 14081, 32140, 50352, 16658, 14223, 16002, 50566, 65552 or 65577 protein such that the presence of 27877, 18080, 14081, 32140, 50352, 16658, 14223, 16002, 50566, 65552 or 65577 protein or nucleic acid is detected in the biological sample. The term "biological sample" includes tissues, cells and biological fluids isolated from a subject, as well as tissues, cells and fluids present within a subject. A preferred biological sample is serum. The level of expression of the 27877, 18080, 14081, 32140, 50352, 16658, 14223, 16002, 50566, 65552 or 65577 gene can be measured in a number of ways, including, but not limited to: measuring the mRNA encoded by the 27877, 18080, 14081, 32140, 50352, 16658, 14223, 16002, 50566, 65552 or 65577 genes; measuring the amount of protein encoded by the 27877, 18080, 14081, 32140, 50352, 16658, 14223, 16002, 50566, 65552 or 65577 genes; or measuring the activity of the protein encoded by the 27877, 18080, 14081, 32140, 50352, 16658, 14223, 16002, 50566, 65552 or 65577 genes.

The level of mRNA corresponding to the 27877, 18080, 14081, 32140, 50352, 16658, 14223, 16002, 50566, 65552 or 65577 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 27877, 18080, 14081, 32140, 50352, 16658, 14223, 16002, 50566, 65552 or 65577 nucleic acid, such as the nucleic acid of SEQ ID NO: 1, 4, 11, 20, 25, 29, 35, 38, 41, 73, 76 or 86, or a portion thereof, such as an oligonucleotide of at least 7, 15, 30, 50, 100, 250 or 500 nucleotides in length and sufficient to specifically hybridize under stringent conditions to 27877, 18080, 14081, 32140, 50352, 16658, 14223, 16002, 50566, 65552 or 65577 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 27877, 18080, 14081, 32140, 50352, 16658, 14223, 16002, 50566, 65552 or 65577 genes.

The level of mRNA in a sample that is encoded by one of 27877, 18080, 14081, 32140, 50352, 16658, 14223, 16002, 50566, 65552 or 65577 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189-193), self sustained sequence replication (Guatelli et al., (1990) *Proc. Natl. Acad. Sci. USA* 87:1874-1878), transcriptional amplification system (Kwoh et al., (1989), *Proc. Natl. Acad. Sci. USA* 86:1173-1177), Q-Beta Replicase (Lizardi et al., (1988) *Biotechnology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 27877, 18080, 14081, 32140, 50352, 16658, 14223, 16002, 50566, 65552 or 65577 gene being analyzed.

In another embodiment, the methods further contacting a control sample with a compound or agent capable of detecting 27877, 18080, 14081, 32140, 50352, 16658, 14223, 16002, 50566, 65552 or 65577 mRNA, or genomic DNA, and comparing the presence of 27877, 18080, 14081, 32140, 50352, 16658, 14223, 16002, 50566, 65552 or 65577 mRNA or genomic DNA in the control sample with the presence of 27877, 18080, 14081, 32140, 50352, 16658, 14223, 16002, 50566, 65552 or 65577 mRNA or genomic DNA in the test sample.

A variety of methods can be used to determine the level of protein encoded by 27877, 18080, 14081, 32140, 50352, 16658, 14223, 16002, 50566, 65552 or 65577. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 27877, 18080, 14081, 32140, 50352, 16658, 14223, 16002, 50566, 65552 or 65577 protein in a biological sample in vitro as well as in vivo. In vitro techniques for detection of 27877, 18080, 14081, 32140, 50352, 16658, 14223, 16002, 50566, 65552 or 65577 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 27877, 18080, 14081, 32140, 50352, 16658, 14223, 16002, 50566, 65552 or 65577 protein include introducing into a subject a labeled anti-27877, 18080, 14081, 32140, 50352, 16658, 14223, 16002, 50566, 65552 or 65577 antibody. For example, the antibody can be labeled with a radioactive marker whose presence and location in a subject can be detected by standard imaging techniques.

In another embodiment, the methods further include contacting the control sample with a compound or agent capable of detecting 27877, 18080, 14081, 32140, 50352, 16658, 14223, 16002, 50566, 65552 or 65577 protein, and comparing the presence of 27877, 18080, 14081, 32140, 50352, 16658, 14223, 16002, 50566, 65552 or 65577 protein in the control sample with the presence of 27877, 18080, 14081, 32140, 50352, 16658, 14223, 16002, 50566, 65552 or 65577 protein in the test sample.

The invention also includes kits for detecting the presence of 27877, 18080, 14081, 32140, 50352, 16658, 14223, 16002, 50566, 65552 or 65577 in a biological sample. For example, the kit can include a compound or agent capable of detecting 27877, 18080, 14081, 32140, 50352, 16658, 14223, 16002, 50566, 65552 or 65577 protein or mRNA in a biological sample; and a standard. The compound or agent can be packaged in a suitable container. The kit can further comprise instructions for using the kit to detect 27877, 18080, 14081, 32140, 50352, 16658, 14223, 16002, 50566, 65552 or 65577 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 27877, 18080, 14081, 32140, 50352, 16658, 14223, 16002, 50566, 65552 or 65577 expression or activity. As used herein, the term "unwanted" includes an unwanted phenomenon involved in a biological response such as pain or deregulated cell proliferation.

In one embodiment, a disease or disorder associated with aberrant or unwanted 27877, 18080, 14081, 32140, 50352, 16658, 14223, 16002, 50566, 65552 or 65577 expression or activity is identified. A test sample is obtained from a subject and 27877, 18080, 14081, 32140, 50352, 16658, 14223, 16002, 50566, 65552 or 65577 protein or nucleic acid (e.g., mRNA or genomic DNA) is evaluated, wherein the level, e.g., the presence or absence, of 27877, 18080, 14081, 32140, 50352, 16658, 14223, 16002, 50566, 65552 or 65577 protein or nucleic acid is diagnostic for a subject having or at risk of developing a disease or disorder associated with aberrant or unwanted 27877, 18080, 14081, 32140, 50352, 16658, 14223, 16002, 50566, 65552 or 65577 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 27877, 18080, 14081, 32140, 50352, 16658, 14223, 16002, 50566, 65552 or 65577 expression or activity. For example, such methods can be used to determine whether a subject can be effectively treated with an agent for a cellular proliferative and/or differentiative disorder, brain, blood vessel, platelet, breast, colon, kidney, lung, ovarian, prostate, hematopoeitic, pancreatic, skeletal muscle, testicular, skin, hormonal, associated with bone metabolism, immune e.g., inflammatory, cardiovascular, endothelial cell, liver, viral diseases, pain, metabolic, anemias, angiogenesis, neoplastic, endocrine, neurological or heart disorder.

The methods of the invention can also be used to detect genetic alterations in a 27877, 18080, 14081, 32140, 50352, 16658, 14223, 16002, 50566, 65552 or 65577 gene, thereby determining if a subject with the altered gene is at risk for a disorder characterized by misregulation in 27877, 18080, 14081, 32140, 50352, 16658, 14223, 16002, 50566, 65552 or 65577 protein activity or nucleic acid expression, such as a cellular proliferative and/or differentiative disorder, brain, blood vessel, platelet, breast, colon, kidney, lung, ovarian, prostate, hematopoeitic, pancreatic, skeletal muscle, testicular, skin, hormonal, associated with bone metabolism, immune e.g., inflammatory, cardiovascular, endothelial cell, liver, viral diseases, pain, metabolic, anemias, angiogenesis, neoplastic, endocrine, neurological or heart disorder. In preferred embodiments, the methods include detecting, in a sample from the subject, the presence or absence of a genetic alteration characterized by at least one of an alteration affecting the integrity of a gene encoding a 27877, 18080, 14081, 32140, 50352, 16658, 14223, 16002, 50566, 65552 or 65577-protein, or the mis-expression of the 27877, 18080, 14081, 32140, 50352, 16658, 14223, 16002, 50566, 65552 or 65577 gene. For example, such genetic alterations can be detected by ascertaining the existence of at least one of 1) a deletion of one or more nucleotides from a 27877, 18080, 14081, 32140, 50352, 16658, 14223, 16002, 50566, 65552 or 65577 gene; 2) an addition of one or more nucleotides to a 27877, 18080, 14081, 32140, 50352, 16658, 14223, 16002, 50566, 65552 or 65577 gene; 3) a substitution of one or more nucleotides of a 27877, 18080, 14081, 32140, 50352, 16658, 14223, 16002, 50566, 65552 or 65577 gene, 4) a chromosomal rearrangement of a 27877, 18080, 14081, 32140, 50352, 16658, 14223, 16002, 50566, 65552 or 65577 gene; 5) an alteration in the level of a messenger RNA transcript of a 27877, 18080, 14081, 32140, 50352, 16658, 14223, 16002, 50566, 65552 or 65577 gene, 6) aberrant modification of a 27877, 18080, 14081, 32140, 50352, 16658, 14223, 16002, 50566, 65552 or 65577 gene, such as of the methylation pattern of the genomic DNA, 7) the presence of a non-wild type splicing pattern of a messenger RNA transcript of a 27877, 18080, 14081, 32140, 50352, 16658, 14223, 16002, 50566, 65552 or 65577 gene, 8) a non-wild type level of a 27877, 18080, 14081, 32140, 50352, 16658, 14223, 16002, 50566, 65552 or 65577-protein, 9) allelic loss of a 27877, 18080, 14081, 32140, 50352, 16658, 14223, 16002, 50566, 65552 or 65577 gene, and 10) inappropriate post-translational modification of a 27877, 18080, 14081, 32140, 50352, 16658, 14223, 16002, 50566, 65552 or 65577-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 27877, 18080, 14081, 32140, 50352, 16658, 14223, 16002, 50566, 65552 or 65577-gene. This method can include the steps of collecting a sample of cells from a subject, isolating nucleic acid (e.g., genomic, mRNA or both) from the sample, contacting the nucleic acid sample with one or more primers which specifically hybridize to a 27877, 18080, 14081, 32140, 50352, 16658, 14223, 16002, 50566, 65552 or 65577 gene under conditions such that hybridization and amplification of the 27877, 18080, 14081, 32140, 50352, 16658, 14223, 16002, 50566, 65552 or 65577 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 27877, 18080, 14081, 32140, 50352, 16658, 14223, 16002, 50566, 65552 or 65577 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498, 531) can be used to score for the presence of specific mutations by development or loss of a ribozyme cleavage site.

In other embodiments, genetic mutations in 27877, 18080, 14081, 32140, 50352, 16658, 14223, 16002, 50566, 65552 or 65577 can be identified by hybridizing a sample and control nucleic acids, e.g., DNA or RNA, two dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin et al. (1996) *Human Mutation* 7: 244-255; Kozal et al. (1996) *Nature Medicine* 2: 753-759). For example, genetic mutations in 27877, 18080, 14081, 32140, 50352, 16658, 14223, 16002, 50566, 65552 or 65577 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 27877, 18080, 14081, 32140, 50352, 16658, 14223, 16002, 50566, 65552 or 65577 gene and detect mutations by comparing the sequence of the sample 27877, 18080, 14081, 32140, 50352, 16658, 14223, 16002, 50566, 65552 or 65577 with the corresponding wild-type (control) sequence. Automated sequencing procedures can be utilized when performing the diagnostic assays (Naeve et al. (1995) *Biotechniques* 19:448-53), including sequencing by mass spectrometry.

Other methods for detecting mutations in the 27877, 18080, 14081, 32140, 50352, 16658, 14223, 16002, 50566, 65552 or 65577 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl. Acad Sci USA* 85:4397; Saleeba et al. (1992) *Methods Enzymol.* 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 27877, 18080, 14081, 32140, 50352, 16658, 14223, 16002, 50566, 65552 or 65577 cDNAs obtained from samples of cells. For example, the mutY enzyme of *E. coli* cleaves A at G/A mismatches and the thymidine DNA glycosylase from HeLa cells cleaves T at G/F mismatches (Hsu et al. (1994) *Carcinogenesis* 15:1657-1662; U.S. Pat. No. 5,459,039).

In other embodiments, alterations in electrophoretic mobility will be used to identify mutations in 27877, 18080, 14081, 32140, 50352, 16658, 14223, 16002, 50566, 65552 or 65577 genes. For example, single strand conformation polymorphism (SSCP) can be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control 27877, 18080, 14081, 32140, 50352, 16658, 14223, 16002, 50566, 65552 or 65577 nucleic acids will be denatured and allowed to renature. The secondary structure of single-stranded nucleic acids varies according to sequence, the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl. Acad. Sci USA* 86:6230).

Alternatively, allele specific amplification technology which depends on selective PCR amplification can be used in conjunction with the instant invention. Oligonucleotides used as primers for specific amplification can carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell. Probes* 6:1). It is anticipated that in certain embodiments amplification can also be performed using Taq ligase for amplification (Barany (1991) *Proc. Natl. Acad. Sci USA* 88:189-93). In such cases, ligation will occur only if there is a perfect match at the 3' end of the 5' sequence making it possible to detect the presence of a known mutation at a specific site by looking for the presence or absence of amplification.

The methods described herein can be performed, for example, by utilizing pre-packaged diagnostic kits comprising at least one probe nucleic acid or antibody reagent described herein, which can be conveniently used, e.g., in clinical settings to diagnose patients exhibiting symptoms or family history of a disease or illness involving a 27877, 18080, 14081, 32140, 50352, 16658, 14223, 16002, 50566, 65552 or 65577 gene.

Use of 27877, 18080, 14081, 32140, 50352, 16658, 14223, 16002, 50566, 65552 or 65577 Molecules as Surrogate Markers The 27877, 18080, 14081, 32140, 50352, 16658, 14223, 16002, 50566, 65552 or 65577 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 27877, 18080, 14081, 32140, 50352, 16658, 14223, 16002, 50566, 65552 or 65577 molecules of the invention can be detected, and can be correlated with one or more biological states in vivo. For example, the 27877, 18080, 14081, 32140, 50352, 16658, 14223, 16002, 50566, 65552 or 65577 molecules of the invention can serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers can serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease can be made using cholesterol levels as a surrogate marker, and an analysis of HIV infection can be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) AIDS Treatment News Archive 209.

The 27877, 18080, 14081, 32140, 50352, 16658, 14223, 16002, 50566, 65552 or 65577 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker can be indicative of the concentration of the drug in a biological tissue, in that the marker is either expressed or transcribed or not expressed or transcribed in that tissue in relationship to the level of the drug. In this fashion, the distribution or uptake of the drug can be monitored by the pharmacodynamic marker. Similarly, the presence or quantity of the pharmacodynamic marker can be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug can be sufficient to activate multiple rounds of marker (e.g., a 27877, 18080, 14081, 32140, 50352, 16658, 14223, 16002, 50566, 65552 or 65577 marker) transcription or expression, the amplified marker can be in a quantity which is more readily detectable than the drug itself. Also, the marker can be more easily detected due to the nature of the marker itself; for example, using the methods described herein, anti-27877, 18080, 14081, 32140, 50352, 16658, 14223, 16002, 50566, 65552 or 65577 antibodies can be employed in an immune-based detection system for a 27877, 18080, 14081, 32140, 50352, 16658, 14223, 16002, 50566, 65552 or 65577 protein marker, or 27877, 18080, 14081, 32140, 50352, 16658, 14223, 16002, 50566, 65552 or 65577-specific radiolabeled probes can be used to detect a 27877, 18080, 14081, 32140, 50352, 16658, 14223, 16002, 50566, 65552 or 65577 mRNA marker. Furthermore, the use of a pharmacodynamic marker can offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am. J. Health-Syst. Pharm.* 56 Suppl. 3: S16-S20.

The 27877, 18080, 14081, 32140, 50352, 16658, 14223, 16002, 50566, 65552 or 65577 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, can be selected. For example, based on the presence or quantity of RNA, or protein (e.g., 27877, 18080, 14081, 32140, 50352, 16658, 14223, 16002, 50566, 65552 or 65577 protein or RNA) for specific tumor markers in a subject, a drug or course of treatment can be selected that is optimized for the treatment of the specific tumor likely to be present in the subject. Similarly, the presence or absence of a specific sequence mutation in 27877, 18080, 14081, 32140, 50352, 16658, 14223, 16002, 50566, 65552 or 65577 DNA can correlate with a 27877, 18080, 14081, 32140, 50352, 16658, 14223, 16002, 50566, 65552 or 65577 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-27877, 18080, 14081, 32140, 50352, 16658, 14223, 16002, 50566, 65552 or 65577 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody, unconjugated or conjugated as described herein, can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent can, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment:

The present invention provides for both prophylactic and therapeutic methods of treating a subject at risk of (or susceptible to) a disorder or having a disorder associated with aberrant or unwanted 27877, 18080, 14081, 32140, 50352, 16658, 14223, 16002, 50566, 65552 or 65577 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments can be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 27877, 18080, 14081, 32140, 50352, 16658, 14223, 16002, 50566, 65552 or 65577 molecules of the present invention or 27877, 18080, 14081, 32140, 50352, 16658, 14223, 16002, 50566, 65552 or 65577 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 27877, 18080, 14081, 32140, 50352, 16658, 14223, 16002, 50566, 65552 or 65577 expression or activity, by administering to the subject a 27877, 18080, 14081, 32140, 50352, 16658, 14223, 16002, 50566, 65552 or 65577 or an agent which modulates 27877, 18080, 14081, 32140, 50352, 16658, 14223, 16002, 50566, 65552 or 65577 expression or at least one 27877, 18080, 14081, 32140, 50352, 16658, 14223, 16002, 50566, 65552 or 65577 activity. Subjects at risk for a disease which is caused or contributed to by aberrant or unwanted 27877, 18080, 14081, 32140, 50352, 16658, 14223, 16002, 50566, 65552 or 65577 expression or activity can be identified by, for example, any or a combination of diagnostic or prognostic assays as described herein. Administration of a prophylactic agent can occur prior to the manifestation of symptoms characteristic of the 27877, 18080, 14081, 32140, 50352, 16658, 14223, 16002, 50566, 65552 or 65577 aberrance, such that a disease or disorder is prevented or, alternatively, delayed in its progression. Depending on the type of 27877, 18080, 14081, 32140, 50352, 16658, 14223, 16002, 50566, 65552 or 65577 aberrance, for example, a 27877, 18080, 14081, 32140, 50352, 16658, 14223, 16002, 50566, 65552 or 65577, 27877, 18080, 14081, 32140, 50352, 16658, 14223, 16002, 50566, 65552 or 65577 agonist or 27877, 18080, 14081, 32140, 50352, 16658, 14223, 16002, 50566, 65552 or 65577 antagonist agent can be used for treating the subject. The appropriate agent can be determined based on screening assays described herein.

It is possible that some 27877, 18080, 14081, 32140, 50352, 16658, 14223, 16002, 50566, 65552 or 65577 disorders can be caused, at least in part, by an abnormal level of gene product, or by the presence of a gene product exhibiting abnormal activity. As such, the reduction in the level and/or activity of such gene products would bring about the amelioration of disorder symptoms.

The 27877, 18080, 14081, 32140, 50352, 16658, 14223, 16002, 50566, 65552 or 65577 molecules can act as novel diagnostic targets and therapeutic agents for controlling one or more of a cellular proliferative and/or differentiative disorder, brain, blood vessel, platelet, breast, colon, kidney, lung, ovarian, prostate, hematopoeitic, pancreatic, skeletal muscle, testicular, skin, hormonal, associated with bone metabolism, immune e.g., inflammatory, cardiovascular, endothelial cell, liver, viral diseases, pain, metabolic, anemias, angiogenesis, neoplastic, endocrine, neurological or heart disorder, all of which are described above.

As discussed, successful treatment of 27877, 18080, 14081, 32140, 50352, 16658, 14223, 16002, 50566, 65552 or 65577 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 27877, 18080, 14081, 32140, 50352, 16658, 14223, 16002, 50566, 65552 or 65577 disorders. Such molecules can include, but are not limited to peptides, phosphopeptides, small organic or inorganic molecules, or antibodies (including, for example, polyclonal, monoclonal, humanized, human, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules can be utilized in treating or preventing a disease characterized by 27877, 18080, 14081, 32140, 50352, 16658, 14223, 16002, 50566, 65552 or 65577 expression is through the use of aptamer molecules specific for 27877, 18080, 14081, 32140, 50352, 16658, 14223, 16002, 50566, 65552 or 65577 protein. Aptamers are nucleic acid molecules having a tertiary structure which permits them to specifically or selectively bind to protein ligands (see, e.g., Osborne et al. (1997) *Curr. Opin. Chem. Biol.* 1: 5-9; and Patel (1997) *Curr Opin Chem Biol* 1:32-46). Since nucleic acid molecules can in many cases be more conveniently introduced into target cells than therapeutic protein molecules can be, aptamers offer a method by which 27877, 18080, 14081, 32140, 50352, 16658, 14223, 16002, 50566, 65552 or 65577 protein activity can be specifically decreased without the introduction of drugs or other molecules which can have pluripotent effects.

Antibodies can be generated that are both specific for target gene product and that reduce target gene product activity. Such antibodies can, therefore, by administered in instances whereby negative modulatory techniques are appropriate for the treatment of 27877, 18080, 14081, 32140, 50352, 16658, 14223, 16002, 50566, 65552 or 65577 disorders. For a description of antibodies, see the Antibody section above.

In circumstances wherein injection of an animal or a human subject with a 27877, 18080, 14081, 32140, 50352, 16658, 14223, 16002, 50566, 65552 or 65577 protein or epitope for stimulating antibody production is harmful to the subject, it is possible to generate an immune response against 27877, 18080, 14081, 32140, 50352, 16658, 14223, 16002, 50566, 65552 or 65577 through the use of anti-idiotypic antibodies (see, for example, Herlyn (1999) *Ann Med* 31:66-78; and Bhattacharya-Chatterjee and Foon (1998) *Cancer Treat Res.* 94:51-68). If an anti-idiotypic antibody is introduced into a mammal or human subject, it should stimulate the production of anti-anti-idiotypic antibodies, which should be specific to the 27877, 18080, 14081, 32140, 50352, 16658, 14223, 16002, 50566, 65552 or 65577 protein.

Vaccines directed to a disease characterized by 27877, 18080, 14081, 32140, 50352, 16658, 14223, 16002, 50566, 65552 or 65577 expression can also be generated in this fashion.

In instances where the target antigen is intracellular and whole antibodies are used, internalizing antibodies can be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889-7893).

The identified compounds that inhibit target gene expression, synthesis and/or activity can be administered to a patient at therapeutically effective doses to prevent, treat or ameliorate 27877, 18080, 14081, 32140, 50352, 16658, 14223, 16002, 50566, 65552 or 65577 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays can utilize antibody mimics and/or "biosensors" that have been created through molecular imprinting techniques. The compound which is able to modulate 27877, 18080, 14081, 32140, 50352, 16658, 14223, 16002, 50566, 65552 or 65577 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell et al (1996) *Current Opinion in Biotechnology* 7:89-94 and in Shea (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis et al (1993) *Nature* 361:645-647. Through the use of isotope-labeling, the "free" concentration of compound which modulates the expression or activity of 27877, 18080, 14081, 32140, 50352, 16658, 14223, 16002, 50566, 65552 or 65577 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz et al (1995) *Analytical Chemistry* 67:2142-2144.

Another aspect of the invention pertains to methods of modulating 27877, 18080, 14081, 32140, 50352, 16658, 14223, 16002, 50566, 65552 or 65577 expression or activity for therapeutic purposes. Accordingly, in an exemplary embodiment, the modulatory method of the invention involves contacting a cell with a 27877, 18080, 14081, 32140, 50352, 16658, 14223, 16002, 50566, 65552 or 65577 or agent that modulates one or more of the activities of 27877, 18080, 14081, 32140, 50352, 16658, 14223, 16002, 50566, 65552 or 65577 protein activity associated with the cell. An agent that modulates 27877, 18080, 14081, 32140, 50352, 16658, 14223, 16002, 50566, 65552 or 65577 protein activity can be an agent as described herein, such as a nucleic acid or a protein, a naturally-occurring target molecule of a 27877, 18080, 14081, 32140, 50352, 16658, 14223, 16002, 50566, 65552 or 65577 protein (e.g., a 27877, 18080, 14081, 32140, 50352, 16658, 14223, 16002, 50566, 65552 or 65577 substrate or receptor), a 27877, 18080, 14081, 32140, 50352, 16658, 14223, 16002, 50566, 65552 or 65577 antibody, a 27877, 18080, 14081, 32140, 50352, 16658, 14223, 16002, 50566, 65552 or 65577 agonist or antagonist, a peptidomimetic of a 27877, 18080, 14081, 32140, 50352, 16658, 14223, 16002, 50566, 65552 or 65577 agonist or antagonist, or other small molecule.

In one embodiment, the agent stimulates one or 27877, 18080, 14081, 32140, 50352, 16658, 14223, 16002, 50566, 65552 or 65577 activities. Examples of such stimulatory agents include active 27877, 18080, 14081, 32140, 50352, 16658, 14223, 16002, 50566, 65552 or 65577 protein and a nucleic acid molecule encoding 27877, 18080, 14081, 32140, 50352, 16658, 14223, 16002, 50566, 65552 or 65577. In another embodiment, the agent inhibits one or more 27877, 18080, 14081, 32140, 50352, 16658, 14223, 16002, 50566, 65552 or 65577 activities. Examples of such inhibitory agents include antisense 27877, 18080, 14081, 32140, 50352, 16658, 14223, 16002, 50566, 65552 or 65577 nucleic acid molecules, anti-27877, 18080, 14081, 32140, 50352, 16658, 14223, 16002, 50566, 65552 or 65577 antibodies, and 27877, 18080, 14081, 32140, 50352, 16658, 14223, 16002, 50566, 65552 or 65577 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 27877, 18080, 14081, 32140, 50352, 16658, 14223, 16002, 50566, 65552 or 65577 protein or nucleic acid molecule. In one embodiment, the method involves administering an agent (e.g., an agent identified by a screening assay described herein), or combination of agents that modulates (e.g., up regulates or down regulates) 27877, 18080, 14081, 32140, 50352, 16658, 14223, 16002, 50566, 65552 or 65577 expression or activity. In another embodiment, the method involves administering a 27877, 18080, 14081, 32140, 50352, 16658, 14223, 16002, 50566, 65552 or 65577 protein or nucleic acid molecule as therapy to compensate for reduced, aberrant, or unwanted 27877, 18080, 14081, 32140, 50352, 16658, 14223, 16002, 50566, 65552 or 65577 expression or activity.

Stimulation of 27877, 18080, 14081, 32140, 50352, 16658, 14223, 16002, 50566, 65552 or 65577 activity is desirable in situations in which 27877, 18080, 14081, 32140, 50352, 16658, 14223, 16002, 50566, 65552 or 65577 is abnormally downregulated and/or in which increased 27877, 18080, 14081, 32140, 50352, 16658, 14223, 16002, 50566, 65552 or 65577 activity is likely to have a beneficial effect. For example, stimulation of 27877, 18080, 14081, 32140, 50352, 16658, 14223, 16002, 50566, 65552 or 65577 activity is desirable in situations in which a 27877, 18080, 14081, 32140, 50352, 16658, 14223, 16002, 50566, 65552 or 65577 is downregulated and/or in which increased 27877, 18080, 14081, 32140, 50352, 16658, 14223, 16002, 50566, 65552 or 65577 activity is likely to have a beneficial effect. Likewise, inhibition of 27877, 18080, 14081, 32140, 50352, 16658, 14223, 16002, 50566, 65552 or 65577 activity is desirable in situations in which 27877, 18080, 14081, 32140, 50352, 16658, 14223, 16002, 50566, 65552 or 65577 is abnormally upregulated and/or in which decreased 27877, 18080, 14081, 32140, 50352, 16658, 14223, 16002, 50566, 65552 or 65577 activity is likely to have a beneficial effect.

Pharmacogenomics

The 27877, 18080, 14081, 32140, 50352, 16658, 14223, 16002, 50566, 65552 or 65577 molecules of the present invention, as well as agents, or modulators which have a stimulatory or inhibitory effect on 27877, 18080, 14081, 32140, 50352, 16658, 14223, 16002, 50566, 65552 or 65577 activity (e.g., 27877, 18080, 14081, 32140, 50352, 16658, 14223, 16002, 50566, 65552 or 65577 gene expression) as identified by a screening assay described herein can be administered to individuals to treat (prophylactically or therapeutically) 27877, 18080, 14081, 32140, 50352, 16658, 14223, 16002, 50566, 65552 or 65577-associated disorders (e.g., aberrant or deficient phospholipase activity, serine carboxypeptidase activity, trypsin-like serine protease activity, aldehyde dehydrogenase activity, ubiquitin-protein ligase activity, protein kinase activity, hydrolase activity or matrix metalloproteinase activity.) associated with aberrant or unwanted 27877, 18080, 14081, 32140, 50352, 16658, 14223, 16002, 50566, 65552 or 65577 activity.

In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a 27877, 18080, 14081, 32140, 50352, 16658, 14223, 16002, 50566, 65552 or 65577 molecule or 27877, 18080, 14081, 32140, 50352, 16658, 14223, 16002, 50566, 65552 or 65577 modulator as well as tailoring the dosage and/or therapeutic regimen of treatment with a 27877, 18080, 14081, 32140, 50352, 16658, 14223, 16002, 50566, 65552 or 65577 molecule or 27877, 18080, 14081, 32140, 50352, 16658, 14223, 16002, 50566, 65552 or 65577 modulator.

Pharmacogenomics deals with clinically significant hereditary variations in the response to drugs due to altered drug disposition and abnormal action in affected persons. See, for example, Eichelbaum et al. (1996) *Clin. Exp. Pharmacol. Physiol.* 23:983-985 and Linder et al. (1997) *Clin. Chem.* 43:254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP can occur once per every 1000 bases of DNA. A SNP can be involved in a disease process, however, the vast majority can not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that can be common among such genetically similar individuals.

Alternatively, a method termed the "candidate gene approach", can be utilized to identify genes that predict drug response. According to this method, if a gene that encodes a drug's target is known (e.g., a 27877, 18080, 14081, 32140, 50352, 16658, 14223, 16002, 50566, 65552 or 65577 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 27877, 18080, 14081, 32140, 50352, 16658, 14223, 16002, 50566, 65552 or 65577 molecule or 27877, 18080, 14081, 32140, 50352, 16658, 14223, 16002, 50566, 65552 or 65577 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 27877, 18080, 14081, 32140, 50352, 16658, 14223, 16002, 50566, 65552 or 65577 molecule or 27877, 18080, 14081, 32140, 50352, 16658, 14223, 16002, 50566, 65552 or 65577 modulator, such as a modulator identified by one of the exemplary screening assays described herein.

The present invention further provides methods for identifying new agents, or combinations, that are based on identifying agents that modulate the activity of one or more of the gene products encoded by one or more of the 27877, 18080, 14081, 32140, 50352, 16658, 14223, 16002, 50566, 65552 or 65577 genes of the present invention, wherein these products can be associated with resistance of the cells to a therapeutic agent. Specifically, the activity of the proteins encoded by the 27877, 18080, 14081, 32140, 50352, 16658, 14223, 16002, 50566, 65552 or 65577 genes of the present invention can be used as a basis for identifying agents for overcoming agent resistance. By blocking the activity of one or more of the resistance proteins, target cells, e.g., human cells, will become sensitive to treatment with an agent to which the unmodified target cells were resistant.

Monitoring the influence of agents (e.g., drugs) on the expression or activity of a 27877, 18080, 14081, 32140, 50352, 16658, 14223, 16002, 50566, 65552 or 65577 protein can be applied in clinical trials. For example, the effectiveness of an agent determined by a screening assay as described herein to increase 27877, 18080, 14081, 32140, 50352, 16658, 14223, 16002, 50566, 65552 or 65577 gene expression, protein levels, or upregulate 27877, 18080, 14081, 32140, 50352, 16658, 14223, 16002, 50566, 65552 or 65577 activity, can be monitored in clinical trials of subjects exhibiting decreased 27877, 18080, 14081, 32140, 50352, 16658, 14223, 16002, 50566, 65552 or 65577 gene expression, protein levels, or downregulated 27877, 18080, 14081, 32140, 50352, 16658, 14223, 16002, 50566, 65552 or 65577 activity. Alternatively, the effectiveness of an agent determined by a screening assay to decrease 27877, 18080, 14081, 32140, 50352, 16658, 14223, 16002, 50566, 65552 or 65577 gene expression, protein levels, or downregulate 27877, 18080, 14081, 32140, 50352, 16658, 14223, 16002, 50566, 65552 or 65577 activity, can be monitored in clinical trials of subjects exhibiting increased 27877, 18080, 14081, 32140, 50352, 16658, 14223, 16002, 50566, 65552 or 65577 gene expression, protein levels, or upregulated 27877, 18080, 14081, 32140, 50352, 16658, 14223, 16002, 50566, 65552 or 65577 activity. In such clinical trials, the expression or activity of a 27877, 18080, 14081, 32140, 50352, 16658, 14223, 16002, 50566, 65552 or 65577 gene, and preferably, other genes that have been implicated in, for example, a protein kinase-associated or another 27877, 18080, 14081, 32140, 50352, 16658, 14223, 16002, 50566, 65552 or 65577-associated disorder can be used as a "read out" or markers of the phenotype of a particular cell.

OTHER EMBODIMENTS

In another aspect, the invention features a method of analyzing a plurality of capture probes. The method is useful, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence, wherein the capture probes are from a cell or subject which expresses 27877, 18080, 14081, 32140, 50352, 16658, 14223, 16002, 50566, 65552 or 65577 or from a cell or subject in which a 27877, 18080, 14081, 32140, 50352, 16658, 14223, 16002, 50566, 65552 or 65577 mediated response has been elicited; contacting the array with a 27877, 18080, 14081, 32140, 50352, 16658, 14223, 16002, 50566, 65552 or 65577 nucleic acid (preferably purified), a 27877, 18080, 14081, 32140, 50352, 16658, 14223, 16002, 50566, 65552 or 65577 polypeptide (preferably purified), or an anti-27877, 18080, 14081, 32140, 50352, 16658, 14223, 16002, 50566, 65552 or 65577 antibody, and thereby evaluating the plurality of capture probes. Binding, e.g., in the case of a nucleic acid, hybridization with a capture probe at an address of the plurality, is detected, e.g., by a signal generated from a label attached to the 27877, 18080, 14081, 32140, 50352, 16658, 14223, 16002, 50566, 65552 or 65577 nucleic acid, polypeptide, or antibody.

The capture probes can be a set of nucleic acids from a selected sample, e.g., a sample of nucleic acids derived from a control or non-stimulated tissue or cell.

The method can include contacting the 27877, 18080, 14081, 32140, 50352, 16658, 14223, 16002, 50566, 65552 or 65577 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 27877, 18080, 14081, 32140, 50352, 16658, 14223, 16002, 50566, 65552 or 65577. Such methods can be used to diagnose a subject, e.g., to evaluate risk for a disease or disorder, to evaluate suitability of a selected treatment for a subject, to evaluate whether a subject has a disease or disorder.

The method can be used to detect SNPs, as described above.

In another aspect, the invention features, a method of analyzing 27877, 18080, 14081, 32140, 50352, 16658, 14223, 16002, 50566, 65552 or 65577, e.g., analyzing structure, function, or relatedness to other nucleic acid or amino acid sequences. The method includes: providing a 27877, 18080, 14081, 32140, 50352, 16658, 14223, 16002, 50566, 65552 or 65577 nucleic acid or amino acid sequence; comparing the 27877, 18080, 14081, 32140, 50352, 16658, 14223, 16002, 50566, 65552 or 65577 sequence with one or more preferably a plurality of sequences from a collection of sequences, e.g., a nucleic acid or protein sequence database; to thereby analyze 27877, 18080, 14081, 32140, 50352, 16658, 14223, 16002, 50566, 65552 or 65577.

The method can include evaluating the sequence identity between a 27877, 18080, 14081, 32140, 50352, 16658, 14223, 16002, 50566, 65552 or 65577 sequence and a database sequence. The method can be performed by accessing the database at a second site, e.g., over the internet. Preferred databases include GenBank™ and SwissProt.

In another aspect, the invention features, a set of oligonucleotides, useful, e.g., for identifying SNP's, or identifying specific alleles of 27877, 18080, 14081, 32140, 50352, 16658, 14223, 16002, 50566, 65552 or 65577. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotide which hybridizes to one allele provides a signal that is distinguishable from an oligonucleotides which hybridizes to a second allele.

The sequences of 27877, 18080, 14081, 32140, 50352, 16658, 14223, 16002, 50566, 65552 or 65577 molecules are provided in a variety of mediums to facilitate use thereof. A sequence can be provided as a manufacture, other than an isolated nucleic acid or amino acid molecule, which contains a 27877, 18080, 14081, 32140, 50352, 16658, 14223, 16002, 50566, 65552 or 65577 molecule. Such a manufacture can provide a nucleotide or amino acid sequence, e.g., an open reading frame, in a form which allows examination of the manufacture using means not directly applicable to examining the nucleotide or amino acid sequences, or a subset thereof, as they exist in nature or in purified form.

A 27877, 18080, 14081, 32140, 50352, 16658, 14223, 16002, 50566, 65552 or 65577 nucleotide or amino acid sequence can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as compact disc and CD-ROM; electrical storage media such as RAM, ROM, EPROM, EEPROM, and the like; and general hard disks and hybrids of these categories such as magnetic/optical storage media. The medium is adapted or configured for having thereon 27877, 18080, 14081, 32140, 50352, 16658, 14223, 16002, 50566, 65552 or 65577 sequence information of the present invention.

As used herein, the term "electronic apparatus" is intended to include any suitable computing or processing apparatus of other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as personal digital assistants (PDAs), cellular phones, pagers, and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the 27877, 18080, 14081, 32140, 50352, 16658, 14223, 16002, 50566, 65552 or 65577 sequence information.

A variety of data storage structures are available to a skilled artisan for creating a computer readable medium having recorded thereon a 27877, 18080, 14081, 32140, 50352, 16658, 14223, 16002, 50566, 65552 or 65577 nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the 27877, 18080, 14081, 32140, 50352, 16658, 14223, 16002, 50566, 65552 or 65577 nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The present invention therefore provides a medium for holding instructions for performing a method for determining whether a subject has a phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder or a pre-disposition to a phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder, wherein the method comprises the steps of determining 27877, 18080, 14081, 32140, 50352, 16658, 14223, 16002, 50566, 65552 or 65577 sequence information associated with the subject and based on the 27877, 18080, 14081, 32140, 50352, 16658, 14223, 16002, 50566, 65552 or 65577 sequence information, determining whether the subject has a phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder and/or recommending a particular treatment for the disease, disorder, or pre-disease condition.

The present invention further provides in an electronic system and/or in a network, a method for determining whether a subject has a phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder or a pre-disposition to a disease associated with 27877, 18080, 14081, 32140, 50352, 16658, 14223, 16002, 50566, 65552 or 65577, wherein the method comprises the steps of determining 27877, 18080, 14081, 32140, 50352, 16658, 14223, 16002, 50566, 65552 or 65577 sequence information associated with the subject, and based on the 27877, 18080, 14081, 32140, 50352, 16658, 14223, 16002, 50566, 65552 or 65577 sequence information, determining whether the subject has a phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder or a pre-disposition to a phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder, and/or recommending a particular treatment for the disease, disorder, or pre-disease condition. The method may further comprise the step of receiving phenotypic information associated with the subject and/or acquiring from a network phenotypic information associated with the subject.

The present invention also provides in a network, a method for determining whether a subject has a phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder or a pre-disposition to a phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder, said method comprising the steps of receiving 27877, 18080, 14081, 32140, 50352, 16658, 14223, 16002, 50566, 65552 or 65577 sequence information from the subject and/or information related thereto, receiving phenotypic information associated with the subject, acquiring information from the network corresponding to 27877, 18080, 14081, 32140, 50352, 16658, 14223, 16002, 50566, 65552 or 65577 and/or corresponding to a phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder, and based on one or more of the phenotypic information, the 27877, 18080, 14081, 32140, 50352, 16658, 14223, 16002, 50566, 65552 or 65577 information (e.g., sequence information and/or information related thereto), and the acquired information, determining whether the subject has a phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder or a pre-disposition to a phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder. The method may further comprise the step of recommending a particular treatment for the disease, disorder, or pre-disease condition.

The present invention also provides a business method for determining whether a subject has a phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder or a pre-disposition to a phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder, said method comprising the steps of receiving information related to 27877, 18080, 14081, 32140, 50352, 16658, 14223, 16002, 50566, 65552 or 65577 (e.g., sequence information and/or information related thereto), receiving phenotypic information associated with the subject, acquiring information from the network related to 27877, 18080, 14081, 32140, 50352, 16658, 14223, 16002, 50566, 65552 or 65577 and/or related to a phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder, and based on one or more of the phenotypic information, the 27877, 18080, 14081, 32140, 50352, 16658, 14223, 16002, 50566, 65552 or 65577 information, and the acquired information, determining whether the subject has a phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder or a pre-disposition to a phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder. The method may further comprise the step of recommending a particular treatment for the disease, disorder, or pre-disease condition.

The invention also includes an array comprising a 27877, 18080, 14081, 32140, 50352, 16658, 14223, 16002, 50566, 65552 or 65577 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be 27877, 18080, 14081, 32140, 50352, 16658, 14223, 16002, 50566, 65552 or 65577. This allows a profile to be developed showing a battery of genes specifically expressed in one or more tissues.

In addition to such qualitative information, the invention allows the quantitation of gene expression. Thus, not only tissue specificity, but also the level of expression of a battery of genes in the tissue if ascertainable. Thus, genes can be grouped on the basis of their tissue expression per se and level of expression in that tissue. This is useful, for example, in ascertaining the relationship of gene expression in that tissue. Thus, one tissue can be perturbed and the effect on gene expression in a second tissue can be determined. In this context, the effect of one cell type on another cell type in response to a biological stimulus can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a protein kinase, methyltransferase, acyl-CoA dehydrogenase, short chain dehyrdogenase, reductase, acyltransferase, phosphatase, transferase, ATP-ase or synthase-associated or another 27877, 18080, 14081, 32140, 50352, 16658, 14223, 16002, 50566, 65552 or 65577-associated disease or disorder, progression of protein kinase, methyltransferase, acyl-CoA dehydrogenase, short chain dehyrdogenase, reductase, acyl-transferase, phosphatase, transferase, ATP-ase or synthase-associated or another 27877, 18080, 14081, 32140, 50352, 16658, 14223, 16002, 50566, 65552 or 65577-associated disease or disorder, and processes, such a cellular transformation associated with the phospholipase, serine carboxypeptidase, trypsin-like serine protease, aldehyde dehydrogenase, ubiquitin-protein ligase, protein kinase, hydrolase or matrix metalloproteinase-associated or another 27877, 18080, 14081, 32140, 50352, 16658, 14223, 16002, 50566, 65552 or 65577-associated disease or disorder.

The array is also useful for ascertaining the effect of the expression of a gene on the expression of other genes in the same cell or in different cells (e.g., acertaining the effect of 27877, 18080, 14081, 32140, 50352, 16658, 14223, 16002, 50566, 65552 or 65577 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including 27877, 18080, 14081, 32140, 50352, 16658, 14223, 16002, 50566, 65552 or 65577) that could serve as a molecular target for diagnosis or therapeutic intervention.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 27877, 18080, 14081, 32140, 50352, 16658, 14223, 16002, 50566, 65552 or 65577 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features a method of analyzing a sequence. The method includes: providing a 27877, 18080, 14081, 32140, 50352, 16658, 14223, 16002, 50566, 65552 or 65577 sequence, or record, in computer readable form; comparing a second sequence to the 27877, 18080, 14081, 32140, 50352, 16658, 14223, 16002, 50566, 65552 or 65577 sequence; thereby analyzing a sequence. Comparison can include comparing to sequences for sequence identity or determining if one sequence is included within the other, e.g., determining if the 27877, 18080, 14081, 32140, 50352, 16658, 14223, 16002, 50566, 65552 or 65577 sequence includes a sequence being compared. In a preferred embodiment the 27877, 18080, 14081, 32140, 50352, 16658, 14223, 16002, 50566, 65552 or 65577 or second sequence is stored on a first computer, e.g., at a first site and the comparison is performed, read, or recorded on a second computer, e.g., at a second site. E.g., the 27877, 18080, 14081, 32140, 50352, 16658, 14223, 16002, 50566, 65552 or 65577 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

EXEMPLIFICATION

Example 1

Tissue Distribution of 27877, 18080, 14081, 32140, 50352, 16658, 14223, 16002, 50566, 65552 or 65577 mRNA Northern blot hybridizations with various RNA samples can be performed under standard conditions and washed under stringent conditions, i.e., 0.2×SSC at 65° C. A DNA probe corresponding to all or a portion of the 27877, 18080, 14081, 32140, 50352, 16658, 14223, 16002, 50566, 65552 or 65577 cDNA (SEQ ID NO:1, 3, 4, 6, 11, 13, 20, 22, 25, 27, 29, 31, 35, 37, 38, 40, 41, 43, 73, 75, 76, 78, 86 or 88) or 27877, 18080, 14081, 32140, 50352, 16658, 14223, 16002, 50566, 65552 or 65577 cDNA can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 2

Recombinant Expression of 27877, 18080, 14081, 32140, 50352, 16658, 14223, 16002, 50566, 65552 or 65577 in Bacterial Cells In this example, 27877, 18080, 14081, 32140, 50352, 16658, 14223, 16002, 50566, 65552 or 65577 is expressed as a recombinant glutathione-S-transferase (GST) fusion polypeptide in *E. coli* and the fusion polypeptide is isolated and characterized. Specifically, 27877, 18080, 14081, 32140, 50352, 16658, 14223, 16002, 50566, 65552 or 65577 is fused to GST and this fusion polypeptide is expressed in *E. coli*, e.g., strain PEB199. Expression of the GST-27877, -18080, -14081, -32140, -50352, -16658, -14223, -16002, -50566, -65552 or -65577 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant 27877, 18080, 14081, 32140, 50352, 16658, 14223, 16002, 50566, 65552 or 65577 Protein in COS Cells To express the 27877, 18080, 14081, 32140, 50352, 16658, 14223, 16002, 50566, 65552 or 65577 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 27877, 18080, 14081, 32140, 50352, 16658, 14223, 16002, 50566, 65552 or 65577 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 27877, 18080, 14081, 32140, 50352, 16658, 14223, 16002, 50566, 65552 or 65577 DNA sequence is amplified by PCR using two primers. The 5' primer contains the restriction site of interest followed by approximately twenty nucleotides of the 27877, 18080, 14081, 32140, 50352, 16658, 14223, 16002, 50566, 65552 or 65577 coding sequence starting from the initiation codon; the 3' end sequence contains complementary sequences to the other restriction site of interest, a translation stop codon, the HA tag or FLAG tag and the last 20 nucleotides of the 27877, 18080, 14081, 32140, 50352, 16658, 14223, 16002, 50566, 65552 or 65577 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 27877, 18080, 14081, 32140, 50352, 16658, 14223, 16002, 50566, 65552 or 65577 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 27877-, 18080-, 14081-, 32140-, 50352-, 16658-, 14223-, 16002-, 50566-, 65552- or 65577- pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the 27877, 18080, 14081, 32140, 50352, 16658, 14223, 16002, 50566, 65552 or 65577 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 27877, 18080, 14081, 32140, 50352, 16658, 14223, 16002, 50566, 65552 or 65577 coding sequence is cloned directly into the polylinker of the pcDNA/Amp vector using the appropriate restriction sites. The resulting plasmid is transfected into COS cells in the manner described above, and the expression of the 27877, 18080, 14081, 32140, 50352, 16658, 14223, 16002, 50566, 65552 or 65577 polypeptide is detected by radiolabelling and immunoprecipitation using a 27877, 18080, 14081, 32140, 50352, 16658, 14223, 16002, 50566, 65552 or 65577 specific monoclonal antibody.

Example 4

TaqMan Analysis of 27877, 18080, 14081, 32140, 50352, 16658, 14223, 16002, 50566, 65552 or 65577

Human 27877, 18080, 14081, 32140, 50352, 16658, 14223, 16002, 50566, 65552 or 65577 expression was measured by TaqMan® quantitative PCR (Perkin Elmer Applied Biosystems) in cDNA prepared from a variety of normal and diseased (e.g., cancerous) human tissues or cell lines.

Probes were designed by PrimerExpress software (PE Biosystems) based on the sequence of the human 27877, 18080, 14081, 32140, 50352, 16658, 14223, 16002, 50566, 65552 or 65577 gene. Each human 27877, 18080, 14081, 32140, 50352, 16658, 14223, 16002, 50566, 65552 or 65577 gene probe was labeled using FAM (6-carboxyfluorescein), and the β2-microglobulin reference probe was labeled with a different fluorescent dye, VIC. The differential labeling of the target gene and internal reference gene thus enabled measurement in same well. Forward and reverse primers and the probes for both P2-microglobulin and target gene were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forward and reverse primers plus 200 nM probe for the target gene. TaqMan matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate human 27877, 18080, 14081, 32140, 50352, 16658, 14223, 16002, 50566, 65552 or 65577 gene expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the human 27877, 18080, 14081, 32140, 50352, 16658, 14223, 16002, 50566, 65552 or 65577 gene is normalized by subtracting the Ct value of the β-2 microglobulin gene to obtain a $_\Delta$Ct value using the following formula: $_\Delta Ct = Ct_{human\ 59914\ and\ 59921} - Ct_{\beta 2\ microglobulin}$. Expression is then calibrated against a cDNA sample showing a comparatively low level of expression of the human 27877, 18080, 14081, 32140, 50352, 16658, 14223, 16002, 50566, 65552 or 65577 gene. The $_\Delta$Ct value for the calibrator sample is then subtracted from $_\Delta$Ct for each tissue sample according to the following formula: $_{\Delta\Delta}Ct = _\Delta Ct_{sample} - _\Delta Ct_{calibrator}$. Relative expression is then calculated using the arithmetic formula given by $2^{-\Delta\Delta Ct}$.

Example 5

In Situ Hybridization of 27877, 18080, 14081, 32140, 50352, 16658, 14223, 16002, 50566, 65552 or 65577

The following describes the tissue distribution of 27877, 18080, 14081, 32140, 50352, 16658, 14223, 16002, 50566, 65552 or 65577 mRNA, as may be determined by in situ hybridization analysis using oligonucleotide probes based on the human G2RF sequence.

For in situ analysis, various tissues, e.g. tissues obtained from brain, are first frozen on dry ice. Ten-micrometer-thick sections of the tissues are postfixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections are rinsed in DEPC 2×SSC (1×SSC is 0.15M NaCl plus 0.015M sodium citrate). Tissue is then dehydrated through a series of ethanol washes, incubated in 100% chloroform for 5 minutes, and then rinsed in 100% ethanol for 1 minute and 95% ethanol for 1 minute and allowed to air dry.

Hybridizations are performed with $^{35}$S-radiolabeled (5×10$^7$ cpm/ml) cRNA probes. Probes are incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides are washed with 2×SSC. Sections are then sequentially incubated at 37° C. in TNE (a solution containing 10 mM Tris-HCl (pH 7.6), 500 mM NaCl, and 1 mM EDTA), for 10 minutes, in TNE with 10 μg of RNase A per ml for 30 minutes, and finally in TNE for 10 minutes. Slides are then rinsed with 2×SSC at room temperature, washed with 2×SSC at 50° C. for 1 hour, washed with 0.2×SSC at 55° C. for 1 hour, and 0.2×SSC at 60° C. for 1 hour. Sections are then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

The contents of all references, patents and published patent applications cited throughout this application are incorporated herein by reference.

EQUIVALENTS

Those skilled in the art will recognize, or be able to ascertain using no more than routine experimentation, many equivalents to the specific embodiments of the invention described herein.

What is claimed is:

1. An isolated polypeptide selected from the group consisting of:
    a) a polypeptide which is encoded by a nucleic acid comprising the nucleotide sequence of SEQ ID NO:25 or SEQ ID NO:27;
    b) a polypeptide comprising the amino acid sequence of SEQ ID NO:26.

2. The polypeptide of claim 1, wherein the polypeptide is encoded by a nucleic acid comprising the nucleotide sequence of SEQ ID NO:25 or SEQ ID NO:27.

3. The polypeptide of claim 1, wherein the polypeptide comprises the amino acid sequence of SEQ ID NO:26.

4. The polypeptide of claim 1, further comprising heterologous amino acid sequences.

5. The polypeptide of claim 2, further comprising hetrologous amino acid sequences.

6. The polypeptide of claim 3, further comprising hetrologous amino acid sequences.

* * * * *